(12) United States Patent
Sasahara et al.

(10) Patent No.: US 7,312,208 B2
(45) Date of Patent: Dec. 25, 2007

(54) QUATERNARY AMMONIUM COMPOUNDS

(75) Inventors: Takehiko Sasahara, Numazu (JP); Mitsunobu Mohri, Mishima (JP)

(73) Assignee: Asahi Kasei Pharma Corporation, Tokyo (JP)

( * ) Notice: Subject to any disclaimer, the term of this patent is extended or adjusted under 35 U.S.C. 154(b) by 383 days.

(21) Appl. No.: 10/647,455

(22) Filed: Aug. 26, 2003

(65) Prior Publication Data

US 2005/0009805 A1    Jan. 13, 2005

Related U.S. Application Data

(60) Provisional application No. 60/407,291, filed on Sep. 3, 2002, provisional application No. 60/434,416, filed on Dec. 19, 2002.

(30) Foreign Application Priority Data

Aug. 28, 2002 (JP) ............. 2002-248586
Dec. 17, 2002 (JP) ............. 2002-364725

(51) Int. Cl.
| A61P 9/00 | (2006.01) |
| A61K 31/553 | (2006.01) |
| A61K 31/554 | (2006.01) |
| C07D 281/10 | (2006.01) |
| C07D 513/02 | (2006.01) |

(52) U.S. Cl. ................. 514/211.09; 540/552
(58) Field of Classification Search ........... 514/211.09; 540/552
See application file for complete search history.

(56) References Cited

FOREIGN PATENT DOCUMENTS

| EP | 0 864 582 A2 | 9/1998 |
| WO | 93/16055 | 8/1993 |
| WO | 94/18183 | 8/1994 |
| WO | 94/18184 | 8/1994 |
| WO | 96/05188 | 2/1996 |
| WO | 97/33882 | 9/1997 |
| WO | 00/01687 | 1/2000 |
| WO | 00/47568 | 8/2000 |
| WO | 00/61568 | 10/2000 |
| WO | 02/08211 A2 | 1/2002 |
| WO | 03/022825 A1 | 3/2003 |

*Primary Examiner*—Brenda Coleman
(74) *Attorney, Agent, or Firm*—Young & Thompson

(57) ABSTRACT

Drugs useful for the treatment and prevention of hyperlipidemia, moreover drugs useful for the treatment and prevention of cholestasis-caused hepatopathy, particularly primary biliary cirrhosis and primary sclerosing cholangitis, and drugs for the treatment and prevention of obesity, fatty liver and steatohepatitis, containing as active ingredients benzothiazepine compounds having a thioamide bond and a quaternary ammonium substituent, represented by formula (1) below are provided.

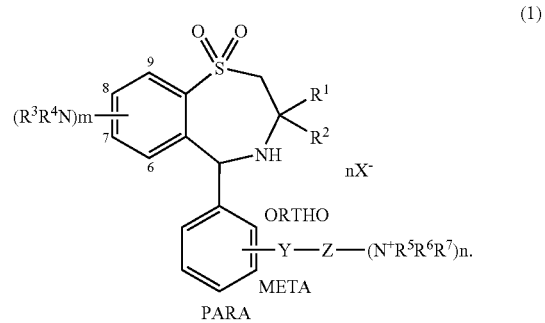

Also, drugs containing ileal bile acid transporter inhibiting compounds as active ingredients for the treatment and prevention of cholestasis-caused hepatopathy are provided.

22 Claims, No Drawings

QUATERNARY AMMONIUM COMPOUNDS

DESCRIPTION OF RELATED APPLICATIONS

This application claims priority under 35 U.S.C. § 119 to Japanese Patent Application No. 2002-248586 filed on Aug. 28, 2002, Japanese Patent Application No. 2002-364725 filed on Dec. 17, 2002, U.S. Provisional Application Ser. No. 60/407291 filed Sep. 3, 2002, and U.S. Provisional Application Ser. No. 60/434416 filed Dec. 19, 2002. The contents of these applications are incorporated herein by reference.

BACKGROUND OF THE INVENTION

1) Field of the Invention

The present invention relates to novel benzothiazepine compounds having a thioamide bond and a quaternary ammonium substituent and to pharmaceutical compositions which contain them. Moreover, the present invention relates to pharmaceutical compositions for the treatment of cholestasis-caused hepatopathy and the like.

2) Description of the Related Art

Hyperlipidemia means a state where neutral fat, cholesterol and the like in blood are at higher levels than the normal levels and has been known to deserve a treatment since it is a main risk factor in ischemic diseases. Moreover, hyperlipidemia is also known to cause arteriosclerosis and in particular, to decrease blood cholesterol level is effective for the prevention and treatment of arteriosclerosis. Arteriosclerosis is also known as a cause of myocardial infarction cerebral thrombosis, peripheral arterial obstruction, and arteriosclerosis obliterans. Syndrome X was advocated by Reavens et al. ("Diabetes", 37, 1595-1607, 1988) and means a multiple risk factor syndrome which develops arteriosclerosis by accumulation of risk factors such as hyperinsulinemia, hyperlipidemia, hypertension, and abnormality of glucose tolerance on an individual, although the factors are not so serious as to indicate the conditions of diseases when they exist independently of each other. A cholesterol-lowering agent is considered to be effective for the prevention or treatment of these diseases (Japan Clinical Hyperlipidemia - Volume 1 -ISSN0047-1 852).

At present, commercially available drugs for the treatment of hyperlipidemia include HMG-CoA reductase inhibitors, anion exchange resins and so forth. These drugs are used for the prevention and treatment of hyperlipidemia, in particular, hypercholesterolemia and arteriosclerosis. Furthermore, these drugs are also used in the prevention or treatment of myocardial infarction, cerebral thrombosis, peripheral arterial obstruction, and arteriosclerosis obliterans, which are diseases caused by hypercholesterolemia or arteriosclerosis.

SUMMARY OF THE INVENTION

It has heretofore been demanded to provide novel drugs useful as therapeutic and prophylactic agents for hyperlipidemia, and furthermore drugs which are also useful as therapeutic and prophylactic agents for cholestasis-caused hepatopathy, in particular primary biliary cirrhosis, and primary sclerosing cholangitis, as well as drugs which are useful as therapeutic and prophylactic agents for obesity, fatty liver, and steatohepatitis.

To solve the above-mentioned problem, the inventors of the present invention synthesized various compounds and studied their activity. As a result, they have verified that novel benzothiazepine compounds represented by formula (1) below having a thioamide bond and a quaternary ammonium substituent have high therapeutic and preventive effects for hyperlipidemia and moreover extremely potent ileal bile acid transporter inhibiting activity and blood cholesterol-lowering activity, so that they can be used as cholesterol-lowering agents, in particular as a therapeutic agent and preventive agent for hyperlipidemia, arteriosclerosis, syndrome X, etc. Furthermore, the inventors have verified that the novel benzothiazepine compounds have therapeutic and preventive effects for cholestasis-caused hepatopathy, so that the compounds can be used as therapeutic and preventive agents for cholestasis-caused hepatopathy, particularly for primary biliary cirrhosis and primary sclerosing cholangitis. Also, the inventors have verified that the compounds have a body weight reducing effect and a fatty liver improving effect, so that they can be used as therapeutic and preventive agents for obesity and fatty liver. Moreover, the inventors have verified that the compounds have a therapeutic effect and preventive effects for steatohepatitis, so that they can be used as therapeutic and preventive agents for steatohepatitis.

That is, the present invention provides a compound represented by formula (1) below.

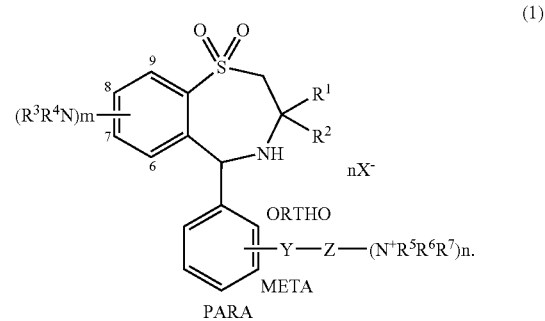

[wherein $R^1$ and $R^2$, which may be mutually different, each represents an alkyl group having from 1 to 10 carbon atoms;

m represents an integer of 1 or 2, and $R^3$ and $R^4$, which may be mutually different, each represents an alkyl group having from 1 to 5 carbon atoms;

Y represents any one of —NHCS—, —NHCSNH—, and —NHCSO— where the —NH in the —NHCS— represents a bond which links with an adjacent benzene ring and the CS— in the —NHCS— represents a bond which links with an adjacent Z, and the —NH in the —NHCSO— represents a bond which links with an adjacent benzene ring and the OSO— in the —NHCSO— represents a bond which links with an adjacent Z;

Z—$(N^+R^5R^6R^7)_n$ represents an alkyl group having from 2 to 10 carbon atoms or an alkenyl group having from 2 to 10 carbon atoms which is substituted with n (—$N^+R^5R^6R^7$)s, where at least one of methylenes which constitute Z may be replaced by any one of a phenylene and an —O—;

n is an integer of 1 or 2; and $N^+R^5R^6R^7$ is any one of I), II), and III) given below which are mutually independent:

I) $R^5$, $R^6$, and $R^7$, which may be mutually different, each represents any one of an alkyl group having from 1 to 10 carbon atoms, an alkenyl group having from 2 to 10 carbon atoms, and an alkynyl group having from 2 to 10 carbon atoms, where the alkyl group, the alkenyl group, and the alkynyl group may be substituted with at least one of a phenyl group, a naphthyl group, a pyridyl group, a quinolyl group, a thienyl group, a furyl group, a piperidyl group, a pyrrolidyl group, a morpholyl group, a cycloalkyl group having from 3 to 7 carbon atoms, a cyano group, a nitro group, a hydroxyl group, an oxo group, a thioxo group, a carboxyl group, a —CON H$_2$ group, an —SO$_3$H group, and further, at least one of methylenes which constitute the alkyl group, the alkenyl group, and the alkynyl group may be replaced by any one of a phenylene, a thienylene, a furylene, a cyclohexylene, a cyclopentylene, an —O—, an —S—, a —CO$_2$—, an —NHCO—, an —NR$^8$—, and an —N$^+$W$^-$R$^9$R$^{10}$— where R$^8$ represents an alkyl group having from 1 to 5 carbon atoms or an alkenyl group having from 2 to 5 carbon atoms and the alkyl group and alkenyl group represented by R$^8$ may be substituted with at least one of a phenyl group, a cycloalkyl group having from 3 to 7 carbon atoms, and a hydroxyl group; R$^9$ and R$^{10}$ which may be mutually different, each represents an alkyl group having from 1 to 5 carbon atoms or an alkenyl group having from 2 to 5 carbon atoms and may be substituted with at least one of a phenyl group, a cycloalkyl group having from 3 to 7 carbon atoms, and a hydroxyl group; and W$^-$represents a counter anion, II) N$^+$R$^5$R$^6$R$^7$ represents a monocyclic ring or a bicyclic ring which is formed by 4 to 9 carbon atoms in addition to an ammonium nitrogen atom, provided that the position of its bonding with Z is the ammonium nitrogen atom, where one of the carbon atoms which constitute the ring in the monocyclic ring and bicyclic ring may be replaced by any one atom of oxygen, nitrogen, and sulfur, and moreover, the monocyclic ring and the bicyclic ring may be substituted with at least one of a hydroxyl group, an oxo group, a thioxo group, a cyano group, a phenyl group, a naphthyl group, a thienyl group, a pyridyl group, a cycloalkyl group having from 3 to 7 carbon atoms, a carboxyl group, a —CON H$_2$ group, an —SO$_3$H group, and an —R$^{11}$group; R$^{11}$ represents an alkyl group having from 1 to 8 carbon atoms or an alkenyl group having from 2 to 8 carbon atoms, where the alkyl group and the alkenyl group represented by R$^{11}$ may be substituted with at least one of a phenyl group, a naphthyl group, a pyridyl group, a quinolyl group, a thienyl group, a furyl group, a piperidyl group, a pyrrolidyl group, a morpholyl group, a cycloalkyl group having from 3 to 7 carbon atoms, a cyano group, a nitro group, a hydroxyl group, an oxo group, a thioxo group, a carboxyl group, a —CONH$_2$ group, and an —SO$_3$H group; moreover, at least one of methylenes which constitute the alkyl group and the alkenyl group may be replaced by any one of a phenylene, a thienylene, a furylene, a cyclohexylene, a cyclopentylene, an —O—, an —S—, a —CO$_2$—, an —NHCO—, an —NR$^8$—, and an —N$^{30}$ W$^-$R$^9$R$^{10}$—, where R$^8$, R$^9$, R$^{10}$, and W$^-$are as described above; among R$^5$, R$^6$, and R$^7$, those groups which are not involved in formation of the monocyclic ring and the bicyclic ring are the same as those in I) described above, III) N$^+$R$^5$R$^6$R$^7$ represents a pyridinium ring, a quinolinium ring, or an isoquinolinium ring, provided that the position of its bonding with Z is an ammonium nitrogen atom; the pyridinium ring, the quinolinium ring, and the isoquinolinium ring may be substituted with at least one of a cyano group, a nitro group, a phenyl group, a naphthyl group, a thienyl group, a pyridyl group, a cycloalkyl group having from 3 to 7 carbon atoms, an alkoxy group having from 1 to 5 carbon atoms, a carboxyl group, a —CONH$_2$ group, an —SO$_3$H group, and an —R$^{12}$ group; R$^{12}$ represents an alkyl group having from 1 to 9 carbon atoms or an alkenyl group having from 2 to 9 carbon atoms; and the alkyl group and the alkenyl group represented by R$^{12}$ may be substituted with at least one of a phenyl group, a naphthyl group, a pyridyl group, a quinolyl group, a thienyl group, a furyl group, a cycloalkyl group having from 3 to 7 carbon atoms, a cyano group, a nitro group, a hydroxyl group, an oxo group, a thioxo group, a carboxyl group, a —CONH$_2$ group, and an —SO$_3$H group; and further, at least one of methylenes which constitute the alkyl group and the alkenyl group may be replaced by any one of a phenylene, a thienylene, a furylene, a cyclohexylene, a cyclopentylene, an —S—, a —CO$_2$—, an —NHCO—, an —NR$^8$—, and an —N$^+$W$^-$R$^9$R$^{10}$—, where R$^8$, R$^9$, R$^{10}$, and W$^-$ are as described above, and X represents a counter anion].

Further, each of the substituents will be explained as follows.

R$^1$and R$^2$, which may be mutually different, each represents a straight chain or branched alkyl group having from 1 to 10 carbon atoms. Particularly, a straight chain alkyl group having from 1 to 10 carbon atoms is preferable and a straight chain alkyl group having from 2 to 6 carbon atoms is more preferable. Preferably R$^1$ and R$^2$ are mutually different and more preferably R$^1$and R$^2$ are the same alkyl groups. Specific preferable modes of R$^1$and R$^2$ include one in which both R$^1$and are an n— propyl group, an n— butyl group, an n— pentyl group, or an n— hexyl group, or one in which R$^1$ is an ethyl group and R$^2$is an n— butyl group.

(NR$^3$R$^4$)$_m$ means that any one of the 6-position to the 9-position is substituted with m (NR$^3$R$^4$)s. m is an integer of 1 or 2. Either 1 or 2 is preferable, with 1 being more preferable. Regarding the position of substitution, when m is 1, the 7-position or the 9-position is preferable, with the 7-position being more preferable; and when m is 2, it is preferable that the two positions consisting of the 7-position and the 9-position are substituted with the same NR$^3$R$^4$. R$^3$ and R$^4$, which may be mutually different, each represents a straight chain or branched alkyl group having from 1 to 5 carbon atoms. In particular, a straight chain alkyl group having from 1 to 3 carbon atoms is preferable, a methyl group or an ethyl group is more preferable, and a methyl group is most preferable. Specific preferable modes of (NR$_3$R$^4$)$_m$ include a 7-dimethylamino group, a 7-diethylamino group, a 7-ethylmethylamino group, a 9-dimethylamino group, and a 7,9-bis (dimethylamino) group.

Y represents any one of an —NHCS—, an —NHCSNH—, and an —NHCSO—. Here, the —NH in the —NHCS— represents a bond which links with an adjacent benzene ring and the CS — represents a bond which links with an adjacent Z, and the —NH in —NHCSO— represents a bond which links with an adjacent benzene ring, and the OSO — represents a bond which links with an adjacent Z. Regarding Y, particularly preferable is —NHCS — or —NHCSNH—, with —NHCSNH — being particularly preferable; the position of its substitution on the benzene ring is any one of an ortho-position, a meta-position, and a para-position. A meta- or para-position is preferable, and a meta-position is most preferable.

Z-(N$^+$R$^5$R$^6$R$^7$)$_n$ is an alkyl group having from 2 to 10 carbon atoms or an alkenyl group having from 2 to 10 carbon atoms which is substituted with n (-N$^+$R$^5$R$^6$R$^7$)s and at least one of methylenes which constitute Z may be replaced by any one of a phenylene and an —O—; n is an integer of 1 or 2, both 1 and 2 are preferable, and 1 is more preferable.

Among the alkyl groups having 2 to 10 carbon atoms and alkenyl groups having from 2 to 10 carbon atoms that are substituted with n (-N$^+$R$^5$R$^6$R$^7$)s, a straight chain or branched alkyl group having from 2 to 10 carbon atoms is preferable, and a straight chain alkyl group having from 2 to 10 carbon atoms or a branched alkyl group having from 3 to 7 carbon atoms is more preferable. When the alkyl group or the alkenyl group is substituted with one $-N^+R^5R^6R^7$, both the straight chain alkyl group having from 2 to 10 carbon atoms and the branched alkyl group having from 3 to 7 carbon atoms are preferable and the straight chain alkyl group having from 2 to 10 carbon atoms is more preferable. When the alkyl group or the alkenyl group is substituted with two $(-N^+R^5R^6R^7)$s, a branched chain alkyl group having from 3 to 6 carbon atoms is preferable. In the case of the straight chain alkyl group having from 2 to 10 carbon atoms which is substituted with one $-N^+R^5R^6R^7$, it is particularly preferable that Z represents a straight chain methylene group having from 2 to 10 carbon atoms.

It is preferable that the at least one of methylenes which constitute Z is replaced by any one of a phenylene and an —O—; however, more preferably the at least one of methylenes is not at all replaced when Y represents —NHCS—. When Y represents —NHCSNH—, more preferably the at least one of methylenes is replaced by a phenylene and a preferable mode of Z in this case is as mentioned earlier. Even when the at least one of methylenes which constitute Z is replaced by any one of a phenylene and an —O—, a straight chain alkyl group having from 2 to 10 carbon atoms which is substituted with one $-N^+R^5R^6R^7$, is preferable, and it is particularly preferable that Z represents a straight chain methylene group having from 2 to 10 carbon atoms. A preferable mode of replacement is any one of replacement of one methylene by a phenylene, replacement of one methylene by an —O—, and replacement of one methylene by a phenylene and another methylene by an —O—. A more preferable mode of replacement is replacement of one methylene by a phenylene. However, the —O— by which one methylene is replaced referred to herein is different from the oxygen atom in the —NHCSO— represented by Y. The phenylene is any one of those represented by the following formulae (phe-1), (phe-2), and (phe-3), among which the formulae (phe-1) or (phe-2) is preferable, and the formula (phe-1) is more preferable.

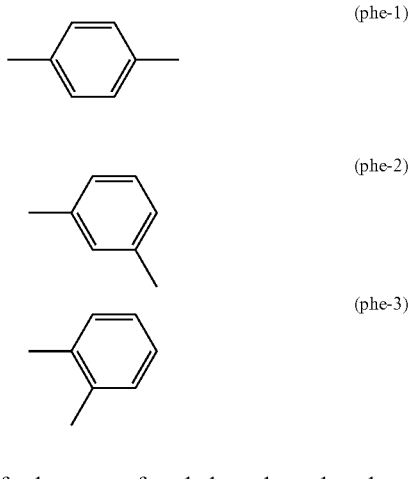

Replacement of at least one of methylenes by a phenylene or an —O— is, for example, as illustrated in a figure below.

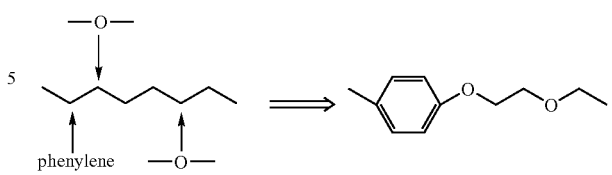

Specific preferable modes of Z include formulae from (sp-1) to (sp-22) and further formulae from (sp-23) to (sp-25) below. In the formulae, *a is bonded to Y in the formula (1) and *b is bonded to $N^+R^5R^6R^7$. The formulae (sp-19) and (sp-20) are specific examples when n is 2 and the remaining formulae are specific examples when n is 1.

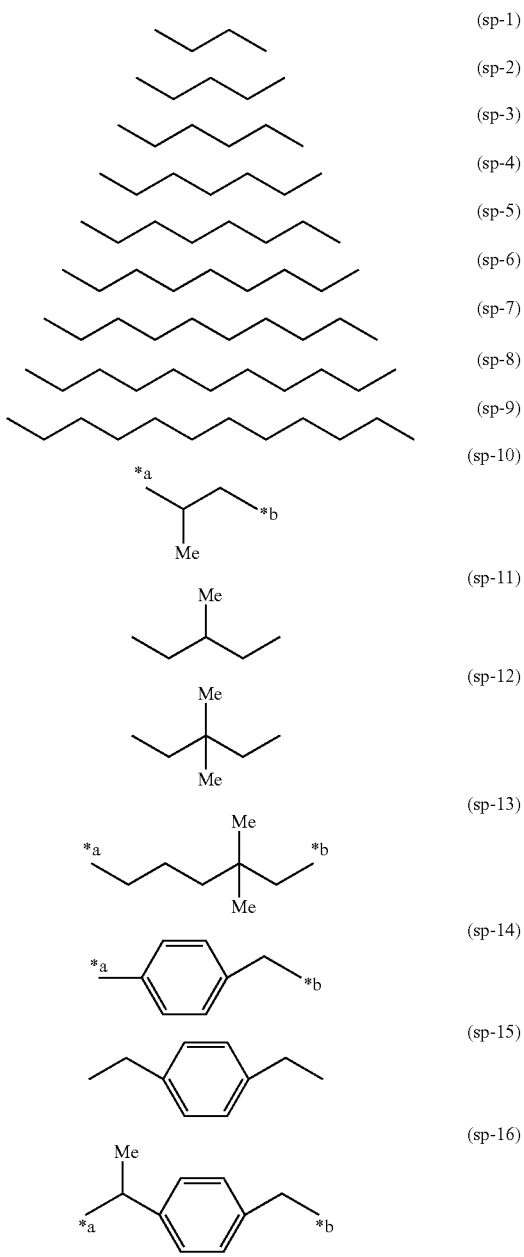

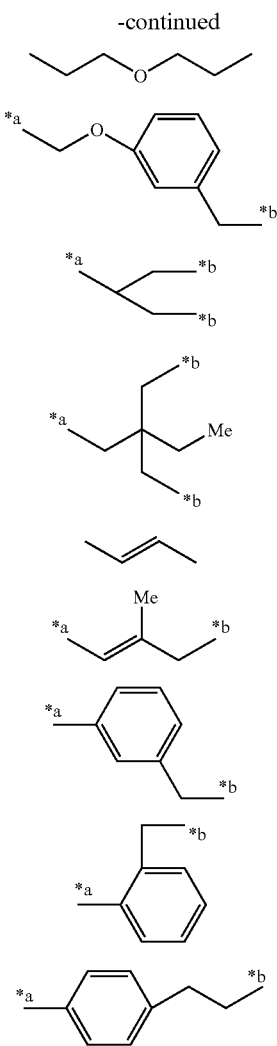

(sp-17)
(sp-18)
(sp-19)
(sp-20)
(sp-21)
(sp-22)
(sp-23)
(sp-24)
(sp-25)

When Y represents —NHCS—, it is particularly preferable that Z is represented by any one of formulae from (sp-1) to (sp-10), from (sp-14) to (sp-16), (sp-18), (sp-19), (sp-21), and (sp-22); among these, the formulae from (sp-1) to (sp-9) are more preferable and (sp-4) is most preferable. When Y represents —NHCSNH—, it is particularly preferable that Z is represented by any one of the formulae from (sp-1) to (sp-9), from (sp-12) to (sp-14), (sp-17), and (sp-20) and the formulae from (sp-23) to (sp-25) are also particularly preferable. Among them, the formulae (sp-1) to (sp-9), and further (sp-14), or (sp-23), and (sp-24), are more preferable, with (sp-14) being most preferable. When Y represents —NHCSO—, it is particularly preferable that Z is any one of the formulae from (sp-1) to (sp-9) and (sp-11); among these, the formulae from (sp-1) to (sp-9) are more preferable.

$N^+R^5R^6R^7$ is any one of I), II), and III) given below which are mutually independent.

I) $R^5$, $R^6$, and $R^7$, which may be mutually different, each represents an alkyl group having from 1 to 10 carbon atoms, an alkenyl group having from 2 to 10 carbon atoms, or an alkynyl group having from 2 to 10 carbon atoms. The alkyl group, the alkenyl group, and the alkynyl group may be substituted with at least one of a phenyl group, a naphthyl group, a pyridyl group, a quinolyl group, a thienyl group, a furyl group, a piperidyl group, a pyrrolidyl group, a morpholyl group, a cycloalkyl group having from 3 to 7 carbon atoms, a cyano group, a nitro group, a hydroxyl group, an oxo group, a thioxo group, a carboxyl group, a —CON $H_2$ group, and an —$SO_3H$ group, and further, at least one of methylenes which constitute the alkyl group, the alkenyl group, and the alkynyl group may be replaced by any one of a phenylene, a thienylene, a furylene, a cyclohexylene, a cyclopentylene, an —O—, an —S—, a —$CO_2$—, an —NHCO—, an —$NR^8$—, and an —$N^+W^-R^9R^{10}$—. $R^8$ represents an alkyl group having from 1 to 5 carbon atoms or an alkenyl group having from 2 to 5 carbon atoms. The alkyl group and the alkenyl group may be substituted with at least one of a phenyl group, a cycloalkyl group having from 3 to 7 carbon atoms, and a hydroxyl group. $R^9$ and $R^{10}$, which may be mutually different, each represents an alkyl group having from 1 to 5 carbon atoms or an alkenyl group having from 2 to 5 carbon atoms and may be substituted with at least one of a phenyl group, a cycloalkyl group having from 3 to 7 carbon atoms, and a hydroxyl group. $W^-$ represents a counter anion.

When $R^5$, $R^6$, and $R^7$ each represents an alkyl group, the alkyl group has preferably from 1 to 10 carbon atoms, any one of 1 to 10 is preferable as the number of carbon atom(s), and more preferably the alkyl group is a straight chain alkyl group having from 1 to 10 carbon atoms. Specific preferable examples of the alkyl group include a methyl group, an ethyl group, an n-propyl group, an n-butyl group, an i—butyl group, an n-pentyl group, an —pentyl group, an n-hexyl group, a 3,3-dimethylbutyl group, an n-heptyl group, a 2,2-dimethylpentyl group, an n-octyl group, an n-nonyl group, an n-decanyl group, and a 2,3-diethylhexyl group. When $R^5$, $R^6$, and $R^7$ each represents an alkenyl group, the alkenyl group has preferably from 3 to 8 carbon atoms, and more preferably the alkenyl group is a straight chain alkenyl group having 3, 4, 5, 6, or 8 carbon atoms or a branched alkenyl group having 4, 6, or 7 carbon atoms. Specific preferable examples of the alkenyl group include a 2-propenyl group, a 2-methyl-2-propenyl group, a 3-butenyl group, a 4-pentenyl group, a 4-methyl-4-pentenyl group, a 5-hexenyl group, a 2-hexenyl group, a 5-methyl-5-hexenyl group, and a 2,7-octadienyl group. When R5, R6, and R7 each represents an alkynyl group, the alkynyl group has preferably from 3 to 9 carbon atoms, and more preferably the alkynyl group is a straight chain alkynyl group having 3, 5, 6, 7, or 9 carbon atoms or a branched alkynyl group having 6 carbon atoms. Specific preferable examples of the alkynyl group include a 2-propynyl group, a 2-pentynyl group, a 4-methyl-2-pentynyl group, a 2-hexynyl group, a 2-heptynyl group, and a 2-nonynyl group.

These preferable alkyl groups, alkenyl groups, and alkynyl groups, particularly alkyl groups, may be substituted with at least one of a phenyl group, a thienyl group, a cyclohexyl group, a cyano group, a hydroxyl group, an oxo group, a carboxyl group, a —CON $H_2$ group, and a —$SO_3H$ group. Moreover, at least one of methylenes which constitute the alkyl group, the alkenyl group, and the alkynyl group, particularly at least one of methylenes which constitute the alkyl group, may be replaced by any one of a phenylene, a thienylene, a furylene, an —O—, a —$CO_2$—, an —NHCO—, an —$NR^8$— (where $R^8$ represents an alkyl group having from 1 to 3 carbon atoms or an alkenyl group having 3 carbon atoms, preferably a straight chain alkyl group having from 1 to 3 carbon atoms or a straight chain alkenyl group having 3 carbon atoms, and the alkyl group may be substituted with at least one of a phenyl group and a hydroxyl group), and an —$N^+W^-R^9R^{10}$— (where $R^9$ and $R^{10}$, which may be mutually different, each represents an alkyl group having from 1 to 3 carbon atoms or an alkenyl group having 3 carbon atoms, preferably a straight chain alkyl group having from 1 to 3 carbon atoms or a straight chain alkenyl group having 3 carbon atoms, and the alkyl group may be substituted with at least one of a phenyl group and a hydroxyl group). It is more preferable that the alkenyl group and the alkynyl group are neither substituted nor replaced.

More preferable modes include any one of 1) a mode in which the preferable alkyl group, alkenyl group, and alkynyl group, in particular the alkyl group, represented by $R^5$, $R^6$, and $R^7$ is substituted with any one of a phenyl group, a thienyl group, a cyclohexyl group, a cyano group, a hydroxyl group, an oxo group, a carboxyl group, a —$CONH_2$ group, and an —$SO_3H$ group, 2) a mode in which the alkyl group, the alkenyl group, and the alkynyl group, particularly the alkyl group is substituted with two hydroxyl groups, 3) a mode in which the alkyl group, the alkenyl group, and the alkynyl group, particularly the alkyl group is substituted with one hydroxyl group and one —$SO_3H$ group, 4) a mode in which the alkyl group, the alkenyl group, and the alkynyl group, particularly the alkyl group is substituted with one oxo group and one phenyl group, 5) a mode in which the alkyl group, the alkenyl group, and the alkynyl group, particularly the alkyl group is substituted with one hydroxyl group and two phenyl groups, 6) a mode in which one methylene which constitutes the alkyl group, the alkenyl group, and the alkynyl group, particularly at least one of methylenes which constitute the alkyl group is replaced by any one of a phenylene, a furylene, a —$CO_2$—, an —NHCO—, an —$NR^8$— (where $R^8$ represents any one of a straight chain alkyl group having from 1 to 3 carbon atoms, a straight chain alkenyl group having 3 carbon atoms, a straight chain alkyl group having from 1 to 3 carbon atoms which is substituted with one hydroxyl group, and a straight chain alkyl group having from 1 to 3 carbon atoms which is substituted with one phenyl group, with specific examples thereof including a methyl group, an ethyl group, an n-propyl group, a 2-propenyl group, a 2-hydroxyethyl group, a 2-hydroxypropyl group, and a benzyl group), and an —$N^+W^-R^9R^{10}$— (where $R^9$ and $R^{10}$, which may be mutually different, each represents a straight chain alkyl group having from 1 to 3 carbon atoms, a straight chain alkenyl group having 3 carbon atoms, a straight chain alkyl group having from 1 to 3 carbon atoms which is substituted with one hydroxyl group, and a straight chain alkyl group having from 1 to 3 carbon atoms which is substituted with one phenyl group, with specific examples thereof including a methyl group, an ethyl group, an n-propyl group, a 2-propenyl group, a 2-hydroxyethyl group, and a benzyl group), 7) a mode in which two methylenes which constitute the alkyl group, the alkenyl group, and the alkynyl group, particularly two methylenes which constitute the alkyl group are replaced by any one selected from two (—O—)s, one phenylene and one —O—, one —O— and one —$NR^8$—, and one —NHCO — and one —O—, 8) a mode in which three methylenes which constitute the alkyl group, the alkenyl group, and the alkynyl group, particularly three methylenes which constitute the alkyl group are replaced by two (—O—)s and one —$NR^8$, or one phenylene and two (—NHCO—)s, 9) a mode in which the alkyl group, the alkenyl group, and the alkynyl group, particularly the alkyl group is substituted with one hydroxyl group, and moreover, one of methylenes which constitute the alkyl group, the alkenyl group, and the alkynyl group, particularly one of methylenes which constitute the alkyl group is replaced by an —O—, 10) a mode in which the alkyl group, the alkenyl group, and the alkynyl group, particularly the alkyl group is substituted with one hydroxyl group, and moreover, one of methylenes which constitute the alkyl group, the alkenyl group, and the alkynyl group, particularly one of methylenes which constitute the alkyl group is replaced by an —$NR^8$—, 11) a mode in which the alkyl group, the alkenyl group, and the alkynyl group, particularly the alkyl group is substituted with one hydroxyl group, and moreover one of methylenes which constitute the alkyl group, the alkenyl group, and the alkynyl group, particularly one of methylenes which constitute the alkyl group is replaced by a furylene, 12) a mode in which the alkyl group, the alkenyl group, and the alkynyl group, particularly the alkyl group is substituted with one oxo group, and moreover, one of methylenes which constitute the alkyl group, the alkenyl group, and the alkynyl group, particularly one of methylenes which constitute the alkyl group is replaced by a thienylene, 13) a mode in which the alkyl group, the alkenyl group, and the alkynyl group, particularly the alkyl group is substituted with one oxo group, and moreover, two of methylenes which constitute the alkyl group, the alkenyl group, and the alkynyl group, particularly two of methylenes which constitute the alkyl group are replaced by one —O— and one phenylene, or the preferable alkyl group, alkenyl group, and alkynyl group represented by $R^5$, $R^6$, and $R^7$ are neither substituted nor replaced.

In the most preferable mode, $R^5$, $R^6$, and $R^7$ each represents any one of a straight chain alkyl group having from 1 to 10 carbon atoms, a straight chain alkyl group having from 1 to 10 carbon atoms which is substituted with one phenyl group, a straight chain alkyl group having from 1 to 10 carbon atoms which is substituted with one hydroxyl group, a straight chain alkenyl group having from 3 to 6 or 8 carbon atoms, a branched alkenyl group having 4, 6, or 7 carbon atoms, a straight chain alkynyl group having 3, 5, 6, 7, or 9 carbon atoms, and a branched alkynyl group having 6 carbon atoms.

Specifically, N,N-dimethyl-N-(n-hexyl)ammonium, N-benzyl- N,N-dimethylammonium, N-benzyl-N-methyl-N-(propargyl)ammonium, or N,N-dimethyl-N-(n-butyl)ammonium is preferable, and N-benzyl- N,N-dimethylammonium or N-benzyl -N-methyl-N-propargylammonium is particularly preferable.

II) —$N^+R^5R^6R^7$ represents a monocyclic ring or a bicyclic ring which is formed by 4 to 9 carbon atoms in addition to an ammonium nitrogen atom, provided that the position of its bonding with Z is the ammonium nitrogen atom. In the monocyclic ring and the bicyclic ring, one of the carbon atoms which constitute the ring may be replaced by any one atom of oxygen, nitrogen, and sulfur, and moreover, the monocyclic ring and the bicyclic ring may be substituted with at least one of a hydroxyl group, an oxo group, a thioxo group, a cyano group, a phenyl group, a naphthyl group, a thienyl group, a pyridyl group, a cycloalkyl group having from 3 to 7 carbon atoms, a carboxyl group, a —$CONH_2$ group, an —$SO_3H$ group, and an —$R^{11}$. $R^{11}$ represents an alkyl group having from 1 to 8 carbon atoms or an alkenyl group having from 2 to 8 carbon atoms. The alkyl group and the alkenyl group may be substituted with at least one of a phenyl group, a naphthyl group, a pyridyl group, a quinolyl group, a thienyl group, a furyl group, a piperidyl group, a pyrrolidyl group, a morpholyl group, a cycloalkyl group having from 3 to 7 carbon atoms, a cyano group, a nitro group, a hydroxyl group, an oxo group, a thioxo group, a carboxyl group, a —$CONH_2$ group, and an —$SO_3H$ group. Moreover, at least one of methylenes which constitute the alkyl and the alkenyl group may be replaced by any one of a phenylene, a thienylene, a furylene, a cyclohexylene, a cyclopentylene, an —O—, an —S—, a —CO$_2$—, an —NHCO—, an —NR$^8$—, and an —N$^+$W$^-$R$^9$R$^{10}$—. R$^8$ represents an alkyl group or alkenyl group having from 1 to 5 carbon atoms. The alkyl group and the alkenyl group may be substituted with at least one of a phenyl group, a cycloalkyl group having from 3 to 7 carbon atoms, and a hydroxyl group. R$^9$ and R$^{10}$, which may be mutually different, each represents an alkyl group having from 1 to 5 carbon atoms or an alkenyl group having from 2 to 5 carbon atoms, and may be substituted with at least one of a phenyl group, a cycloalkyl group having from 3 to 7 carbon atoms, and a hydroxyl group. W represents a counter anion. Among R$^5$, R$^6$, and R$^7$, a group which is not involved in the formation of the monocyclic and the bicyclic ring represents an alkyl group having from 1 to 10 carbon atoms, an alkenyl group having from 2 to 10 carbon atoms, or an alkynyl group having from 2 to 10 carbon atoms. The alkyl group, the alkenyl group, and the alkynyl group may be substituted with at least one of a phenyl group, a naphthyl group, a pyridyl group, a quinolyl group, a thienyl group, a furyl group, a piperidyl group, a pyrrolidyl group, a morpholyl group, a cycloalkyl group having from 3 to 7 carbon atoms, a cyano group, a nitro group, a hydroxyl group, an oxo group, a thioxo group, a carboxyl group, a —CONH$_2$ group, and an —SO$_3$H group. Moreover, at least one of methylenes which constitute the alkyl group, the alkenyl group, and the alkynyl group may be replaced by any one of a phenylene, a naphthylene, a thienylene, a furylene, a pyridylene, a cyclohexylene, a cyclopentylene, an —O—, an —S—, a —CO$_2$—, an —NHCO—, an —NR$^8$—, and an —N$^+$W$^-$R$^9$R$^{10}$—. R$^8$ represents an alkyl group having from 1 to 5 carbon atoms or an alkenyl group having from 2 to 5 carbon atoms. The alkyl group and the alkenyl group may be substituted with at least one of a phenyl group, a cycloalkyl group having from 3 to 7 carbon atoms, and a hydroxyl group. R9 and R10, which may be mutually different, each represents an alkyl group having from 1 to 5 carbon atoms or an alkenyl group having from 2 to 5 carbon atoms, and may be substituted with at least one of a phenyl group, a cycloalkyl group having from 3 to 7 carbon atoms, and a hydroxyl group. W represents a counter anion.

The monocyclic ring or bicyclic ring represented by the N$^+$R$^5$R$^6$R$^7$ is preferably any one of a pyrrolidinium ring, a piperidinium ring, a morpholinium ring, a thiomorpholinium ring, a piperazinium ring, an azepanium ring, a quinuclidinium ring, and a 1,4-diazabicyclo[2.2.2] octanium ring. The monocyclic ring and the bicyclic ring may be substituted with at least one of a hydroxyl group, an oxo group, a cyano group, a phenyl group, a —CONH$_2$— group, and an —R$^{11}$. Here, R$^{11}$ is preferably an alkyl group having from 1 to 6 carbon atoms or an alkenyl group having 3 carbon atoms and more preferably a straight chain alkyl group having from 1 to 5 carbon atoms (for example, a methyl group, an ethyl group, an n-propyl group, an n-butyl group, or an n-pentyl group), a branched alkyl group having 6 carbon atoms (for example, a 3,3-dimethylbutyl group), a straight chain alkenyl group having 3 carbon atoms (for example, a 2-propenyl group). The alkyl group may be substituted with at least one of a hydroxyl group, a cyano group, a phenyl group, and a —CONH$_2$ group. Moreover, at least one of methylenes which constitute the alkyl group may be replaced by any one of an —O—, a —CO$_2$—, and an —NHCO—. Among R$^5$, R$^6$, and R$^7$, a group which is not involved in the formation of the ring represents an alkyl group having from 1 to 6 carbon atoms (preferably a straight chain alkyl group having from 1 to 6 carbon atoms), an alkenyl group having from 3 to 4 carbon atoms (preferably a straight chain alkenyl group having from 3 to 4 carbon atoms), or an alkynyl group having from 3 to 6 carbon atoms (preferably a straight chain alkynyl group having 3, 4, or 6 carbon atoms). The alkyl group, the alkenyl group, and the alkynyl group, particularly the alkyl group may be substituted with at least one of a phenyl group, a thienyl group, a furyl group, a piperidyl group, a pyrrolidyl group, a morpholyl group, a cyclopropyl group, a cyclopentyl group, a cyano group, a hydroxyl group, an oxo group, a nitro group, a carboxyl group, and an —SO$_3$H group. Moreover, at least one of methylenes which constitute the alkyl group may be replaced by any one of a phenylene, an —O—, and a —CO$_2$—. It is more preferable that the alkenyl group and the alkynyl group are neither substituted nor replaced.

In a more preferable mode, the pyrrolidinium ring, the piperidinium ring, the morpholinium ring, the thiomorpholinium ring, the piperazinium ring, the azepanium ring, the quinuclidinium ring, and the 1,4-diazabicyclo[2.2.2]octanium ring are 1) substituted with any one of a hydroxyl group, an oxo group, a cyano group, a phenyl group, a —CONH$_2$ group, and an —R$^{11}$ group, 2) substituted with one cyano group and one hydroxyl group, 3) substituted with one hydroxyl group and one —R$^{11}$, 4) substituted with one oxo group and one —R$^{11}$, 5) substituted with two oxo groups, or 6) substituted with two (—R$^{11}$)s. Alternatively, the pyrrolidinium ring, the piperidinium ring, the morpholinium ring, the thiomorpholinium ring, the piperazinium ring, the azepanium ring, the quinuclidinium ring, and the 1,4-diazabicyclo[2.2.2]octanium ring are unsubstituted. Here, R$^{11}$ represents a straight chain alkyl group having from 1 to 5 carbon atoms (for example, a methyl group, an ethyl group, an n-propyl group, an n-butyl group, or an n-pentyl group), a branched alkyl group having 6 carbon atoms (for example, a 3,3-dimethylbutyl group), or a straight chain alkenyl group having 3 carbon atoms (for example, a 2-propenyl group), in which 1) the alkyl group is substituted with one hydroxyl group or one phenyl group, 2) one of methylenes which constitute the alkyl group is replaced by either a —CO$_2$— or an —NHCO—, 3) two methylenes which constitute the alkyl group are replaced by one —O— and one —NHCO—, 4) the alkyl group is substituted with one cyano group and moreover, one of methylenes which constitute the alkyl group is replaced by an —O—, 5) the alkyl group is substituted with one —CONH$_2$ and moreover, one of methylenes which constitute the alkyl group is replaced by an —O—, 6) the alkyl group is substituted with one phenyl group and moreover, one of methylenes which constitute the alkyl group is replaced by a —CO$_2$—, 7) the alkyl group is substituted with one phenyl group and moreover, one of methylenes which constitute the alkyl group is replaced by an —NHCO—, or 8) the alkyl group is neither substituted nor replaced. Specific examples of R$^{11}$ include a methyl group, an ethyl group, an n-propyl group, an n-butyl group, an n-pentyl group, a 2-propenyl group, a benzyl group, an acetylamino group, a t-butoxycarbonylamino group, a hydroxymethyl group, a 2-hydroxyethyl group, a 3-hydroxypropyl group, a 2-cyanoethoxy group, a (2-cyanoethoxy)methyl group, a 2-carbamoylethoxy group, an ethoxycarbonyl group, a t-butoxycarbonyl group, a benzoyloxy group, a phenylacetylamino group, a butanoylamino group, and a pentanoylamino group. Among R$^5$, R$^6$, and R$^7$, a group which is not involved in the formation of the ring represents a straight chain alkyl group having from 1 to 6 carbon atoms, a straight chain alkenyl group having from 3 to 4 carbon atoms, or a straight chain alkynyl group having 3, 4, or 6 carbon atoms, in which 1) the alkyl group, the alkenyl group, and the alkynyl group, particularly the alkyl group is substituted with any one of a phenyl group, a thienyl group, a furyl group, a piperidyl group, a pyrrolidyl group, a morpholyl group, a cyclopropyl group, a cyclopentyl group, a cyano group, a hydroxyl group, a carboxyl group, and an —$SO_3H$ group, 2) the alkyl group, the alkenyl group, and the alkynyl group, particularly the alkyl group is substituted with two hydroxyl groups, 3) the alkyl group, the alkenyl group, and the alkynyl group, particularly the alkyl group is substituted with one hydroxyl group and one —$SO_3H$, 4) the alkyl group, the alkenyl group, and the alkynyl group, particularly the alkyl group is substituted with four hydroxyl groups and one oxo group, 5) the alkyl group, the alkenyl group, and the alkynyl group, particularly the alkyl group is substituted with one nitro group and one morpholyl group, 6) one of methylenes which constitute the alkyl group, the alkenyl group, and the alkynyl group, particularly one of methylenes which constitute the alkyl group is replaced by a —$CO_2$—, or 7) the alkyl group, the alkenyl group, and the alkynyl group, particularly the alkyl group is substituted with one morpholyl group and moreover, one of methylenes which constitute the alkyl group, the alkenyl group, and the alkynyl group, particularly one of methylenes which constitute the alkyl group is replaced by an —O—, or the alkyl group, the alkenyl group, and the alkynyl group are neither substituted nor replaced.

A particularly preferable mode is one in which the ring is a pyrrolidinium ring, a piperidinium ring, an azepanium ring, a quinuclidinium ring, or a 1,4-diazabicyclo[2.2.2]octanium ring which is substituted with any one of a methyl group, an ethyl group, an n-propyl group, an n-butyl group, an n-pentyl group, a 2-propenyl group, a phenyl group, a benzyl group, a hydroxyl group, a hydroxymethyl group, a 2-hydroxyethyl group, and a 3-hydroxypropyl group; or unsubstituted. Among $R^5$, $R^6$, and $R^7$, a group which is not involved in the formation of the ring represents any one of a straight chain alkyl group having from 1 to 6 carbon atoms, a straight chain alkyl group having from 1 to 6 carbon atoms which is substituted with one phenyl group, a straight chain alkyl group which is substituted with one hydroxyl group, a straight chain alkenyl group having from 3 to 4 carbon atoms, and a straight chain alkynyl group having 3, 4, or 6 carbon atoms.

Regarding the group which is not involved in the formation of the ring, specific preferable examples of the straight chain alkyl group having from 1 to 6 carbon atoms include a methyl group, an ethyl group, an n-propyl group, an n-butyl group, an n-pentyl group, and an n-hexyl group; specific preferable examples of the straight chain alkenyl group having from 3 to 4 carbon atoms include a 2-propenyl group, a 3-butenyl group, and a 2,7-octadienyl group; and specific preferable examples of the straight chain alkynyl group having 3, 4, or 6 carbon atoms include a 2-propynyl group, a 2-butynyl group, and a 2,4-hexadiynyl group.

In the most preferable mode, the ring is a quinuclidinium ring or a 1,4-diazabicyclo[2.2.2]octanium ring which is either substituted with any one of an n-butyl group, a phenyl group, a benzyl group and a hydroxyl group, or unsubstituted.

Specifically, quinuclidinium-1 -yl, 4-phenylquinuclidinium-1 -yl, 3-hydroxyquinuclidinium-1-yl, 1 ,4-diazabicyclo[2.2.2]octanium-1 -yl, 4-n-butyl.-1 ,4-diazabicyclo [2.2.2]octanium-1 -yl, and 4-benzyl-1 ,4-diazabicyclo[2.2.2] octanium-1-yl are preferable, and particularly preferable examples include quinuclidinium-1 -yl, 4-phenylquinuclidinium-1-yl, and 1 ,4-diazabicyclo[2.2.2]octanium-1 -yl.

Among these, 4-phenylquinuclidinium-1-yl is most preferable. Also, in some cases, 1,4-diazabicyclo[2.2.2]octanium-1-yl is most preferable. Furthermore, in some other cases, quinuclidinium-1-yl is most preferable.

In another most preferable mode, the ring is a pyrrolidinium ring, a piperidinium ring, or an azepanium ring which is either substituted with any one of a methyl group, a phenyl group, a benzyl group, a hydroxyl group, a hydroxymethyl group, a 2-hydroxyethyl group, and a 3-hydroxypropyl group, or unsubstituted. Among $R^5$, $R^6$, and $R^7$, a group which is not involved in the formation of the ring represents any one of a straight chain alkyl group having from 1 to 6 carbon atoms, a straight chain alkyl group having from 1 to 6 carbon atoms which is substituted with one phenyl group, a straight chain alkyl group which is substituted with one hydroxyl group, a straight chain alkenyl group having from 3 to 4 carbon atoms, and a straight chain alkynyl group having 3, 4, or 6 carbon atoms. Specifically, 1 -methyl-pyrrolidinium-1 -yl, 1 -ethyl-pyrrolidinium-1-yl, 1 -n-butyl-pyrrolidinium-1-yl, 1-n-pentyl-pyrrolidinium-1 -yl, 3-hydroxy-1 -methyl-pyrrolidinium-1 -yl, 1-ethyl-3-hydroxy-pyrrolidinium-1-yl, 1-benzyl-3-hydroxy-pyrrolidinium-1-yl, 1-methyl-piperidinium-1-yl, 1-ethyl-piperidinium-1-yl, 1-n-butyl-piperidinium-1-yl, 1-n-pentyl-piperidinium-1-yl, 4-benzyl-1-n-butyl-piperidinium-1-yl, 4-benzyl-1-n-pentyl-piperidinium-1-yl, 3-hydroxy-1-methyl-piperidinium-1-yl, 4-hydroxy-1-methyl-piperidinium-1-yl, 3-hydroxymethyl-1-methyl-piperidinium-1-yl, 1-benzyl-4-hydroxymethyl-piperidinium-1-yl, 1-benzyl-4-hydoxyethyl-piperidinium-1-yl, 1-benzyl-4-hydroxy-piperidinium-1-yl, 1-ethyl-azepanium-1 -yl, 1-n-butyl-azepanium-1-yl, 1-n-pentyl-azepanium-1-yl, 1-benzyl-azepanium-1-yl, and 1-hydroxyethyl-azepanium-1-yl are preferable; 1-n-butyl-pyrrolidinium-1-yl, 1-ethyl-piperidinium-1-yl, 4-benzyl-1-n-butyl-piperidinium-1-yl, 4-benzyl-1-n-pentyl-piperidinium-1-yl, and 1-benzyl-4-hydroxy-piperidinium-1-yl are more preferable, with 1-benzyl-4-hydroxy-piperidinium-1-yl being most preferable.

III) $N^+R^5R^6R^7$ represents a pyridinium ring, a quinolinium ring, or an isoquinolinium ring, provided which the position of its bonding with Z is the ammonium nitrogen atom. The pyridinium ring, the quinolinium ring, and the isoquinolinium ring may be substituted with at least one of a cyano group, a nitro group, a phenyl group, a naphthyl group, a thienyl group, a pyridyl group, a cycloalkyl group having from 3 to 7 carbon atoms, an alkoxy group having from 1 to 5 carbon atoms, a carboxyl group, a —$CONH_2$ group, an —$SO_3H$ group, and an group. R12 represents an alkyl group having from 1 to 9 carbon atoms or an alkenyl group having from 2 to 9 carbon atoms. The alkyl group and the alkenyl group may be substituted with at least one of a phenyl group a naphthyl group, a pyridyl group, a quinolyl group, a thienyl group, a furyl group, a cycloalkyl group having from 3 to 7 carbon atoms, a cyano group, a nitro group, a hydroxyl group, an oxo group, thioxo group, a carboxyl group, a —$CON H_2$ group, and an —$SO_3H$ group. Further, at least one of methylenes which constitute the alkyl group and the alkenyl group may be replaced by any one of a phenylene, a thienylene, a furylene, a cyclohexylene, a cyclopentylene, an —S—, a —$CO_2$—, an —NHCO—, an —$NR^8$—, and an —$N^+W^-R^9R^{10}$—. $R^8$ represents an alkyl group having from 1 to 5 carbon atoms or an alkenyl group having from 2 to 5 carbon atoms. The alkyl group and the alkenyl group may be substituted with at least one of a phenyl group, a cycloalkyl group having from 3 to 7 carbon atoms, and a hydroxyl group. $R^9$ and $R^{10}$, which may be mutually different, each represents an alkyl group having from 1 to 5 carbon atoms or an alkenyl group having from 2 to 5 carbon atoms, and may be substituted with at least one of a phenyl group, a cycloalkyl group having from 3 to 7 carbon atoms, and a hydroxyl group W⁻ represents a counter anion.

It is preferable that among the pyridinium ring, the quinolinium ring, and the isoquinolinium ring, the pyridinium ring and the quinolinium ring, particularly the pyridinium ring, is substituted with at least one of a cyano group, a nitro group, a phenyl group, a thienyl group, a pyridyl group, an alkoxy group having from 1 to 3 carbon atoms, a carboxyl group, a —CONH2— group, and an —$R^{12}$ group. Here, $R^{12}$ represents an alkyl group having from 1 to 9 carbon atoms (preferably a straight chain alkyl group having from 1 to 7 carbon atoms, or a branched alkyl group having from 3 to 5 or 9 carbon atoms) or an alkenyl group having from 2 to 4 carbon atoms (preferably a straight chain alkenyl group having from 2 to 4 carbon atoms). The alkyl group and the alkenyl group, particularly the alkyl group may be substituted with at least one of a phenyl group, a naphthyl group, a pyridyl group, a cyano group, a nitro group, a hydroxyl group, an oxo group, a carboxyl group, and an —SO₃H group, and moreover, at least one of methylenes which constitute the alkyl group and the alkenyl group, particularly one of methylenes which constitute the alkyl group may be replaced by any one of an —S—, a —CO₂—, an —NHCO—, and an —$NR^8$—, where $R^8$ represents an alkyl group having from 1 to 3 carbon atoms (preferably a straight chain alkyl group having from 1 to 3 carbon atoms) and the alkyl group may be substituted with at least one (preferably one) hydroxyl group.

In a more preferable mode, the ring is any one of 1) a pyridinium ring substituted with any one of a cyano group, a phenyl group, a thienyl group, a pyridyl group, a methoxy group, an ethoxy group, a propoxy group, a carboxyl group, a —$CONH^2$— group, and an —$R^{12}$ group, 2) a pyridinium ring substituted with two cyano groups, 3) a pyridinium ring substituted with two (—$R^{12}$)s, 4) a pyridinium ring substituted with one cyano group and one —$R^{12}$, 5) a pyridinium ring substituted with one phenyl group and one —$R^{12}$, 6) a quinolinium ring substituted with any one of a cyano group, a nitro group, a carboxyl group, a methoxy group, an ethoxy group, a propoxy group, and an —$R^{12}$ group, 7) a quinolinium ring substituted with one methoxy group and one —$R^{12}$, 8) a quinolinium ring substituted with one nitro group and one —$R^{12}$, 9) an unsubstituted pyridinium ring, 10) an unsubstituted quinolinium ring, and 11) an unsubstituted isoquinolinium ring. Here, $R^{12}$ represents a straight chain alkyl group having from 1 to 7 carbon atoms (for example, a methyl group, an ethyl group, an n-propyl group, an n-butyl group, an n-pentyl group, or an n-heptyl group), a branched alkyl group having from 3 to 5 or 9 carbon atoms (for example, an i-propyl group, a t-butyl group, a 3-pentyl group, or a 5-nonyl group), , or a straight chain alkenyl group having 2 to 4 carbon atoms (for example, a vinyl group or a 3-butenyl group), and 1) the alkyl group and the alkenyl group, particularly the alkyl group is substituted with any one of a phenyl group, a naphthyl group, a pyridyl group, a cyano group, a nitro group, a hydroxyl group, an oxo group, a carboxyl group, and an —SO₃H group, 2) the alkyl group and the alkenyl group, particularly the alkyl group is substituted with one oxo group and one phenyl group, 3) the alkyl group and the alkenyl group, particularly the alkyl group is substituted with two hydroxyl groups and one one pyridyl group, 4) one of methylenes which constitute the alkyl group and the alkenyl group, particularly one of methylenes which constitute the alkyl group is replaced by a —CO₂—, 5) the alkyl group and the alkenyl group, particularly the alkyl group is substituted with one hydroxyl group and moreover, one of methylenes which constitute the alkyl group and the alkenyl group, particularly one of methylenes which constitute the alkyl group is replaced by an —NHCO—, 6) the alkyl group and the alkenyl group, particularly the alkyl group is substituted with one oxo group, and moreover, one of methylenes which constitute the alkyl group and the alkenyl group, particularly one of methylenes which constitute the alkyl group is replaced by a —CO₂—, 7) the alkyl group and the alkenyl group, particularly the alkyl group is substituted with one phenyl group, and moreover, one of methylenes which constitute the alkyl group and the alkenyl group, particularly one of methylenes which constitute the alkyl group is replaced by a —CO₂—, 8) the alkyl group and the alkenyl group, particularly the alkyl group is substituted with one carboxyl group, and moreover, one of methylenes which constitute the alkyl group and the alkenyl group, particularly one of methylenes which constitute the alkyl group is replaced by an —S—, 9) the alkyl group and the alkenyl group, particularly the alkyl group is substituted with one hydroxyl group and one oxo group, and moreover, one of methylenes which constitute the alkyl group and the alkenyl group, particularly one of methylenes which constitute the alkyl group is replaced by an —$NR^8$— (where $R^8$ represents a methyl group, an ethyl group, an n-propyl group, a 2-hydroxyethyl group, or a 3-hydroxypropyl group), or 10) the alkyl group and the alkenyl group are neither substituted nor replaced. Specific examples of R12 include a methyl group, an ethyl group, an n-propyl group, an -propyl group, an n-butyl group, a t-butyl group, an n-pentyl group, a 3-pentyl group, a 5-nonyl group, a vinyl group, a benzyl group, a 3-phenylpropyl group, a 2-(1-naphthyl)vinyl group, a hydroxymethyl group, a 2-hydroxyethyl group, a 3-hydroxypropyl group, a formyl group, an acetyl group, a propionyl group, a benzoyl group, a methoxycarbonyl group, an ethoxycarbonyl group, a butoxycarbonyl group, a hexoxycarbonyl group, a benzyloxycarbonyl group, a 2-propenyloxycarbonyl group, an ethoxycarbonylmethyl group, a 2-(methoxycarbonyl)ethyl group, an ethoxycarbonylmethylcarbonyl group, a 2-hydroxyethylaminocarbonyl group, a bis(2-hydroxyethyl)aminocarbonyl group, a 2-carboxyvinyl group, a carboxymethylthio group, a cyanomethyl group, a 2-nitrovinyl group, a 2-(4-pyridyl)ethyl group, a 2-(4-pyridyl)vinyl group, a 3-(4-pyridyl)propyl group, a 2-(4-pyridyl)-1,2-dihydroxyethyl group, and a 2-sulfoethyl group.

In a particularly preferable mode, the ring is any one of an unsubstituted pyridinium ring, an unsubstituted quinolinium ring, an unsubstituted isoquinolinium ring, a pyridinium ring substituted with any one of a methyl group, an ethyl group, an n-propyl group, an i-propyl group, an n-butyl group, a t-butyl group, an n-pentyl group, a vinyl group, a phenyl group, a benzyl group, a 3-phenylpropyl group, a hydroxymethyl group, a 2-hydroxyethyl group, and a 3-hydroxypropyl group, a pyridinium ring substituted with either two methyl groups or two ethyl groups, a pyridinium ring substituted with one phenyl group and one methyl group, and a quinolinium ring substituted with either one methyl group or one i-propyl group. In the most preferable mode, the ring is a pyridinium ring which is either substituted with any one of a t-butyl group, an n-butyl group, an n-propyl group, an ethyl group, a methyl group, a hydroxypropyl group, and a methoxycarbonylethyl group, or unsubstituted.

Specifically, isoquinolinium-1-yl, 4-methylpyridinium-1-yl, 3-(n-butyl)pyridinium-1-yl, 4-ethyl-pyridinium-1-yl, 4-(t-butyl)pyridinium-1-yl, 3-(3-hydroxypropyl)-pyridinium-1-yl, 3-(3-hydroxypropyl)-pyridinium-1-yl, 3-[2-(methoxycarbonyl)ethyl]- pyridinium-1-yl, and 2-(n-propyl)-pyridinium-1-yl are preferable, and 4-(t-butyl) pyridinium-1-yl, 3-(3-hydroxypropyl)-pyridinium-1-yl, 3-[2-(methoxycarbonyl)ethyl]-pyridinium-1-yl, and 2-(n-propyl)- pyridinium-1-yl are particularly preferable.

After all, the $N^+R^5R^6R^7$ is preferably one group selected from the group consisting of N-benzyl-N,N-dimethylammonium, N-benzyl-N-methyl-N-propargylammonium, 4-phenylquinuclidinium-1-yl, 1 ,4-diazabicyclo[2. 2.2]octanium-1-yl, 1-benzyl-4-hydroxy-piperidinium-1-yl, 4-(t-butyl) pyridinium-1-yl, 3-(3-hydroxypropyl)-pyridinium-1-yl, 3-[2-(methoxycarbonyl)ethyl]- pyridinium-1-yl, and 2-(n-propyl)-pyridinium-1-yl.

Examples of the naphthyl group used in the explanation from I) to Ill) above include a 1-naphthyl group and a 2-naphthyl group, with a 1-naphthyl group being preferable. Examples of the pyridyl group include a 1-pyridyl group, a 2-pyridyl group, a 3-pyridyl group, and a 4-pyridyl group, preferably a 1-pyridyl group and a 4-pyridyl group, and more preferably a 4-pyridyl group. Examples of the quinolyl group include a 1-quinolyl group, a 2-quinolyl group, a 3-quinolyl group, a 4-quinolyl group, a 5-quinolyl group, a 6-quinolyl group, a 7-quinolyl group, and a 8-quinolyl group, preferably a 1-quinolyl group and a 4-quinolyl group. Examples of the thienyl group include a 2-thienyl group and a 3-thienyl group, preferably a 2-thienyl group. Examples of the furyl group include a 2-furyl group, and a 3-furyl group, preferably a 2-furyl group. Examples of the piperidyl group include a 1-piperidyl group, a 2-piperidyl group, a 3-piperidyl group, and a 4-piperidyl group, preferably a 1-piperidyl group and a 4-piperidyl group, and more preferably a 1-piperidyl group. Examples of the pyrrolidyl group include a 1-pyrrolidyl group, a 2-pyrrolidyl group, and a 3-pyrrolidyl group, preferably a 1-pyrrolidyl group. Examples of the morpholyl group include a 2-morpholyl group, a 3-morpholyl group, and a 4-morpholyl group, particularly preferably a 4-morpholyl group. Preferable examples of the cycloalkyl group having from 3 to 7 carbon atoms include a cyclopropyl group, a cyclobutyl group, a cyclopentyl group, a cyclohexyl group, and a cycloheptyl group. The phenylene group is represented by any one of the formulae (phe-1) to (phe-3) mentioned earlier and preferably the formula (phe-1) or (phe-2), and more preferably the formula (phe-1). The thienylene group is represented by any one of the formulae (thi-1) to (thi-4) given below, with the formula (thi-1) being particularly preferable.

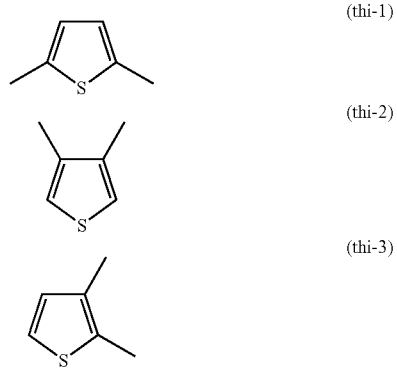

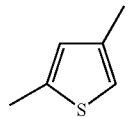

The furylene group is represented by any one of the formulae (fur-i) to (fur-4) given below, with formula (fur-i) being particularly preferable.

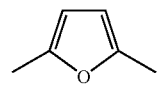

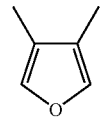

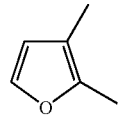

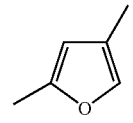

The cyclohexylene group is represented by any one of the formulae (hex-1) to (hex-3) given below, preferably the formula (hex-1) or the formula (hex-2), and more preferably the formula (hex-1). The cyclopentylene group is represented by any one of the formulae (pen-1) and (pen-2) given below, preferably the formula (pen-1).

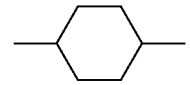

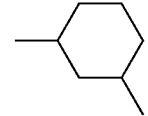

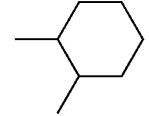

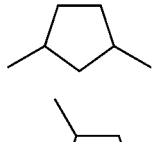

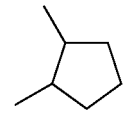

Specific examples of the —N⁺R⁵R⁶R⁷ which correspond to I) include the formulae (an-1) to (an-158) and further (an-380) and (an-381) given below.
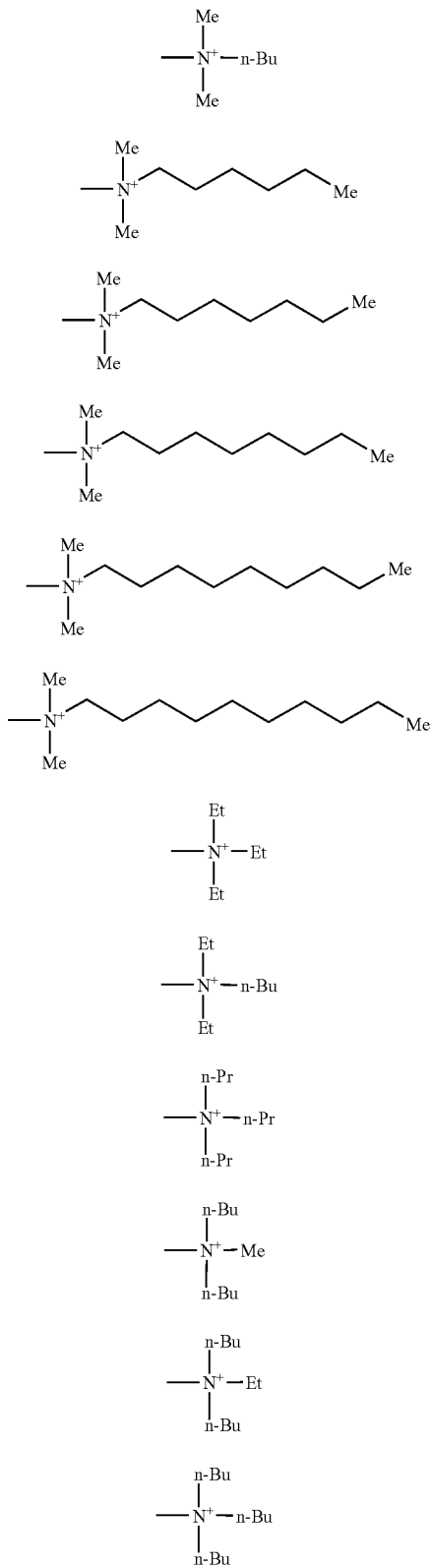
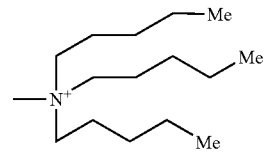
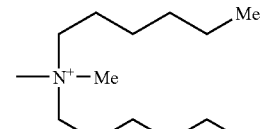
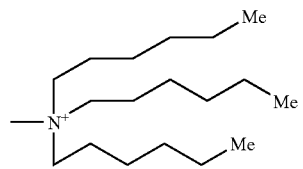
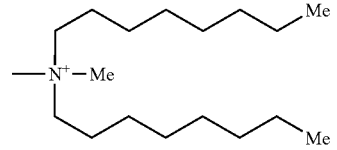
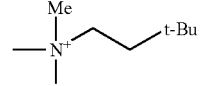
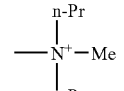
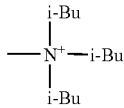
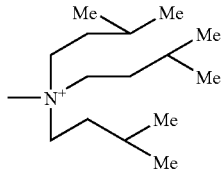
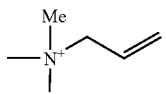
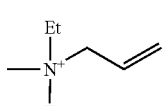
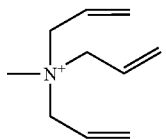

-continued
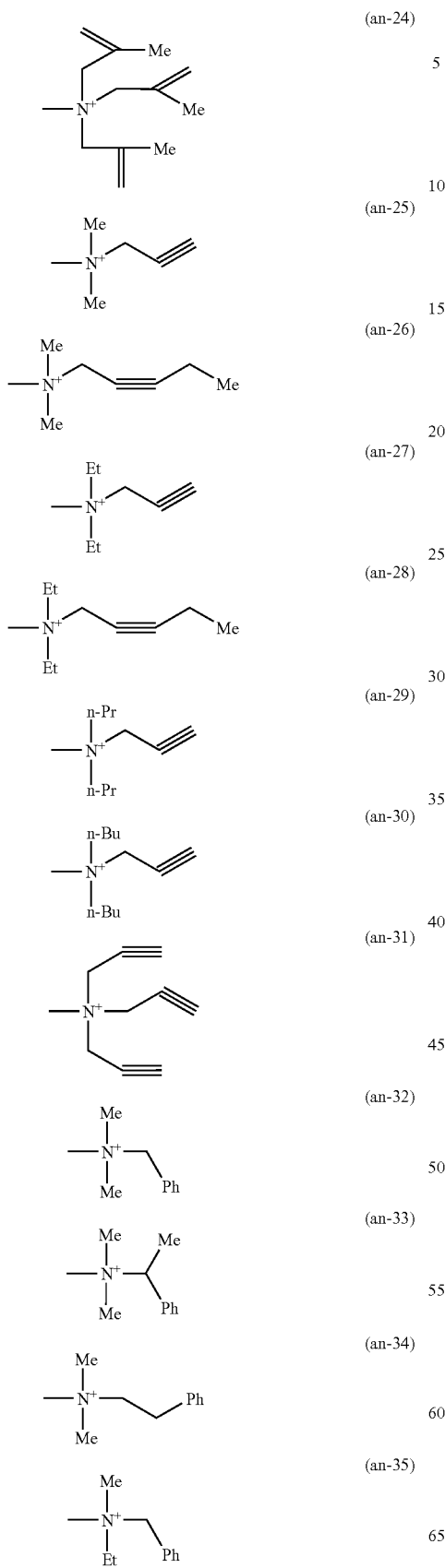
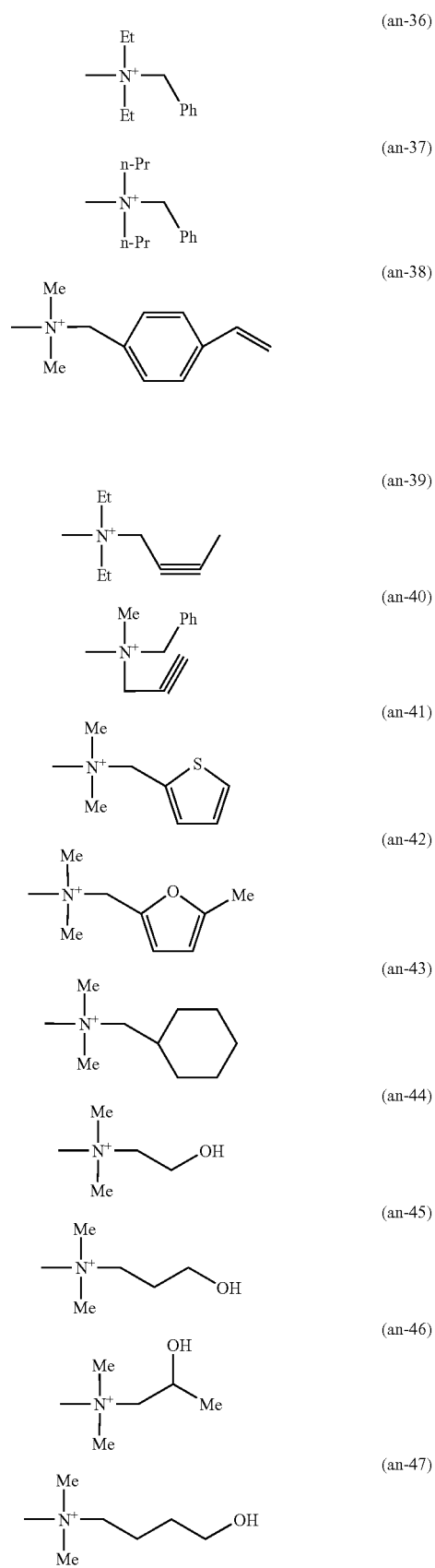

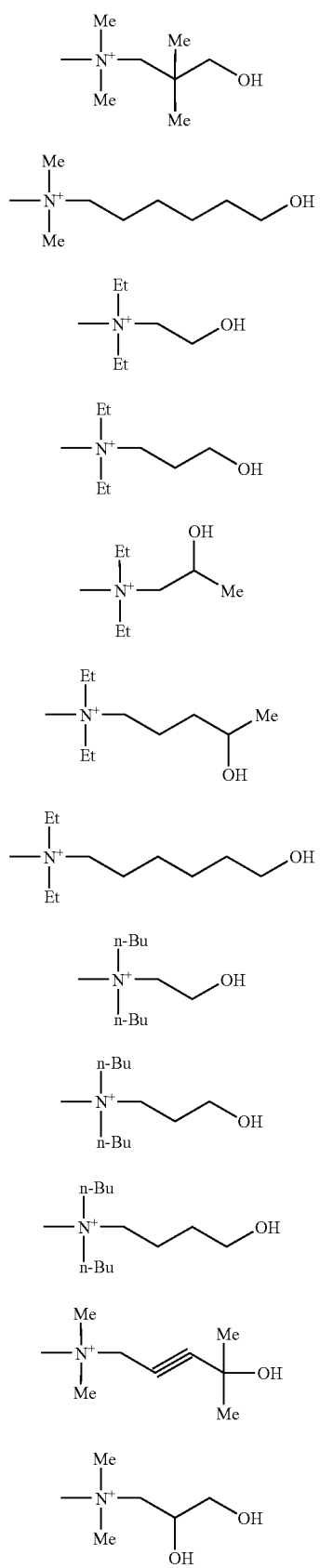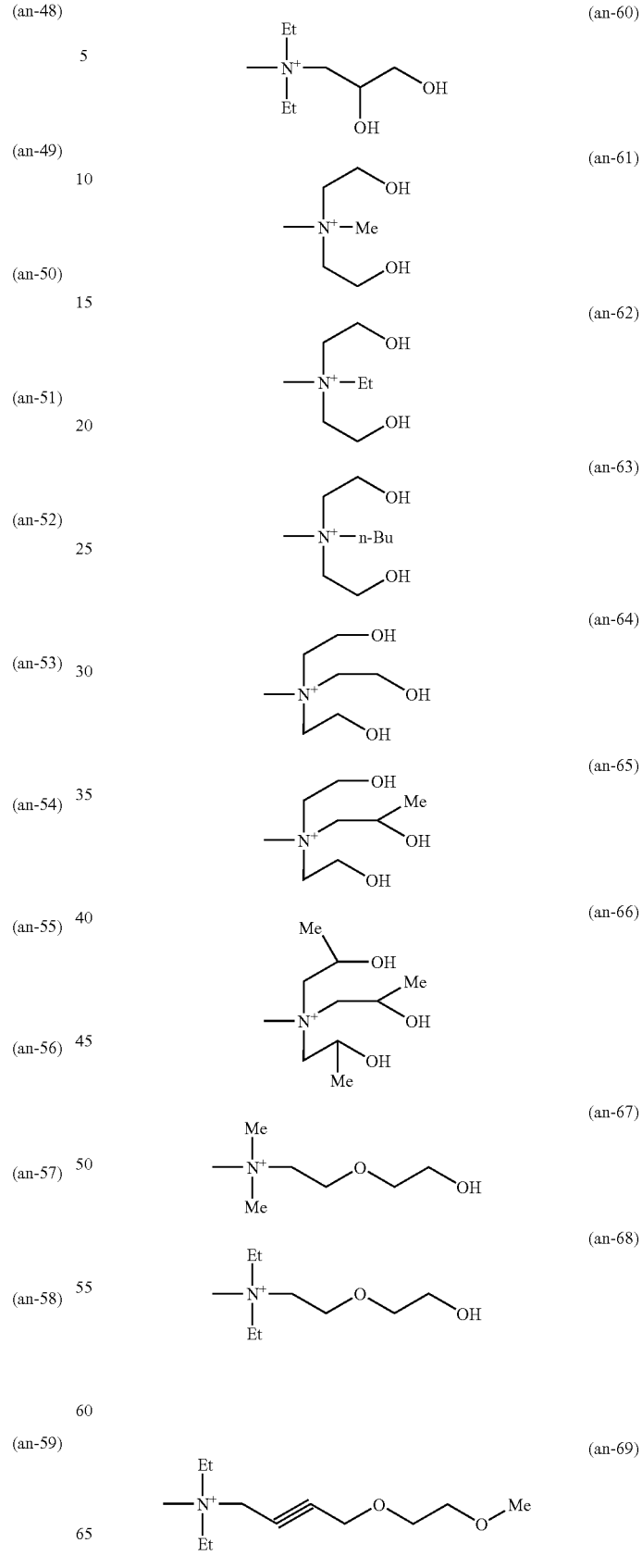

-continued
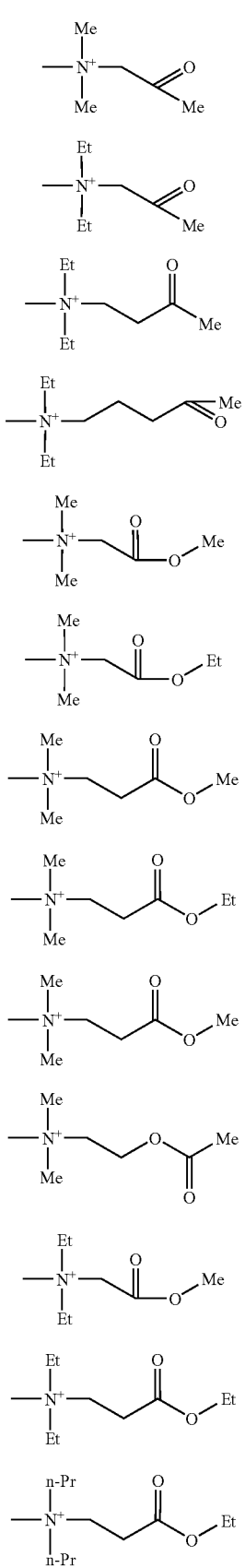
(an-70)
(an-71)
(an-72)
(an-73)
(an-74)
(an-75)
(an-76)
(an-77)
(an-78)
(an-79)
(an-80)
(an-81)
(an-82)
-continued
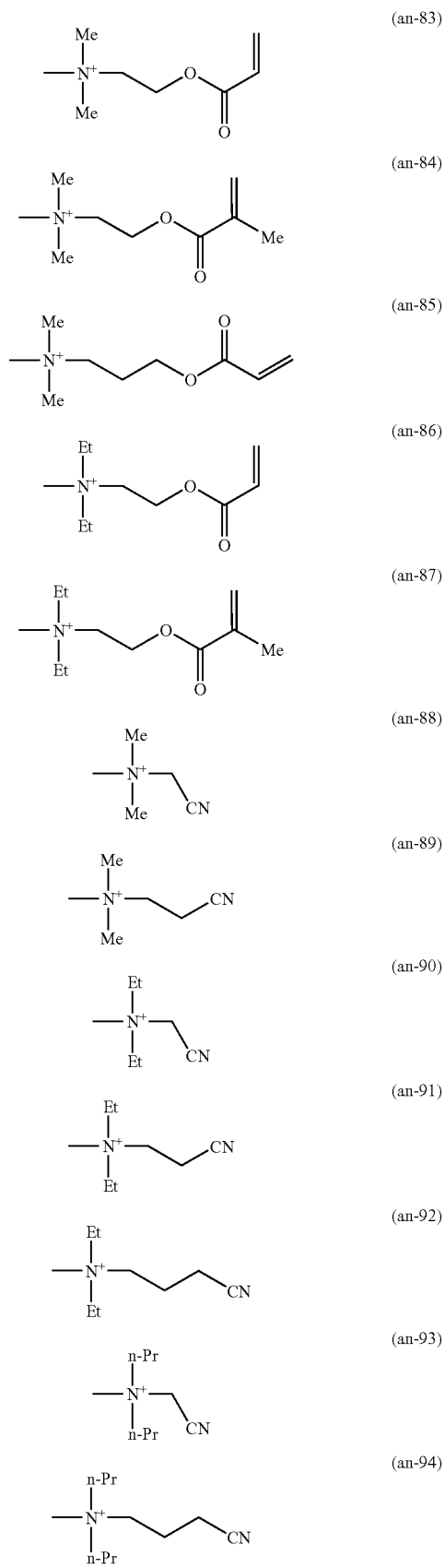
(an-83)
(an-84)
(an-85)
(an-86)
(an-87)
(an-88)
(an-89)
(an-90)
(an-91)
(an-92)
(an-93)
(an-94)

-continued (an-95) through (an-117): chemical structures of quaternary ammonium compounds.

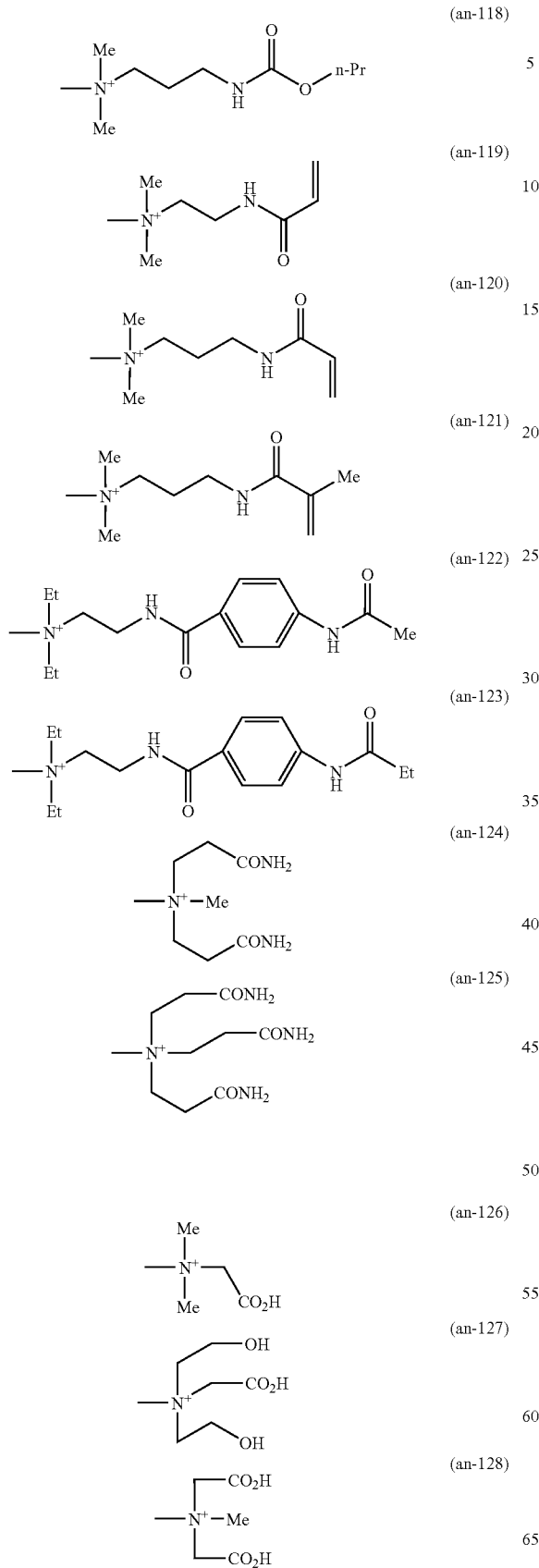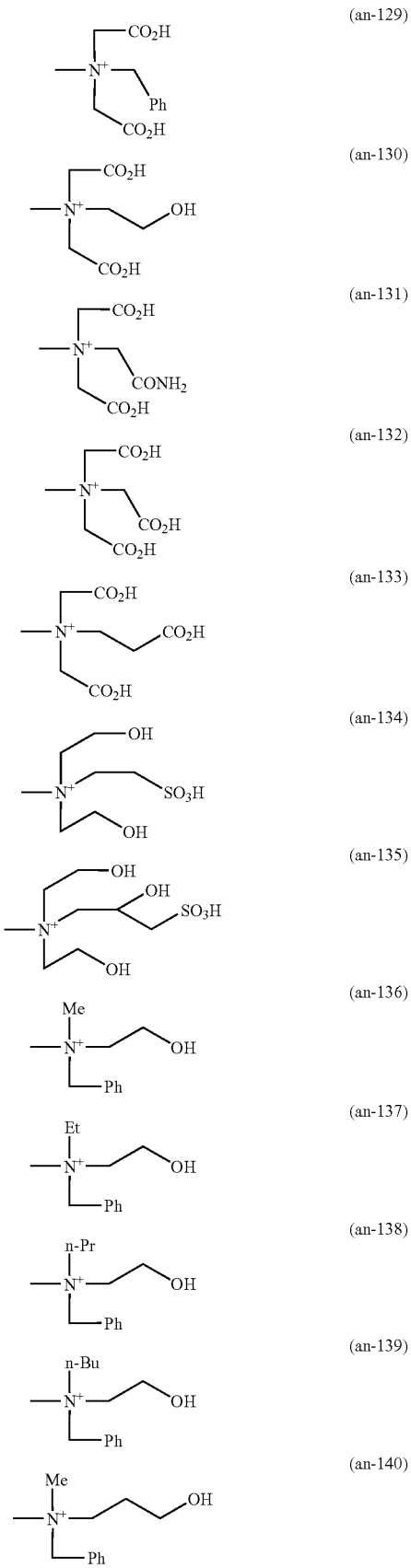

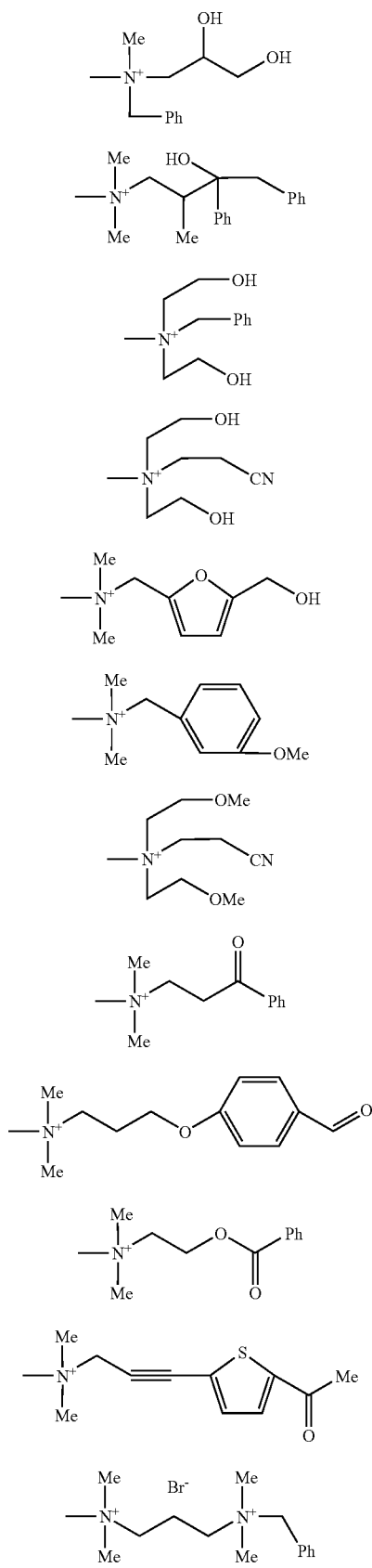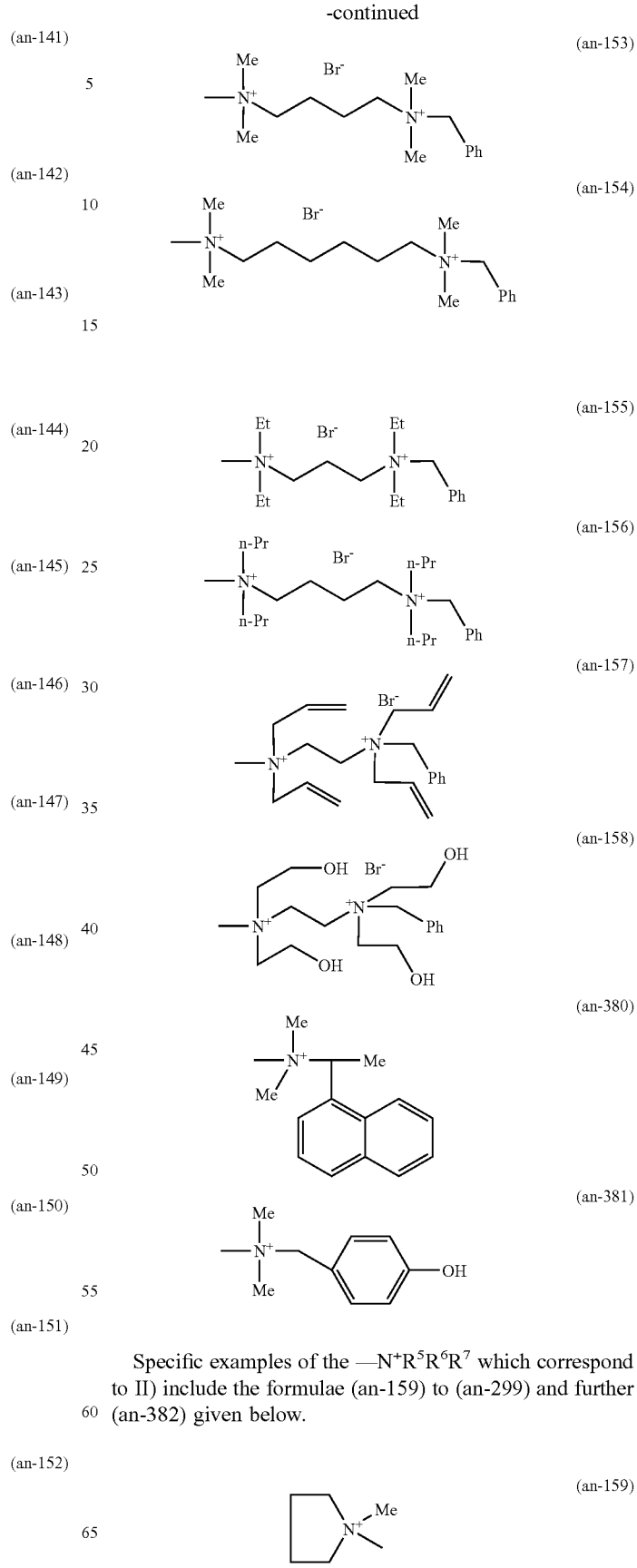
Specific examples of the —N⁺R⁵R⁶R⁷ which correspond to II) include the formulae (an-159) to (an-299) and further (an-382) given below.

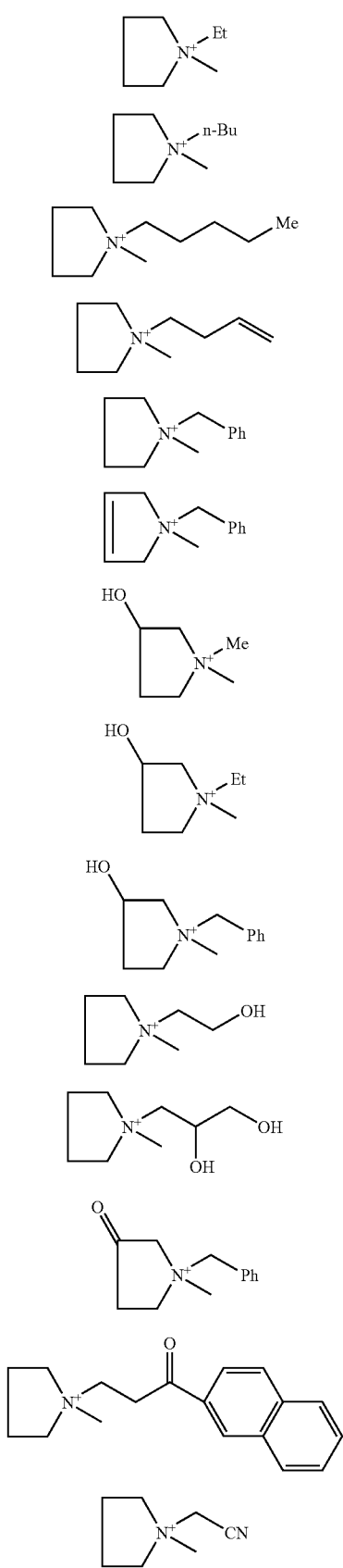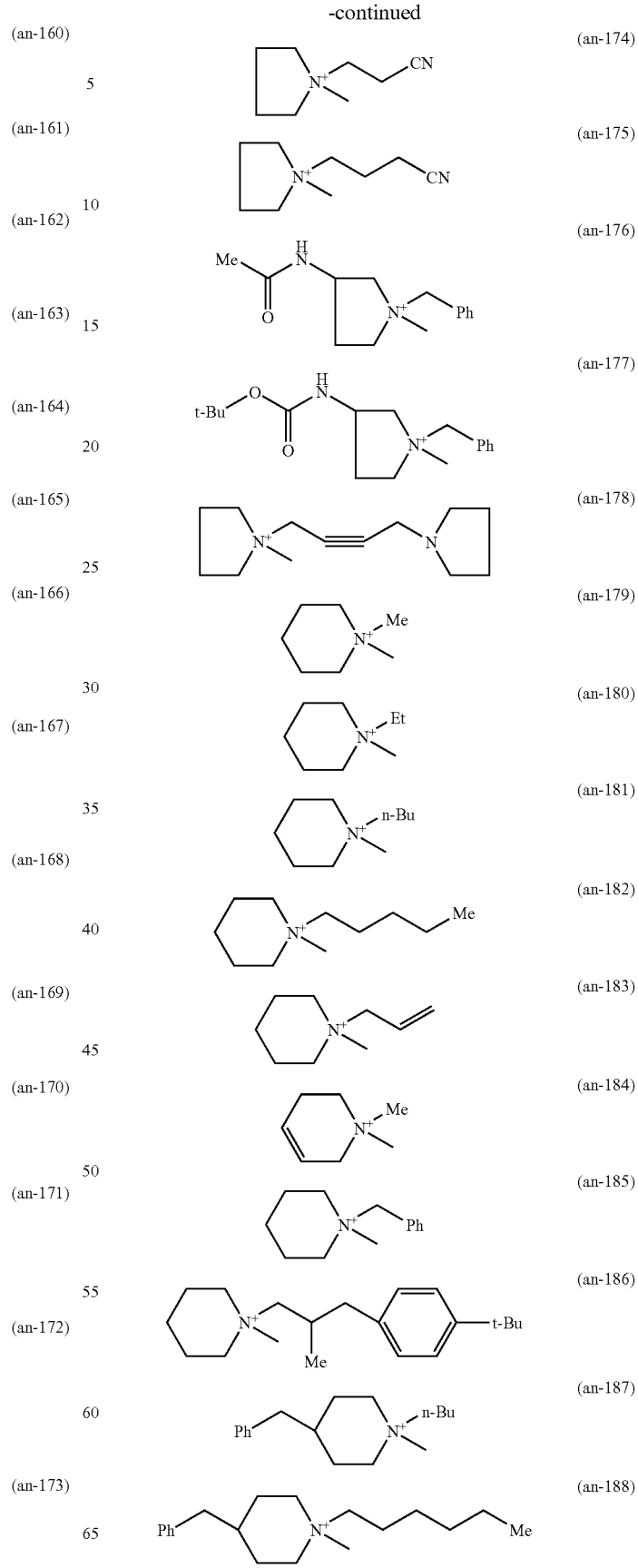

-continued
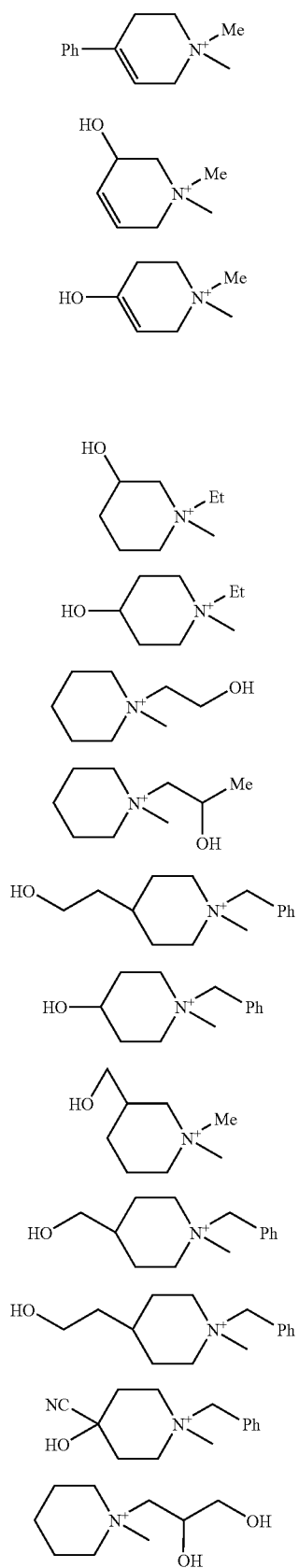
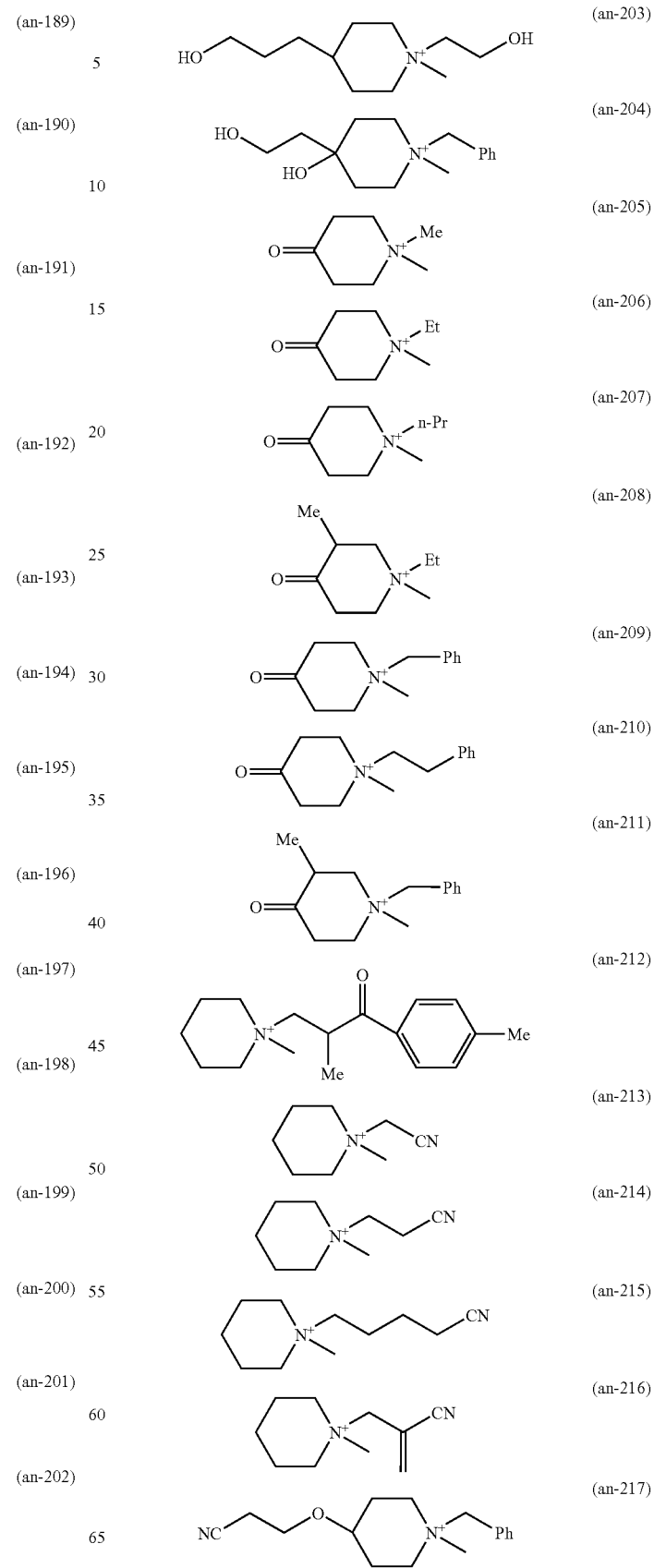

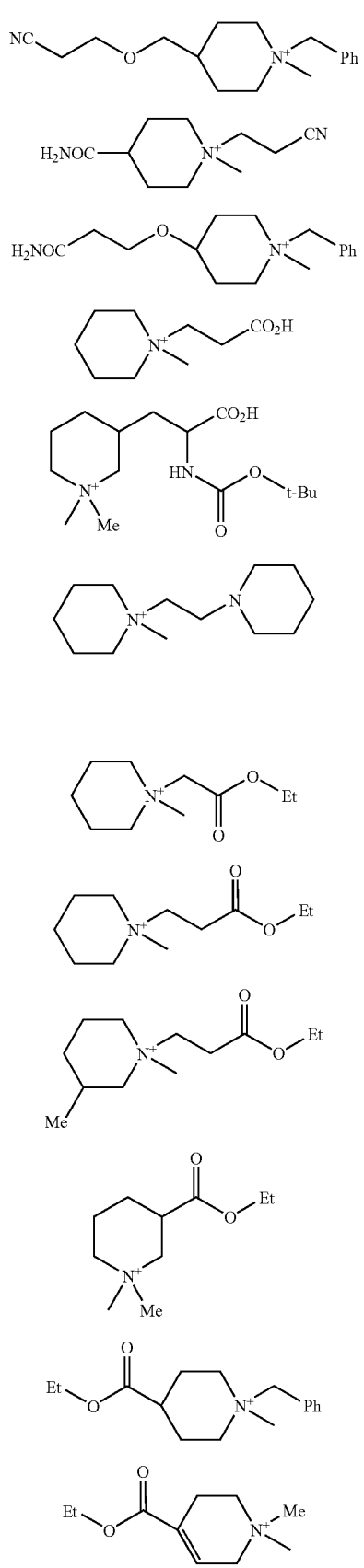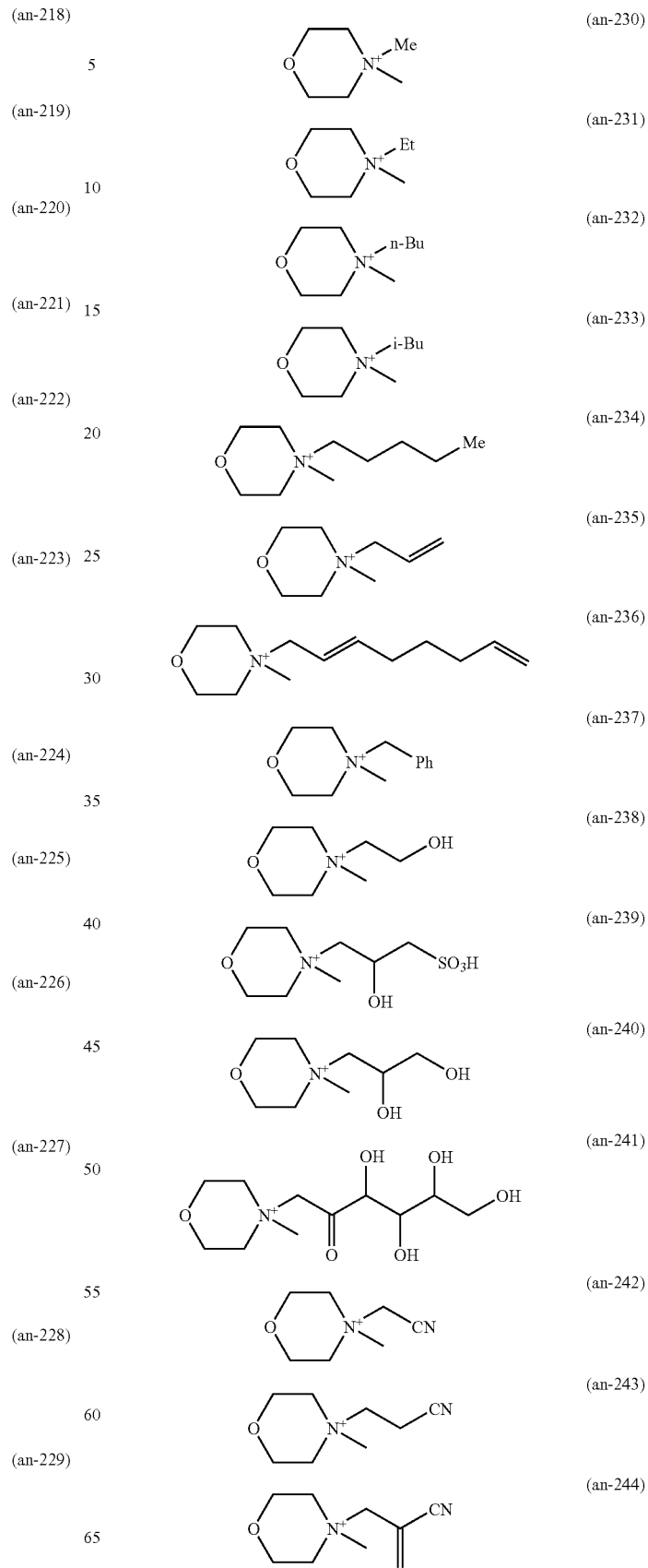

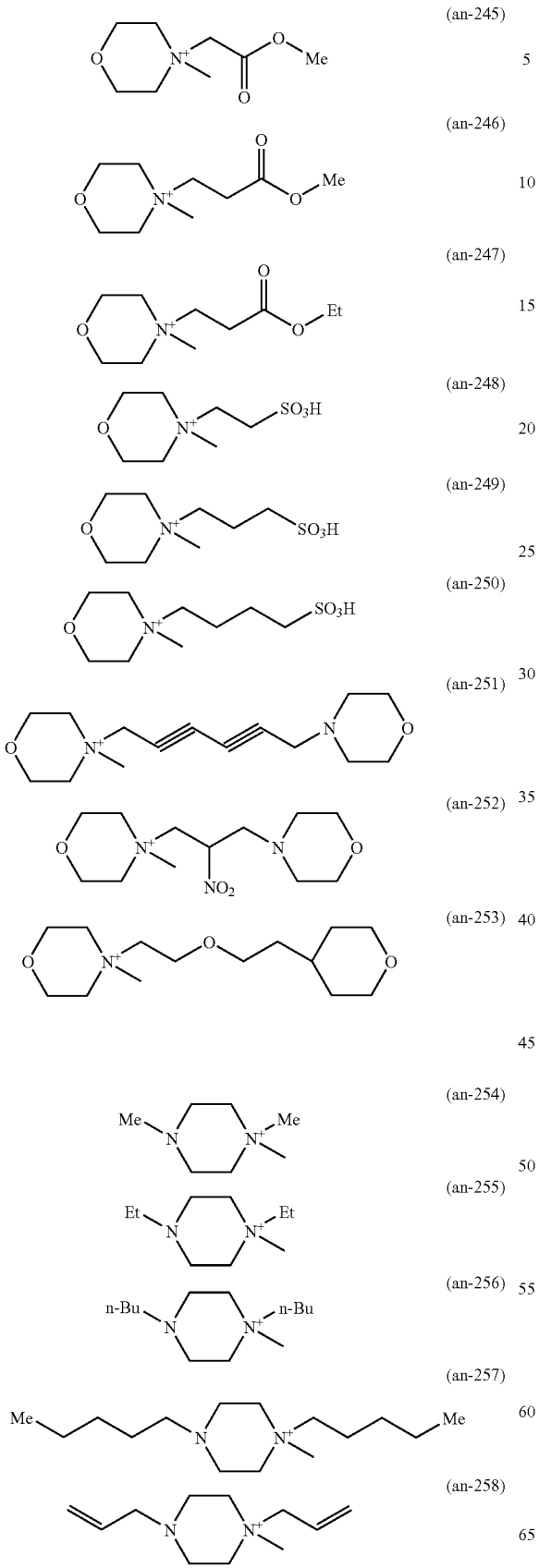
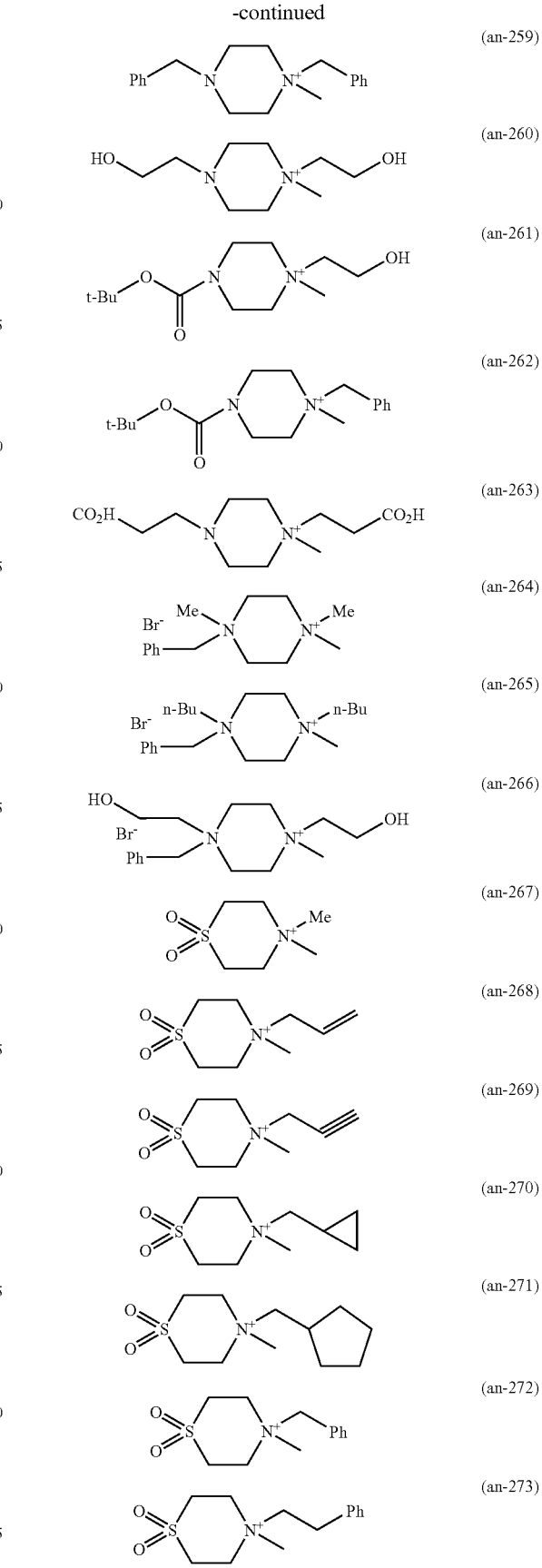

-continued (an-274)
(an-275)
(an-276)
(an-277)
(an-278)
(an-279)
(an-280)
(an-281)
(an-282)
(an-283)
(an-284)
(an-285)
(an-286)

-continued (an-287)
(an-288)
(an-289)
(an-290)
(an-291)
(an-292)
(an-293)
(an-294)
(an-295)
(an-296)
(an-297)
(an-298)

-continued
(an-299)
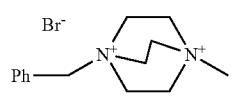
(an-382)
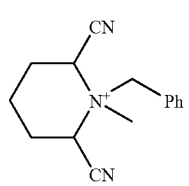
Specific examples of the —N⁺R⁵R⁶R⁷ which correspond to III) include formulae from (an-300) to (an-377), further (an-378), (an-379), and moreover (an-394) to (an-402) given below.
(an-300)
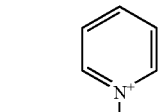
(an-301)
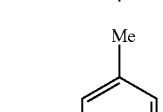
(an-302)
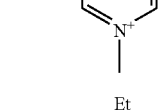
(an-303)
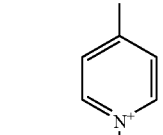
(an-304)
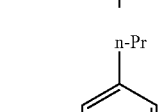
(an-305)
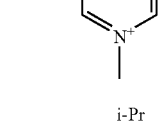
-continued
(an-306)
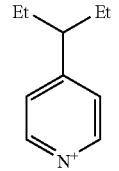
(an-307)
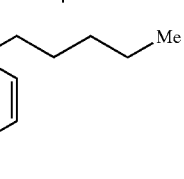
(an-308)
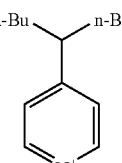
(an-309)
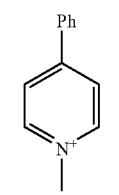
(an-310)
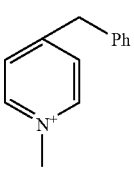
(an-311)
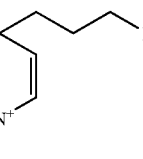
(an-312)
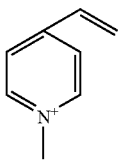
(an-313)
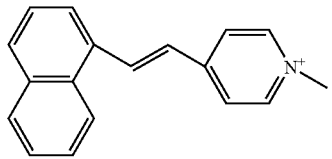
(an-314)
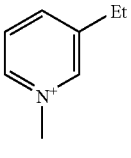

-continued
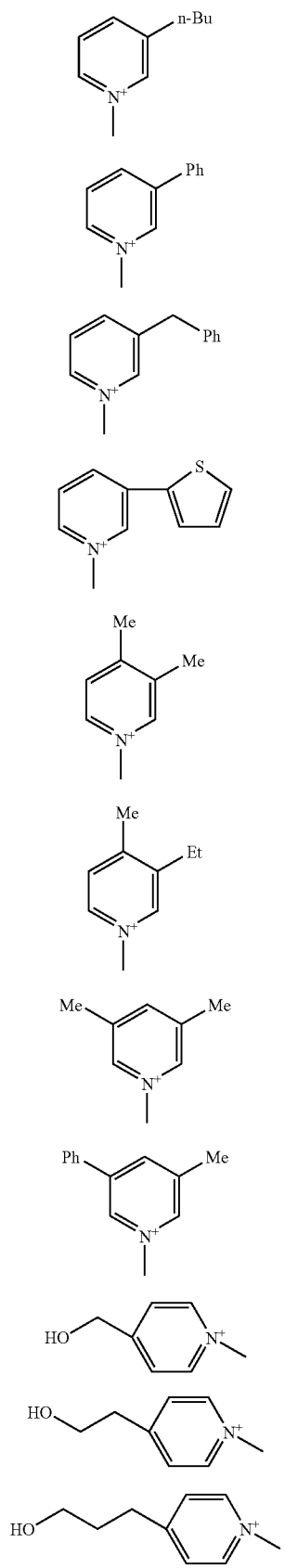
(an-315)
(an-316)
(an-317)
(an-318)
(an-319)
(an-320)
(an-321)
(an-322)
(an-323)
(an-324)
(an-325)
-continued
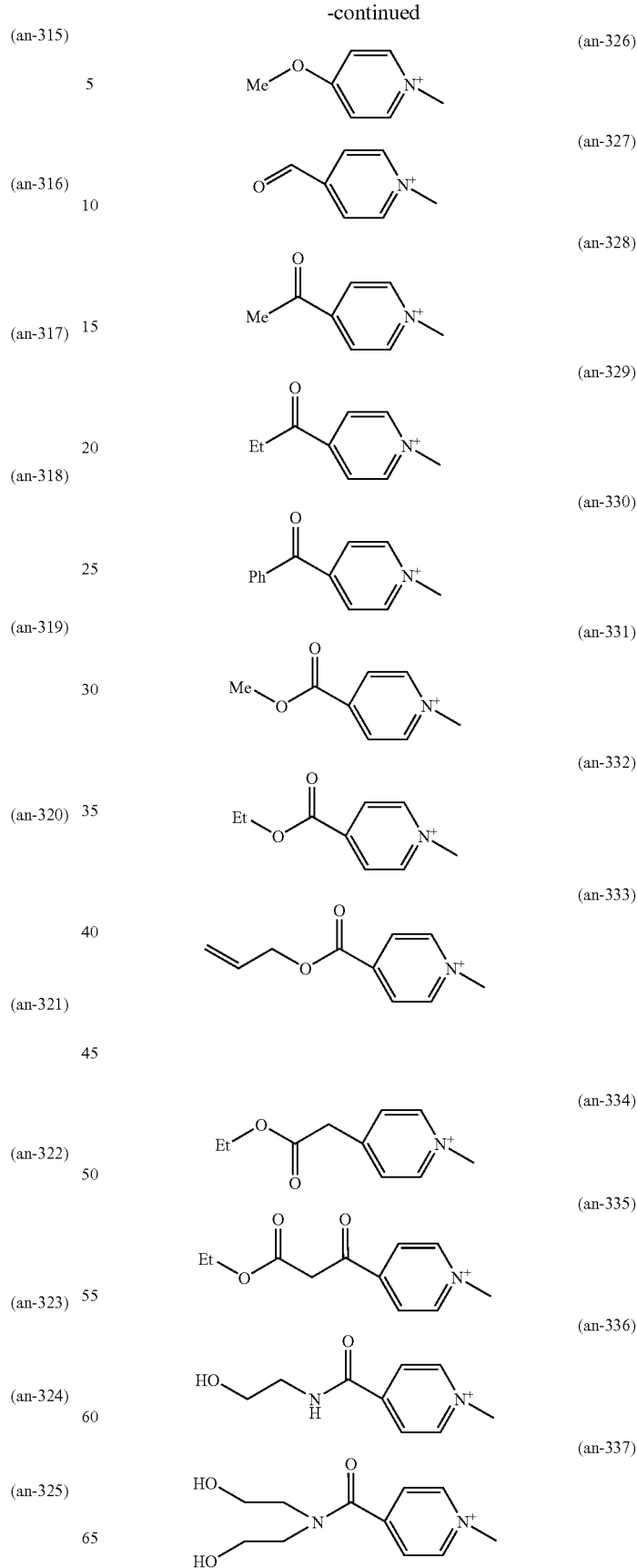
(an-326)
(an-327)
(an-328)
(an-329)
(an-330)
(an-331)
(an-332)
(an-333)
(an-334)
(an-335)
(an-336)
(an-337)

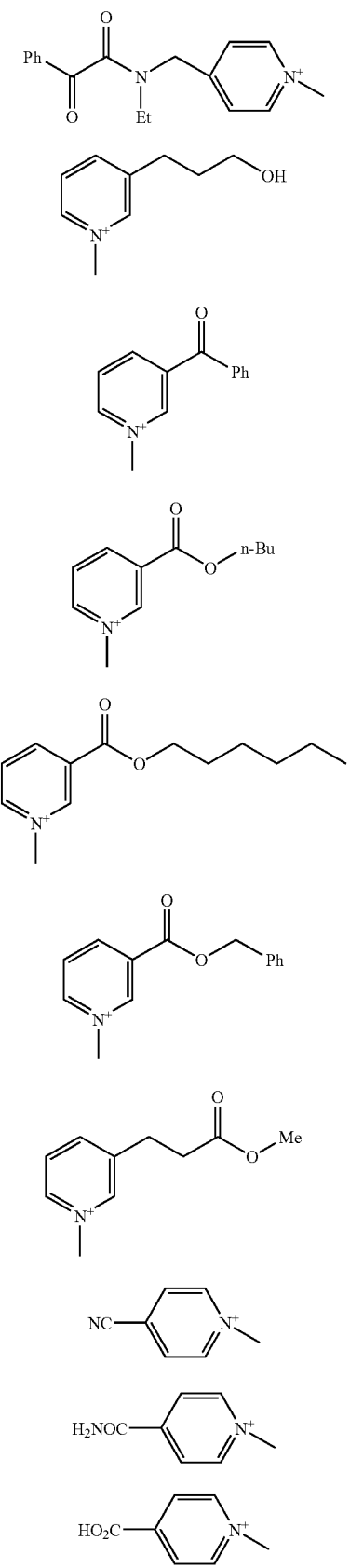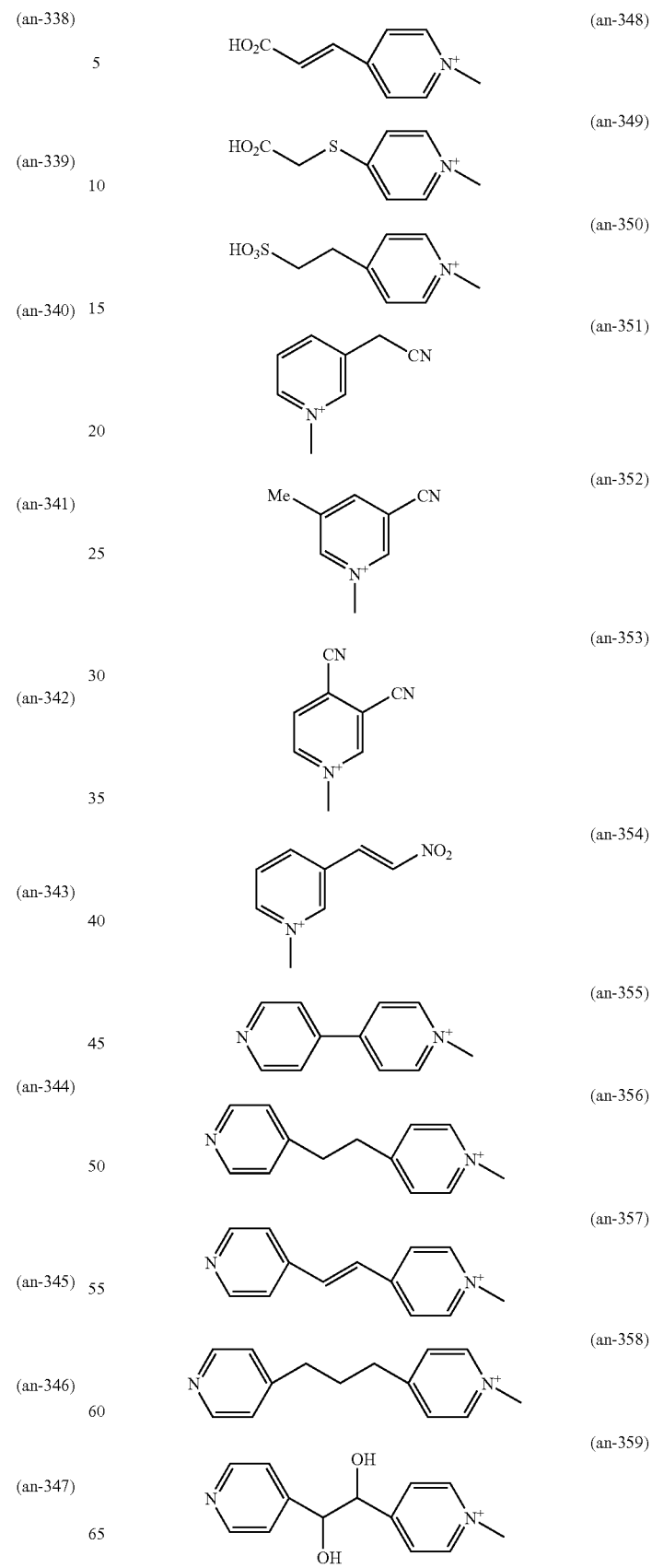

-continued
(an-367) 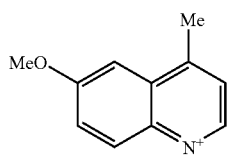
(an-368) 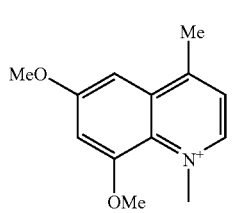
(an-369) 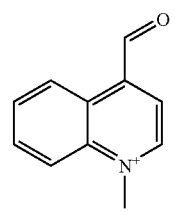
(an-370) 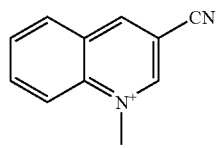
(an-371) 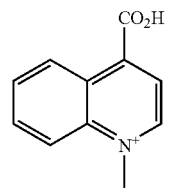
(an-372) 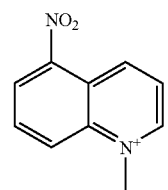
(an-373) 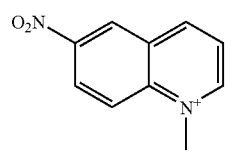
(an-374) 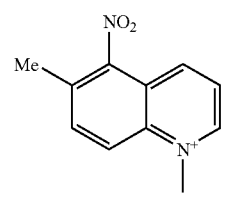
(an-375) 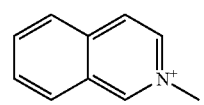
-continued
(an-376) 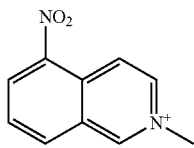
(an-377) 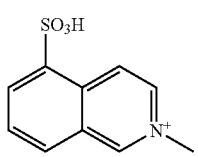
(an-360) 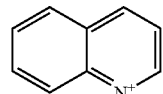
(an-361) 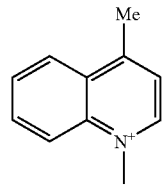
(an-362) 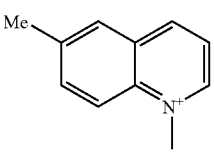
(an-363) 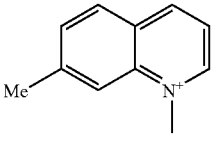
(an-364) 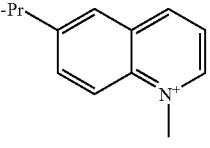
(an-365) 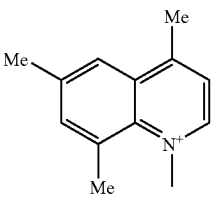
(an-366) 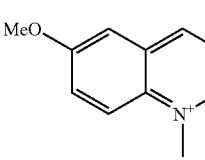

(an-367) 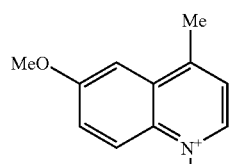
(an-368) 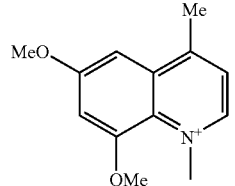
(an-369) 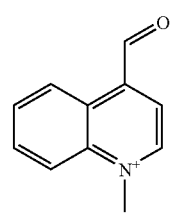
(an-370) 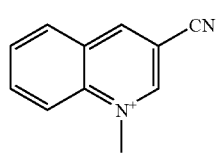
(an-371) 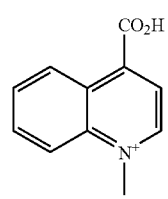
(an-372) 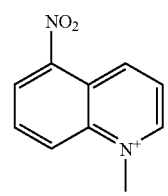
(an-373) 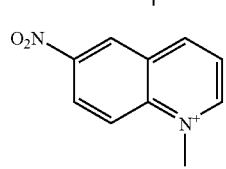
(an-374) 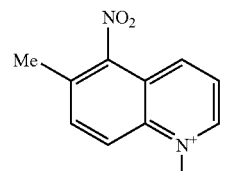
(an-375) 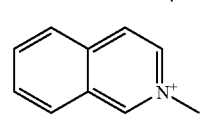
(an-376) 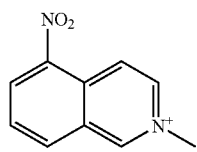
(an-377) 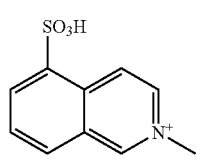
(an-378) 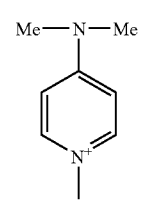
(an-379) 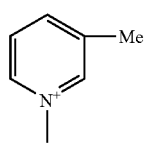
(an-394) 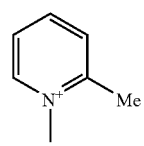
(an-395) 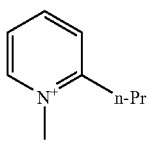
(an-396) 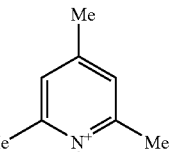
(an-397) 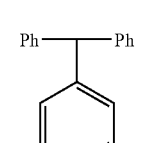
(an-398) 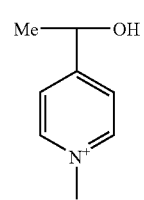

Specific examples of the —N⁺R⁵R⁶R⁷ other than those which correspond to I) to III) above include the formulae (an-383) to (an-393) and further (an-403) to (an-407) given below.

-continued

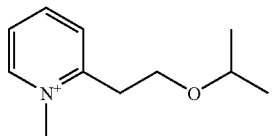
(an-407)

W⁻ and X⁻ each represents a counter anion which may be negatively charged ions regardless of their valence and can electrically neutralize a positively charged ammonium ion in the compound of the present invention, and it is preferable that they are pharmaceutically acceptable anions. Examples of preferable anion include $F^-$, $Cl^-$, $Br^-$, $I^-$, $OH^-$, $CH_3SO_3^-$, $CF_3SO_3^-$, $HCO_2^-$, $CH_3CO_2^-$, $CF_3CO_2^-$, $ClO_4^-$, $IO_4^-$, $HCO_3^-$, $CO_3^{2-}$, $NO_3^-$, $HSO_4^-$, $SO_4^{2-}$, $H_2PO_4^{2-}$, $HPO_4^{2-}$, $PO_4^{3-}$, among which $Cl^-$ and $Br^-$ are particularly preferable. W⁻ and X⁻ may be mutually different but more preferably they are the same.

Combinations of the substituents are not particularly limited; examples of particularly preferable compounds include (1) compounds in which Z-$(N^+R^5R^6R^7)_n$ represents an alkyl group having 2 to 10 carbon atoms which is substituted with n (—$N^+R^5R^6R^7$)s and at least one of methylenes which constitute Z may be replaced by any one of a phenylene and an —O—;

(2) the compounds described in (1) above, in which n is 1;

(3) the compounds described in (2) above, in which Z is a straight chain alkyl group having 2 to 10 carbon atoms, a straight chain alkyl group having 2 to 10 carbon atoms with one of methylenes which constitute Z being replaced by a phenylene, a straight chain alkyl group having 2 to 10 carbon atoms with one of methylenes which constitute Z being replaced by an —O—, or a straight chain alkyl group having 2 to 10 carbon atoms with one of methylenes which constitute Z being replaced by a phenylene and another methylene being replaced by —O—;

(4) the compounds described in (3) above, in which Z is a straight chain methylene group having from 2 to 10 carbon atoms, a straight chain methylene group having from 2 to 10 carbon atoms with one of methylenes thereof being replaced by a phenylene, a straight chain methylene group having from 2 to 10 carbon atoms with one of methylenes thereof being replaced by an —O—, or a straight chain methylene group having from 2 to 10 carbon atoms with one of methylenes thereof being replaced by a phenylene and another being replaced by an —O—;

(5) the compounds described in (4) above, in which Z is a straight chain methylene group having from 2 to 10 carbon atoms;

(6) the compounds described in (4) or (5) above, in which Y is —NHCS— or NHCSNH— at the para—position or meta—position;

(7) the compounds described in (6) above, in which Y is —NHCSNH—at the meta—position and Z is a straight chain methylene group having from 2 to 10 carbon atoms;

(8) the compounds described in (6) above, in which Y is —NHCS— at the meta—position and Z is a straight chain methylene group having from 2 to 10 carbon atoms;

(9) the compounds described in (8) above, in which Y is —NHCS— at the meta—position and Z is a straight chain methylene group having 5 carbon atoms;

(10) the compounds described in (4) above, in which Y is —NHCSNH— at the meta-position and Z is a straight chain methylene group having from 2 to 10 carbon atoms with one of methylenes thereof being replaced by a phenylene;

(11) the compounds described in (6) above, in which Y is —NHCS— or —NHCSNH— at the meta-position and Z is represented by formula (sp-4) below

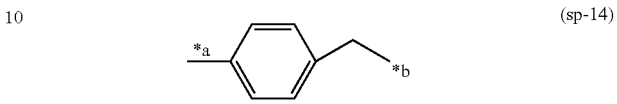
(sp-14)

[wherein *a is bonded to a bond with Y in the formula (1) and *b is bonded to a bond with $N^+R^5R^6R^7$];

(12) the compounds described in (10) or (11) above, in which Y is —NHCSNH— at the meta-position;

(13) the compounds described in any one of (1) to (12) above, in which the $N^+R^5R^6R^7$ is any one of I), II), and III) given below which are mutually independent:

I) $R^5$, $R^6$, and $R^7$, which may be mutually different, each represents any one of an alkyl group having from 1 to 10 carbon atoms, an alkenyl group having from 3 to 8 carbon atoms, and an alkynyl group having from 3 to 9 carbon atoms, where the alkyl group, the alkenyl group, and the alkynyl group may be substituted with at least one of a phenyl group, a thienyl group, a cyclohexyl group, a cyano group, a hydroxyl group, an oxo group, a carboxyl group, a —$CONH_2$ group, and an —$SO_3H$ group, and further, at least one of methylenes which constitute the alkyl group, the alkenyl group, and the alkynyl group may be replaced by any one of a phenylene, a thienylene, a furylene, an —O—, a —$CO_2$—, an —NHCO—, an —$NR^8$—, and an —$N^+W^-R^9R^{10}$— in which R5 represents an alkyl group having from 1 to 3 carbon atoms or an alkenyl group having 3 carbon atoms and the alkyl group may be substituted with at least one of a phenyl group and a hydroxyl group; $R^9$ and $R^{10}$ which may be mutually different, each represents an alkyl group having from 1 to 3 carbon atoms or an alkenyl group having 3 carbon atoms and the alkyl group may be substituted with at least one of a phenyl group and a hydroxyl group, II) $N^+R^5R^6R^7$ represents a monocyclic ring or a bicyclic ring which is any one of a pyrrolidinium ring, a piperidinium ring, a morpholinium ring, a thiomorpholinium ring, a piperazinium ring, an azepanium ring, a quinuclidinium ring, or a 1,4-diazabicyclo[2.2.2]octanium ring, provided that the position of its bonding with Z is an ammonium nitrogen atom; the monocyclic ring and the bicyclic ring may be substituted with at least one of a hydroxyl group, an oxo group, a cyano group, a phenyl group, a —CON $H_2$ group, and an —$R^{11}$ group; $R^{11}$ represents an alkyl group having from 1 to 6 carbon atoms or an alkenyl group having 3 carbon atoms, where the alkyl group represented by $R^{11}$ may be substituted with at least one of a hydroxyl group, a cyano group, a phenyl group, and a —$CONH_2$ group; moreover, at least one of methylenes which constitute the alkyl group may be replaced by any one of an —O—, a —$CO_2$—, and an —NHCO—; among $R^5$, $R^6$, and $R^7$, a group which is not involved in formation of the ring represents an alkyl group having 1 to 6 carbon atoms, an alkenyl group having 3 to 4 carbon atoms, or an alkynyl group having 3 to 6 carbon atoms; the alkyl group, the alkenyl group, and the alkynyl group represented by $R^5$, $R^6$, or $R^7$ may be substituted with at least one of a phenyl group, a thienyl group, a furyl group, a piperidyl group, a pyrrolidyl group, a morpholyl group, a cyclopropyl group, a cyclopentyl group, a cyano group, a hydroxyl group, an oxo group, a nitro group, a carboxyl group, an $CONH_2$ group, and an $SO_3H$ group; and moreover, at least one of methylenes which constitute the alkyl group may be replaced by any one of a phenylene, an —O—, and a —$CO_2$—, III) $N^+R^5R^6R^7$ represents a pyridinium ring, a quinolinium ring, or an isoquinolinium ring, provided that the position of its bonding with Z is an ammonium nitrogen atom; the pyridinium ring and the quinolinium ring may be substituted with at least one of a cyano group, a nitro group, a phenyl group, a thienyl group, a pyridyl group, an alkoxy group having from 1 to 3 carbon atoms, a carboxyl group, a —$CONH_2$ group, and an —$R^{12}$ group; $R^{12}$ represents an alkyl group having from 1 to 9 carbon atoms or an alkenyl group having from 2 to 4 carbon atoms; and the alkyl group and the alkenyl group represented by $R^{12}$ may be substituted with at least one of a phenyl group, a naphthyl group, a pyridyl group, a cyano group, a nitro group, a hydroxyl group, an oxo group, a carboxyl group, and an —$SO_3H$ group; and further, at least one of methylenes which constitute the alkyl group and the alkenyl group may be replaced by any one of an —S—, a —$CO_2$—, an —NHCO—, and an —$NR^8$— where $R^8$ represents an alkyl group having 1 to 3 carbon atoms and the alkyl group may be substituted with at least one hydroxyl group;

(14) the compounds described in any one of (1) to (13), in which the $N^+R^5R^6R^7$ is any one of I), II), and III) given below which are mutually independent;

I) $R^5$, $R^6$, and $R^7$, which may be mutually different, each represents an alkyl group having from 1 to 10 carbon atoms, a straight chain alkenyl group having from 3 to 6 or 8 carbon atoms, a branched alkenyl group having 4, 6 or 7 carbon atoms, a straight chain alkynyl group having from 3, 5, 6, 7 or 9 carbon atoms, or a branched alkynyl group having 6 carbon atoms, in which 1) the preferable alkyl group, alkenyl group, and alkynyl group represented by $R^5$, $R^6$, and $R^7$ are substituted with any one of a phenyl group, a thienyl group, a cyclohexyl group, a cyano group, a hydroxyl group, an oxo group, a carboxyl group, a —$CONH_2$ group, and an —$SO_3H$ group, 2) the alkyl group, the alkenyl group, and the alkynyl group are substituted with two hydroxyl groups, 3) the alkyl group, the alkenyl group, and the alkynyl group are substituted with one hydroxyl group and one —$SO_3H$ group, 4) the alkyl group, the alkenyl group, and the alkynyl group are substituted with one oxo group and one phenyl group, 5) the alkyl group, the alkenyl group, and the alkynyl group are substituted with one hydroxyl group and two phenyl groups, 6) one of methylenes which constitutes the alkyl group, the alkenyl group, and the alkynyl group is replaced by any one of a phenylene, a furylene, a —$CO_2$—, an —NHCO—, an —$NR^8$— (where $R^8$ represents a methyl group, an ethyl group, an n-propyl group, a 2-propenyl group, a 2-hydroxyethyl group, a 2-hydroxypropyl group, or a benzyl group), and an —$N^+W^-R^9R^{10}$— (where $R^9$ and $R^{10}$ each represents a methyl group, an ethyl group, an n-propyl group, a 2-propenyl group, a 2-hydroxyethyl group, or a benzyl group), 7) two of methylenes which constitute the alkyl group, the alkenyl group, and the alkynyl group are replaced by any one selected from two (—O—)s, one phenylene and one —O—, one —O— and one —$NR^8$—, and one —NHCO— and one —O—, 8) three of methylenes which constitute the alkyl group, the alkenyl group, and the alkynyl group are replaced by any one selected from two (—O—)s and one or one phenylene and two (—NHCO—)s, 9) the alkyl group, the alkenyl group, and the alkynyl group are substituted with one hydroxyl group, and moreover, one of methylenes which constitute the alkyl group, the alkenyl group, and the alkynyl group is replaced by an —O—, 10) the alkyl group, the alkenyl group, and the alkynyl group are substituted with one hydroxyl group, and moreover, one of methylenes which constitute the alkyl group, the alkenyl group, and the alkynyl group is replaced by an —$NR^8$—, 11) the alkyl group, the alkenyl group, and the alkynyl group are substituted with one hydroxyl group, and moreover one of methylenes which constitute the alkyl group, the alkenyl group, and the alkynyl group is replaced by a furylene, 12) the alkyl group, the alkenyl group, and the alkynyl group are substituted with one oxo group, and moreover, one of methylenes which constitute the alkyl group, the alkenyl group, and the alkynyl group is replaced by a thienylene, 13) the alkyl group, the alkenyl group, and the alkynyl group are substituted with one oxo group, and moreover, two of methylenes which constitute the alkyl group, the alkenyl group, and the alkynyl group are replaced by one —O— and one phenylene, or the alkyl group, alkenyl group, and alkynyl group are neither substituted nor replaced, II) $N^+R^5R^6R^7$ represents a monocyclic ring or a bicyclic ring which is any one of a pyrrolidinium ring, a piperidinium ring, a morpholinium ring, a thiomorpholinium ring, a piperazinium ring, an azepanium ring, a quinuclidinium ring, and a 1,4-diazabicyclo[2.2.2]octanium ring, provided that the position of its bonding with Z is an ammonium nitrogen atom; the monocyclic ring and the bicyclic ring are 1) substituted with any one of a hydroxyl group, an oxo group, a cyano group, a phenyl group, a —$CONH_2$ group, and an —$R^{11}$ group, 2) substituted with one cyano group and one hydroxyl group, 3) substituted with one hydroxyl group and one —$R^{11}$, 4) substituted with one oxo group and one —$R^{11}$, 5) substituted with two oxo groups, or 6) substituted with two (—$R^{11}$)s, or the monocyclic ring and the bicyclic ring are unsubstituted, where $R^{11}$ represents any one of a methyl group, an ethyl group, an n-propyl group, an n-butyl group, an n-pentyl group, a 2-propenyl group, a benzyl group, an acetylamino group, a t-butoxycarbonylamino group, a hydroxymethyl group, a 2-hydroxyethyl group, a 3-hydroxypropyl group, a 2-cyanoethoxy group, a (2-cyanoethoxy)methyl group, a 2-carbamoylethoxy group, an ethoxycarbonyl group, a t-butoxycarbonyl group, a benzoyloxy group, a phenylacetylamino group, a butanoylamino group, and a pentanoylamino group;

Among $R^5$, $R^6$, and $R^7$, a group which is not involved in the formation of the ring represents a straight chain alkyl group having from 1 to 6 carbon atoms, a straight chain alkenyl group having from 3 to 4 carbon atoms, or a straight chain alkynyl group having 3, 4, or 6 carbon atoms, in which 1) the alkyl group, the alkenyl group, and the alkynyl group represented by $R^5$, $R^6$, or $R^7$ are substituted with any one of a phenyl group, a thienyl group, a furyl group, a piperidyl group, a pyrrolidyl group, a morpholyl group, a cyclopropyl group, a cyclopentyl group, a cyano group, a hydroxyl group, a carboxyl group, and an —$SO_3H$ group, 2) the alkyl group, the alkenyl group, and the alkynyl group are substituted with two hydroxyl groups, 3) the alkyl group, the alkenyl group, and the alkynyl group are substituted with one hydroxyl group and one —$SO_3H$, 4) the alkyl group, the alkenyl group, and the alkynyl group are substituted with four hydroxyl groups and one oxo group, 5) the alkyl group, the alkenyl group, and the alkynyl group are substituted with one nitro group and one morpholyl group, 6) one of methylenes which constitute the alkyl group, the alkenyl group, and the alkynyl group is replaced by a —$CO_2$—, or 7) the alkyl group, the alkenyl group, and the alkynyl group are substituted with one morpholyl group and moreover, one of methylenes which constitute the alkyl group, the alkenyl group, and the alkynyl group is replaced by an —O—, or the alkyl group, the alkenyl group, and the alkynyl group are neither substituted nor replaced, III) $N^+R^5R^6R^7$ represents any one of 1) a pyridinium ring substituted with any one of a cyano group, a phenyl group, a thienyl group, a pyridyl group, a methoxy group, an ethoxy group, a propoxy group, a carboxyl group, a —$CONH_2$— group, and a —$R^{12}$ group, 2) a pyridinium ring substituted with two cyano groups, 3) a pyridinium group substituted with two (—$R^{12}$)s, 4) a pyridinium ring substituted with one cyano group and one —$R^{12}$, 5) a pyridinium ring substituted with one phenyl group and one —$R^{12}$, 6) a quinolinium ring substituted with any one of a cyano group, a nitro group, a carboxyl group, a methoxy group, an ethoxy group, a propoxy group, and —$R^{12}$, 7) a quinolinium ring substituted with one methoxy group and one —$R^{12}$, 8) a quinolinium ring substituted with one nitro group and one —$R^{12}$, 9) an unsubstituted pyridinium ring, 10) an unsubstituted quinolinium ring, or 11) an unsubstituted isoquinolinium ring, where $R^{12}$ represents any one of a methyl group, an ethyl group, an n—propyl group, an i-propyl group, an n-butyl group, a t-butyl group, an n-pentyl group, a 3-pentyl group, a 5-nonyl group, a vinyl group, a benzyl group, a 3-phenylpropyl group, a 2-(1-naphthyl)vinyl group, a hydroxymethyl group, a 2-hydroxyethyl group, a 3-hydroxypropyl group, a formyl group, an acetyl group, a propionyl group, a benzoyl group, a methoxycarbonyl group, an ethoxycarbonyl group, a butoxycarbonyl group, a hexoxycarbonyl group, a benzyloxycarbonyl group, a 2-propenyloxycarbonyl group, an ethoxycarbonylmethyl group, a 2-(methoxycarbonyl)ethyl group, an ethoxycarbonylmethylcarbonyl group, a 2-hydroxyethylaminocarbonyl group, a bis(2-hydroxyethyl)aminocarbonyl group, a 2-carboxyvinyl group, a carboxymethylthio group, a cyanomethyl group, a 2-nitrovinyl group, a 2-(4-pyridyl)ethyl group, a 2-(4-pyridyl)vinyl group, a 3-(4-pyridyl)propyl group, a 2-(4-pyridyl)-1,2-dihydroxyethyl group, and a 2-sulfoethyl group, provided that the position of its bonding with Z is an ammonium nitrogen atom;

(15) the compounds described in any one of (1) to (14), in which the $N^+R^5R^6R^7$ is any one of I), II), and III) given below which are mutually independent;

I) $R^5$, $R^6$, and $R^7$, which may be mutually different, each represents any one of a straight chain alkyl group having from 1 to 10 carbon atoms, a straight chain alkyl group having from 1 to 10 carbon atoms which is substituted with one phenyl group, a straight chain alkyl group having from 1 to 10 carbon atoms which is substituted with one hydroxyl group, an alkenyl group having from 3 to 6, or 8 carbon atoms, a branched alkenyl group having 4, 6, or 7 carbon atoms, a straight chain alkynyl group having 3, 5, 6, 7, or 9 carbon atoms, and a branched alkynyl group having 6 carbon atoms, II) $N^+R^5R^6R^7$ represents a pyrrolidinium ring, a piperidinium ring, an azepanium ring, a quinuclidinium ring, or a 1,4-diazabicyclo[2 22]- octanium ring, substituted with any one of a methyl group, an ethyl group, an n-propyl group, an n-butyl group, an n-pentyl group, a 2-propenyl group, a benzyl group, a hydroxyl group, a hydroxyl group, a hydroxymethyl group, a 2-hydroxyethyl group, and a 3-hydroxypropyl group, or unsubstituted, provided that the position of its bonding with Z is an ammonium nitrogen atom; among $R^5$, $R^6$, and $R^7$, any group that is not involved in the formation of the ring represents any one of a straight chain alkyl group having from 1 to 6 carbon atoms, a straight chain alkyl group having from 1 to 6 carbon atoms which is substituted with one phenyl group, a straight chain alkyl group having from 1 to 6 carbon atoms which is substituted with one hydroxyl group, a straight chain alkenyl group having from 3 to 4 carbon atoms, and a straight chain alkynyl group having 3, 4, or 6 carbon atoms, III) $N^+R^5R^6R^7$ represents an unsubstituted pyridinium ring, an unsubstituted quinolinium ring, an unsubstituted isoquinolinium ring, a pyridinium ring substituted with any one of a methyl group, an ethyl group, an n-propyl group, an i-propyl group, an n-butyl group, a t-butyl group, an n-pentyl group, a vinyl group, a phenyl group, a benzyl group, a 3-phenylpropyl group, a hydroxymethyl group, a 2-hydroxyethyl group, and a 3-hydroxypropyl group, a pyridinium ring substituted with any two of a methyl group and an ethyl group, a pyridinium ring substituted with one phenyl group and one methyl group, and a quinolinium ring substituted with any one of a methyl group and an -propyl group, provided that the position of its bonding with Z is ammonium nitrogen atom.

(16) the compounds described in any one of (13) to (15), in which R1 and $R^2$, which may be mutually different, each represents a straight chain alkyl group having 2 to 6 carbon atoms, and $(NR^3R^4)_m$ represents any one of a dimethylamino group substituting at the 7-position, a diethylamino group substituting at the 7-position, an ethylmethylamino group substituting at the 7-position, a dimethylamino group substituting at the 9-position, and dimethylamino groups substituting at the 7- and 9-positions;

(17) the compounds described in (16) above, in which $(NR_3R^4)_m$ is any one of a dimethylamino group substituting at the 7-position, a diethylamino group substituting at the 7-position, and an ethylmethylamino group substituting at the 7-position, and $N^+R^5R^6R^7$ is any one of a 4-t-butylpyridinium group, a 3-(3-hydroxypropyl)-pyridinium group, a 3-[2-(methoxycarbonyl)ethyl]-pyridinium group, a 2-(n-propyl)-pyridinium group, a 4-phenylquinuclidinium group, and a 1,4-diazabicyclo[2.2.2]octanium group; and (18) the compounds described in (17), in which both R1 and R2 are n-butyl groups, and $(NR^3R^4)_m$ is a dimethylamino group substituting at the 7-position.

In the compounds of the present invention, asymmetric centers can exist also in Z and $(N^+R^5R^6R^7)$ in addition to the 3-position and the 5-position in the formula (1), so that there can be a plurality of stereo isomers depending on the number of asymmetric centers. Not only pure stereoisomers but also mixtures of any plural number of isomers are included in the scope of the present invention. Moreover, there can exist a plurality of geometrical isomers depending on the types of Z and $(N^+R^5R^6R^7)$ in the compounds of the present invention. Not only pure geometrical isomers but also mixtures of any plural number of the isomers are included in the scope of the present invention.

Further, the present invention provides pharmaceutical compositions which contain the compounds of the present invention as active ingredients; a pharmaceutical composition which is a cholesterol-lowering agent, a pharmaceutical composition which is a therapeutic or preventive agent for any one of hyperlipidemia, arteriosclerosis, and syndrome X, a pharmaceutical composition which is a treating or preventing agent for cholestasis-caused hepatopathy, a pharmaceutical composition which is a treating or preventing agent for any one of primary biliary cirrhosis and primary sclerosing cholangitis, a pharmaceutical composition which is a treating or preventing agent for obesity and fatty liver, and a pharmaceutical composition which is a treating or preventing agent for steatohepatitis.

Due to their characteristic of having a thioamide bond in the molecule, the compounds of the present invention can be fully expected to act as radical scavengers. Radicals have high cytotoxicities; for example, when they act on alimentary canal, they are considered to cause alimentary canal disorder, for example, inflammatory enteritis (see Thomson A et al., Dig Dis, 16: 152-158, 1998). Furthermore, thiourea has been reported to have a protective effect against disorder of amino acid transporter (that is, inhibition of amino acid absorption) in small intestine caused by hydroxy radical and to be useful as a radical scavenger (see Hayashi K. et al., Scand. J. Gastroenterol, 28, 261-266, 1993). Taking this into consideration, the compounds of the present invention are considered to have an effect as a radical scavenger which can be used in the treatment or prevention of the disorder of alimentary canal, for example, inflammatory enteritis. A method for examining the radical scavenging effect includes a method of mixing the compound of the present invention with a compound which generates a hydroxy radical, for example, a hydrogen peroxide solution, t-BuOOH or the like and measuring the remaining quantity of radical using a physicochemical or a biochemical method. Moreover, the method for examining the radical scavenging effect includes a method of allowing the compound of the present invention to coexist in a model of causing disorder in a tissue of small intestine or small intestine epithelial cell line with a compound which generates a hydroxy radical, and an effect of decreasing the degree of disorder is examined. Note that the method of Hayashi et al. (see Hayashi K. et al., Scand. J. Gastroenterol, 28, 262-266, 1993) may be exemplified as a more specific method.

The 1,4-benzothiazepine skeleton, which is the basic skeleton of the compounds of the present invention, has a basic nitrogen at the 4-position which is a position adjacent to the center of asymmetry, so that optical isomers can be readily acquired by using various optical resolving agents such as camphor-sulfonic acid derivatives and tartaric acid derivatives. Moreover, since the 1,4-benzothiazepine skeleton forms pharmaceutically acceptable salts with various acids due to the existence of the basic nitrogen therein, compounds having acceptable water solubilities can be acquired, so that the skeleton is a basic skeleton which is useful for producing pharmaceuticals. The compounds of the present invention, which include the skeleton and a thioamide bond and a quaternary ammonium substituent introduced therein, are novel compounds which exhibit a very potent ileal bile acid transportation inhibiting activity and have stability in that the compounds are less susceptible to metabolism in vivo and have a reduced toxicity to the alimentary canal. The test examples described above have verified that the compounds of the present invention are useful as cholesterol-lowering agents, and furthermore they are useful for use in pharmaceutical compositions for treating or preventing hyperlipidemia, arteriosclerosis, syndrome X and the like. Also, it has been verified that the compounds of the present invention are useful as agents for ameliorating cholestasis-caused hepatopathy, and furthermore it has been verified that they are useful for use in pharmaceutical compositions for the treatment and prevention of cholestasis-caused hepatopathy, for example, primary biliary cirrhosis or primary sclerosing cholangitis. Further, it has been verified that the compounds of the present invention are useful for use in pharmaceutical compositions for the treatment and prevention of obesity and fatty liver. Moreover, it has been verified that the compounds of the present invention are useful for use in pharmaceutical compositions for treating and preventing steatohepatitis. In addition, it has been verified that the pharmaceutical compositions which contain ileal bile acid transporter inhibiting compounds as active ingredients are effective on cholestasis-caused hepatopathy and are useful for use in pharmaceutical compositions for the treatment and prevention of, in particular, primary biliary cirrhosis or primary sclerosing cholangitis.

The other objects, features and advantages of the present invention are specifically set forth in or will become apparent from the following detailed descriptions of the invention.

DETAILED DESCRIPTION

Specific examples of the compound represented by formula (1) include the following compounds and acid addition salts thereof.

Compounds in which both $R^1$ and $R^2$ are butyl groups, $NR^3R^4$ is a 7-dimethylamino group, $X^-$ is $Br^-$, and the bonding position of Y is the meta-position include those compounds described in Table 1 (from 1A0001 to 1A6681, from 1U0001 to 1U6681, and from 1C0001 to 1C3930). From (sp-1) to (sp-25) and from (an-1) to (an-393) in Table 1, are as mentioned earlier.

TABLE 1

| Y = NHCS | | | Y = NHCSNH | | | Y = NHCSO | | |
|---|---|---|---|---|---|---|---|---|
| Exemplification | Z | $N^+R^5R^6R^7$ | Exemplification | Z | $N^+R^5R^6R^7$ | Exemplification | Z | $N^+R^5R^6R^7$ |
| 1A0001 | sp-1 | an-1 | 1U0001 | sp-1 | an-1 | 1C0001 | sp-1 | an-1 |
| 1A0002 | sp-1 | an-2 | 1U0002 | sp-1 | an-2 | 1C0002 | sp-1 | an-2 |
| 1A0003 | sp-1 | an-3 | 1U0003 | sp-1 | an-3 | 1C0003 | sp-1 | an-3 |
| 1A0004 | sp-1 | an-4 | 1U0004 | sp-1 | an-4 | 1C0004 | sp-1 | an-4 |
| 1A0005 | sp-1 | an-5 | 1U0005 | sp-1 | an-5 | 1C0005 | sp-1 | an-5 |
| 1A0006 | sp-1 | an-6 | 1U0006 | sp-1 | an-6 | 1C0006 | sp-1 | an-6 |
| 1A0007 | sp-1 | an-7 | 1U0007 | sp-1 | an-7 | 1C0007 | sp-1 | an-7 |
| 1A0008 | sp-1 | an-8 | 1U0008 | sp-1 | an-8 | 1C0008 | sp-1 | an-8 |
| 1A0009 | sp-1 | an-9 | 1U0009 | sp-1 | an-9 | 1C0009 | sp-1 | an-9 |
| 1A0010 | sp-1 | an-10 | 1U0010 | sp-1 | an-10 | 1C0010 | sp-1 | an-10 |
| 1A0011 | sp-1 | an-11 | 1U0011 | sp-1 | an-11 | 1C0011 | sp-1 | an-11 |
| 1A0012 | sp-1 | an-12 | 1U0012 | sp-1 | an-12 | 1C0012 | sp-1 | an-12 |
| 1A0013 | sp-1 | an-13 | 1U0013 | sp-1 | an-13 | 1C0013 | sp-1 | an-13 |
| 1A0014 | sp-1 | an-14 | 1U0014 | sp-1 | an-14 | 1C0014 | sp-1 | an-14 |
| 1A0015 | sp-1 | an-15 | 1U0015 | sp-1 | an-15 | 1C0015 | sp-1 | an-15 |
| 1A0016 | sp-1 | an-16 | 1U0016 | sp-1 | an-16 | 1C0016 | sp-1 | an-16 |
| 1A0017 | sp-1 | an-17 | 1U0017 | sp-1 | an-17 | 1C0017 | sp-1 | an-17 |

TABLE 1-continued

| | | | | | | | | |
|---|---|---|---|---|---|---|---|---|
| 1A0018 | sp-1 | an-18 | 1U0018 | sp-1 | an-18 | 1C0018 | sp-1 | an-18 |
| 1A0019 | sp-1 | an-19 | 1U0019 | sp-1 | an-19 | 1C0019 | sp-1 | an-19 |
| 1A0020 | sp-1 | an-20 | 1U0020 | sp-1 | an-20 | 1C0020 | sp-1 | an-20 |
| 1A0021 | sp-1 | an-21 | 1U0021 | sp-1 | an-21 | 1C0021 | sp-1 | an-21 |
| 1A0022 | sp-1 | an-22 | 1U0022 | sp-1 | an-22 | 1C0022 | sp-1 | an-22 |
| 1A0023 | sp-1 | an-23 | 1U0023 | sp-1 | an-23 | 1C0023 | sp-1 | an-23 |
| 1A0024 | sp-1 | an-24 | 1U0024 | sp-1 | an-24 | 1C0024 | sp-1 | an-24 |
| 1A0025 | sp-1 | an-25 | 1U0025 | sp-1 | an-25 | 1C0025 | sp-1 | an-25 |
| 1A0026 | sp-1 | an-26 | 1U0026 | sp-1 | an-26 | 1C0026 | sp-1 | an-26 |
| 1A0027 | sp-1 | an-27 | 1U0027 | sp-1 | an-27 | 1C0027 | sp-1 | an-27 |
| 1A0028 | sp-1 | an-28 | 1U0028 | sp-1 | an-28 | 1C0028 | sp-1 | an-28 |
| 1A0029 | sp-1 | an-29 | 1U0029 | sp-1 | an-29 | 1C0029 | sp-1 | an-29 |
| 1A0030 | sp-1 | an-30 | 1U0030 | sp-1 | an-30 | 1C0030 | sp-1 | an-30 |
| 1A0031 | sp-1 | an-31 | 1U0031 | sp-1 | an-31 | 1C0031 | sp-1 | an-31 |
| 1A0032 | sp-1 | an-32 | 1U0032 | sp-1 | an-32 | 1C0032 | sp-1 | an-32 |
| 1A0033 | sp-1 | an-33 | 1U0033 | sp-1 | an-33 | 1C0033 | sp-1 | an-33 |
| 1A0034 | sp-1 | an-34 | 1U0034 | sp-1 | an-34 | 1C0034 | sp-1 | an-34 |
| 1A0035 | sp-1 | an-35 | 1U0035 | sp-1 | an-35 | 1C0035 | sp-1 | an-35 |
| 1A0036 | sp-1 | an-36 | 1U0036 | sp-1 | an-36 | 1C0036 | sp-1 | an-36 |
| 1A0037 | sp-1 | an-37 | 1U0037 | sp-1 | an-37 | 1C0037 | sp-1 | an-37 |
| 1A0038 | sp-1 | an-38 | 1U0038 | sp-1 | an-38 | 1C0038 | sp-1 | an-38 |
| 1A0039 | sp-1 | an-39 | 1U0039 | sp-1 | an-39 | 1C0039 | sp-1 | an-39 |
| 1A0040 | sp-1 | an-40 | 1U0040 | sp-1 | an-40 | 1C0040 | sp-1 | an-40 |
| 1A0041 | sp-1 | an-41 | 1U0041 | sp-1 | an-41 | 1C0041 | sp-1 | an-41 |
| 1A0042 | sp-1 | an-42 | 1U0042 | sp-1 | an-42 | 1C0042 | sp-1 | an-42 |
| 1A0043 | sp-1 | an-43 | 1U0043 | sp-1 | an-43 | 1C0043 | sp-1 | an-43 |
| 1A0044 | sp-1 | an-44 | 1U0044 | sp-1 | an-44 | 1C0044 | sp-1 | an-44 |
| 1A0045 | sp-1 | an-45 | 1U0045 | sp-1 | an-45 | 1C0045 | sp-1 | an-45 |
| 1A0046 | sp-1 | an-46 | 1U0046 | sp-1 | an-46 | 1C0046 | sp-1 | an-46 |
| 1A0047 | sp-1 | an-47 | 1U0047 | sp-1 | an-47 | 1C0047 | sp-1 | an-47 |
| 1A0048 | sp-1 | an-48 | 1U0048 | sp-1 | an-48 | 1C0048 | sp-1 | an-48 |
| 1A0049 | sp-1 | an-49 | 1U0049 | sp-1 | an-49 | 1C0049 | sp-1 | an-49 |
| 1A0050 | sp-1 | an-50 | 1U0050 | sp-1 | an-50 | 1C0050 | sp-1 | an-50 |
| 1A0051 | sp-1 | an-51 | 1U0051 | sp-1 | an-51 | 1C0051 | sp-1 | an-51 |
| 1A0052 | sp-1 | an-52 | 1U0052 | sp-1 | an-52 | 1C0052 | sp-1 | an-52 |
| 1A0053 | sp-1 | an-53 | 1U0053 | sp-1 | an-53 | 1C0053 | sp-1 | an-53 |
| 1A0054 | sp-1 | an-54 | 1U0054 | sp-1 | an-54 | 1C0054 | sp-1 | an-54 |
| 1A0055 | sp-1 | an-55 | 1U0055 | sp-1 | an-55 | 1C0055 | sp-1 | an-55 |
| 1A0056 | sp-1 | an-56 | 1U0056 | sp-1 | an-56 | 1C0056 | sp-1 | an-56 |
| 1A0057 | sp-1 | an-57 | 1U0057 | sp-1 | an-57 | 1C0057 | sp-1 | an-57 |
| 1A0058 | sp-1 | an-58 | 1U0058 | sp-1 | an-58 | 1C0058 | sp-1 | an-58 |
| 1A0059 | sp-1 | an-59 | 1U0059 | sp-1 | an-59 | 1C0059 | sp-1 | an-59 |
| 1A0060 | sp-1 | an-60 | 1U0060 | sp-1 | an-60 | 1C0060 | sp-1 | an-60 |
| 1A0061 | sp-1 | an-61 | 1U0061 | sp-1 | an-61 | 1C0061 | sp-1 | an-61 |
| 1A0062 | sp-1 | an-62 | 1U0062 | sp-1 | an-62 | 1C0062 | sp-1 | an-62 |
| 1A0063 | sp-1 | an-63 | 1U0063 | sp-1 | an-63 | 1C0063 | sp-1 | an-63 |
| 1A0064 | sp-1 | an-64 | 1U0064 | sp-1 | an-64 | 1C0064 | sp-1 | an-64 |
| 1A0065 | sp-1 | an-65 | 1U0065 | sp-1 | an-65 | 1C0065 | sp-1 | an-65 |
| 1A0066 | sp-1 | an-66 | 1U0066 | sp-1 | an-66 | 1C0066 | sp-1 | an-66 |
| 1A0067 | sp-1 | an-67 | 1U0067 | sp-1 | an-67 | 1C0067 | sp-1 | an-67 |
| 1A0068 | sp-1 | an-68 | 1U0068 | sp-1 | an-68 | 1C0068 | sp-1 | an-68 |
| 1A0069 | sp-1 | an-69 | 1U0069 | sp-1 | an-69 | 1C0069 | sp-1 | an-69 |
| 1A0070 | sp-1 | an-70 | 1U0070 | sp-1 | an-70 | 1C0070 | sp-1 | an-70 |
| 1A0071 | sp-1 | an-71 | 1U0071 | sp-1 | an-71 | 1C0071 | sp-1 | an-71 |
| 1A0072 | sp-1 | an-72 | 1U0072 | sp-1 | an-72 | 1C0072 | sp-1 | an-72 |
| 1A0073 | sp-1 | an-73 | 1U0073 | sp-1 | an-73 | 1C0073 | sp-1 | an-73 |
| 1A0074 | sp-1 | an-74 | 1U0074 | sp-1 | an-74 | 1C0074 | sp-1 | an-74 |
| 1A0075 | sp-1 | an-75 | 1U0075 | sp-1 | an-75 | 1C0075 | sp-1 | an-75 |
| 1A0076 | sp-1 | an-76 | 1U0076 | sp-1 | an-76 | 1C0076 | sp-1 | an-76 |
| 1A0077 | sp-1 | an-77 | 1U0077 | sp-1 | an-77 | 1C0077 | sp-1 | an-77 |
| 1A0078 | sp-1 | an-78 | 1U0078 | sp-1 | an-78 | 1C0078 | sp-1 | an-78 |
| 1A0079 | sp-1 | an-79 | 1U0079 | sp-1 | an-79 | 1C0079 | sp-1 | an-79 |
| 1A0080 | sp-1 | an-80 | 1U0080 | sp-1 | an-80 | 1C0080 | sp-1 | an-80 |
| 1A0081 | sp-1 | an-81 | 1U0081 | sp-1 | an-81 | 1C0081 | sp-1 | an-81 |
| 1A0082 | sp-1 | an-82 | 1U0082 | sp-1 | an-82 | 1C0082 | sp-1 | an-82 |
| 1A0083 | sp-1 | an-83 | 1U0083 | sp-1 | an-83 | 1C0083 | sp-1 | an-83 |
| 1A0084 | sp-1 | an-84 | 1U0084 | sp-1 | an-84 | 1C0084 | sp-1 | an-84 |
| 1A0085 | sp-1 | an-85 | 1U0085 | sp-1 | an-85 | 1C0085 | sp-1 | an-85 |
| 1A0086 | sp-1 | an-86 | 1U0086 | sp-1 | an-86 | 1C0086 | sp-1 | an-86 |
| 1A0087 | sp-1 | an-87 | 1U0087 | sp-1 | an-87 | 1C0087 | sp-1 | an-87 |
| 1A0088 | sp-1 | an-88 | 1U0088 | sp-1 | an-88 | 1C0088 | sp-1 | an-88 |
| 1A0089 | sp-1 | an-89 | 1U0089 | sp-1 | an-89 | 1C0089 | sp-1 | an-89 |
| 1A0090 | sp-1 | an-90 | 1U0090 | sp-1 | an-90 | 1C0090 | sp-1 | an-90 |
| 1A0091 | sp-1 | an-91 | 1U0091 | sp-1 | an-91 | 1C0091 | sp-1 | an-91 |
| 1A0092 | sp-1 | an-92 | 1U0092 | sp-1 | an-92 | 1C0092 | sp-1 | an-92 |
| 1A0093 | sp-1 | an-93 | 1U0093 | sp-1 | an-93 | 1C0093 | sp-1 | an-93 |
| 1A0094 | sp-1 | an-94 | 1U0094 | sp-1 | an-94 | 1C0094 | sp-1 | an-94 |
| 1A0095 | sp-1 | an-95 | 1U0095 | sp-1 | an-95 | 1C0095 | sp-1 | an-95 |
| 1A0096 | sp-1 | an-96 | 1U0096 | sp-1 | an-96 | 1C0096 | sp-1 | an-96 |

TABLE 1-continued

| | | | | | | | | |
|---|---|---|---|---|---|---|---|---|
| 1A0097 | sp-1 | an-97 | 1U0097 | sp-1 | an-97 | 1C0097 | sp-1 | an-97 |
| 1A0098 | sp-1 | an-98 | 1U0098 | sp-1 | an-98 | 1C0098 | sp-1 | an-98 |
| 1A0099 | sp-1 | an-99 | 1U0099 | sp-1 | an-99 | 1C0099 | sp-1 | an-99 |
| 1A0100 | sp-1 | an-100 | 1U0100 | sp-1 | an-100 | 1C0100 | sp-1 | an-100 |
| 1A0101 | sp-1 | an-101 | 1U0101 | sp-1 | an-101 | 1C0101 | sp-1 | an-101 |
| 1A0102 | sp-1 | an-102 | 1U0102 | sp-1 | an-102 | 1C0102 | sp-1 | an-102 |
| 1A0103 | sp-1 | an-103 | 1U0103 | sp-1 | an-103 | 1C0103 | sp-1 | an-103 |
| 1A0104 | sp-1 | an-104 | 1U0104 | sp-1 | an-104 | 1C0104 | sp-1 | an-104 |
| 1A0105 | sp-1 | an-105 | 1U0105 | sp-1 | an-105 | 1C0105 | sp-1 | an-105 |
| 1A0106 | sp-1 | an-106 | 1U0106 | sp-1 | an-106 | 1C0106 | sp-1 | an-106 |
| 1A0107 | sp-1 | an-107 | 1U0107 | sp-1 | an-107 | 1C0107 | sp-1 | an-107 |
| 1A0108 | sp-1 | an-108 | 1U0108 | sp-1 | an-108 | 1C0108 | sp-1 | an-108 |
| 1A0109 | sp-1 | an-109 | 1U0109 | sp-1 | an-109 | 1C0109 | sp-1 | an-109 |
| 1A0110 | sp-1 | an-110 | 1U0110 | sp-1 | an-110 | 1C0110 | sp-1 | an-110 |
| 1A0111 | sp-1 | an-111 | 1U0111 | sp-1 | an-111 | 1C0111 | sp-1 | an-111 |
| 1A0112 | sp-1 | an-112 | 1U0112 | sp-1 | an-112 | 1C0112 | sp-1 | an-112 |
| 1A0113 | sp-1 | an-113 | 1U0113 | sp-1 | an-113 | 1C0113 | sp-1 | an-113 |
| 1A0114 | sp-1 | an-114 | 1U0114 | sp-1 | an-114 | 1C0114 | sp-1 | an-114 |
| 1A0115 | sp-1 | an-115 | 1U0115 | sp-1 | an-115 | 1C0115 | sp-1 | an-115 |
| 1A0116 | sp-1 | an-116 | 1U0116 | sp-1 | an-116 | 1C0116 | sp-1 | an-116 |
| 1A0117 | sp-1 | an-117 | 1U0117 | sp-1 | an-117 | 1C0117 | sp-1 | an-117 |
| 1A0118 | sp-1 | an-118 | 1U0118 | sp-1 | an-118 | 1C0118 | sp-1 | an-118 |
| 1A0119 | sp-1 | an-119 | 1U0119 | sp-1 | an-119 | 1C0119 | sp-1 | an-119 |
| 1A0120 | sp-1 | an-120 | 1U0120 | sp-1 | an-120 | 1C0120 | sp-1 | an-120 |
| 1A0121 | sp-1 | an-121 | 1U0121 | sp-1 | an-121 | 1C0121 | sp-1 | an-121 |
| 1A0122 | sp-1 | an-122 | 1U0122 | sp-1 | an-122 | 1C0122 | sp-1 | an-122 |
| 1A0123 | sp-1 | an-123 | 1U0123 | sp-1 | an-123 | 1C0123 | sp-1 | an-123 |
| 1A0124 | sp-1 | an-124 | 1U0124 | sp-1 | an-124 | 1C0124 | sp-1 | an-124 |
| 1A0125 | sp-1 | an-125 | 1U0125 | sp-1 | an-125 | 1C0125 | sp-1 | an-125 |
| 1A0126 | sp-1 | an-126 | 1U0126 | sp-1 | an-126 | 1C0126 | sp-1 | an-126 |
| 1A0127 | sp-1 | an-127 | 1U0127 | sp-1 | an-127 | 1C0127 | sp-1 | an-127 |
| 1A0128 | sp-1 | an-128 | 1U0128 | sp-1 | an-128 | 1C0128 | sp-1 | an-128 |
| 1A0129 | sp-1 | an-129 | 1U0129 | sp-1 | an-129 | 1C0129 | sp-1 | an-129 |
| 1A0130 | sp-1 | an-130 | 1U0130 | sp-1 | an-130 | 1C0130 | sp-1 | an-130 |
| 1A0131 | sp-1 | an-131 | 1U0131 | sp-1 | an-131 | 1C0131 | sp-1 | an-131 |
| 1A0132 | sp-1 | an-132 | 1U0132 | sp-1 | an-132 | 1C0132 | sp-1 | an-132 |
| 1A0133 | sp-1 | an-133 | 1U0133 | sp-1 | an-133 | 1C0133 | sp-1 | an-133 |
| 1A0134 | sp-1 | an-134 | 1U0134 | sp-1 | an-134 | 1C0134 | sp-1 | an-134 |
| 1A0135 | sp-1 | an-135 | 1U0135 | sp-1 | an-135 | 1C0135 | sp-1 | an-135 |
| 1A0136 | sp-1 | an-136 | 1U0136 | sp-1 | an-136 | 1C0136 | sp-1 | an-136 |
| 1A0137 | sp-1 | an-137 | 1U0137 | sp-1 | an-137 | 1C0137 | sp-1 | an-137 |
| 1A0138 | sp-1 | an-138 | 1U0138 | sp-1 | an-138 | 1C0138 | sp-1 | an-138 |
| 1A0139 | sp-1 | an-139 | 1U0139 | sp-1 | an-139 | 1C0139 | sp-1 | an-139 |
| 1A0140 | sp-1 | an-140 | 1U0140 | sp-1 | an-140 | 1C0140 | sp-1 | an-140 |
| 1A0141 | sp-1 | an-141 | 1U0141 | sp-1 | an-141 | 1C0141 | sp-1 | an-141 |
| 1A0142 | sp-1 | an-142 | 1U0142 | sp-1 | an-142 | 1C0142 | sp-1 | an-142 |
| 1A0143 | sp-1 | an-143 | 1U0143 | sp-1 | an-143 | 1C0143 | sp-1 | an-143 |
| 1A0144 | sp-1 | an-144 | 1U0144 | sp-1 | an-144 | 1C0144 | sp-1 | an-144 |
| 1A0145 | sp-1 | an-145 | 1U0145 | sp-1 | an-145 | 1C0145 | sp-1 | an-145 |
| 1A0146 | sp-1 | an-146 | 1U0146 | sp-1 | an-146 | 1C0146 | sp-1 | an-146 |
| 1A0147 | sp-1 | an-147 | 1U0147 | sp-1 | an-147 | 1C0147 | sp-1 | an-147 |
| 1A0148 | sp-1 | an-148 | 1U0148 | sp-1 | an-148 | 1C0148 | sp-1 | an-148 |
| 1A0149 | sp-1 | an-149 | 1U0149 | sp-1 | an-149 | 1C0149 | sp-1 | an-149 |
| 1A0150 | sp-1 | an-150 | 1U0150 | sp-1 | an-150 | 1C0150 | sp-1 | an-150 |
| 1A0151 | sp-1 | an-151 | 1U0151 | sp-1 | an-151 | 1C0151 | sp-1 | an-151 |
| 1A0152 | sp-1 | an-152 | 1U0152 | sp-1 | an-152 | 1C0152 | sp-1 | an-152 |
| 1A0153 | sp-1 | an-153 | 1U0153 | sp-1 | an-153 | 1C0153 | sp-1 | an-153 |
| 1A0154 | sp-1 | an-154 | 1U0154 | sp-1 | an-154 | 1C0154 | sp-1 | an-154 |
| 1A0155 | sp-1 | an-155 | 1U0155 | sp-1 | an-155 | 1C0155 | sp-1 | an-155 |
| 1A0156 | sp-1 | an-156 | 1U0156 | sp-1 | an-156 | 1C0156 | sp-1 | an-156 |
| 1A0157 | sp-1 | an-157 | 1U0157 | sp-1 | an-157 | 1C0157 | sp-1 | an-157 |
| 1A0158 | sp-1 | an-158 | 1U0158 | sp-1 | an-158 | 1C0158 | sp-1 | an-158 |
| 1A0159 | sp-1 | an-159 | 1U0159 | sp-1 | an-159 | 1C0159 | sp-1 | an-159 |
| 1A0160 | sp-1 | an-160 | 1U0160 | sp-1 | an-160 | 1C0160 | sp-1 | an-160 |
| 1A0161 | sp-1 | an-161 | 1U0161 | sp-1 | an-161 | 1C0161 | sp-1 | an-161 |
| 1A0162 | sp-1 | an-162 | 1U0162 | sp-1 | an-162 | 1C0162 | sp-1 | an-162 |
| 1A0163 | sp-1 | an-163 | 1U0163 | sp-1 | an-163 | 1C0163 | sp-1 | an-163 |
| 1A0164 | sp-1 | an-164 | 1U0164 | sp-1 | an-164 | 1C0164 | sp-1 | an-164 |
| 1A0165 | sp-1 | an-165 | 1U0165 | sp-1 | an-165 | 1C0165 | sp-1 | an-165 |
| 1A0166 | sp-1 | an-166 | 1U0166 | sp-1 | an-166 | 1C0166 | sp-1 | an-166 |
| 1A0167 | sp-1 | an-167 | 1U0167 | sp-1 | an-167 | 1C0167 | sp-1 | an-167 |
| 1A0168 | sp-1 | an-168 | 1U0168 | sp-1 | an-168 | 1C0168 | sp-1 | an-168 |
| 1A0169 | sp-1 | an-169 | 1U0169 | sp-1 | an-169 | 1C0169 | sp-1 | an-169 |
| 1A0170 | sp-1 | an-170 | 1U0170 | sp-1 | an-170 | 1C0170 | sp-1 | an-170 |
| 1A0171 | sp-1 | an-171 | 1U0171 | sp-1 | an-171 | 1C0171 | sp-1 | an-171 |
| 1A0172 | sp-1 | an-172 | 1U0172 | sp-1 | an-172 | 1C0172 | sp-1 | an-172 |
| 1A0173 | sp-1 | an-173 | 1U0173 | sp-1 | an-173 | 1C0173 | sp-1 | an-173 |
| 1A0174 | sp-1 | an-174 | 1U0174 | sp-1 | an-174 | 1C0174 | sp-1 | an-174 |
| 1A0175 | sp-1 | an-175 | 1U0175 | sp-1 | an-175 | 1C0175 | sp-1 | an-175 |

TABLE 1-continued

| | | | | | | | | |
|---|---|---|---|---|---|---|---|---|
| 1A0176 | sp-1 | an-176 | 1U0176 | sp-1 | an-176 | 1C0176 | sp-1 | an-176 |
| 1A0177 | sp-1 | an-177 | 1U0177 | sp-1 | an-177 | 1C0177 | sp-1 | an-177 |
| 1A0178 | sp-1 | an-178 | 1U0178 | sp-1 | an-178 | 1C0178 | sp-1 | an-178 |
| 1A0179 | sp-1 | an-179 | 1U0179 | sp-1 | an-179 | 1C0179 | sp-1 | an-179 |
| 1A0180 | sp-1 | an-180 | 1U0180 | sp-1 | an-180 | 1C0180 | sp-1 | an-180 |
| 1A0181 | sp-1 | an-181 | 1U0181 | sp-1 | an-181 | 1C0181 | sp-1 | an-181 |
| 1A0182 | sp-1 | an-182 | 1U0182 | sp-1 | an-182 | 1C0182 | sp-1 | an-182 |
| 1A0183 | sp-1 | an-183 | 1U0183 | sp-1 | an-183 | 1C0183 | sp-1 | an-183 |
| 1A0184 | sp-1 | an-184 | 1U0184 | sp-1 | an-184 | 1C0184 | sp-1 | an-184 |
| 1A0185 | sp-1 | an-185 | 1U0185 | sp-1 | an-185 | 1C0185 | sp-1 | an-185 |
| 1A0186 | sp-1 | an-186 | 1U0186 | sp-1 | an-186 | 1C0186 | sp-1 | an-186 |
| 1A0187 | sp-1 | an-187 | 1U0187 | sp-1 | an-187 | 1C0187 | sp-1 | an-187 |
| 1A0188 | sp-1 | an-188 | 1U0188 | sp-1 | an-188 | 1C0188 | sp-1 | an-188 |
| 1A0189 | sp-1 | an-189 | 1U0189 | sp-1 | an-189 | 1C0189 | sp-1 | an-189 |
| 1A0190 | sp-1 | an-190 | 1U0190 | sp-1 | an-190 | 1C0190 | sp-1 | an-190 |
| 1A0191 | sp-1 | an-191 | 1U0191 | sp-1 | an-191 | 1C0191 | sp-1 | an-191 |
| 1A0192 | sp-1 | an-192 | 1U0192 | sp-1 | an-192 | 1C0192 | sp-1 | an-192 |
| 1A0193 | sp-1 | an-193 | 1U0193 | sp-1 | an-193 | 1C0193 | sp-1 | an-193 |
| 1A0194 | sp-1 | an-194 | 1U0194 | sp-1 | an-194 | 1C0194 | sp-1 | an-194 |
| 1A0195 | sp-1 | an-195 | 1U0195 | sp-1 | an-195 | 1C0195 | sp-1 | an-195 |
| 1A0196 | sp-1 | an-196 | 1U0196 | sp-1 | an-196 | 1C0196 | sp-1 | an-196 |
| 1A0197 | sp-1 | an-197 | 1U0197 | sp-1 | an-197 | 1C0197 | sp-1 | an-197 |
| 1A0198 | sp-1 | an-198 | 1U0198 | sp-1 | an-198 | 1C0198 | sp-1 | an-198 |
| 1A0199 | sp-1 | an-199 | 1U0199 | sp-1 | an-199 | 1C0199 | sp-1 | an-199 |
| 1A0200 | sp-1 | an-200 | 1U0200 | sp-1 | an-200 | 1C0200 | sp-1 | an-200 |
| 1A0201 | sp-1 | an-201 | 1U0201 | sp-1 | an-201 | 1C0201 | sp-1 | an-201 |
| 1A0202 | sp-1 | an-202 | 1U0202 | sp-1 | an-202 | 1C0202 | sp-1 | an-202 |
| 1A0203 | sp-1 | an-203 | 1U0203 | sp-1 | an-203 | 1C0203 | sp-1 | an-203 |
| 1A0204 | sp-1 | an-204 | 1U0204 | sp-1 | an-204 | 1C0204 | sp-1 | an-204 |
| 1A0205 | sp-1 | an-205 | 1U0205 | sp-1 | an-205 | 1C0205 | sp-1 | an-205 |
| 1A0206 | sp-1 | an-206 | 1U0206 | sp-1 | an-206 | 1C0206 | sp-1 | an-206 |
| 1A0207 | sp-1 | an-207 | 1U0207 | sp-1 | an-207 | 1C0207 | sp-1 | an-207 |
| 1A0208 | sp-1 | an-208 | 1U0208 | sp-1 | an-208 | 1C0208 | sp-1 | an-208 |
| 1A0209 | sp-1 | an-209 | 1U0209 | sp-1 | an-209 | 1C0209 | sp-1 | an-209 |
| 1A0210 | sp-1 | an-210 | 1U0210 | sp-1 | an-210 | 1C0210 | sp-1 | an-210 |
| 1A0211 | sp-1 | an-211 | 1U0211 | sp-1 | an-211 | 1C0211 | sp-1 | an-211 |
| 1A0212 | sp-1 | an-212 | 1U0212 | sp-1 | an-212 | 1C0212 | sp-1 | an-212 |
| 1A0213 | sp-1 | an-213 | 1U0213 | sp-1 | an-213 | 1C0213 | sp-1 | an-213 |
| 1A0214 | sp-1 | an-214 | 1U0214 | sp-1 | an-214 | 1C0214 | sp-1 | an-214 |
| 1A0215 | sp-1 | an-215 | 1U0215 | sp-1 | an-215 | 1C0215 | sp-1 | an-215 |
| 1A0216 | sp-1 | an-216 | 1U0216 | sp-1 | an-216 | 1C0216 | sp-1 | an-216 |
| 1A0217 | sp-1 | an-217 | 1U0217 | sp-1 | an-217 | 1C0217 | sp-1 | an-217 |
| 1A0218 | sp-1 | an-218 | 1U0218 | sp-1 | an-218 | 1C0218 | sp-1 | an-218 |
| 1A0219 | sp-1 | an-219 | 1U0219 | sp-1 | an-219 | 1C0219 | sp-1 | an-219 |
| 1A0220 | sp-1 | an-220 | 1U0220 | sp-1 | an-220 | 1C0220 | sp-1 | an-220 |
| 1A0221 | sp-1 | an-221 | 1U0221 | sp-1 | an-221 | 1C0221 | sp-1 | an-221 |
| 1A0222 | sp-1 | an-222 | 1U0222 | sp-1 | an-222 | 1C0222 | sp-1 | an-222 |
| 1A0223 | sp-1 | an-223 | 1U0223 | sp-1 | an-223 | 1C0223 | sp-1 | an-223 |
| 1A0224 | sp-1 | an-224 | 1U0224 | sp-1 | an-224 | 1C0224 | sp-1 | an-224 |
| 1A0225 | sp-1 | an-225 | 1U0225 | sp-1 | an-225 | 1C0225 | sp-1 | an-225 |
| 1A0226 | sp-1 | an-226 | 1U0226 | sp-1 | an-226 | 1C0226 | sp-1 | an-226 |
| 1A0227 | sp-1 | an-227 | 1U0227 | sp-1 | an-227 | 1C0227 | sp-1 | an-227 |
| 1A0228 | sp-1 | an-228 | 1U0228 | sp-1 | an-228 | 1C0228 | sp-1 | an-228 |
| 1A0229 | sp-1 | an-229 | 1U0229 | sp-1 | an-229 | 1C0229 | sp-1 | an-229 |
| 1A0230 | sp-1 | an-230 | 1U0230 | sp-1 | an-230 | 1C0230 | sp-1 | an-230 |
| 1A0231 | sp-1 | an-231 | 1U0231 | sp-1 | an-231 | 1C0231 | sp-1 | an-231 |
| 1A0232 | sp-1 | an-232 | 1U0232 | sp-1 | an-232 | 1C0232 | sp-1 | an-232 |
| 1A0233 | sp-1 | an-233 | 1U0233 | sp-1 | an-233 | 1C0233 | sp-1 | an-233 |
| 1A0234 | sp-1 | an-234 | 1U0234 | sp-1 | an-234 | 1C0234 | sp-1 | an-234 |
| 1A0235 | sp-1 | an-235 | 1U0235 | sp-1 | an-235 | 1C0235 | sp-1 | an-235 |
| 1A0236 | sp-1 | an-236 | 1U0236 | sp-1 | an-236 | 1C0236 | sp-1 | an-236 |
| 1A0237 | sp-1 | an-237 | 1U0237 | sp-1 | an-237 | 1C0237 | sp-1 | an-237 |
| 1A0238 | sp-1 | an-238 | 1U0238 | sp-1 | an-238 | 1C0238 | sp-1 | an-238 |
| 1A0239 | sp-1 | an-239 | 1U0239 | sp-1 | an-239 | 1C0239 | sp-1 | an-239 |
| 1A0240 | sp-1 | an-240 | 1U0240 | sp-1 | an-240 | 1C0240 | sp-1 | an-240 |
| 1A0241 | sp-1 | an-241 | 1U0241 | sp-1 | an-241 | 1C0241 | sp-1 | an-241 |
| 1A0242 | sp-1 | an-242 | 1U0242 | sp-1 | an-242 | 1C0242 | sp-1 | an-242 |
| 1A0243 | sp-1 | an-243 | 1U0243 | sp-1 | an-243 | 1C0243 | sp-1 | an-243 |
| 1A0244 | sp-1 | an-244 | 1U0244 | sp-1 | an-244 | 1C0244 | sp-1 | an-244 |
| 1A0245 | sp-1 | an-245 | 1U0245 | sp-1 | an-245 | 1C0245 | sp-1 | an-245 |
| 1A0246 | sp-1 | an-246 | 1U0246 | sp-1 | an-246 | 1C0246 | sp-1 | an-246 |
| 1A0247 | sp-1 | an-247 | 1U0247 | sp-1 | an-247 | 1C0247 | sp-1 | an-247 |
| 1A0248 | sp-1 | an-248 | 1U0248 | sp-1 | an-248 | 1C0248 | sp-1 | an-248 |
| 1A0249 | sp-1 | an-249 | 1U0249 | sp-1 | an-249 | 1C0249 | sp-1 | an-249 |
| 1A0250 | sp-1 | an-250 | 1U0250 | sp-1 | an-250 | 1C0250 | sp-1 | an-250 |
| 1A0251 | sp-1 | an-251 | 1U0251 | sp-1 | an-251 | 1C0251 | sp-1 | an-251 |
| 1A0252 | sp-1 | an-252 | 1U0252 | sp-1 | an-252 | 1C0252 | sp-1 | an-252 |
| 1A0253 | sp-1 | an-253 | 1U0253 | sp-1 | an-253 | 1C0253 | sp-1 | an-253 |
| 1A0254 | sp-1 | an-254 | 1U0254 | sp-1 | an-254 | 1C0254 | sp-1 | an-254 |

TABLE 1-continued

| | | | | | | | | |
|---|---|---|---|---|---|---|---|---|
| 1A0255 | sp-1 | an-255 | 1U0255 | sp-1 | an-255 | 1C0255 | sp-1 | an-255 |
| 1A0256 | sp-1 | an-258 | 1U0256 | sp-1 | an-256 | 1C0256 | sp-1 | an-256 |
| 1A0257 | sp-1 | an-257 | 1U0257 | sp-1 | an-257 | 1C0257 | sp-1 | an-257 |
| 1A0258 | sp-1 | an-258 | 1U0258 | sp-1 | an-258 | 1C0258 | sp-1 | an-258 |
| 1A0259 | sp-1 | an-259 | 1U0259 | sp-1 | an-259 | 1C0259 | sp-1 | an-259 |
| 1A0260 | sp-1 | an-260 | 1U0260 | sp-1 | an-260 | 1C0260 | sp-1 | an-260 |
| 1A0261 | sp-1 | an-261 | 1U0261 | sp-1 | an-261 | 1C0261 | sp-1 | an-261 |
| 1A0262 | sp-1 | an-262 | 1U0262 | sp-1 | an-262 | 1C0262 | sp-1 | an-262 |
| 1A0263 | sp-1 | an-263 | 1U0263 | sp-1 | an-263 | 1C0263 | sp-1 | an-263 |
| 1A0264 | sp-1 | an-264 | 1U0264 | sp-1 | an-264 | 1C0264 | sp-1 | an-264 |
| 1A0265 | sp-1 | an-265 | 1U0265 | sp-1 | an-265 | 1C0265 | sp-1 | an-265 |
| 1A0266 | sp-1 | an-266 | 1U0266 | sp-1 | an-266 | 1C0266 | sp-1 | an-266 |
| 1A0267 | sp-1 | an-267 | 1U0267 | sp-1 | an-267 | 1C0267 | sp-1 | an-267 |
| 1A0268 | sp-1 | an-268 | 1U0268 | sp-1 | an-268 | 1C0268 | sp-1 | an-268 |
| 1A0269 | sp-1 | an-269 | 1U0269 | sp-1 | an-269 | 1C0269 | sp-1 | an-269 |
| 1A0270 | sp-1 | an-270 | 1U0270 | sp-1 | an-270 | 1C0270 | sp-1 | an-270 |
| 1A0271 | sp-1 | an-271 | 1U0271 | sp-1 | an-271 | 1C0271 | sp-1 | an-271 |
| 1A0272 | sp-1 | an-272 | 1U0272 | sp-1 | an-272 | 1C0272 | sp-1 | an-272 |
| 1A0273 | sp-1 | an-273 | 1U0273 | sp-1 | an-273 | 1C0273 | sp-1 | an-273 |
| 1A0274 | sp-1 | an-274 | 1U0274 | sp-1 | an-274 | 1C0274 | sp-1 | an-274 |
| 1A0275 | sp-1 | an-275 | 1U0275 | sp-1 | an-275 | 1C0275 | sp-1 | an-275 |
| 1A0276 | sp-1 | an-276 | 1U0276 | sp-1 | an-276 | 1C0276 | sp-1 | an-276 |
| 1A0277 | sp-1 | an-277 | 1U0277 | sp-1 | an-277 | 1C0277 | sp-1 | an-277 |
| 1A0278 | sp-1 | an-278 | 1U0278 | sp-1 | an-278 | 1C0278 | sp-1 | an-278 |
| 1A0279 | sp-1 | an-279 | 1U0279 | sp-1 | an-279 | 1C0279 | sp-1 | an-279 |
| 1A0280 | sp-1 | an-280 | 1U0280 | sp-1 | an-280 | 1C0280 | sp-1 | an-280 |
| 1A0281 | sp-1 | an-281 | 1U0281 | sp-1 | an-281 | 1C0281 | sp-1 | an-281 |
| 1A0282 | sp-1 | an-282 | 1U0282 | sp-1 | an-282 | 1C0282 | sp-1 | an-282 |
| 1A0283 | sp-1 | an-283 | 1U0283 | sp-1 | an-283 | 1C0283 | sp-1 | an-283 |
| 1A0284 | sp-1 | an-284 | 1U0284 | sp-1 | an-284 | 1C0284 | sp-1 | an-284 |
| 1A0285 | sp-1 | an-285 | 1U0285 | sp-1 | an-285 | 1C0285 | sp-1 | an-285 |
| 1A0286 | sp-1 | an-286 | 1U0286 | sp-1 | an-286 | 1C0286 | sp-1 | an-286 |
| 1A0287 | sp-1 | an-287 | 1U0287 | sp-1 | an-287 | 1C0287 | sp-1 | an-287 |
| 1A0288 | sp-1 | an-288 | 1U0288 | sp-1 | an-288 | 1C0288 | sp-1 | an-288 |
| 1A0289 | sp-1 | an-289 | 1U0289 | sp-1 | an-289 | 1C0289 | sp-1 | an-289 |
| 1A0290 | sp-1 | an-290 | 1U0290 | sp-1 | an-290 | 1C0290 | sp-1 | an-290 |
| 1A0291 | sp-1 | an-291 | 1U0291 | sp-1 | an-291 | 1C0291 | sp-1 | an-291 |
| 1A0292 | sp-1 | an-292 | 1U0292 | sp-1 | an-292 | 1C0292 | sp-1 | an-292 |
| 1A0293 | sp-1 | an-293 | 1U0293 | sp-1 | an-293 | 1C0293 | sp-1 | an-293 |
| 1A0294 | sp-1 | an-294 | 1U0294 | sp-1 | an-294 | 1C0294 | sp-1 | an-294 |
| 1A0295 | sp-1 | an-295 | 1U0295 | sp-1 | an-295 | 1C0295 | sp-1 | an-295 |
| 1A0296 | sp-1 | an-296 | 1U0296 | sp-1 | an-296 | 1C0296 | sp-1 | an-296 |
| 1A0297 | sp-1 | an-297 | 1U0297 | sp-1 | an-297 | 1C0297 | sp-1 | an-297 |
| 1A0298 | sp-1 | an-298 | 1U0298 | sp-1 | an-298 | 1C0298 | sp-1 | an-298 |
| 1A0299 | sp-1 | an-299 | 1U0299 | sp-1 | an-299 | 1C0299 | sp-1 | an-299 |
| 1A0300 | sp-1 | an-300 | 1U0300 | sp-1 | an-300 | 1C0300 | sp-1 | an-300 |
| 1A0301 | sp-1 | an-301 | 1U0301 | sp-1 | an-301 | 1C0301 | sp-1 | an-301 |
| 1A0302 | sp-1 | an-302 | 1U0302 | sp-1 | an-302 | 1C0302 | sp-1 | an-302 |
| 1A0303 | sp-1 | an-303 | 1U0303 | sp-1 | an-303 | 1C0303 | sp-1 | an-303 |
| 1A0304 | sp-1 | an-304 | 1U0304 | sp-1 | an-304 | 1C0304 | sp-1 | an-304 |
| 1A0305 | sp-1 | an-305 | 1U0305 | sp-1 | an-305 | 1C0305 | sp-1 | an-305 |
| 1A0306 | sp-1 | an-306 | 1U0306 | sp-1 | an-306 | 1C0306 | sp-1 | an-306 |
| 1A0307 | sp-1 | an-307 | 1U0307 | sp-1 | an-307 | 1C0307 | sp-1 | an-307 |
| 1A0308 | sp-1 | an-308 | 1U0308 | sp-1 | an-308 | 1C0308 | sp-1 | an-308 |
| 1A0309 | sp-1 | an-309 | 1U0309 | sp-1 | an-309 | 1C0309 | sp-1 | an-309 |
| 1A0310 | sp-1 | an-310 | 1U0310 | sp-1 | an-310 | 1C0310 | sp-1 | an-310 |
| 1A0311 | sp-1 | an-311 | 1U0311 | sp-1 | an-311 | 1C0311 | sp-1 | an-311 |
| 1A0312 | sp-1 | an-312 | 1U0312 | sp-1 | an-312 | 1C0312 | sp-1 | an-312 |
| 1A0313 | sp-1 | an-313 | 1U0313 | sp-1 | an-313 | 1C0313 | sp-1 | an-313 |
| 1A0314 | sp-1 | an-314 | 1U0314 | sp-1 | an-314 | 1C0314 | sp-1 | an-314 |
| 1A0315 | sp-1 | an-315 | 1U0315 | sp-1 | an-315 | 1C0315 | sp-1 | an-315 |
| 1A0316 | sp-1 | an-316 | 1U0316 | sp-1 | an-316 | 1C0316 | sp-1 | an-316 |
| 1A0317 | sp-1 | an-317 | 1U0317 | sp-1 | an-317 | 1C0317 | sp-1 | an-317 |
| 1A0318 | sp-1 | an-318 | 1U0318 | sp-1 | an-318 | 1C0318 | sp-1 | an-318 |
| 1A0319 | sp-1 | an-319 | 1U0319 | sp-1 | an-319 | 1C0319 | sp-1 | an-319 |
| 1A0320 | sp-1 | an-320 | 1U0320 | sp-1 | an-320 | 1C0320 | sp-1 | an-320 |
| 1A0321 | sp-1 | an-321 | 1U0321 | sp-1 | an-321 | 1C0321 | sp-1 | an-321 |
| 1A0322 | sp-1 | an-322 | 1U0322 | sp-1 | an-322 | 1C0322 | sp-1 | an-322 |
| 1A0323 | sp-1 | an-323 | 1U0323 | sp-1 | an-323 | 1C0323 | sp-1 | an-323 |
| 1A0324 | sp-1 | an-324 | 1U0324 | sp-1 | an-324 | 1C0324 | sp-1 | an-324 |
| 1A0325 | sp-1 | an-325 | 1U0325 | sp-1 | an-325 | 1C0325 | sp-1 | an-325 |
| 1A0326 | sp-1 | an-326 | 1U0326 | sp-1 | an-326 | 1C0326 | sp-1 | an-326 |
| 1A0327 | sp-1 | an-327 | 1U0327 | sp-1 | an-327 | 1C0327 | sp-1 | an-327 |
| 1A0328 | sp-1 | an-328 | 1U0328 | sp-1 | an-328 | 1C0328 | sp-1 | an-328 |
| 1A0329 | sp-1 | an-329 | 1U0329 | sp-1 | an-329 | 1C0329 | sp-1 | an-329 |
| 1A0330 | sp-1 | an-330 | 1U0330 | sp-1 | an-330 | 1C0330 | sp-1 | an-330 |
| 1A0331 | sp-1 | an-331 | 1U0331 | sp-1 | an-331 | 1C0331 | sp-1 | an-331 |
| 1A0332 | sp-1 | an-332 | 1U0332 | sp-1 | an-332 | 1C0332 | sp-1 | an-332 |
| 1A0333 | sp-1 | an-333 | 1U0333 | sp-1 | an-333 | 1C0333 | sp-1 | an-333 |

TABLE 1-continued

| | | | | | | | | |
|---|---|---|---|---|---|---|---|---|
| 1A0334 | sp-1 | an-334 | 1U0334 | sp-1 | an-334 | 1C0334 | sp-1 | an-334 |
| 1A0335 | sp-1 | an-335 | 1U0335 | sp-1 | an-335 | 1C0335 | sp-1 | an-335 |
| 1A0336 | sp-1 | an-336 | 1U0336 | sp-1 | an-336 | 1C0336 | sp-1 | an-336 |
| 1A0337 | sp-1 | an-337 | 1U0337 | sp-1 | an-337 | 1C0337 | sp-1 | an-337 |
| 1A0338 | sp-1 | an-338 | 1U0338 | sp-1 | an-338 | 1C0338 | sp-1 | an-338 |
| 1A0339 | sp-1 | an-339 | 1U0339 | sp-1 | an-339 | 1C0339 | sp-1 | an-339 |
| 1A0340 | sp-1 | an-340 | 1U0340 | sp-1 | an-340 | 1C0340 | sp-1 | an-340 |
| 1A0341 | sp-1 | an-341 | 1U0341 | sp-1 | an-341 | 1C0341 | sp-1 | an-341 |
| 1A0342 | sp-1 | an-342 | 1U0342 | sp-1 | an-342 | 1C0342 | sp-1 | an-342 |
| 1A0343 | sp-1 | an-343 | 1U0343 | sp-1 | an-343 | 1C0343 | sp-1 | an-343 |
| 1A0344 | sp-1 | an-344 | 1U0344 | sp-1 | an-344 | 1C0344 | sp-1 | an-344 |
| 1A0345 | sp-1 | an-345 | 1U0345 | sp-1 | an-345 | 1C0345 | sp-1 | an-345 |
| 1A0346 | sp-1 | an-346 | 1U0346 | sp-1 | an-346 | 1C0346 | sp-1 | an-346 |
| 1A0347 | sp-1 | an-347 | 1U0347 | sp-1 | an-347 | 1C0347 | sp-1 | an-347 |
| 1A0348 | sp-1 | an-348 | 1U0348 | sp-1 | an-348 | 1C0348 | sp-1 | an-348 |
| 1A0349 | sp-1 | an-349 | 1U0349 | sp-1 | an-349 | 1C0349 | sp-1 | an-349 |
| 1A0350 | sp-1 | an-350 | 1U0350 | sp-1 | an-350 | 1C0350 | sp-1 | an-350 |
| 1A0351 | sp-1 | an-351 | 1U0351 | sp-1 | an-351 | 1C0351 | sp-1 | an-351 |
| 1A0352 | sp-1 | an-352 | 1U0352 | sp-1 | an-352 | 1C0352 | sp-1 | an-352 |
| 1A0353 | sp-1 | an-353 | 1U0353 | sp-1 | an-353 | 1C0353 | sp-1 | an-353 |
| 1A0354 | sp-1 | an-354 | 1U0354 | sp-1 | an-354 | 1C0354 | sp-1 | an-354 |
| 1A0355 | sp-1 | an-355 | 1U0355 | sp-1 | an-355 | 1C0355 | sp-1 | an-355 |
| 1A0356 | sp-1 | an-356 | 1U0356 | sp-1 | an-356 | 1C0356 | sp-1 | an-356 |
| 1A0357 | sp-1 | an-357 | 1U0357 | sp-1 | an-357 | 1C0357 | sp-1 | an-357 |
| 1A0358 | sp-1 | an-358 | 1U0358 | sp-1 | an-358 | 1C0358 | sp-1 | an-358 |
| 1A0359 | sp-1 | an-359 | 1U0359 | sp-1 | an-359 | 1C0359 | sp-1 | an-359 |
| 1A0360 | sp-1 | an-360 | 1U0360 | sp-1 | an-360 | 1C0360 | sp-1 | an-360 |
| 1A0361 | sp-1 | an-361 | 1U0361 | sp-1 | an-361 | 1C0361 | sp-1 | an-361 |
| 1A0362 | sp-1 | an-362 | 1U0362 | sp-1 | an-362 | 1C0362 | sp-1 | an-362 |
| 1A0363 | sp-1 | an-363 | 1U0363 | sp-1 | an-363 | 1C0363 | sp-1 | an-363 |
| 1A0364 | sp-1 | an-364 | 1U0364 | sp-1 | an-364 | 1C0364 | sp-1 | an-364 |
| 1A0365 | sp-1 | an-365 | 1U0365 | sp-1 | an-365 | 1C0365 | sp-1 | an-365 |
| 1A0366 | sp-1 | an-366 | 1U0366 | sp-1 | an-366 | 1C0366 | sp-1 | an-366 |
| 1A0367 | sp-1 | an-367 | 1U0367 | sp-1 | an-367 | 1C0367 | sp-1 | an-367 |
| 1A0368 | sp-1 | an-368 | 1U0368 | sp-1 | an-368 | 1C0368 | sp-1 | an-368 |
| 1A0369 | sp-1 | an-369 | 1U0369 | sp-1 | an-369 | 1C0369 | sp-1 | an-369 |
| 1A0370 | sp-1 | an-370 | 1U0370 | sp-1 | an-370 | 1C0370 | sp-1 | an-370 |
| 1A0371 | sp-1 | an-371 | 1U0371 | sp-1 | an-371 | 1C0371 | sp-1 | an-371 |
| 1A0372 | sp-1 | an-372 | 1U0372 | sp-1 | an-372 | 1C0372 | sp-1 | an-372 |
| 1A0373 | sp-1 | an-373 | 1U0373 | sp-1 | an-373 | 1C0373 | sp-1 | an-373 |
| 1A0374 | sp-1 | an-374 | 1U0374 | sp-1 | an-374 | 1C0374 | sp-1 | an-374 |
| 1A0375 | sp-1 | an-375 | 1U0375 | sp-1 | an-375 | 1C0375 | sp-1 | an-375 |
| 1A0376 | sp-1 | an-376 | 1U0376 | sp-1 | an-376 | 1C0376 | sp-1 | an-376 |
| 1A0377 | sp-1 | an-377 | 1U0377 | sp-1 | an-377 | 1C0377 | sp-1 | an-377 |
| 1A0378 | sp-2 | an-1 | 1U0378 | sp-2 | an-1 | 1C0378 | sp-2 | an-1 |
| 1A0379 | sp-2 | an-2 | 1U0379 | sp-2 | an-2 | 1C0379 | sp-2 | an-2 |
| 1A0380 | sp-2 | an-3 | 1U0380 | sp-2 | an-3 | 1C0380 | sp-2 | an-3 |
| 1A0381 | sp-2 | an-4 | 1U0381 | sp-2 | an-4 | 1C0381 | sp-2 | an-4 |
| 1A0382 | sp-2 | an-5 | 1U0382 | sp-2 | an-5 | 1C0382 | sp-2 | an-5 |
| 1A0383 | sp-2 | an-6 | 1U0383 | sp-2 | an-6 | 1C0383 | sp-2 | an-6 |
| 1A0384 | sp-2 | an-7 | 1U0384 | sp-2 | an-7 | 1C0384 | sp-2 | an-7 |
| 1A0385 | sp-2 | an-8 | 1U0385 | sp-2 | an-8 | 1C0385 | sp-2 | an-8 |
| 1A0386 | sp-2 | an-9 | 1U0386 | sp-2 | an-9 | 1C0386 | sp-2 | an-9 |
| 1A0387 | sp-2 | an-10 | 1U0387 | sp-2 | an-10 | 1C0387 | sp-2 | an-10 |
| 1A0388 | sp-2 | an-11 | 1U0388 | sp-2 | an-11 | 1C0388 | sp-2 | an-11 |
| 1A0389 | sp-2 | an-12 | 1U0389 | sp-2 | an-12 | 1C0389 | sp-2 | an-12 |
| 1A0390 | sp-2 | an-13 | 1U0390 | sp-2 | an-13 | 1C0390 | sp-2 | an-13 |
| 1A0391 | sp-2 | an-14 | 1U0391 | sp-2 | an-14 | 1C0391 | sp-2 | an-14 |
| 1A0392 | sp-2 | an-15 | 1U0392 | sp-2 | an-15 | 1C0392 | sp-2 | an-15 |
| 1A0393 | sp-2 | an-16 | 1U0393 | sp-2 | an-16 | 1C0393 | sp-2 | an-16 |
| 1A0394 | sp-2 | an-17 | 1U0394 | sp-2 | an-17 | 1C0394 | sp-2 | an-17 |
| 1A0395 | sp-2 | an-18 | 1U0395 | sp-2 | an-18 | 1C0395 | sp-2 | an-18 |
| 1A0396 | sp-2 | an-19 | 1U0396 | sp-2 | an-19 | 1C0396 | sp-2 | an-19 |
| 1A0397 | sp-2 | an-20 | 1U0397 | sp-2 | an-20 | 1C0397 | sp-2 | an-20 |
| 1A0398 | sp-2 | an-21 | 1U0398 | sp-2 | an-21 | 1C0398 | sp-2 | an-21 |
| 1A0399 | sp-2 | an-22 | 1U0399 | sp-2 | an-22 | 1C0399 | sp-2 | an-22 |
| 1A0400 | sp-2 | an-23 | 1U0400 | sp-2 | an-23 | 1C0400 | sp-2 | an-23 |
| 1A0401 | sp-2 | an-24 | 1U0401 | sp-2 | an-24 | 1C0401 | sp-2 | an-24 |
| 1A0402 | sp-2 | an-25 | 1U0402 | sp-2 | an-25 | 1C0402 | sp-2 | an-25 |
| 1A0403 | sp-2 | an-26 | 1U0403 | sp-2 | an-26 | 1C0403 | sp-2 | an-26 |
| 1A0404 | sp-2 | an-27 | 1U0404 | sp-2 | an-27 | 1C0404 | sp-2 | an-27 |
| 1A0405 | sp-2 | an-28 | 1U0405 | sp-2 | an-28 | 1C0405 | sp-2 | an-28 |
| 1A0406 | sp-2 | an-29 | 1U0406 | sp-2 | an-29 | 1C0406 | sp-2 | an-29 |
| 1A0407 | sp-2 | an-30 | 1U0407 | sp-2 | an-30 | 1C0407 | sp-2 | an-30 |
| 1A0408 | sp-2 | an-31 | 1U0408 | sp-2 | an-31 | 1C0408 | sp-2 | an-31 |
| 1A0409 | sp-2 | an-32 | 1U0409 | sp-2 | an-32 | 1C0409 | sp-2 | an-32 |
| 1A0410 | sp-2 | an-33 | 1U0410 | sp-2 | an-33 | 1C0410 | sp-2 | an-33 |
| 1A0411 | sp-2 | an-34 | 1U0411 | sp-2 | an-34 | 1C0411 | sp-2 | an-34 |
| 1A0412 | sp-2 | an-35 | 1U0412 | sp-2 | an-35 | 1C0412 | sp-2 | an-35 |

TABLE 1-continued

| | | | | | | | | |
|---|---|---|---|---|---|---|---|---|
| 1A0413 | sp-2 | an-36 | 1U0413 | sp-2 | an-36 | 1C0413 | sp-2 | an-36 |
| 1A0414 | sp-2 | an-37 | 1U0414 | sp-2 | an-37 | 1C0414 | sp-2 | an-37 |
| 1A0415 | sp-2 | an-38 | 1U0415 | sp-2 | an-38 | 1C0415 | sp-2 | an-38 |
| 1A0416 | sp-2 | an-39 | 1U0416 | sp-2 | an-39 | 1C0416 | sp-2 | an-39 |
| 1A0417 | sp-2 | an-40 | 1U0417 | sp-2 | an-40 | 1C0417 | sp-2 | an-40 |
| 1A0418 | sp-2 | an-41 | 1U0418 | sp-2 | an-41 | 1C0418 | sp-2 | an-41 |
| 1A0419 | sp-2 | an-42 | 1U0419 | sp-2 | an-42 | 1C0419 | sp-2 | an-42 |
| 1A0420 | sp-2 | an-43 | 1U0420 | sp-2 | an-43 | 1C0420 | sp-2 | an-43 |
| 1A0421 | sp-2 | an-44 | 1U0421 | sp-2 | an-44 | 1C0421 | sp-2 | an-44 |
| 1A0422 | sp-2 | an-45 | 1U0422 | sp-2 | an-45 | 1C0422 | sp-2 | an-45 |
| 1A0423 | sp-2 | an-46 | 1U0423 | sp-2 | an-46 | 1C0423 | sp-2 | an-46 |
| 1A0424 | sp-2 | an-47 | 1U0424 | sp-2 | an-47 | 1C0424 | sp-2 | an-47 |
| 1A0425 | sp-2 | an-48 | 1U0425 | sp-2 | an-48 | 1C0425 | sp-2 | an-48 |
| 1A0426 | sp-2 | an-49 | 1U0426 | sp-2 | an-49 | 1C0426 | sp-2 | an-49 |
| 1A0427 | sp-2 | an-50 | 1U0427 | sp-2 | an-50 | 1C0427 | sp-2 | an-50 |
| 1A0428 | sp-2 | an-51 | 1U0428 | sp-2 | an-51 | 1C0428 | sp-2 | an-51 |
| 1A0429 | sp-2 | an-52 | 1U0429 | sp-2 | an-52 | 1C0429 | sp-2 | an-52 |
| 1A0430 | sp-2 | an-53 | 1U0430 | sp-2 | an-53 | 1C0430 | sp-2 | an-53 |
| 1A0431 | sp-2 | an-54 | 1U0431 | sp-2 | an-54 | 1C0431 | sp-2 | an-54 |
| 1A0432 | sp-2 | an-55 | 1U0432 | sp-2 | an-55 | 1C0432 | sp-2 | an-55 |
| 1A0433 | sp-2 | an-56 | 1U0433 | sp-2 | an-56 | 1C0433 | sp-2 | an-56 |
| 1A0434 | sp-2 | an-57 | 1U0434 | sp-2 | an-57 | 1C0434 | sp-2 | an-57 |
| 1A0435 | sp-2 | an-58 | 1U0435 | sp-2 | an-58 | 1C0435 | sp-2 | an-58 |
| 1A0436 | sp-2 | an-59 | 1U0436 | sp-2 | an-59 | 1C0436 | sp-2 | an-59 |
| 1A0437 | sp-2 | an-60 | 1U0437 | sp-2 | an-60 | 1C0437 | sp-2 | an-60 |
| 1A0438 | sp-2 | an-61 | 1U0438 | sp-2 | an-61 | 1C0438 | sp-2 | an-61 |
| 1A0439 | sp-2 | an-62 | 1U0439 | sp-2 | an-62 | 1C0439 | sp-2 | an-62 |
| 1A0440 | sp-2 | an-63 | 1U0440 | sp-2 | an-63 | 1C0440 | sp-2 | an-63 |
| 1A0441 | sp-2 | an-64 | 1U0441 | sp-2 | an-64 | 1C0441 | sp-2 | an-64 |
| 1A0442 | sp-2 | an-65 | 1U0442 | sp-2 | an-65 | 1C0442 | sp-2 | an-65 |
| 1A0443 | sp-2 | an-66 | 1U0443 | sp-2 | an-66 | 1C0443 | sp-2 | an-66 |
| 1A0444 | sp-2 | an-67 | 1U0444 | sp-2 | an-67 | 1C0444 | sp-2 | an-67 |
| 1A0445 | sp-2 | an-68 | 1U0445 | sp-2 | an-68 | 1C0445 | sp-2 | an-68 |
| 1A0446 | sp-2 | an-69 | 1U0446 | sp-2 | an-69 | 1C0446 | sp-2 | an-69 |
| 1A0447 | sp-2 | an-70 | 1U0447 | sp-2 | an-70 | 1C0447 | sp-2 | an-70 |
| 1A0448 | sp-2 | an-71 | 1U0448 | sp-2 | an-71 | 1C0448 | sp-2 | an-71 |
| 1A0449 | sp-2 | an-72 | 1U0449 | sp-2 | an-72 | 1C0449 | sp-2 | an-72 |
| 1A0450 | sp-2 | an-73 | 1U0450 | sp-2 | an-73 | 1C0450 | sp-2 | an-73 |
| 1A0451 | sp-2 | an-74 | 1U0451 | sp-2 | an-74 | 1C0451 | sp-2 | an-74 |
| 1A0452 | sp-2 | an-75 | 1U0452 | sp-2 | an-75 | 1C0452 | sp-2 | an-75 |
| 1A0453 | sp-2 | an-76 | 1U0453 | sp-2 | an-76 | 1C0453 | sp-2 | an-76 |
| 1A0454 | sp-2 | an-77 | 1U0454 | sp-2 | an-77 | 1C0454 | sp-2 | an-77 |
| 1A0455 | sp-2 | an-78 | 1U0455 | sp-2 | an-78 | 1C0455 | sp-2 | an-78 |
| 1A0456 | sp-2 | an-79 | 1U0456 | sp-2 | an-79 | 1C0456 | sp-2 | an-79 |
| 1A0457 | sp-2 | an-80 | 1U0457 | sp-2 | an-80 | 1C0457 | sp-2 | an-80 |
| 1A0458 | sp-2 | an-81 | 1U0458 | sp-2 | an-81 | 1C0458 | sp-2 | an-81 |
| 1A0459 | sp-2 | an-82 | 1U0459 | sp-2 | an-82 | 1C0459 | sp-2 | an-82 |
| 1A0460 | sp-2 | an-83 | 1U0460 | sp-2 | an-83 | 1C0460 | sp-2 | an-83 |
| 1A0461 | sp-2 | an-84 | 1U0461 | sp-2 | an-84 | 1C0461 | sp-2 | an-84 |
| 1A0462 | sp-2 | an-85 | 1U0462 | sp-2 | an-85 | 1C0462 | sp-2 | an-85 |
| 1A0463 | sp-2 | an-86 | 1U0463 | sp-2 | an-86 | 1C0463 | sp-2 | an-86 |
| 1A0464 | sp-2 | an-87 | 1U0464 | sp-2 | an-87 | 1C0464 | sp-2 | an-87 |
| 1A0465 | sp-2 | an-88 | 1U0465 | sp-2 | an-88 | 1C0465 | sp-2 | an-88 |
| 1A0466 | sp-2 | an-89 | 1U0466 | sp-2 | an-89 | 1C0466 | sp-2 | an-89 |
| 1A0467 | sp-2 | an-90 | 1U0467 | sp-2 | an-90 | 1C0467 | sp-2 | an-90 |
| 1A0468 | sp-2 | an-91 | 1U0468 | sp-2 | an-91 | 1C0468 | sp-2 | an-91 |
| 1A0469 | sp-2 | an-92 | 1U0469 | sp-2 | an-92 | 1C0469 | sp-2 | an-92 |
| 1A0470 | sp-2 | an-93 | 1U0470 | sp-2 | an-93 | 1C0470 | sp-2 | an-93 |
| 1A0471 | sp-2 | an-94 | 1U0471 | sp-2 | an-94 | 1C0471 | sp-2 | an-94 |
| 1A0472 | sp-2 | an-95 | 1U0472 | sp-2 | an-95 | 1C0472 | sp-2 | an-95 |
| 1A0473 | sp-2 | an-96 | 1U0473 | sp-2 | an-96 | 1C0473 | sp-2 | an-96 |
| 1A0474 | sp-2 | an-97 | 1U0474 | sp-2 | an-97 | 1C0474 | sp-2 | an-97 |
| 1A0475 | sp-2 | an-98 | 1U0475 | sp-2 | an-98 | 1C0475 | sp-2 | an-98 |
| 1A0476 | sp-2 | an-99 | 1U0476 | sp-2 | an-99 | 1C0476 | sp-2 | an-99 |
| 1A0477 | sp-2 | an-100 | 1U0477 | sp-2 | an-100 | 1C0477 | sp-2 | an-100 |
| 1A0478 | sp-2 | an-101 | 1U0478 | sp-2 | an-101 | 1C0478 | sp-2 | an-101 |
| 1A0479 | sp-2 | an-102 | 1U0479 | sp-2 | an-102 | 1C0479 | sp-2 | an-102 |
| 1A0480 | sp-2 | an-103 | 1U0480 | sp-2 | an-103 | 1C0480 | sp-2 | an-103 |
| 1A0481 | sp-2 | an-104 | 1U0481 | sp-2 | an-104 | 1C0481 | sp-2 | an-104 |
| 1A0482 | sp-2 | an-105 | 1U0482 | sp-2 | an-105 | 1C0482 | sp-2 | an-105 |
| 1A0483 | sp-2 | an-106 | 1U0483 | sp-2 | an-106 | 1C0483 | sp-2 | an-106 |
| 1A0484 | sp-2 | an-107 | 1U0484 | sp-2 | an-107 | 1C0484 | sp-2 | an-107 |
| 1A0485 | sp-2 | an-108 | 1U0485 | sp-2 | an-108 | 1C0485 | sp-2 | an-108 |
| 1A0486 | sp-2 | an-109 | 1U0486 | sp-2 | an-109 | 1C0486 | sp-2 | an-109 |
| 1A0487 | sp-2 | an-110 | 1U0487 | sp-2 | an-110 | 1C0487 | sp-2 | an-110 |
| 1A0488 | sp-2 | an-111 | 1U0488 | sp-2 | an-111 | 1C0488 | sp-2 | an-111 |
| 1A0489 | sp-2 | an-112 | 1U0489 | sp-2 | an-112 | 1C0489 | sp-2 | an-112 |
| 1A0490 | sp-2 | an-113 | 1U0490 | sp-2 | an-113 | 1C0490 | sp-2 | an-113 |
| 1A0491 | sp-2 | an-114 | 1U0491 | sp-2 | an-114 | 1C0491 | sp-2 | an-114 |

TABLE 1-continued

| | | | | | | | | |
|---|---|---|---|---|---|---|---|---|
| 1A0492 | sp-2 | an-115 | 1U0492 | sp-2 | an-115 | 1C0492 | sp-2 | an-115 |
| 1A0493 | sp-2 | an-116 | 1U0493 | sp-2 | an-116 | 1C0493 | sp-2 | an-116 |
| 1A0494 | sp-2 | an-117 | 1U0494 | sp-2 | an-117 | 1C0494 | sp-2 | an-117 |
| 1A0495 | sp-2 | an-118 | 1U0495 | sp-2 | an-118 | 1C0495 | sp-2 | an-118 |
| 1A0496 | sp-2 | an-119 | 1U0496 | sp-2 | an-119 | 1C0496 | sp-2 | an-119 |
| 1A0497 | sp-2 | an-120 | 1U0497 | sp-2 | an-120 | 1C0497 | sp-2 | an-120 |
| 1A0498 | sp-2 | an-121 | 1U0498 | sp-2 | an-121 | 1C0498 | sp-2 | an-121 |
| 1A0499 | sp-2 | an-122 | 1U0499 | sp-2 | an-122 | 1C0499 | sp-2 | an-122 |
| 1A0500 | sp-2 | an-123 | 1U0500 | sp-2 | an-123 | 1C0500 | sp-2 | an-123 |
| 1A0501 | sp-2 | an-124 | 1U0501 | sp-2 | an-124 | 1C0501 | sp-2 | an-124 |
| 1A0502 | sp-2 | an-125 | 1U0502 | sp-2 | an-125 | 1C0502 | sp-2 | an-125 |
| 1A0503 | sp-2 | an-126 | 1U0503 | sp-2 | an-126 | 1C0503 | sp-2 | an-126 |
| 1A0504 | sp-2 | an-127 | 1U0504 | sp-2 | an-127 | 1C0504 | sp-2 | an-127 |
| 1A0505 | sp-2 | an-128 | 1U0505 | sp-2 | an-128 | 1C0505 | sp-2 | an-128 |
| 1A0506 | sp-2 | an-129 | 1U0506 | sp-2 | an-129 | 1C0506 | sp-2 | an-129 |
| 1A0507 | sp-2 | an-130 | 1U0507 | sp-2 | an-130 | 1C0507 | sp-2 | an-130 |
| 1A0508 | sp-2 | an-131 | 1U0508 | sp-2 | an-131 | 1C0508 | sp-2 | an-131 |
| 1A0509 | sp-2 | an-132 | 1U0509 | sp-2 | an-132 | 1C0509 | sp-2 | an-132 |
| 1A0510 | sp-2 | an-133 | 1U0510 | sp-2 | an-133 | 1C0510 | sp-2 | an-133 |
| 1A0511 | sp-2 | an-134 | 1U0511 | sp-2 | an-134 | 1C0511 | sp-2 | an-134 |
| 1A0512 | sp-2 | an-135 | 1U0512 | sp-2 | an-135 | 1C0512 | sp-2 | an-135 |
| 1A0513 | sp-2 | an-136 | 1U0513 | sp-2 | an-136 | 1C0513 | sp-2 | an-136 |
| 1A0514 | sp-2 | an-137 | 1U0514 | sp-2 | an-137 | 1C0514 | sp-2 | an-137 |
| 1A0515 | sp-2 | an-138 | 1U0515 | sp-2 | an-138 | 1C0515 | sp-2 | an-138 |
| 1A0516 | sp-2 | an-139 | 1U0516 | sp-2 | an-139 | 1C0516 | sp-2 | an-139 |
| 1A0517 | sp-2 | an-140 | 1U0517 | sp-2 | an-140 | 1C0517 | sp-2 | an-140 |
| 1A0518 | sp-2 | an-141 | 1U0518 | sp-2 | an-141 | 1C0518 | sp-2 | an-141 |
| 1A0519 | sp-2 | an-142 | 1U0519 | sp-2 | an-142 | 1C0519 | sp-2 | an-142 |
| 1A0520 | sp-2 | an-143 | 1U0520 | sp-2 | an-143 | 1C0520 | sp-2 | an-143 |
| 1A0521 | sp-2 | an-144 | 1U0521 | sp-2 | an-144 | 1C0521 | sp-2 | an-144 |
| 1A0522 | sp-2 | an-145 | 1U0522 | sp-2 | an-145 | 1C0522 | sp-2 | an-145 |
| 1A0523 | sp-2 | an-146 | 1U0523 | sp-2 | an-146 | 1C0523 | sp-2 | an-146 |
| 1A0524 | sp-2 | an-147 | 1U0524 | sp-2 | an-147 | 1C0524 | sp-2 | an-147 |
| 1A0525 | sp-2 | an-148 | 1U0525 | sp-2 | an-148 | 1C0525 | sp-2 | an-148 |
| 1A0526 | sp-2 | an-149 | 1U0526 | sp-2 | an-149 | 1C0526 | sp-2 | an-149 |
| 1A0527 | sp-2 | an-150 | 1U0527 | sp-2 | an-150 | 1C0527 | sp-2 | an-150 |
| 1A0528 | sp-2 | an-151 | 1U0528 | sp-2 | an-151 | 1C0528 | sp-2 | an-151 |
| 1A0529 | sp-2 | an-152 | 1U0529 | sp-2 | an-152 | 1C0529 | sp-2 | an-152 |
| 1A0530 | sp-2 | an-153 | 1U0530 | sp-2 | an-153 | 1C0530 | sp-2 | an-153 |
| 1A0531 | sp-2 | an-154 | 1U0531 | sp-2 | an-154 | 1C0531 | sp-2 | an-154 |
| 1A0532 | sp-2 | an-155 | 1U0532 | sp-2 | an-155 | 1C0532 | sp-2 | an-155 |
| 1A0533 | sp-2 | an-156 | 1U0533 | sp-2 | an-156 | 1C0533 | sp-2 | an-156 |
| 1A0534 | sp-2 | an-157 | 1U0534 | sp-2 | an-157 | 1C0534 | sp-2 | an-157 |
| 1A0535 | sp-2 | an-158 | 1U0535 | sp-2 | an-158 | 1C0535 | sp-2 | an-158 |
| 1A0536 | sp-2 | an-159 | 1U0536 | sp-2 | an-159 | 1C0536 | sp-2 | an-159 |
| 1A0537 | sp-2 | an-160 | 1U0537 | sp-2 | an-160 | 1C0537 | sp-2 | an-160 |
| 1A0538 | sp-2 | an-161 | 1U0538 | sp-2 | an-161 | 1C0538 | sp-2 | an-161 |
| 1A0539 | sp-2 | an-162 | 1U0539 | sp-2 | an-162 | 1C0539 | sp-2 | an-162 |
| 1A0540 | sp-2 | an-163 | 1U0540 | sp-2 | an-163 | 1C0540 | sp-2 | an-163 |
| 1A0541 | sp-2 | an-164 | 1U0541 | sp-2 | an-164 | 1C0541 | sp-2 | an-164 |
| 1A0542 | sp-2 | an-165 | 1U0542 | sp-2 | an-165 | 1C0542 | sp-2 | an-165 |
| 1A0543 | sp-2 | an-166 | 1U0543 | sp-2 | an-166 | 1C0543 | sp-2 | an-166 |
| 1A0544 | sp-2 | an-167 | 1U0544 | sp-2 | an-167 | 1C0544 | sp-2 | an-167 |
| 1A0545 | sp-2 | an-168 | 1U0545 | sp-2 | an-168 | 1C0545 | sp-2 | an-168 |
| 1A0546 | sp-2 | an-169 | 1U0546 | sp-2 | an-169 | 1C0546 | sp-2 | an-169 |
| 1A0547 | sp-2 | an-170 | 1U0547 | sp-2 | an-170 | 1C0547 | sp-2 | an-170 |
| 1A0548 | sp-2 | an-171 | 1U0548 | sp-2 | an-171 | 1C0548 | sp-2 | an-171 |
| 1A0549 | sp-2 | an-172 | 1U0549 | sp-2 | an-172 | 1C0549 | sp-2 | an-172 |
| 1A0550 | sp-2 | an-173 | 1U0550 | sp-2 | an-173 | 1C0550 | sp-2 | an-173 |
| 1A0551 | sp-2 | an-174 | 1U0551 | sp-2 | an-174 | 1C0551 | sp-2 | an-174 |
| 1A0552 | sp-2 | an-175 | 1U0552 | sp-2 | an-175 | 1C0552 | sp-2 | an-175 |
| 1A0553 | sp-2 | an-176 | 1U0553 | sp-2 | an-176 | 1C0553 | sp-2 | an-176 |
| 1A0554 | sp-2 | an-177 | 1U0554 | sp-2 | an-177 | 1C0554 | sp-2 | an-177 |
| 1A0555 | sp-2 | an-178 | 1U0555 | sp-2 | an-178 | 1C0555 | sp-2 | an-178 |
| 1A0556 | sp-2 | an-179 | 1U0556 | sp-2 | an-179 | 1C0556 | sp-2 | an-179 |
| 1A0557 | sp-2 | an-180 | 1U0557 | sp-2 | an-180 | 1C0557 | sp-2 | an-180 |
| 1A0558 | sp-2 | an-181 | 1U0558 | sp-2 | an-181 | 1C0558 | sp-2 | an-181 |
| 1A0559 | sp-2 | an-182 | 1U0559 | sp-2 | an-182 | 1C0559 | sp-2 | an-182 |
| 1A0560 | sp-2 | an-183 | 1U0560 | sp-2 | an-183 | 1C0560 | sp-2 | an-183 |
| 1A0561 | sp-2 | an-184 | 1U0561 | sp-2 | an-184 | 1C0561 | sp-2 | an-184 |
| 1A0562 | sp-2 | an-185 | 1U0562 | sp-2 | an-185 | 1C0562 | sp-2 | an-185 |
| 1A0563 | sp-2 | an-186 | 1U0563 | sp-2 | an-186 | 1C0563 | sp-2 | an-186 |
| 1A0564 | sp-2 | an-187 | 1U0564 | sp-2 | an-187 | 1C0564 | sp-2 | an-187 |
| 1A0565 | sp-2 | an-188 | 1U0565 | sp-2 | an-188 | 1C0565 | sp-2 | an-188 |
| 1A0566 | sp-2 | an-189 | 1U0566 | sp-2 | an-189 | 1C0566 | sp-2 | an-189 |
| 1A0567 | sp-2 | an-190 | 1U0567 | sp-2 | an-190 | 1C0567 | sp-2 | an-190 |
| 1A0568 | sp-2 | an-191 | 1U0568 | sp-2 | an-191 | 1C0568 | sp-2 | an-191 |
| 1A0569 | sp-2 | an-192 | 1U0569 | sp-2 | an-192 | 1C0569 | sp-2 | an-192 |
| 1A0570 | sp-2 | an-193 | 1U0570 | sp-2 | an-193 | 1C0570 | sp-2 | an-193 |

TABLE 1-continued

| | | | | | | | | |
|---|---|---|---|---|---|---|---|---|
| 1A0571 | sp-2 | an-194 | 1U0571 | sp-2 | an-194 | 1C0571 | sp-2 | an-194 |
| 1A0572 | sp-2 | an-195 | 1U0572 | sp-2 | an-195 | 1C0572 | sp-2 | an-195 |
| 1A0573 | sp-2 | an-196 | 1U0573 | sp-2 | an-196 | 1C0573 | sp-2 | an-196 |
| 1A0574 | sp-2 | an-197 | 1U0574 | sp-2 | an-197 | 1C0574 | sp-2 | an-197 |
| 1A0575 | sp-2 | an-198 | 1U0575 | sp-2 | an-198 | 1C0575 | sp-2 | an-198 |
| 1A0576 | sp-2 | an-199 | 1U0576 | sp-2 | an-199 | 1C0576 | sp-2 | an-199 |
| 1A0577 | sp-2 | an-200 | 1U0577 | sp-2 | an-200 | 1C0577 | sp-2 | an-200 |
| 1A0578 | sp-2 | an-201 | 1U0578 | sp-2 | an-201 | 1C0578 | sp-2 | an-201 |
| 1A0579 | sp-2 | an-202 | 1U0579 | sp-2 | an-202 | 1C0579 | sp-2 | an-202 |
| 1A0580 | sp-2 | an-203 | 1U0580 | sp-2 | an-203 | 1C0580 | sp-2 | an-203 |
| 1A0581 | sp-2 | an-204 | 1U0581 | sp-2 | an-204 | 1C0581 | sp-2 | an-204 |
| 1A0582 | sp-2 | an-205 | 1U0582 | sp-2 | an-205 | 1C0582 | sp-2 | an-205 |
| 1A0583 | sp-2 | an-206 | 1U0583 | sp-2 | an-206 | 1C0583 | sp-2 | an-206 |
| 1A0584 | sp-2 | an-207 | 1U0584 | sp-2 | an-207 | 1C0584 | sp-2 | an-207 |
| 1A0585 | sp-2 | an-208 | 1U0585 | sp-2 | an-208 | 1C0585 | sp-2 | an-208 |
| 1A0586 | sp-2 | an-209 | 1U0586 | sp-2 | an-209 | 1C0586 | sp-2 | an-209 |
| 1A0587 | sp-2 | an-210 | 1U0587 | sp-2 | an-210 | 1C0587 | sp-2 | an-210 |
| 1A0588 | sp-2 | an-211 | 1U0588 | sp-2 | an-211 | 1C0588 | sp-2 | an-211 |
| 1A0589 | sp-2 | an-212 | 1U0589 | sp-2 | an-212 | 1C0589 | sp-2 | an-212 |
| 1A0590 | sp-2 | an-213 | 1U0590 | sp-2 | an-213 | 1C0590 | sp-2 | an-213 |
| 1A0591 | sp-2 | an-214 | 1U0591 | sp-2 | an-214 | 1C0591 | sp-2 | an-214 |
| 1A0592 | sp-2 | an-215 | 1U0592 | sp-2 | an-215 | 1C0592 | sp-2 | an-215 |
| 1A0593 | sp-2 | an-216 | 1U0593 | sp-2 | an-216 | 1C0593 | sp-2 | an-216 |
| 1A0594 | sp-2 | an-217 | 1U0594 | sp-2 | an-217 | 1C0594 | sp-2 | an-217 |
| 1A0595 | sp-2 | an-218 | 1U0595 | sp-2 | an-218 | 1C0595 | sp-2 | an-218 |
| 1A0596 | sp-2 | an-219 | 1U0596 | sp-2 | an-219 | 1C0596 | sp-2 | an-219 |
| 1A0597 | sp-2 | an-220 | 1U0597 | sp-2 | an-220 | 1C0597 | sp-2 | an-220 |
| 1A0598 | sp-2 | an-221 | 1U0598 | sp-2 | an-221 | 1C0598 | sp-2 | an-221 |
| 1A0599 | sp-2 | an-222 | 1U0599 | sp-2 | an-222 | 1C0599 | sp-2 | an-222 |
| 1A0600 | sp-2 | an-223 | 1U0600 | sp-2 | an-223 | 1C0600 | sp-2 | an-223 |
| 1A0601 | sp-2 | an-224 | 1U0601 | sp-2 | an-224 | 1C0601 | sp-2 | an-224 |
| 1A0602 | sp-2 | an-225 | 1U0602 | sp-2 | an-225 | 1C0602 | sp-2 | an-225 |
| 1A0603 | sp-2 | an-226 | 1U0603 | sp-2 | an-226 | 1C0603 | sp-2 | an-226 |
| 1A0604 | sp-2 | an-227 | 1U0604 | sp-2 | an-227 | 1C0604 | sp-2 | an-227 |
| 1A0605 | sp-2 | an-228 | 1U0605 | sp-2 | an-228 | 1C0605 | sp-2 | an-228 |
| 1A0606 | sp-2 | an-229 | 1U0606 | sp-2 | an-229 | 1C0606 | sp-2 | an-229 |
| 1A0607 | sp-2 | an-230 | 1U0607 | sp-2 | an-230 | 1C0607 | sp-2 | an-230 |
| 1A0608 | sp-2 | an-231 | 1U0608 | sp-2 | an-231 | 1C0608 | sp-2 | an-231 |
| 1A0609 | sp-2 | an-232 | 1U0609 | sp-2 | an-232 | 1C0609 | sp-2 | an-232 |
| 1A0610 | sp-2 | an-233 | 1U0610 | sp-2 | an-233 | 1C0610 | sp-2 | an-233 |
| 1A0611 | sp-2 | an-234 | 1U0611 | sp-2 | an-234 | 1C0611 | sp-2 | an-234 |
| 1A0612 | sp-2 | an-235 | 1U0612 | sp-2 | an-235 | 1C0612 | sp-2 | an-235 |
| 1A0613 | sp-2 | an-236 | 1U0613 | sp-2 | an-236 | 1C0613 | sp-2 | an-236 |
| 1A0614 | sp-2 | an-237 | 1U0614 | sp-2 | an-237 | 1C0614 | sp-2 | an-237 |
| 1A0615 | sp-2 | an-238 | 1U0615 | sp-2 | an-238 | 1C0615 | sp-2 | an-238 |
| 1A0616 | sp-2 | an-239 | 1U0616 | sp-2 | an-239 | 1C0616 | sp-2 | an-239 |
| 1A0617 | sp-2 | an-240 | 1U0617 | sp-2 | an-240 | 1C0617 | sp-2 | an-240 |
| 1A0618 | sp-2 | an-241 | 1U0618 | sp-2 | an-241 | 1C0618 | sp-2 | an-241 |
| 1A0619 | sp-2 | an-242 | 1U0619 | sp-2 | an-242 | 1C0619 | sp-2 | an-242 |
| 1A0620 | sp-2 | an-243 | 1U0620 | sp-2 | an-243 | 1C0620 | sp-2 | an-243 |
| 1A0621 | sp-2 | an-244 | 1U0621 | sp-2 | an-244 | 1C0621 | sp-2 | an-244 |
| 1A0622 | sp-2 | an-245 | 1U0622 | sp-2 | an-245 | 1C0622 | sp-2 | an-245 |
| 1A0623 | sp-2 | an-246 | 1U0623 | sp-2 | an-246 | 1C0623 | sp-2 | an-246 |
| 1A0624 | sp-2 | an-247 | 1U0624 | sp-2 | an-247 | 1C0624 | sp-2 | an-247 |
| 1A0625 | sp-2 | an-248 | 1U0625 | sp-2 | an-248 | 1C0625 | sp-2 | an-248 |
| 1A0626 | sp-2 | an-249 | 1U0626 | sp-2 | an-249 | 1C0626 | sp-2 | an-249 |
| 1A0627 | sp-2 | an-250 | 1U0627 | sp-2 | an-250 | 1C0627 | sp-2 | an-250 |
| 1A0628 | sp-2 | an-251 | 1U0628 | sp-2 | an-251 | 1C0628 | sp-2 | an-251 |
| 1A0629 | sp-2 | an-252 | 1U0629 | sp-2 | an-252 | 1C0629 | sp-2 | an-252 |
| 1A0630 | sp-2 | an-253 | 1U0630 | sp-2 | an-253 | 1C0630 | sp-2 | an-253 |
| 1A0631 | sp-2 | an-254 | 1U0631 | sp-2 | an-254 | 1C0631 | sp-2 | an-254 |
| 1A0632 | sp-2 | an-255 | 1U0632 | sp-2 | an-255 | 1C0632 | sp-2 | an-255 |
| 1A0633 | sp-2 | an-256 | 1U0633 | sp-2 | an-256 | 1C0633 | sp-2 | an-256 |
| 1A0634 | sp-2 | an-257 | 1U0634 | sp-2 | an-257 | 1C0634 | sp-2 | an-257 |
| 1A0635 | sp-2 | an-258 | 1U0635 | sp-2 | an-258 | 1C0635 | sp-2 | an-258 |
| 1A0636 | sp-2 | an-259 | 1U0636 | sp-2 | an-259 | 1C0636 | sp-2 | an-259 |
| 1A0637 | sp-2 | an-260 | 1U0637 | sp-2 | an-260 | 1C0637 | sp-2 | an-260 |
| 1A0638 | sp-2 | an-261 | 1U0638 | sp-2 | an-261 | 1C0638 | sp-2 | an-261 |
| 1A0639 | sp-2 | an-262 | 1U0639 | sp-2 | an-262 | 1C0639 | sp-2 | an-262 |
| 1A0640 | sp-2 | an-263 | 1U0640 | sp-2 | an-263 | 1C0640 | sp-2 | an-263 |
| 1A0641 | sp-2 | an-264 | 1U0641 | sp-2 | an-264 | 1C0641 | sp-2 | an-264 |
| 1A0642 | sp-2 | an-265 | 1U0642 | sp-2 | an-265 | 1C0642 | sp-2 | an-265 |
| 1A0643 | sp-2 | an-266 | 1U0643 | sp-2 | an-266 | 1C0643 | sp-2 | an-266 |
| 1A0644 | sp-2 | an-267 | 1U0644 | sp-2 | an-267 | 1C0644 | sp-2 | an-267 |
| 1A0645 | sp-2 | an-268 | 1U0645 | sp-2 | an-268 | 1C0645 | sp-2 | an-268 |
| 1A0646 | sp-2 | an-269 | 1U0646 | sp-2 | an-269 | 1C0646 | sp-2 | an-269 |
| 1A0647 | sp-2 | an-270 | 1U0647 | sp-2 | an-270 | 1C0647 | sp-2 | an-270 |
| 1A0648 | sp-2 | an-271 | 1U0648 | sp-2 | an-271 | 1C0648 | sp-2 | an-271 |
| 1A0649 | sp-2 | an-272 | 1U0649 | sp-2 | an-272 | 1C0649 | sp-2 | an-272 |

TABLE 1-continued

| | | | | | | | | |
|---|---|---|---|---|---|---|---|---|
| 1A0650 | sp-2 | an-273 | 1U0650 | sp-2 | an-273 | 1C0650 | sp-2 | an-273 |
| 1A0651 | sp-2 | an-274 | 1U0651 | sp-2 | an-274 | 1C0651 | sp-2 | an-274 |
| 1A0652 | sp-2 | an-275 | 1U0652 | sp-2 | an-275 | 1C0652 | sp-2 | an-275 |
| 1A0653 | sp-2 | an-276 | 1U0653 | sp-2 | an-276 | 1C0653 | sp-2 | an-276 |
| 1A0654 | sp-2 | an-277 | 1U0654 | sp-2 | an-277 | 1C0654 | sp-2 | an-277 |
| 1A0655 | sp-2 | an-278 | 1U0655 | sp-2 | an-278 | 1C0655 | sp-2 | an-278 |
| 1A0656 | sp-2 | an-279 | 1U0656 | sp-2 | an-279 | 1C0656 | sp-2 | an-279 |
| 1A0657 | sp-2 | an-280 | 1U0657 | sp-2 | an-280 | 1C0657 | sp-2 | an-280 |
| 1A0658 | sp-2 | an-281 | 1U0658 | sp-2 | an-281 | 1C0658 | sp-2 | an-281 |
| 1A0659 | sp-2 | an-282 | 1U0659 | sp-2 | an-282 | 1C0659 | sp-2 | an-282 |
| 1A0660 | sp-2 | an-283 | 1U0660 | sp-2 | an-283 | 1C0660 | sp-2 | an-283 |
| 1A0661 | sp-2 | an-284 | 1U0661 | sp-2 | an-284 | 1C0661 | sp-2 | an-284 |
| 1A0662 | sp-2 | an-285 | 1U0662 | sp-2 | an-285 | 1C0662 | sp-2 | an-285 |
| 1A0663 | sp-2 | an-286 | 1U0663 | sp-2 | an-286 | 1C0663 | sp-2 | an-286 |
| 1A0664 | sp-2 | an-287 | 1U0664 | sp-2 | an-287 | 1C0664 | sp-2 | an-287 |
| 1A0665 | sp-2 | an-288 | 1U0665 | sp-2 | an-288 | 1C0665 | sp-2 | an-288 |
| 1A0666 | sp-2 | an-289 | 1U0666 | sp-2 | an-289 | 1C0666 | sp-2 | an-289 |
| 1A0667 | sp-2 | an-290 | 1U0667 | sp-2 | an-290 | 1C0667 | sp-2 | an-290 |
| 1A0668 | sp-2 | an-291 | 1U0668 | sp-2 | an-291 | 1C0668 | sp-2 | an-291 |
| 1A0669 | sp-2 | an-292 | 1U0669 | sp-2 | an-292 | 1C0669 | sp-2 | an-292 |
| 1A0670 | sp-2 | an-293 | 1U0670 | sp-2 | an-293 | 1C0670 | sp-2 | an-293 |
| 1A0671 | sp-2 | an-294 | 1U0671 | sp-2 | an-294 | 1C0671 | sp-2 | an-294 |
| 1A0672 | sp-2 | an-295 | 1U0672 | sp-2 | an-295 | 1C0672 | sp-2 | an-295 |
| 1A0673 | sp-2 | an-296 | 1U0673 | sp-2 | an-296 | 1C0673 | sp-2 | an-296 |
| 1A0674 | sp-2 | an-297 | 1U0674 | sp-2 | an-297 | 1C0674 | sp-2 | an-297 |
| 1A0675 | sp-2 | an-298 | 1U0675 | sp-2 | an-298 | 1C0675 | sp-2 | an-298 |
| 1A0676 | sp-2 | an-299 | 1U0676 | sp-2 | an-299 | 1C0676 | sp-2 | an-299 |
| 1A0677 | sp-2 | an-300 | 1U0677 | sp-2 | an-300 | 1C0677 | sp-2 | an-300 |
| 1A0678 | sp-2 | an-301 | 1U0678 | sp-2 | an-301 | 1C0678 | sp-2 | an-301 |
| 1A0679 | sp-2 | an-302 | 1U0679 | sp-2 | an-302 | 1C0679 | sp-2 | an-302 |
| 1A0680 | sp-2 | an-303 | 1U0680 | sp-2 | an-303 | 1C0680 | sp-2 | an-303 |
| 1A0681 | sp-2 | an-304 | 1U0681 | sp-2 | an-304 | 1C0681 | sp-2 | an-304 |
| 1A0682 | sp-2 | an-305 | 1U0682 | sp-2 | an-305 | 1C0682 | sp-2 | an-305 |
| 1A0683 | sp-2 | an-306 | 1U0683 | sp-2 | an-306 | 1C0683 | sp-2 | an-306 |
| 1A0684 | sp-2 | an-307 | 1U0684 | sp-2 | an-307 | 1C0684 | sp-2 | an-307 |
| 1A0685 | sp-2 | an-308 | 1U0685 | sp-2 | an-308 | 1C0685 | sp-2 | an-308 |
| 1A0686 | sp-2 | an-309 | 1U0686 | sp-2 | an-309 | 1C0686 | sp-2 | an-309 |
| 1A0687 | sp-2 | an-310 | 1U0687 | sp-2 | an-310 | 1C0687 | sp-2 | an-310 |
| 1A0688 | sp-2 | an-311 | 1U0688 | sp-2 | an-311 | 1C0688 | sp-2 | an-311 |
| 1A0689 | sp-2 | an-312 | 1U0689 | sp-2 | an-312 | 1C0689 | sp-2 | an-312 |
| 1A0690 | sp-2 | an-313 | 1U0690 | sp-2 | an-313 | 1C0690 | sp-2 | an-313 |
| 1A0691 | sp-2 | an-314 | 1U0691 | sp-2 | an-314 | 1C0691 | sp-2 | an-314 |
| 1A0692 | sp-2 | an-315 | 1U0692 | sp-2 | an-315 | 1C0692 | sp-2 | an-315 |
| 1A0693 | sp-2 | an-316 | 1U0693 | sp-2 | an-316 | 1C0693 | sp-2 | an-316 |
| 1A0694 | sp-2 | an-317 | 1U0694 | sp-2 | an-317 | 1C0694 | sp-2 | an-317 |
| 1A0695 | sp-2 | an-318 | 1U0695 | sp-2 | an-318 | 1C0695 | sp-2 | an-318 |
| 1A0696 | sp-2 | an-319 | 1U0696 | sp-2 | an-319 | 1C0696 | sp-2 | an-319 |
| 1A0697 | sp-2 | an-320 | 1U0697 | sp-2 | an-320 | 1C0697 | sp-2 | an-320 |
| 1A0698 | sp-2 | an-321 | 1U0698 | sp-2 | an-321 | 1C0698 | sp-2 | an-321 |
| 1A0699 | sp-2 | an-322 | 1U0699 | sp-2 | an-322 | 1C0699 | sp-2 | an-322 |
| 1A0700 | sp-2 | an-323 | 1U0700 | sp-2 | an-323 | 1C0700 | sp-2 | an-323 |
| 1A0701 | sp-2 | an-324 | 1U0701 | sp-2 | an-324 | 1C0701 | sp-2 | an-324 |
| 1A0702 | sp-2 | an-325 | 1U0702 | sp-2 | an-325 | 1C0702 | sp-2 | an-325 |
| 1A0703 | sp-2 | an-326 | 1U0703 | sp-2 | an-326 | 1C0703 | sp-2 | an-326 |
| 1A0704 | sp-2 | an-327 | 1U0704 | sp-2 | an-327 | 1C0704 | sp-2 | an-327 |
| 1A0705 | sp-2 | an-328 | 1U0705 | sp-2 | an-328 | 1C0705 | sp-2 | an-328 |
| 1A0706 | sp-2 | an-329 | 1U0706 | sp-2 | an-329 | 1C0706 | sp-2 | an-329 |
| 1A0707 | sp-2 | an-330 | 1U0707 | sp-2 | an-330 | 1C0707 | sp-2 | an-330 |
| 1A0708 | sp-2 | an-331 | 1U0708 | sp-2 | an-331 | 1C0708 | sp-2 | an-331 |
| 1A0709 | sp-2 | an-332 | 1U0709 | sp-2 | an-332 | 1C0709 | sp-2 | an-332 |
| 1A0710 | sp-2 | an-333 | 1U0710 | sp-2 | an-333 | 1C0710 | sp-2 | an-333 |
| 1A0711 | sp-2 | an-334 | 1U0711 | sp-2 | an-334 | 1C0711 | sp-2 | an-334 |
| 1A0712 | sp-2 | an-335 | 1U0712 | sp-2 | an-335 | 1C0712 | sp-2 | an-335 |
| 1A0713 | sp-2 | an-336 | 1U0713 | sp-2 | an-336 | 1C0713 | sp-2 | an-336 |
| 1A0714 | sp-2 | an-337 | 1U0714 | sp-2 | an-337 | 1C0714 | sp-2 | an-337 |
| 1A0715 | sp-2 | an-338 | 1U0715 | sp-2 | an-338 | 1C0715 | sp-2 | an-338 |
| 1A0716 | sp-2 | an-339 | 1U0716 | sp-2 | an-339 | 1C0716 | sp-2 | an-339 |
| 1A0717 | sp-2 | an-340 | 1U0717 | sp-2 | an-340 | 1C0717 | sp-2 | an-340 |
| 1A0718 | sp-2 | an-341 | 1U0718 | sp-2 | an-341 | 1C0718 | sp-2 | an-341 |
| 1A0719 | sp-2 | an-342 | 1U0719 | sp-2 | an-342 | 1C0719 | sp-2 | an-342 |
| 1A0720 | sp-2 | an-343 | 1U0720 | sp-2 | an-343 | 1C0720 | sp-2 | an-343 |
| 1A0721 | sp-2 | an-344 | 1U0721 | sp-2 | an-344 | 1C0721 | sp-2 | an-344 |
| 1A0722 | sp-2 | an-345 | 1U0722 | sp-2 | an-345 | 1C0722 | sp-2 | an-345 |
| 1A0723 | sp-2 | an-346 | 1U0723 | sp-2 | an-346 | 1C0723 | sp-2 | an-346 |
| 1A0724 | sp-2 | an-347 | 1U0724 | sp-2 | an-347 | 1C0724 | sp-2 | an-347 |
| 1A0725 | sp-2 | an-348 | 1U0725 | sp-2 | an-348 | 1C0725 | sp-2 | an-348 |
| 1A0726 | sp-2 | an-349 | 1U0726 | sp-2 | an-349 | 1C0726 | sp-2 | an-349 |
| 1A0727 | sp-2 | an-350 | 1U0727 | sp-2 | an-350 | 1C0727 | sp-2 | an-350 |
| 1A0728 | sp-2 | an-351 | 1U0728 | sp-2 | an-351 | 1C0728 | sp-2 | an-351 |

TABLE 1-continued

| | | | | | | | | |
|---|---|---|---|---|---|---|---|---|
| 1A0729 | sp-2 | an-352 | 1U0729 | sp-2 | an-352 | 1C0729 | sp-2 | an-352 |
| 1A0730 | sp-2 | an-353 | 1U0730 | sp-2 | an-353 | 1C0730 | sp-2 | an-353 |
| 1A0731 | sp-2 | an-354 | 1U0731 | sp-2 | an-354 | 1C0731 | sp-2 | an-354 |
| 1A0732 | sp-2 | an-355 | 1U0732 | sp-2 | an-355 | 1C0732 | sp-2 | an-355 |
| 1A0733 | sp-2 | an-356 | 1U0733 | sp-2 | an-356 | 1C0733 | sp-2 | an-356 |
| 1A0734 | sp-2 | an-357 | 1U0734 | sp-2 | an-357 | 1C0734 | sp-2 | an-357 |
| 1A0735 | sp-2 | an-358 | 1U0735 | sp-2 | an-358 | 1C0735 | sp-2 | an-358 |
| 1A0736 | sp-2 | an-359 | 1U0736 | sp-2 | an-359 | 1C0736 | sp-2 | an-359 |
| 1A0737 | sp-2 | an-360 | 1U0737 | sp-2 | an-360 | 1C0737 | sp-2 | an-360 |
| 1A0738 | sp-2 | an-361 | 1U0738 | sp-2 | an-361 | 1C0738 | sp-2 | an-361 |
| 1A0739 | sp-2 | an-362 | 1U0739 | sp-2 | an-362 | 1C0739 | sp-2 | an-362 |
| 1A0740 | sp-2 | an-363 | 1U0740 | sp-2 | an-363 | 1C0740 | sp-2 | an-363 |
| 1A0741 | sp-2 | an-364 | 1U0741 | sp-2 | an-364 | 1C0741 | sp-2 | an-364 |
| 1A0742 | sp-2 | an-365 | 1U0742 | sp-2 | an-365 | 1C0742 | sp-2 | an-365 |
| 1A0743 | sp-2 | an-366 | 1U0743 | sp-2 | an-366 | 1C0743 | sp-2 | an-366 |
| 1A0744 | sp-2 | an-367 | 1U0744 | sp-2 | an-367 | 1C0744 | sp-2 | an-367 |
| 1A0745 | sp-2 | an-368 | 1U0745 | sp-2 | an-368 | 1C0745 | sp-2 | an-368 |
| 1A0746 | sp-2 | an-369 | 1U0746 | sp-2 | an-369 | 1C0746 | sp-2 | an-369 |
| 1A0747 | sp-2 | an-370 | 1U0747 | sp-2 | an-370 | 1C0747 | sp-2 | an-370 |
| 1A0748 | sp-2 | an-371 | 1U0748 | sp-2 | an-371 | 1C0748 | sp-2 | an-371 |
| 1A0749 | sp-2 | an-372 | 1U0749 | sp-2 | an-372 | 1C0749 | sp-2 | an-372 |
| 1A0750 | sp-2 | an-373 | 1U0750 | sp-2 | an-373 | 1C0750 | sp-2 | an-373 |
| 1A0751 | sp-2 | an-374 | 1U0751 | sp-2 | an-374 | 1C0751 | sp-2 | an-374 |
| 1A0752 | sp-2 | an-375 | 1U0752 | sp-2 | an-375 | 1C0752 | sp-2 | an-375 |
| 1A0753 | sp-2 | an-376 | 1U0753 | sp-2 | an-376 | 1C0753 | sp-2 | an-376 |
| 1A0754 | sp-2 | an-377 | 1U0754 | sp-2 | an-377 | 1C0754 | sp-2 | an-377 |
| 1A0755 | sp-3 | an-1 | 1U0755 | sp-3 | an-1 | 1C0755 | sp-3 | an-1 |
| 1A0756 | sp-3 | an-2 | 1U0756 | sp-3 | an-2 | 1C0756 | sp-3 | an-2 |
| 1A0757 | sp-3 | an-3 | 1U0757 | sp-3 | an-3 | 1C0757 | sp-3 | an-3 |
| 1A0758 | sp-3 | an-4 | 1U0758 | sp-3 | an-4 | 1C0758 | sp-3 | an-4 |
| 1A0759 | sp-3 | an-5 | 1U0759 | sp-3 | an-5 | 1C0759 | sp-3 | an-5 |
| 1A0760 | sp-3 | an-6 | 1U0760 | sp-3 | an-6 | 1C0760 | sp-3 | an-6 |
| 1A0761 | sp-3 | an-7 | 1U0761 | sp-3 | an-7 | 1C0761 | sp-3 | an-7 |
| 1A0762 | sp-3 | an-8 | 1U0762 | sp-3 | an-8 | 1C0762 | sp-3 | an-8 |
| 1A0763 | sp-3 | an-9 | 1U0763 | sp-3 | an-9 | 1C0763 | sp-3 | an-9 |
| 1A0764 | sp-3 | an-10 | 1U0764 | sp-3 | an-10 | 1C0764 | sp-3 | an-10 |
| 1A0765 | sp-3 | an-11 | 1U0765 | sp-3 | an-11 | 1C0765 | sp-3 | an-11 |
| 1A0766 | sp-3 | an-12 | 1U0766 | sp-3 | an-12 | 1C0766 | sp-3 | an-12 |
| 1A0767 | sp-3 | an-13 | 1U0767 | sp-3 | an-13 | 1C0767 | sp-3 | an-13 |
| 1A0768 | sp-3 | an-14 | 1U0768 | sp-3 | an-14 | 1C0768 | sp-3 | an-14 |
| 1A0769 | sp-3 | an-15 | 1U0769 | sp-3 | an-15 | 1C0769 | sp-3 | an-15 |
| 1A0770 | sp-3 | an-16 | 1U0770 | sp-3 | an-16 | 1C0770 | sp-3 | an-16 |
| 1A0771 | sp-3 | an-17 | 1U0771 | sp-3 | an-17 | 1C0771 | sp-3 | an-17 |
| 1A0772 | sp-3 | an-18 | 1U0772 | sp-3 | an-18 | 1C0772 | sp-3 | an-18 |
| 1A0773 | sp-3 | an-19 | 1U0773 | sp-3 | an-19 | 1C0773 | sp-3 | an-19 |
| 1A0774 | sp-3 | an-20 | 1U0774 | sp-3 | an-20 | 1C0774 | sp-3 | an-20 |
| 1A0775 | sp-3 | an-21 | 1U0775 | sp-3 | an-21 | 1C0775 | sp-3 | an-21 |
| 1A0776 | sp-3 | an-22 | 1U0776 | sp-3 | an-22 | 1C0776 | sp-3 | an-22 |
| 1A0777 | sp-3 | an-23 | 1U0777 | sp-3 | an-23 | 1C0777 | sp-3 | an-23 |
| 1A0778 | sp-3 | an-24 | 1U0778 | sp-3 | an-24 | 1C0778 | sp-3 | an-24 |
| 1A0779 | sp-3 | an-25 | 1U0779 | sp-3 | an-25 | 1C0779 | sp-3 | an-25 |
| 1A0780 | sp-3 | an-26 | 1U0780 | sp-3 | an-26 | 1C0780 | sp-3 | an-26 |
| 1A0781 | sp-3 | an-27 | 1U0781 | sp-3 | an-27 | 1C0781 | sp-3 | an-27 |
| 1A0782 | sp-3 | an-28 | 1U0782 | sp-3 | an-28 | 1C0782 | sp-3 | an-28 |
| 1A0783 | sp-3 | an-29 | 1U0783 | sp-3 | an-29 | 1C0783 | sp-3 | an-29 |
| 1A0784 | sp-3 | an-30 | 1U0784 | sp-3 | an-30 | 1C0784 | sp-3 | an-30 |
| 1A0785 | sp-3 | an-31 | 1U0785 | sp-3 | an-31 | 1C0785 | sp-3 | an-31 |
| 1A0786 | sp-3 | an-32 | 1U0786 | sp-3 | an-32 | 1C0786 | sp-3 | an-32 |
| 1A0787 | sp-3 | an-33 | 1U0787 | sp-3 | an-33 | 1C0787 | sp-3 | an-33 |
| 1A0788 | sp-3 | an-34 | 1U0788 | sp-3 | an-34 | 1C0788 | sp-3 | an-34 |
| 1A0789 | sp-3 | an-35 | 1U0789 | sp-3 | an-35 | 1C0789 | sp-3 | an-35 |
| 1A0790 | sp-3 | an-36 | 1U0790 | sp-3 | an-36 | 1C0790 | sp-3 | an-36 |
| 1A0791 | sp-3 | an-37 | 1U0791 | sp-3 | an-37 | 1C0791 | sp-3 | an-37 |
| 1A0792 | sp-3 | an-38 | 1U0792 | sp-3 | an-38 | 1C0792 | sp-3 | an-38 |
| 1A0793 | sp-3 | an-39 | 1U0793 | sp-3 | an-39 | 1C0793 | sp-3 | an-39 |
| 1A0794 | sp-3 | an-40 | 1U0794 | sp-3 | an-40 | 1C0794 | sp-3 | an-40 |
| 1A0795 | sp-3 | an-41 | 1U0795 | sp-3 | an-41 | 1C0795 | sp-3 | an-41 |
| 1A0796 | sp-3 | an-42 | 1U0796 | sp-3 | an-42 | 1C0796 | sp-3 | an-42 |
| 1A0797 | sp-3 | an-43 | 1U0797 | sp-3 | an-43 | 1C0797 | sp-3 | an-43 |
| 1A0798 | sp-3 | an-44 | 1U0798 | sp-3 | an-44 | 1C0798 | sp-3 | an-44 |
| 1A0799 | sp-3 | an-45 | 1U0799 | sp-3 | an-45 | 1C0799 | sp-3 | an-45 |
| 1A0800 | sp-3 | an-46 | 1U0800 | sp-3 | an-46 | 1C0800 | sp-3 | an-46 |
| 1A0801 | sp-3 | an-47 | 1U0801 | sp-3 | an-47 | 1C0801 | sp-3 | an-47 |
| 1A0802 | sp-3 | an-48 | 1U0802 | sp-3 | an-48 | 1C0802 | sp-3 | an-48 |
| 1A0803 | sp-3 | an-49 | 1U0803 | sp-3 | an-49 | 1C0803 | sp-3 | an-49 |
| 1A0804 | sp-3 | an-50 | 1U0804 | sp-3 | an-50 | 1C0804 | sp-3 | an-50 |
| 1A0805 | sp-3 | an-51 | 1U0805 | sp-3 | an-51 | 1C0805 | sp-3 | an-51 |
| 1A0806 | sp-3 | an-52 | 1U0806 | sp-3 | an-52 | 1C0806 | sp-3 | an-52 |
| 1A0807 | sp-3 | an-53 | 1U0807 | sp-3 | an-53 | 1C0807 | sp-3 | an-53 |

TABLE 1-continued

| | | | | | | | | |
|---|---|---|---|---|---|---|---|---|
| 1A0808 | sp-3 | an-54 | 1U0808 | sp-3 | an-54 | 1C0808 | sp-3 | an-54 |
| 1A0809 | sp-3 | an-55 | 1U0809 | sp-3 | an-55 | 1C0809 | sp-3 | an-55 |
| 1A0810 | sp-3 | an-56 | 1U0810 | sp-3 | an-56 | 1C0810 | sp-3 | an-56 |
| 1A0811 | sp-3 | an-57 | 1U0811 | sp-3 | an-57 | 1C0811 | sp-3 | an-57 |
| 1A0812 | sp-3 | an-58 | 1U0812 | sp-3 | an-58 | 1C0812 | sp-3 | an-58 |
| 1A0813 | sp-3 | an-59 | 1U0813 | sp-3 | an-59 | 1C0813 | sp-3 | an-59 |
| 1A0814 | sp-3 | an-60 | 1U0814 | sp-3 | an-60 | 1C0814 | sp-3 | an-60 |
| 1A0815 | sp-3 | an-61 | 1U0815 | sp-3 | an-61 | 1C0815 | sp-3 | an-61 |
| 1A0816 | sp-3 | an-62 | 1U0816 | sp-3 | an-62 | 1C0816 | sp-3 | an-62 |
| 1A0817 | sp-3 | an-63 | 1U0817 | sp-3 | an-63 | 1C0817 | sp-3 | an-63 |
| 1A0818 | sp-3 | an-64 | 1U0818 | sp-3 | an-64 | 1C0818 | sp-3 | an-64 |
| 1A0819 | sp-3 | an-65 | 1U0819 | sp-3 | an-65 | 1C0819 | sp-3 | an-65 |
| 1A0820 | sp-3 | an-66 | 1U0820 | sp-3 | an-66 | 1C0820 | sp-3 | an-66 |
| 1A0821 | sp-3 | an-67 | 1U0821 | sp-3 | an-67 | 1C0821 | sp-3 | an-67 |
| 1A0822 | sp-3 | an-68 | 1U0822 | sp-3 | an-68 | 1C0822 | sp-3 | an-68 |
| 1A0823 | sp-3 | an-69 | 1U0823 | sp-3 | an-69 | 1C0823 | sp-3 | an-69 |
| 1A0824 | sp-3 | an-70 | 1U0824 | sp-3 | an-70 | 1C0824 | sp-3 | an-70 |
| 1A0825 | sp-3 | an-71 | 1U0825 | sp-3 | an-71 | 1C0825 | sp-3 | an-71 |
| 1A0826 | sp-3 | an-72 | 1U0826 | sp-3 | an-72 | 1C0826 | sp-3 | an-72 |
| 1A0827 | sp-3 | an-73 | 1U0827 | sp-3 | an-73 | 1C0827 | sp-3 | an-73 |
| 1A0828 | sp-3 | an-74 | 1U0828 | sp-3 | an-74 | 1C0828 | sp-3 | an-74 |
| 1A0829 | sp-3 | an-75 | 1U0829 | sp-3 | an-75 | 1C0829 | sp-3 | an-75 |
| 1A0830 | sp-3 | an-76 | 1U0830 | sp-3 | an-76 | 1C0830 | sp-3 | an-76 |
| 1A0831 | sp-3 | an-77 | 1U0831 | sp-3 | an-77 | 1C0831 | sp-3 | an-77 |
| 1A0832 | sp-3 | an-78 | 1U0832 | sp-3 | an-78 | 1C0832 | sp-3 | an-78 |
| 1A0833 | sp-3 | an-79 | 1U0833 | sp-3 | an-79 | 1C0833 | sp-3 | an-79 |
| 1A0834 | sp-3 | an-80 | 1U0834 | sp-3 | an-80 | 1C0834 | sp-3 | an-80 |
| 1A0835 | sp-3 | an-81 | 1U0835 | sp-3 | an-81 | 1C0835 | sp-3 | an-81 |
| 1A0836 | sp-3 | an-82 | 1U0836 | sp-3 | an-82 | 1C0836 | sp-3 | an-82 |
| 1A0837 | sp-3 | an-83 | 1U0837 | sp-3 | an-83 | 1C0837 | sp-3 | an-83 |
| 1A0838 | sp-3 | an-84 | 1U0838 | sp-3 | an-84 | 1C0838 | sp-3 | an-84 |
| 1A0839 | sp-3 | an-85 | 1U0839 | sp-3 | an-85 | 1C0839 | sp-3 | an-85 |
| 1A0840 | sp-3 | an-86 | 1U0840 | sp-3 | an-86 | 1C0840 | sp-3 | an-86 |
| 1A0841 | sp-3 | an-87 | 1U0841 | sp-3 | an-87 | 1C0841 | sp-3 | an-87 |
| 1A0842 | sp-3 | an-88 | 1U0842 | sp-3 | an-88 | 1C0842 | sp-3 | an-88 |
| 1A0843 | sp-3 | an-89 | 1U0843 | sp-3 | an-89 | 1C0843 | sp-3 | an-89 |
| 1A0844 | sp-3 | an-90 | 1U0844 | sp-3 | an-90 | 1C0844 | sp-3 | an-90 |
| 1A0845 | sp-3 | an-91 | 1U0845 | sp-3 | an-91 | 1C0845 | sp-3 | an-91 |
| 1A0846 | sp-3 | an-92 | 1U0846 | sp-3 | an-92 | 1C0846 | sp-3 | an-92 |
| 1A0847 | sp-3 | an-93 | 1U0847 | sp-3 | an-93 | 1C0847 | sp-3 | an-93 |
| 1A0848 | sp-3 | an-94 | 1U0848 | sp-3 | an-94 | 1C0848 | sp-3 | an-94 |
| 1A0849 | sp-3 | an-95 | 1U0849 | sp-3 | an-95 | 1C0849 | sp-3 | an-95 |
| 1A0850 | sp-3 | an-96 | 1U0850 | sp-3 | an-96 | 1C0850 | sp-3 | an-96 |
| 1A0851 | sp-3 | an-97 | 1U0851 | sp-3 | an-97 | 1C0851 | sp-3 | an-97 |
| 1A0852 | sp-3 | an-98 | 1U0852 | sp-3 | an-98 | 1C0852 | sp-3 | an-98 |
| 1A0853 | sp-3 | an-99 | 1U0853 | sp-3 | an-99 | 1C0853 | sp-3 | an-99 |
| 1A0854 | sp-3 | an-100 | 1U0854 | sp-3 | an-100 | 1C0854 | sp-3 | an-100 |
| 1A0855 | sp-3 | an-101 | 1U0855 | sp-3 | an-101 | 1C0855 | sp-3 | an-101 |
| 1A0856 | sp-3 | an-102 | 1U0856 | sp-3 | an-102 | 1C0856 | sp-3 | an-102 |
| 1A0857 | sp-3 | an-103 | 1U0857 | sp-3 | an-103 | 1C0857 | sp-3 | an-103 |
| 1A0858 | sp-3 | an-104 | 1U0858 | sp-3 | an-104 | 1C0858 | sp-3 | an-104 |
| 1A0859 | sp-3 | an-105 | 1U0859 | sp-3 | an-105 | 1C0859 | sp-3 | an-105 |
| 1A0860 | sp-3 | an-106 | 1U0860 | sp-3 | an-106 | 1C0860 | sp-3 | an-106 |
| 1A0861 | sp-3 | an-107 | 1U0861 | sp-3 | an-107 | 1C0861 | sp-3 | an-107 |
| 1A0862 | sp-3 | an-108 | 1U0862 | sp-3 | an-108 | 1C0862 | sp-3 | an-108 |
| 1A0863 | sp-3 | an-109 | 1U0863 | sp-3 | an-109 | 1C0863 | sp-3 | an-109 |
| 1A0864 | sp-3 | an-110 | 1U0864 | sp-3 | an-110 | 1C0864 | sp-3 | an-110 |
| 1A0865 | sp-3 | an-111 | 1U0865 | sp-3 | an-111 | 1C0865 | sp-3 | an-111 |
| 1A0866 | sp-3 | an-112 | 1U0866 | sp-3 | an-112 | 1C0866 | sp-3 | an-112 |
| 1A0867 | sp-3 | an-113 | 1U0867 | sp-3 | an-113 | 1C0867 | sp-3 | an-113 |
| 1A0868 | sp-3 | an-114 | 1U0868 | sp-3 | an-114 | 1C0868 | sp-3 | an-114 |
| 1A0869 | sp-3 | an-115 | 1U0869 | sp-3 | an-115 | 1C0869 | sp-3 | an-115 |
| 1A0870 | sp-3 | an-116 | 1U0870 | sp-3 | an-116 | 1C0870 | sp-3 | an-116 |
| 1A0871 | sp-3 | an-117 | 1U0871 | sp-3 | an-117 | 1C0871 | sp-3 | an-117 |
| 1A0872 | sp-3 | an-118 | 1U0872 | sp-3 | an-118 | 1C0872 | sp-3 | an-118 |
| 1A0873 | sp-3 | an-119 | 1U0873 | sp-3 | an-119 | 1C0873 | sp-3 | an-119 |
| 1A0874 | sp-3 | an-120 | 1U0874 | sp-3 | an-120 | 1C0874 | sp-3 | an-120 |
| 1A0875 | sp-3 | an-121 | 1U0875 | sp-3 | an-121 | 1C0875 | sp-3 | an-121 |
| 1A0876 | sp-3 | an-122 | 1U0876 | sp-3 | an-122 | 1C0876 | sp-3 | an-122 |
| 1A0877 | sp-3 | an-123 | 1U0877 | sp-3 | an-123 | 1C0877 | sp-3 | an-123 |
| 1A0878 | sp-3 | an-124 | 1U0878 | sp-3 | an-124 | 1C0878 | sp-3 | an-124 |
| 1A0879 | sp-3 | an-125 | 1U0879 | sp-3 | an-125 | 1C0879 | sp-3 | an-125 |
| 1A0880 | sp-3 | an-126 | 1U0880 | sp-3 | an-126 | 1C0880 | sp-3 | an-126 |
| 1A0881 | sp-3 | an-127 | 1U0881 | sp-3 | an-127 | 1C0881 | sp-3 | an-127 |
| 1A0882 | sp-3 | an-128 | 1U0882 | sp-3 | an-128 | 1C0882 | sp-3 | an-128 |
| 1A0883 | sp-3 | an-129 | 1U0883 | sp-3 | an-129 | 1C0883 | sp-3 | an-129 |
| 1A0884 | sp-3 | an-130 | 1U0884 | sp-3 | an-130 | 1C0884 | sp-3 | an-130 |
| 1A0885 | sp-3 | an-131 | 1U0885 | sp-3 | an-131 | 1C0885 | sp-3 | an-131 |
| 1A0886 | sp-3 | an-132 | 1U0886 | sp-3 | an-132 | 1C0886 | sp-3 | an-132 |

TABLE 1-continued

| | | | | | | | | |
|---|---|---|---|---|---|---|---|---|
| 1A0887 | sp-3 | an-133 | 1U0887 | sp-3 | an-133 | 1C0887 | sp-3 | an-133 |
| 1A0888 | sp-3 | an-134 | 1U0888 | sp-3 | an-134 | 1C0888 | sp-3 | an-134 |
| 1A0889 | sp-3 | an-135 | 1U0889 | sp-3 | an-135 | 1C0889 | sp-3 | an-135 |
| 1A0890 | sp-3 | an-136 | 1U0890 | sp-3 | an-136 | 1C0890 | sp-3 | an-136 |
| 1A0891 | sp-3 | an-137 | 1U0891 | sp-3 | an-137 | 1C0891 | sp-3 | an-137 |
| 1A0892 | sp-3 | an-138 | 1U0892 | sp-3 | an-138 | 1C0892 | sp-3 | an-138 |
| 1A0893 | sp-3 | an-139 | 1U0893 | sp-3 | an-139 | 1C0893 | sp-3 | an-139 |
| 1A0894 | sp-3 | an-140 | 1U0894 | sp-3 | an-140 | 1C0894 | sp-3 | an-140 |
| 1A0895 | sp-3 | an-141 | 1U0895 | sp-3 | an-141 | 1C0895 | sp-3 | an-141 |
| 1A0896 | sp-3 | an-142 | 1U0896 | sp-3 | an-142 | 1C0896 | sp-3 | an-142 |
| 1A0897 | sp-3 | an-143 | 1U0897 | sp-3 | an-143 | 1C0897 | sp-3 | an-143 |
| 1A0898 | sp-3 | an-144 | 1U0898 | sp-3 | an-144 | 1C0898 | sp-3 | an-144 |
| 1A0899 | sp-3 | an-145 | 1U0899 | sp-3 | an-145 | 1C0899 | sp-3 | an-145 |
| 1A0900 | sp-3 | an-146 | 1U0900 | sp-3 | an-146 | 1C0900 | sp-3 | an-146 |
| 1A0901 | sp-3 | an-147 | 1U0901 | sp-3 | an-147 | 1C0901 | sp-3 | an-147 |
| 1A0902 | sp-3 | an-148 | 1U0902 | sp-3 | an-148 | 1C0902 | sp-3 | an-148 |
| 1A0903 | sp-3 | an-149 | 1U0903 | sp-3 | an-149 | 1C0903 | sp-3 | an-149 |
| 1A0904 | sp-3 | an-150 | 1U0904 | sp-3 | an-150 | 1C0904 | sp-3 | an-150 |
| 1A0905 | sp-3 | an-151 | 1U0905 | sp-3 | an-151 | 1C0905 | sp-3 | an-151 |
| 1A0906 | sp-3 | an-152 | 1U0906 | sp-3 | an-152 | 1C0906 | sp-3 | an-152 |
| 1A0907 | sp-3 | an-153 | 1U0907 | sp-3 | an-153 | 1C0907 | sp-3 | an-153 |
| 1A0908 | sp-3 | an-154 | 1U0908 | sp-3 | an-154 | 1C0908 | sp-3 | an-154 |
| 1A0909 | sp-3 | an-155 | 1U0909 | sp-3 | an-155 | 1C0909 | sp-3 | an-155 |
| 1A0910 | sp-3 | an-156 | 1U0910 | sp-3 | an-156 | 1C0910 | sp-3 | an-156 |
| 1A0911 | sp-3 | an-157 | 1U0911 | sp-3 | an-157 | 1C0911 | sp-3 | an-157 |
| 1A0912 | sp-3 | an-158 | 1U0912 | sp-3 | an-158 | 1C0912 | sp-3 | an-158 |
| 1A0913 | sp-3 | an-159 | 1U0913 | sp-3 | an-159 | 1C0913 | sp-3 | an-159 |
| 1A0914 | sp-3 | an-160 | 1U0914 | sp-3 | an-160 | 1C0914 | sp-3 | an-160 |
| 1A0915 | sp-3 | an-161 | 1U0915 | sp-3 | an-161 | 1C0915 | sp-3 | an-161 |
| 1A0916 | sp-3 | an-162 | 1U0916 | sp-3 | an-162 | 1C0916 | sp-3 | an-162 |
| 1A0917 | sp-3 | an-163 | 1U0917 | sp-3 | an-163 | 1C0917 | sp-3 | an-163 |
| 1A0918 | sp-3 | an-164 | 1U0918 | sp-3 | an-164 | 1C0918 | sp-3 | an-164 |
| 1A0919 | sp-3 | an-165 | 1U0919 | sp-3 | an-165 | 1C0919 | sp-3 | an-165 |
| 1A0920 | sp-3 | an-166 | 1U0920 | sp-3 | an-166 | 1C0920 | sp-3 | an-166 |
| 1A0921 | sp-3 | an-167 | 1U0921 | sp-3 | an-167 | 1C0921 | sp-3 | an-167 |
| 1A0922 | sp-3 | an-168 | 1U0922 | sp-3 | an-168 | 1C0922 | sp-3 | an-168 |
| 1A0923 | sp-3 | an-169 | 1U0923 | sp-3 | an-169 | 1C0923 | sp-3 | an-169 |
| 1A0924 | sp-3 | an-170 | 1U0924 | sp-3 | an-170 | 1C0924 | sp-3 | an-170 |
| 1A0925 | sp-3 | an-171 | 1U0925 | sp-3 | an-171 | 1C0925 | sp-3 | an-171 |
| 1A0926 | sp-3 | an-172 | 1U0926 | sp-3 | an-172 | 1C0926 | sp-3 | an-172 |
| 1A0927 | sp-3 | an-173 | 1U0927 | sp-3 | an-173 | 1C0927 | sp-3 | an-173 |
| 1A0928 | sp-3 | an-174 | 1U0928 | sp-3 | an-174 | 1C0928 | sp-3 | an-174 |
| 1A0929 | sp-3 | an-175 | 1U0929 | sp-3 | an-175 | 1C0929 | sp-3 | an-175 |
| 1A0930 | sp-3 | an-176 | 1U0930 | sp-3 | an-176 | 1C0930 | sp-3 | an-176 |
| 1A0931 | sp-3 | an-177 | 1U0931 | sp-3 | an-177 | 1C0931 | sp-3 | an-177 |
| 1A0932 | sp-3 | an-178 | 1U0932 | sp-3 | an-178 | 1C0932 | sp-3 | an-178 |
| 1A0933 | sp-3 | an-179 | 1U0933 | sp-3 | an-179 | 1C0933 | sp-3 | an-179 |
| 1A0934 | sp-3 | an-180 | 1U0934 | sp-3 | an-180 | 1C0934 | sp-3 | an-180 |
| 1A0935 | sp-3 | an-181 | 1U0935 | sp-3 | an-181 | 1C0935 | sp-3 | an-181 |
| 1A0936 | sp-3 | an-182 | 1U0936 | sp-3 | an-182 | 1C0936 | sp-3 | an-182 |
| 1A0937 | sp-3 | an-183 | 1U0937 | sp-3 | an-183 | 1C0937 | sp-3 | an-183 |
| 1A0938 | sp-3 | an-184 | 1U0938 | sp-3 | an-184 | 1C0938 | sp-3 | an-184 |
| 1A0939 | sp-3 | an-185 | 1U0939 | sp-3 | an-185 | 1C0939 | sp-3 | an-185 |
| 1A0940 | sp-3 | an-186 | 1U0940 | sp-3 | an-186 | 1C0940 | sp-3 | an-186 |
| 1A0941 | sp-3 | an-187 | 1U0941 | sp-3 | an-187 | 1C0941 | sp-3 | an-187 |
| 1A0942 | sp-3 | an-188 | 1U0942 | sp-3 | an-188 | 1C0942 | sp-3 | an-188 |
| 1A0943 | sp-3 | an-189 | 1U0943 | sp-3 | an-189 | 1C0943 | sp-3 | an-189 |
| 1A0944 | sp-3 | an-190 | 1U0944 | sp-3 | an-190 | 1C0944 | sp-3 | an-190 |
| 1A0945 | sp-3 | an-191 | 1U0945 | sp-3 | an-191 | 1C0945 | sp-3 | an-191 |
| 1A0946 | sp-3 | an-192 | 1U0946 | sp-3 | an-192 | 1C0946 | sp-3 | an-192 |
| 1A0947 | sp-3 | an-193 | 1U0947 | sp-3 | an-193 | 1C0947 | sp-3 | an-193 |
| 1A0948 | sp-3 | an-194 | 1U0948 | sp-3 | an-194 | 1C0948 | sp-3 | an-194 |
| 1A0949 | sp-3 | an-195 | 1U0949 | sp-3 | an-195 | 1C0949 | sp-3 | an-195 |
| 1A0950 | sp-3 | an-196 | 1U0950 | sp-3 | an-196 | 1C0950 | sp-3 | an-196 |
| 1A0951 | sp-3 | an-197 | 1U0951 | sp-3 | an-197 | 1C0951 | sp-3 | an-197 |
| 1A0952 | sp-3 | an-198 | 1U0952 | sp-3 | an-198 | 1C0952 | sp-3 | an-198 |
| 1A0953 | sp-3 | an-199 | 1U0953 | sp-3 | an-199 | 1C0953 | sp-3 | an-199 |
| 1A0954 | sp-3 | an-200 | 1U0954 | sp-3 | an-200 | 1C0954 | sp-3 | an-200 |
| 1A0955 | sp-3 | an-201 | 1U0955 | sp-3 | an-201 | 1C0955 | sp-3 | an-201 |
| 1A0956 | sp-3 | an-202 | 1U0956 | sp-3 | an-202 | 1C0956 | sp-3 | an-202 |
| 1A0957 | sp-3 | an-203 | 1U0957 | sp-3 | an-203 | 1C0957 | sp-3 | an-203 |
| 1A0958 | sp-3 | an-204 | 1U0958 | sp-3 | an-204 | 1C0958 | sp-3 | an-204 |
| 1A0959 | sp-3 | an-205 | 1U0959 | sp-3 | an-205 | 1C0959 | sp-3 | an-205 |
| 1A0960 | sp-3 | an-206 | 1U0960 | sp-3 | an-206 | 1C0960 | sp-3 | an-206 |
| 1A0961 | sp-3 | an-207 | 1U0961 | sp-3 | an-207 | 1C0961 | sp-3 | an-207 |
| 1A0962 | sp-3 | an-208 | 1U0962 | sp-3 | an-208 | 1C0962 | sp-3 | an-208 |
| 1A0963 | sp-3 | an-209 | 1U0963 | sp-3 | an-209 | 1C0963 | sp-3 | an-209 |
| 1A0964 | sp-3 | an-210 | 1U0964 | sp-3 | an-210 | 1C0964 | sp-3 | an-210 |
| 1A0965 | sp-3 | an-211 | 1U0965 | sp-3 | an-211 | 1C0965 | sp-3 | an-211 |

TABLE 1-continued

| | | | | | | | | |
|---|---|---|---|---|---|---|---|---|
| 1A0966 | sp-3 | an-212 | 1U0966 | sp-3 | an-212 | 1C0966 | sp-3 | an-212 |
| 1A0967 | sp-3 | an-213 | 1U0967 | sp-3 | an-213 | 1C0967 | sp-3 | an-213 |
| 1A0968 | sp-3 | an-214 | 1U0968 | sp-3 | an-214 | 1C0968 | sp-3 | an-214 |
| 1A0969 | sp-3 | an-215 | 1U0969 | sp-3 | an-215 | 1C0969 | sp-3 | an-215 |
| 1A0970 | sp-3 | an-216 | 1U0970 | sp-3 | an-216 | 1C0970 | sp-3 | an-216 |
| 1A0971 | sp-3 | an-217 | 1U0971 | sp-3 | an-217 | 1C0971 | sp-3 | an-217 |
| 1A0972 | sp-3 | an-218 | 1U0972 | sp-3 | an-218 | 1C0972 | sp-3 | an-218 |
| 1A0973 | sp-3 | an-219 | 1U0973 | sp-3 | an-219 | 1C0973 | sp-3 | an-219 |
| 1A0974 | sp-3 | an-220 | 1U0974 | sp-3 | an-220 | 1C0974 | sp-3 | an-220 |
| 1A0975 | sp-3 | an-221 | 1U0975 | sp-3 | an-221 | 1C0975 | sp-3 | an-221 |
| 1A0976 | sp-3 | an-222 | 1U0976 | sp-3 | an-222 | 1C0976 | sp-3 | an-222 |
| 1A0977 | sp-3 | an-223 | 1U0977 | sp-3 | an-223 | 1C0977 | sp-3 | an-223 |
| 1A0978 | sp-3 | an-224 | 1U0978 | sp-3 | an-224 | 1C0978 | sp-3 | an-224 |
| 1A0979 | sp-3 | an-225 | 1U0979 | sp-3 | an-225 | 1C0979 | sp-3 | an-225 |
| 1A0980 | sp-3 | an-226 | 1U0980 | sp-3 | an-226 | 1C0980 | sp-3 | an-226 |
| 1A0981 | sp-3 | an-227 | 1U0981 | sp-3 | an-227 | 1C0981 | sp-3 | an-227 |
| 1A0982 | sp-3 | an-228 | 1U0982 | sp-3 | an-228 | 1C0982 | sp-3 | an-228 |
| 1A0983 | sp-3 | an-229 | 1U0983 | sp-3 | an-229 | 1C0983 | sp-3 | an-229 |
| 1A0984 | sp-3 | an-230 | 1U0984 | sp-3 | an-230 | 1C0984 | sp-3 | an-230 |
| 1A0985 | sp-3 | an-231 | 1U0985 | sp-3 | an-231 | 1C0985 | sp-3 | an-231 |
| 1A0986 | sp-3 | an-232 | 1U0986 | sp-3 | an-232 | 1C0986 | sp-3 | an-232 |
| 1A0987 | sp-3 | an-233 | 1U0987 | sp-3 | an-233 | 1C0987 | sp-3 | an-233 |
| 1A0988 | sp-3 | an-234 | 1U0988 | sp-3 | an-234 | 1C0988 | sp-3 | an-234 |
| 1A0989 | sp-3 | an-235 | 1U0989 | sp-3 | an-235 | 1C0989 | sp-3 | an-235 |
| 1A0990 | sp-3 | an-236 | 1U0990 | sp-3 | an-236 | 1C0990 | sp-3 | an-236 |
| 1A0991 | sp-3 | an-237 | 1U0991 | sp-3 | an-237 | 1C0991 | sp-3 | an-237 |
| 1A0992 | sp-3 | an-238 | 1U0992 | sp-3 | an-238 | 1C0992 | sp-3 | an-238 |
| 1A0993 | sp-3 | an-239 | 1U0993 | sp-3 | an-239 | 1C0993 | sp-3 | an-239 |
| 1A0994 | sp-3 | an-240 | 1U0994 | sp-3 | an-240 | 1C0994 | sp-3 | an-240 |
| 1A0995 | sp-3 | an-241 | 1U0995 | sp-3 | an-241 | 1C0995 | sp-3 | an-241 |
| 1A0996 | sp-3 | an-242 | 1U0996 | sp-3 | an-242 | 1C0996 | sp-3 | an-242 |
| 1A0997 | sp-3 | an-243 | 1U0997 | sp-3 | an-243 | 1C0997 | sp-3 | an-243 |
| 1A0998 | sp-3 | an-244 | 1U0998 | sp-3 | an-244 | 1C0998 | sp-3 | an-244 |
| 1A0999 | sp-3 | an-245 | 1U0999 | sp-3 | an-245 | 1C0999 | sp-3 | an-245 |
| 1A1000 | sp-3 | an-246 | 1U1000 | sp-3 | an-246 | 1C1000 | sp-3 | an-246 |
| 1A1001 | sp-3 | an-247 | 1U1001 | sp-3 | an-247 | 1C1001 | sp-3 | an-247 |
| 1A1002 | sp-3 | an-248 | 1U1002 | sp-3 | an-248 | 1C1002 | sp-3 | an-248 |
| 1A1003 | sp-3 | an-249 | 1U1003 | sp-3 | an-249 | 1C1003 | sp-3 | an-249 |
| 1A1004 | sp-3 | an-250 | 1U1004 | sp-3 | an-250 | 1C1004 | sp-3 | an-250 |
| 1A1005 | sp-3 | an-251 | 1U1005 | sp-3 | an-251 | 1C1005 | sp-3 | an-251 |
| 1A1006 | sp-3 | an-252 | 1U1006 | sp-3 | an-252 | 1C1006 | sp-3 | an-252 |
| 1A1007 | sp-3 | an-253 | 1U1007 | sp-3 | an-253 | 1C1007 | sp-3 | an-253 |
| 1A1008 | sp-3 | an-254 | 1U1008 | sp-3 | an-254 | 1C1008 | sp-3 | an-254 |
| 1A1009 | sp-3 | an-255 | 1U1009 | sp-3 | an-255 | 1C1009 | sp-3 | an-255 |
| 1A1010 | sp-3 | an-256 | 1U1010 | sp-3 | an-256 | 1C1010 | sp-3 | an-256 |
| 1A1011 | sp-3 | an-257 | 1U1011 | sp-3 | an-257 | 1C1011 | sp-3 | an-257 |
| 1A1012 | sp-3 | an-258 | 1U1012 | sp-3 | an-258 | 1C1012 | sp-3 | an-258 |
| 1A1013 | sp-3 | an-259 | 1U1013 | sp-3 | an-259 | 1C1013 | sp-3 | an-259 |
| 1A1014 | sp-3 | an-260 | 1U1014 | sp-3 | an-260 | 1C1014 | sp-3 | an-260 |
| 1A1015 | sp-3 | an-261 | 1U1015 | sp-3 | an-261 | 1C1015 | sp-3 | an-261 |
| 1A1016 | sp-3 | an-262 | 1U1016 | sp-3 | an-262 | 1C1016 | sp-3 | an-262 |
| 1A1017 | sp-3 | an-263 | 1U1017 | sp-3 | an-263 | 1C1017 | sp-3 | an-263 |
| 1A1018 | sp-3 | an-264 | 1U1018 | sp-3 | an-264 | 1C1018 | sp-3 | an-264 |
| 1A1019 | sp-3 | an-265 | 1U1019 | sp-3 | an-265 | 1C1019 | sp-3 | an-265 |
| 1A1020 | sp-3 | an-266 | 1U1020 | sp-3 | an-266 | 1C1020 | sp-3 | an-266 |
| 1A1021 | sp-3 | an-267 | 1U1021 | sp-3 | an-267 | 1C1021 | sp-3 | an-267 |
| 1A1022 | sp-3 | an-268 | 1U1022 | sp-3 | an-268 | 1C1022 | sp-3 | an-268 |
| 1A1023 | sp-3 | an-269 | 1U1023 | sp-3 | an-269 | 1C1023 | sp-3 | an-269 |
| 1A1024 | sp-3 | an-270 | 1U1024 | sp-3 | an-270 | 1C1024 | sp-3 | an-270 |
| 1A1025 | sp-3 | an-271 | 1U1025 | sp-3 | an-271 | 1C1025 | sp-3 | an-271 |
| 1A1026 | sp-3 | an-272 | 1U1026 | sp-3 | an-272 | 1C1026 | sp-3 | an-272 |
| 1A1027 | sp-3 | an-273 | 1U1027 | sp-3 | an-273 | 1C1027 | sp-3 | an-273 |
| 1A1028 | sp-3 | an-274 | 1U1028 | sp-3 | an-274 | 1C1028 | sp-3 | an-274 |
| 1A1029 | sp-3 | an-275 | 1U1029 | sp-3 | an-275 | 1C1029 | sp-3 | an-275 |
| 1A1030 | sp-3 | an-276 | 1U1030 | sp-3 | an-276 | 1C1030 | sp-3 | an-276 |
| 1A1031 | sp-3 | an-277 | 1U1031 | sp-3 | an-277 | 1C1031 | sp-3 | an-277 |
| 1A1032 | sp-3 | an-278 | 1U1032 | sp-3 | an-278 | 1C1032 | sp-3 | an-278 |
| 1A1033 | sp-3 | an-279 | 1U1033 | sp-3 | an-279 | 1C1033 | sp-3 | an-279 |
| 1A1034 | sp-3 | an-280 | 1U1034 | sp-3 | an-280 | 1C1034 | sp-3 | an-280 |
| 1A1035 | sp-3 | an-281 | 1U1035 | sp-3 | an-281 | 1C1035 | sp-3 | an-281 |
| 1A1036 | sp-3 | an-282 | 1U1036 | sp-3 | an-282 | 1C1036 | sp-3 | an-282 |
| 1A1037 | sp-3 | an-283 | 1U1037 | sp-3 | an-283 | 1C1037 | sp-3 | an-283 |
| 1A1038 | sp-3 | an-284 | 1U1038 | sp-3 | an-284 | 1C1038 | sp-3 | an-284 |
| 1A1039 | sp-3 | an-285 | 1U1039 | sp-3 | an-285 | 1C1039 | sp-3 | an-285 |
| 1A1040 | sp-3 | an-286 | 1U1040 | sp-3 | an-286 | 1C1040 | sp-3 | an-286 |
| 1A1041 | sp-3 | an-287 | 1U1041 | sp-3 | an-287 | 1C1041 | sp-3 | an-287 |
| 1A1042 | sp-3 | an-288 | 1U1042 | sp-3 | an-288 | 1C1042 | sp-3 | an-288 |
| 1A1043 | sp-3 | an-289 | 1U1043 | sp-3 | an-289 | 1C1043 | sp-3 | an-289 |
| 1A1044 | sp-3 | an-290 | 1U1044 | sp-3 | an-290 | 1C1044 | sp-3 | an-290 |

TABLE 1-continued

| | | | | | | | | |
|---|---|---|---|---|---|---|---|---|
| 1A1045 | sp-3 | an-291 | 1U1045 | sp-3 | an-291 | 1C1045 | sp-3 | an-291 |
| 1A1046 | sp-3 | an-292 | 1U1046 | sp-3 | an-292 | 1C1046 | sp-3 | an-292 |
| 1A1047 | sp-3 | an-293 | 1U1047 | sp-3 | an-293 | 1C1047 | sp-3 | an-293 |
| 1A1048 | sp-3 | an-294 | 1U1048 | sp-3 | an-294 | 1C1048 | sp-3 | an-294 |
| 1A1049 | sp-3 | an-295 | 1U1049 | sp-3 | an-295 | 1C1049 | sp-3 | an-295 |
| 1A1050 | sp-3 | an-296 | 1U1050 | sp-3 | an-296 | 1C1050 | sp-3 | an-296 |
| 1A1051 | sp-3 | an-297 | 1U1051 | sp-3 | an-297 | 1C1051 | sp-3 | an-297 |
| 1A1052 | sp-3 | an-298 | 1U1052 | sp-3 | an-298 | 1C1052 | sp-3 | an-298 |
| 1A1053 | sp-3 | an-299 | 1U1053 | sp-3 | an-299 | 1C1053 | sp-3 | an-299 |
| 1A1054 | sp-3 | an-300 | 1U1054 | sp-3 | an-300 | 1C1054 | sp-3 | an-300 |
| 1A1055 | sp-3 | an-301 | 1U1055 | sp-3 | an-301 | 1C1055 | sp-3 | an-301 |
| 1A1056 | sp-3 | an-302 | 1U1056 | sp-3 | an-302 | 1C1056 | sp-3 | an-302 |
| 1A1057 | sp-3 | an-303 | 1U1057 | sp-3 | an-303 | 1C1057 | sp-3 | an-303 |
| 1A1058 | sp-3 | an-304 | 1U1058 | sp-3 | an-304 | 1C1058 | sp-3 | an-304 |
| 1A1059 | sp-3 | an-305 | 1U1059 | sp-3 | an-305 | 1C1059 | sp-3 | an-305 |
| 1A1060 | sp-3 | an-306 | 1U1060 | sp-3 | an-306 | 1C1060 | sp-3 | an-306 |
| 1A1061 | sp-3 | an-307 | 1U1061 | sp-3 | an-307 | 1C1061 | sp-3 | an-307 |
| 1A1062 | sp-3 | an-308 | 1U1062 | sp-3 | an-308 | 1C1062 | sp-3 | an-308 |
| 1A1063 | sp-3 | an-309 | 1U1063 | sp-3 | an-309 | 1C1063 | sp-3 | an-309 |
| 1A1064 | sp-3 | an-310 | 1U1064 | sp-3 | an-310 | 1C1064 | sp-3 | an-310 |
| 1A1065 | sp-3 | an-311 | 1U1065 | sp-3 | an-311 | 1C1065 | sp-3 | an-311 |
| 1A1066 | sp-3 | an-312 | 1U1066 | sp-3 | an-312 | 1C1066 | sp-3 | an-312 |
| 1A1067 | sp-3 | an-313 | 1U1067 | sp-3 | an-313 | 1C1067 | sp-3 | an-313 |
| 1A1068 | sp-3 | an-314 | 1U1068 | sp-3 | an-314 | 1C1068 | sp-3 | an-314 |
| 1A1069 | sp-3 | an-315 | 1U1069 | sp-3 | an-315 | 1C1069 | sp-3 | an-315 |
| 1A1070 | sp-3 | an-316 | 1U1070 | sp-3 | an-316 | 1C1070 | sp-3 | an-316 |
| 1A1071 | sp-3 | an-317 | 1U1071 | sp-3 | an-317 | 1C1071 | sp-3 | an-317 |
| 1A1072 | sp-3 | an-318 | 1U1072 | sp-3 | an-318 | 1C1072 | sp-3 | an-318 |
| 1A1073 | sp-3 | an-319 | 1U1073 | sp-3 | an-319 | 1C1073 | sp-3 | an-319 |
| 1A1074 | sp-3 | an-320 | 1U1074 | sp-3 | an-320 | 1C1074 | sp-3 | an-320 |
| 1A1075 | sp-3 | an-321 | 1U1075 | sp-3 | an-321 | 1C1075 | sp-3 | an-321 |
| 1A1076 | sp-3 | an-322 | 1U1076 | sp-3 | an-322 | 1C1076 | sp-3 | an-322 |
| 1A1077 | sp-3 | an-323 | 1U1077 | sp-3 | an-323 | 1C1077 | sp-3 | an-323 |
| 1A1078 | sp-3 | an-324 | 1U1078 | sp-3 | an-324 | 1C1078 | sp-3 | an-324 |
| 1A1079 | sp-3 | an-325 | 1U1079 | sp-3 | an-325 | 1C1079 | sp-3 | an-325 |
| 1A1080 | sp-3 | an-326 | 1U1080 | sp-3 | an-326 | 1C1080 | sp-3 | an-326 |
| 1A1081 | sp-3 | an-327 | 1U1081 | sp-3 | an-327 | 1C1081 | sp-3 | an-327 |
| 1A1082 | sp-3 | an-328 | 1U1082 | sp-3 | an-328 | 1C1082 | sp-3 | an-328 |
| 1A1083 | sp-3 | an-329 | 1U1083 | sp-3 | an-329 | 1C1083 | sp-3 | an-329 |
| 1A1084 | sp-3 | an-330 | 1U1084 | sp-3 | an-330 | 1C1084 | sp-3 | an-330 |
| 1A1085 | sp-3 | an-331 | 1U1085 | sp-3 | an-331 | 1C1085 | sp-3 | an-331 |
| 1A1086 | sp-3 | an-332 | 1U1086 | sp-3 | an-332 | 1C1086 | sp-3 | an-332 |
| 1A1087 | sp-3 | an-333 | 1U1087 | sp-3 | an-333 | 1C1087 | sp-3 | an-333 |
| 1A1088 | sp-3 | an-334 | 1U1088 | sp-3 | an-334 | 1C1088 | sp-3 | an-334 |
| 1A1089 | sp-3 | an-335 | 1U1089 | sp-3 | an-335 | 1C1089 | sp-3 | an-335 |
| 1A1090 | sp-3 | an-336 | 1U1090 | sp-3 | an-336 | 1C1090 | sp-3 | an-336 |
| 1A1091 | sp-3 | an-337 | 1U1091 | sp-3 | an-337 | 1C1091 | sp-3 | an-337 |
| 1A1092 | sp-3 | an-338 | 1U1092 | sp-3 | an-338 | 1C1092 | sp-3 | an-338 |
| 1A1093 | sp-3 | an-339 | 1U1093 | sp-3 | an-339 | 1C1093 | sp-3 | an-339 |
| 1A1094 | sp-3 | an-340 | 1U1094 | sp-3 | an-340 | 1C1094 | sp-3 | an-340 |
| 1A1095 | sp-3 | an-341 | 1U1095 | sp-3 | an-341 | 1C1095 | sp-3 | an-341 |
| 1A1096 | sp-3 | an-342 | 1U1096 | sp-3 | an-342 | 1C1096 | sp-3 | an-342 |
| 1A1097 | sp-3 | an-343 | 1U1097 | sp-3 | an-343 | 1C1097 | sp-3 | an-343 |
| 1A1098 | sp-3 | an-344 | 1U1098 | sp-3 | an-344 | 1C1098 | sp-3 | an-344 |
| 1A1099 | sp-3 | an-345 | 1U1099 | sp-3 | an-345 | 1C1099 | sp-3 | an-345 |
| 1A1100 | sp-3 | an-346 | 1U1100 | sp-3 | an-346 | 1C1100 | sp-3 | an-346 |
| 1A1101 | sp-3 | an-347 | 1U1101 | sp-3 | an-347 | 1C1101 | sp-3 | an-347 |
| 1A1102 | sp-3 | an-348 | 1U1102 | sp-3 | an-348 | 1C1102 | sp-3 | an-348 |
| 1A1103 | sp-3 | an-349 | 1U1103 | sp-3 | an-349 | 1C1103 | sp-3 | an-349 |
| 1A1104 | sp-3 | an-350 | 1U1104 | sp-3 | an-350 | 1C1104 | sp-3 | an-350 |
| 1A1105 | sp-3 | an-351 | 1U1105 | sp-3 | an-351 | 1C1105 | sp-3 | an-351 |
| 1A1106 | sp-3 | an-352 | 1U1106 | sp-3 | an-352 | 1C1106 | sp-3 | an-352 |
| 1A1107 | sp-3 | an-353 | 1U1107 | sp-3 | an-353 | 1C1107 | sp-3 | an-353 |
| 1A1108 | sp-3 | an-354 | 1U1108 | sp-3 | an-354 | 1C1108 | sp-3 | an-354 |
| 1A1109 | sp-3 | an-355 | 1U1109 | sp-3 | an-355 | 1C1109 | sp-3 | an-355 |
| 1A1110 | sp-3 | an-356 | 1U1110 | sp-3 | an-356 | 1C1110 | sp-3 | an-356 |
| 1A1111 | sp-3 | an-357 | 1U1111 | sp-3 | an-357 | 1C1111 | sp-3 | an-357 |
| 1A1112 | sp-3 | an-358 | 1U1112 | sp-3 | an-358 | 1C1112 | sp-3 | an-358 |
| 1A1113 | sp-3 | an-359 | 1U1113 | sp-3 | an-359 | 1C1113 | sp-3 | an-359 |
| 1A1114 | sp-3 | an-360 | 1U1114 | sp-3 | an-360 | 1C1114 | sp-3 | an-360 |
| 1A1115 | sp-3 | an-361 | 1U1115 | sp-3 | an-361 | 1C1115 | sp-3 | an-361 |
| 1A1116 | sp-3 | an-362 | 1U1116 | sp-3 | an-362 | 1C1116 | sp-3 | an-362 |
| 1A1117 | sp-3 | an-363 | 1U1117 | sp-3 | an-363 | 1C1117 | sp-3 | an-363 |
| 1A1118 | sp-3 | an-364 | 1U1118 | sp-3 | an-364 | 1C1118 | sp-3 | an-364 |
| 1A1119 | sp-3 | an-365 | 1U1119 | sp-3 | an-365 | 1C1119 | sp-3 | an-365 |
| 1A1120 | sp-3 | an-366 | 1U1120 | sp-3 | an-366 | 1C1120 | sp-3 | an-366 |
| 1A1121 | sp-3 | an-367 | 1U1121 | sp-3 | an-367 | 1C1121 | sp-3 | an-367 |
| 1A1122 | sp-3 | an-368 | 1U1122 | sp-3 | an-368 | 1C1122 | sp-3 | an-368 |
| 1A1123 | sp-3 | an-369 | 1U1123 | sp-3 | an-369 | 1C1123 | sp-3 | an-369 |

TABLE 1-continued

| | | | | | | | | |
|---|---|---|---|---|---|---|---|---|
| 1A1124 | sp-3 | an-370 | 1U1124 | sp-3 | an-370 | 1C1124 | sp-3 | an-370 |
| 1A1125 | sp-3 | an-371 | 1U1125 | sp-3 | an-371 | 1C1125 | sp-3 | an-371 |
| 1A1126 | sp-3 | an-372 | 1U1126 | sp-3 | an-372 | 1C1126 | sp-3 | an-372 |
| 1A1127 | sp-3 | an-373 | 1U1127 | sp-3 | an-373 | 1C1127 | sp-3 | an-373 |
| 1A1128 | sp-3 | an-374 | 1U1128 | sp-3 | an-374 | 1C1128 | sp-3 | an-374 |
| 1A1129 | sp-3 | an-375 | 1U1129 | sp-3 | an-375 | 1C1129 | sp-3 | an-375 |
| 1A1130 | sp-3 | an-376 | 1U1130 | sp-3 | an-376 | 1C1130 | sp-3 | an-376 |
| 1A1131 | sp-3 | an-377 | 1U1131 | sp-3 | an-377 | 1C1131 | sp-3 | an-377 |
| 1A1132 | sp-4 | an-1 | 1U1132 | sp-4 | an-1 | 1C1132 | sp-4 | an-1 |
| 1A1133 | sp-4 | an-2 | 1U1133 | sp-4 | an-2 | 1C1133 | sp-4 | an-2 |
| 1A1134 | sp-4 | an-3 | 1U1134 | sp-4 | an-3 | 1C1134 | sp-4 | an-3 |
| 1A1135 | sp-4 | an-4 | 1U1135 | sp-4 | an-4 | 1C1135 | sp-4 | an-4 |
| 1A1136 | sp-4 | an-5 | 1U1136 | sp-4 | an-5 | 1C1136 | sp-4 | an-5 |
| 1A1137 | sp-4 | an-6 | 1U1137 | sp-4 | an-6 | 1C1137 | sp-4 | an-6 |
| 1A1138 | sp-4 | an-7 | 1U1138 | sp-4 | an-7 | 1C1138 | sp-4 | an-7 |
| 1A1139 | sp-4 | an-8 | 1U1139 | sp-4 | an-8 | 1C1139 | sp-4 | an-8 |
| 1A1140 | sp-4 | an-9 | 1U1140 | sp-4 | an-9 | 1C1140 | sp-4 | an-9 |
| 1A1141 | sp-4 | an-10 | 1U1141 | sp-4 | an-10 | 1C1141 | sp-4 | an-10 |
| 1A1142 | sp-4 | an-11 | 1U1142 | sp-4 | an-11 | 1C1142 | sp-4 | an-11 |
| 1A1143 | sp-4 | an-12 | 1U1143 | sp-4 | an-12 | 1C1143 | sp-4 | an-12 |
| 1A1144 | sp-4 | an-13 | 1U1144 | sp-4 | an-13 | 1C1144 | sp-4 | an-13 |
| 1A1145 | sp-4 | an-14 | 1U1145 | sp-4 | an-14 | 1C1145 | sp-4 | an-14 |
| 1A1146 | sp-4 | an-15 | 1U1146 | sp-4 | an-15 | 1C1146 | sp-4 | an-15 |
| 1A1147 | sp-4 | an-16 | 1U1147 | sp-4 | an-16 | 1C1147 | sp-4 | an-16 |
| 1A1148 | sp-4 | an-17 | 1U1148 | sp-4 | an-17 | 1C1148 | sp-4 | an-17 |
| 1A1149 | sp-4 | an-18 | 1U1149 | sp-4 | an-18 | 1C1149 | sp-4 | an-18 |
| 1A1150 | sp-4 | an-19 | 1U1150 | sp-4 | an-19 | 1C1150 | sp-4 | an-19 |
| 1A1151 | sp-4 | an-20 | 1U1151 | sp-4 | an-20 | 1C1151 | sp-4 | an-20 |
| 1A1152 | sp-4 | an-21 | 1U1152 | sp-4 | an-21 | 1C1152 | sp-4 | an-21 |
| 1A1153 | sp-4 | an-22 | 1U1153 | sp-4 | an-22 | 1C1153 | sp-4 | an-22 |
| 1A1154 | sp-4 | an-23 | 1U1154 | sp-4 | an-23 | 1C1154 | sp-4 | an-23 |
| 1A1155 | sp-4 | an-24 | 1U1155 | sp-4 | an-24 | 1C1155 | sp-4 | an-24 |
| 1A1156 | sp-4 | an-25 | 1U1156 | sp-4 | an-25 | 1C1156 | sp-4 | an-25 |
| 1A1157 | sp-4 | an-26 | 1U1157 | sp-4 | an-26 | 1C1157 | sp-4 | an-26 |
| 1A1158 | sp-4 | an-27 | 1U1158 | sp-4 | an-27 | 1C1158 | sp-4 | an-27 |
| 1A1159 | sp-4 | an-28 | 1U1159 | sp-4 | an-28 | 1C1159 | sp-4 | an-28 |
| 1A1160 | sp-4 | an-29 | 1U1160 | sp-4 | an-29 | 1C1160 | sp-4 | an-29 |
| 1A1161 | sp-4 | an-30 | 1U1161 | sp-4 | an-30 | 1C1161 | sp-4 | an-30 |
| 1A1162 | sp-4 | an-31 | 1U1162 | sp-4 | an-31 | 1C1162 | sp-4 | an-31 |
| 1A1163 | sp-4 | an-32 | 1U1163 | sp-4 | an-32 | 1C1163 | sp-4 | an-32 |
| 1A1164 | sp-4 | an-33 | 1U1164 | sp-4 | an-33 | 1C1164 | sp-4 | an-33 |
| 1A1165 | sp-4 | an-34 | 1U1165 | sp-4 | an-34 | 1C1165 | sp-4 | an-34 |
| 1A1166 | sp-4 | an-35 | 1U1166 | sp-4 | an-35 | 1C1166 | sp-4 | an-35 |
| 1A1167 | sp-4 | an-36 | 1U1167 | sp-4 | an-36 | 1C1167 | sp-4 | an-36 |
| 1A1168 | sp-4 | an-37 | 1U1168 | sp-4 | an-37 | 1C1168 | sp-4 | an-37 |
| 1A1169 | sp-4 | an-38 | 1U1169 | sp-4 | an-38 | 1C1169 | sp-4 | an-38 |
| 1A1170 | sp-4 | an-39 | 1U1170 | sp-4 | an-39 | 1C1170 | sp-4 | an-39 |
| 1A1171 | sp-4 | an-40 | 1U1171 | sp-4 | an-40 | 1C1171 | sp-4 | an-40 |
| 1A1172 | sp-4 | an-41 | 1U1172 | sp-4 | an-41 | 1C1172 | sp-4 | an-41 |
| 1A1173 | sp-4 | an-42 | 1U1173 | sp-4 | an-42 | 1C1173 | sp-4 | an-42 |
| 1A1174 | sp-4 | an-43 | 1U1174 | sp-4 | an-43 | 1C1174 | sp-4 | an-43 |
| 1A1175 | sp-4 | an-44 | 1U1175 | sp-4 | an-44 | 1C1175 | sp-4 | an-44 |
| 1A1176 | sp-4 | an-45 | 1U1176 | sp-4 | an-45 | 1C1176 | sp-4 | an-45 |
| 1A1177 | sp-4 | an-46 | 1U1177 | sp-4 | an-46 | 1C1177 | sp-4 | an-46 |
| 1A1178 | sp-4 | an-47 | 1U1178 | sp-4 | an-47 | 1C1178 | sp-4 | an-47 |
| 1A1179 | sp-4 | an-48 | 1U1179 | sp-4 | an-48 | 1C1179 | sp-4 | an-48 |
| 1A1180 | sp-4 | an-49 | 1U1180 | sp-4 | an-49 | 1C1180 | sp-4 | an-49 |
| 1A1181 | sp-4 | an-50 | 1U1181 | sp-4 | an-50 | 1C1181 | sp-4 | an-50 |
| 1A1182 | sp-4 | an-51 | 1U1182 | sp-4 | an-51 | 1C1182 | sp-4 | an-51 |
| 1A1183 | sp-4 | an-52 | 1U1183 | sp-4 | an-52 | 1C1183 | sp-4 | an-52 |
| 1A1184 | sp-4 | an-53 | 1U1184 | sp-4 | an-53 | 1C1184 | sp-4 | an-53 |
| 1A1185 | sp-4 | an-54 | 1U1185 | sp-4 | an-54 | 1C1185 | sp-4 | an-54 |
| 1A1186 | sp-4 | an-55 | 1U1186 | sp-4 | an-55 | 1C1186 | sp-4 | an-55 |
| 1A1187 | sp-4 | an-56 | 1U1187 | sp-4 | an-56 | 1C1187 | sp-4 | an-56 |
| 1A1188 | sp-4 | an-57 | 1U1188 | sp-4 | an-57 | 1C1188 | sp-4 | an-57 |
| 1A1189 | sp-4 | an-58 | 1U1189 | sp-4 | an-58 | 1C1189 | sp-4 | an-58 |
| 1A1190 | sp-4 | an-59 | 1U1190 | sp-4 | an-59 | 1C1190 | sp-4 | an-59 |
| 1A1191 | sp-4 | an-60 | 1U1191 | sp-4 | an-60 | 1C1191 | sp-4 | an-60 |
| 1A1192 | sp-4 | an-61 | 1U1192 | sp-4 | an-61 | 1C1192 | sp-4 | an-61 |
| 1A1193 | sp-4 | an-62 | 1U1193 | sp-4 | an-62 | 1C1193 | sp-4 | an-62 |
| 1A1194 | sp-4 | an-63 | 1U1194 | sp-4 | an-63 | 1C1194 | sp-4 | an-63 |
| 1A1195 | sp-4 | an-64 | 1U1195 | sp-4 | an-64 | 1C1195 | sp-4 | an-64 |
| 1A1196 | sp-4 | an-65 | 1U1196 | sp-4 | an-65 | 1C1196 | sp-4 | an-65 |
| 1A1197 | sp-4 | an-66 | 1U1197 | sp-4 | an-66 | 1C1197 | sp-4 | an-66 |
| 1A1198 | sp-4 | an-67 | 1U1198 | sp-4 | an-67 | 1C1198 | sp-4 | an-67 |
| 1A1199 | sp-4 | an-68 | 1U1199 | sp-4 | an-68 | 1C1199 | sp-4 | an-68 |
| 1A1200 | sp-4 | an-69 | 1U1200 | sp-4 | an-69 | 1C1200 | sp-4 | an-69 |
| 1A1201 | sp-4 | an-70 | 1U1201 | sp-4 | an-70 | 1C1201 | sp-4 | an-70 |
| 1A1202 | sp-4 | an-71 | 1U1202 | sp-4 | an-71 | 1C1202 | sp-4 | an-71 |

TABLE 1-continued

| | | | | | | | | |
|---|---|---|---|---|---|---|---|---|
| 1A1203 | sp-4 | an-72 | 1U1203 | sp-4 | an-72 | 1C1203 | sp-4 | an-72 |
| 1A1204 | sp-4 | an-73 | 1U1204 | sp-4 | an-73 | 1C1204 | sp-4 | an-73 |
| 1A1205 | sp-4 | an-74 | 1U1205 | sp-4 | an-74 | 1C1205 | sp-4 | an-74 |
| 1A1206 | sp-4 | an-75 | 1U1206 | sp-4 | an-75 | 1C1206 | sp-4 | an-75 |
| 1A1207 | sp-4 | an-76 | 1U1207 | sp-4 | an-76 | 1C1207 | sp-4 | an-76 |
| 1A1208 | sp-4 | an-77 | 1U1208 | sp-4 | an-77 | 1C1208 | sp-4 | an-77 |
| 1A1209 | sp-4 | an-78 | 1U1209 | sp-4 | an-78 | 1C1209 | sp-4 | an-78 |
| 1A1210 | sp-4 | an-79 | 1U1210 | sp-4 | an-79 | 1C1210 | sp-4 | an-79 |
| 1A1211 | sp-4 | an-80 | 1U1211 | sp-4 | an-80 | 1C1211 | sp-4 | an-80 |
| 1A1212 | sp-4 | an-81 | 1U1212 | sp-4 | an-81 | 1C1212 | sp-4 | an-81 |
| 1A1213 | sp-4 | an-82 | 1U1213 | sp-4 | an-82 | 1C1213 | sp-4 | an-82 |
| 1A1214 | sp-4 | an-83 | 1U1214 | sp-4 | an-83 | 1C1214 | sp-4 | an-83 |
| 1A1215 | sp-4 | an-84 | 1U1215 | sp-4 | an-84 | 1C1215 | sp-4 | an-84 |
| 1A1216 | sp-4 | an-85 | 1U1216 | sp-4 | an-85 | 1C1216 | sp-4 | an-85 |
| 1A1217 | sp-4 | an-86 | 1U1217 | sp-4 | an-86 | 1C1217 | sp-4 | an-86 |
| 1A1218 | sp-4 | an-87 | 1U1218 | sp-4 | an-87 | 1C1218 | sp-4 | an-87 |
| 1A1219 | sp-4 | an-88 | 1U1219 | sp-4 | an-88 | 1C1219 | sp-4 | an-88 |
| 1A1220 | sp-4 | an-89 | 1U1220 | sp-4 | an-89 | 1C1220 | sp-4 | an-89 |
| 1A1221 | sp-4 | an-90 | 1U1221 | sp-4 | an-90 | 1C1221 | sp-4 | an-90 |
| 1A1222 | sp-4 | an-91 | 1U1222 | sp-4 | an-91 | 1C1222 | sp-4 | an-91 |
| 1A1223 | sp-4 | an-92 | 1U1223 | sp-4 | an-92 | 1C1223 | sp-4 | an-92 |
| 1A1224 | sp-4 | an-93 | 1U1224 | sp-4 | an-93 | 1C1224 | sp-4 | an-93 |
| 1A1225 | sp-4 | an-94 | 1U1225 | sp-4 | an-94 | 1C1225 | sp-4 | an-94 |
| 1A1226 | sp-4 | an-95 | 1U1226 | sp-4 | an-95 | 1C1226 | sp-4 | an-95 |
| 1A1227 | sp-4 | an-96 | 1U1227 | sp-4 | an-96 | 1C1227 | sp-4 | an-96 |
| 1A1228 | sp-4 | an-97 | 1U1228 | sp-4 | an-97 | 1C1228 | sp-4 | an-97 |
| 1A1229 | sp-4 | an-98 | 1U1229 | sp-4 | an-98 | 1C1229 | sp-4 | an-98 |
| 1A1230 | sp-4 | an-99 | 1U1230 | sp-4 | an-99 | 1C1230 | sp-4 | an-99 |
| 1A1231 | sp-4 | an-100 | 1U1231 | sp-4 | an-100 | 1C1231 | sp-4 | an-100 |
| 1A1232 | sp-4 | an-101 | 1U1232 | sp-4 | an-101 | 1C1232 | sp-4 | an-101 |
| 1A1233 | sp-4 | an-102 | 1U1233 | sp-4 | an-102 | 1C1233 | sp-4 | an-102 |
| 1A1234 | sp-4 | an-103 | 1U1234 | sp-4 | an-103 | 1C1234 | sp-4 | an-103 |
| 1A1235 | sp-4 | an-104 | 1U1235 | sp-4 | an-104 | 1C1235 | sp-4 | an-104 |
| 1A1236 | sp-4 | an-105 | 1U1236 | sp-4 | an-105 | 1C1236 | sp-4 | an-105 |
| 1A1237 | sp-4 | an-106 | 1U1237 | sp-4 | an-106 | 1C1237 | sp-4 | an-106 |
| 1A1238 | sp-4 | an-107 | 1U1238 | sp-4 | an-107 | 1C1238 | sp-4 | an-107 |
| 1A1239 | sp-4 | an-108 | 1U1239 | sp-4 | an-108 | 1C1239 | sp-4 | an-108 |
| 1A1240 | sp-4 | an-109 | 1U1240 | sp-4 | an-109 | 1C1240 | sp-4 | an-109 |
| 1A1241 | sp-4 | an-110 | 1U1241 | sp-4 | an-110 | 1C1241 | sp-4 | an-110 |
| 1A1242 | sp-4 | an-111 | 1U1242 | sp-4 | an-111 | 1C1242 | sp-4 | an-111 |
| 1A1243 | sp-4 | an-112 | 1U1243 | sp-4 | an-112 | 1C1243 | sp-4 | an-112 |
| 1A1244 | sp-4 | an-113 | 1U1244 | sp-4 | an-113 | 1C1244 | sp-4 | an-113 |
| 1A1245 | sp-4 | an-114 | 1U1245 | sp-4 | an-114 | 1C1245 | sp-4 | an-114 |
| 1A1246 | sp-4 | an-115 | 1U1246 | sp-4 | an-115 | 1C1246 | sp-4 | an-115 |
| 1A1247 | sp-4 | an-116 | 1U1247 | sp-4 | an-116 | 1C1247 | sp-4 | an-116 |
| 1A1248 | sp-4 | an-117 | 1U1248 | sp-4 | an-117 | 1C1248 | sp-4 | an-117 |
| 1A1249 | sp-4 | an-118 | 1U1249 | sp-4 | an-118 | 1C1249 | sp-4 | an-118 |
| 1A1250 | sp-4 | an-119 | 1U1250 | sp-4 | an-119 | 1C1250 | sp-4 | an-119 |
| 1A1251 | sp-4 | an-120 | 1U1251 | sp-4 | an-120 | 1C1251 | sp-4 | an-120 |
| 1A1252 | sp-4 | an-121 | 1U1252 | sp-4 | an-121 | 1C1252 | sp-4 | an-121 |
| 1A1253 | sp-4 | an-122 | 1U1253 | sp-4 | an-122 | 1C1253 | sp-4 | an-122 |
| 1A1254 | sp-4 | an-123 | 1U1254 | sp-4 | an-123 | 1C1254 | sp-4 | an-123 |
| 1A1255 | sp-4 | an-124 | 1U1255 | sp-4 | an-124 | 1C1255 | sp-4 | an-124 |
| 1A1256 | sp-4 | an-125 | 1U1256 | sp-4 | an-125 | 1C1256 | sp-4 | an-125 |
| 1A1257 | sp-4 | an-126 | 1U1257 | sp-4 | an-126 | 1C1257 | sp-4 | an-126 |
| 1A1258 | sp-4 | an-127 | 1U1258 | sp-4 | an-127 | 1C1258 | sp-4 | an-127 |
| 1A1259 | sp-4 | an-128 | 1U1259 | sp-4 | an-128 | 1C1259 | sp-4 | an-128 |
| 1A1260 | sp-4 | an-129 | 1U1260 | sp-4 | an-129 | 1C1260 | sp-4 | an-129 |
| 1A1261 | sp-4 | an-130 | 1U1261 | sp-4 | an-130 | 1C1261 | sp-4 | an-130 |
| 1A1262 | sp-4 | an-131 | 1U1262 | sp-4 | an-131 | 1C1262 | sp-4 | an-131 |
| 1A1263 | sp-4 | an-132 | 1U1263 | sp-4 | an-132 | 1C1263 | sp-4 | an-132 |
| 1A1264 | sp-4 | an-133 | 1U1264 | sp-4 | an-133 | 1C1264 | sp-4 | an-133 |
| 1A1265 | sp-4 | an-134 | 1U1265 | sp-4 | an-134 | 1C1265 | sp-4 | an-134 |
| 1A1266 | sp-4 | an-135 | 1U1266 | sp-4 | an-135 | 1C1266 | sp-4 | an-135 |
| 1A1267 | sp-4 | an-136 | 1U1267 | sp-4 | an-136 | 1C1267 | sp-4 | an-136 |
| 1A1268 | sp-4 | an-137 | 1U1268 | sp-4 | an-137 | 1C1268 | sp-4 | an-137 |
| 1A1269 | sp-4 | an-138 | 1U1269 | sp-4 | an-138 | 1C1269 | sp-4 | an-138 |
| 1A1270 | sp-4 | an-139 | 1U1270 | sp-4 | an-139 | 1C1270 | sp-4 | an-139 |
| 1A1271 | sp-4 | an-140 | 1U1271 | sp-4 | an-140 | 1C1271 | sp-4 | an-140 |
| 1A1272 | sp-4 | an-141 | 1U1272 | sp-4 | an-141 | 1C1272 | sp-4 | an-141 |
| 1A1273 | sp-4 | an-142 | 1U1273 | sp-4 | an-142 | 1C1273 | sp-4 | an-142 |
| 1A1274 | sp-4 | an-143 | 1U1274 | sp-4 | an-143 | 1C1274 | sp-4 | an-143 |
| 1A1275 | sp-4 | an-144 | 1U1275 | sp-4 | an-144 | 1C1275 | sp-4 | an-144 |
| 1A1276 | sp-4 | an-145 | 1U1276 | sp-4 | an-145 | 1C1276 | sp-4 | an-145 |
| 1A1277 | sp-4 | an-146 | 1U1277 | sp-4 | an-146 | 1C1277 | sp-4 | an-146 |
| 1A1278 | sp-4 | an-147 | 1U1278 | sp-4 | an-147 | 1C1278 | sp-4 | an-147 |
| 1A1279 | sp-4 | an-148 | 1U1279 | sp-4 | an-148 | 1C1279 | sp-4 | an-148 |
| 1A1280 | sp-4 | an-149 | 1U1280 | sp-4 | an-149 | 1C1280 | sp-4 | an-149 |
| 1A1281 | sp-4 | an-150 | 1U1281 | sp-4 | an-150 | 1C1281 | sp-4 | an-150 |

TABLE 1-continued

| | | | | | | | | |
|---|---|---|---|---|---|---|---|---|
| 1A1282 | sp-4 | an-151 | 1U1282 | sp-4 | an-151 | 1C1282 | sp-4 | an-151 |
| 1A1283 | sp-4 | an-152 | 1U1283 | sp-4 | an-152 | 1C1283 | sp-4 | an-152 |
| 1A1284 | sp-4 | an-153 | 1U1284 | sp-4 | an-153 | 1C1284 | sp-4 | an-153 |
| 1A1285 | sp-4 | an-154 | 1U1285 | sp-4 | an-154 | 1C1285 | sp-4 | an-154 |
| 1A1286 | sp-4 | an-155 | 1U1286 | sp-4 | an-155 | 1C1286 | sp-4 | an-155 |
| 1A1287 | sp-4 | an-156 | 1U1287 | sp-4 | an-156 | 1C1287 | sp-4 | an-156 |
| 1A1288 | sp-4 | an-157 | 1U1288 | sp-4 | an-157 | 1C1288 | sp-4 | an-157 |
| 1A1289 | sp-4 | an-158 | 1U1289 | sp-4 | an-158 | 1C1289 | sp-4 | an-158 |
| 1A1290 | sp-4 | an-159 | 1U1290 | sp-4 | an-159 | 1C1290 | sp-4 | an-159 |
| 1A1291 | sp-4 | an-160 | 1U1291 | sp-4 | an-160 | 1C1291 | sp-4 | an-160 |
| 1A1292 | sp-4 | an-161 | 1U1292 | sp-4 | an-161 | 1C1292 | sp-4 | an-161 |
| 1A1293 | sp-4 | an-162 | 1U1293 | sp-4 | an-162 | 1C1293 | sp-4 | an-162 |
| 1A1294 | sp-4 | an-163 | 1U1294 | sp-4 | an-163 | 1C1294 | sp-4 | an-163 |
| 1A1295 | sp-4 | an-164 | 1U1295 | sp-4 | an-164 | 1C1295 | sp-4 | an-164 |
| 1A1296 | sp-4 | an-165 | 1U1296 | sp-4 | an-165 | 1C1296 | sp-4 | an-165 |
| 1A1297 | sp-4 | an-166 | 1U1297 | sp-4 | an-166 | 1C1297 | sp-4 | an-166 |
| 1A1298 | sp-4 | an-167 | 1U1298 | sp-4 | an-167 | 1C1298 | sp-4 | an-167 |
| 1A1299 | sp-4 | an-168 | 1U1299 | sp-4 | an-168 | 1C1299 | sp-4 | an-168 |
| 1A1300 | sp-4 | an-169 | 1U1300 | sp-4 | an-169 | 1C1300 | sp-4 | an-169 |
| 1A1301 | sp-4 | an-170 | 1U1301 | sp-4 | an-170 | 1C1301 | sp-4 | an-170 |
| 1A1302 | sp-4 | an-171 | 1U1302 | sp-4 | an-171 | 1C1302 | sp-4 | an-171 |
| 1A1303 | sp-4 | an-172 | 1U1303 | sp-4 | an-172 | 1C1303 | sp-4 | an-172 |
| 1A1304 | sp-4 | an-173 | 1U1304 | sp-4 | an-173 | 1C1304 | sp-4 | an-173 |
| 1A1305 | sp-4 | an-174 | 1U1305 | sp-4 | an-174 | 1C1305 | sp-4 | an-174 |
| 1A1306 | sp-4 | an-175 | 1U1306 | sp-4 | an-175 | 1C1306 | sp-4 | an-175 |
| 1A1307 | sp-4 | an-176 | 1U1307 | sp-4 | an-176 | 1C1307 | sp-4 | an-176 |
| 1A1308 | sp-4 | an-177 | 1U1308 | sp-4 | an-177 | 1C1308 | sp-4 | an-177 |
| 1A1309 | sp-4 | an-178 | 1U1309 | sp-4 | an-178 | 1C1309 | sp-4 | an-178 |
| 1A1310 | sp-4 | an-179 | 1U1310 | sp-4 | an-179 | 1C1310 | sp-4 | an-179 |
| 1A1311 | sp-4 | an-180 | 1U1311 | sp-4 | an-180 | 1C1311 | sp-4 | an-180 |
| 1A1312 | sp-4 | an-181 | 1U1312 | sp-4 | an-181 | 1C1312 | sp-4 | an-181 |
| 1A1313 | sp-4 | an-182 | 1U1313 | sp-4 | an-182 | 1C1313 | sp-4 | an-182 |
| 1A1314 | sp-4 | an-183 | 1U1314 | sp-4 | an-183 | 1C1314 | sp-4 | an-183 |
| 1A1315 | sp-4 | an-184 | 1U1315 | sp-4 | an-184 | 1C1315 | sp-4 | an-184 |
| 1A1316 | sp-4 | an-185 | 1U1316 | sp-4 | an-185 | 1C1316 | sp-4 | an-185 |
| 1A1317 | sp-4 | an-186 | 1U1317 | sp-4 | an-186 | 1C1317 | sp-4 | an-186 |
| 1A1318 | sp-4 | an-187 | 1U1318 | sp-4 | an-187 | 1C1318 | sp-4 | an-187 |
| 1A1319 | sp-4 | an-188 | 1U1319 | sp-4 | an-183 | 1C1319 | sp-4 | an-188 |
| 1A1320 | sp-4 | an-189 | 1U1320 | sp-4 | an-189 | 1C1320 | sp-4 | an-189 |
| 1A1321 | sp-4 | an-190 | 1U1321 | sp-4 | an-190 | 1C1321 | sp-4 | an-190 |
| 1A1322 | sp-4 | an-191 | 1U1322 | sp-4 | an-191 | 1C1322 | sp-4 | an-191 |
| 1A1323 | sp-4 | an-192 | 1U1323 | sp-4 | an-192 | 1C1323 | sp-4 | an-192 |
| 1A1324 | sp-4 | an-193 | 1U1324 | sp-4 | an-193 | 1C1324 | sp-4 | an-193 |
| 1A1325 | sp-4 | an-194 | 1U1325 | sp-4 | an-194 | 1C1325 | sp-4 | an-194 |
| 1A1326 | sp-4 | an-195 | 1U1326 | sp-4 | an-195 | 1C1326 | sp-4 | an-195 |
| 1A1327 | sp-4 | an-196 | 1U1327 | sp-4 | an-196 | 1C1327 | sp-4 | an-196 |
| 1A1328 | sp-4 | an-197 | 1U1328 | sp-4 | an-197 | 1C1328 | sp-4 | an-197 |
| 1A1329 | sp-4 | an-198 | 1U1329 | sp-4 | an-198 | 1C1329 | sp-4 | an-198 |
| 1A1330 | sp-4 | an-199 | 1U1330 | sp-4 | an-199 | 1C1330 | sp-4 | an-199 |
| 1A1331 | sp-4 | an-200 | 1U1331 | sp-4 | an-200 | 1C1331 | sp-4 | an-200 |
| 1A1332 | sp-4 | an-201 | 1U1332 | sp-4 | an-201 | 1C1332 | sp-4 | an-201 |
| 1A1333 | sp-4 | an-202 | 1U1333 | sp-4 | an-202 | 1C1333 | sp-4 | an-202 |
| 1A1334 | sp-4 | an-203 | 1U1334 | sp-4 | an-203 | 1C1334 | sp-4 | an-203 |
| 1A1335 | sp-4 | an-204 | 1U1335 | sp-4 | an-204 | 1C1335 | sp-4 | an-204 |
| 1A1336 | sp-4 | an-205 | 1U1336 | sp-4 | an-205 | 1C1336 | sp-4 | an-205 |
| 1A1337 | sp-4 | an-206 | 1U1337 | sp-4 | an-206 | 1C1337 | sp-4 | an-206 |
| 1A1338 | sp-4 | an-207 | 1U1338 | sp-4 | an-207 | 1C1338 | sp-4 | an-207 |
| 1A1339 | sp-4 | an-208 | 1U1339 | sp-4 | an-208 | 1C1339 | sp-4 | an-208 |
| 1A1340 | sp-4 | an-209 | 1U1340 | sp-4 | an-209 | 1C1340 | sp-4 | an-209 |
| 1A1341 | sp-4 | an-210 | 1U1341 | sp-4 | an-210 | 1C1341 | sp-4 | an-210 |
| 1A1342 | sp-4 | an-211 | 1U1342 | sp-4 | an-211 | 1C1342 | sp-4 | an-211 |
| 1A1343 | sp-4 | an-212 | 1U1343 | sp-4 | an-212 | 1C1343 | sp-4 | an-212 |
| 1A1344 | sp-4 | an-213 | 1U1344 | sp-4 | an-213 | 1C1344 | sp-4 | an-213 |
| 1A1345 | sp-4 | an-214 | 1U1345 | sp-4 | an-214 | 1C1345 | sp-4 | an-214 |
| 1A1346 | sp-4 | an-215 | 1U1346 | sp-4 | an-215 | 1C1346 | sp-4 | an-215 |
| 1A1347 | sp-4 | an-216 | 1U1347 | sp-4 | an-216 | 1C1347 | sp-4 | an-216 |
| 1A1348 | sp-4 | an-217 | 1U1348 | sp-4 | an-217 | 1C1348 | sp-4 | an-217 |
| 1A1349 | sp-4 | an-218 | 1U1349 | sp-4 | an-218 | 1C1349 | sp-4 | an-218 |
| 1A1350 | sp-4 | an-219 | 1U1350 | sp-4 | an-219 | 1C1350 | sp-4 | an-219 |
| 1A1351 | sp-4 | an-220 | 1U1351 | sp-4 | an-220 | 1C1351 | sp-4 | an-220 |
| 1A1352 | sp-4 | an-221 | 1U1352 | sp-4 | an-221 | 1C1352 | sp-4 | an-221 |
| 1A1353 | sp-4 | an-222 | 1U1353 | sp-4 | an-222 | 1C1353 | sp-4 | an-222 |
| 1A1354 | sp-4 | an-223 | 1U1354 | sp-4 | an-223 | 1C1354 | sp-4 | an-223 |
| 1A1355 | sp-4 | an-224 | 1U1355 | sp-4 | an-224 | 1C1355 | sp-4 | an-224 |
| 1A1356 | sp-4 | an-225 | 1U1356 | sp-4 | an-225 | 1C1356 | sp-4 | an-225 |
| 1A1357 | sp-4 | an-226 | 1U1357 | sp-4 | an-226 | 1C1357 | sp-4 | an-226 |
| 1A1358 | sp-4 | an-227 | 1U1358 | sp-4 | an-227 | 1C1358 | sp-4 | an-227 |
| 1A1359 | sp-4 | an-228 | 1U1359 | sp-4 | an-228 | 1C1359 | sp-4 | an-228 |
| 1A1360 | sp-4 | an-229 | 1U1360 | sp-4 | an-229 | 1C1360 | sp-4 | an-229 |

TABLE 1-continued

| | | | | | | | | |
|---|---|---|---|---|---|---|---|---|
| 1A1361 | sp-4 | an-230 | 1U1361 | sp-4 | an-230 | 1C1361 | sp-4 | an-230 |
| 1A1362 | sp-4 | an-231 | 1U1362 | sp-4 | an-231 | 1C1362 | sp-4 | an-231 |
| 1A1363 | sp-4 | an-232 | 1U1363 | sp-4 | an-232 | 1C1363 | sp-4 | an-232 |
| 1A1364 | sp-4 | an-233 | 1U1364 | sp-4 | an-233 | 1C1364 | sp-4 | an-233 |
| 1A1365 | sp-4 | an-234 | 1U1365 | sp-4 | an-234 | 1C1365 | sp-4 | an-234 |
| 1A1366 | sp-4 | an-235 | 1U1366 | sp-4 | an-235 | 1C1366 | sp-4 | an-235 |
| 1A1367 | sp-4 | an-236 | 1U1367 | sp-4 | an-236 | 1C1367 | sp-4 | an-236 |
| 1A1368 | sp-4 | an-237 | 1U1368 | sp-4 | an-237 | 1C1368 | sp-4 | an-237 |
| 1A1369 | sp-4 | an-238 | 1U1369 | sp-4 | an-238 | 1C1369 | sp-4 | an-238 |
| 1A1370 | sp-4 | an-239 | 1U1370 | sp-4 | an-239 | 1C1370 | sp-4 | an-239 |
| 1A1371 | sp-4 | an-240 | 1U1371 | sp-4 | an-240 | 1C1371 | sp-4 | an-240 |
| 1A1372 | sp-4 | an-241 | 1U1372 | sp-4 | an-241 | 1C1372 | sp-4 | an-241 |
| 1A1373 | sp-4 | an-242 | 1U1373 | sp-4 | an-242 | 1C1373 | sp-4 | an-242 |
| 1A1374 | sp-4 | an-243 | 1U1374 | sp-4 | an-243 | 1C1374 | sp-4 | an-243 |
| 1A1375 | sp-4 | an-244 | 1U1375 | sp-4 | an-244 | 1C1375 | sp-4 | an-244 |
| 1A1376 | sp-4 | an-245 | 1U1376 | sp-4 | an-245 | 1C1376 | sp-4 | an-245 |
| 1A1377 | sp-4 | an-246 | 1U1377 | sp-4 | an-246 | 1C1377 | sp-4 | an-246 |
| 1A1378 | sp-4 | an-247 | 1U1378 | sp-4 | an-247 | 1C1378 | sp-4 | an-247 |
| 1A1379 | sp-4 | an-248 | 1U1379 | sp-4 | an-248 | 1C1379 | sp-4 | an-248 |
| 1A1380 | sp-4 | an-249 | 1U1380 | sp-4 | an-249 | 1C1380 | sp-4 | an-249 |
| 1A1381 | sp-4 | an-250 | 1U1381 | sp-4 | an-250 | 1C1381 | sp-4 | an-250 |
| 1A1382 | sp-4 | an-251 | 1U1382 | sp-4 | an-251 | 1C1382 | sp-4 | an-251 |
| 1A1383 | sp-4 | an-252 | 1U1383 | sp-4 | an-252 | 1C1383 | sp-4 | an-252 |
| 1A1384 | sp-4 | an-253 | 1U1384 | sp-4 | an-253 | 1C1384 | sp-4 | an-253 |
| 1A1385 | sp-4 | an-254 | 1U1385 | sp-4 | an-254 | 1C1385 | sp-4 | an-254 |
| 1A1386 | sp-4 | an-255 | 1U1386 | sp-4 | an-255 | 1C1386 | sp-4 | an-255 |
| 1A1387 | sp-4 | an-256 | 1U1387 | sp-4 | an-256 | 1C1387 | sp-4 | an-256 |
| 1A1388 | sp-4 | an-257 | 1U1388 | sp-4 | an-257 | 1C1388 | sp-4 | an-257 |
| 1A1389 | sp-4 | an-258 | 1U1389 | sp-4 | an-258 | 1C1389 | sp-4 | an-258 |
| 1A1390 | sp-4 | an-259 | 1U1390 | sp-4 | an-259 | 1C1390 | sp-4 | an-259 |
| 1A1391 | sp-4 | an-260 | 1U1391 | sp-4 | an-260 | 1C1391 | sp-4 | an-260 |
| 1A1392 | sp-4 | an-261 | 1U1392 | sp-4 | an-261 | 1C1392 | sp-4 | an-261 |
| 1A1393 | sp-4 | an-262 | 1U1393 | sp-4 | an-262 | 1C1393 | sp-4 | an-262 |
| 1A1394 | sp-4 | an-263 | 1U1394 | sp-4 | an-263 | 1C1394 | sp-4 | an-263 |
| 1A1395 | sp-4 | an-264 | 1U1395 | sp-4 | an-264 | 1C1395 | sp-4 | an-264 |
| 1A1396 | sp-4 | an-265 | 1U1396 | sp-4 | an-265 | 1C1396 | sp-4 | an-265 |
| 1A1397 | sp-4 | an-266 | 1U1397 | sp-4 | an-266 | 1C1397 | sp-4 | an-266 |
| 1A1398 | sp-4 | an-267 | 1U1398 | sp-4 | an-267 | 1C1398 | sp-4 | an-267 |
| 1A1399 | sp-4 | an-268 | 1U1399 | sp-4 | an-268 | 1C1399 | sp-4 | an-268 |
| 1A1400 | sp-4 | an-269 | 1U1400 | sp-4 | an-269 | 1C1400 | sp-4 | an-269 |
| 1A1401 | sp-4 | an-270 | 1U1401 | sp-4 | an-270 | 1C1401 | sp-4 | an-270 |
| 1A1402 | sp-4 | an-271 | 1U1402 | sp-4 | an-271 | 1C1402 | sp-4 | an-271 |
| 1A1403 | sp-4 | an-272 | 1U1403 | sp-4 | an-272 | 1C1403 | sp-4 | an-272 |
| 1A1404 | sp-4 | an-273 | 1U1404 | sp-4 | an-273 | 1C1404 | sp-4 | an-273 |
| 1A1405 | sp-4 | an-274 | 1U1405 | sp-4 | an-274 | 1C1405 | sp-4 | an-274 |
| 1A1406 | sp-4 | an-275 | 1U1406 | sp-4 | an-275 | 1C1406 | sp-4 | an-275 |
| 1A1407 | sp-4 | an-276 | 1U1407 | sp-4 | an-276 | 1C1407 | sp-4 | an-276 |
| 1A1408 | sp-4 | an-277 | 1U1408 | sp-4 | an-277 | 1C1408 | sp-4 | an-277 |
| 1A1409 | sp-4 | an-278 | 1U1409 | sp-4 | an-278 | 1C1409 | sp-4 | an-278 |
| 1A1410 | sp-4 | an-279 | 1U1410 | sp-4 | an-279 | 1C1410 | sp-4 | an-279 |
| 1A1411 | sp-4 | an-280 | 1U1411 | sp-4 | an-280 | 1C1411 | sp-4 | an-280 |
| 1A1412 | sp-4 | an-281 | 1U1412 | sp-4 | an-281 | 1C1412 | sp-4 | an-281 |
| 1A1413 | sp-4 | an-282 | 1U1413 | sp-4 | an-282 | 1C1413 | sp-4 | an-282 |
| 1A1414 | sp-4 | an-283 | 1U1414 | sp-4 | an-283 | 1C1414 | sp-4 | an-283 |
| 1A1415 | sp-4 | an-284 | 1U1415 | sp-4 | an-284 | 1C1415 | sp-4 | an-284 |
| 1A1416 | sp-4 | an-285 | 1U1416 | sp-4 | an-285 | 1C1416 | sp-4 | an-285 |
| 1A1417 | sp-4 | an-286 | 1U1417 | sp-4 | an-286 | 1C1417 | sp-4 | an-286 |
| 1A1418 | sp-4 | an-287 | 1U1418 | sp-4 | an-287 | 1C1418 | sp-4 | an-287 |
| 1A1419 | sp-4 | an-288 | 1U1419 | sp-4 | an-288 | 1C1419 | sp-4 | an-288 |
| 1A1420 | sp-4 | an-289 | 1U1420 | sp-4 | an-289 | 1C1420 | sp-4 | an-289 |
| 1A1421 | sp-4 | an-290 | 1U1421 | sp-4 | an-290 | 1C1421 | sp-4 | an-290 |
| 1A1422 | sp-4 | an-291 | 1U1422 | sp-4 | an-291 | 1C1422 | sp-4 | an-291 |
| 1A1423 | sp-4 | an-292 | 1U1423 | sp-4 | an-292 | 1C1423 | sp-4 | an-292 |
| 1A1424 | sp-4 | an-293 | 1U1424 | sp-4 | an-293 | 1C1424 | sp-4 | an-293 |
| 1A1425 | sp-4 | an-294 | 1U1425 | sp-4 | an-294 | 1C1425 | sp-4 | an-294 |
| 1A1426 | sp-4 | an-295 | 1U1426 | sp-4 | an-295 | 1C1426 | sp-4 | an-295 |
| 1A1427 | sp-4 | an-296 | 1U1427 | sp-4 | an-296 | 1C1427 | sp-4 | an-296 |
| 1A1428 | sp-4 | an-297 | 1U1428 | sp-4 | an-297 | 1C1428 | sp-4 | an-297 |
| 1A1429 | sp-4 | an-298 | 1U1429 | sp-4 | an-298 | 1C1429 | sp-4 | an-298 |
| 1A1430 | sp-4 | an-299 | 1U1430 | sp-4 | an-299 | 1C1430 | sp-4 | an-299 |
| 1A1431 | sp-4 | an-300 | 1U1431 | sp-4 | an-300 | 1C1431 | sp-4 | an-300 |
| 1A1432 | sp-4 | an-301 | 1U1432 | sp-4 | an-301 | 1C1432 | sp-4 | an-301 |
| 1A1433 | sp-4 | an-302 | 1U1433 | sp-4 | an-302 | 1C1433 | sp-4 | an-302 |
| 1A1434 | sp-4 | an-303 | 1U1434 | sp-4 | an-303 | 1C1434 | sp-4 | an-303 |
| 1A1435 | sp-4 | an-304 | 1U1435 | sp-4 | an-304 | 1C1435 | sp-4 | an-304 |
| 1A1436 | sp-4 | an-305 | 1U1436 | sp-4 | an-305 | 1C1436 | sp-4 | an-305 |
| 1A1437 | sp-4 | an-306 | 1U1437 | sp-4 | an-306 | 1C1437 | sp-4 | an-306 |
| 1A1438 | sp-4 | an-307 | 1U1438 | sp-4 | an-307 | 1C1438 | sp-4 | an-307 |
| 1A1439 | sp-4 | an-308 | 1U1439 | sp-4 | an-308 | 1C1439 | sp-4 | an-308 |

TABLE 1-continued

| | | | | | | | | |
|---|---|---|---|---|---|---|---|---|
| 1A1440 | sp-4 | an-309 | 1U1440 | sp-4 | an-309 | 1C1440 | sp-4 | an-309 |
| 1A1441 | sp-4 | an-310 | 1U1441 | sp-4 | an-310 | 1C1441 | sp-4 | an-310 |
| 1A1442 | sp-4 | an-311 | 1U1442 | sp-4 | an-311 | 1C1442 | sp-4 | an-311 |
| 1A1443 | sp-4 | an-312 | 1U1443 | sp-4 | an-312 | 1C1443 | sp-4 | an-312 |
| 1A1444 | sp-4 | an-313 | 1U1444 | sp-4 | an-313 | 1C1444 | sp-4 | an-313 |
| 1A1445 | sp-4 | an-314 | 1U1445 | sp-4 | an-314 | 1C1445 | sp-4 | an-314 |
| 1A1446 | sp-4 | an-315 | 1U1446 | sp-4 | an-315 | 1C1446 | sp-4 | an-315 |
| 1A1447 | sp-4 | an-316 | 1U1447 | sp-4 | an-316 | 1C1447 | sp-4 | an-316 |
| 1A1448 | sp-4 | an-317 | 1U1448 | sp-4 | an-317 | 1C1448 | sp-4 | an-317 |
| 1A1449 | sp-4 | an-318 | 1U1449 | sp-4 | an-318 | 1C1449 | sp-4 | an-318 |
| 1A1450 | sp-4 | an-319 | 1U1450 | sp-4 | an-319 | 1C1450 | sp-4 | an-319 |
| 1A1451 | sp-4 | an-320 | 1U1451 | sp-4 | an-320 | 1C1451 | sp-4 | an-320 |
| 1A1452 | sp-4 | an-321 | 1U1452 | sp-4 | an-321 | 1C1452 | sp-4 | an-321 |
| 1A1453 | sp-4 | an-322 | 1U1453 | sp-4 | an-322 | 1C1453 | sp-4 | an-322 |
| 1A1454 | sp-4 | an-323 | 1U1454 | sp-4 | an-323 | 1C1454 | sp-4 | an-323 |
| 1A1455 | sp-4 | an-324 | 1U1455 | sp-4 | an-324 | 1C1455 | sp-4 | an-324 |
| 1A1456 | sp-4 | an-325 | 1U1456 | sp-4 | an-325 | 1C1456 | sp-4 | an-325 |
| 1A1457 | sp-4 | an-326 | 1U1457 | sp-4 | an-326 | 1C1457 | sp-4 | an-326 |
| 1A1458 | sp-4 | an-327 | 1U1458 | sp-4 | an-327 | 1C1458 | sp-4 | an-327 |
| 1A1459 | sp-4 | an-328 | 1U1459 | sp-4 | an-328 | 1C1459 | sp-4 | an-328 |
| 1A1460 | sp-4 | an-329 | 1U1460 | sp-4 | an-329 | 1C1460 | sp-4 | an-329 |
| 1A1461 | sp-4 | an-330 | 1U1461 | sp-4 | an-330 | 1C1461 | sp-4 | an-330 |
| 1A1462 | sp-4 | an-331 | 1U1462 | sp-4 | an-331 | 1C1462 | sp-4 | an-331 |
| 1A1463 | sp-4 | an-332 | 1U1463 | sp-4 | an-332 | 1C1463 | sp-4 | an-332 |
| 1A1464 | sp-4 | an-333 | 1U1464 | sp-4 | an-333 | 1C1464 | sp-4 | an-333 |
| 1A1465 | sp-4 | an-334 | 1U1465 | sp-4 | an-334 | 1C1465 | sp-4 | an-334 |
| 1A1466 | sp-4 | an-335 | 1U1466 | sp-4 | an-335 | 1C1466 | sp-4 | an-335 |
| 1A1467 | sp-4 | an-336 | 1U1467 | sp-4 | an-336 | 1C1467 | sp-4 | an-336 |
| 1A1468 | sp-4 | an-337 | 1U1468 | sp-4 | an-337 | 1C1468 | sp-4 | an-337 |
| 1A1469 | sp-4 | an-338 | 1U1469 | sp-4 | an-338 | 1C1469 | sp-4 | an-338 |
| 1A1470 | sp-4 | an-339 | 1U1470 | sp-4 | an-339 | 1C1470 | sp-4 | an-339 |
| 1A1471 | sp-4 | an-340 | 1U1471 | sp-4 | an-340 | 1C1471 | sp-4 | an-340 |
| 1A1472 | sp-4 | an-341 | 1U1472 | sp-4 | an-341 | 1C1472 | sp-4 | an-341 |
| 1A1473 | sp-4 | an-342 | 1U1473 | sp-4 | an-342 | 1C1473 | sp-4 | an-342 |
| 1A1474 | sp-4 | an-343 | 1U1474 | sp-4 | an-343 | 1C1474 | sp-4 | an-343 |
| 1A1475 | sp-4 | an-344 | 1U1475 | sp-4 | an-344 | 1C1475 | sp-4 | an-344 |
| 1A1476 | sp-4 | an-345 | 1U1476 | sp-4 | an-345 | 1C1476 | sp-4 | an-345 |
| 1A1477 | sp-4 | an-346 | 1U1477 | sp-4 | an-346 | 1C1477 | sp-4 | an-346 |
| 1A1478 | sp-4 | an-347 | 1U1478 | sp-4 | an-347 | 1C1478 | sp-4 | an-347 |
| 1A1479 | sp-4 | an-348 | 1U1479 | sp-4 | an-348 | 1C1479 | sp-4 | an-348 |
| 1A1480 | sp-4 | an-349 | 1U1480 | sp-4 | an-349 | 1C1480 | sp-4 | an-349 |
| 1A1481 | sp-4 | an-350 | 1U1481 | sp-4 | an-350 | 1C1481 | sp-4 | an-350 |
| 1A1482 | sp-4 | an-351 | 1U1482 | sp-4 | an-351 | 1C1482 | sp-4 | an-351 |
| 1A1483 | sp-4 | an-352 | 1U1483 | sp-4 | an-352 | 1C1483 | sp-4 | an-352 |
| 1A1484 | sp-4 | an-353 | 1U1484 | sp-4 | an-353 | 1C1484 | sp-4 | an-353 |
| 1A1485 | sp-4 | an-354 | 1U1485 | sp-4 | an-354 | 1C1485 | sp-4 | an-354 |
| 1A1486 | sp-4 | an-355 | 1U1486 | sp-4 | an-355 | 1C1486 | sp-4 | an-355 |
| 1A1487 | sp-4 | an-356 | 1U1487 | sp-4 | an-356 | 1C1487 | sp-4 | an-356 |
| 1A1488 | sp-4 | an-357 | 1U1488 | sp-4 | an-357 | 1C1488 | sp-4 | an-357 |
| 1A1489 | sp-4 | an-358 | 1U1489 | sp-4 | an-358 | 1C1489 | sp-4 | an-358 |
| 1A1490 | sp-4 | an-359 | 1U1490 | sp-4 | an-359 | 1C1490 | sp-4 | an-359 |
| 1A1491 | sp-4 | an-360 | 1U1491 | sp-4 | an-360 | 1C1491 | sp-4 | an-360 |
| 1A1492 | sp-4 | an-361 | 1U1492 | sp-4 | an-361 | 1C1492 | sp-4 | an-361 |
| 1A1493 | sp-4 | an-362 | 1U1493 | sp-4 | an-362 | 1C1493 | sp-4 | an-362 |
| 1A1494 | sp-4 | an-363 | 1U1494 | sp-4 | an-363 | 1C1494 | sp-4 | an-363 |
| 1A1495 | sp-4 | an-364 | 1U1495 | sp-4 | an-364 | 1C1495 | sp-4 | an-364 |
| 1A1496 | sp-4 | an-365 | 1U1496 | sp-4 | an-365 | 1C1496 | sp-4 | an-365 |
| 1A1497 | sp-4 | an-366 | 1U1497 | sp-4 | an-366 | 1C1497 | sp-4 | an-366 |
| 1A1498 | sp-4 | an-367 | 1U1498 | sp-4 | an-367 | 1C1498 | sp-4 | an-367 |
| 1A1499 | sp-4 | an-368 | 1U1499 | sp-4 | an-368 | 1C1499 | sp-4 | an-368 |
| 1A1500 | sp-4 | an-369 | 1U1500 | sp-4 | an-369 | 1C1500 | sp-4 | an-369 |
| 1A1501 | sp-4 | an-370 | 1U1501 | sp-4 | an-370 | 1C1501 | sp-4 | an-370 |
| 1A1502 | sp-4 | an-371 | 1U1502 | sp-4 | an-371 | 1C1502 | sp-4 | an-371 |
| 1A1503 | sp-4 | an-372 | 1U1503 | sp-4 | an-372 | 1C1503 | sp-4 | an-372 |
| 1A1504 | sp-4 | an-373 | 1U1504 | sp-4 | an-373 | 1C1504 | sp-4 | an-373 |
| 1A1505 | sp-4 | an-374 | 1U1505 | sp-4 | an-374 | 1C1505 | sp-4 | an-374 |
| 1A1506 | sp-4 | an-375 | 1U1506 | sp-4 | an-375 | 1C1506 | sp-4 | an-375 |
| 1A1507 | sp-4 | an-376 | 1U1507 | sp-4 | an-376 | 1C1507 | sp-4 | an-376 |
| 1A1508 | sp-4 | an-377 | 1U1508 | sp-4 | an-377 | 1C1508 | sp-4 | an-377 |
| 1A1509 | sp-5 | an-1 | 1U1509 | sp-5 | an-1 | 1C1509 | sp-5 | an-1 |
| 1A1510 | sp-5 | an-2 | 1U1510 | sp-5 | an-2 | 1C1510 | sp-5 | an-2 |
| 1A1511 | sp-5 | an-3 | 1U1511 | sp-5 | an-3 | 1C1511 | sp-5 | an-3 |
| 1A1512 | sp-5 | an-4 | 1U1512 | sp-5 | an-4 | 1C1512 | sp-5 | an-4 |
| 1A1513 | sp-5 | an-5 | 1U1513 | sp-5 | an-5 | 1C1513 | sp-5 | an-5 |
| 1A1514 | sp-5 | an-6 | 1U1514 | sp-5 | an-6 | 1C1514 | sp-5 | an-6 |
| 1A1515 | sp-5 | an-7 | 1U1515 | sp-5 | an-7 | 1C1515 | sp-5 | an-7 |
| 1A1516 | sp-5 | an-8 | 1U1516 | sp-5 | an-8 | 1C1516 | sp-5 | an-8 |
| 1A1517 | sp-5 | an-9 | 1U1517 | sp-5 | an-9 | 1C1517 | sp-5 | an-9 |
| 1A1518 | sp-5 | an-10 | 1U1518 | sp-5 | an-10 | 1C1518 | sp-5 | an-10 |

TABLE 1-continued

| | | | | | | | | |
|---|---|---|---|---|---|---|---|---|
| 1A1519 | sp-5 | an-11 | 1U1519 | sp-5 | an-11 | 1C1519 | sp-5 | an-11 |
| 1A1520 | sp-5 | an-12 | 1U1520 | sp-5 | an-12 | 1C1520 | sp-5 | an-12 |
| 1A1521 | sp-5 | an-13 | 1U1521 | sp-5 | an-13 | 1C1521 | sp-5 | an-13 |
| 1A1522 | sp-5 | an-14 | 1U1522 | sp-5 | an-14 | 1C1522 | sp-5 | an-14 |
| 1A1523 | sp-5 | an-15 | 1U1523 | sp-5 | an-15 | 1C1523 | sp-5 | an-15 |
| 1A1524 | sp-5 | an-16 | 1U1524 | sp-5 | an-16 | 1C1524 | sp-5 | an-16 |
| 1A1525 | sp-5 | an-17 | 1U1525 | sp-5 | an-17 | 1C1525 | sp-5 | an-17 |
| 1A1526 | sp-5 | an-18 | 1U1526 | sp-5 | an-18 | 1C1526 | sp-5 | an-18 |
| 1A1527 | sp-5 | an-19 | 1U1527 | sp-5 | an-19 | 1C1527 | sp-5 | an-19 |
| 1A1528 | sp-5 | an-20 | 1U1528 | sp-5 | an-20 | 1C1528 | sp-5 | an-20 |
| 1A1529 | sp-5 | an-21 | 1U1529 | sp-5 | an-21 | 1C1529 | sp-5 | an-21 |
| 1A1530 | sp-5 | an-22 | 1U1530 | sp-5 | an-22 | 1C1530 | sp-5 | an-22 |
| 1A1531 | sp-5 | an-23 | 1U1531 | sp-5 | an-23 | 1C1531 | sp-5 | an-23 |
| 1A1532 | sp-5 | an-24 | 1U1532 | sp-5 | an-24 | 1C1532 | sp-5 | an-24 |
| 1A1533 | sp-5 | an-25 | 1U1533 | sp-5 | an-25 | 1C1533 | sp-5 | an-25 |
| 1A1534 | sp-5 | an-26 | 1U1534 | sp-5 | an-26 | 1C1534 | sp-5 | an-26 |
| 1A1535 | sp-5 | an-27 | 1U1535 | sp-5 | an-27 | 1C1535 | sp-5 | an-27 |
| 1A1536 | sp-5 | an-28 | 1U1536 | sp-5 | an-28 | 1C1536 | sp-5 | an-28 |
| 1A1537 | sp-5 | an-29 | 1U1537 | sp-5 | an-29 | 1C1537 | sp-5 | an-29 |
| 1A1538 | sp-5 | an-30 | 1U1538 | sp-5 | an-30 | 1C1538 | sp-5 | an-30 |
| 1A1539 | sp-5 | an-31 | 1U1539 | sp-5 | an-31 | 1C1539 | sp-5 | an-31 |
| 1A1540 | sp-5 | an-32 | 1U1540 | sp-5 | an-32 | 1C1540 | sp-5 | an-32 |
| 1A1541 | sp-5 | an-33 | 1U1541 | sp-5 | an-33 | 1C1541 | sp-5 | an-33 |
| 1A1542 | sp-5 | an-34 | 1U1542 | sp-5 | an-34 | 1C1542 | sp-5 | an-34 |
| 1A1543 | sp-5 | an-35 | 1U1543 | sp-5 | an-35 | 1C1543 | sp-5 | an-35 |
| 1A1544 | sp-5 | an-36 | 1U1544 | sp-5 | an-36 | 1C1544 | sp-5 | an-36 |
| 1A1545 | sp-5 | an-37 | 1U1545 | sp-5 | an-37 | 1C1545 | sp-5 | an-37 |
| 1A1546 | sp-5 | an-38 | 1U1546 | sp-5 | an-38 | 1C1546 | sp-5 | an-38 |
| 1A1547 | sp-5 | an-39 | 1U1547 | sp-5 | an-39 | 1C1547 | sp-5 | an-39 |
| 1A1548 | sp-5 | an-40 | 1U1548 | sp-5 | an-40 | 1C1548 | sp-5 | an-40 |
| 1A1549 | sp-5 | an-41 | 1U1549 | sp-5 | an-41 | 1C1549 | sp-5 | an-41 |
| 1A1550 | sp-5 | an-42 | 1U1550 | sp-5 | an-42 | 1C1550 | sp-5 | an-42 |
| 1A1551 | sp-5 | an-43 | 1U1551 | sp-5 | an-43 | 1C1551 | sp-5 | an-43 |
| 1A1552 | sp-5 | an-44 | 1U1552 | sp-5 | an-44 | 1C1552 | sp-5 | an-44 |
| 1A1553 | sp-5 | an-45 | 1U1553 | sp-5 | an-45 | 1C1553 | sp-5 | an-45 |
| 1A1554 | sp-5 | an-46 | 1U1554 | sp-5 | an-46 | 1C1554 | sp-5 | an-46 |
| 1A1555 | sp-5 | an-47 | 1U1555 | sp-5 | an-47 | 1C1555 | sp-5 | an-47 |
| 1A1556 | sp-5 | an-48 | 1U1556 | sp-5 | an-48 | 1C1556 | sp-5 | an-48 |
| 1A1557 | sp-5 | an-49 | 1U1557 | sp-5 | an-49 | 1C1557 | sp-5 | an-49 |
| 1A1558 | sp-5 | an-50 | 1U1558 | sp-5 | an-50 | 1C1558 | sp-5 | an-50 |
| 1A1559 | sp-5 | an-51 | 1U1559 | sp-5 | an-51 | 1C1559 | sp-5 | an-51 |
| 1A1560 | sp-5 | an-52 | 1U1560 | sp-5 | an-52 | 1C1560 | sp-5 | an-52 |
| 1A1561 | sp-5 | an-53 | 1U1561 | sp-5 | an-53 | 1C1561 | sp-5 | an-53 |
| 1A1562 | sp-5 | an-54 | 1U1562 | sp-5 | an-54 | 1C1562 | sp-5 | an-54 |
| 1A1563 | sp-5 | an-55 | 1U1563 | sp-5 | an-55 | 1C1563 | sp-5 | an-55 |
| 1A1564 | sp-5 | an-56 | 1U1564 | sp-5 | an-56 | 1C1564 | sp-5 | an-56 |
| 1A1565 | sp-5 | an-57 | 1U1565 | sp-5 | an-57 | 1C1565 | sp-5 | an-57 |
| 1A1566 | sp-5 | an-58 | 1U1566 | sp-5 | an-58 | 1C1566 | sp-5 | an-58 |
| 1A1567 | sp-5 | an-59 | 1U1567 | sp-5 | an-59 | 1C1567 | sp-5 | an-59 |
| 1A1568 | sp-5 | an-60 | 1U1568 | sp-5 | an-60 | 1C1568 | sp-5 | an-60 |
| 1A1569 | sp-5 | an-61 | 1U1569 | sp-5 | an-61 | 1C1569 | sp-5 | an-61 |
| 1A1570 | sp-5 | an-62 | 1U1570 | sp-5 | an-62 | 1C1570 | sp-5 | an-62 |
| 1A1571 | sp-5 | an-63 | 1U1571 | sp-5 | an-63 | 1C1571 | sp-5 | an-63 |
| 1A1572 | sp-5 | an-64 | 1U1572 | sp-5 | an-64 | 1C1572 | sp-5 | an-64 |
| 1A1573 | sp-5 | an-65 | 1U1573 | sp-5 | an-65 | 1C1573 | sp-5 | an-65 |
| 1A1574 | sp-5 | an-66 | 1U1574 | sp-5 | an-66 | 1C1574 | sp-5 | an-66 |
| 1A1575 | sp-5 | an-67 | 1U1575 | sp-5 | an-67 | 1C1575 | sp-5 | an-67 |
| 1A1576 | sp-5 | an-68 | 1U1576 | sp-5 | an-68 | 1C1576 | sp-5 | an-68 |
| 1A1577 | sp-5 | an-69 | 1U1577 | sp-5 | an-69 | 1C1577 | sp-5 | an-69 |
| 1A1578 | sp-5 | an-70 | 1U1578 | sp-5 | an-70 | 1C1578 | sp-5 | an-70 |
| 1A1579 | sp-5 | an-71 | 1U1579 | sp-5 | an-71 | 1C1579 | sp-5 | an-71 |
| 1A1580 | sp-5 | an-72 | 1U1580 | sp-5 | an-72 | 1C1580 | sp-5 | an-72 |
| 1A1581 | sp-5 | an-73 | 1U1581 | sp-5 | an-73 | 1C1581 | sp-5 | an-73 |
| 1A1582 | sp-5 | an-74 | 1U1582 | sp-5 | an-74 | 1C1582 | sp-5 | an-74 |
| 1A1583 | sp-5 | an-75 | 1U1583 | sp-5 | an-75 | 1C1583 | sp-5 | an-75 |
| 1A1584 | sp-5 | an-76 | 1U1584 | sp-5 | an-76 | 1C1584 | sp-5 | an-76 |
| 1A1585 | sp-5 | an-77 | 1U1585 | sp-5 | an-77 | 1C1585 | sp-5 | an-77 |
| 1A1586 | sp-5 | an-78 | 1U1586 | sp-5 | an-78 | 1C1586 | sp-5 | an-78 |
| 1A1587 | sp-5 | an-79 | 1U1587 | sp-5 | an-79 | 1C1587 | sp-5 | an-79 |
| 1A1588 | sp-5 | an-80 | 1U1588 | sp-5 | an-80 | 1C1588 | sp-5 | an-80 |
| 1A1589 | sp-5 | an-81 | 1U1589 | sp-5 | an-81 | 1C1589 | sp-5 | an-81 |
| 1A1590 | sp-5 | an-82 | 1U1590 | sp-5 | an-82 | 1C1590 | sp-5 | an-82 |
| 1A1591 | sp-5 | an-83 | 1U1591 | sp-5 | an-83 | 1C1591 | sp-5 | an-83 |
| 1A1592 | sp-5 | an-84 | 1U1592 | sp-5 | an-84 | 1C1592 | sp-5 | an-84 |
| 1A1593 | sp-5 | an-85 | 1U1593 | sp-5 | an-85 | 1C1593 | sp-5 | an-85 |
| 1A1594 | sp-5 | an-86 | 1U1594 | sp-5 | an-86 | 1C1594 | sp-5 | an-86 |
| 1A1595 | sp-5 | an-87 | 1U1595 | sp-5 | an-87 | 1C1595 | sp-5 | an-87 |
| 1A1596 | sp-5 | an-88 | 1U1596 | sp-5 | an-88 | 1C1596 | sp-5 | an-88 |
| 1A1597 | sp-5 | an-89 | 1U1597 | sp-5 | an-89 | 1C1597 | sp-5 | an-89 |

TABLE 1-continued

| | | | | | | | | |
|---|---|---|---|---|---|---|---|---|
| 1A1598 | sp-5 | an-90 | 1U1598 | sp-5 | an-90 | 1C1598 | sp-5 | an-90 |
| 1A1599 | sp-5 | an-91 | 1U1599 | sp-5 | an-91 | 1C1599 | sp-5 | an-91 |
| 1A1600 | sp-5 | an-92 | 1U1600 | sp-5 | an-92 | 1C1600 | sp-5 | an-92 |
| 1A1601 | sp-5 | an-93 | 1U1601 | sp-5 | an-93 | 1C1601 | sp-5 | an-93 |
| 1A1602 | sp-5 | an-94 | 1U1602 | sp-5 | an-94 | 1C1602 | sp-5 | an-94 |
| 1A1603 | sp-5 | an-95 | 1U1603 | sp-5 | an-95 | 1C1603 | sp-5 | an-95 |
| 1A1604 | sp-5 | an-96 | 1U1604 | sp-5 | an-96 | 1C1604 | sp-5 | an-96 |
| 1A1605 | sp-5 | an-97 | 1U1605 | sp-5 | an-97 | 1C1605 | sp-5 | an-97 |
| 1A1606 | sp-5 | an-98 | 1U1606 | sp-5 | an-98 | 1C1606 | sp-5 | an-98 |
| 1A1607 | sp-5 | an-99 | 1U1607 | sp-5 | an-99 | 1C1607 | sp-5 | an-99 |
| 1A1608 | sp-5 | an-100 | 1U1608 | sp-5 | an-100 | 1C1608 | sp-5 | an-100 |
| 1A1609 | sp-5 | an-101 | 1U1609 | sp-5 | an-101 | 1C1609 | sp-5 | an-101 |
| 1A1610 | sp-5 | an-102 | 1U1610 | sp-5 | an-102 | 1C1610 | sp-5 | an-102 |
| 1A1611 | sp-5 | an-103 | 1U1611 | sp-5 | an-103 | 1C1611 | sp-5 | an-103 |
| 1A1612 | sp-5 | an-104 | 1U1612 | sp-5 | an-104 | 1C1612 | sp-5 | an-104 |
| 1A1613 | sp-5 | an-105 | 1U1613 | sp-5 | an-105 | 1C1613 | sp-5 | an-105 |
| 1A1614 | sp-5 | an-106 | 1U1614 | sp-5 | an-106 | 1C1614 | sp-5 | an-106 |
| 1A1615 | sp-5 | an-107 | 1U1615 | sp-5 | an-107 | 1C1615 | sp-5 | an-107 |
| 1A1616 | sp-5 | an-108 | 1U1616 | sp-5 | an-108 | 1C1616 | sp-5 | an-108 |
| 1A1617 | sp-5 | an-109 | 1U1617 | sp-5 | an-109 | 1C1617 | sp-5 | an-109 |
| 1A1618 | sp-5 | an-110 | 1U1618 | sp-5 | an-110 | 1C1618 | sp-5 | an-110 |
| 1A1619 | sp-5 | an-111 | 1U1619 | sp-5 | an-111 | 1C1619 | sp-5 | an-111 |
| 1A1620 | sp-5 | an-112 | 1U1620 | sp-5 | an-112 | 1C1620 | sp-5 | an-112 |
| 1A1621 | sp-5 | an-113 | 1U1621 | sp-5 | an-113 | 1C1621 | sp-5 | an-113 |
| 1A1622 | sp-5 | an-114 | 1U1622 | sp-5 | an-114 | 1C1622 | sp-5 | an-114 |
| 1A1623 | sp-5 | an-115 | 1U1623 | sp-5 | an-115 | 1C1623 | sp-5 | an-115 |
| 1A1624 | sp-5 | an-116 | 1U1624 | sp-5 | an-116 | 1C1624 | sp-5 | an-116 |
| 1A1625 | sp-5 | an-117 | 1U1625 | sp-5 | an-117 | 1C1625 | sp-5 | an-117 |
| 1A1626 | sp-5 | an-118 | 1U1626 | sp-5 | an-118 | 1C1626 | sp-5 | an-118 |
| 1A1627 | sp-5 | an-119 | 1U1627 | sp-5 | an-119 | 1C1627 | sp-5 | an-119 |
| 1A1628 | sp-5 | an-120 | 1U1628 | sp-5 | an-120 | 1C1628 | sp-5 | an-120 |
| 1A1629 | sp-5 | an-121 | 1U1629 | sp-5 | an-121 | 1C1629 | sp-5 | an-121 |
| 1A1630 | sp-5 | an-122 | 1U1630 | sp-5 | an-122 | 1C1630 | sp-5 | an-122 |
| 1A1631 | sp-5 | an-123 | 1U1631 | sp-5 | an-123 | 1C1631 | sp-5 | an-123 |
| 1A1632 | sp-5 | an-124 | 1U1632 | sp-5 | an-124 | 1C1632 | sp-5 | an-124 |
| 1A1633 | sp-5 | an-125 | 1U1633 | sp-5 | an-125 | 1C1633 | sp-5 | an-125 |
| 1A1634 | sp-5 | an-126 | 1U1634 | sp-5 | an-126 | 1C1634 | sp-5 | an-126 |
| 1A1635 | sp-5 | an-127 | 1U1635 | sp-5 | an-127 | 1C1635 | sp-5 | an-127 |
| 1A1636 | sp-5 | an-128 | 1U1636 | sp-5 | an-128 | 1C1636 | sp-5 | an-128 |
| 1A1637 | sp-5 | an-129 | 1U1637 | sp-5 | an-129 | 1C1637 | sp-5 | an-129 |
| 1A1638 | sp-5 | an-130 | 1U1638 | sp-5 | an-130 | 1C1638 | sp-5 | an-130 |
| 1A1639 | sp-5 | an-131 | 1U1639 | sp-5 | an-131 | 1C1639 | sp-5 | an-131 |
| 1A1640 | sp-5 | an-132 | 1U1640 | sp-5 | an-132 | 1C1640 | sp-5 | an-132 |
| 1A1641 | sp-5 | an-133 | 1U1641 | sp-5 | an-133 | 1C1641 | sp-5 | an-133 |
| 1A1642 | sp-5 | an-134 | 1U1642 | sp-5 | an-134 | 1C1642 | sp-5 | an-134 |
| 1A1643 | sp-5 | an-135 | 1U1643 | sp-5 | an-135 | 1C1643 | sp-5 | an-135 |
| 1A1644 | sp-5 | an-136 | 1U1644 | sp-5 | an-136 | 1C1644 | sp-5 | an-136 |
| 1A1645 | sp-5 | an-137 | 1U1645 | sp-5 | an-137 | 1C1645 | sp-5 | an-137 |
| 1A1646 | sp-5 | an-138 | 1U1646 | sp-5 | an-138 | 1C1646 | sp-5 | an-138 |
| 1A1647 | sp-5 | an-139 | 1U1647 | sp-5 | an-139 | 1C1647 | sp-5 | an-139 |
| 1A1648 | sp-5 | an-140 | 1U1648 | sp-5 | an-140 | 1C1648 | sp-5 | an-140 |
| 1A1649 | sp-5 | an-141 | 1U1649 | sp-5 | an-141 | 1C1649 | sp-5 | an-141 |
| 1A1650 | sp-5 | an-142 | 1U1650 | sp-5 | an-142 | 1C1650 | sp-5 | an-142 |
| 1A1651 | sp-5 | an-143 | 1U1651 | sp-5 | an-143 | 1C1651 | sp-5 | an-143 |
| 1A1652 | sp-5 | an-144 | 1U1652 | sp-5 | an-144 | 1C1652 | sp-5 | an-144 |
| 1A1653 | sp-5 | an-145 | 1U1653 | sp-5 | an-145 | 1C1653 | sp-5 | an-145 |
| 1A1654 | sp-5 | an-146 | 1U1654 | sp-5 | an-146 | 1C1654 | sp-5 | an-146 |
| 1A1655 | sp-5 | an-147 | 1U1655 | sp-5 | an-147 | 1C1655 | sp-5 | an-147 |
| 1A1656 | sp-5 | an-148 | 1U1656 | sp-5 | an-148 | 1C1656 | sp-5 | an-148 |
| 1A1657 | sp-5 | an-149 | 1U1657 | sp-5 | an-149 | 1C1657 | sp-5 | an-149 |
| 1A1658 | sp-5 | an-150 | 1U1658 | sp-5 | an-150 | 1C1658 | sp-5 | an-150 |
| 1A1659 | sp-5 | an-151 | 1U1659 | sp-5 | an-151 | 1C1659 | sp-5 | an-151 |
| 1A1660 | sp-5 | an-152 | 1U1660 | sp-5 | an-152 | 1C1660 | sp-5 | an-152 |
| 1A1661 | sp-5 | an-153 | 1U1661 | sp-5 | an-153 | 1C1661 | sp-5 | an-153 |
| 1A1662 | sp-5 | an-154 | 1U1662 | sp-5 | an-154 | 1C1662 | sp-5 | an-154 |
| 1A1663 | sp-5 | an-155 | 1U1663 | sp-5 | an-155 | 1C1663 | sp-5 | an-155 |
| 1A1664 | sp-5 | an-156 | 1U1664 | sp-5 | an-156 | 1C1664 | sp-5 | an-156 |
| 1A1665 | sp-5 | an-157 | 1U1665 | sp-5 | an-157 | 1C1665 | sp-5 | an-157 |
| 1A1666 | sp-5 | an-158 | 1U1666 | sp-5 | an-158 | 1C1666 | sp-5 | an-158 |
| 1A1667 | sp-5 | an-159 | 1U1667 | sp-5 | an-159 | 1C1667 | sp-5 | an-159 |
| 1A1668 | sp-5 | an-160 | 1U1668 | sp-5 | an-160 | 1C1668 | sp-5 | an-160 |
| 1A1669 | sp-5 | an-161 | 1U1669 | sp-5 | an-161 | 1C1669 | sp-5 | an-161 |
| 1A1670 | sp-5 | an-162 | 1U1670 | sp-5 | an-162 | 1C1670 | sp-5 | an-162 |
| 1A1671 | sp-5 | an-163 | 1U1671 | sp-5 | an-163 | 1C1671 | sp-5 | an-163 |
| 1A1672 | sp-5 | an-164 | 1U1672 | sp-5 | an-164 | 1C1672 | sp-5 | an-164 |
| 1A1673 | sp-5 | an-165 | 1U1673 | sp-5 | an-165 | 1C1673 | sp-5 | an-165 |
| 1A1674 | sp-5 | an-166 | 1U1674 | sp-5 | an-166 | 1C1674 | sp-5 | an-166 |
| 1A1675 | sp-5 | an-167 | 1U1675 | sp-5 | an-167 | 1C1675 | sp-5 | an-167 |
| 1A1676 | sp-5 | an-168 | 1U1676 | sp-5 | an-168 | 1C1676 | sp-5 | an-168 |

TABLE 1-continued

| | | | | | | | | |
|---|---|---|---|---|---|---|---|---|
| 1A1677 | sp-5 | an-169 | 1U1677 | sp-5 | an-169 | 1C1677 | sp-5 | an-169 |
| 1A1678 | sp-5 | an-170 | 1U1678 | sp-5 | an-170 | 1C1678 | sp-5 | an-170 |
| 1A1679 | sp-5 | an-171 | 1U1679 | sp-5 | an-171 | 1C1679 | sp-5 | an-171 |
| 1A1680 | sp-5 | an-172 | 1U1680 | sp-5 | an-172 | 1C1680 | sp-5 | an-172 |
| 1A1681 | sp-5 | an-173 | 1U1681 | sp-5 | an-173 | 1C1681 | sp-5 | an-173 |
| 1A1682 | sp-5 | an-174 | 1U1682 | sp-5 | an-174 | 1C1682 | sp-5 | an-174 |
| 1A1683 | sp-5 | an-175 | 1U1683 | sp-5 | an-175 | 1C1683 | sp-5 | an-175 |
| 1A1684 | sp-5 | an-176 | 1U1684 | sp-5 | an-176 | 1C1684 | sp-5 | an-176 |
| 1A1685 | sp-5 | an-177 | 1U1685 | sp-5 | an-177 | 1C1685 | sp-5 | an-177 |
| 1A1686 | sp-5 | an-178 | 1U1686 | sp-5 | an-178 | 1C1686 | sp-5 | an-178 |
| 1A1687 | sp-5 | an-179 | 1U1687 | sp-5 | an-179 | 1C1687 | sp-5 | an-179 |
| 1A1688 | sp-5 | an-180 | 1U1688 | sp-5 | an-180 | 1C1688 | sp-5 | an-180 |
| 1A1689 | sp-5 | an-181 | 1U1689 | sp-5 | an-181 | 1C1689 | sp-5 | an-181 |
| 1A1690 | sp-5 | an-182 | 1U1690 | sp-5 | an-182 | 1C1690 | sp-5 | an-182 |
| 1A1691 | sp-5 | an-183 | 1U1691 | sp-5 | an-183 | 1C1691 | sp-5 | an-183 |
| 1A1692 | sp-5 | an-184 | 1U1692 | sp-5 | an-184 | 1C1692 | sp-5 | an-184 |
| 1A1693 | sp-5 | an-185 | 1U1693 | sp-5 | an-185 | 1C1693 | sp-5 | an-185 |
| 1A1694 | sp-5 | an-186 | 1U1694 | sp-5 | an-186 | 1C1694 | sp-5 | an-186 |
| 1A1695 | sp-5 | an-187 | 1U1695 | sp-5 | an-187 | 1C1695 | sp-5 | an-187 |
| 1A1696 | sp-5 | an-188 | 1U1696 | sp-5 | an-188 | 1C1696 | sp-5 | an-188 |
| 1A1697 | sp-5 | an-189 | 1U1697 | sp-5 | an-189 | 1C1697 | sp-5 | an-189 |
| 1A1698 | sp-5 | an-190 | 1U1698 | sp-5 | an-190 | 1C1698 | sp-5 | an-190 |
| 1A1699 | sp-5 | an-191 | 1U1699 | sp-5 | an-191 | 1C1699 | sp-5 | an-191 |
| 1A1700 | sp-5 | an-192 | 1U1700 | sp-5 | an-192 | 1C1700 | sp-5 | an-192 |
| 1A1701 | sp-5 | an-193 | 1U1701 | sp-5 | an-193 | 1C1701 | sp-5 | an-193 |
| 1A1702 | sp-5 | an-194 | 1U1702 | sp-5 | an-194 | 1C1702 | sp-5 | an-194 |
| 1A1703 | sp-5 | an-195 | 1U1703 | sp-5 | an-195 | 1C1703 | sp-5 | an-195 |
| 1A1704 | sp-5 | an-196 | 1U1704 | sp-5 | an-196 | 1C1704 | sp-5 | an-196 |
| 1A1705 | sp-5 | an-197 | 1U1705 | sp-5 | an-197 | 1C1705 | sp-5 | an-197 |
| 1A1706 | sp-5 | an-198 | 1U1706 | sp-5 | an-198 | 1C1706 | sp-5 | an-198 |
| 1A1707 | sp-5 | an-199 | 1U1707 | sp-5 | an-199 | 1C1707 | sp-5 | an-199 |
| 1A1708 | sp-5 | an-200 | 1U1708 | sp-5 | an-200 | 1C1708 | sp-5 | an-200 |
| 1A1709 | sp-5 | an-201 | 1U1709 | sp-5 | an-201 | 1C1709 | sp-5 | an-201 |
| 1A1710 | sp-5 | an-202 | 1U1710 | sp-5 | an-202 | 1C1710 | sp-5 | an-202 |
| 1A1711 | sp-5 | an-203 | 1U1711 | sp-5 | an-203 | 1C1711 | sp-5 | an-203 |
| 1A1712 | sp-5 | an-204 | 1U1712 | sp-5 | an-204 | 1C1712 | sp-5 | an-204 |
| 1A1713 | sp-5 | an-205 | 1U1713 | sp-5 | an-205 | 1C1713 | sp-5 | an-205 |
| 1A1714 | sp-5 | an-206 | 1U1714 | sp-5 | an-206 | 1C1714 | sp-5 | an-206 |
| 1A1715 | sp-5 | an-207 | 1U1715 | sp-5 | an-207 | 1C1715 | sp-5 | an-207 |
| 1A1716 | sp-5 | an-208 | 1U1716 | sp-5 | an-208 | 1C1716 | sp-5 | an-208 |
| 1A1717 | sp-5 | an-209 | 1U1717 | sp-5 | an-209 | 1C1717 | sp-5 | an-209 |
| 1A1718 | sp-5 | an-210 | 1U1718 | sp-5 | an-210 | 1C1718 | sp-5 | an-210 |
| 1A1719 | sp-5 | an-211 | 1U1719 | sp-5 | an-211 | 1C1719 | sp-5 | an-211 |
| 1A1720 | sp-5 | an-212 | 1U1720 | sp-5 | an-212 | 1C1720 | sp-5 | an-212 |
| 1A1721 | sp-5 | an-213 | 1U1721 | sp-5 | an-213 | 1C1721 | sp-5 | an-213 |
| 1A1722 | sp-5 | an-214 | 1U1722 | sp-5 | an-214 | 1C1722 | sp-5 | an-214 |
| 1A1723 | sp-5 | an-215 | 1U1723 | sp-5 | an-215 | 1C1723 | sp-5 | an-215 |
| 1A1724 | sp-5 | an-216 | 1U1724 | sp-5 | an-216 | 1C1724 | sp-5 | an-216 |
| 1A1725 | sp-5 | an-217 | 1U1725 | sp-5 | an-217 | 1C1725 | sp-5 | an-217 |
| 1A1726 | sp-5 | an-218 | 1U1726 | sp-5 | an-218 | 1C1726 | sp-5 | an-218 |
| 1A1727 | sp-5 | an-219 | 1U1727 | sp-5 | an-219 | 1C1727 | sp-5 | an-219 |
| 1A1728 | sp-5 | an-220 | 1U1728 | sp-5 | an-220 | 1C1728 | sp-5 | an-220 |
| 1A1729 | sp-5 | an-221 | 1U1729 | sp-5 | an-221 | 1C1729 | sp-5 | an-221 |
| 1A1730 | sp-5 | an-222 | 1U1730 | sp-5 | an-222 | 1C1730 | sp-5 | an-222 |
| 1A1731 | sp-5 | an-223 | 1U1731 | sp-5 | an-223 | 1C1731 | sp-5 | an-223 |
| 1A1732 | sp-5 | an-224 | 1U1732 | sp-5 | an-224 | 1C1732 | sp-5 | an-224 |
| 1A1733 | sp-5 | an-225 | 1U1733 | sp-5 | an-225 | 1C1733 | sp-5 | an-225 |
| 1A1734 | sp-5 | an-226 | 1U1734 | sp-5 | an-226 | 1C1734 | sp-5 | an-226 |
| 1A1735 | sp-5 | an-227 | 1U1735 | sp-5 | an-227 | 1C1735 | sp-5 | an-227 |
| 1A1736 | sp-5 | an-228 | 1U1736 | sp-5 | an-228 | 1C1736 | sp-5 | an-228 |
| 1A1737 | sp-5 | an-229 | 1U1737 | sp-5 | an-229 | 1C1737 | sp-5 | an-229 |
| 1A1738 | sp-5 | an-230 | 1U1738 | sp-5 | an-230 | 1C1738 | sp-5 | an-230 |
| 1A1739 | sp-5 | an-231 | 1U1739 | sp-5 | an-231 | 1C1739 | sp-5 | an-231 |
| 1A1740 | sp-5 | an-232 | 1U1740 | sp-5 | an-232 | 1C1740 | sp-5 | an-232 |
| 1A1741 | sp-5 | an-233 | 1U1741 | sp-5 | an-233 | 1C1741 | sp-5 | an-233 |
| 1A1742 | sp-5 | an-234 | 1U1742 | sp-5 | an-234 | 1C1742 | sp-5 | an-234 |
| 1A1743 | sp-5 | an-235 | 1U1743 | sp-5 | an-235 | 1C1743 | sp-5 | an-235 |
| 1A1744 | sp-5 | an-236 | 1U1744 | sp-5 | an-236 | 1C1744 | sp-5 | an-236 |
| 1A1745 | sp-5 | an-237 | 1U1745 | sp-5 | an-237 | 1C1745 | sp-5 | an-237 |
| 1A1746 | sp-5 | an-238 | 1U1746 | sp-5 | an-238 | 1C1746 | sp-5 | an-238 |
| 1A1747 | sp-5 | an-239 | 1U1747 | sp-5 | an-239 | 1C1747 | sp-5 | an-239 |
| 1A1748 | sp-5 | an-240 | 1U1748 | sp-5 | an-240 | 1C1748 | sp-5 | an-240 |
| 1A1749 | sp-5 | an-241 | 1U1749 | sp-5 | an-241 | 1C1749 | sp-5 | an-241 |
| 1A1750 | sp-5 | an-242 | 1U1750 | sp-5 | an-242 | 1C1750 | sp-5 | an-242 |
| 1A1751 | sp-5 | an-243 | 1U1751 | sp-5 | an-243 | 1C1751 | sp-5 | an-243 |
| 1A1752 | sp-5 | an-244 | 1U1752 | sp-5 | an-244 | 1C1752 | sp-5 | an-244 |
| 1A1753 | sp-5 | an-245 | 1U1753 | sp-5 | an-245 | 1C1753 | sp-5 | an-245 |
| 1A1754 | sp-5 | an-246 | 1U1754 | sp-5 | an-246 | 1C1754 | sp-5 | an-246 |
| 1A1755 | sp-5 | an-247 | 1U1755 | sp-5 | an-247 | 1C1755 | sp-5 | an-247 |

TABLE 1-continued

| | | | | | | | | |
|---|---|---|---|---|---|---|---|---|
| 1A1756 | sp-5 | an-248 | 1U1756 | sp-5 | an-248 | 1C1756 | sp-5 | an-248 |
| 1A1757 | sp-5 | an-249 | 1U1757 | sp-5 | an-249 | 1C1757 | sp-5 | an-249 |
| 1A1758 | sp-5 | an-250 | 1U1758 | sp-5 | an-250 | 1C1758 | sp-5 | an-250 |
| 1A1759 | sp-5 | an-251 | 1U1759 | sp-5 | an-251 | 1C1759 | sp-5 | an-251 |
| 1A1760 | sp-5 | an-252 | 1U1760 | sp-5 | an-252 | 1C1760 | sp-5 | an-252 |
| 1A1761 | sp-5 | an-253 | 1U1761 | sp-5 | an-253 | 1C1761 | sp-5 | an-253 |
| 1A1762 | sp-5 | an-254 | 1U1762 | sp-5 | an-254 | 1C1762 | sp-5 | an-254 |
| 1A1763 | sp-5 | an-255 | 1U1763 | sp-5 | an-255 | 1C1763 | sp-5 | an-255 |
| 1A1764 | sp-5 | an-256 | 1U1764 | sp-5 | an-256 | 1C1764 | sp-5 | an-256 |
| 1A1765 | sp-5 | an-257 | 1U1765 | sp-5 | an-257 | 1C1765 | sp-5 | an-257 |
| 1A1766 | sp-5 | an-258 | 1U1766 | sp-5 | an-258 | 1C1766 | sp-5 | an-258 |
| 1A1767 | sp-5 | an-259 | 1U1767 | sp-5 | an-259 | 1C1767 | sp-5 | an-259 |
| 1A1768 | sp-5 | an-260 | 1U1768 | sp-5 | an-260 | 1C1768 | sp-5 | an-260 |
| 1A1769 | sp-5 | an-261 | 1U1769 | sp-5 | an-261 | 1C1769 | sp-5 | an-261 |
| 1A1770 | sp-5 | an-262 | 1U1770 | sp-5 | an-262 | 1C1770 | sp-5 | an-262 |
| 1A1771 | sp-5 | an-263 | 1U1771 | sp-5 | an-263 | 1C1771 | sp-5 | an-263 |
| 1A1772 | sp-5 | an-264 | 1U1772 | sp-5 | an-264 | 1C1772 | sp-5 | an-264 |
| 1A1773 | sp-5 | an-265 | 1U1773 | sp-5 | an-265 | 1C1773 | sp-5 | an-265 |
| 1A1774 | sp-5 | an-266 | 1U1774 | sp-5 | an-266 | 1C1774 | sp-5 | an-266 |
| 1A1775 | sp-5 | an-267 | 1U1775 | sp-5 | an-267 | 1C1775 | sp-5 | an-267 |
| 1A1776 | sp-5 | an-268 | 1U1776 | sp-5 | an-268 | 1C1776 | sp-5 | an-268 |
| 1A1777 | sp-5 | an-269 | 1U1777 | sp-5 | an-269 | 1C1777 | sp-5 | an-269 |
| 1A1778 | sp-5 | an-270 | 1U1778 | sp-5 | an-270 | 1C1778 | sp-5 | an-270 |
| 1A1779 | sp-5 | an-271 | 1U1779 | sp-5 | an-271 | 1C1779 | sp-5 | an-271 |
| 1A1780 | sp-5 | an-272 | 1U1780 | sp-5 | an-272 | 1C1780 | sp-5 | an-272 |
| 1A1781 | sp-5 | an-273 | 1U1781 | sp-5 | an-273 | 1C1781 | sp-5 | an-273 |
| 1A1782 | sp-5 | an-274 | 1U1782 | sp-5 | an-274 | 1C1782 | sp-5 | an-274 |
| 1A1783 | sp-5 | an-275 | 1U1783 | sp-5 | an-275 | 1C1783 | sp-5 | an-275 |
| 1A1784 | sp-5 | an-276 | 1U1784 | sp-5 | an-276 | 1C1784 | sp-5 | an-276 |
| 1A1785 | sp-5 | an-277 | 1U1785 | sp-5 | an-277 | 1C1785 | sp-5 | an-277 |
| 1A1786 | sp-5 | an-278 | 1U1786 | sp-5 | an-278 | 1C1786 | sp-5 | an-278 |
| 1A1787 | sp-5 | an-279 | 1U1787 | sp-5 | an-279 | 1C1787 | sp-5 | an-279 |
| 1A1788 | sp-5 | an-280 | 1U1788 | sp-5 | an-280 | 1C1788 | sp-5 | an-280 |
| 1A1789 | sp-5 | an-281 | 1U1789 | sp-5 | an-281 | 1C1789 | sp-5 | an-281 |
| 1A1790 | sp-5 | an-282 | 1U1790 | sp-5 | an-282 | 1C1790 | sp-5 | an-282 |
| 1A1791 | sp-5 | an-283 | 1U1791 | sp-5 | an-283 | 1C1791 | sp-5 | an-283 |
| 1A1792 | sp-5 | an-284 | 1U1792 | sp-5 | an-284 | 1C1792 | sp-5 | an-234 |
| 1A1793 | sp-5 | an-285 | 1U1793 | sp-5 | an-285 | 1C1793 | sp-5 | an-285 |
| 1A1794 | sp-5 | an-286 | 1U1794 | sp-5 | an-286 | 1C1794 | sp-5 | an-286 |
| 1A1795 | sp-5 | an-287 | 1U1795 | sp-5 | an-287 | 1C1795 | sp-5 | an-287 |
| 1A1796 | sp-5 | an-288 | 1U1796 | sp-5 | an-288 | 1C1796 | sp-5 | an-288 |
| 1A1797 | sp-5 | an-289 | 1U1797 | sp-5 | an-289 | 1C1797 | sp-5 | an-289 |
| 1A1798 | sp-5 | an-290 | 1U1798 | sp-5 | an-290 | 1C1798 | sp-5 | an-290 |
| 1A1799 | sp-5 | an-291 | 1U1799 | sp-5 | an-291 | 1C1799 | sp-5 | an-291 |
| 1A1800 | sp-5 | an-292 | 1U1800 | sp-5 | an-292 | 1C1800 | sp-5 | an-292 |
| 1A1801 | sp-5 | an-293 | 1U1801 | sp-5 | an-293 | 1C1801 | sp-5 | an-293 |
| 1A1802 | sp-5 | an-294 | 1U1802 | sp-5 | an-294 | 1C1802 | sp-5 | an-294 |
| 1A1803 | sp-5 | an-295 | 1U1803 | sp-5 | an-295 | 1C1803 | sp-5 | an-295 |
| 1A1804 | sp-5 | an-296 | 1U1804 | sp-5 | an-296 | 1C1804 | sp-5 | an-296 |
| 1A1805 | sp-5 | an-297 | 1U1805 | sp-5 | an-297 | 1C1805 | sp-5 | an-297 |
| 1A1806 | sp-5 | an-298 | 1U1806 | sp-5 | an-298 | 1C1806 | sp-5 | an-298 |
| 1A1807 | sp-5 | an-299 | 1U1807 | sp-5 | an-299 | 1C1807 | sp-5 | an-299 |
| 1A1808 | sp-5 | an-300 | 1U1808 | sp-5 | an-300 | 1C1808 | sp-5 | an-300 |
| 1A1809 | sp-5 | an-301 | 1U1809 | sp-5 | an-301 | 1C1809 | sp-5 | an-301 |
| 1A1810 | sp-5 | an-302 | 1U1810 | sp-5 | an-302 | 1C1810 | sp-5 | an-302 |
| 1A1811 | sp-5 | an-303 | 1U1811 | sp-5 | an-303 | 1C1811 | sp-5 | an-303 |
| 1A1812 | sp-5 | an-304 | 1U1812 | sp-5 | an-304 | 1C1812 | sp-5 | an-304 |
| 1A1813 | sp-5 | an-305 | 1U1813 | sp-5 | an-305 | 1C1813 | sp-5 | an-305 |
| 1A1814 | sp-5 | an-306 | 1U1814 | sp-5 | an-306 | 1C1814 | sp-5 | an-306 |
| 1A1815 | sp-5 | an-307 | 1U1815 | sp-5 | an-307 | 1C1815 | sp-5 | an-307 |
| 1A1816 | sp-5 | an-308 | 1U1816 | sp-5 | an-308 | 1C1816 | sp-5 | an-308 |
| 1A1817 | sp-5 | an-309 | 1U1817 | sp-5 | an-309 | 1C1817 | sp-5 | an-309 |
| 1A1818 | sp-5 | an-310 | 1U1818 | sp-5 | an-310 | 1C1818 | sp-5 | an-310 |
| 1A1819 | sp-5 | an-311 | 1U1819 | sp-5 | an-311 | 1C1819 | sp-5 | an-311 |
| 1A1820 | sp-5 | an-312 | 1U1820 | sp-5 | an-312 | 1C1820 | sp-5 | an-312 |
| 1A1821 | sp-5 | an-313 | 1U1821 | sp-5 | an-313 | 1C1821 | sp-5 | an-313 |
| 1A1822 | sp-5 | an-314 | 1U1822 | sp-5 | an-314 | 1C1822 | sp-5 | an-314 |
| 1A1823 | sp-5 | an-315 | 1U1823 | sp-5 | an-315 | 1C1823 | sp-5 | an-315 |
| 1A1824 | sp-5 | an-316 | 1U1824 | sp-5 | an-316 | 1C1824 | sp-5 | an-316 |
| 1A1825 | sp-5 | an-317 | 1U1825 | sp-5 | an-317 | 1C1825 | sp-5 | an-317 |
| 1A1826 | sp-5 | an-318 | 1U1826 | sp-5 | an-318 | 1C1826 | sp-5 | an-318 |
| 1A1827 | sp-5 | an-319 | 1U1827 | sp-5 | an-319 | 1C1827 | sp-5 | an-319 |
| 1A1828 | sp-5 | an-320 | 1U1828 | sp-5 | an-320 | 1C1828 | sp-5 | an-320 |
| 1A1829 | sp-5 | an-321 | 1U1829 | sp-5 | an-321 | 1C1829 | sp-5 | an-321 |
| 1A1830 | sp-5 | an-322 | 1U1830 | sp-5 | an-322 | 1C1830 | sp-5 | an-322 |
| 1A1831 | sp-5 | an-323 | 1U1831 | sp-5 | an-323 | 1C1831 | sp-5 | an-323 |
| 1A1832 | sp-5 | an-324 | 1U1832 | sp-5 | an-324 | 1C1832 | sp-5 | an-324 |
| 1A1833 | sp-5 | an-325 | 1U1833 | sp-5 | an-325 | 1C1833 | sp-5 | an-325 |
| 1A1834 | sp-5 | an-326 | 1U1834 | sp-5 | an-326 | 1C1834 | sp-5 | an-326 |

TABLE 1-continued

| | | | | | | | | |
|---|---|---|---|---|---|---|---|---|
| 1A1835 | sp-5 | an-327 | 1U1835 | sp-5 | an-327 | 1C1835 | sp-5 | an-327 |
| 1A1836 | sp-5 | an-328 | 1U1836 | sp-5 | an-328 | 1C1836 | sp-5 | an-328 |
| 1A1837 | sp-5 | an-329 | 1U1837 | sp-5 | an-329 | 1C1837 | sp-5 | an-329 |
| 1A1838 | sp-5 | an-330 | 1U1838 | sp-5 | an-330 | 1C1838 | sp-5 | an-330 |
| 1A1839 | sp-5 | an-331 | 1U1839 | sp-5 | an-331 | 1C1839 | sp-5 | an-331 |
| 1A1840 | sp-5 | an-332 | 1U1840 | sp-5 | an-332 | 1C1840 | sp-5 | an-332 |
| 1A1841 | sp-5 | an-333 | 1U1841 | sp-5 | an-333 | 1C1841 | sp-5 | an-333 |
| 1A1842 | sp-5 | an-334 | 1U1842 | sp-5 | an-334 | 1C1842 | sp-5 | an-334 |
| 1A1843 | sp-5 | an-335 | 1U1843 | sp-5 | an-335 | 1C1843 | sp-5 | an-335 |
| 1A1844 | sp-5 | an-336 | 1U1844 | sp-5 | an-336 | 1C1844 | sp-5 | an-336 |
| 1A1845 | sp-5 | an-337 | 1U1845 | sp-5 | an-337 | 1C1845 | sp-5 | an-337 |
| 1A1846 | sp-5 | an-338 | 1U1846 | sp-5 | an-338 | 1C1846 | sp-5 | an-338 |
| 1A1847 | sp-5 | an-339 | 1U1847 | sp-5 | an-339 | 1C1847 | sp-5 | an-339 |
| 1A1848 | sp-5 | an-340 | 1U1848 | sp-5 | an-340 | 1C1848 | sp-5 | an-340 |
| 1A1849 | sp-5 | an-341 | 1U1849 | sp-5 | an-341 | 1C1849 | sp-5 | an-341 |
| 1A1850 | sp-5 | an-342 | 1U1850 | sp-5 | an-342 | 1C1850 | sp-5 | an-342 |
| 1A1851 | sp-5 | an-343 | 1U1851 | sp-5 | an-343 | 1C1851 | sp-5 | an-343 |
| 1A1852 | sp-5 | an-344 | 1U1852 | sp-5 | an-344 | 1C1852 | sp-5 | an-344 |
| 1A1853 | sp-5 | an-345 | 1U1853 | sp-5 | an-345 | 1C1853 | sp-5 | an-345 |
| 1A1854 | sp-5 | an-346 | 1U1854 | sp-5 | an-346 | 1C1854 | sp-5 | an-346 |
| 1A1855 | sp-5 | an-347 | 1U1855 | sp-5 | an-347 | 1C1855 | sp-5 | an-347 |
| 1A1856 | sp-5 | an-348 | 1U1856 | sp-5 | an-348 | 1C1856 | sp-5 | an-348 |
| 1A1857 | sp-5 | an-349 | 1U1857 | sp-5 | an-349 | 1C1857 | sp-5 | an-349 |
| 1A1858 | sp-5 | an-350 | 1U1858 | sp-5 | an-350 | 1C1858 | sp-5 | an-350 |
| 1A1859 | sp-5 | an-351 | 1U1859 | sp-5 | an-351 | 1C1859 | sp-5 | an-351 |
| 1A1860 | sp-5 | an-352 | 1U1860 | sp-5 | an-352 | 1C1860 | sp-5 | an-352 |
| 1A1861 | sp-5 | an-353 | 1U1861 | sp-5 | an-353 | 1C1861 | sp-5 | an-353 |
| 1A1862 | sp-5 | an-354 | 1U1862 | sp-5 | an-354 | 1C1862 | sp-5 | an-354 |
| 1A1863 | sp-5 | an-355 | 1U1863 | sp-5 | an-355 | 1C1863 | sp-5 | an-355 |
| 1A1864 | sp-5 | an-356 | 1U1864 | sp-5 | an-356 | 1C1864 | sp-5 | an-356 |
| 1A1865 | sp-5 | an-357 | 1U1865 | sp-5 | an-357 | 1C1865 | sp-5 | an-357 |
| 1A1866 | sp-5 | an-358 | 1U1866 | sp-5 | an-358 | 1C1866 | sp-5 | an-358 |
| 1A1867 | sp-5 | an-359 | 1U1867 | sp-5 | an-359 | 1C1867 | sp-5 | an-359 |
| 1A1868 | sp-5 | an-360 | 1U1868 | sp-5 | an-360 | 1C1868 | sp-5 | an-360 |
| 1A1869 | sp-5 | an-361 | 1U1869 | sp-5 | an-361 | 1C1869 | sp-5 | an-361 |
| 1A1870 | sp-5 | an-362 | 1U1870 | sp-5 | an-362 | 1C1870 | sp-5 | an-362 |
| 1A1871 | sp-5 | an-363 | 1U1871 | sp-5 | an-363 | 1C1871 | sp-5 | an-363 |
| 1A1872 | sp-5 | an-364 | 1U1872 | sp-5 | an-364 | 1C1872 | sp-5 | an-364 |
| 1A1873 | sp-5 | an-365 | 1U1873 | sp-5 | an-365 | 1C1873 | sp-5 | an-365 |
| 1A1874 | sp-5 | an-366 | 1U1874 | sp-5 | an-366 | 1C1874 | sp-5 | an-366 |
| 1A1875 | sp-5 | an-367 | 1U1875 | sp-5 | an-367 | 1C1875 | sp-5 | an-367 |
| 1A1876 | sp-5 | an-368 | 1U1876 | sp-5 | an-368 | 1C1876 | sp-5 | an-368 |
| 1A1877 | sp-5 | an-369 | 1U1877 | sp-5 | an-369 | 1C1877 | sp-5 | an-369 |
| 1A1878 | sp-5 | an-370 | 1U1878 | sp-5 | an-370 | 1C1878 | sp-5 | an-370 |
| 1A1879 | sp-5 | an-371 | 1U1879 | sp-5 | an-371 | 1C1879 | sp-5 | an-371 |
| 1A1880 | sp-5 | an-372 | 1U1880 | sp-5 | an-372 | 1C1880 | sp-5 | an-372 |
| 1A1881 | sp-5 | an-373 | 1U1881 | sp-5 | an-373 | 1C1881 | sp-5 | an-373 |
| 1A1882 | sp-5 | an-374 | 1U1882 | sp-5 | an-374 | 1C1882 | sp-5 | an-374 |
| 1A1883 | sp-5 | an-375 | 1U1883 | sp-5 | an-375 | 1C1883 | sp-5 | an-375 |
| 1A1884 | sp-5 | an-376 | 1U1884 | sp-5 | an-376 | 1C1884 | sp-5 | an-376 |
| 1A1885 | sp-5 | an-377 | 1U1885 | sp-5 | an-377 | 1C1885 | sp-5 | an-377 |
| 1A1886 | sp-6 | an-1 | 1U1886 | sp-6 | an-1 | 1C1886 | sp-6 | an-1 |
| 1A1887 | sp-6 | an-2 | 1U1887 | sp-6 | an-2 | 1C1887 | sp-6 | an-2 |
| 1A1888 | sp-6 | an-3 | 1U1888 | sp-6 | an-3 | 1C1888 | sp-6 | an-3 |
| 1A1889 | sp-6 | an-4 | 1U1889 | sp-6 | an-4 | 1C1889 | sp-6 | an-4 |
| 1A1890 | sp-6 | an-5 | 1U1890 | sp-6 | an-5 | 1C1890 | sp-6 | an-5 |
| 1A1891 | sp-6 | an-6 | 1U1891 | sp-6 | an-6 | 1C1891 | sp-6 | an-6 |
| 1A1892 | sp-6 | an-7 | 1U1892 | sp-6 | an-7 | 1C1892 | sp-6 | an-7 |
| 1A1893 | sp-6 | an-8 | 1U1893 | sp-6 | an-8 | 1C1893 | sp-6 | an-8 |
| 1A1894 | sp-6 | an-9 | 1U1894 | sp-6 | an-9 | 1C1894 | sp-6 | an-9 |
| 1A1895 | sp-6 | an-10 | 1U1895 | sp-6 | an-10 | 1C1895 | sp-6 | an-10 |
| 1A1896 | sp-6 | an-11 | 1U1896 | sp-6 | an-11 | 1C1896 | sp-6 | an-11 |
| 1A1897 | sp-6 | an-12 | 1U1897 | sp-6 | an-12 | 1C1897 | sp-6 | an-12 |
| 1A1898 | sp-6 | an-13 | 1U1898 | sp-6 | an-13 | 1C1898 | sp-6 | an-13 |
| 1A1899 | sp-6 | an-14 | 1U1899 | sp-6 | an-14 | 1C1899 | sp-6 | an-14 |
| 1A1900 | sp-6 | an-15 | 1U1900 | sp-6 | an-15 | 1C1900 | sp-6 | an-15 |
| 1A1901 | sp-6 | an-16 | 1U1901 | sp-6 | an-16 | 1C1901 | sp-6 | an-16 |
| 1A1902 | sp-6 | an-17 | 1U1902 | sp-6 | an-17 | 1C1902 | sp-6 | an-17 |
| 1A1903 | sp-6 | an-18 | 1U1903 | sp-6 | an-18 | 1C1903 | sp-6 | an-18 |
| 1A1904 | sp-6 | an-19 | 1U1904 | sp-6 | an-19 | 1C1904 | sp-6 | an-19 |
| 1A1905 | sp-6 | an-20 | 1U1905 | sp-6 | an-20 | 1C1905 | sp-6 | an-20 |
| 1A1906 | sp-6 | an-21 | 1U1906 | sp-6 | an-21 | 1C1906 | sp-6 | an-21 |
| 1A1907 | sp-6 | an-22 | 1U1907 | sp-6 | an-22 | 1C1907 | sp-6 | an-22 |
| 1A1908 | sp-6 | an-23 | 1U1908 | sp-6 | an-23 | 1C1908 | sp-6 | an-23 |
| 1A1909 | sp-6 | an-24 | 1U1909 | sp-6 | an-24 | 1C1909 | sp-6 | an-24 |
| 1A1910 | sp-6 | an-25 | 1U1910 | sp-6 | an-25 | 1C1910 | sp-6 | an-25 |
| 1A1911 | sp-6 | an-26 | 1U1911 | sp-6 | an-26 | 1C1911 | sp-6 | an-26 |
| 1A1912 | sp-6 | an-27 | 1U1912 | sp-6 | an-27 | 1C1912 | sp-6 | an-27 |
| 1A1913 | sp-6 | an-28 | 1U1913 | sp-6 | an-28 | 1C1913 | sp-6 | an-28 |

TABLE 1-continued

| | | | | | | | | |
|---|---|---|---|---|---|---|---|---|
| 1A1914 | sp-6 | an-29 | 1U1914 | sp-6 | an-29 | 1C1914 | sp-6 | an-29 |
| 1A1915 | sp-6 | an-30 | 1U1915 | sp-6 | an-30 | 1C1915 | sp-6 | an-30 |
| 1A1916 | sp-6 | an-31 | 1U1916 | sp-6 | an-31 | 1C1916 | sp-6 | an-31 |
| 1A1917 | sp-6 | an-32 | 1U1917 | sp-6 | an-32 | 1C1917 | sp-6 | an-32 |
| 1A1918 | sp-6 | an-33 | 1U1918 | sp-6 | an-33 | 1C1918 | sp-6 | an-33 |
| 1A1919 | sp-6 | an-34 | 1U1919 | sp-6 | an-34 | 1C1919 | sp-6 | an-34 |
| 1A1920 | sp-6 | an-35 | 1U1920 | sp-6 | an-35 | 1C1920 | sp-6 | an-35 |
| 1A1921 | sp-6 | an-36 | 1U1921 | sp-6 | an-36 | 1C1921 | sp-6 | an-36 |
| 1A1922 | sp-6 | an-37 | 1U1922 | sp-6 | an-37 | 1C1922 | sp-6 | an-37 |
| 1A1923 | sp-6 | an-38 | 1U1923 | sp-6 | an-38 | 1C1923 | sp-6 | an-38 |
| 1A1924 | sp-6 | an-39 | 1U1924 | sp-6 | an-39 | 1C1924 | sp-6 | an-39 |
| 1A1925 | sp-6 | an-40 | 1U1925 | sp-6 | an-40 | 1C1925 | sp-6 | an-40 |
| 1A1926 | sp-6 | an-41 | 1U1926 | sp-6 | an-41 | 1C1926 | sp-6 | an-41 |
| 1A1927 | sp-6 | an-42 | 1U1927 | sp-6 | an-42 | 1C1927 | sp-6 | an-42 |
| 1A1928 | sp-6 | an-43 | 1U1928 | sp-6 | an-43 | 1C1928 | sp-6 | an-43 |
| 1A1929 | sp-6 | an-44 | 1U1929 | sp-6 | an-44 | 1C1929 | sp-6 | an-44 |
| 1A1930 | sp-6 | an-45 | 1U1930 | sp-6 | an-45 | 1C1930 | sp-6 | an-45 |
| 1A1931 | sp-6 | an-46 | 1U1931 | sp-6 | an-46 | 1C1931 | sp-6 | an-46 |
| 1A1932 | sp-6 | an-47 | 1U1932 | sp-6 | an-47 | 1C1932 | sp-6 | an-47 |
| 1A1933 | sp-6 | an-48 | 1U1933 | sp-6 | an-48 | 1C1933 | sp-6 | an-48 |
| 1A1934 | sp-6 | an-49 | 1U1934 | sp-6 | an-49 | 1C1934 | sp-6 | an-49 |
| 1A1935 | sp-6 | an-50 | 1U1935 | sp-6 | an-50 | 1C1935 | sp-6 | an-50 |
| 1A1936 | sp-6 | an-51 | 1U1936 | sp-6 | an-51 | 1C1936 | sp-6 | an-51 |
| 1A1937 | sp-6 | an-52 | 1U1937 | sp-6 | an-52 | 1C1937 | sp-6 | an-52 |
| 1A1938 | sp-6 | an-53 | 1U1938 | sp-6 | an-53 | 1C1938 | sp-6 | an-53 |
| 1A1939 | sp-6 | an-54 | 1U1939 | sp-6 | an-54 | 1C1939 | sp-6 | an-54 |
| 1A1940 | sp-6 | an-55 | 1U1940 | sp-6 | an-55 | 1C1940 | sp-6 | an-55 |
| 1A1941 | sp-6 | an-56 | 1U1941 | sp-6 | an-56 | 1C1941 | sp-6 | an-56 |
| 1A1942 | sp-6 | an-57 | 1U1942 | sp-6 | an-57 | 1C1942 | sp-6 | an-57 |
| 1A1943 | sp-6 | an-58 | 1U1943 | sp-6 | an-58 | 1C1943 | sp-6 | an-58 |
| 1A1944 | sp-6 | an-59 | 1U1944 | sp-6 | an-59 | 1C1944 | sp-6 | an-59 |
| 1A1945 | sp-6 | an-60 | 1U1945 | sp-6 | an-60 | 1C1945 | sp-6 | an-60 |
| 1A1946 | sp-6 | an-61 | 1U1946 | sp-6 | an-61 | 1C1946 | sp-6 | an-61 |
| 1A1947 | sp-6 | an-62 | 1U1947 | sp-6 | an-62 | 1C1947 | sp-6 | an-62 |
| 1A1948 | sp-6 | an-63 | 1U1948 | sp-6 | an-63 | 1C1948 | sp-6 | an-63 |
| 1A1949 | sp-6 | an-64 | 1U1949 | sp-6 | an-64 | 1C1949 | sp-6 | an-64 |
| 1A1950 | sp-6 | an-65 | 1U1950 | sp-6 | an-65 | 1C1950 | sp-6 | an-65 |
| 1A1951 | sp-6 | an-66 | 1U1951 | sp-6 | an-66 | 1C1951 | sp-6 | an-66 |
| 1A1952 | sp-6 | an-67 | 1U1952 | sp-6 | an-67 | 1C1952 | sp-6 | an-67 |
| 1A1953 | sp-6 | an-68 | 1U1953 | sp-6 | an-68 | 1C1953 | sp-6 | an-68 |
| 1A1954 | sp-6 | an-69 | 1U1954 | sp-6 | an-69 | 1C1954 | sp-6 | an-69 |
| 1A1955 | sp-6 | an-70 | 1U1955 | sp-6 | an-70 | 1C1955 | sp-6 | an-70 |
| 1A1956 | sp-6 | an-71 | 1U1956 | sp-6 | an-71 | 1C1956 | sp-6 | an-71 |
| 1A1957 | sp-6 | an-72 | 1U1957 | sp-6 | an-72 | 1C1957 | sp-6 | an-72 |
| 1A1958 | sp-6 | an-73 | 1U1958 | sp-6 | an-73 | 1C1958 | sp-6 | an-73 |
| 1A1959 | sp-6 | an-74 | 1U1959 | sp-6 | an-74 | 1C1959 | sp-6 | an-74 |
| 1A1960 | sp-6 | an-75 | 1U1960 | sp-6 | an-75 | 1C1960 | sp-6 | an-75 |
| 1A1961 | sp-6 | an-76 | 1U1961 | sp-6 | an-76 | 1C1961 | sp-6 | an-76 |
| 1A1962 | sp-6 | an-77 | 1U1962 | sp-6 | an-77 | 1C1962 | sp-6 | an-77 |
| 1A1963 | sp-6 | an-78 | 1U1963 | sp-6 | an-78 | 1C1963 | sp-6 | an-78 |
| 1A1964 | sp-6 | an-79 | 1U1964 | sp-6 | an-79 | 1C1964 | sp-6 | an-79 |
| 1A1965 | sp-6 | an-80 | 1U1965 | sp-6 | an-80 | 1C1965 | sp-6 | an-80 |
| 1A1966 | sp-6 | an-81 | 1U1966 | sp-6 | an-81 | 1C1966 | sp-6 | an-81 |
| 1A1967 | sp-6 | an-82 | 1U1967 | sp-6 | an-82 | 1C1967 | sp-6 | an-82 |
| 1A1968 | sp-6 | an-83 | 1U1968 | sp-6 | an-83 | 1C1968 | sp-6 | an-83 |
| 1A1969 | sp-6 | an-84 | 1U1969 | sp-6 | an-84 | 1C1969 | sp-6 | an-84 |
| 1A1970 | sp-6 | an-85 | 1U1970 | sp-6 | an-85 | 1C1970 | sp-6 | an-85 |
| 1A1971 | sp-6 | an-86 | 1U1971 | sp-6 | an-86 | 1C1971 | sp-6 | an-86 |
| 1A1972 | sp-6 | an-87 | 1U1972 | sp-6 | an-87 | 1C1972 | sp-6 | an-87 |
| 1A1973 | sp-6 | an-88 | 1U1973 | sp-6 | an-88 | 1C1973 | sp-6 | an-88 |
| 1A1974 | sp-6 | an-89 | 1U1974 | sp-6 | an-89 | 1C1974 | sp-6 | an-89 |
| 1A1975 | sp-6 | an-90 | 1U1975 | sp-6 | an-90 | 1C1975 | sp-6 | an-90 |
| 1A1976 | sp-6 | an-91 | 1U1976 | sp-6 | an-91 | 1C1976 | sp-6 | an-91 |
| 1A1977 | sp-6 | an-92 | 1U1977 | sp-6 | an-92 | 1C1977 | sp-6 | an-92 |
| 1A1978 | sp-6 | an-93 | 1U1978 | sp-6 | an-93 | 1C1978 | sp-6 | an-93 |
| 1A1979 | sp-6 | an-94 | 1U1979 | sp-6 | an-94 | 1C1979 | sp-6 | an-94 |
| 1A1980 | sp-6 | an-95 | 1U1980 | sp-6 | an-95 | 1C1980 | sp-6 | an-95 |
| 1A1981 | sp-6 | an-96 | 1U1981 | sp-6 | an-96 | 1C1981 | sp-6 | an-96 |
| 1A1982 | sp-6 | an-97 | 1U1982 | sp-6 | an-97 | 1C1982 | sp-6 | an-97 |
| 1A1983 | sp-6 | an-98 | 1U1983 | sp-6 | an-98 | 1C1983 | sp-6 | an-98 |
| 1A1984 | sp-6 | an-99 | 1U1984 | sp-6 | an-99 | 1C1984 | sp-6 | an-99 |
| 1A1985 | sp-6 | an-100 | 1U1985 | sp-6 | an-100 | 1C1985 | sp-6 | an-100 |
| 1A1986 | sp-6 | an-101 | 1U1986 | sp-6 | an-101 | 1C1986 | sp-6 | an-101 |
| 1A1987 | sp-6 | an-102 | 1U1987 | sp-6 | an-102 | 1C1987 | sp-6 | an-102 |
| 1A1988 | sp-6 | an-103 | 1U1988 | sp-6 | an-103 | 1C1988 | sp-6 | an-103 |
| 1A1989 | sp-6 | an-104 | 1U1989 | sp-6 | an-104 | 1C1989 | sp-6 | an-104 |
| 1A1990 | sp-6 | an-105 | 1U1990 | sp-6 | an-105 | 1C1990 | sp-6 | an-105 |
| 1A1991 | sp-6 | an-106 | 1U1991 | sp-6 | an-106 | 1C1991 | sp-6 | an-106 |
| 1A1992 | sp-6 | an-107 | 1U1992 | sp-6 | an-107 | 1C1992 | sp-6 | an-107 |

TABLE 1-continued

| | | | | | | | | |
|---|---|---|---|---|---|---|---|---|
| 1A1993 | sp-6 | an-108 | 1U1993 | sp-6 | an-108 | 1C1993 | sp-6 | an-108 |
| 1A1994 | sp-6 | an-109 | 1U1994 | sp-6 | an-109 | 1C1994 | sp-6 | an-109 |
| 1A1995 | sp-6 | an-110 | 1U1995 | sp-6 | an-110 | 1C1995 | sp-6 | an-110 |
| 1A1996 | sp-6 | an-111 | 1U1996 | sp-6 | an-111 | 1C1996 | sp-6 | an-111 |
| 1A1997 | sp-6 | an-112 | 1U1997 | sp-6 | an-112 | 1C1997 | sp-6 | an-112 |
| 1A1998 | sp-6 | an-113 | 1U1998 | sp-6 | an-113 | 1C1998 | sp-6 | an-113 |
| 1A1999 | sp-6 | an-114 | 1U1999 | sp-6 | an-114 | 1C1999 | sp-6 | an-114 |
| 1A2000 | sp-6 | an-115 | 1U2000 | sp-6 | an-115 | 1C2000 | sp-6 | an-115 |
| 1A2001 | sp-6 | an-116 | 1U2001 | sp-6 | an-116 | 1C2001 | sp-6 | an-116 |
| 1A2002 | sp-6 | an-117 | 1U2002 | sp-6 | an-117 | 1C2002 | sp-6 | an-117 |
| 1A2003 | sp-6 | an-118 | 1U2003 | sp-6 | an-118 | 1C2003 | sp-6 | an-118 |
| 1A2004 | sp-6 | an-119 | 1U2004 | sp-6 | an-119 | 1C2004 | sp-6 | an-119 |
| 1A2005 | sp-6 | an-120 | 1U2005 | sp-6 | an-120 | 1C2005 | sp-6 | an-120 |
| 1A2006 | sp-6 | an-121 | 1U2006 | sp-6 | an-121 | 1C2006 | sp-6 | an-121 |
| 1A2007 | sp-6 | an-122 | 1U2007 | sp-6 | an-122 | 1C2007 | sp-6 | an-122 |
| 1A2008 | sp-6 | an-123 | 1U2008 | sp-6 | an-123 | 1C2008 | sp-6 | an-123 |
| 1A2009 | sp-6 | an-124 | 1U2009 | sp-6 | an-124 | 1C2009 | sp-6 | an-124 |
| 1A2010 | sp-6 | an-125 | 1U2010 | sp-6 | an-125 | 1C2010 | sp-6 | an-125 |
| 1A2011 | sp-6 | an-126 | 1U2011 | sp-6 | an-126 | 1C2011 | sp-6 | an-126 |
| 1A2012 | sp-6 | an-127 | 1U2012 | sp-6 | an-127 | 1C2012 | sp-6 | an-127 |
| 1A2013 | sp-6 | an-128 | 1U2013 | sp-6 | an-128 | 1C2013 | sp-6 | an-128 |
| 1A2014 | sp-6 | an-129 | 1U2014 | sp-6 | an-129 | 1C2014 | sp-6 | an-129 |
| 1A2015 | sp-6 | an-130 | 1U2015 | sp-6 | an-130 | 1C2015 | sp-6 | an-130 |
| 1A2016 | sp-6 | an-131 | 1U2016 | sp-6 | an-131 | 1C2016 | sp-6 | an-131 |
| 1A2017 | sp-6 | an-132 | 1U2017 | sp-6 | an-132 | 1C2017 | sp-6 | an-132 |
| 1A2018 | sp-6 | an-133 | 1U2018 | sp-6 | an-133 | 1C2018 | sp-6 | an-133 |
| 1A2019 | sp-6 | an-134 | 1U2019 | sp-6 | an-134 | 1C2019 | sp-6 | an-134 |
| 1A2020 | sp-6 | an-135 | 1U2020 | sp-6 | an-135 | 1C2020 | sp-6 | an-135 |
| 1A2021 | sp-6 | an-136 | 1U2021 | sp-6 | an-136 | 1C2021 | sp-6 | an-136 |
| 1A2022 | sp-6 | an-137 | 1U2022 | sp-6 | an-137 | 1C2022 | sp-6 | an-137 |
| 1A2023 | sp-6 | an-138 | 1U2023 | sp-6 | an-138 | 1C2023 | sp-6 | an-138 |
| 1A2024 | sp-6 | an-139 | 1U2024 | sp-6 | an-139 | 1C2024 | sp-6 | an-139 |
| 1A2025 | sp-6 | an-140 | 1U2025 | sp-6 | an-140 | 1C2025 | sp-6 | an-140 |
| 1A2026 | sp-6 | an-141 | 1U2026 | sp-6 | an-141 | 1C2026 | sp-6 | an-141 |
| 1A2027 | sp-6 | an-142 | 1U2027 | sp-6 | an-142 | 1C2027 | sp-6 | an-142 |
| 1A2028 | sp-6 | an-143 | 1U2028 | sp-6 | an-143 | 1C2028 | sp-6 | an-143 |
| 1A2029 | sp-6 | an-144 | 1U2029 | sp-6 | an-144 | 1C2029 | sp-6 | an-144 |
| 1A2030 | sp-6 | an-145 | 1U2030 | sp-6 | an-145 | 1C2030 | sp-6 | an-145 |
| 1A2031 | sp-6 | an-146 | 1U2031 | sp-6 | an-146 | 1C2031 | sp-6 | an-146 |
| 1A2032 | sp-6 | an-147 | 1U2032 | sp-6 | an-147 | 1C2032 | sp-6 | an-147 |
| 1A2033 | sp-6 | an-148 | 1U2033 | sp-6 | an-148 | 1C2033 | sp-6 | an-148 |
| 1A2034 | sp-6 | an-149 | 1U2034 | sp-6 | an-149 | 1C2034 | sp-6 | an-149 |
| 1A2035 | sp-6 | an-150 | 1U2035 | sp-6 | an-150 | 1C2035 | sp-6 | an-150 |
| 1A2036 | sp-6 | an-151 | 1U2036 | sp-6 | an-151 | 1C2036 | sp-6 | an-151 |
| 1A2037 | sp-6 | an-152 | 1U2037 | sp-6 | an-152 | 1C2037 | sp-6 | an-152 |
| 1A2038 | sp-6 | an-153 | 1U2038 | sp-6 | an-153 | 1C2038 | sp-6 | an-153 |
| 1A2039 | sp-6 | an-154 | 1U2039 | sp-6 | an-154 | 1C2039 | sp-6 | an-154 |
| 1A2040 | sp-6 | an-155 | 1U2040 | sp-6 | an-155 | 1C2040 | sp-6 | an-155 |
| 1A2041 | sp-6 | an-156 | 1U2041 | sp-6 | an-156 | 1C2041 | sp-6 | an-156 |
| 1A2042 | sp-6 | an-157 | 1U2042 | sp-6 | an-157 | 1C2042 | sp-6 | an-157 |
| 1A2043 | sp-6 | an-158 | 1U2043 | sp-6 | an-158 | 1C2043 | sp-6 | an-158 |
| 1A2044 | sp-6 | an-159 | 1U2044 | sp-6 | an-159 | 1C2044 | sp-6 | an-159 |
| 1A2045 | sp-6 | an-160 | 1U2045 | sp-6 | an-160 | 1C2045 | sp-6 | an-160 |
| 1A2046 | sp-6 | an-161 | 1U2046 | sp-6 | an-161 | 1C2046 | sp-6 | an-161 |
| 1A2047 | sp-6 | an-162 | 1U2047 | sp-6 | an-162 | 1C2047 | sp-6 | an-162 |
| 1A2048 | sp-6 | an-163 | 1U2048 | sp-6 | an-163 | 1C2048 | sp-6 | an-163 |
| 1A2049 | sp-6 | an-164 | 1U2049 | sp-6 | an-164 | 1C2049 | sp-6 | an-164 |
| 1A2050 | sp-6 | an-165 | 1U2050 | sp-6 | an-165 | 1C2050 | sp-6 | an-165 |
| 1A2051 | sp-6 | an-166 | 1U2051 | sp-6 | an-166 | 1C2051 | sp-6 | an-166 |
| 1A2052 | sp-6 | an-167 | 1U2052 | sp-6 | an-167 | 1C2052 | sp-6 | an-167 |
| 1A2053 | sp-6 | an-168 | 1U2053 | sp-6 | an-168 | 1C2053 | sp-6 | an-168 |
| 1A2054 | sp-6 | an-169 | 1U2054 | sp-6 | an-169 | 1C2054 | sp-6 | an-169 |
| 1A2055 | sp-6 | an-170 | 1U2055 | sp-6 | an-170 | 1C2055 | sp-6 | an-170 |
| 1A2056 | sp-6 | an-171 | 1U2056 | sp-6 | an-171 | 1C2056 | sp-6 | an-171 |
| 1A2057 | sp-6 | an-172 | 1U2057 | sp-6 | an-172 | 1C2057 | sp-6 | an-172 |
| 1A2058 | sp-6 | an-173 | 1U2058 | sp-6 | an-173 | 1C2058 | sp-6 | an-173 |
| 1A2059 | sp-6 | an-174 | 1U2059 | sp-6 | an-174 | 1C2059 | sp-6 | an-174 |
| 1A2060 | sp-6 | an-175 | 1U2060 | sp-6 | an-175 | 1C2060 | sp-6 | an-175 |
| 1A2061 | sp-6 | an-176 | 1U2061 | sp-6 | an-176 | 1C2061 | sp-6 | an-176 |
| 1A2062 | sp-6 | an-177 | 1U2062 | sp-6 | an-177 | 1C2062 | sp-6 | an-177 |
| 1A2063 | sp-6 | an-178 | 1U2063 | sp-6 | an-178 | 1C2063 | sp-6 | an-178 |
| 1A2064 | sp-6 | an-179 | 1U2064 | sp-6 | an-179 | 1C2064 | sp-6 | an-179 |
| 1A2065 | sp-6 | an-180 | 1U2065 | sp-6 | an-180 | 1C2065 | sp-6 | an-180 |
| 1A2066 | sp-6 | an-181 | 1U2066 | sp-6 | an-181 | 1C2066 | sp-6 | an-181 |
| 1A2067 | sp-6 | an-182 | 1U2067 | sp-6 | an-182 | 1C2067 | sp-6 | an-182 |
| 1A2068 | sp-6 | an-183 | 1U2068 | sp-6 | an-183 | 1C2068 | sp-6 | an-183 |
| 1A2069 | sp-6 | an-184 | 1U2069 | sp-6 | an-184 | 1C2069 | sp-6 | an-184 |
| 1A2070 | sp-6 | an-185 | 1U2070 | sp-6 | an-185 | 1C2070 | sp-6 | an-185 |
| 1A2071 | sp-6 | an-186 | 1U2071 | sp-6 | an-186 | 1C2071 | sp-6 | an-186 |

TABLE 1-continued

| | | | | | | | | |
|---|---|---|---|---|---|---|---|---|
| 1A2072 | sp-6 | an-187 | 1U2072 | sp-6 | an-187 | 1C2072 | sp-6 | an-187 |
| 1A2073 | sp-6 | an-188 | 1U2073 | sp-6 | an-188 | 1C2073 | sp-6 | an-188 |
| 1A2074 | sp-6 | an-189 | 1U2074 | sp-6 | an-189 | 1C2074 | sp-6 | an-189 |
| 1A2075 | sp-6 | an-190 | 1U2075 | sp-6 | an-190 | 1C2075 | sp-6 | an-190 |
| 1A2076 | sp-6 | an-191 | 1U2076 | sp-6 | an-191 | 1C2076 | sp-6 | an-191 |
| 1A2077 | sp-6 | an-192 | 1U2077 | sp-6 | an-192 | 1C2077 | sp-6 | an-192 |
| 1A2078 | sp-6 | an-193 | 1U2078 | sp-6 | an-193 | 1C2078 | sp-6 | an-193 |
| 1A2079 | sp-6 | an-194 | 1U2079 | sp-6 | an-194 | 1C2079 | sp-6 | an-194 |
| 1A2080 | sp-6 | an-195 | 1U2080 | sp-6 | an-195 | 1C2080 | sp-6 | an-195 |
| 1A2081 | sp-6 | an-196 | 1U2081 | sp-6 | an-196 | 1C2081 | sp-6 | an-196 |
| 1A2082 | sp-6 | an-197 | 1U2082 | sp-6 | an-197 | 1C2082 | sp-6 | an-197 |
| 1A2083 | sp-6 | an-198 | 1U2083 | sp-6 | an-198 | 1C2083 | sp-6 | an-198 |
| 1A2084 | sp-6 | an-199 | 1U2084 | sp-6 | an-199 | 1C2084 | sp-6 | an-199 |
| 1A2085 | sp-6 | an-200 | 1U2085 | sp-6 | an-200 | 1C2085 | sp-6 | an-200 |
| 1A2086 | sp-6 | an-201 | 1U2086 | sp-6 | an-201 | 1C2086 | sp-6 | an-201 |
| 1A2087 | sp-6 | an-202 | 1U2087 | sp-6 | an-202 | 1C2087 | sp-6 | an-202 |
| 1A2088 | sp-6 | an-203 | 1U2088 | sp-6 | an-203 | 1C2088 | sp-6 | an-203 |
| 1A2089 | sp-6 | an-204 | 1U2089 | sp-6 | an-204 | 1C2089 | sp-6 | an-204 |
| 1A2090 | sp-6 | an-205 | 1U2090 | sp-6 | an-205 | 1C2090 | sp-6 | an-205 |
| 1A2091 | sp-6 | an-206 | 1U2091 | sp-6 | an-206 | 1C2091 | sp-6 | an-206 |
| 1A2092 | sp-6 | an-207 | 1U2092 | sp-6 | an-207 | 1C2092 | sp-6 | an-207 |
| 1A2093 | sp-6 | an-208 | 1U2093 | sp-6 | an-208 | 1C2093 | sp-6 | an-208 |
| 1A2094 | sp-6 | an-209 | 1U2094 | sp-6 | an-209 | 1C2094 | sp-6 | an-209 |
| 1A2095 | sp-6 | an-210 | 1U2095 | sp-6 | an-210 | 1C2095 | sp-6 | an-210 |
| 1A2096 | sp-6 | an-211 | 1U2096 | sp-6 | an-211 | 1C2096 | sp-6 | an-211 |
| 1A2097 | sp-6 | an-212 | 1U2097 | sp-6 | an-212 | 1C2097 | sp-6 | an-212 |
| 1A2098 | sp-6 | an-213 | 1U2098 | sp-6 | an-213 | 1C2098 | sp-6 | an-213 |
| 1A2099 | sp-6 | an-214 | 1U2099 | sp-6 | an-214 | 1C2099 | sp-6 | an-214 |
| 1A2100 | sp-6 | an-215 | 1U2100 | sp-6 | an-215 | 1C2100 | sp-6 | an-215 |
| 1A2101 | sp-6 | an-216 | 1U2101 | sp-6 | an-216 | 1C2101 | sp-6 | an-216 |
| 1A2102 | sp-6 | an-217 | 1U2102 | sp-6 | an-217 | 1C2102 | sp-6 | an-217 |
| 1A2103 | sp-6 | an-218 | 1U2103 | sp-6 | an-218 | 1C2103 | sp-6 | an-218 |
| 1A2104 | sp-6 | an-219 | 1U2104 | sp-6 | an-219 | 1C2104 | sp-6 | an-219 |
| 1A2105 | sp-6 | an-220 | 1U2105 | sp-6 | an-220 | 1C2105 | sp-6 | an-220 |
| 1A2106 | sp-6 | an-221 | 1U2106 | sp-6 | an-221 | 1C2106 | sp-6 | an-221 |
| 1A2107 | sp-6 | an-222 | 1U2107 | sp-6 | an-222 | 1C2107 | sp-6 | an-222 |
| 1A2108 | sp-6 | an-223 | 1U2108 | sp-6 | an-223 | 1C2108 | sp-6 | an-223 |
| 1A2109 | sp-6 | an-224 | 1U2109 | sp-6 | an-224 | 1C2109 | sp-6 | an-224 |
| 1A2110 | sp-6 | an-225 | 1U2110 | sp-6 | an-225 | 1C2110 | sp-6 | an-225 |
| 1A2111 | sp-6 | an-226 | 1U2111 | sp-6 | an-226 | 1C2111 | sp-6 | an-226 |
| 1A2112 | sp-6 | an-227 | 1U2112 | sp-6 | an-227 | 1C2112 | sp-6 | an-227 |
| 1A2113 | sp-6 | an-228 | 1U2113 | sp-6 | an-228 | 1C2113 | sp-6 | an-228 |
| 1A2114 | sp-6 | an-229 | 1U2114 | sp-6 | an-229 | 1C2114 | sp-6 | an-229 |
| 1A2115 | sp-6 | an-230 | 1U2115 | sp-6 | an-230 | 1C2115 | sp-6 | an-230 |
| 1A2116 | sp-6 | an-231 | 1U2116 | sp-6 | an-231 | 1C2116 | sp-6 | an-231 |
| 1A2117 | sp-6 | an-232 | 1U2117 | sp-6 | an-232 | 1C2117 | sp-6 | an-232 |
| 1A2118 | sp-6 | an-233 | 1U2118 | sp-6 | an-233 | 1C2118 | sp-6 | an-233 |
| 1A2119 | sp-6 | an-234 | 1U2119 | sp-6 | an-234 | 1C2119 | sp-6 | an-234 |
| 1A2120 | sp-6 | an-235 | 1U2120 | sp-6 | an-235 | 1C2120 | sp-6 | an-235 |
| 1A2121 | sp-6 | an-236 | 1U2121 | sp-6 | an-236 | 1C2121 | sp-6 | an-236 |
| 1A2122 | sp-6 | an-237 | 1U2122 | sp-6 | an-237 | 1C2122 | sp-6 | an-237 |
| 1A2123 | sp-6 | an-238 | 1U2123 | sp-6 | an-238 | 1C2123 | sp-6 | an-238 |
| 1A2124 | sp-6 | an-239 | 1U2124 | sp-6 | an-239 | 1C2124 | sp-6 | an-239 |
| 1A2125 | sp-6 | an-240 | 1U2125 | sp-6 | an-240 | 1C2125 | sp-6 | an-240 |
| 1A2126 | sp-6 | an-241 | 1U2126 | sp-6 | an-241 | 1C2126 | sp-6 | an-241 |
| 1A2127 | sp-6 | an-242 | 1U2127 | sp-6 | an-242 | 1C2127 | sp-6 | an-242 |
| 1A2128 | sp-6 | an-243 | 1U2128 | sp-6 | an-243 | 1C2128 | sp-6 | an-243 |
| 1A2129 | sp-6 | an-244 | 1U2129 | sp-6 | an-244 | 1C2129 | sp-6 | an-244 |
| 1A2130 | sp-6 | an-245 | 1U2130 | sp-6 | an-245 | 1C2130 | sp-6 | an-245 |
| 1A2131 | sp-6 | an-246 | 1U2131 | sp-6 | an-246 | 1C2131 | sp-6 | an-246 |
| 1A2132 | sp-6 | an-247 | 1U2132 | sp-6 | an-247 | 1C2132 | sp-6 | an-247 |
| 1A2133 | sp-6 | an-248 | 1U2133 | sp-6 | an-248 | 1C2133 | sp-6 | an-248 |
| 1A2134 | sp-6 | an-249 | 1U2134 | sp-6 | an-249 | 1C2134 | sp-6 | an-249 |
| 1A2135 | sp-6 | an-250 | 1U2135 | sp-6 | an-250 | 1C2135 | sp-6 | an-250 |
| 1A2136 | sp-6 | an-251 | 1U2136 | sp-6 | an-251 | 1C2136 | sp-6 | an-251 |
| 1A2137 | sp-6 | an-252 | 1U2137 | sp-6 | an-252 | 1C2137 | sp-6 | an-252 |
| 1A2138 | sp-6 | an-253 | 1U2138 | sp-6 | an-253 | 1C2138 | sp-6 | an-253 |
| 1A2139 | sp-6 | an-254 | 1U2139 | sp-6 | an-254 | 1C2139 | sp-6 | an-254 |
| 1A2140 | sp-6 | an-255 | 1U2140 | sp-6 | an-255 | 1C2140 | sp-6 | an-255 |
| 1A2141 | sp-6 | an-256 | 1U2141 | sp-6 | an-256 | 1C2141 | sp-6 | an-256 |
| 1A2142 | sp-6 | an-257 | 1U2142 | sp-6 | an-257 | 1C2142 | sp-6 | an-257 |
| 1A2143 | sp-6 | an-258 | 1U2143 | sp-6 | an-258 | 1C2143 | sp-6 | an-258 |
| 1A2144 | sp-6 | an-259 | 1U2144 | sp-6 | an-259 | 1C2144 | sp-6 | an-259 |
| 1A2145 | sp-6 | an-260 | 1U2145 | sp-6 | an-260 | 1C2145 | sp-6 | an-260 |
| 1A2146 | sp-6 | an-261 | 1U2146 | sp-6 | an-261 | 1C2146 | sp-6 | an-261 |
| 1A2147 | sp-6 | an-262 | 1U2147 | sp-6 | an-262 | 1C2147 | sp-6 | an-262 |
| 1A2148 | sp-6 | an-263 | 1U2148 | sp-6 | an-263 | 1C2148 | sp-6 | an-263 |
| 1A2149 | sp-6 | an-264 | 1U2149 | sp-6 | an-264 | 1C2149 | sp-6 | an-264 |
| 1A2150 | sp-6 | an-265 | 1U2150 | sp-6 | an-265 | 1C2150 | sp-6 | an-265 |

TABLE 1-continued

| | | | | | | | | |
|---|---|---|---|---|---|---|---|---|
| 1A2151 | sp-6 | an-266 | 1U2151 | sp-6 | an-266 | 1C2151 | sp-6 | an-266 |
| 1A2152 | sp-6 | an-267 | 1U2152 | sp-6 | an-267 | 1C2152 | sp-6 | an-267 |
| 1A2153 | sp-6 | an-268 | 1U2153 | sp-6 | an-268 | 1C2153 | sp-6 | an-268 |
| 1A2154 | sp-6 | an-269 | 1U2154 | sp-6 | an-269 | 1C2154 | sp-6 | an-269 |
| 1A2155 | sp-6 | an-270 | 1U2155 | sp-6 | an-270 | 1C2155 | sp-6 | an-270 |
| 1A2156 | sp-6 | an-271 | 1U2156 | sp-6 | an-271 | 1C2156 | sp-6 | an-271 |
| 1A2157 | sp-6 | an-272 | 1U2157 | sp-6 | an-272 | 1C2157 | sp-6 | an-272 |
| 1A2158 | sp-6 | an-273 | 1U2158 | sp-6 | an-273 | 1C2158 | sp-6 | an-273 |
| 1A2159 | sp-6 | an-274 | 1U2159 | sp-6 | an-274 | 1C2159 | sp-6 | an-274 |
| 1A2160 | sp-6 | an-275 | 1U2160 | sp-6 | an-275 | 1C2160 | sp-6 | an-275 |
| 1A2161 | sp-6 | an-276 | 1U2161 | sp-6 | an-276 | 1C2161 | sp-6 | an-276 |
| 1A2162 | sp-6 | an-277 | 1U2162 | sp-6 | an-277 | 1C2162 | sp-6 | an-277 |
| 1A2163 | sp-6 | an-278 | 1U2163 | sp-6 | an-278 | 1C2163 | sp-6 | an-278 |
| 1A2164 | sp-6 | an-279 | 1U2164 | sp-6 | an-279 | 1C2164 | sp-6 | an-279 |
| 1A2165 | sp-6 | an-280 | 1U2165 | sp-6 | an-280 | 1C2165 | sp-6 | an-280 |
| 1A2166 | sp-6 | an-281 | 1U2166 | sp-6 | an-281 | 1C2166 | sp-6 | an-281 |
| 1A2167 | sp-6 | an-282 | 1U2167 | sp-6 | an-282 | 1C2167 | sp-6 | an-282 |
| 1A2168 | sp-6 | an-283 | 1U2168 | sp-6 | an-283 | 1C2168 | sp-6 | an-283 |
| 1A2169 | sp-6 | an-284 | 1U2169 | sp-6 | an-284 | 1C2169 | sp-6 | an-284 |
| 1A2170 | sp-6 | an-285 | 1U2170 | sp-6 | an-285 | 1C2170 | sp-6 | an-285 |
| 1A2171 | sp-6 | an-286 | 1U2171 | sp-6 | an-286 | 1C2171 | sp-6 | an-286 |
| 1A2172 | sp-6 | an-287 | 1U2172 | sp-6 | an-287 | 1C2172 | sp-6 | an-287 |
| 1A2173 | sp-6 | an-288 | 1U2173 | sp-6 | an-288 | 1C2173 | sp-6 | an-288 |
| 1A2174 | sp-6 | an-289 | 1U2174 | sp-6 | an-289 | 1C2174 | sp-6 | an-289 |
| 1A2175 | sp-6 | an-290 | 1U2175 | sp-6 | an-290 | 1C2175 | sp-6 | an-290 |
| 1A2176 | sp-6 | an-291 | 1U2176 | sp-6 | an-291 | 1C2176 | sp-6 | an-291 |
| 1A2177 | sp-6 | an-292 | 1U2177 | sp-6 | an-292 | 1C2177 | sp-6 | an-292 |
| 1A2178 | sp-6 | an-293 | 1U2178 | sp-6 | an-293 | 1C2178 | sp-6 | an-293 |
| 1A2179 | sp-6 | an-294 | 1U2179 | sp-6 | an-294 | 1C2179 | sp-6 | an-294 |
| 1A2180 | sp-6 | an-295 | 1U2180 | sp-6 | an-295 | 1C2180 | sp-6 | an-295 |
| 1A2181 | sp-6 | an-296 | 1U2181 | sp-6 | an-296 | 1C2181 | sp-6 | an-296 |
| 1A2182 | sp-6 | an-297 | 1U2182 | sp-6 | an-297 | 1C2182 | sp-6 | an-297 |
| 1A2183 | sp-6 | an-298 | 1U2183 | sp-6 | an-298 | 1C2183 | sp-6 | an-298 |
| 1A2184 | sp-6 | an-299 | 1U2184 | sp-6 | an-299 | 1C2184 | sp-6 | an-299 |
| 1A2185 | sp-6 | an-300 | 1U2185 | sp-6 | an-300 | 1C2185 | sp-6 | an-300 |
| 1A2186 | sp-6 | an-301 | 1U2186 | sp-6 | an-301 | 1C2186 | sp-6 | an-301 |
| 1A2187 | sp-6 | an-302 | 1U2187 | sp-6 | an-302 | 1C2187 | sp-6 | an-302 |
| 1A2188 | sp-6 | an-303 | 1U2188 | sp-6 | an-303 | 1C2188 | sp-6 | an-303 |
| 1A2189 | sp-6 | an-304 | 1U2189 | sp-6 | an-304 | 1C2189 | sp-6 | an-304 |
| 1A2190 | sp-6 | an-305 | 1U2190 | sp-6 | an-305 | 1C2190 | sp-6 | an-305 |
| 1A2191 | sp-6 | an-306 | 1U2191 | sp-6 | an-306 | 1C2191 | sp-6 | an-306 |
| 1A2192 | sp-6 | an-307 | 1U2192 | sp-6 | an-307 | 1C2192 | sp-6 | an-307 |
| 1A2193 | sp-6 | an-308 | 1U2193 | sp-6 | an-308 | 1C2193 | sp-6 | an-308 |
| 1A2194 | sp-6 | an-309 | 1U2194 | sp-6 | an-309 | 1C2194 | sp-6 | an-309 |
| 1A2195 | sp-6 | an-310 | 1U2195 | sp-6 | an-310 | 1C2195 | sp-6 | an-310 |
| 1A2196 | sp-6 | an-311 | 1U2196 | sp-6 | an-311 | 1C2196 | sp-6 | an-311 |
| 1A2197 | sp-6 | an-312 | 1U2197 | sp-6 | an-312 | 1C2197 | sp-6 | an-312 |
| 1A2198 | sp-6 | an-313 | 1U2198 | sp-6 | an-313 | 1C2198 | sp-6 | an-313 |
| 1A2199 | sp-6 | an-314 | 1U2199 | sp-6 | an-314 | 1C2199 | sp-6 | an-314 |
| 1A2200 | sp-6 | an-315 | 1U2200 | sp-6 | an-315 | 1C2200 | sp-6 | an-315 |
| 1A2201 | sp-6 | an-316 | 1U2201 | sp-6 | an-316 | 1C2201 | sp-6 | an-316 |
| 1A2202 | sp-6 | an-317 | 1U2202 | sp-6 | an-317 | 1C2202 | sp-6 | an-317 |
| 1A2203 | sp-6 | an-318 | 1U2203 | sp-6 | an-318 | 1C2203 | sp-6 | an-318 |
| 1A2204 | sp-6 | an-319 | 1U2204 | sp-6 | an-319 | 1C2204 | sp-6 | an-319 |
| 1A2205 | sp-6 | an-320 | 1U2205 | sp-6 | an-320 | 1C2205 | sp-6 | an-320 |
| 1A2206 | sp-6 | an-321 | 1U2206 | sp-6 | an-321 | 1C2206 | sp-6 | an-321 |
| 1A2207 | sp-6 | an-322 | 1U2207 | sp-6 | an-322 | 1C2207 | sp-6 | an-322 |
| 1A2208 | sp-6 | an-323 | 1U2208 | sp-6 | an-323 | 1C2208 | sp-6 | an-323 |
| 1A2209 | sp-6 | an-324 | 1U2209 | sp-6 | an-324 | 1C2209 | sp-6 | an-324 |
| 1A2210 | sp-6 | an-325 | 1U2210 | sp-6 | an-325 | 1C2210 | sp-6 | an-325 |
| 1A2211 | sp-6 | an-326 | 1U2211 | sp-6 | an-326 | 1C2211 | sp-6 | an-326 |
| 1A2212 | sp-6 | an-327 | 1U2212 | sp-6 | an-327 | 1C2212 | sp-6 | an-327 |
| 1A2213 | sp-6 | an-328 | 1U2213 | sp-6 | an-328 | 1C2213 | sp-6 | an-328 |
| 1A2214 | sp-6 | an-329 | 1U2214 | sp-6 | an-329 | 1C2214 | sp-6 | an-329 |
| 1A2215 | sp-6 | an-330 | 1U2215 | sp-6 | an-330 | 1C2215 | sp-6 | an-330 |
| 1A2216 | sp-6 | an-331 | 1U2216 | sp-6 | an-331 | 1C2216 | sp-6 | an-331 |
| 1A2217 | sp-6 | an-332 | 1U2217 | sp-6 | an-332 | 1C2217 | sp-6 | an-332 |
| 1A2218 | sp-6 | an-333 | 1U2218 | sp-6 | an-333 | 1C2218 | sp-6 | an-333 |
| 1A2219 | sp-6 | an-334 | 1U2219 | sp-6 | an-334 | 1C2219 | sp-6 | an-334 |
| 1A2220 | sp-6 | an-335 | 1U2220 | sp-6 | an-335 | 1C2220 | sp-6 | an-335 |
| 1A2221 | sp-6 | an-336 | 1U2221 | sp-6 | an-336 | 1C2221 | sp-6 | an-336 |
| 1A2222 | sp-6 | an-337 | 1U2222 | sp-6 | an-337 | 1C2222 | sp-6 | an-337 |
| 1A2223 | sp-6 | an-338 | 1U2223 | sp-6 | an-338 | 1C2223 | sp-6 | an-338 |
| 1A2224 | sp-6 | an-339 | 1U2224 | sp-6 | an-339 | 1C2224 | sp-6 | an-339 |
| 1A2225 | sp-6 | an-340 | 1U2225 | sp-6 | an-340 | 1C2225 | sp-6 | an-340 |
| 1A2226 | sp-6 | an-341 | 1U2226 | sp-6 | an-341 | 1C2226 | sp-6 | an-341 |
| 1A2227 | sp-6 | an-342 | 1U2227 | sp-6 | an-342 | 1C2227 | sp-6 | an-342 |
| 1A2228 | sp-6 | an-343 | 1U2228 | sp-6 | an-343 | 1C2228 | sp-6 | an-343 |
| 1A2229 | sp-6 | an-344 | 1U2229 | sp-6 | an-344 | 1C2229 | sp-6 | an-344 |

TABLE 1-continued

| | | | | | | | | |
|---|---|---|---|---|---|---|---|---|
| 1A2230 | sp-6 | an-345 | 1U2230 | sp-6 | an-345 | 1C2230 | sp-6 | an-345 |
| 1A2231 | sp-6 | an-346 | 1U2231 | sp-6 | an-346 | 1C2231 | sp-6 | an-346 |
| 1A2232 | sp-6 | an-347 | 1U2232 | sp-6 | an-347 | 1C2232 | sp-6 | an-347 |
| 1A2233 | sp-6 | an-348 | 1U2233 | sp-6 | an-348 | 1C2233 | sp-6 | an-348 |
| 1A2234 | sp-6 | an-349 | 1U2234 | sp-6 | an-349 | 1C2234 | sp-6 | an-349 |
| 1A2235 | sp-6 | an-350 | 1U2235 | sp-6 | an-350 | 1C2235 | sp-6 | an-350 |
| 1A2236 | sp-6 | an-351 | 1U2236 | sp-6 | an-351 | 1C2236 | sp-6 | an-351 |
| 1A2237 | sp-6 | an-352 | 1U2237 | sp-6 | an-352 | 1C2237 | sp-6 | an-352 |
| 1A2238 | sp-6 | an-353 | 1U2238 | sp-6 | an-353 | 1C2238 | sp-6 | an-353 |
| 1A2239 | sp-6 | an-354 | 1U2239 | sp-6 | an-354 | 1C2239 | sp-6 | an-354 |
| 1A2240 | sp-6 | an-355 | 1U2240 | sp-6 | an-355 | 1C2240 | sp-6 | an-355 |
| 1A2241 | sp-6 | an-356 | 1U2241 | sp-6 | an-356 | 1C2241 | sp-6 | an-356 |
| 1A2242 | sp-6 | an-357 | 1U2242 | sp-6 | an-357 | 1C2242 | sp-6 | an-357 |
| 1A2243 | sp-6 | an-358 | 1U2243 | sp-6 | an-358 | 1C2243 | sp-6 | an-358 |
| 1A2244 | sp-6 | an-359 | 1U2244 | sp-6 | an-359 | 1C2244 | sp-6 | an-359 |
| 1A2245 | sp-6 | an-360 | 1U2245 | sp-6 | an-360 | 1C2245 | sp-6 | an-360 |
| 1A2246 | sp-6 | an-361 | 1U2246 | sp-6 | an-361 | 1C2246 | sp-6 | an-361 |
| 1A2247 | sp-6 | an-362 | 1U2247 | sp-6 | an-362 | 1C2247 | sp-6 | an-362 |
| 1A2248 | sp-6 | an-363 | 1U2248 | sp-6 | an-363 | 1C2248 | sp-6 | an-363 |
| 1A2249 | sp-6 | an-364 | 1U2249 | sp-6 | an-364 | 1C2249 | sp-6 | an-364 |
| 1A2250 | sp-6 | an-365 | 1U2250 | sp-6 | an-365 | 1C2250 | sp-6 | an-365 |
| 1A2251 | sp-6 | an-366 | 1U2251 | sp-6 | an-366 | 1C2251 | sp-6 | an-366 |
| 1A2252 | sp-6 | an-367 | 1U2252 | sp-6 | an-367 | 1C2252 | sp-6 | an-367 |
| 1A2253 | sp-6 | an-368 | 1U2253 | sp-6 | an-368 | 1C2253 | sp-6 | an-368 |
| 1A2254 | sp-6 | an-369 | 1U2254 | sp-6 | an-369 | 1C2254 | sp-6 | an-369 |
| 1A2255 | sp-6 | an-370 | 1U2255 | sp-6 | an-370 | 1C2255 | sp-6 | an-370 |
| 1A2256 | sp-6 | an-371 | 1U2256 | sp-6 | an-371 | 1C2256 | sp-6 | an-371 |
| 1A2257 | sp-6 | an-372 | 1U2257 | sp-6 | an-372 | 1C2257 | sp-6 | an-372 |
| 1A2258 | sp-6 | an-373 | 1U2258 | sp-6 | an-373 | 1C2258 | sp-6 | an-373 |
| 1A2259 | sp-6 | an-374 | 1U2259 | sp-6 | an-374 | 1C2259 | sp-6 | an-374 |
| 1A2260 | sp-6 | an-375 | 1U2260 | sp-6 | an-375 | 1C2260 | sp-6 | an-375 |
| 1A2261 | sp-6 | an-376 | 1U2261 | sp-6 | an-376 | 1C2261 | sp-6 | an-376 |
| 1A2262 | sp-6 | an-377 | 1U2262 | sp-6 | an-377 | 1C2262 | sp-6 | an-377 |
| 1A2263 | sp-7 | an-1 | 1U2263 | sp-7 | an-1 | 1C2263 | sp-7 | an-1 |
| 1A2264 | sp-7 | an-2 | 1U2264 | sp-7 | an-2 | 1C2264 | sp-7 | an-2 |
| 1A2265 | sp-7 | an-3 | 1U2265 | sp-7 | an-3 | 1C2265 | sp-7 | an-3 |
| 1A2266 | sp-7 | an-4 | 1U2266 | sp-7 | an-4 | 1C2266 | sp-7 | an-4 |
| 1A2267 | sp-7 | an-5 | 1U2267 | sp-7 | an-5 | 1C2267 | sp-7 | an-5 |
| 1A2268 | sp-7 | an-6 | 1U2268 | sp-7 | an-6 | 1C2268 | sp-7 | an-6 |
| 1A2269 | sp-7 | an-7 | 1U2269 | sp-7 | an-7 | 1C2269 | sp-7 | an-7 |
| 1A2270 | sp-7 | an-8 | 1U2270 | sp-7 | an-8 | 1C2270 | sp-7 | an-8 |
| 1A2271 | sp-7 | an-9 | 1U2271 | sp-7 | an-9 | 1C2271 | sp-7 | an-9 |
| 1A2272 | sp-7 | an-10 | 1U2272 | sp-7 | an-10 | 1C2272 | sp-7 | an-10 |
| 1A2273 | sp-7 | an-11 | 1U2273 | sp-7 | an-11 | 1C2273 | sp-7 | an-11 |
| 1A2274 | sp-7 | an-12 | 1U2274 | sp-7 | an-12 | 1C2274 | sp-7 | an-12 |
| 1A2275 | sp-7 | an-13 | 1U2275 | sp-7 | an-13 | 1C2275 | sp-7 | an-13 |
| 1A2276 | sp-7 | an-14 | 1U2276 | sp-7 | an-14 | 1C2276 | sp-7 | an-14 |
| 1A2277 | sp-7 | an-15 | 1U2277 | sp-7 | an-15 | 1C2277 | sp-7 | an-15 |
| 1A2278 | sp-7 | an-16 | 1U2278 | sp-7 | an-16 | 1C2278 | sp-7 | an-16 |
| 1A2279 | sp-7 | an-17 | 1U2279 | sp-7 | an-17 | 1C2279 | sp-7 | an-17 |
| 1A2280 | sp-7 | an-18 | 1U2280 | sp-7 | an-18 | 1C2280 | sp-7 | an-18 |
| 1A2281 | sp-7 | an-19 | 1U2281 | sp-7 | an-19 | 1C2281 | sp-7 | an-19 |
| 1A2282 | sp-7 | an-20 | 1U2282 | sp-7 | an-20 | 1C2282 | sp-7 | an-20 |
| 1A2283 | sp-7 | an-21 | 1U2283 | sp-7 | an-21 | 1C2283 | sp-7 | an-21 |
| 1A2284 | sp-7 | an-22 | 1U2284 | sp-7 | an-22 | 1C2284 | sp-7 | an-22 |
| 1A2285 | sp-7 | an-23 | 1U2285 | sp-7 | an-23 | 1C2285 | sp-7 | an-23 |
| 1A2286 | sp-7 | an-24 | 1U2286 | sp-7 | an-24 | 1C2286 | sp-7 | an-24 |
| 1A2287 | sp-7 | an-25 | 1U2287 | sp-7 | an-25 | 1C2287 | sp-7 | an-25 |
| 1A2288 | sp-7 | an-26 | 1U2288 | sp-7 | an-26 | 1C2288 | sp-7 | an-26 |
| 1A2289 | sp-7 | an-27 | 1U2289 | sp-7 | an-27 | 1C2289 | sp-7 | an-27 |
| 1A2290 | sp-7 | an-28 | 1U2290 | sp-7 | an-28 | 1C2290 | sp-7 | an-28 |
| 1A2291 | sp-7 | an-29 | 1U2291 | sp-7 | an-29 | 1C2291 | sp-7 | an-29 |
| 1A2292 | sp-7 | an-30 | 1U2292 | sp-7 | an-30 | 1C2292 | sp-7 | an-30 |
| 1A2293 | sp-7 | an-31 | 1U2293 | sp-7 | an-31 | 1C2293 | sp-7 | an-31 |
| 1A2294 | sp-7 | an-32 | 1U2294 | sp-7 | an-32 | 1C2294 | sp-7 | an-32 |
| 1A2295 | sp-7 | an-33 | 1U2295 | sp-7 | an-33 | 1C2295 | sp-7 | an-33 |
| 1A2296 | sp-7 | an-34 | 1U2296 | sp-7 | an-34 | 1C2296 | sp-7 | an-34 |
| 1A2297 | sp-7 | an-35 | 1U2297 | sp-7 | an-35 | 1C2297 | sp-7 | an-35 |
| 1A2298 | sp-7 | an-36 | 1U2298 | sp-7 | an-36 | 1C2298 | sp-7 | an-36 |
| 1A2299 | sp-7 | an-37 | 1U2299 | sp-7 | an-37 | 1C2299 | sp-7 | an-37 |
| 1A2300 | sp-7 | an-38 | 1U2300 | sp-7 | an-38 | 1C2300 | sp-7 | an-38 |
| 1A2301 | sp-7 | an-39 | 1U2301 | sp-7 | an-39 | 1C2301 | sp-7 | an-39 |
| 1A2302 | sp-7 | an-40 | 1U2302 | sp-7 | an-40 | 1C2302 | sp-7 | an-40 |
| 1A2303 | sp-7 | an-41 | 1U2303 | sp-7 | an-41 | 1C2303 | sp-7 | an-41 |
| 1A2304 | sp-7 | an-42 | 1U2304 | sp-7 | an-42 | 1C2304 | sp-7 | an-42 |
| 1A2305 | sp-7 | an-43 | 1U2305 | sp-7 | an-43 | 1C2305 | sp-7 | an-43 |
| 1A2306 | sp-7 | an-44 | 1U2306 | sp-7 | an-44 | 1C2306 | sp-7 | an-44 |
| 1A2307 | sp-7 | an-45 | 1U2307 | sp-7 | an-45 | 1C2307 | sp-7 | an-45 |
| 1A2308 | sp-7 | an-46 | 1U2308 | sp-7 | an-46 | 1C2308 | sp-7 | an-46 |

TABLE 1-continued

| | | | | | | | | |
|---|---|---|---|---|---|---|---|---|
| 1A2309 | sp-7 | an-47 | 1U2309 | sp-7 | an-47 | 1C2309 | sp-7 | an-47 |
| 1A2310 | sp-7 | an-48 | 1U2310 | sp-7 | an-48 | 1C2310 | sp-7 | an-48 |
| 1A2311 | sp-7 | an-49 | 1U2311 | sp-7 | an-49 | 1C2311 | sp-7 | an-49 |
| 1A2312 | sp-7 | an-50 | 1U2312 | sp-7 | an-50 | 1C2312 | sp-7 | an-50 |
| 1A2313 | sp-7 | an-51 | 1U2313 | sp-7 | an-51 | 1C2313 | sp-7 | an-51 |
| 1A2314 | sp-7 | an-52 | 1U2314 | sp-7 | an-52 | 1C2314 | sp-7 | an-52 |
| 1A2315 | sp-7 | an-53 | 1U2315 | sp-7 | an-53 | 1C2315 | sp-7 | an-53 |
| 1A2316 | sp-7 | an-54 | 1U2316 | sp-7 | an-54 | 1C2316 | sp-7 | an-54 |
| 1A2317 | sp-7 | an-55 | 1U2317 | sp-7 | an-55 | 1C2317 | sp-7 | an-55 |
| 1A2318 | sp-7 | an-56 | 1U2318 | sp-7 | an-56 | 1C2318 | sp-7 | an-56 |
| 1A2319 | sp-7 | an-57 | 1U2319 | sp-7 | an-57 | 1C2319 | sp-7 | an-57 |
| 1A2320 | sp-7 | an-58 | 1U2320 | sp-7 | an-58 | 1C2320 | sp-7 | an-58 |
| 1A2321 | sp-7 | an-59 | 1U2321 | sp-7 | an-59 | 1C2321 | sp-7 | an-59 |
| 1A2322 | sp-7 | an-60 | 1U2322 | sp-7 | an-60 | 1C2322 | sp-7 | an-60 |
| 1A2323 | sp-7 | an-61 | 1U2323 | sp-7 | an-61 | 1C2323 | sp-7 | an-61 |
| 1A2324 | sp-7 | an-62 | 1U2324 | sp-7 | an-62 | 1C2324 | sp-7 | an-62 |
| 1A2325 | sp-7 | an-63 | 1U2325 | sp-7 | an-63 | 1C2325 | sp-7 | an-63 |
| 1A2326 | sp-7 | an-64 | 1U2326 | sp-7 | an-64 | 1C2326 | sp-7 | an-64 |
| 1A2327 | sp-7 | an-65 | 1U2327 | sp-7 | an-65 | 1C2327 | sp-7 | an-65 |
| 1A2328 | sp-7 | an-66 | 1U2328 | sp-7 | an-66 | 1C2328 | sp-7 | an-66 |
| 1A2329 | sp-7 | an-67 | 1U2329 | sp-7 | an-67 | 1C2329 | sp-7 | an-67 |
| 1A2330 | sp-7 | an-68 | 1U2330 | sp-7 | an-68 | 1C2330 | sp-7 | an-68 |
| 1A2331 | sp-7 | an-69 | 1U2331 | sp-7 | an-69 | 1C2331 | sp-7 | an-69 |
| 1A2332 | sp-7 | an-70 | 1U2332 | sp-7 | an-70 | 1C2332 | sp-7 | an-70 |
| 1A2333 | sp-7 | an-71 | 1U2333 | sp-7 | an-71 | 1C2333 | sp-7 | an-71 |
| 1A2334 | sp-7 | an-72 | 1U2334 | sp-7 | an-72 | 1C2334 | sp-7 | an-72 |
| 1A2335 | sp-7 | an-73 | 1U2335 | sp-7 | an-73 | 1C2335 | sp-7 | an-73 |
| 1A2336 | sp-7 | an-74 | 1U2336 | sp-7 | an-74 | 1C2336 | sp-7 | an-74 |
| 1A2337 | sp-7 | an-75 | 1U2337 | sp-7 | an-75 | 1C2337 | sp-7 | an-75 |
| 1A2338 | sp-7 | an-76 | 1U2338 | sp-7 | an-76 | 1C2338 | sp-7 | an-76 |
| 1A2339 | sp-7 | an-77 | 1U2339 | sp-7 | an-77 | 1C2339 | sp-7 | an-77 |
| 1A2340 | sp-7 | an-78 | 1U2340 | sp-7 | an-78 | 1C2340 | sp-7 | an-78 |
| 1A2341 | sp-7 | an-79 | 1U2341 | sp-7 | an-79 | 1C2341 | sp-7 | an-79 |
| 1A2342 | sp-7 | an-80 | 1U2342 | sp-7 | an-80 | 1C2342 | sp-7 | an-80 |
| 1A2343 | sp-7 | an-81 | 1U2343 | sp-7 | an-81 | 1C2343 | sp-7 | an-81 |
| 1A2344 | sp-7 | an-82 | 1U2344 | sp-7 | an-82 | 1C2344 | sp-7 | an-82 |
| 1A2345 | sp-7 | an-83 | 1U2345 | sp-7 | an-83 | 1C2345 | sp-7 | an-83 |
| 1A2346 | sp-7 | an-84 | 1U2346 | sp-7 | an-84 | 1C2346 | sp-7 | an-84 |
| 1A2347 | sp-7 | an-85 | 1U2347 | sp-7 | an-85 | 1C2347 | sp-7 | an-85 |
| 1A2348 | sp-7 | an-86 | 1U2348 | sp-7 | an-86 | 1C2348 | sp-7 | an-86 |
| 1A2349 | sp-7 | an-87 | 1U2349 | sp-7 | an-87 | 1C2349 | sp-7 | an-87 |
| 1A2350 | sp-7 | an-88 | 1U2350 | sp-7 | an-88 | 1C2350 | sp-7 | an-88 |
| 1A2351 | sp-7 | an-89 | 1U2351 | sp-7 | an-89 | 1C2351 | sp-7 | an-89 |
| 1A2352 | sp-7 | an-90 | 1U2352 | sp-7 | an-90 | 1C2352 | sp-7 | an-90 |
| 1A2353 | sp-7 | an-91 | 1U2353 | sp-7 | an-91 | 1C2353 | sp-7 | an-91 |
| 1A2354 | sp-7 | an-92 | 1U2354 | sp-7 | an-92 | 1C2354 | sp-7 | an-92 |
| 1A2355 | sp-7 | an-93 | 1U2355 | sp-7 | an-93 | 1C2355 | sp-7 | an-93 |
| 1A2356 | sp-7 | an-94 | 1U2356 | sp-7 | an-94 | 1C2356 | sp-7 | an-94 |
| 1A2357 | sp-7 | an-95 | 1U2357 | sp-7 | an-95 | 1C2357 | sp-7 | an-95 |
| 1A2358 | sp-7 | an-96 | 1U2358 | sp-7 | an-96 | 1C2358 | sp-7 | an-96 |
| 1A2359 | sp-7 | an-97 | 1U2359 | sp-7 | an-97 | 1C2359 | sp-7 | an-97 |
| 1A2360 | sp-7 | an-98 | 1U2360 | sp-7 | an-98 | 1C2360 | sp-7 | an-98 |
| 1A2361 | sp-7 | an-99 | 1U2361 | sp-7 | an-99 | 1C2361 | sp-7 | an-99 |
| 1A2362 | sp-7 | an-100 | 1U2362 | sp-7 | an-100 | 1C2362 | sp-7 | an-100 |
| 1A2363 | sp-7 | an-101 | 1U2363 | sp-7 | an-101 | 1C2363 | sp-7 | an-101 |
| 1A2364 | sp-7 | an-102 | 1U2364 | sp-7 | an-102 | 1C2364 | sp-7 | an-102 |
| 1A2365 | sp-7 | an-103 | 1U2365 | sp-7 | an-103 | 1C2365 | sp-7 | an-103 |
| 1A2366 | sp-7 | an-104 | 1U2366 | sp-7 | an-104 | 1C2366 | sp-7 | an-104 |
| 1A2367 | sp-7 | an-105 | 1U2367 | sp-7 | an-105 | 1C2367 | sp-7 | an-105 |
| 1A2368 | sp-7 | an-106 | 1U2368 | sp-7 | an-106 | 1C2368 | sp-7 | an-106 |
| 1A2369 | sp-7 | an-107 | 1U2369 | sp-7 | an-107 | 1C2369 | sp-7 | an-107 |
| 1A2370 | sp-7 | an-108 | 1U2370 | sp-7 | an-108 | 1C2370 | sp-7 | an-108 |
| 1A2371 | sp-7 | an-109 | 1U2371 | sp-7 | an-109 | 1C2371 | sp-7 | an-109 |
| 1A2372 | sp-7 | an-110 | 1U2372 | sp-7 | an-110 | 1C2372 | sp-7 | an-110 |
| 1A2373 | sp-7 | an-111 | 1U2373 | sp-7 | an-111 | 1C2373 | sp-7 | an-111 |
| 1A2374 | sp-7 | an-112 | 1U2374 | sp-7 | an-112 | 1C2374 | sp-7 | an-112 |
| 1A2375 | sp-7 | an-113 | 1U2375 | sp-7 | an-113 | 1C2375 | sp-7 | an-113 |
| 1A2376 | sp-7 | an-114 | 1U2376 | sp-7 | an-114 | 1C2376 | sp-7 | an-114 |
| 1A2377 | sp-7 | an-115 | 1U2377 | sp-7 | an-115 | 1C2377 | sp-7 | an-115 |
| 1A2378 | sp-7 | an-116 | 1U2378 | sp-7 | an-116 | 1G2378 | sp-7 | an-116 |
| 1A2379 | sp-7 | an-117 | 1U2379 | sp-7 | an-117 | 1C2379 | sp-7 | an-117 |
| 1A2380 | sp-7 | an-118 | 1U2380 | sp-7 | an-118 | 1C2380 | sp-7 | an-118 |
| 1A2381 | sp-7 | an-119 | 1U2381 | sp-7 | an-119 | 1C2381 | sp-7 | an-119 |
| 1A2382 | sp-7 | an-120 | 1U2382 | sp-7 | an-120 | 1C2382 | sp-7 | an-120 |
| 1A2383 | sp-7 | an-121 | 1U2383 | sp-7 | an-121 | 1C2383 | sp-7 | an-121 |
| 1A2384 | sp-7 | an-122 | 1U2384 | sp-7 | an-122 | 1C2384 | sp-7 | an-122 |
| 1A2385 | sp-7 | an-123 | 1U2385 | sp-7 | an-123 | 1C2385 | sp-7 | an-123 |
| 1A2386 | sp-7 | an-124 | 1U2386 | sp-7 | an-124 | 1C2386 | sp-7 | an-124 |
| 1A2387 | sp-7 | an-125 | 1U2387 | sp-7 | an-125 | 1C2387 | sp-7 | an-125 |

TABLE 1-continued

| | | | | | | | | |
|---|---|---|---|---|---|---|---|---|
| 1A2388 | sp-7 | an-126 | 1U2388 | sp-7 | an-126 | 1C2388 | sp-7 | an-126 |
| 1A2389 | sp-7 | an-127 | 1U2389 | sp-7 | an-127 | 1C2389 | sp-7 | an-127 |
| 1A2390 | sp-7 | an-128 | 1U2390 | sp-7 | an-128 | 1C2390 | sp-7 | an-128 |
| 1A2391 | sp-7 | an-129 | 1U2391 | sp-7 | an-129 | 1C2391 | sp-7 | an-129 |
| 1A2392 | sp-7 | an-130 | 1U2392 | sp-7 | an-130 | 1C2392 | sp-7 | an-130 |
| 1A2393 | sp-7 | an-131 | 1U2393 | sp-7 | an-131 | 1C2393 | sp-7 | an-131 |
| 1A2394 | sp-7 | an-132 | 1U2394 | sp-7 | an-132 | 1C2394 | sp-7 | an-132 |
| 1A2395 | sp-7 | an-133 | 1U2395 | sp-7 | an-133 | 1C2395 | sp-7 | an-133 |
| 1A2396 | sp-7 | an-134 | 1U2396 | sp-7 | an-134 | 1C2396 | sp-7 | an-134 |
| 1A2397 | sp-7 | an-135 | 1U2397 | sp-7 | an-135 | 1C2397 | sp-7 | an-135 |
| 1A2398 | sp-7 | an-136 | 1U2398 | sp-7 | an-136 | 1C2398 | sp-7 | an-136 |
| 1A2399 | sp-7 | an-137 | 1U2399 | sp-7 | an-137 | 1C2399 | sp-7 | an-137 |
| 1A2400 | sp-7 | an-138 | 1U2400 | sp-7 | an-138 | 1C2400 | sp-7 | an-138 |
| 1A2401 | sp-7 | an-139 | 1U2401 | sp-7 | an-139 | 1C2401 | sp-7 | an-139 |
| 1A2402 | sp-7 | an-140 | 1U2402 | sp-7 | an-140 | 1C2402 | sp-7 | an-140 |
| 1A2403 | sp-7 | an-141 | 1U2403 | sp-7 | an-141 | 1C2403 | sp-7 | an-141 |
| 1A2404 | sp-7 | an-142 | 1U2404 | sp-7 | an-142 | 1G2404 | sp-7 | an-142 |
| 1A2405 | sp-7 | an-143 | 1U2405 | sp-7 | an-143 | 1C2405 | sp-7 | an-143 |
| 1A2406 | sp-7 | an-144 | 1U2406 | sp-7 | an-144 | 1C2406 | sp-7 | an-144 |
| 1A2407 | sp-7 | an-145 | 1U2407 | sp-7 | an-145 | 1C2407 | sp-7 | an-145 |
| 1A2408 | sp-7 | an-146 | 1U2408 | sp-7 | an-146 | 1C2408 | sp-7 | an-146 |
| 1A2409 | sp-7 | an-147 | 1U2409 | sp-7 | an-147 | 1C2409 | sp-7 | an-147 |
| 1A2410 | sp-7 | an-148 | 1U2410 | sp-7 | an-148 | 1C2410 | sp-7 | an-148 |
| 1A2411 | sp-7 | an-149 | 1U2411 | sp-7 | an-149 | 1C2411 | sp-7 | an-149 |
| 1A2412 | sp-7 | an-150 | 1U2412 | sp-7 | an-150 | 1C2412 | sp-7 | an-150 |
| 1A2413 | sp-7 | an-151 | 1U2413 | sp-7 | an-151 | 1C2413 | sp-7 | an-151 |
| 1A2414 | sp-7 | an-152 | 1U2414 | sp-7 | an-152 | 1C2414 | sp-7 | an-152 |
| 1A2415 | sp-7 | an-153 | 1U2415 | sp-7 | an-153 | 1C2415 | sp-7 | an-153 |
| 1A2416 | sp-7 | an-154 | 1U2416 | sp-7 | an-154 | 1C2416 | sp-7 | an-154 |
| 1A2417 | sp-7 | an-155 | 1U2417 | sp-7 | an-155 | 1C2417 | sp-7 | an-155 |
| 1A2418 | sp-7 | an-156 | 1U2418 | sp-7 | an-156 | 1C2418 | sp-7 | an-156 |
| 1A2419 | sp-7 | an-157 | 1U2419 | sp-7 | an-157 | 1C2419 | sp-7 | an-157 |
| 1A2420 | sp-7 | an-158 | 1U2420 | sp-7 | an-158 | 1C2420 | sp-7 | an-158 |
| 1A2421 | sp-7 | an-159 | 1U2421 | sp-7 | an-159 | 1C2421 | sp-7 | an-159 |
| 1A2422 | sp-7 | an-160 | 1U2422 | sp-7 | an-160 | 1C2422 | sp-7 | an-160 |
| 1A2423 | sp-7 | an-161 | 1U2423 | sp-7 | an-161 | 1C2423 | sp-7 | an-161 |
| 1A2424 | sp-7 | an-162 | 1U2424 | sp-7 | an-162 | 1C2424 | sp-7 | an-162 |
| 1A2425 | sp-7 | an-163 | 1U2425 | sp-7 | an-163 | 1C2425 | sp-7 | an-163 |
| 1A2426 | sp-7 | an-164 | 1U2426 | sp-7 | an-164 | 1C2426 | sp-7 | an-164 |
| 1A2427 | sp-7 | an-165 | 1U2427 | sp-7 | an-165 | 1C2427 | sp-7 | an-165 |
| 1A2428 | sp-7 | an-166 | 1U2428 | sp-7 | an-166 | 1G2428 | sp-7 | an-166 |
| 1A2429 | sp-7 | an-167 | 1U2429 | sp-7 | an-167 | 1C2429 | sp-7 | an-167 |
| 1A2430 | sp-7 | an-168 | 1U2430 | sp-7 | an-168 | 1C2430 | sp-7 | an-168 |
| 1A2431 | sp-7 | an-169 | 1U2431 | sp-7 | an-169 | 1C2431 | sp-7 | an-169 |
| 1A2432 | sp-7 | an-170 | 1U2432 | sp-7 | an-170 | 1C2432 | sp-7 | an-170 |
| 1A2433 | sp-7 | an-171 | 1U2433 | sp-7 | an-171 | 1C2433 | sp-7 | an-171 |
| 1A2434 | sp-7 | an-172 | 1U2434 | sp-7 | an-172 | 1C2434 | sp-7 | an-172 |
| 1A2435 | sp-7 | an-173 | 1U2435 | sp-7 | an-173 | 1C2435 | sp-7 | an-173 |
| 1A2436 | sp-7 | an-174 | 1U2436 | sp-7 | an-174 | 1C2436 | sp-7 | an-174 |
| 1A2437 | sp-7 | an-175 | 1U2437 | sp-7 | an-175 | 1C2437 | sp-7 | an-175 |
| 1A2438 | sp-7 | an-176 | 1U2438 | sp-7 | an-176 | 1C2438 | sp-7 | an-176 |
| 1A2439 | sp-7 | an-177 | 1U2439 | sp-7 | an-177 | 1C2439 | sp-7 | an-177 |
| 1A2440 | sp-7 | an-178 | 1U2440 | sp-7 | an-178 | 1C2440 | sp-7 | an-178 |
| 1A2441 | sp-7 | an-179 | 1U2441 | sp-7 | an-179 | 1C2441 | sp-7 | an-179 |
| 1A2442 | sp-7 | an-180 | 1U2442 | sp-7 | an-180 | 1C2442 | sp-7 | an-180 |
| 1A2443 | sp-7 | an-181 | 1U2443 | sp-7 | an-181 | 1C2443 | sp-7 | an-181 |
| 1A2444 | sp-7 | an-132 | 1U2444 | sp-7 | an-182 | 1C2444 | sp-7 | an-182 |
| 1A2445 | sp-7 | an-183 | 1U2445 | sp-7 | an-183 | 1C2445 | sp-7 | an-183 |
| 1A2446 | sp-7 | an-184 | 1U2446 | sp-7 | an-184 | 1C2446 | sp-7 | an-184 |
| 1A2447 | sp-7 | an-185 | 1U2447 | sp-7 | an-185 | 1C2447 | sp-7 | an-185 |
| 1A2448 | sp-7 | an-186 | 1U2448 | sp-7 | an-186 | 1C2448 | sp-7 | an-186 |
| 1A2449 | sp-7 | an-187 | 1U2449 | sp-7 | an-187 | 1C2449 | sp-7 | an-187 |
| 1A2450 | sp-7 | an-188 | 1U2450 | sp-7 | an-188 | 1C2450 | sp-7 | an-188 |
| 1A2451 | sp-7 | an-189 | 1U2451 | sp-7 | an-189 | 1C2451 | sp-7 | an-189 |
| 1A2452 | sp-7 | an-190 | 1U2452 | sp-7 | an-190 | 1C2452 | sp-7 | an-190 |
| 1A2453 | sp-7 | an-191 | 1U2453 | sp-7 | an-191 | 1C2453 | sp-7 | an-191 |
| 1A2454 | sp-7 | an-192 | 1U2454 | sp-7 | an-192 | 1C2454 | sp-7 | an-192 |
| 1A2455 | sp-7 | an-193 | 1U2455 | sp-7 | an-193 | 1C2455 | sp-7 | an-193 |
| 1A2456 | sp-7 | an-194 | 1U2456 | sp-7 | an-194 | 1C2456 | sp-7 | an-194 |
| 1A2457 | sp-7 | an-195 | 1U2457 | sp-7 | an-195 | 1C2457 | sp-7 | an-195 |
| 1A2458 | sp-7 | an-196 | 1U2458 | sp-7 | an-196 | 1C2458 | sp-7 | an-196 |
| 1A2459 | sp-7 | an-197 | 1U2459 | sp-7 | an-197 | 1C2459 | sp-7 | an-197 |
| 1A2460 | sp-7 | an-198 | 1U2460 | sp-7 | an-198 | 1C2460 | sp-7 | an-198 |
| 1A2461 | sp-7 | an-199 | 1U2461 | sp-7 | an-199 | 1C2461 | sp-7 | an-199 |
| 1A2462 | sp-7 | an-200 | 1U2462 | sp-7 | an-200 | 1C2462 | sp-7 | an-200 |
| 1A2463 | sp-7 | an-201 | 1U2463 | sp-7 | an-201 | 1C2463 | sp-7 | an-201 |
| 1A2464 | sp-7 | an-202 | 1U2464 | sp-7 | an-202 | 1C2464 | sp-7 | an-202 |
| 1A2465 | sp-7 | an-203 | 1U2465 | sp-7 | an-203 | 1C2465 | sp-7 | an-203 |
| 1A2466 | sp-7 | an-204 | 1U2466 | sp-7 | an-204 | 1C2466 | sp-7 | an-204 |

TABLE 1-continued

| | | | | | | | | |
|---|---|---|---|---|---|---|---|---|
| 1A2467 | sp-7 | an-205 | 1U2467 | sp-7 | an-205 | 1C2467 | sp-7 | an-205 |
| 1A2468 | sp-7 | an-206 | 1U2468 | sp-7 | an-206 | 1C2468 | sp-7 | an-206 |
| 1A2469 | sp-7 | an-207 | 1U2469 | sp-7 | an-207 | 1C2469 | sp-7 | an-207 |
| 1A2470 | sp-7 | an-208 | 1U2470 | sp-7 | an-208 | 1C2470 | sp-7 | an-208 |
| 1A2471 | sp-7 | an-209 | 1U2471 | sp-7 | an-209 | 1C2471 | sp-7 | an-209 |
| 1A2472 | sp-7 | an-210 | 1U2472 | sp-7 | an-210 | 1C2472 | sp-7 | an-210 |
| 1A2473 | sp-7 | an-211 | 1U2473 | sp-7 | an-211 | 1C2473 | sp-7 | an-211 |
| 1A2474 | sp-7 | an-212 | 1U2474 | sp-7 | an-212 | 1C2474 | sp-7 | an-212 |
| 1A2475 | sp-7 | an-213 | 1U2475 | sp-7 | an-213 | 1C2475 | sp-7 | an-213 |
| 1A2476 | sp-7 | an-214 | 1U2476 | sp-7 | an-214 | 1C2476 | sp-7 | an-214 |
| 1A2477 | sp-7 | an-215 | 1U2477 | sp-7 | an-215 | 1C2477 | sp-7 | an-215 |
| 1A2478 | sp-7 | an-216 | 1U2478 | sp-7 | an-216 | 1C2478 | sp-7 | an-216 |
| 1A2479 | sp-7 | an-217 | 1U2479 | sp-7 | an-217 | 1C2479 | sp-7 | an-217 |
| 1A2480 | sp-7 | an-218 | 1U2480 | sp-7 | an-218 | 1C2480 | sp-7 | an-218 |
| 1A2481 | sp-7 | an-219 | 1U2481 | sp-7 | an-219 | 1C2481 | sp-7 | an-219 |
| 1A2482 | sp-7 | an-220 | 1U2482 | sp-7 | an-220 | 1C2482 | sp-7 | an-220 |
| 1A2483 | sp-7 | an-221 | 1U2483 | sp-7 | an-221 | 1C2483 | sp-7 | an-221 |
| 1A2484 | sp-7 | an-222 | 1U2484 | sp-7 | an-222 | 1C2484 | sp-7 | an-222 |
| 1A2485 | sp-7 | an-223 | 1U2485 | sp-7 | an-223 | 1C2485 | sp-7 | an-223 |
| 1A2486 | sp-7 | an-224 | 1U2486 | sp-7 | an-224 | 1C2486 | sp-7 | an-224 |
| 1A2487 | sp-7 | an-225 | 1U2487 | sp-7 | an-225 | 1C2487 | sp-7 | an-225 |
| 1A2488 | sp-7 | an-226 | 1U2488 | sp-7 | an-226 | 1C2488 | sp-7 | an-226 |
| 1A2489 | sp-7 | an-227 | 1U2489 | sp-7 | an-227 | 1C2489 | sp-7 | an-227 |
| 1A2490 | sp-7 | an-228 | 1U2490 | sp-7 | an-228 | 1C2490 | sp-7 | an-228 |
| 1A2491 | sp-7 | an-229 | 1U2491 | sp-7 | an-229 | 1C2491 | sp-7 | an-229 |
| 1A2492 | sp-7 | an-230 | 1U2492 | sp-7 | an-230 | 1C2492 | sp-7 | an-230 |
| 1A2493 | sp-7 | an-231 | 1U2493 | sp-7 | an-231 | 1C2493 | sp-7 | an-231 |
| 1A2494 | sp-7 | an-232 | 1U2494 | sp-7 | an-232 | 1C2494 | sp-7 | an-232 |
| 1A2495 | sp-7 | an-233 | 1U2495 | sp-7 | an-233 | 1C2495 | sp-7 | an-233 |
| 1A2496 | sp-7 | an-234 | 1U2496 | sp-7 | an-234 | 1C2496 | sp-7 | an-234 |
| 1A2497 | sp-7 | an-235 | 1U2497 | sp-7 | an-235 | 1C2497 | sp-7 | an-235 |
| 1A2498 | sp-7 | an-236 | 1U2498 | sp-7 | an-236 | 1C2498 | sp-7 | an-236 |
| 1A2499 | sp-7 | an-237 | 1U2499 | sp-7 | an-237 | 1C2499 | sp-7 | an-237 |
| 1A2500 | sp-7 | an-238 | 1U2500 | sp-7 | an-238 | 1C2500 | sp-7 | an-238 |
| 1A2501 | sp-7 | an-239 | 1U2501 | sp-7 | an-239 | 1C2501 | sp-7 | an-239 |
| 1A2502 | sp-7 | an-240 | 1U2502 | sp-7 | an-240 | 1C2502 | sp-7 | an-240 |
| 1A2503 | sp-7 | an-241 | 1U2503 | sp-7 | an-241 | 1C2503 | sp-7 | an-241 |
| 1A2504 | sp-7 | an-242 | 1U2504 | sp-7 | an-242 | 1C2504 | sp-7 | an-242 |
| 1A2505 | sp-7 | an-243 | 1U2505 | sp-7 | an-243 | 1C2505 | sp-7 | an-243 |
| 1A2506 | sp-7 | an-244 | 1U2506 | sp-7 | an-244 | 1C2506 | sp-7 | an-244 |
| 1A2507 | sp-7 | an-245 | 1U2507 | sp-7 | an-245 | 1C2507 | sp-7 | an-245 |
| 1A2508 | sp-7 | an-246 | 1U2508 | sp-7 | an-246 | 1C2508 | sp-7 | an-246 |
| 1A2509 | sp-7 | an-247 | 1U2509 | sp-7 | an-247 | 1C2509 | sp-7 | an-247 |
| 1A2510 | sp-7 | an-248 | 1U2510 | sp-7 | an-248 | 1C2510 | sp-7 | an-248 |
| 1A2511 | sp-7 | an-249 | 1U2511 | sp-7 | an-249 | 1C2511 | sp-7 | an-249 |
| 1A2512 | sp-7 | an-250 | 1U2512 | sp-7 | an-250 | 1C2512 | sp-7 | an-250 |
| 1A2513 | sp-7 | an-251 | 1U2513 | sp-7 | an-251 | 1C2513 | sp-7 | an-251 |
| 1A2514 | sp-7 | an-252 | 1U2514 | sp-7 | an-252 | 1C2514 | sp-7 | an-252 |
| 1A2515 | sp-7 | an-253 | 1U2515 | sp-7 | an-253 | 1C2515 | sp-7 | an-253 |
| 1A2516 | sp-7 | an-254 | 1U2516 | sp-7 | an-254 | 1C2516 | sp-7 | an-254 |
| 1A2517 | sp-7 | an-255 | 1U2517 | sp-7 | an-255 | 1C2517 | sp-7 | an-255 |
| 1A2518 | sp-7 | an-256 | 1U2518 | sp-7 | an-256 | 1C2518 | sp-7 | an-256 |
| 1A2519 | sp-7 | an-257 | 1U2519 | sp-7 | an-257 | 1C2519 | sp-7 | an-257 |
| 1A2520 | sp-7 | an-258 | 1U2520 | sp-7 | an-258 | 1C2520 | sp-7 | an-258 |
| 1A2521 | sp-7 | an-259 | 1U2521 | sp-7 | an-259 | 1C2521 | sp-7 | an-259 |
| 1A2522 | sp-7 | an-260 | 1U2522 | sp-7 | an-260 | 1C2522 | sp-7 | an-260 |
| 1A2523 | sp-7 | an-261 | 1U2523 | sp-7 | an-261 | 1C2523 | sp-7 | an-261 |
| 1A2524 | sp-7 | an-262 | 1U2524 | sp-7 | an-262 | 1C2524 | sp-7 | an-262 |
| 1A2525 | sp-7 | an-263 | 1U2525 | sp-7 | an-263 | 1C2525 | sp-7 | an-263 |
| 1A2526 | sp-7 | an-264 | 1U2526 | sp-7 | an-264 | 1C2526 | sp-7 | an-264 |
| 1A2527 | sp-7 | an-265 | 1U2527 | sp-7 | an-265 | 1C2527 | sp-7 | an-265 |
| 1A2528 | sp-7 | an-266 | 1U2528 | sp-7 | an-266 | 1C2528 | sp-7 | an-266 |
| 1A2529 | sp-7 | an-267 | 1U2529 | sp-7 | an-267 | 1C2529 | sp-7 | an-267 |
| 1A2530 | sp-7 | an-268 | 1U2530 | sp-7 | an-268 | 1C2530 | sp-7 | an-268 |
| 1A2531 | sp-7 | an-269 | 1U2531 | sp-7 | an-269 | 1C2531 | sp-7 | an-269 |
| 1A2532 | sp-7 | an-270 | 1U2532 | sp-7 | an-270 | 1C2532 | sp-7 | an-270 |
| 1A2533 | sp-7 | an-271 | 1U2533 | sp-7 | an-271 | 1C2533 | sp-7 | an-271 |
| 1A2534 | sp-7 | an-272 | 1U2534 | sp-7 | an-272 | 1C2534 | sp-7 | an-272 |
| 1A2535 | sp-7 | an-273 | 1U2535 | sp-7 | an-273 | 1C2535 | sp-7 | an-273 |
| 1A2536 | sp-7 | an-274 | 1U2536 | sp-7 | an-274 | 1C2536 | sp-7 | an-274 |
| 1A2537 | sp-7 | an-275 | 1U2537 | sp-7 | an-275 | 1C2537 | sp-7 | an-275 |
| 1A2538 | sp-7 | an-276 | 1U2538 | sp-7 | an-276 | 1C2538 | sp-7 | an-276 |
| 1A2539 | sp-7 | an-277 | 1U2539 | sp-7 | an-277 | 1C2539 | sp-7 | an-277 |
| 1A2540 | sp-7 | an-278 | 1U2540 | sp-7 | an-278 | 1C2540 | sp-7 | an-278 |
| 1A2541 | sp-7 | an-279 | 1U2541 | sp-7 | an-279 | 1C2541 | sp-7 | an-279 |
| 1A2542 | sp-7 | an-280 | 1U2542 | sp-7 | an-280 | 1C2542 | sp-7 | an-280 |
| 1A2543 | sp-7 | an-281 | 1U2543 | sp-7 | an-231 | 1C2543 | sp-7 | an-281 |
| 1A2544 | sp-7 | an-282 | 1U2544 | sp-7 | an-282 | 1C2544 | sp-7 | an-282 |
| 1A2545 | sp-7 | an-283 | 1U2545 | sp-7 | an-283 | 1C2545 | sp-7 | an-283 |

TABLE 1-continued

| | | | | | | | | |
|---|---|---|---|---|---|---|---|---|
| 1A2546 | sp-7 | an-284 | 1U2546 | sp-7 | an-284 | 1C2546 | sp-7 | an-284 |
| 1A2547 | sp-7 | an-285 | 1U2547 | sp-7 | an-285 | 1C2547 | sp-7 | an-285 |
| 1A2548 | sp-7 | an-286 | 1U2548 | sp-7 | an-286 | 1C2548 | sp-7 | an-286 |
| 1A2549 | sp-7 | an-287 | 1U2549 | sp-7 | an-287 | 1C2549 | sp-7 | an-287 |
| 1A2550 | sp-7 | an-288 | 1U2550 | sp-7 | an-288 | 1C2550 | sp-7 | an-288 |
| 1A2551 | sp-7 | an-289 | 1U2551 | sp-7 | an-289 | 1C2551 | sp-7 | an-289 |
| 1A2552 | sp-7 | an-290 | 1U2552 | sp-7 | an-290 | 1C2552 | sp-7 | an-290 |
| 1A2553 | sp-7 | an-291 | 1U2553 | sp-7 | an-291 | 1C2553 | sp-7 | an-291 |
| 1A2554 | sp-7 | an-292 | 1U2554 | sp-7 | an-292 | 1C2554 | sp-7 | an-292 |
| 1A2555 | sp-7 | an-293 | 1U2555 | sp-7 | an-293 | 1C2555 | sp-7 | an-293 |
| 1A2556 | sp-7 | an-294 | 1U2556 | sp-7 | an-294 | 1C2556 | sp-7 | an-294 |
| 1A2557 | sp-7 | an-295 | 1U2557 | sp-7 | an-295 | 1C2557 | sp-7 | an-295 |
| 1A2558 | sp-7 | an-296 | 1U2558 | sp-7 | an-296 | 1C2558 | sp-7 | an-296 |
| 1A2559 | sp-7 | an-297 | 1U2559 | sp-7 | an-297 | 1C2559 | sp-7 | an-297 |
| 1A2560 | sp-7 | an-298 | 1U2560 | sp-7 | an-298 | 1C2560 | sp-7 | an-298 |
| 1A2561 | sp-7 | an-299 | 1U2561 | sp-7 | an-299 | 1C2561 | sp-7 | an-299 |
| 1A2562 | sp-7 | an-300 | 1U2562 | sp-7 | an-300 | 1C2562 | sp-7 | an-300 |
| 1A2563 | sp-7 | an-301 | 1U2563 | sp-7 | an-301 | 1C2563 | sp-7 | an-301 |
| 1A2564 | sp-7 | an-302 | 1U2564 | sp-7 | an-302 | 1C2564 | sp-7 | an-302 |
| 1A2565 | sp-7 | an-303 | 1U2565 | sp-7 | an-303 | 1C2565 | sp-7 | an-303 |
| 1A2566 | sp-7 | an-304 | 1U2566 | sp-7 | an-304 | 1C2566 | sp-7 | an-304 |
| 1A2567 | sp-7 | an-305 | 1U2567 | sp-7 | an-305 | 1C2567 | sp-7 | an-305 |
| 1A2568 | sp-7 | an-306 | 1U2568 | sp-7 | an-306 | 1C2568 | sp-7 | an-306 |
| 1A2569 | sp-7 | an-307 | 1U2569 | sp-7 | an-307 | 1C2569 | sp-7 | an-307 |
| 1A2570 | sp-7 | an-308 | 1U2570 | sp-7 | an-308 | 1C2570 | sp-7 | an-308 |
| 1A2571 | sp-7 | an-309 | 1U2571 | sp-7 | an-309 | 1C2571 | sp-7 | an-309 |
| 1A2572 | sp-7 | an-310 | 1U2572 | sp-7 | an-310 | 1C2572 | sp-7 | an-310 |
| 1A2573 | sp-7 | an-311 | 1U2573 | sp-7 | an-311 | 1C2573 | sp-7 | an-311 |
| 1A2574 | sp-7 | an-312 | 1U2574 | sp-7 | an-312 | 1C2574 | sp-7 | an-312 |
| 1A2575 | sp-7 | an-313 | 1U2575 | sp-7 | an-313 | 1C2575 | sp-7 | an-313 |
| 1A2576 | sp-7 | an-314 | 1U2576 | sp-7 | an-314 | 1C2576 | sp-7 | an-314 |
| 1A2577 | sp-7 | an-315 | 1U2577 | sp-7 | an-315 | 1C2577 | sp-7 | an-315 |
| 1A2578 | sp-7 | an-316 | 1U2578 | sp-7 | an-316 | 1C2578 | sp-7 | an-316 |
| 1A2579 | sp-7 | an-317 | 1U2579 | sp-7 | an-317 | 1C2579 | sp-7 | an-317 |
| 1A2580 | sp-7 | an-318 | 1U2580 | sp-7 | an-318 | 1C2580 | sp-7 | an-318 |
| 1A2581 | sp-7 | an-319 | 1U2581 | sp-7 | an-319 | 1C2581 | sp-7 | an-319 |
| 1A2582 | sp-7 | an-320 | 1U2582 | sp-7 | an-320 | 1C2582 | sp-7 | an-320 |
| 1A2583 | sp-7 | an-321 | 1U2583 | sp-7 | an-321 | 1C2583 | sp-7 | an-321 |
| 1A2584 | sp-7 | an-322 | 1U2584 | sp-7 | an-322 | 1C2584 | sp-7 | an-322 |
| 1A2585 | sp-7 | an-323 | 1U2585 | sp-7 | an-323 | 1C2585 | sp-7 | an-323 |
| 1A2586 | sp-7 | an-324 | 1U2586 | sp-7 | an-324 | 1C2586 | sp-7 | an-324 |
| 1A2587 | sp-7 | an-325 | 1U2587 | sp-7 | an-325 | 1C2587 | sp-7 | an-325 |
| 1A2588 | sp-7 | an-326 | 1U2588 | sp-7 | an-326 | 1C2588 | sp-7 | an-326 |
| 1A2589 | sp-7 | an-327 | 1U2589 | sp-7 | an-327 | 1C2589 | sp-7 | an-327 |
| 1A2590 | sp-7 | an-328 | 1U2590 | sp-7 | an-328 | 1C2590 | sp-7 | an-328 |
| 1A2591 | sp-7 | an-329 | 1U2591 | sp-7 | an-329 | 1C2591 | sp-7 | an-329 |
| 1A2592 | sp-7 | an-330 | 1U2592 | sp-7 | an-330 | 1C2592 | sp-7 | an-330 |
| 1A2593 | sp-7 | an-331 | 1U2593 | sp-7 | an-331 | 1C2593 | sp-7 | an-331 |
| 1A2594 | sp-7 | an-332 | 1U2594 | sp-7 | an-332 | 1C2594 | sp-7 | an-332 |
| 1A2595 | sp-7 | an-333 | 1U2595 | sp-7 | an-333 | 1C2595 | sp-7 | an-333 |
| 1A2596 | sp-7 | an-334 | 1U2596 | sp-7 | an-334 | 1C2596 | sp-7 | an-334 |
| 1A2597 | sp-7 | an-335 | 1U2597 | sp-7 | an-335 | 1C2597 | sp-7 | an-335 |
| 1A2598 | sp-7 | an-336 | 1U2598 | sp-7 | an-336 | 1C2598 | sp-7 | an-336 |
| 1A2599 | sp-7 | an-337 | 1U2599 | sp-7 | an-337 | 1C2599 | sp-7 | an-337 |
| 1A2600 | sp-7 | an-338 | 1U2600 | sp-7 | an-338 | 1C2600 | sp-7 | an-338 |
| 1A2601 | sp-7 | an-339 | 1U2601 | sp-7 | an-339 | 1C2601 | sp-7 | an-339 |
| 1A2602 | sp-7 | an-340 | 1U2602 | sp-7 | an-340 | 1C2602 | sp-7 | an-340 |
| 1A2603 | sp-7 | an-341 | 1U2603 | sp-7 | an-341 | 1C2603 | sp-7 | an-341 |
| 1A2604 | sp-7 | an-342 | 1U2604 | sp-7 | an-342 | 1C2604 | sp-7 | an-342 |
| 1A2605 | sp-7 | an-343 | 1U2605 | sp-7 | an-343 | 1C2605 | sp-7 | an-343 |
| 1A2606 | sp-7 | an-344 | 1U2606 | sp-7 | an-344 | 1C2606 | sp-7 | an-344 |
| 1A2607 | sp-7 | an-345 | 1U2607 | sp-7 | an-345 | 1C2607 | sp-7 | an-345 |
| 1A2608 | sp-7 | an-346 | 1U2608 | sp-7 | an-346 | 1C2608 | sp-7 | an-346 |
| 1A2609 | sp-7 | an-347 | 1U2609 | sp-7 | an-347 | 1C2609 | sp-7 | an-347 |
| 1A2610 | sp-7 | an-348 | 1U2610 | sp-7 | an-343 | 1C2610 | sp-7 | an-348 |
| 1A2611 | sp-7 | an-349 | 1U2611 | sp-7 | an-349 | 1C2611 | sp-7 | an-349 |
| 1A2612 | sp-7 | an-350 | 1U2612 | sp-7 | an-350 | 1C2612 | sp-7 | an-350 |
| 1A2613 | sp-7 | an-351 | 1U2613 | sp-7 | an-351 | 1C2613 | sp-7 | an-351 |
| 1A2614 | sp-7 | an-352 | 1U2614 | sp-7 | an-352 | 1C2614 | sp-7 | an-352 |
| 1A2615 | sp-7 | an-353 | 1U2615 | sp-7 | an-353 | 1C2615 | sp-7 | an-353 |
| 1A2616 | sp-7 | an-354 | 1U2616 | sp-7 | an-354 | 1C2616 | sp-7 | an-354 |
| 1A2617 | sp-7 | an-355 | 1U2617 | sp-7 | an-355 | 1C2617 | sp-7 | an-355 |
| 1A2618 | sp-7 | an-356 | 1U2618 | sp-7 | an-356 | 1C2618 | sp-7 | an-356 |
| 1A2619 | sp-7 | an-357 | 1U2619 | sp-7 | an-357 | 1C2619 | sp-7 | an-357 |
| 1A2620 | sp-7 | an-358 | 1U2620 | sp-7 | an-358 | 1C2620 | sp-7 | an-358 |
| 1A2621 | sp-7 | an-359 | 1U2621 | sp-7 | an-359 | 1C2621 | sp-7 | an-359 |
| 1A2622 | sp-7 | an-360 | 1U2622 | sp-7 | an-360 | 1C2622 | sp-7 | an-360 |
| 1A2623 | sp-7 | an-361 | 1U2623 | sp-7 | an-361 | 1C2623 | sp-7 | an-361 |
| 1A2624 | sp-7 | an-362 | 1U2624 | sp-7 | an-362 | 1C2624 | sp-7 | an-362 |

TABLE 1-continued

| | | | | | | | | |
|---|---|---|---|---|---|---|---|---|
| 1A2625 | sp-7 | an-363 | 1U2625 | sp-7 | an-363 | 1C2625 | sp-7 | an-363 |
| 1A2626 | sp-7 | an-364 | 1U2626 | sp-7 | an-364 | 1C2626 | sp-7 | an-364 |
| 1A2627 | sp-7 | an-365 | 1U2627 | sp-7 | an-365 | 1C2627 | sp-7 | an-365 |
| 1A2628 | sp-7 | an-366 | 1U2628 | sp-7 | an-366 | 1C2628 | sp-7 | an-366 |
| 1A2629 | sp-7 | an-367 | 1U2629 | sp-7 | an-367 | 1C2629 | sp-7 | an-367 |
| 1A2630 | sp-7 | an-368 | 1U2630 | sp-7 | an-368 | 1C2630 | sp-7 | an-368 |
| 1A2631 | sp-7 | an-369 | 1U2631 | sp-7 | an-369 | 1C2631 | sp-7 | an-369 |
| 1A2632 | sp-7 | an-370 | 1U2632 | sp-7 | an-370 | 1C2632 | sp-7 | an-370 |
| 1A2633 | sp-7 | an-371 | 1U2633 | sp-7 | an-371 | 1C2633 | sp-7 | an-371 |
| 1A2634 | sp-7 | an-372 | 1U2634 | sp-7 | an-372 | 1C2634 | sp-7 | an-372 |
| 1A2635 | sp-7 | an-373 | 1U2635 | sp-7 | an-373 | 1C2635 | sp-7 | an-373 |
| 1A2636 | sp-7 | an-374 | 1U2636 | sp-7 | an-374 | 1C2636 | sp-7 | an-374 |
| 1A2637 | sp-7 | an-375 | 1U2637 | sp-7 | an-375 | 1C2637 | sp-7 | an-375 |
| 1A2638 | sp-7 | an-376 | 1U2638 | sp-7 | an-376 | 1C2638 | sp-7 | an-376 |
| 1A2639 | sp-7 | an-377 | 1U2639 | sp-7 | an-377 | 1C2639 | sp-7 | an-377 |
| 1A2640 | sp-8 | an-1 | 1U2640 | sp-8 | an-1 | 1C2640 | sp-8 | an-1 |
| 1A2641 | sp-8 | an-2 | 1U2641 | sp-a | an-2 | 1C2641 | sp-8 | an-2 |
| 1A2642 | sp-8 | an-3 | 1U2642 | sp-8 | an-3 | 1C2642 | sp-8 | an-3 |
| 1A2643 | sp-8 | an-4 | 1U2643 | sp-8 | an-4 | 1C2643 | sp-8 | an-4 |
| 1A2644 | sp-8 | an-5 | 1U2644 | sp-8 | an-5 | 1C2644 | sp-8 | an-5 |
| 1A2645 | sp-8 | an-6 | 1U2645 | sp-8 | an-6 | 1C2645 | sp-8 | an-6 |
| 1A2646 | sp-8 | an-7 | 1U2646 | sp-8 | an-7 | 1C2646 | sp-8 | an-7 |
| 1A2647 | sp-8 | an-8 | 1U2647 | sp-8 | an-8 | 1C2647 | sp-8 | an-8 |
| 1A2648 | sp-8 | an-9 | 1U2648 | sp-8 | an-9 | 1C2648 | sp-8 | an-9 |
| 1A2649 | sp-8 | an-10 | 1U2649 | sp-8 | an-10 | 1C2649 | sp-8 | an-10 |
| 1A2650 | sp-8 | an-11 | 1U2650 | sp-8 | an-11 | 1C2650 | sp-8 | an-11 |
| 1A2651 | sp-8 | an-12 | 1U2651 | sp-8 | an-12 | 1C2651 | sp-8 | an-12 |
| 1A2652 | sp-8 | an-13 | 1U2652 | sp-8 | an-13 | 1C2652 | sp-8 | an-13 |
| 1A2653 | sp-8 | an-14 | 1U2653 | sp-8 | an-14 | 1C2653 | sp-8 | an-14 |
| 1A2654 | sp-8 | an-15 | 1U2654 | sp-8 | an-15 | 1C2654 | sp-8 | an-15 |
| 1A2655 | sp-8 | an-16 | 1U2655 | sp-8 | an-16 | 1C2655 | sp-8 | an-16 |
| 1A2656 | sp-8 | an-17 | 1U2656 | sp-8 | an-17 | 1C2656 | sp-8 | an-17 |
| 1A2657 | sp-8 | an-18 | 1U2657 | sp-8 | an-18 | 1C2657 | sp-8 | an-18 |
| 1A2658 | sp-8 | an-19 | 1U2658 | sp-8 | an-19 | 1C2658 | sp-8 | an-19 |
| 1A2659 | sp-8 | an-20 | 1U2659 | sp-8 | an-20 | 1C2659 | sp-8 | an-20 |
| 1A2660 | sp-8 | an-21 | 1U2660 | sp-8 | an-21 | 1C2660 | sp-8 | an-21 |
| 1A2661 | sp-8 | an-22 | 1U2661 | sp-8 | an-22 | 1C2661 | sp-8 | an-22 |
| 1A2662 | sp-8 | an-23 | 1U2662 | sp-8 | an-23 | 1C2662 | sp-8 | an-23 |
| 1A2663 | sp-8 | an-24 | 1U2663 | sp-8 | an-24 | 1C2663 | sp-8 | an-24 |
| 1A2664 | sp-8 | an-25 | 1U2664 | sp-8 | an-25 | 1C2664 | sp-8 | an-25 |
| 1A2665 | sp-8 | an-26 | 1U2665 | sp-8 | an-26 | 1C2665 | sp-8 | an-26 |
| 1A2666 | sp-8 | an-27 | 1U2666 | sp-8 | an-27 | 1C2666 | sp-8 | an-27 |
| 1A2667 | sp-8 | an-28 | 1U2667 | sp-8 | an-28 | 1C2667 | sp-8 | an-28 |
| 1A2668 | sp-8 | an-29 | 1U2668 | sp-8 | an-29 | 1C2668 | sp-8 | an-29 |
| 1A2669 | sp-8 | an-30 | 1U2669 | sp-8 | an-30 | 1C2669 | sp-8 | an-30 |
| 1A2670 | sp-8 | an-31 | 1U2670 | sp-8 | an-31 | 1C2670 | sp-8 | an-31 |
| 1A2671 | sp-8 | an-32 | 1U2671 | sp-8 | an-32 | 1C2671 | sp-8 | an-32 |
| 1A2672 | sp-8 | an-33 | 1U2672 | sp-8 | an-33 | 1C2672 | sp-8 | an-33 |
| 1A2673 | sp-8 | an-34 | 1U2673 | sp-8 | an-34 | 1C2673 | sp-8 | an-34 |
| 1A2674 | sp-8 | an-35 | 1U2674 | sp-8 | an-35 | 1C2674 | sp-8 | an-35 |
| 1A2675 | sp-8 | an-36 | 1U2675 | sp-8 | an-36 | 1C2675 | sp-8 | an-36 |
| 1A2676 | sp-8 | an-37 | 1U2676 | sp-8 | an-37 | 1C2676 | sp-8 | an-37 |
| 1A2677 | sp-8 | an-38 | 1U2677 | sp-8 | an-38 | 1C2677 | sp-8 | an-38 |
| 1A2678 | sp-8 | an-39 | 1U2678 | sp-8 | an-39 | 1C2678 | sp-8 | an-39 |
| 1A2679 | sp-8 | an-40 | 1U2679 | sp-8 | an-40 | 1C2679 | sp-8 | an-40 |
| 1A2680 | sp-8 | an-41 | 1U2680 | sp-8 | an-41 | 1C2680 | sp-8 | an-41 |
| 1A2681 | sp-8 | an-42 | 1U2681 | sp-8 | an-42 | 1C2681 | sp-8 | an-42 |
| 1A2682 | sp-8 | an-43 | 1U2682 | sp-8 | an-43 | 1C2682 | sp-8 | an-43 |
| 1A2683 | sp-8 | an-44 | 1U2683 | sp-8 | an-44 | 1C2683 | sp-8 | an-44 |
| 1A2684 | sp-8 | an-45 | 1U2684 | sp-8 | an-45 | 1C2684 | sp-8 | an-45 |
| 1A2685 | sp-8 | an-46 | 1U2685 | sp-8 | an-46 | 1C2685 | sp-8 | an-46 |
| 1A2686 | sp-8 | an-47 | 1U2686 | sp-8 | an-47 | 1C2686 | sp-8 | an-47 |
| 1A2687 | sp-8 | an-48 | 1U2687 | sp-8 | an-48 | 1C2687 | sp-8 | an-48 |
| 1A2688 | sp-8 | an-49 | 1U2688 | sp-8 | an-49 | 1C2688 | sp-8 | an-49 |
| 1A2689 | sp-8 | an-50 | 1U2689 | sp-8 | an-50 | 1C2689 | sp-8 | an-50 |
| 1A2690 | sp-8 | an-51 | 1U2690 | sp-8 | an-51 | 1C2690 | sp-8 | an-51 |
| 1A2691 | sp-8 | an-52 | 1U2691 | sp-8 | an-52 | 1C2691 | sp-8 | an-52 |
| 1A2692 | sp-8 | an-53 | 1U2692 | sp-8 | an-53 | 1C2692 | sp-8 | an-53 |
| 1A2693 | sp-8 | an-54 | 1U2693 | sp-8 | an-54 | 1C2693 | sp-8 | an-54 |
| 1A2694 | sp-8 | an-55 | 1U2694 | sp-8 | an-55 | 1C2694 | sp-8 | an-55 |
| 1A2695 | sp-8 | an-56 | 1U2695 | sp-8 | an-56 | 1C2695 | sp-8 | an-56 |
| 1A2696 | sp-8 | an-57 | 1U2696 | sp-8 | an-57 | 1C2696 | sp-8 | an-57 |
| 1A2697 | sp-8 | an-58 | 1U2697 | sp-8 | an-58 | 1C2697 | sp-8 | an-58 |
| 1A2698 | sp-8 | an-59 | 1U2698 | sp-8 | an-59 | 1C2698 | sp-8 | an-59 |
| 1A2699 | sp-8 | an-60 | 1U2699 | sp-8 | an-60 | 1C2699 | sp-8 | an-60 |
| 1A2700 | sp-8 | an-61 | 1U2700 | sp-8 | an-61 | 1C2700 | sp-8 | an-61 |
| 1A2701 | sp-8 | an-62 | 1U2701 | sp-8 | an-62 | 1C2701 | sp-8 | an-62 |
| 1A2702 | sp-8 | an-63 | 1U2702 | sp-8 | an-63 | 1C2702 | sp-8 | an-63 |
| 1A2703 | sp-8 | an-64 | 1U2703 | sp-8 | an-64 | 1C2703 | sp-8 | an-64 |

TABLE 1-continued

| | | | | | | | | |
|---|---|---|---|---|---|---|---|---|
| 1A2704 | sp-8 | an-65 | 1U2704 | sp-8 | an-65 | 1C2704 | sp-8 | an-65 |
| 1A2705 | sp-8 | an-66 | 1U2705 | sp-8 | an-66 | 1C2705 | sp-8 | an-66 |
| 1A2706 | sp-8 | an-67 | 1U2706 | sp-8 | an-67 | 1C2706 | sp-8 | an-67 |
| 1A2707 | sp-8 | an-68 | 1U2707 | sp-8 | an-68 | 1C2707 | sp-8 | an-68 |
| 1A2708 | sp-8 | an-69 | 1U2708 | sp-8 | an-69 | 1C2708 | sp-8 | an-69 |
| 1A2709 | sp-8 | an-70 | 1U2709 | sp-8 | an-70 | 1C2709 | sp-8 | an-70 |
| 1A2710 | sp-8 | an-71 | 1U2710 | sp-8 | an-71 | 1C2710 | sp-8 | an-71 |
| 1A2711 | sp-8 | an-72 | 1U2711 | sp-8 | an-72 | 1C2711 | sp-8 | an-72 |
| 1A2712 | sp-8 | an-73 | 1U2712 | sp-8 | an-73 | 1C2712 | sp-8 | an-73 |
| 1A2713 | sp-8 | an-74 | 1U2713 | sp-8 | an-74 | 1C2713 | sp-8 | an-74 |
| 1A2714 | sp-8 | an-75 | 1U2714 | sp-8 | an-75 | 1C2714 | sp-8 | an-75 |
| 1A2715 | sp-8 | an-76 | 1U2715 | sp-8 | an-76 | 1C2715 | sp-8 | an-76 |
| 1A2716 | sp-8 | an-77 | 1U2716 | sp-8 | an-77 | 1C2716 | sp-8 | an-77 |
| 1A2717 | sp-8 | an-78 | 1U2717 | sp-8 | an-78 | 1C2717 | sp-8 | an-78 |
| 1A2718 | sp-8 | an-79 | 1U2718 | sp-8 | an-79 | 1C2718 | sp-8 | an-79 |
| 1A2719 | sp-8 | an-80 | 1U2719 | sp-8 | an-80 | 1C2719 | sp-8 | an-80 |
| 1A2720 | sp-8 | an-81 | 1U2720 | sp-8 | an-81 | 1C2720 | sp-8 | an-81 |
| 1A2721 | sp-8 | an-82 | 1U2721 | sp-8 | an-82 | 1C2721 | sp-8 | an-82 |
| 1A2722 | sp-8 | an-83 | 1U2722 | sp-8 | an-83 | 1C2722 | sp-8 | an-83 |
| 1A2723 | sp-8 | an-84 | 1U2723 | sp-8 | an-84 | 1C2723 | sp-8 | an-84 |
| 1A2724 | sp-8 | an-85 | 1U2724 | sp-8 | an-85 | 1C2724 | sp-8 | an-85 |
| 1A2725 | sp-8 | an-86 | 1U2725 | sp-8 | an-86 | 1C2725 | sp-8 | an-86 |
| 1A2726 | sp-8 | an-87 | 1U2726 | sp-8 | an-87 | 1C2726 | sp-8 | an-87 |
| 1A2727 | sp-8 | an-88 | 1U2727 | sp-8 | an-88 | 1C2727 | sp-8 | an-88 |
| 1A2728 | sp-8 | an-89 | 1U2728 | sp-8 | an-89 | 1C2728 | sp-8 | an-89 |
| 1A2729 | sp-8 | an-90 | 1U2729 | sp-8 | an-90 | 1C2729 | sp-8 | an-90 |
| 1A2730 | sp-8 | an-91 | 1U2730 | sp-8 | an-91 | 1C2730 | sp-8 | an-91 |
| 1A2731 | sp-8 | an-92 | 1U2731 | sp-8 | an-92 | 1C2731 | sp-8 | an-92 |
| 1A2732 | sp-8 | an-93 | 1U2732 | sp-8 | an-93 | 1C2732 | sp-8 | an-93 |
| 1A2733 | sp-8 | an-94 | 1U2733 | sp-8 | an-94 | 1C2733 | sp-8 | an-94 |
| 1A2734 | sp-8 | an-95 | 1U2734 | sp-8 | an-95 | 1C2734 | sp-8 | an-95 |
| 1A2735 | sp-8 | an-96 | 1U2735 | sp-8 | an-96 | 1C2735 | sp-8 | an-96 |
| 1A2736 | sp-8 | an-97 | 1U2736 | sp-8 | an-97 | 1C2736 | sp-8 | an-97 |
| 1A2737 | sp-8 | an-98 | 1U2737 | sp-8 | an-98 | 1C2737 | sp-8 | an-98 |
| 1A2738 | sp-8 | an-99 | 1U2738 | sp-8 | an-99 | 1C2738 | sp-8 | an-99 |
| 1A2739 | sp-8 | an-100 | 1U2739 | sp-8 | an-100 | 1C2739 | sp-8 | an-100 |
| 1A2740 | sp-8 | an-101 | 1U2740 | sp-8 | an-101 | 1C2740 | sp-8 | an-101 |
| 1A2741 | sp-8 | an-102 | 1U2741 | sp-8 | an-102 | 1C2741 | sp-8 | an-102 |
| 1A2742 | sp-8 | an-103 | 1U2742 | sp-8 | an-103 | 1C2742 | sp-8 | an-103 |
| 1A2743 | sp-8 | an-104 | 1U2743 | sp-8 | an-104 | 1C2743 | sp-8 | an-104 |
| 1A2744 | sp-8 | an-105 | 1U2744 | sp-8 | an-105 | 1C2744 | sp-8 | an-105 |
| 1A2745 | sp-8 | an-106 | 1U2745 | sp-8 | an-106 | 1C2745 | sp-8 | an-106 |
| 1A2746 | sp-8 | an-107 | 1U2746 | sp-8 | an-107 | 1C2746 | sp-8 | an-107 |
| 1A2747 | sp-8 | an-108 | 1U2747 | sp-8 | an-108 | 1C2747 | sp-8 | an-108 |
| 1A2748 | sp-8 | an-109 | 1U2748 | sp-8 | an-109 | 1C2748 | sp-8 | an-109 |
| 1A2749 | sp-8 | an-110 | 1U2749 | sp-8 | an-110 | 1C2749 | sp-8 | an-110 |
| 1A2750 | sp-8 | an-111 | 1U2750 | sp-8 | an-111 | 1C2750 | sp-8 | an-111 |
| 1A2751 | sp-8 | an-112 | 1U2751 | sp-8 | an-112 | 1C2751 | sp-8 | an-112 |
| 1A2752 | sp-8 | an-113 | 1U2752 | sp-8 | an-113 | 1C2752 | sp-8 | an-113 |
| 1A2753 | sp-8 | an-114 | 1U2753 | sp-8 | an-114 | 1C2753 | sp-8 | an-114 |
| 1A2754 | sp-8 | an-115 | 1U2754 | sp-8 | an-115 | 1C2754 | sp-8 | an-115 |
| 1A2755 | sp-8 | an-116 | 1U2755 | sp-8 | an-116 | 1C2755 | sp-8 | an-116 |
| 1A2756 | sp-8 | an-117 | 1U2756 | sp-8 | an-117 | 1C2756 | sp-8 | an-117 |
| 1A2757 | sp-8 | an-118 | 1U2757 | sp-8 | an-118 | 1C2757 | sp-8 | an-118 |
| 1A2758 | sp-8 | an-119 | 1U2758 | sp-8 | an-119 | 1C2758 | sp-8 | an-119 |
| 1A2759 | sp-8 | an-120 | 1U2759 | sp-8 | an-120 | 1C2759 | sp-8 | an-120 |
| 1A2760 | sp-8 | an-121 | 1U2760 | sp-8 | an-121 | 1C2760 | sp-8 | an-121 |
| 1A2761 | sp-8 | an-122 | 1U2761 | sp-8 | an-122 | 1C2761 | sp-8 | an-122 |
| 1A2762 | sp-8 | an-123 | 1U2762 | sp-8 | an-123 | 1C2762 | sp-8 | an-123 |
| 1A2763 | sp-8 | an-124 | 1U2763 | sp-8 | an-124 | 1C2763 | sp-8 | an-124 |
| 1A2764 | sp-8 | an-125 | 1U2764 | sp-8 | an-125 | 1C2764 | sp-8 | an-125 |
| 1A2765 | sp-8 | an-126 | 1U2765 | sp-8 | an-126 | 1C2765 | sp-8 | an-126 |
| 1A2766 | sp-8 | an-127 | 1U2766 | sp-8 | an-127 | 1C2766 | sp-8 | an-127 |
| 1A2767 | sp-8 | an-128 | 1U2767 | sp-8 | an-128 | 1C2767 | sp-a | an-128 |
| 1A2768 | sp-8 | an-129 | 1U2768 | sp-8 | an-129 | 1C2768 | sp-8 | an-129 |
| 1A2769 | sp-8 | an-130 | 1U2769 | sp-8 | an-130 | 1C2769 | sp-8 | an-130 |
| 1A2770 | sp-8 | an-131 | 1U2770 | sp-8 | an-131 | 1C2770 | sp-8 | an-131 |
| 1A2771 | sp-8 | an-132 | 1U2771 | sp-8 | an-132 | 1C2771 | sp-8 | an-132 |
| 1A2772 | sp-8 | an-133 | 1U2772 | sp-8 | an-133 | 1C2772 | sp-8 | an-133 |
| 1A2773 | sp-8 | an-134 | 1U2773 | sp-8 | an-134 | 1C2773 | sp-8 | an-134 |
| 1A2774 | sp-8 | an-135 | 1U2774 | sp-8 | an-135 | 1C2774 | sp-8 | an-135 |
| 1A2775 | sp-8 | an-136 | 1U2775 | sp-8 | an-136 | 1C2775 | sp-8 | an-136 |
| 1A2776 | sp-8 | an-137 | 1U2776 | sp-8 | an-137 | 1C2776 | sp-8 | an-137 |
| 1A2777 | sp-8 | an-138 | 1U2777 | sp-8 | an-138 | 1C2777 | sp-8 | an-138 |
| 1A2778 | sp-8 | an-139 | 1U2778 | sp-8 | an-139 | 1C2778 | sp-8 | an-139 |
| 1A2779 | sp-8 | an-140 | 1U2779 | sp-8 | an-140 | 1C2779 | sp-8 | an-140 |
| 1A2780 | sp-8 | an-141 | 1U2780 | sp-8 | an-141 | 1C2780 | sp-8 | an-141 |
| 1A2781 | sp-8 | an-142 | 1U2781 | sp-8 | an-142 | 1C2781 | sp-8 | an-142 |
| 1A2782 | sp-8 | an-143 | 1U2782 | sp-8 | an-143 | 1C2782 | sp-8 | an-143 |

TABLE 1-continued

| | | | | | | | | |
|---|---|---|---|---|---|---|---|---|
| 1A2783 | sp-8 | an-144 | 1U2783 | sp-8 | an-144 | 1C2783 | sp-8 | an-144 |
| 1A2784 | sp-8 | an-145 | 1U2784 | sp-8 | an-145 | 1C2784 | sp-8 | an-145 |
| 1A2785 | sp-8 | an-146 | 1U2785 | sp-8 | an-146 | 1C2785 | sp-8 | an-146 |
| 1A2786 | sp-8 | an-147 | 1U2786 | sp-8 | an-147 | 1C2786 | sp-8 | an-147 |
| 1A2787 | sp-8 | an-148 | 1U2787 | sp-8 | an-148 | 1C2787 | sp-8 | an-148 |
| 1A2788 | sp-8 | an-149 | 1U2788 | sp-8 | an-149 | 1C2788 | sp-8 | an-149 |
| 1A2789 | sp-8 | an-150 | 1U2789 | sp-8 | an-150 | 1C2789 | sp-8 | an-150 |
| 1A2790 | sp-8 | an-151 | 1U2790 | sp-8 | an-151 | 1C2790 | sp-8 | an-151 |
| 1A2791 | sp-8 | an-152 | 1U2791 | sp-8 | an-152 | 1C2791 | sp-8 | an-152 |
| 1A2792 | sp-8 | an-153 | 1U2792 | sp-8 | an-153 | 1C2792 | sp-8 | an-153 |
| 1A2793 | sp-8 | an-154 | 1U2793 | sp-8 | an-154 | 1C2793 | sp-8 | an-154 |
| 1A2794 | sp-8 | an-155 | 1U2794 | sp-8 | an-155 | 1C2794 | sp-8 | an-155 |
| 1A2795 | sp-8 | an-156 | 1U2795 | sp-8 | an-156 | 1C2795 | sp-8 | an-156 |
| 1A2796 | sp-8 | an-157 | 1U2796 | sp-8 | an-157 | 1C2796 | sp-8 | an-157 |
| 1A2797 | sp-8 | an-158 | 1U2797 | sp-8 | an-158 | 1C2797 | sp-8 | an-158 |
| 1A2798 | sp-8 | an-159 | 1U2798 | sp-8 | an-159 | 1C2798 | sp-8 | an-159 |
| 1A2799 | sp-8 | an-160 | 1U2799 | sp-8 | an-160 | 1C2799 | sp-8 | an-160 |
| 1A2800 | sp-8 | an-161 | 1U2800 | sp-8 | an-161 | 1C2800 | sp-8 | an-161 |
| 1A2801 | sp-8 | an-162 | 1U2801 | sp-8 | an-162 | 1C2801 | sp-8 | an-162 |
| 1A2802 | sp-8 | an-163 | 1U2802 | sp-8 | an-163 | 1C2802 | sp-8 | an-163 |
| 1A2803 | sp-8 | an-164 | 1U2803 | sp-8 | an-164 | 1C2803 | sp-8 | an-164 |
| 1A2804 | sp-8 | an-165 | 1U2804 | sp-8 | an-165 | 1C2804 | sp-8 | an-165 |
| 1A2805 | sp-8 | an-166 | 1U2805 | sp-8 | an-166 | 1C2805 | sp-8 | an-166 |
| 1A2806 | sp-8 | an-167 | 1U2806 | sp-8 | an-167 | 1C2806 | sp-8 | an-167 |
| 1A2807 | sp-8 | an-168 | 1U2807 | sp-8 | an-168 | 1C2807 | sp-8 | an-168 |
| 1A2808 | sp-8 | an-169 | 1U2808 | sp-8 | an-169 | 1C2808 | sp-8 | an-169 |
| 1A2809 | sp-8 | an-170 | 1U2809 | sp-8 | an-170 | 1C2809 | sp-8 | an-170 |
| 1A2810 | sp-8 | an-171 | 1U2810 | sp-8 | an-171 | 1C2810 | sp-8 | an-171 |
| 1A2811 | sp-8 | an-172 | 1U2811 | sp-8 | an-172 | 1C2811 | sp-8 | an-172 |
| 1A2812 | sp-8 | an-173 | 1U2812 | sp-8 | an-173 | 1C2812 | sp-8 | an-173 |
| 1A2813 | sp-8 | an-174 | 1U2813 | sp-8 | an-174 | 1C2813 | sp-8 | an-174 |
| 1A2814 | sp-8 | an-175 | 1U2814 | sp-8 | an-175 | 1C2814 | sp-8 | an-175 |
| 1A2815 | sp-8 | an-176 | 1U2815 | sp-8 | an-176 | 1C2815 | sp-8 | an-176 |
| 1A2816 | sp-8 | an-177 | 1U2816 | sp-8 | an-177 | 1C2816 | sp-8 | an-177 |
| 1A2817 | sp-8 | an-178 | 1U2817 | sp-8 | an-178 | 1C2817 | sp-8 | an-178 |
| 1A2818 | sp-8 | an-179 | 1U2818 | sp-8 | an-179 | 1C2818 | sp-8 | an-179 |
| 1A2819 | sp-8 | an-180 | 1U2819 | sp-8 | an-180 | 1C2819 | sp-8 | an-180 |
| 1A2820 | sp-8 | an-181 | 1U2820 | sp-8 | an-181 | 1C2820 | sp-8 | an-181 |
| 1A2821 | sp-8 | an-182 | 1U2821 | sp-8 | an-182 | 1C2821 | sp-8 | an-182 |
| 1A2822 | sp-8 | an-183 | 1U2822 | sp-8 | an-183 | 1C2822 | sp-8 | an-183 |
| 1A2823 | sp-8 | an-184 | 1U2823 | sp-8 | an-184 | 1C2823 | sp-8 | an-184 |
| 1A2824 | sp-8 | an-185 | 1U2824 | sp-8 | an-185 | 1C2824 | sp-8 | an-185 |
| 1A2825 | sp-8 | an-186 | 1U2825 | sp-8 | an-186 | 1C2825 | sp-8 | an-186 |
| 1A2826 | sp-8 | an-187 | 1U2826 | sp-8 | an-187 | 1C2826 | sp-8 | an-187 |
| 1A2827 | sp-8 | an-188 | 1U2827 | sp-8 | an-188 | 1C2827 | sp-8 | an-188 |
| 1A2828 | sp-8 | an-189 | 1U2828 | sp-8 | an-189 | 1C2828 | sp-8 | an-189 |
| 1A2829 | sp-8 | an-190 | 1U2829 | sp-8 | an-190 | 1C2829 | sp-8 | an-190 |
| 1A2830 | sp-8 | an-191 | 1U2830 | sp-8 | an-191 | 1C2830 | sp-8 | an-191 |
| 1A2831 | sp-8 | an-192 | 1U2831 | sp-8 | an-192 | 1C2831 | sp-8 | an-192 |
| 1A2832 | sp-8 | an-193 | 1U2832 | sp-8 | an-193 | 1C2832 | sp-8 | an-193 |
| 1A2833 | sp-8 | an-194 | 1U2833 | sp-8 | an-194 | 1C2833 | sp-8 | an-194 |
| 1A2834 | sp-8 | an-195 | 1U2834 | sp-8 | an-195 | 1C2834 | sp-8 | an-195 |
| 1A2835 | sp-8 | an-196 | 1U2835 | sp-8 | an-196 | 1C2835 | sp-8 | an-196 |
| 1A2836 | sp-8 | an-197 | 1U2836 | sp-8 | an-197 | 1C2836 | sp-8 | an-197 |
| 1A2837 | sp-8 | an-198 | 1U2837 | sp-8 | an-198 | 1C2837 | sp-8 | an-198 |
| 1A2838 | sp-8 | an-199 | 1U2838 | sp-8 | an-199 | 1C2838 | sp-8 | an-199 |
| 1A2839 | sp-8 | an-200 | 1U2839 | sp-8 | an-200 | 1C2839 | sp-8 | an-200 |
| 1A2840 | sp-8 | an-201 | 1U2840 | sp-8 | an-201 | 1C2840 | sp-8 | an-201 |
| 1A2841 | sp-8 | an-202 | 1U2841 | sp-8 | an-202 | 1C2841 | sp-8 | an-202 |
| 1A2842 | sp-8 | an-203 | 1U2842 | sp-8 | an-203 | 1C2842 | sp-8 | an-203 |
| 1A2843 | sp-8 | an-204 | 1U2843 | sp-8 | an-204 | 1C2843 | sp-8 | an-204 |
| 1A2844 | sp-8 | an-205 | 1U2844 | sp-8 | an-205 | 1C2844 | sp-8 | an-205 |
| 1A2845 | sp-8 | an-206 | 1U2845 | sp-8 | an-206 | 1C2845 | sp-8 | an-206 |
| 1A2846 | sp-8 | an-207 | 1U2846 | sp-8 | an-207 | 1C2846 | sp-8 | an-207 |
| 1A2847 | sp-8 | an-208 | 1U2847 | sp-8 | an-208 | 1C2847 | sp-8 | an-208 |
| 1A2848 | sp-8 | an-209 | 1U2848 | sp-8 | an-209 | 1C2848 | sp-8 | an-209 |
| 1A2849 | sp-8 | an-210 | 1U2849 | sp-8 | an-210 | 1C2849 | sp-8 | an-210 |
| 1A2850 | sp-8 | an-211 | 1U2850 | sp-8 | an-211 | 1C2850 | sp-8 | an-211 |
| 1A2851 | sp-8 | an-212 | 1U2851 | sp-8 | an-212 | 1C2851 | sp-8 | an-212 |
| 1A2852 | sp-8 | an-213 | 1U2852 | sp-8 | an-213 | 1C2852 | sp-8 | an-213 |
| 1A2853 | sp-8 | an-214 | 1U2853 | sp-8 | an-214 | 1C2853 | sp-8 | an-214 |
| 1A2854 | sp-8 | an-215 | 1U2854 | sp-8 | an-215 | 1C2854 | sp-8 | an-215 |
| 1A2855 | sp-8 | an-216 | 1U2855 | sp-8 | an-216 | 1C2855 | sp-8 | an-216 |
| 1A2856 | sp-8 | an-217 | 1U2856 | sp-8 | an-217 | 1C2856 | sp-8 | an-217 |
| 1A2857 | sp-8 | an-218 | 1U2857 | sp-8 | an-218 | 1C2857 | sp-8 | an-218 |
| 1A2858 | sp-8 | an-219 | 1U2858 | sp-8 | an-219 | 1C2858 | sp-8 | an-219 |
| 1A2859 | sp-8 | an-220 | 1U2859 | sp-8 | an-220 | 1C2859 | sp-8 | an-220 |
| 1A2860 | sp-8 | an-221 | 1U2860 | sp-8 | an-221 | 1C2860 | sp-8 | an-221 |
| 1A2861 | sp-8 | an-222 | 1U2861 | sp-8 | an-222 | 1C2861 | sp-8 | an-222 |

TABLE 1-continued

| | | | | | | | | |
|---|---|---|---|---|---|---|---|---|
| 1A2862 | sp-8 | an-223 | 1U2862 | sp-8 | an-223 | 1C2862 | sp-8 | an-223 |
| 1A2863 | sp-8 | an-224 | 1U2863 | sp-8 | an-224 | 1C2863 | sp-8 | an-224 |
| 1A2864 | sp-8 | an-225 | 1U2864 | sp-8 | an-225 | 1C2864 | sp-8 | an-225 |
| 1A2865 | sp-8 | an-226 | 1U2865 | sp-8 | an-226 | 1C2865 | sp-8 | an-226 |
| 1A2866 | sp-8 | an-227 | 1U2866 | sp-8 | an-227 | 1C2866 | sp-8 | an-227 |
| 1A2867 | sp-8 | an-228 | 1U2867 | sp-8 | an-228 | 1C2867 | sp-8 | an-228 |
| 1A2868 | sp-8 | an-229 | 1U2868 | sp-8 | an-229 | 1C2868 | sp-8 | an-229 |
| 1A2869 | sp-8 | an-230 | 1U2869 | sp-8 | an-230 | 1C2869 | sp-8 | an-230 |
| 1A2870 | sp-8 | an-231 | 1U2870 | sp-8 | an-231 | 1C2870 | sp-8 | an-231 |
| 1A2871 | sp-8 | an-232 | 1U2871 | sp-8 | an-232 | 1C2871 | sp-8 | an-232 |
| 1A2872 | sp-8 | an-233 | 1U2872 | sp-8 | an-233 | 1C2872 | sp-8 | an-233 |
| 1A2873 | sp-8 | an-234 | 1U2873 | sp-8 | an-234 | 1C2873 | sp-8 | an-234 |
| 1A2874 | sp-8 | an-235 | 1U2874 | sp-8 | an-235 | 1C2874 | sp-8 | an-235 |
| 1A2875 | sp-8 | an-236 | 1U2875 | sp-8 | an-236 | 1C2875 | sp-8 | an-236 |
| 1A2876 | sp-8 | an-237 | 1U2876 | sp-8 | an-237 | 1C2876 | sp-8 | an-237 |
| 1A2877 | sp-8 | an-238 | 1U2877 | sp-8 | an-238 | 1C2877 | sp-8 | an-238 |
| 1A2878 | sp-8 | an-239 | 1U2878 | sp-8 | an-239 | 1C2878 | sp-8 | an-239 |
| 1A2879 | sp-8 | an-240 | 1U2879 | sp-8 | an-240 | 1C2879 | sp-8 | an-240 |
| 1A2880 | sp-8 | an-241 | 1U2880 | sp-8 | an-241 | 1C2880 | sp-8 | an-241 |
| 1A2881 | sp-8 | an-242 | 1U2881 | sp-8 | an-242 | 1C2881 | sp-8 | an-242 |
| 1A2882 | sp-8 | an-243 | 1U2882 | sp-8 | an-243 | 1C2882 | sp-8 | an-243 |
| 1A2883 | sp-8 | an-244 | 1U2883 | sp-8 | an-244 | 1C2883 | sp-8 | an-244 |
| 1A2884 | sp-8 | an-245 | 1U2884 | sp-8 | an-245 | 1C2884 | sp-8 | an-245 |
| 1A2885 | sp-8 | an-246 | 1U2885 | sp-8 | an-246 | 1C2885 | sp-8 | an-246 |
| 1A2886 | sp-8 | an-247 | 1U2886 | sp-8 | an-247 | 1C2886 | sp-8 | an-247 |
| 1A2887 | sp-8 | an-248 | 1U2887 | sp-8 | an-248 | 1C2887 | sp-8 | an-248 |
| 1A2888 | sp-8 | an-249 | 1U2888 | sp-8 | an-249 | 1C2888 | sp-8 | an-249 |
| 1A2889 | sp-8 | an-250 | 1U2889 | sp-8 | an-250 | 1C2889 | sp-8 | an-250 |
| 1A2890 | sp-8 | an-251 | 1U2890 | sp-8 | an-251 | 1C2890 | sp-8 | an-251 |
| 1A2891 | sp-8 | an-252 | 1U2891 | sp-8 | an-252 | 1C2891 | sp-8 | an-252 |
| 1A2892 | sp-8 | an-253 | 1U2892 | sp-8 | an-253 | 1C2892 | sp-8 | an-253 |
| 1A2893 | sp-8 | an-254 | 1U2893 | sp-8 | an-254 | 1C2893 | sp-8 | an-254 |
| 1A2894 | sp-8 | an-255 | 1U2894 | sp-8 | an-255 | 1C2894 | sp-8 | an-255 |
| 1A2895 | sp-8 | an-256 | 1U2895 | sp-8 | an-256 | 1C2895 | sp-8 | an-256 |
| 1A2896 | sp-8 | an-257 | 1U2896 | sp-8 | an-257 | 1C2896 | sp-8 | an-257 |
| 1A2897 | sp-8 | an-258 | 1U2897 | sp-8 | an-258 | 1C2897 | sp-8 | an-258 |
| 1A2898 | sp-8 | an-259 | 1U2898 | sp-8 | an-259 | 1C2898 | sp-8 | an-259 |
| 1A2899 | sp-8 | an-260 | 1U2899 | sp-8 | an-260 | 1C2899 | sp-8 | an-260 |
| 1A2900 | sp-8 | an-261 | 1U2900 | sp-8 | an-261 | 1C2900 | sp-8 | an-261 |
| 1A2901 | sp-8 | an-262 | 1U2901 | sp-8 | an-262 | 1C2901 | sp-8 | an-262 |
| 1A2902 | sp-8 | an-263 | 1U2902 | sp-8 | an-263 | 1C2902 | sp-8 | an-263 |
| 1A2903 | sp-8 | an-264 | 1U2903 | sp-8 | an-264 | 1C2903 | sp-8 | an-264 |
| 1A2904 | sp-8 | an-265 | 1U2904 | sp-8 | an-265 | 1C2904 | sp-8 | an-265 |
| 1A2905 | sp-8 | an-266 | 1U2905 | sp-8 | an-266 | 1C2905 | sp-8 | an-266 |
| 1A2906 | sp-8 | an-267 | 1U2906 | sp-8 | an-267 | 1C2906 | sp-8 | an-267 |
| 1A2907 | sp-8 | an-268 | 1U2907 | sp-8 | an-268 | 1C2907 | sp-8 | an-268 |
| 1A2908 | sp-8 | an-269 | 1U2908 | sp-8 | an-269 | 1C2908 | sp-8 | an-269 |
| 1A2909 | sp-8 | an-270 | 1U2909 | sp-8 | an-270 | 1C2909 | sp-8 | an-270 |
| 1A2910 | sp-8 | an-271 | 1U2910 | sp-8 | an-271 | 1C2910 | sp-8 | an-271 |
| 1A2911 | sp-8 | an-272 | 1U2911 | sp-8 | an-272 | 1C2911 | sp-8 | an-272 |
| 1A2912 | sp-8 | an-273 | 1U2912 | sp-8 | an-273 | 1C2912 | sp-8 | an-273 |
| 1A2913 | sp-8 | an-274 | 1U2913 | sp-8 | an-274 | 1C2913 | sp-8 | an-274 |
| 1A2914 | sp-8 | an-275 | 1U2914 | sp-8 | an-275 | 1C2914 | sp-8 | an-275 |
| 1A2915 | sp-8 | an-276 | 1U2915 | sp-8 | an-276 | 1C2915 | sp-8 | an-276 |
| 1A2916 | sp-8 | an-277 | 1U2916 | sp-8 | an-277 | 1C2916 | sp-8 | an-277 |
| 1A2917 | sp-8 | an-278 | 1U2917 | sp-8 | an-278 | 1C2917 | sp-8 | an-278 |
| 1A2918 | sp-8 | an-279 | 1U2918 | sp-8 | an-279 | 1C2918 | sp-8 | an-279 |
| 1A2919 | sp-8 | an-280 | 1U2919 | sp-8 | an-280 | 1C2919 | sp-8 | an-280 |
| 1A2920 | sp-8 | an-281 | 1U2920 | sp-8 | an-281 | 1C2920 | sp-8 | an-281 |
| 1A2921 | sp-8 | an-282 | 1U2921 | sp-8 | an-282 | 1C2921 | sp-8 | an-282 |
| 1A2922 | sp-8 | an-283 | 1U2922 | sp-8 | an-283 | 1C2922 | sp-8 | an-283 |
| 1A2923 | sp-8 | an-284 | 1U2923 | sp-8 | an-284 | 1C2923 | sp-8 | an-284 |
| 1A2924 | sp-8 | an-285 | 1U2924 | sp-8 | an-285 | 1C2924 | sp-8 | an-285 |
| 1A2925 | sp-8 | an-286 | 1U2925 | sp-8 | an-286 | 1C2925 | sp-8 | an-286 |
| 1A2926 | sp-8 | an-287 | 1U2926 | sp-8 | an-287 | 1C2926 | sp-8 | an-287 |
| 1A2927 | sp-8 | an-288 | 1U2927 | sp-8 | an-288 | 1C2927 | sp-8 | an-288 |
| 1A2928 | sp-8 | an-289 | 1U2928 | sp-8 | an-289 | 1C2928 | sp-8 | an-289 |
| 1A2929 | sp-8 | an-290 | 1U2929 | sp-8 | an-290 | 1C2929 | sp-8 | an-290 |
| 1A2930 | sp-8 | an-291 | 1U2930 | sp-8 | an-291 | 1C2930 | sp-8 | an-291 |
| 1A2931 | sp-8 | an-292 | 1U2931 | sp-8 | an-292 | 1C2931 | sp-8 | an-292 |
| 1A2932 | sp-8 | an-293 | 1U2932 | sp-8 | an-293 | 1C2932 | sp-8 | an-293 |
| 1A2933 | sp-8 | an-294 | 1U2933 | sp-8 | an-294 | 1C2933 | sp-8 | an-294 |
| 1A2934 | sp-8 | an-295 | 1U2934 | sp-8 | an-295 | 1C2934 | sp-8 | an-295 |
| 1A2935 | sp-8 | an-296 | 1U2935 | sp-8 | an-296 | 1C2935 | sp-8 | an-296 |
| 1A2936 | sp-8 | an-297 | 1U2936 | sp-8 | an-297 | 1C2936 | sp-8 | an-297 |
| 1A2937 | sp-8 | an-298 | 1U2937 | sp-8 | an-298 | 1C2937 | sp-8 | an-298 |
| 1A2938 | sp-8 | an-299 | 1U2938 | sp-8 | an-299 | 1C2938 | sp-8 | an-299 |
| 1A2939 | sp-8 | an-300 | 1U2939 | sp-8 | an-300 | 1C2939 | sp-8 | an-300 |
| 1A2940 | sp-8 | an-301 | 1U2940 | sp-8 | an-301 | 1C2940 | sp-8 | an-301 |

TABLE 1-continued

| | | | | | | | | |
|---|---|---|---|---|---|---|---|---|
| 1A2941 | sp-8 | an-302 | 1U2941 | sp-8 | an-302 | 1C2941 | sp-8 | an-302 |
| 1A2942 | sp-8 | an-303 | 1U2942 | sp-8 | an-303 | 1C2942 | sp-8 | an-303 |
| 1A2943 | sp-8 | an-304 | 1U2943 | sp-8 | an-304 | 1C2943 | sp-8 | an-304 |
| 1A2944 | sp-8 | an-305 | 1U2944 | sp-8 | an-305 | 1C2944 | sp-8 | an-305 |
| 1A2945 | sp-8 | an-306 | 1U2945 | sp-8 | an-306 | 1C2945 | sp-8 | an-306 |
| 1A2946 | sp-8 | an-307 | 1U2946 | sp-8 | an-307 | 1C2946 | sp-8 | an-307 |
| 1A2947 | sp-8 | an-308 | 1U2947 | sp-8 | an-308 | 1C2947 | sp-8 | an-308 |
| 1A2948 | sp-8 | an-309 | 1U2948 | sp-8 | an-309 | 1C2948 | sp-8 | an-309 |
| 1A2949 | sp-8 | an-310 | 1U2949 | sp-8 | an-310 | 1C2949 | sp-8 | an-310 |
| 1A2950 | sp-8 | an-311 | 1U2950 | sp-8 | an-311 | 1C2950 | sp-8 | an-311 |
| 1A2951 | sp-8 | an-312 | 1U2951 | sp-8 | an-312 | 1C2951 | sp-8 | an-312 |
| 1A2952 | sp-8 | an-313 | 1U2952 | sp-8 | an-313 | 1C2952 | sp-8 | an-313 |
| 1A2953 | sp-8 | an-314 | 1U2953 | sp-8 | an-314 | 1C2953 | sp-8 | an-314 |
| 1A2954 | sp-8 | an-315 | 1U2954 | sp-8 | an-315 | 1C2954 | sp-8 | an-315 |
| 1A2955 | sp-8 | an-316 | 1U2955 | sp-8 | an-316 | 1C2955 | sp-8 | an-316 |
| 1A2956 | sp-8 | an-317 | 1U2956 | sp-8 | an-317 | 1C2956 | sp-8 | an-317 |
| 1A2957 | sp-8 | an-318 | 1U2957 | sp-8 | an-318 | 1C2957 | sp-8 | an-318 |
| 1A2958 | sp-8 | an-319 | 1U2958 | sp-8 | an-319 | 1C2958 | sp-8 | an-319 |
| 1A2959 | sp-8 | an-320 | 1U2959 | sp-8 | an-320 | 1C2959 | sp-8 | an-320 |
| 1A2960 | sp-8 | an-321 | 1U2960 | sp-8 | an-321 | 1C2960 | sp-8 | an-321 |
| 1A2961 | sp-8 | an-322 | 1U2961 | sp-8 | an-322 | 1C2961 | sp-8 | an-322 |
| 1A2962 | sp-8 | an-323 | 1U2962 | sp-8 | an-323 | 1C2962 | sp-8 | an-323 |
| 1A2963 | sp-8 | an-324 | 1U2963 | sp-8 | an-324 | 1C2963 | sp-8 | an-324 |
| 1A2964 | sp-8 | an-325 | 1U2964 | sp-8 | an-325 | 1C2964 | sp-8 | an-325 |
| 1A2965 | sp-8 | an-326 | 1U2965 | sp-8 | an-326 | 1C2965 | sp-8 | an-326 |
| 1A2966 | sp-8 | an-327 | 1U2966 | sp-8 | an-327 | 1C2966 | sp-8 | an-327 |
| 1A2967 | sp-8 | an-328 | 1U2967 | sp-8 | an-328 | 1C2967 | sp-8 | an-328 |
| 1A2968 | sp-8 | an-329 | 1U2968 | sp-8 | an-329 | 1C2968 | sp-8 | an-329 |
| 1A2969 | sp-8 | an-330 | 1U2969 | sp-8 | an-330 | 1C2969 | sp-8 | an-330 |
| 1A2970 | sp-8 | an-331 | 1U2970 | sp-8 | an-331 | 1C2970 | sp-8 | an-331 |
| 1A2971 | sp-8 | an-332 | 1U2971 | sp-8 | an-332 | 1C2971 | sp-8 | an-332 |
| 1A2972 | sp-8 | an-333 | 1U2972 | sp-8 | an-333 | 1C2972 | sp-8 | an-333 |
| 1A2973 | sp-8 | an-334 | 1U2973 | sp-8 | an-334 | 1C2973 | sp-8 | an-334 |
| 1A2974 | sp-8 | an-335 | 1U2974 | sp-8 | an-335 | 1C2974 | sp-8 | an-335 |
| 1A2975 | sp-8 | an-336 | 1U2975 | sp-8 | an-336 | 1C2975 | sp-8 | an-336 |
| 1A2976 | sp-8 | an-337 | 1U2976 | sp-8 | an-337 | 1C2976 | sp-8 | an-337 |
| 1A2977 | sp-8 | an-338 | 1U2977 | sp-8 | an-338 | 1C2977 | sp-8 | an-338 |
| 1A2978 | sp-8 | an-339 | 1U2978 | sp-8 | an-339 | 1C2978 | sp-8 | an-339 |
| 1A2979 | sp-8 | an-340 | 1U2979 | sp-8 | an-340 | 1C2979 | sp-8 | an-340 |
| 1A2980 | sp-8 | an-341 | 1U2980 | sp-8 | an-341 | 1C2980 | sp-8 | an-341 |
| 1A2981 | sp-8 | an-342 | 1U2981 | sp-8 | an-342 | 1C2981 | sp-8 | an-342 |
| 1A2982 | sp-8 | an-343 | 1U2982 | sp-8 | an-343 | 1C2982 | sp-8 | an-343 |
| 1A2983 | sp-8 | an-344 | 1U2983 | sp-8 | an-344 | 1C2983 | sp-8 | an-344 |
| 1A2984 | sp-8 | an-345 | 1U2984 | sp-8 | an-345 | 1C2984 | sp-8 | an-345 |
| 1A2985 | sp-8 | an-346 | 1U2985 | sp-8 | an-346 | 1C2985 | sp-8 | an-346 |
| 1A2986 | sp-8 | an-347 | 1U2986 | sp-8 | an-347 | 1C2986 | sp-8 | an-347 |
| 1A2987 | sp-8 | an-348 | 1U2987 | sp-8 | an-348 | 1C2987 | sp-8 | an-348 |
| 1A2988 | sp-8 | an-349 | 1U2988 | sp-8 | an-349 | 1C2988 | sp-8 | an-349 |
| 1A2989 | sp-8 | an-350 | 1U2989 | sp-8 | an-350 | 1C2989 | sp-8 | an-350 |
| 1A2990 | sp-8 | an-351 | 1U2990 | sp-8 | an-351 | 1C2990 | sp-8 | an-351 |
| 1A2991 | sp-8 | an-352 | 1U2991 | sp-8 | an-352 | 1C2991 | sp-8 | an-352 |
| 1A2992 | sp-8 | an-353 | 1U2992 | sp-8 | an-353 | 1C2992 | sp-8 | an-353 |
| 1A2993 | sp-8 | an-354 | 1U2993 | sp-8 | an-354 | 1C2993 | sp-8 | an-354 |
| 1A2994 | sp-8 | an-355 | 1U2994 | sp-8 | an-355 | 1C2994 | sp-8 | an-355 |
| 1A2995 | sp-8 | an-356 | 1U2995 | sp-8 | an-356 | 1C2995 | sp-8 | an-356 |
| 1A2996 | sp-8 | an-357 | 1U2996 | sp-8 | an-357 | 1C2996 | sp-8 | an-357 |
| 1A2997 | sp-8 | an-358 | 1U2997 | sp-8 | an-358 | 1C2997 | sp-8 | an-358 |
| 1A2998 | sp-8 | an-359 | 1U2998 | sp-8 | an-359 | 1C2998 | sp-8 | an-359 |
| 1A2999 | sp-8 | an-360 | 1U2999 | sp-8 | an-360 | 1C2999 | sp-8 | an-360 |
| 1A3000 | sp-8 | an-361 | 1U3000 | sp-8 | an-361 | 1C3000 | sp-8 | an-361 |
| 1A3001 | sp-8 | an-362 | 1U3001 | sp-8 | an-362 | 1C3001 | sp-8 | an-362 |
| 1A3002 | sp-8 | an-363 | 1U3002 | sp-8 | an-363 | 1C3002 | sp-8 | an-363 |
| 1A3003 | sp-8 | an-364 | 1U3003 | sp-8 | an-364 | 1C3003 | sp-8 | an-364 |
| 1A3004 | sp-8 | an-365 | 1U3004 | sp-8 | an-365 | 1C3004 | sp-8 | an-365 |
| 1A3005 | sp-8 | an-366 | 1U3005 | sp-8 | an-366 | 1C3005 | sp-8 | an-366 |
| 1A3006 | sp-8 | an-367 | 1U3006 | sp-8 | an-367 | 1C3006 | sp-8 | an-367 |
| 1A3007 | sp-8 | an-368 | 1U3007 | sp-8 | an-368 | 1C3007 | sp-8 | an-368 |
| 1A3008 | sp-8 | an-369 | 1U3008 | sp-8 | an-369 | 1C3008 | sp-8 | an-369 |
| 1A3009 | sp-8 | an-370 | 1U3009 | sp-8 | an-370 | 1C3009 | sp-8 | an-370 |
| 1A3010 | sp-8 | an-371 | 1U3010 | sp-8 | an-371 | 1C3010 | sp-8 | an-371 |
| 1A3011 | sp-8 | an-372 | 1U3011 | sp-8 | an-372 | 1C3011 | sp-8 | an-372 |
| 1A3012 | sp-8 | an-373 | 1U3012 | sp-8 | an-373 | 1C3012 | sp-8 | an-373 |
| 1A3013 | sp-8 | an-374 | 1U3013 | sp-8 | an-374 | 1C3013 | sp-8 | an-374 |
| 1A3014 | sp-8 | an-375 | 1U3014 | sp-8 | an-375 | 1C3014 | sp-8 | an-375 |
| 1A3015 | sp-8 | an-376 | 1U3015 | sp-8 | an-376 | 1C3015 | sp-8 | an-376 |
| 1A3016 | sp-8 | an-377 | 1U3016 | sp-8 | an-377 | 1C3016 | sp-8 | an-377 |
| 1A3017 | sp-9 | an-1 | 1U3017 | sp-9 | an-1 | 1C3017 | sp-9 | an-1 |
| 1A3018 | sp-9 | an-2 | 1U3018 | sp-9 | an-2 | 1C3018 | sp-9 | an-2 |
| 1A3019 | sp-9 | an-3 | 1U3019 | sp-9 | an-3 | 1C3019 | sp-9 | an-3 |

TABLE 1-continued

| | | | | | | | | |
|---|---|---|---|---|---|---|---|---|
| 1A3020 | sp-9 | an-4 | 1U3020 | sp-9 | an-4 | 1C3020 | sp-9 | an-4 |
| 1A3021 | sp-9 | an-5 | 1U3021 | sp-9 | an-5 | 1C3021 | sp-9 | an-5 |
| 1A3022 | sp-9 | an-6 | 1U3022 | sp-9 | an-6 | 1C3022 | sp-9 | an-6 |
| 1A3023 | sp-9 | an-7 | 1U3023 | sp-9 | an-7 | 1C3023 | sp-9 | an-7 |
| 1A3024 | sp-9 | an-8 | 1U3024 | sp-9 | an-8 | 1C3024 | sp-9 | an-8 |
| 1A3025 | sp-9 | an-9 | 1U3025 | sp-9 | an-9 | 1C3025 | sp-9 | an-9 |
| 1A3026 | sp-9 | an-10 | 1U3026 | sp-9 | an-10 | 1C3026 | sp-9 | an-10 |
| 1A3027 | sp-9 | an-11 | 1U3027 | sp-9 | an-11 | 1C3027 | sp-9 | an-11 |
| 1A3028 | sp-9 | an-12 | 1U3028 | sp-9 | an-12 | 1C3028 | sp-9 | an-12 |
| 1A3029 | sp-9 | an-13 | 1U3029 | sp-9 | an-13 | 1C3029 | sp-9 | an-13 |
| 1A3030 | sp-9 | an-14 | 1U3030 | sp-9 | an-14 | 1C3030 | sp-9 | an-14 |
| 1A3031 | sp-9 | an-15 | 1U3031 | sp-9 | an-15 | 1C3031 | sp-9 | an-15 |
| 1A3032 | sp-9 | an-16 | 1U3032 | sp-9 | an-16 | 1C3032 | sp-9 | an-16 |
| 1A3033 | sp-9 | an-17 | 1U3033 | sp-9 | an-17 | 1C3033 | sp-9 | an-17 |
| 1A3034 | sp-9 | an-18 | 1U3034 | sp-9 | an-18 | 1C3034 | sp-9 | an-18 |
| 1A3035 | sp-9 | an-19 | 1U3035 | sp-9 | an-19 | 1C3035 | sp-9 | an-19 |
| 1A3036 | sp-9 | an-20 | 1U3036 | sp-9 | an-20 | 1C3036 | sp-9 | an-20 |
| 1A3037 | sp-9 | an-21 | 1U3037 | sp-9 | an-21 | 1C3037 | sp-9 | an-21 |
| 1A3038 | sp-9 | an-22 | 1U3038 | sp-9 | an-22 | 1C3038 | sp-9 | an-22 |
| 1A3039 | sp-9 | an-23 | 1U3039 | sp-9 | an-23 | 1C3039 | sp-9 | an-23 |
| 1A3040 | sp-9 | an-24 | 1U3040 | sp-9 | an-24 | 1C3040 | sp-9 | an-24 |
| 1A3041 | sp-9 | an-25 | 1U3041 | sp-9 | an-25 | 1C3041 | sp-9 | an-25 |
| 1A3042 | sp-9 | an-26 | 1U3042 | sp-9 | an-26 | 1C3042 | sp-9 | an-26 |
| 1A3043 | sp-9 | an-27 | 1U3043 | sp-9 | an-27 | 1C3043 | sp-9 | an-27 |
| 1A3044 | sp-9 | an-28 | 1U3044 | sp-9 | an-28 | 1C3044 | sp-9 | an-28 |
| 1A3045 | sp-9 | an-29 | 1U3045 | sp-9 | an-29 | 1C3045 | sp-9 | an-29 |
| 1A3046 | sp-9 | an-30 | 1U3046 | sp-9 | an-30 | 1C3046 | sp-9 | an-30 |
| 1A3047 | sp-9 | an-31 | 1U3047 | sp-9 | an-31 | 1C3047 | sp-9 | an-31 |
| 1A3048 | sp-9 | an-32 | 1U3048 | sp-9 | an-32 | 1C3048 | sp-9 | an-32 |
| 1A3049 | sp-9 | an-33 | 1U3049 | sp-9 | an-33 | 1C3049 | sp-9 | an-33 |
| 1A3050 | sp-9 | an-34 | 1U3050 | sp-9 | an-34 | 1C3050 | sp-9 | an-34 |
| 1A3051 | sp-9 | an-35 | 1U3051 | sp-9 | an-35 | 1C3051 | sp-9 | an-35 |
| 1A3052 | sp-9 | an-36 | 1U3052 | sp-9 | an-36 | 1C3052 | sp-9 | an-36 |
| 1A3053 | sp-9 | an-37 | 1U3053 | sp-9 | an-37 | 1C3053 | sp-9 | an-37 |
| 1A3054 | sp-9 | an-38 | 1U3054 | sp-9 | an-38 | 1C3054 | sp-9 | an-38 |
| 1A3055 | sp-9 | an-39 | 1U3055 | sp-9 | an-39 | 1C3055 | sp-9 | an-39 |
| 1A3056 | sp-9 | an-40 | 1U3056 | sp-9 | an-40 | 1C3056 | sp-9 | an-40 |
| 1A3057 | sp-9 | an-41 | 1U3057 | sp-9 | an-41 | 1C3057 | sp-9 | an-41 |
| 1A3058 | sp-9 | an-42 | 1U3058 | sp-9 | an-42 | 1C3058 | sp-9 | an-42 |
| 1A3059 | sp-9 | an-43 | 1U3059 | sp-9 | an-43 | 1C3059 | sp-9 | an-43 |
| 1A3060 | sp-9 | an-44 | 1U3060 | sp-9 | an-44 | 1C3060 | sp-9 | an-44 |
| 1A3061 | sp-9 | an-45 | 1U3061 | sp-9 | an-45 | 1C3061 | sp-9 | an-45 |
| 1A3062 | sp-9 | an-46 | 1U3062 | sp-9 | an-46 | 1C3062 | sp-9 | an-46 |
| 1A3063 | sp-9 | an-47 | 1U3063 | sp-9 | an-47 | 1C3063 | sp-9 | an-47 |
| 1A3064 | sp-9 | an-48 | 1U3064 | sp-9 | an-48 | 1C3064 | sp-9 | an-48 |
| 1A3065 | sp-9 | an-49 | 1U3065 | sp-9 | an-49 | 1C3065 | sp-9 | an-49 |
| 1A3066 | sp-9 | an-50 | 1U3066 | sp-9 | an-50 | 1C3066 | sp-9 | an-50 |
| 1A3067 | sp-9 | an-51 | 1U3067 | sp-9 | an-51 | 1C3067 | sp-9 | an-51 |
| 1A3068 | sp-9 | an-52 | 1U3068 | sp-9 | an-52 | 1C3068 | sp-9 | an-52 |
| 1A3069 | sp-9 | an-53 | 1U3069 | sp-9 | an-53 | 1C3069 | sp-9 | an-53 |
| 1A3070 | sp-9 | an-54 | 1U3070 | sp-9 | an-54 | 1C3070 | sp-9 | an-54 |
| 1A3071 | sp-9 | an-55 | 1U3071 | sp-9 | an-55 | 1C3071 | sp-9 | an-55 |
| 1A3072 | sp-9 | an-56 | 1U3072 | sp-9 | an-56 | 1C3072 | sp-9 | an-56 |
| 1A3073 | sp-9 | an-57 | 1U3073 | sp-9 | an-57 | 1C3073 | sp-9 | an-57 |
| 1A3074 | sp-9 | an-58 | 1U3074 | sp-9 | an-58 | 1C3074 | sp-9 | an-58 |
| 1A3075 | sp-9 | an-59 | 1U3075 | sp-9 | an-59 | 1C3075 | sp-9 | an-59 |
| 1A3076 | sp-9 | an-60 | 1U3076 | sp-9 | an-60 | 1C3076 | sp-9 | an-60 |
| 1A3077 | sp-9 | an-61 | 1U3077 | sp-9 | an-61 | 1C3077 | sp-9 | an-61 |
| 1A3078 | sp-9 | an-62 | 1U3078 | sp-9 | an-62 | 1C3078 | sp-9 | an-62 |
| 1A3079 | sp-9 | an-63 | 1U3079 | sp-9 | an-63 | 1C3079 | sp-9 | an-63 |
| 1A3080 | sp-9 | an-64 | 1U3080 | sp-9 | an-64 | 1C3080 | sp-9 | an-64 |
| 1A3081 | sp-9 | an-65 | 1U3081 | sp-9 | an-65 | 1C3081 | sp-9 | an-65 |
| 1A3082 | sp-9 | an-66 | 1U3082 | sp-9 | an-66 | 1C3082 | sp-9 | an-66 |
| 1A3083 | sp-9 | an-67 | 1U3083 | sp-9 | an-67 | 1C3083 | sp-9 | an-67 |
| 1A3084 | sp-9 | an-68 | 1U3084 | sp-9 | an-68 | 1C3084 | sp-9 | an-68 |
| 1A3085 | sp-9 | an-69 | 1U3085 | sp-9 | an-69 | 1C3085 | sp-9 | an-69 |
| 1A3086 | sp-9 | an-70 | 1U3086 | sp-9 | an-70 | 1C3086 | sp-9 | an-70 |
| 1A3087 | sp-9 | an-71 | 1U3087 | sp-9 | an-71 | 1C3087 | sp-9 | an-71 |
| 1A3088 | sp-9 | an-72 | 1U3088 | sp-9 | an-72 | 1C3088 | sp-9 | an-72 |
| 1A3089 | sp-9 | an-73 | 1U3089 | sp-9 | an-73 | 1C3089 | sp-9 | an-73 |
| 1A3090 | sp-9 | an-74 | 1U3090 | sp-9 | an-74 | 1C3090 | sp-9 | an-74 |
| 1A3091 | sp-9 | an-75 | 1U3091 | sp-9 | an-75 | 1C3091 | sp-9 | an-75 |
| 1A3092 | sp-9 | an-76 | 1U3092 | sp-9 | an-76 | 1C3092 | sp-9 | an-76 |
| 1A3093 | sp-9 | an-77 | 1U3093 | sp-9 | an-77 | 1C3093 | sp-9 | an-77 |
| 1A3094 | sp-9 | an-78 | 1U3094 | sp-9 | an-78 | 1C3094 | sp-9 | an-78 |
| 1A3095 | sp-9 | an-79 | 1U3095 | sp-9 | an-79 | 1C3095 | sp-9 | an-79 |
| 1A3096 | sp-9 | an-80 | 1U3096 | sp-9 | an-80 | 1C3096 | sp-9 | an-80 |
| 1A3097 | sp-9 | an-81 | 1U3097 | sp-9 | an-81 | 1C3097 | sp-9 | an-81 |
| 1A3098 | sp-9 | an-82 | 1U3098 | sp-9 | an-82 | 1C3098 | sp-9 | an-82 |

TABLE 1-continued

| | | | | | | | | |
|---|---|---|---|---|---|---|---|---|
| 1A3099 | sp-9 | an-83 | 1U3099 | sp-9 | an-83 | 1C3099 | sp-9 | an-83 |
| 1A3100 | sp-9 | an-84 | 1U3100 | sp-9 | an-84 | 1C3100 | sp-9 | an-84 |
| 1A3101 | sp-9 | an-85 | 1U3101 | sp-9 | an-85 | 1C3101 | sp-9 | an-85 |
| 1A3102 | sp-9 | an-86 | 1U3102 | sp-9 | an-86 | 1C3102 | sp-9 | an-86 |
| 1A3103 | sp-9 | an-87 | 1U3103 | sp-9 | an-87 | 1C3103 | sp-9 | an-87 |
| 1A3104 | sp-9 | an-88 | 1U3104 | sp-9 | an-88 | 1C3104 | sp-9 | an-88 |
| 1A3105 | sp-9 | an-89 | 1U3105 | sp-9 | an-89 | 1C3105 | sp-9 | an-89 |
| 1A3106 | sp-9 | an-90 | 1U3106 | sp-9 | an-90 | 1C3106 | sp-9 | an-90 |
| 1A3107 | sp-9 | an-91 | 1U3107 | sp-9 | an-91 | 1C3107 | sp-9 | an-91 |
| 1A3108 | sp-9 | an-92 | 1U3108 | sp-9 | an-92 | 1C3108 | sp-9 | an-92 |
| 1A3109 | sp-9 | an-93 | 1U3109 | sp-9 | an-93 | 1C3109 | sp-9 | an-93 |
| 1A3110 | sp-9 | an-94 | 1U3110 | sp-9 | an-94 | 1C3110 | sp-9 | an-94 |
| 1A3111 | sp-9 | an-95 | 1U3111 | sp-9 | an-95 | 1C3111 | sp-9 | an-95 |
| 1A3112 | sp-9 | an-96 | 1U3112 | sp-9 | an-96 | 1C3112 | sp-9 | an-96 |
| 1A3113 | sp-9 | an-97 | 1U3113 | sp-9 | an-97 | 1C3113 | sp-9 | an-97 |
| 1A3114 | sp-9 | an-98 | 1U3114 | sp-9 | an-98 | 1C3114 | sp-9 | an-98 |
| 1A3115 | sp-9 | an-99 | 1U3115 | sp-9 | an-99 | 1C3115 | sp-9 | an-99 |
| 1A3116 | sp-9 | an-100 | 1U3116 | sp-9 | an-100 | 1C3116 | sp-9 | an-100 |
| 1A3117 | sp-9 | an-101 | 1U3117 | sp-9 | an-101 | 1C3117 | sp-9 | an-101 |
| 1A3118 | sp-9 | an-102 | 1U3118 | sp-9 | an-102 | 1C3118 | sp-9 | an-102 |
| 1A3119 | sp-9 | an-103 | 1U3119 | sp-9 | an-103 | 1C3119 | sp-9 | an-103 |
| 1A3120 | sp-9 | an-104 | 1U3120 | sp-9 | an-104 | 1C3120 | sp-9 | an-104 |
| 1A3121 | sp-9 | an-105 | 1U3121 | sp-9 | an-105 | 1C3121 | sp-9 | an-105 |
| 1A3122 | sp-9 | an-106 | 1U3122 | sp-9 | an-106 | 1C3122 | sp-9 | an-106 |
| 1A3123 | sp-9 | an-107 | 1U3123 | sp-9 | an-107 | 1C3123 | sp-9 | an-107 |
| 1A3124 | sp-9 | an-108 | 1U3124 | sp-9 | an-108 | 1C3124 | sp-9 | an-108 |
| 1A3125 | sp-9 | an-109 | 1U3125 | sp-9 | an-109 | 1C3125 | sp-9 | an-109 |
| 1A3126 | sp-9 | an-110 | 1U3126 | sp-9 | an-110 | 1C3126 | sp-9 | an-110 |
| 1A3127 | sp-9 | an-111 | 1U3127 | sp-9 | an-111 | 1C3127 | sp-9 | an-111 |
| 1A3128 | sp-9 | an-112 | 1U3128 | sp-9 | an-112 | 1C3128 | sp-9 | an-112 |
| 1A3129 | sp-9 | an-113 | 1U3129 | sp-9 | an-113 | 1C3129 | sp-9 | an-113 |
| 1A3130 | sp-9 | an-114 | 1U3130 | sp-9 | an-114 | 1C3130 | sp-9 | an-114 |
| 1A3131 | sp-9 | an-115 | 1U3131 | sp-9 | an-115 | 1C3131 | sp-9 | an-115 |
| 1A3132 | sp-9 | an-116 | 1U3132 | sp-9 | an-116 | 1C3132 | sp-9 | an-116 |
| 1A3133 | sp-9 | an-117 | 1U3133 | sp-9 | an-117 | 1C3133 | sp-9 | an-117 |
| 1A3134 | sp-9 | an-118 | 1U3134 | sp-9 | an-118 | 1C3134 | sp-9 | an-118 |
| 1A3135 | sp-9 | an-119 | 1U3135 | sp-9 | an-119 | 1C3135 | sp-9 | an-119 |
| 1A3136 | sp-9 | an-120 | 1U3136 | sp-9 | an-120 | 1C3136 | sp-9 | an-120 |
| 1A3137 | sp-9 | an-121 | 1U3137 | sp-9 | an-121 | 1C3137 | sp-9 | an-121 |
| 1A3138 | sp-9 | an-122 | 1U3138 | sp-9 | an-122 | 1C3138 | sp-9 | an-122 |
| 1A3139 | sp-9 | an-123 | 1U3139 | sp-9 | an-123 | 1C3139 | sp-9 | an-123 |
| 1A3140 | sp-9 | an-124 | 1U3140 | sp-9 | an-124 | 1C3140 | sp-9 | an-124 |
| 1A3141 | sp-9 | an-125 | 1U3141 | sp-9 | an-125 | 1C3141 | sp-9 | an-125 |
| 1A3142 | sp-9 | an-126 | 1U3142 | sp-9 | an-126 | 1C3142 | sp-9 | an-126 |
| 1A3143 | sp-9 | an-127 | 1U3143 | sp-9 | an-127 | 1O3143 | sp-9 | an-127 |
| 1A3144 | sp-9 | an-128 | 1U3144 | sp-9 | an-128 | 1C3144 | sp-9 | an-128 |
| 1A3145 | sp-9 | an-129 | 1U3145 | sp-9 | an-129 | 1C3145 | sp-9 | an-129 |
| 1A3146 | sp-9 | an-130 | 1U3146 | sp-9 | an-130 | 1C3146 | sp-9 | an-130 |
| 1A3147 | sp-9 | an-131 | 1U3147 | sp-9 | an-131 | 1C3147 | sp-9 | an-131 |
| 1A3148 | sp-9 | an-132 | 1U3148 | sp-9 | an-132 | 1C3148 | sp-9 | an-132 |
| 1A3149 | sp-9 | an-133 | 1U3149 | sp-9 | an-133 | 1C3149 | sp-9 | an-133 |
| 1A3150 | sp-9 | an-134 | 1U3150 | sp-9 | an-134 | 1C3150 | sp-9 | an-134 |
| 1A3151 | sp-9 | an-135 | 1U3151 | sp-9 | an-135 | 1C3151 | sp-9 | an-135 |
| 1A3152 | sp-9 | an-136 | 1U3152 | sp-9 | an-136 | 1C3152 | sp-9 | an-136 |
| 1A3153 | sp-9 | an-137 | 1U3153 | sp-9 | an-137 | 1C3153 | sp-9 | an-137 |
| 1A3154 | sp-9 | an-138 | 1U3154 | sp-9 | an-138 | 1C3154 | sp-9 | an-138 |
| 1A3155 | sp-9 | an-139 | 1U3155 | sp-9 | an-139 | 1C3155 | sp-9 | an-139 |
| 1A3156 | sp-9 | an-140 | 1U3156 | sp-9 | an-140 | 1C3156 | sp-9 | an-140 |
| 1A3157 | sp-9 | an-141 | 1U3157 | sp-9 | an-141 | 1C3157 | sp-9 | an-141 |
| 1A3158 | sp-9 | an-142 | 1U3158 | sp-9 | an-142 | 1C3158 | sp-9 | an-142 |
| 1A3159 | sp-9 | an-143 | 1U3159 | sp-9 | an-143 | 1C3159 | sp-9 | an-143 |
| 1A3160 | sp-9 | an-144 | 1U3160 | sp-9 | an-144 | 1C3160 | sp-9 | an-144 |
| 1A3161 | sp-9 | an-145 | 1U3161 | sp-9 | an-145 | 1C3161 | sp-9 | an-145 |
| 1A3162 | sp-9 | an-146 | 1U3162 | sp-9 | an-146 | 1C3162 | sp-9 | an-146 |
| 1A3163 | sp-9 | an-147 | 1U3163 | sp-9 | an-147 | 1C3163 | sp-9 | an-147 |
| 1A3164 | sp-9 | an-148 | 1U3164 | sp-9 | an-148 | 1C3164 | sp-9 | an-148 |
| 1A3165 | sp-9 | an-149 | 1U3165 | sp-9 | an-149 | 1C3165 | sp-9 | an-149 |
| 1A3166 | sp-9 | an-150 | 1U3166 | sp-9 | an-150 | 1C3166 | sp-9 | an-150 |
| 1A3167 | sp-9 | an-151 | 1U3167 | sp-9 | an-151 | 1C3167 | sp-9 | an-151 |
| 1A3168 | sp-9 | an-152 | 1U3168 | sp-9 | an-152 | 1C3168 | sp-9 | an-152 |
| 1A3169 | sp-9 | an-153 | 1U3169 | sp-9 | an-153 | 1C3169 | sp-9 | an-153 |
| 1A3170 | sp-9 | an-154 | 1U3170 | sp-9 | an-154 | 1C3170 | sp-9 | an-154 |
| 1A3171 | sp-9 | an-155 | 1U3171 | sp-9 | an-155 | 1C3171 | sp-9 | an-155 |
| 1A3172 | sp-9 | an-156 | 1U3172 | sp-9 | an-156 | 1C3172 | sp-9 | an-156 |
| 1A3173 | sp-9 | an-157 | 1U3173 | sp-9 | an-157 | 1C3173 | sp-9 | an-157 |
| 1A3174 | sp-9 | an-158 | 1U3174 | sp-9 | an-158 | 1C3174 | sp-9 | an-158 |
| 1A3175 | sp-9 | an-159 | 1U3175 | sp-9 | an-159 | 1C3175 | sp-9 | an-159 |
| 1A3176 | sp-9 | an-160 | 1U3176 | sp-9 | an-160 | 1C3176 | sp-9 | an-160 |
| 1A3177 | sp-9 | an-161 | 1U3177 | sp-9 | an-161 | 1C3177 | sp-9 | an-161 |

TABLE 1-continued

| | | | | | | | | |
|---|---|---|---|---|---|---|---|---|
| 1A3178 | sp-9 | an-162 | 1U3178 | sp-9 | an-162 | 1C3178 | sp-9 | an-162 |
| 1A3179 | sp-9 | an-163 | 1U3179 | sp-9 | an-163 | 1C3179 | sp-9 | an-163 |
| 1A3180 | sp-9 | an-164 | 1U3180 | sp-9 | an-164 | 1C3180 | sp-9 | an-164 |
| 1A3181 | sp-9 | an-165 | 1U3181 | sp-9 | an-165 | 1C3181 | sp-9 | an-165 |
| 1A3182 | sp-9 | an-166 | 1U3182 | sp-9 | an-166 | 1C3182 | sp-9 | an-166 |
| 1A3183 | sp-9 | an-167 | 1U3183 | sp-9 | an-167 | 1C3183 | sp-9 | an-167 |
| 1A3184 | sp-9 | an-168 | 1U3184 | sp-9 | an-168 | 1C3184 | sp-9 | an-168 |
| 1A3185 | sp-9 | an-169 | 1U3185 | sp-9 | an-169 | 1C3185 | sp-9 | an-169 |
| 1A3186 | sp-9 | an-170 | 1U3186 | sp-9 | an-170 | 1C3186 | sp-9 | an-170 |
| 1A3187 | sp-9 | an-171 | 1U3187 | sp-9 | an-171 | 1C3187 | sp-9 | an-171 |
| 1A3188 | sp-9 | an-172 | 1U3188 | sp-9 | an-172 | 1C3188 | sp-9 | an-172 |
| 1A3189 | sp-9 | an-173 | 1U3189 | sp-9 | an-173 | 1C3189 | sp-9 | an-173 |
| 1A3190 | sp-9 | an-174 | 1U3190 | sp-9 | an-174 | 1C3190 | sp-9 | an-174 |
| 1A3191 | sp-9 | an-175 | 1U3191 | sp-9 | an-175 | 1C3191 | sp-9 | an-175 |
| 1A3192 | sp-9 | an-176 | 1U3192 | sp-9 | an-176 | 1C3192 | sp-9 | an-176 |
| 1A3193 | sp-9 | an-177 | 1U3193 | sp-9 | an-177 | 1C3193 | sp-9 | an-177 |
| 1A3194 | sp-9 | an-178 | 1U3194 | sp-9 | an-178 | 1C3194 | sp-9 | an-178 |
| 1A3195 | sp-9 | an-179 | 1U3195 | sp-9 | an-179 | 1C3195 | sp-9 | an-179 |
| 1A3196 | sp-9 | an-180 | 1U3196 | sp-9 | an-180 | 1C3196 | sp-9 | an-180 |
| 1A3197 | sp-9 | an-181 | 1U3197 | sp-9 | an-181 | 1C3197 | sp-9 | an-181 |
| 1A3198 | sp-9 | an-182 | 1U3198 | sp-9 | an-182 | 1C3198 | sp-9 | an-182 |
| 1A3199 | sp-9 | an-183 | 1U3199 | sp-9 | an-183 | 1C3199 | sp-9 | an-183 |
| 1A3200 | sp-9 | an-184 | 1U3200 | sp-9 | an-184 | 1C3200 | sp-9 | an-184 |
| 1A3201 | sp-9 | an-185 | 1U3201 | sp-9 | an-185 | 1C3201 | sp-9 | an-185 |
| 1A3202 | sp-9 | an-186 | 1U3202 | sp-9 | an-186 | 1C3202 | sp-9 | an-186 |
| 1A3203 | sp-9 | an-187 | 1U3203 | sp-9 | an-187 | 1C3203 | sp-9 | an-187 |
| 1A3204 | sp-9 | an-188 | 1U3204 | sp-9 | an-188 | 1C3204 | sp-9 | an-188 |
| 1A3205 | sp-9 | an-189 | 1U3205 | sp-9 | an-189 | 1C3205 | sp-9 | an-189 |
| 1A3206 | sp-9 | an-190 | 1U3206 | sp-9 | an-190 | 1C3206 | sp-9 | an-190 |
| 1A3207 | sp-9 | an-191 | 1U3207 | sp-9 | an-191 | 1C3207 | sp-9 | an-191 |
| 1A3208 | sp-9 | an-192 | 1U3208 | sp-9 | an-192 | 1C3208 | sp-9 | an-192 |
| 1A3209 | sp-9 | an-193 | 1U3209 | sp-9 | an-193 | 1C3209 | sp-9 | an-193 |
| 1A3210 | sp-9 | an-194 | 1U3210 | sp-9 | an-194 | 1C3210 | sp-9 | an-194 |
| 1A3211 | sp-9 | an-195 | 1U3211 | sp-9 | an-195 | 1C3211 | sp-9 | an-195 |
| 1A3212 | sp-9 | an-196 | 1U3212 | sp-9 | an-196 | 1C3212 | sp-9 | an-196 |
| 1A3213 | sp-9 | an-197 | 1U3213 | sp-9 | an-197 | 1C3213 | sp-9 | an-197 |
| 1A3214 | sp-9 | an-198 | 1U3214 | sp-9 | an-198 | 1C3214 | sp-9 | an-198 |
| 1A3215 | sp-9 | an-199 | 1U3215 | sp-9 | an-199 | 1C3215 | sp-9 | an-199 |
| 1A3216 | sp-9 | an-200 | 1U3216 | sp-9 | an-200 | 1C3216 | sp-9 | an-200 |
| 1A3217 | sp-9 | an-201 | 1U3217 | sp-9 | an-201 | 1C3217 | sp-9 | an-201 |
| 1A3218 | sp-9 | an-202 | 1U3218 | sp-9 | an-202 | 1C3218 | sp-9 | an-202 |
| 1A3219 | sp-9 | an-203 | 1U3219 | sp-9 | an-203 | 1C3219 | sp-9 | an-203 |
| 1A3220 | sp-9 | an-204 | 1U3220 | sp-9 | an-204 | 1C3220 | sp-9 | an-204 |
| 1A3221 | sp-9 | an-205 | 1U3221 | sp-9 | an-205 | 1C3221 | sp-9 | an-205 |
| 1A3222 | sp-9 | an-206 | 1U3222 | sp-9 | an-206 | 1C3222 | sp-9 | an-206 |
| 1A3223 | sp-9 | an-207 | 1U3223 | sp-9 | an-207 | 1C3223 | sp-9 | an-207 |
| 1A3224 | sp-9 | an-208 | 1U3224 | sp-9 | an-208 | 1C3224 | sp-9 | an-208 |
| 1A3225 | sp-9 | an-209 | 1U3225 | sp-9 | an-209 | 1C3225 | sp-9 | an-209 |
| 1A3226 | sp-9 | an-210 | 1U3226 | sp-9 | an-210 | 1C3226 | sp-9 | an-210 |
| 1A3227 | sp-9 | an-211 | 1U3227 | sp-9 | an-211 | 1C3227 | sp-9 | an-211 |
| 1A3228 | sp-9 | an-212 | 1U3228 | sp-9 | an-212 | 1C3228 | sp-9 | an-212 |
| 1A3229 | sp-9 | an-213 | 1U3229 | sp-9 | an-213 | 1C3229 | sp-9 | an-213 |
| 1A3230 | sp-9 | an-214 | 1U3230 | sp-9 | an-214 | 1C3230 | sp-9 | an-214 |
| 1A3231 | sp-9 | an-215 | 1U3231 | sp-9 | an-215 | 1C3231 | sp-9 | an-215 |
| 1A3232 | sp-9 | an-216 | 1U3232 | sp-9 | an-216 | 1C3232 | sp-9 | an-216 |
| 1A3233 | sp-9 | an-217 | 1U3233 | sp-9 | an-217 | 1C3233 | sp-9 | an-217 |
| 1A3234 | sp-9 | an-218 | 1U3234 | sp-9 | an-218 | 1C3234 | sp-9 | an-218 |
| 1A3235 | sp-9 | an-219 | 1U3235 | sp-9 | an-219 | 1C3235 | sp-9 | an-219 |
| 1A3236 | sp-9 | an-220 | 1U3236 | sp-9 | an-220 | 1C3236 | sp-9 | an-220 |
| 1A3237 | sp-9 | an-221 | 1U3237 | sp-9 | an-221 | 1C3237 | sp-9 | an-221 |
| 1A3238 | sp-9 | an-222 | 1U3238 | sp-9 | an-222 | 1C3238 | sp-9 | an-222 |
| 1A3239 | sp-9 | an-223 | 1U3239 | sp-9 | an-223 | 1C3239 | sp-9 | an-223 |
| 1A3240 | sp-9 | an-224 | 1U3240 | sp-9 | an-224 | 1C3240 | sp-9 | an-224 |
| 1A3241 | sp-9 | an-225 | 1U3241 | sp-9 | an-225 | 1C3241 | sp-9 | an-225 |
| 1A3242 | sp-9 | an-226 | 1U3242 | sp-9 | an-226 | 1C3242 | sp-9 | an-226 |
| 1A3243 | sp-9 | an-227 | 1U3243 | sp-9 | an-227 | 1C3243 | sp-9 | an-227 |
| 1A3244 | sp-9 | an-228 | 1U3244 | sp-9 | an-228 | 1C3244 | sp-9 | an-228 |
| 1A3245 | sp-9 | an-229 | 1U3245 | sp-9 | an-229 | 1C3245 | sp-9 | an-229 |
| 1A3246 | sp-9 | an-230 | 1U3246 | sp-9 | an-230 | 1C3246 | sp-9 | an-230 |
| 1A3247 | sp-9 | an-231 | 1U3247 | sp-9 | an-231 | 1C3247 | sp-9 | an-231 |
| 1A3248 | sp-9 | an-232 | 1U3248 | sp-9 | an-232 | 1C3248 | sp-9 | an-232 |
| 1A3249 | sp-9 | an-233 | 1U3249 | sp-9 | an-233 | 1C3249 | sp-9 | an-233 |
| 1A3250 | sp-9 | an-234 | 1U3250 | sp-9 | an-234 | 1C3250 | sp-9 | an-234 |
| 1A3251 | sp-9 | an-235 | 1U3251 | sp-9 | an-235 | 1C3251 | sp-9 | an-235 |
| 1A3252 | sp-9 | an-236 | 1U3252 | sp-9 | an-236 | 1C3252 | sp-9 | an-236 |
| 1A3253 | sp-9 | an-237 | 1U3253 | sp-9 | an-237 | 1C3253 | sp-9 | an-237 |
| 1A3254 | sp-9 | an-233 | 1U3254 | sp-9 | an-238 | 1C3254 | sp-9 | an-238 |
| 1A3255 | sp-9 | an-239 | 1U3255 | sp-9 | an-239 | 1C3255 | sp-9 | an-239 |
| 1A3256 | sp-9 | an-240 | 1U3256 | sp-9 | an-240 | 1C3256 | sp-9 | an-240 |

TABLE 1-continued

| | | | | | | | | |
|---|---|---|---|---|---|---|---|---|
| 1A3257 | sp-9 | an-241 | 1U3257 | sp-9 | an-241 | 1C3257 | sp-9 | an-241 |
| 1A3258 | sp-9 | an-242 | 1U3258 | sp-9 | an-242 | 1C3258 | sp-9 | an-242 |
| 1A3259 | sp-9 | an-243 | 1U3259 | sp-9 | an-243 | 1C3259 | sp-9 | an-243 |
| 1A3260 | sp-9 | an-244 | 1U3260 | sp-9 | an-244 | 1C3260 | sp-9 | an-244 |
| 1A3261 | sp-9 | an-245 | 1U3261 | sp-9 | an-245 | 1C3261 | sp-9 | an-245 |
| 1A3262 | sp-9 | an-246 | 1U3262 | sp-9 | an-246 | 1C3262 | sp-9 | an-246 |
| 1A3263 | sp-9 | an-247 | 1U3263 | sp-9 | an-247 | 1C3263 | sp-9 | an-247 |
| 1A3264 | sp-9 | an-248 | 1U3264 | sp-9 | an-248 | 1C3264 | sp-9 | an-248 |
| 1A3265 | sp-9 | an-249 | 1U3265 | sp-9 | an-249 | 1C3265 | sp-9 | an-249 |
| 1A3266 | sp-9 | an-250 | 1U3266 | sp-9 | an-250 | 1C3266 | sp-9 | an-250 |
| 1A3267 | sp-9 | an-251 | 1U3267 | sp-9 | an-251 | 1C3267 | sp-9 | an-251 |
| 1A3268 | sp-9 | an-252 | 1U3268 | sp-9 | an-252 | 1C3268 | sp-9 | an-252 |
| 1A3269 | sp-9 | an-253 | 1U3269 | sp-9 | an-253 | 1C3269 | sp-9 | an-253 |
| 1A3270 | sp-9 | an-254 | 1U3270 | sp-9 | an-254 | 1C3270 | sp-9 | an-254 |
| 1A3271 | sp-9 | an-255 | 1U3271 | sp-9 | an-255 | 1C3271 | sp-9 | an-255 |
| 1A3272 | sp-9 | an-256 | 1U3272 | sp-9 | an-256 | 1C3272 | sp-9 | an-256 |
| 1A3273 | sp-9 | an-257 | 1U3273 | sp-9 | an-257 | 1C3273 | sp-9 | an-257 |
| 1A3274 | sp-9 | an-258 | 1U3274 | sp-9 | an-258 | 1C3274 | sp-9 | an-258 |
| 1A3275 | sp-9 | an-259 | 1U3275 | sp-9 | an-259 | 1C3275 | sp-9 | an-259 |
| 1A3276 | sp-9 | an-260 | 1U3276 | sp-9 | an-260 | 1C3276 | sp-9 | an-260 |
| 1A3277 | sp-9 | an-261 | 1U3277 | sp-9 | an-261 | 1C3277 | sp-9 | an-261 |
| 1A3278 | sp-9 | an-262 | 1U3278 | sp-9 | an-262 | 1C3278 | sp-9 | an-262 |
| 1A3279 | sp-9 | an-263 | 1U3279 | sp-9 | an-263 | 1C3279 | sp-9 | an-263 |
| 1A3280 | sp-9 | an-264 | 1U3280 | sp-9 | an-264 | 1C3280 | sp-9 | an-264 |
| 1A3281 | sp-9 | an-265 | 1U3281 | sp-9 | an-265 | 1C3281 | sp-9 | an-265 |
| 1A3282 | sp-9 | an-266 | 1U3282 | sp-9 | an-266 | 1C3282 | sp-9 | an-266 |
| 1A3283 | sp-9 | an-267 | 1U3283 | sp-9 | an-267 | 1C3283 | sp-9 | an-267 |
| 1A3284 | sp-9 | an-268 | 1U3284 | sp-9 | an-268 | 1C3284 | sp-9 | an-268 |
| 1A3285 | sp-9 | an-269 | 1U3285 | sp-9 | an-269 | 1C3285 | sp-9 | an-269 |
| 1A3286 | sp-9 | an-270 | 1U3286 | sp-9 | an-270 | 1C3286 | sp-9 | an-270 |
| 1A3287 | sp-9 | an-271 | 1U3287 | sp-9 | an-271 | 1C3287 | sp-9 | an-271 |
| 1A3288 | sp-9 | an-272 | 1U3288 | sp-9 | an-272 | 1C3288 | sp-9 | an-272 |
| 1A3289 | sp-9 | an-273 | 1U3289 | sp-9 | an-273 | 1C3289 | sp-9 | an-273 |
| 1A3290 | sp-9 | an-274 | 1U3290 | sp-9 | an-274 | 1C3290 | sp-9 | an-274 |
| 1A3291 | sp-9 | an-275 | 1U3291 | sp-9 | an-275 | 1C3291 | sp-9 | an-275 |
| 1A3292 | sp-9 | an-276 | 1U3292 | sp-9 | an-276 | 1C3292 | sp-9 | an-276 |
| 1A3293 | sp-9 | an-277 | 1U3293 | sp-9 | an-277 | 1C3293 | sp-9 | an-277 |
| 1A3294 | sp-9 | an-278 | 1U3294 | sp-9 | an-278 | 1C3294 | sp-9 | an-278 |
| 1A3295 | sp-9 | an-279 | 1U3295 | sp-9 | an-279 | 1C3295 | sp-9 | an-279 |
| 1A3296 | sp-9 | an-280 | 1U3296 | sp-9 | an-280 | 1C3296 | sp-9 | an-280 |
| 1A3297 | sp-9 | an-281 | 1U3297 | sp-9 | an-281 | 1C3297 | sp-9 | an-281 |
| 1A3298 | sp-9 | an-282 | 1U3298 | sp-9 | an-282 | 1C3298 | sp-9 | an-282 |
| 1A3299 | sp-9 | an-283 | 1U3299 | sp-9 | an-283 | 1C3299 | sp-9 | an-283 |
| 1A3300 | sp-9 | an-284 | 1U3300 | sp-9 | an-284 | 1C3300 | sp-9 | an-284 |
| 1A3301 | sp-9 | an-285 | 1U3301 | sp-9 | an-285 | 1C3301 | sp-9 | an-285 |
| 1A3302 | sp-9 | an-286 | 1U3302 | sp-9 | an-286 | 1C3302 | sp-9 | an-286 |
| 1A3303 | sp-9 | an-287 | 1U3303 | sp-9 | an-287 | 1C3303 | sp-9 | an-287 |
| 1A3304 | sp-9 | an-288 | 1U3304 | sp-9 | an-288 | 1C3304 | sp-9 | an-288 |
| 1A3305 | sp-9 | an-289 | 1U3305 | sp-9 | an-289 | 1C3305 | sp-9 | an-289 |
| 1A3306 | sp-9 | an-290 | 1U3306 | sp-9 | an-290 | 1C3306 | sp-9 | an-290 |
| 1A3307 | sp-9 | an-291 | 1U3307 | sp-9 | an-291 | 1C3307 | sp-9 | an-291 |
| 1A3308 | sp-9 | an-292 | 1U3308 | sp-9 | an-292 | 1C3308 | sp-9 | an-292 |
| 1A3309 | sp-9 | an-293 | 1U3309 | sp-9 | an-293 | 1C3309 | sp-9 | an-293 |
| 1A3310 | sp-9 | an-294 | 1U3310 | sp-9 | an-294 | 1C3310 | sp-9 | an-294 |
| 1A3311 | sp-9 | an-295 | 1U3311 | sp-9 | an-295 | 1C3311 | sp-9 | an-295 |
| 1A3312 | sp-9 | an-296 | 1U3312 | sp-9 | an-296 | 1C3312 | sp-9 | an-296 |
| 1A3313 | sp-9 | an-297 | 1U3313 | sp-9 | an-297 | 1C3313 | sp-9 | an-297 |
| 1A3314 | sp-9 | an-298 | 1U3314 | sp-9 | an-298 | 1C3314 | sp-9 | an-298 |
| 1A3315 | sp-9 | an-299 | 1U3315 | sp-9 | an-299 | 1C3315 | sp-9 | an-299 |
| 1A3316 | sp-9 | an-300 | 1U3316 | sp-9 | an-300 | 1C3316 | sp-9 | an-300 |
| 1A3317 | sp-9 | an-301 | 1U3317 | sp-9 | an-301 | 1C3317 | sp-9 | an-301 |
| 1A3318 | sp-9 | an-302 | 1U3318 | sp-9 | an-302 | 1C3318 | sp-9 | an-302 |
| 1A3319 | sp-9 | an-303 | 1U3319 | sp-9 | an-303 | 1C3319 | sp-9 | an-303 |
| 1A3320 | sp-9 | an-304 | 1U3320 | sp-9 | an-304 | 1C3320 | sp-9 | an-304 |
| 1A3321 | sp-9 | an-305 | 1U3321 | sp-9 | an-305 | 1C3321 | sp-9 | an-305 |
| 1A3322 | sp-9 | an-306 | 1U3322 | sp-9 | an-306 | 1C3322 | sp-9 | an-306 |
| 1A3323 | sp-9 | an-307 | 1U3323 | sp-9 | an-307 | 1C3323 | sp-9 | an-307 |
| 1A3324 | sp-9 | an-308 | 1U3324 | sp-9 | an-308 | 1C3324 | sp-9 | an-308 |
| 1A3325 | sp-9 | an-309 | 1U3325 | sp-9 | an-309 | 1C3325 | sp-9 | an-309 |
| 1A3326 | sp-9 | an-310 | 1U3326 | sp-9 | an-310 | 1C3326 | sp-9 | an-310 |
| 1A3327 | sp-9 | an-311 | 1U3327 | sp-9 | an-311 | 1C3327 | sp-9 | an-311 |
| 1A3328 | sp-9 | an-312 | 1U3328 | sp-9 | an-312 | 1C3328 | sp-9 | an-312 |
| 1A3329 | sp-9 | an-313 | 1U3329 | sp-9 | an-313 | 1C3329 | sp-9 | an-313 |
| 1A3330 | sp-9 | an-314 | 1U3330 | sp-9 | an-314 | 1C3330 | sp-9 | an-314 |
| 1A3331 | sp-9 | an-315 | 1U3331 | sp-9 | an-315 | 1C3331 | sp-9 | an-315 |
| 1A3332 | sp-9 | an-316 | 1U3332 | sp-9 | an-316 | 1C3332 | sp-9 | an-316 |
| 1A3333 | sp-9 | an-317 | 1U3333 | sp-9 | an-317 | 1C3333 | sp-9 | an-317 |
| 1A3334 | sp-9 | an-318 | 1U3334 | sp-9 | an-318 | 1C3334 | sp-9 | an-318 |
| 1A3335 | sp-9 | an-319 | 1U3335 | sp-9 | an-319 | 1C3335 | sp-9 | an-319 |

TABLE 1-continued

| | | | | | | | | |
|---|---|---|---|---|---|---|---|---|
| 1A3336 | sp-9 | an-320 | 1U3336 | sp-9 | an-320 | 1C3336 | sp-9 | an-320 |
| 1A3337 | sp-9 | an-321 | 1U3337 | sp-9 | an-321 | 1C3337 | sp-9 | an-321 |
| 1A3338 | sp-9 | an-322 | 1U3338 | sp-9 | an-322 | 1C3338 | sp-9 | an-322 |
| 1A3339 | sp-9 | an-323 | 1U3339 | sp-9 | an-323 | 1C3339 | sp-9 | an-323 |
| 1A3340 | sp-9 | an-324 | 1U3340 | sp-9 | an-324 | 1C3340 | sp-9 | an-324 |
| 1A3341 | sp-9 | an-325 | 1U3341 | sp-9 | an-325 | 1C3341 | sp-9 | an-325 |
| 1A3342 | sp-9 | an-326 | 1U3342 | sp-9 | an-326 | 1C3342 | sp-9 | an-326 |
| 1A3343 | sp-9 | an-327 | 1U3343 | sp-9 | an-327 | 1C3343 | sp-9 | an-327 |
| 1A3344 | sp-9 | an-328 | 1U3344 | sp-9 | an-328 | 1C3344 | sp-9 | an-328 |
| 1A3345 | sp-9 | an-329 | 1U3345 | sp-9 | an-329 | 1C3345 | sp-9 | an-329 |
| 1A3346 | sp-9 | an-330 | 1U3346 | sp-9 | an-330 | 1C3346 | sp-9 | an-330 |
| 1A3347 | sp-9 | an-331 | 1U3347 | sp-9 | an-331 | 1C3347 | sp-9 | an-331 |
| 1A3348 | sp-9 | an-332 | 1U3348 | sp-9 | an-332 | 1C3348 | sp-9 | an-332 |
| 1A3349 | sp-9 | an-333 | 1U3349 | sp-9 | an-333 | 1C3349 | sp-9 | an-333 |
| 1A3350 | sp-9 | an-334 | 1U3350 | sp-9 | an-334 | 1C3350 | sp-9 | an-334 |
| 1A3351 | sp-9 | an-335 | 1U3351 | sp-9 | an-335 | 1C3351 | sp-9 | an-335 |
| 1A3352 | sp-9 | an-336 | 1U3352 | sp-9 | an-336 | 1C3352 | sp-9 | an-336 |
| 1A3353 | sp-9 | an-337 | 1U3353 | sp-9 | an-337 | 1C3353 | sp-9 | an-337 |
| 1A3354 | sp-9 | an-338 | 1U3354 | sp-9 | an-338 | 1C3354 | sp-9 | an-338 |
| 1A3355 | sp-9 | an-339 | 1U3355 | sp-9 | an-339 | 1C3355 | sp-9 | an-339 |
| 1A3356 | sp-9 | an-340 | 1U3356 | sp-9 | an-340 | 1C3356 | sp-9 | an-340 |
| 1A3357 | sp-9 | an-341 | 1U3357 | sp-9 | an-341 | 1C3357 | sp-9 | an-341 |
| 1A3358 | sp-9 | an-342 | 1U3358 | sp-9 | an-342 | 1C3358 | sp-9 | an-342 |
| 1A3359 | sp-9 | an-343 | 1U3359 | sp-9 | an-343 | 1C3359 | sp-9 | an-343 |
| 1A3360 | sp-9 | an-344 | 1U3360 | sp-9 | an-344 | 1C3360 | sp-9 | an-344 |
| 1A3361 | sp-9 | an-345 | 1U3361 | sp-9 | an-345 | 1C3361 | sp-9 | an-345 |
| 1A3362 | sp-9 | an-346 | 1U3362 | sp-9 | an-346 | 1C3362 | sp-9 | an-346 |
| 1A3363 | sp-9 | an-347 | 1U3363 | sp-9 | an-347 | 1C3363 | sp-9 | an-347 |
| 1A3364 | sp-9 | an-348 | 1U3364 | sp-9 | an-348 | 1C3364 | sp-9 | an-348 |
| 1A3365 | sp-9 | an-349 | 1U3365 | sp-9 | an-349 | 1C3365 | sp-9 | an-349 |
| 1A3366 | sp-9 | an-350 | 1U3366 | sp-9 | an-350 | 1C3366 | sp-9 | an-350 |
| 1A3367 | sp-9 | an-351 | 1U3367 | sp-9 | an-351 | 1C3367 | sp-9 | an-351 |
| 1A3368 | sp-9 | an-352 | 1U3368 | sp-9 | an-352 | 1C3368 | sp-9 | an-352 |
| 1A3369 | sp-9 | an-353 | 1U3369 | sp-9 | an-353 | 1C3369 | sp-9 | an-353 |
| 1A3370 | sp-9 | an-354 | 1U3370 | sp-9 | an-354 | 1C3370 | sp-9 | an-354 |
| 1A3371 | sp-9 | an-355 | 1U3371 | sp-9 | an-355 | 1C3371 | sp-9 | an-355 |
| 1A3372 | sp-9 | an-356 | 1U3372 | sp-9 | an-356 | 1C3372 | sp-9 | an-356 |
| 1A3373 | sp-9 | an-357 | 1U3373 | sp-9 | an-357 | 1C3373 | sp-9 | an-357 |
| 1A3374 | sp-9 | an-358 | 1U3374 | sp-9 | an-358 | 1C3374 | sp-9 | an-358 |
| 1A3375 | sp-9 | an-359 | 1U3375 | sp-9 | an-359 | 1C3375 | sp-9 | an-359 |
| 1A3376 | sp-9 | an-360 | 1U3376 | sp-9 | an-360 | 1C3376 | sp-9 | an-360 |
| 1A3377 | sp-9 | an-361 | 1U3377 | sp-9 | an-361 | 1C3377 | sp-9 | an-361 |
| 1A3378 | sp-9 | an-362 | 1U3378 | sp-9 | an-362 | 1C3378 | sp-9 | an-362 |
| 1A3379 | sp-9 | an-363 | 1U3379 | sp-9 | an-363 | 1C3379 | sp-9 | an-363 |
| 1A3380 | sp-9 | an-364 | 1U3380 | sp-9 | an-364 | 1C3380 | sp-9 | an-364 |
| 1A3381 | sp-9 | an-365 | 1U3381 | sp-9 | an-365 | 1C3381 | sp-9 | an-365 |
| 1A3382 | sp-9 | an-366 | 1U3382 | sp-9 | an-366 | 1C3382 | sp-9 | an-366 |
| 1A3383 | sp-9 | an-367 | 1U3383 | sp-9 | an-367 | 1C3383 | sp-9 | an-367 |
| 1A3384 | sp-9 | an-368 | 1U3384 | sp-9 | an-368 | 1C3384 | sp-9 | an-368 |
| 1A3385 | sp-9 | an-369 | 1U3385 | sp-9 | an-369 | 1C3385 | sp-9 | an-369 |
| 1A3386 | sp-9 | an-370 | 1U3386 | sp-9 | an-370 | 1C3386 | sp-9 | an-370 |
| 1A3387 | sp-9 | an-371 | 1U3387 | sp-9 | an-371 | 1C3387 | sp-9 | an-371 |
| 1A3388 | sp-9 | an-372 | 1U3388 | sp-9 | an-372 | 1C3388 | sp-9 | an-372 |
| 1A3389 | sp-9 | an-373 | 1U3389 | sp-9 | an-373 | 1C3389 | sp-9 | an-373 |
| 1A3390 | sp-9 | an-374 | 1U3390 | sp-9 | an-374 | 1C3390 | sp-9 | an-374 |
| 1A3391 | sp-9 | an-375 | 1U3391 | sp-9 | an-375 | 1C3391 | sp-9 | an-375 |
| 1A3392 | sp-9 | an-376 | 1U3392 | sp-9 | an-376 | 1C3392 | sp-9 | an-376 |
| 1A3393 | sp-9 | an-377 | 1U3393 | sp-9 | an-377 | 1C3393 | sp-9 | an-377 |
| 1A3394 | sp-10 | an-1 | 1U3394 | sp-12 | an-1 | 1C3394 | sp-11 | an-1 |
| 1A3395 | sp-10 | an-2 | 1U3395 | sp-12 | an-2 | 1C3395 | sp-11 | an-2 |
| 1A3396 | sp-10 | an-3 | 1U3396 | sp-12 | an-3 | 1C3396 | sp-11 | an-3 |
| 1A3397 | sp-10 | an-4 | 1U3397 | sp-12 | an-4 | 1C3397 | sp-11 | an-4 |
| 1A3398 | sp-10 | an-5 | 1U3398 | sp-12 | an-5 | 1C3398 | sp-11 | an-5 |
| 1A3399 | sp-10 | an-6 | 1U3399 | sp-12 | an-6 | 1C3399 | sp-11 | an-6 |
| 1A3400 | sp-10 | an-7 | 1U3400 | sp-12 | an-7 | 1C3400 | sp-11 | an-7 |
| 1A3401 | sp-10 | an-8 | 1U3401 | sp-12 | an-8 | 1C3401 | sp-11 | an-8 |
| 1A3402 | sp-10 | an-9 | 1U3402 | sp-12 | an-9 | 1C3402 | sp-11 | an-9 |
| 1A3403 | sp-10 | an-10 | 1U3403 | sp-12 | an-10 | 1C3403 | sp-11 | an-10 |
| 1A3404 | sp-10 | an-11 | 1U3404 | sp-12 | an-11 | 1C3404 | sp-11 | an-11 |
| 1A3405 | sp-10 | an-12 | 1U3405 | sp-12 | an-12 | 1C3405 | sp-11 | an-12 |
| 1A3406 | sp-10 | an-13 | 1U3406 | sp-12 | an-13 | 1C3406 | sp-11 | an-13 |
| 1A3407 | sp-10 | an-14 | 1U3407 | sp-12 | an-14 | 1C3407 | sp-11 | an-14 |
| 1A3408 | sp-10 | an-15 | 1U3408 | sp-12 | an-15 | 1C3408 | sp-11 | an-15 |
| 1A3409 | sp-10 | an-16 | 1U3409 | sp-12 | an-16 | 1C3409 | sp-11 | an-16 |
| 1A3410 | sp-10 | an-17 | 1U3410 | sp-12 | an-17 | 1C3410 | sp-11 | an-17 |
| 1A3411 | sp-10 | an-18 | 1U3411 | sp-12 | an-18 | 1C3411 | sp-11 | an-18 |
| 1A3412 | sp-10 | an-19 | 1U3412 | sp-12 | an-19 | 1C3412 | sp-11 | an-19 |
| 1A3413 | sp-10 | an-20 | 1U3413 | sp-12 | an-20 | 1C3413 | sp-11 | an-20 |
| 1A3414 | sp-10 | an-21 | 1U3414 | sp-12 | an-21 | 1C3414 | sp-11 | an-21 |

TABLE 1-continued

| | | | | | | | | |
|---|---|---|---|---|---|---|---|---|
| 1A3415 | sp-10 | an-22 | 1U3415 | sp-12 | an-22 | 1C3415 | sp-11 | an-22 |
| 1A3416 | sp-10 | an-23 | 1U3416 | sp-12 | an-23 | 1C3416 | sp-11 | an-23 |
| 1A3417 | sp-10 | an-24 | 1U3417 | sp-12 | an-24 | 1C3417 | sp-11 | an-24 |
| 1A3418 | sp-10 | an-25 | 1U3418 | sp-12 | an-25 | 1C3418 | sp-11 | an-25 |
| 1A3419 | sp-10 | an-26 | 1U3419 | sp-12 | an-26 | 1C3419 | sp-11 | an-26 |
| 1A3420 | sp-10 | an-27 | 1U3420 | sp-12 | an-27 | 1C3420 | sp-11 | an-27 |
| 1A3421 | sp-10 | an-28 | 1U3421 | sp-12 | an-28 | 1C3421 | sp-11 | an-28 |
| 1A3422 | sp-10 | an-29 | 1U3422 | sp-12 | an-29 | 1C3422 | sp-11 | an-29 |
| 1A3423 | sp-10 | an-30 | 1U3423 | sp-12 | an-30 | 1C3423 | sp-11 | an-30 |
| 1A3424 | sp-10 | an-31 | 1U3424 | sp-12 | an-31 | 1C3424 | sp-11 | an-31 |
| 1A3425 | sp-10 | an-32 | 1U3425 | sp-12 | an-32 | 1C3425 | sp-11 | an-32 |
| 1A3426 | sp-10 | an-33 | 1U3426 | sp-12 | an-33 | 1C3426 | sp-11 | an-33 |
| 1A3427 | sp-10 | an-34 | 1U3427 | sp-12 | an-34 | 1C3427 | sp-11 | an-34 |
| 1A3428 | sp-10 | an-35 | 1U3428 | sp-12 | an-35 | 1C3428 | sp-11 | an-35 |
| 1A3429 | sp-10 | an-36 | 1U3429 | sp-12 | an-36 | 1C3429 | sp-11 | an-36 |
| 1A3430 | sp-10 | an-37 | 1U3430 | sp-12 | an-37 | 1C3430 | sp-11 | an-37 |
| 1A3431 | sp-10 | an-38 | 1U3431 | sp-12 | an-38 | 1C3431 | sp-11 | an-38 |
| 1A3432 | sp-10 | an-39 | 1U3432 | sp-12 | an-39 | 1C3432 | sp-11 | an-39 |
| 1A3433 | sp-10 | an-40 | 1U3433 | sp-12 | an-40 | 1C3433 | sp-11 | an-40 |
| 1A3434 | sp-10 | an-41 | 1U3434 | sp-12 | an-41 | 1C3434 | sp-11 | an-41 |
| 1A3435 | sp-10 | an-42 | 1U3435 | sp-12 | an-42 | 1C3435 | sp-11 | an-42 |
| 1A3436 | sp-10 | an-43 | 1U3436 | sp-12 | an-43 | 1C3436 | sp-11 | an-43 |
| 1A3437 | sp-10 | an-44 | 1U3437 | sp-12 | an-44 | 1C3437 | sp-11 | an-44 |
| 1A3438 | sp-10 | an-45 | 1U3438 | sp-12 | an-45 | 1C3438 | sp-11 | an-45 |
| 1A3439 | sp-10 | an-46 | 1U3439 | sp-12 | an-46 | 1C3439 | sp-11 | an-46 |
| 1A3440 | sp-10 | an-47 | 1U3440 | sp-12 | an-47 | 1C3440 | sp-11 | an-47 |
| 1A3441 | sp-10 | an-48 | 1U3441 | sp-12 | an-48 | 1C3441 | sp-11 | an-48 |
| 1A3442 | sp-10 | an-49 | 1U3442 | sp-12 | an-49 | 1C3442 | sp-11 | an-49 |
| 1A3443 | sp-10 | an-50 | 1U3443 | sp-12 | an-50 | 1C3443 | sp-11 | an-50 |
| 1A3444 | sp-10 | an-51 | 1U3444 | sp-12 | an-51 | 1C3444 | sp-11 | an-51 |
| 1A3445 | sp-10 | an-52 | 1U3445 | sp-12 | an-52 | 1C3445 | sp-11 | an-52 |
| 1A3446 | sp-10 | an-53 | 1U3446 | sp-12 | an-53 | 1C3446 | sp-11 | an-53 |
| 1A3447 | sp-10 | an-54 | 1U3447 | sp-12 | an-54 | 1C3447 | sp-11 | an-54 |
| 1A3448 | sp-10 | an-55 | 1U3448 | sp-12 | an-55 | 1C3448 | sp-11 | an-55 |
| 1A3449 | sp-10 | an-56 | 1U3449 | sp-12 | an-56 | 1C3449 | sp-11 | an-56 |
| 1A3450 | sp-10 | an-57 | 1U3450 | sp-12 | an-57 | 1C3450 | sp-11 | an-57 |
| 1A3451 | sp-10 | an-58 | 1U3451 | sp-12 | an-58 | 1C3451 | sp-11 | an-58 |
| 1A3452 | sp-10 | an-59 | 1U3452 | sp-12 | an-59 | 1C3452 | sp-11 | an-59 |
| 1A3453 | sp-10 | an-60 | 1U3453 | sp-12 | an-60 | 1C3453 | sp-11 | an-60 |
| 1A3454 | sp-10 | an-61 | 1U3454 | sp-12 | an-61 | 1C3454 | sp-11 | an-61 |
| 1A3455 | sp-10 | an-62 | 1U3455 | sp-12 | an-62 | 1C3455 | sp-11 | an-62 |
| 1A3456 | sp-10 | an-63 | 1U3456 | sp-12 | an-63 | 1C3456 | sp-11 | an-63 |
| 1A3457 | sp-10 | an-64 | 1U3457 | sp-12 | an-64 | 1C3457 | sp-11 | an-64 |
| 1A3458 | sp-10 | an-65 | 1U3458 | sp-12 | an-65 | 1C3458 | sp-11 | an-65 |
| 1A3459 | sp-10 | an-66 | 1U3459 | sp-12 | an-66 | 1C3459 | sp-11 | an-66 |
| 1A3460 | sp-10 | an-67 | 1U3460 | sp-12 | an-67 | 1C3460 | sp-11 | an-67 |
| 1A3461 | sp-10 | an-68 | 1U3461 | sp-12 | an-68 | 1C3461 | sp-11 | an-68 |
| 1A3462 | sp-10 | an-69 | 1U3462 | sp-12 | an-69 | 1C3462 | sp-11 | an-69 |
| 1A3463 | sp-10 | an-70 | 1U3463 | sp-12 | an-70 | 1C3463 | sp-11 | an-70 |
| 1A3464 | sp-10 | an-71 | 1U3464 | sp-12 | an-71 | 1C3464 | sp-11 | an-71 |
| 1A3465 | sp-10 | an-72 | 1U3465 | sp-12 | an-72 | 1C3465 | sp-11 | an-72 |
| 1A3466 | sp-10 | an-73 | 1U3466 | sp-12 | an-73 | 1C3466 | sp-11 | an-73 |
| 1A3467 | sp-10 | an-74 | 1U3467 | sp-12 | an-74 | 1C3467 | sp-11 | an-74 |
| 1A3468 | sp-10 | an-75 | 1U3468 | sp-12 | an-75 | 1C3468 | sp-11 | an-75 |
| 1A3469 | sp-10 | an-76 | 1U3469 | sp-12 | an-76 | 1C3469 | sp-11 | an-76 |
| 1A3470 | sp-10 | an-77 | 1U3470 | sp-12 | an-77 | 1C3470 | sp-11 | an-77 |
| 1A3471 | sp-10 | an-78 | 1U3471 | sp-12 | an-78 | 1C3471 | sp-11 | an-78 |
| 1A3472 | sp-10 | an-79 | 1U3472 | sp-12 | an-79 | 1C3472 | sp-11 | an-79 |
| 1A3473 | sp-10 | an-80 | 1U3473 | sp-12 | an-80 | 1C3473 | sp-11 | an-80 |
| 1A3474 | sp-10 | an-81 | 1U3474 | sp-12 | an-81 | 1C3474 | sp-11 | an-81 |
| 1A3475 | sp-10 | an-82 | 1U3475 | sp-12 | an-82 | 1C3475 | sp-11 | an-82 |
| 1A3476 | sp-10 | an-83 | 1U3476 | sp-12 | an-83 | 1C3476 | sp-11 | an-83 |
| 1A3477 | sp-10 | an-84 | 1U3477 | sp-12 | an-84 | 1C3477 | sp-11 | an-84 |
| 1A3478 | sp-10 | an-85 | 1U3478 | sp-12 | an-85 | 1C3478 | sp-11 | an-85 |
| 1A3479 | sp-10 | an-86 | 1U3479 | sp-12 | an-86 | 1C3479 | sp-11 | an-86 |
| 1A3480 | sp-10 | an-87 | 1U3480 | sp-12 | an-87 | 1C3480 | sp-11 | an-87 |
| 1A3481 | sp-10 | an-88 | 1U3481 | sp-12 | an-88 | 1C3481 | sp-11 | an-88 |
| 1A3482 | sp-10 | an-89 | 1U3482 | sp-12 | an-89 | 1C3482 | sp-11 | an-89 |
| 1A3483 | sp-10 | an-90 | 1U3483 | sp-12 | an-90 | 1C3483 | sp-11 | an-90 |
| 1A3484 | sp-10 | an-91 | 1U3484 | sp-12 | an-91 | 1C3484 | sp-11 | an-91 |
| 1A3485 | sp-10 | an-92 | 1U3485 | sp-12 | an-92 | 1C3485 | sp-11 | an-92 |
| 1A3486 | sp-10 | an-93 | 1U3486 | sp-12 | an-93 | 1C3486 | sp-11 | an-93 |
| 1A3487 | sp-10 | an-94 | 1U3487 | sp-12 | an-94 | 1C3487 | sp-11 | an-94 |
| 1A3488 | sp-10 | an-95 | 1U3488 | sp-12 | an-95 | 1C3488 | sp-11 | an-95 |
| 1A3489 | sp-10 | an-96 | 1U3489 | sp-12 | an-96 | 1C3489 | sp-11 | an-96 |
| 1A3490 | sp-10 | an-97 | 1U3490 | sp-12 | an-97 | 1C3490 | sp-11 | an-97 |
| 1A3491 | sp-10 | an-98 | 1U3491 | sp-12 | an-98 | 1C3491 | sp-11 | an-98 |
| 1A3492 | sp-10 | an-99 | 1U3492 | sp-12 | an-99 | 1C3492 | sp-11 | an-99 |
| 1A3493 | sp-10 | an-100 | 1U3493 | sp-12 | an-100 | 1C3493 | sp-11 | an-100 |

TABLE 1-continued

| | | | | | | | | |
|---|---|---|---|---|---|---|---|---|
| 1A3494 | sp-10 | an-101 | 1U3494 | sp-12 | an-101 | 1C3494 | sp-11 | an-101 |
| 1A3495 | sp-10 | an-102 | 1U3495 | sp-12 | an-102 | 1C3495 | sp-11 | an-102 |
| 1A3496 | sp-10 | an-103 | 1U3496 | sp-12 | an-103 | 1C3496 | sp-11 | an-103 |
| 1A3497 | sp-10 | an-104 | 1U3497 | sp-12 | an-104 | 1C3497 | sp-11 | an-104 |
| 1A3498 | sp-10 | an-105 | 1U3498 | sp-12 | an-105 | 1C3498 | sp-11 | an-105 |
| 1A3499 | sp-10 | an-106 | 1U3499 | sp-12 | an-106 | 1C3499 | sp-11 | an-106 |
| 1A3500 | sp-10 | an-107 | 1U3500 | sp-12 | an-107 | 1C3500 | sp-11 | an-107 |
| 1A3501 | sp-10 | an-108 | 1U3501 | sp-12 | an-108 | 1C3501 | sp-11 | an-108 |
| 1A3502 | sp-10 | an-109 | 1U3502 | sp-12 | an-109 | 1C3502 | sp-11 | an-109 |
| 1A3503 | sp-10 | an-110 | 1U3503 | sp-12 | an-110 | 1C3503 | sp-11 | an-110 |
| 1A3504 | sp-10 | an-111 | 1U3504 | sp-12 | an-111 | 1C3504 | sp-11 | an-111 |
| 1A3505 | sp-10 | an-112 | 1U3505 | sp-12 | an-112 | 1C3505 | sp-11 | an-112 |
| 1A3506 | sp-10 | an-113 | 1U3506 | sp-12 | an-113 | 1C3506 | sp-11 | an-113 |
| 1A3507 | sp-10 | an-114 | 1U3507 | sp-12 | an-114 | 1C3507 | sp-11 | an-114 |
| 1A3508 | sp-10 | an-115 | 1U3508 | sp-12 | an-115 | 1C3508 | sp-11 | an-115 |
| 1A3509 | sp-10 | an-116 | 1U3509 | sp-12 | an-116 | 1C3509 | sp-11 | an-116 |
| 1A3510 | sp-10 | an-117 | 1U3510 | sp-12 | an-117 | 1C3510 | sp-11 | an-117 |
| 1A3511 | sp-10 | an-118 | 1U3511 | sp-12 | an-118 | 1C3511 | sp-11 | an-118 |
| 1A3512 | sp-10 | an-119 | 1U3512 | sp-12 | an-119 | 1C3512 | sp-11 | an-119 |
| 1A3513 | sp-10 | an-120 | 1U3513 | sp-12 | an-120 | 1C3513 | sp-11 | an-120 |
| 1A3514 | sp-10 | an-121 | 1U3514 | sp-12 | an-121 | 1C3514 | sp-11 | an-121 |
| 1A3515 | sp-10 | an-122 | 1U3515 | sp-12 | an-122 | 1C3515 | sp-11 | an-122 |
| 1A3516 | sp-10 | an-123 | 1U3516 | sp-12 | an-123 | 1C3516 | sp-11 | an-123 |
| 1A3517 | sp-10 | an-124 | 1U3517 | sp-12 | an-124 | 1C3517 | sp-11 | an-124 |
| 1A3518 | sp-10 | an-125 | 1U3518 | sp-12 | an-125 | 1C3518 | sp-11 | an-125 |
| 1A3519 | sp-10 | an-126 | 1U3519 | sp-12 | an-126 | 1C3519 | sp-11 | an-126 |
| 1A3520 | sp-10 | an-127 | 1U3520 | sp-12 | an-127 | 1C3520 | sp-11 | an-127 |
| 1A3521 | sp-10 | an-128 | 1U3521 | sp-12 | an-128 | 1C3521 | sp-11 | an-128 |
| 1A3522 | sp-10 | an-129 | 1U3522 | sp-12 | an-129 | 1C3522 | sp-11 | an-129 |
| 1A3523 | sp-10 | an-130 | 1U3523 | sp-12 | an-130 | 1C3523 | sp-11 | an-130 |
| 1A3524 | sp-10 | an-131 | 1U3524 | sp-12 | an-131 | 1C3524 | sp-11 | an-131 |
| 1A3525 | sp-10 | an-132 | 1U3525 | sp-12 | an-132 | 1C3525 | sp-11 | an-132 |
| 1A3526 | sp-10 | an-133 | 1U3526 | sp-12 | an-133 | 1C3526 | sp-11 | an-133 |
| 1A3527 | sp-10 | an-134 | 1U3527 | sp-12 | an-134 | 1C3527 | sp-11 | an-134 |
| 1A3528 | sp-10 | an-135 | 1U3528 | sp-12 | an-135 | 1C3528 | sp-11 | an-135 |
| 1A3529 | sp-10 | an-136 | 1U3529 | sp-12 | an-136 | 1C3529 | sp-11 | an-136 |
| 1A3530 | sp-10 | an-137 | 1U3530 | sp-12 | an-137 | 1C3530 | sp-11 | an-137 |
| 1A3531 | sp-10 | an-138 | 1U3531 | sp-12 | an-138 | 1C3531 | sp-11 | an-138 |
| 1A3532 | sp-10 | an-139 | 1U3532 | sp-12 | an-139 | 1C3532 | sp-11 | an-139 |
| 1A3533 | sp-10 | an-140 | 1U3533 | sp-12 | an-140 | 1C3533 | sp-11 | an-140 |
| 1A3534 | sp-10 | an-141 | 1U3534 | sp-12 | an-141 | 1C3534 | sp-11 | an-141 |
| 1A3535 | sp-10 | an-142 | 1U3535 | sp-12 | an-142 | 1C3535 | sp-11 | an-142 |
| 1A3536 | sp-10 | an-143 | 1U3536 | sp-12 | an-143 | 1C3536 | sp-11 | an-143 |
| 1A3537 | sp-10 | an-144 | 1U3537 | sp-12 | an-144 | 1C3537 | sp-11 | an-144 |
| 1A3538 | sp-10 | an-145 | 1U3538 | sp-12 | an-145 | 1C3538 | sp-11 | an-145 |
| 1A3539 | sp-10 | an-146 | 1U3539 | sp-12 | an-146 | 1C3539 | sp-11 | an-146 |
| 1A3540 | sp-10 | an-147 | 1U3540 | sp-12 | an-147 | 1C3540 | sp-11 | an-147 |
| 1A3541 | sp-10 | an-148 | 1U3541 | sp-12 | an-148 | 1C3541 | sp-11 | an-148 |
| 1A3542 | sp-10 | an-149 | 1U3542 | sp-12 | an-149 | 1C3542 | sp-11 | an-149 |
| 1A3543 | sp-10 | an-150 | 1U3543 | sp-12 | an-150 | 1C3543 | sp-11 | an-150 |
| 1A3544 | sp-10 | an-151 | 1U3544 | sp-12 | an-151 | 1C3544 | sp-11 | an-151 |
| 1A3545 | sp-10 | an-152 | 1U3545 | sp-12 | an-152 | 1C3545 | sp-11 | an-152 |
| 1A3546 | sp-10 | an-153 | 1U3546 | sp-12 | an-153 | 1C3546 | sp-11 | an-153 |
| 1A3547 | sp-10 | an-154 | 1U3547 | sp-12 | an-154 | 1C3547 | sp-11 | an-154 |
| 1A3548 | sp-10 | an-155 | 1U3548 | sp-12 | an-155 | 1C3548 | sp-11 | an-155 |
| 1A3549 | sp-10 | an-156 | 1U3549 | sp-12 | an-156 | 1C3549 | sp-11 | an-156 |
| 1A3550 | sp-10 | an-157 | 1U3550 | sp-12 | an-157 | 1C3550 | sp-11 | an-157 |
| 1A3551 | sp-10 | an-158 | 1U3551 | sp-12 | an-158 | 1C3551 | sp-11 | an-158 |
| 1A3552 | sp-10 | an-159 | 1U3552 | sp-12 | an-159 | 1C3552 | sp-11 | an-159 |
| 1A3553 | sp-10 | an-160 | 1U3553 | sp-12 | an-160 | 1C3553 | sp-11 | an-160 |
| 1A3554 | sp-10 | an-161 | 1U3554 | sp-12 | an-161 | 1C3554 | sp-11 | an-161 |
| 1A3555 | sp-10 | an-162 | 1U3555 | sp-12 | an-162 | 1C3555 | sp-11 | an-162 |
| 1A3556 | sp-10 | an-163 | 1U3556 | sp-12 | an-163 | 1C3556 | sp-11 | an-163 |
| 1A3557 | sp-10 | an-164 | 1U3557 | sp-12 | an-164 | 1C3557 | sp-11 | an-164 |
| 1A3558 | sp-10 | an-165 | 1U3558 | sp-12 | an-165 | 1C3558 | sp-11 | an-165 |
| 1A3559 | sp-10 | an-166 | 1U3559 | sp-12 | an-166 | 1C3559 | sp-11 | an-166 |
| 1A3560 | sp-10 | an-167 | 1U3560 | sp-12 | an-167 | 1C3560 | sp-11 | an-167 |
| 1A3561 | sp-10 | an-168 | 1U3561 | sp-12 | an-168 | 1C3561 | sp-11 | an-168 |
| 1A3562 | sp-10 | an-169 | 1U3562 | sp-12 | an-169 | 1C3562 | sp-11 | an-169 |
| 1A3563 | sp-10 | an-170 | 1U3563 | sp-12 | an-170 | 1C3563 | sp-11 | an-170 |
| 1A3564 | sp-10 | an-171 | 1U3564 | sp-12 | an-171 | 1C3564 | sp-11 | an-171 |
| 1A3565 | sp-10 | an-172 | 1U3565 | sp-12 | an-172 | 1G3565 | sp-11 | an-172 |
| 1A3566 | sp-10 | an-173 | 1U3566 | sp-12 | an-173 | 1C3566 | sp-11 | an-173 |
| 1A3567 | sp-10 | an-174 | 1U3567 | sp-12 | an-174 | 1C3567 | sp-11 | an-174 |
| 1A3568 | sp-10 | an-175 | 1U3568 | sp-12 | an-175 | 1C3568 | sp-11 | an-175 |
| 1A3569 | sp-10 | an-176 | 1U3569 | sp-12 | an-176 | 1C3569 | sp-11 | an-176 |
| 1A3570 | sp-10 | an-177 | 1U3570 | sp-12 | an-177 | 1C3570 | sp-11 | an-177 |
| 1A3571 | sp-10 | an-178 | 1U3571 | sp-12 | an-178 | 1C3571 | sp-11 | an-178 |
| 1A3572 | sp-10 | an-179 | 1U3572 | sp-12 | an-179 | 1C3572 | sp-11 | an-179 |

TABLE 1-continued

| | | | | | | | | |
|---|---|---|---|---|---|---|---|---|
| 1A3573 | sp-10 | an-180 | 1U3573 | sp-12 | an-180 | 1C3573 | sp-11 | an-180 |
| 1A3574 | sp-10 | an-181 | 1U3574 | sp-12 | an-181 | 1C3574 | sp-11 | an-181 |
| 1A3575 | sp-10 | an-182 | 1U3575 | sp-12 | an-182 | 1C3575 | sp-11 | an-182 |
| 1A3576 | sp-10 | an-183 | 1U3576 | sp-12 | an-183 | 1C3576 | sp-11 | an-183 |
| 1A3577 | sp-10 | an-184 | 1U3577 | sp-12 | an-184 | 1C3577 | sp-11 | an-184 |
| 1A3578 | sp-10 | an-185 | 1U3578 | sp-12 | an-185 | 1C3578 | sp-11 | an-185 |
| 1A3579 | sp-10 | an-186 | 1U3579 | sp-12 | an-186 | 1C3579 | sp-11 | an-186 |
| 1A3580 | sp-10 | an-187 | 1U3580 | sp-12 | an-187 | 1C3580 | sp-11 | an-187 |
| 1A3581 | sp-10 | an-188 | 1U3581 | sp-12 | an-188 | 1C3581 | sp-11 | an-188 |
| 1A3582 | sp-10 | an-189 | 1U3582 | sp-12 | an-189 | 1C3582 | sp-11 | an-189 |
| 1A3583 | sp-10 | an-190 | 1U3583 | sp-12 | an-190 | 1C3583 | sp-11 | an-190 |
| 1A3584 | sp-10 | an-191 | 1U3584 | sp-12 | an-191 | 1C3584 | sp-11 | an-191 |
| 1A3585 | sp-10 | an-192 | 1U3585 | sp-12 | an-192 | 1C3585 | sp-11 | an-192 |
| 1A3586 | sp-10 | an-193 | 1U3586 | sp-12 | an-193 | 1C3586 | sp-11 | an-193 |
| 1A3587 | sp-10 | an-194 | 1U3587 | sp-12 | an-194 | 1C3587 | sp-11 | an-194 |
| 1A3588 | sp-10 | an-195 | 1U3588 | sp-12 | an-195 | 1C3588 | sp-11 | an-195 |
| 1A3589 | sp-10 | an-196 | 1U3589 | sp-12 | an-196 | 1C3589 | sp-11 | an-196 |
| 1A3590 | sp-10 | an-197 | 1U3590 | sp-12 | an-197 | 1C3590 | sp-11 | an-197 |
| 1A3591 | sp-10 | an-198 | 1U3591 | sp-12 | an-198 | 1C3591 | sp-11 | an-198 |
| 1A3592 | sp-10 | an-199 | 1U3592 | sp-12 | an-199 | 1C3592 | sp-11 | an-199 |
| 1A3593 | sp-10 | an-200 | 1U3593 | sp-12 | an-200 | 1C3593 | sp-11 | an-200 |
| 1A3594 | sp-10 | an-201 | 1U3594 | sp-12 | an-201 | 1C3594 | sp-11 | an-201 |
| 1A3595 | sp-10 | an-202 | 1U3595 | sp-12 | an-202 | 1C3595 | sp-11 | an-202 |
| 1A3596 | sp-10 | an-203 | 1U3596 | sp-12 | an-203 | 1C3596 | sp-11 | an-203 |
| 1A3597 | sp-10 | an-204 | 1U3597 | sp-12 | an-204 | 1C3597 | sp-11 | an-204 |
| 1A3598 | sp-10 | an-205 | 1U3598 | sp-12 | an-205 | 1C3598 | sp-11 | an-205 |
| 1A3599 | sp-10 | an-206 | 1U3599 | sp-12 | an-206 | 1C3599 | sp-11 | an-206 |
| 1A3600 | sp-10 | an-207 | 1U3600 | sp-12 | an-207 | 1C3600 | sp-11 | an-207 |
| 1A3601 | sp-10 | an-208 | 1U3601 | sp-12 | an-208 | 1C3601 | sp-11 | an-208 |
| 1A3602 | sp-10 | an-209 | 1U3602 | sp-12 | an-209 | 1C3602 | sp-11 | an-209 |
| 1A3603 | sp-10 | an-210 | 1U3603 | sp-12 | an-210 | 1C3603 | sp-11 | an-210 |
| 1A3604 | sp-10 | an-211 | 1U3604 | sp-12 | an-211 | 1C3604 | sp-11 | an-211 |
| 1A3605 | sp-10 | an-212 | 1U3605 | sp-12 | an-212 | 1C3605 | sp-11 | an-212 |
| 1A3606 | sp-10 | an-213 | 1U3606 | sp-12 | an-213 | 1C3606 | sp-11 | an-213 |
| 1A3607 | sp-10 | an-214 | 1U3607 | sp-12 | an-214 | 1C3607 | sp-11 | an-214 |
| 1A3608 | sp-10 | an-215 | 1U3608 | sp-12 | an-215 | 1C3608 | sp-11 | an-215 |
| 1A3609 | sp-10 | an-216 | 1U3609 | sp-12 | an-216 | 1C3609 | sp-11 | an-216 |
| 1A3610 | sp-10 | an-217 | 1U3610 | sp-12 | an-217 | 1C3610 | sp-11 | an-217 |
| 1A3611 | sp-10 | an-218 | 1U3611 | sp-12 | an-218 | 1C3611 | sp-11 | an-218 |
| 1A3612 | sp-10 | an-219 | 1U3612 | sp-12 | an-219 | 1C3612 | sp-11 | an-219 |
| 1A3613 | sp-10 | an-220 | 1U3613 | sp-12 | an-220 | 1C3613 | sp-11 | an-220 |
| 1A3614 | sp-10 | an-221 | 1U3614 | sp-12 | an-221 | 1C3614 | sp-11 | an-221 |
| 1A3615 | sp-10 | an-222 | 1U3615 | sp-12 | an-222 | 1C3615 | sp-11 | an-222 |
| 1A3616 | sp-10 | an-223 | 1U3616 | sp-12 | an-223 | 1C3616 | sp-11 | an-223 |
| 1A3617 | sp-10 | an-224 | 1U3617 | sp-12 | an-224 | 1C3617 | sp-11 | an-224 |
| 1A3618 | sp-10 | an-225 | 1U3618 | sp-12 | an-225 | 1C3618 | sp-11 | an-225 |
| 1A3619 | sp-10 | an-226 | 1U3619 | sp-12 | an-226 | 1C3619 | sp-11 | an-226 |
| 1A3620 | sp-10 | an-227 | 1U3620 | sp-12 | an-227 | 1C3620 | sp-11 | an-227 |
| 1A3621 | sp-10 | an-228 | 1U3621 | sp-12 | an-228 | 1C3621 | sp-11 | an-228 |
| 1A3622 | sp-10 | an-229 | 1U3622 | sp-12 | an-229 | 1C3622 | sp-11 | an-229 |
| 1A3623 | sp-10 | an-230 | 1U3623 | sp-12 | an-230 | 1C3623 | sp-11 | an-230 |
| 1A3624 | sp-10 | an-231 | 1U3624 | sp-12 | an-231 | 1C3624 | sp-11 | an-231 |
| 1A3625 | sp-10 | an-232 | 1U3625 | sp-12 | an-232 | 1C3625 | sp-11 | an-232 |
| 1A3626 | sp-10 | an-233 | 1U3626 | sp-12 | an-233 | 1C3626 | sp-11 | an-233 |
| 1A3627 | sp-10 | an-234 | 1U3627 | sp-12 | an-234 | 1C3627 | sp-11 | an-234 |
| 1A3628 | sp-10 | an-235 | 1U3628 | sp-12 | an-235 | 1C3628 | sp-11 | an-235 |
| 1A3629 | sp-10 | an-236 | 1U3629 | sp-12 | an-236 | 1C3629 | sp-11 | an-236 |
| 1A3630 | sp-10 | an-237 | 1U3630 | sp-12 | an-237 | 1C3630 | sp-11 | an-237 |
| 1A3631 | sp-10 | an-238 | 1U3631 | sp-12 | an-238 | 1C3631 | sp-11 | an-238 |
| 1A3632 | sp-10 | an-239 | 1U3632 | sp-12 | an-239 | 1C3632 | sp-11 | an-239 |
| 1A3633 | sp-10 | an-240 | 1U3633 | sp-12 | an-240 | 1C3633 | sp-11 | an-240 |
| 1A3634 | sp-10 | an-241 | 1U3634 | sp-12 | an-241 | 1C3634 | sp-11 | an-241 |
| 1A3635 | sp-10 | an-242 | 1U3635 | sp-12 | an-242 | 1C3635 | sp-11 | an-242 |
| 1A3636 | sp-10 | an-243 | 1U3636 | sp-12 | an-243 | 1C3636 | sp-11 | an-243 |
| 1A3637 | sp-10 | an-244 | 1U3637 | sp-12 | an-244 | 1C3637 | sp-11 | an-244 |
| 1A3638 | sp-10 | an-245 | 1U3638 | sp-12 | an-245 | 1C3638 | sp-11 | an-245 |
| 1A3639 | sp-10 | an-246 | 1U3639 | sp-12 | an-246 | 1C3639 | sp-11 | an-246 |
| 1A3640 | sp-10 | an-247 | 1U3640 | sp-12 | an-247 | 1C3640 | sp-11 | an-247 |
| 1A3641 | sp-10 | an-248 | 1U3641 | sp-12 | an-248 | 1C3641 | sp-11 | an-248 |
| 1A3642 | sp-10 | an-249 | 1U3642 | sp-12 | an-249 | 1C3642 | sp-11 | an-249 |
| 1A3643 | sp-10 | an-250 | 1U3643 | sp-12 | an-250 | 1C3643 | sp-11 | an-250 |
| 1A3644 | sp-10 | an-251 | 1U3644 | sp-12 | an-251 | 1C3644 | sp-11 | an-251 |
| 1A3645 | sp-10 | an-252 | 1U3645 | sp-12 | an-252 | 1C3645 | sp-11 | an-252 |
| 1A3646 | sp-10 | an-253 | 1U3646 | sp-12 | an-253 | 1C3646 | sp-11 | an-253 |
| 1A3647 | sp-10 | an-254 | 1U3647 | sp-12 | an-254 | 1C3647 | sp-11 | an-254 |
| 1A3648 | sp-10 | an-255 | 1U3648 | sp-12 | an-255 | 1C3648 | sp-11 | an-255 |
| 1A3649 | sp-10 | an-256 | 1U3649 | sp-12 | an-256 | 1C3649 | sp-11 | an-256 |
| 1A3650 | sp-10 | an-257 | 1U3650 | sp-12 | an-257 | 1C3650 | sp-11 | an-257 |
| 1A3651 | sp-10 | an-258 | 1U3651 | sp-12 | an-258 | 1C3651 | sp-11 | an-258 |

TABLE 1-continued

| | | | | | | | | |
|---|---|---|---|---|---|---|---|---|
| 1A3652 | sp-10 | an-259 | 1U3652 | sp-12 | an-259 | 1C3652 | sp-11 | an-259 |
| 1A3653 | sp-10 | an-260 | 1U3653 | sp-12 | an-260 | 1C3653 | sp-11 | an-260 |
| 1A3654 | sp-10 | an-261 | 1U3654 | sp-12 | an-261 | 1C3654 | sp-11 | an-261 |
| 1A3655 | sp-10 | an-262 | 1U3655 | sp-12 | an-262 | 1C3655 | sp-11 | an-262 |
| 1A3656 | sp-10 | an-263 | 1U3656 | sp-12 | an-263 | 1C3656 | sp-11 | an-263 |
| 1A3657 | sp-10 | an-264 | 1U3657 | sp-12 | an-264 | 1C3657 | sp-11 | an-264 |
| 1A3658 | sp-10 | an-265 | 1U3658 | sp-12 | an-265 | 1C3658 | sp-11 | an-265 |
| 1A3659 | sp-10 | an-266 | 1U3659 | sp-12 | an-266 | 1C3659 | sp-11 | an-266 |
| 1A3660 | sp-10 | an-267 | 1U3660 | sp-12 | an-267 | 1C3660 | sp-11 | an-267 |
| 1A3661 | sp-10 | an-268 | 1U3661 | sp-12 | an-268 | 1C3661 | sp-11 | an-268 |
| 1A3662 | sp-10 | an-269 | 1U3662 | sp-12 | an-269 | 1C3662 | sp-11 | an-269 |
| 1A3663 | sp-10 | an-270 | 1U3663 | sp-12 | an-270 | 1C3663 | sp-11 | an-270 |
| 1A3664 | sp-10 | an-271 | 1U3664 | sp-12 | an-271 | 1C3664 | sp-11 | an-271 |
| 1A3665 | sp-10 | an-272 | 1U3665 | sp-12 | an-272 | 1C3665 | sp-11 | an-272 |
| 1A3666 | sp-10 | an-273 | 1U3666 | sp-12 | an-273 | 1C3666 | sp-11 | an-273 |
| 1A3667 | sp-10 | an-274 | 1U3667 | sp-12 | an-274 | 1C3667 | sp-11 | an-274 |
| 1A3668 | sp-10 | an-275 | 1U3668 | sp-12 | an-275 | 1C3668 | sp-11 | an-275 |
| 1A3669 | sp-10 | an-276 | 1U3669 | sp-12 | an-276 | 1C3669 | sp-11 | an-276 |
| 1A3670 | sp-10 | an-277 | 1U3570 | sp-12 | an-277 | 1C3670 | sp-11 | an-277 |
| 1A3671 | sp-10 | an-278 | 1U3671 | sp-12 | an-278 | 1C3671 | sp-11 | an-278 |
| 1A3672 | sp-10 | an-279 | 1U3672 | sp-12 | an-279 | 1C3672 | sp-11 | an-279 |
| 1A3673 | sp-10 | an-280 | 1U3673 | sp-12 | an-280 | 1C3673 | sp-11 | an-280 |
| 1A3874 | sp-10 | an-281 | 1U3674 | sp-12 | an-281 | 1C3674 | sp-11 | an-281 |
| 1A3675 | sp-10 | an-282 | 1U3675 | sp-12 | an-282 | 1C3675 | sp-11 | an-282 |
| 1A3676 | sp-10 | an-283 | 1U3676 | sp-12 | an-283 | 1C3676 | sp-11 | an-283 |
| 1A3677 | sp-10 | an-284 | 1U3677 | sp-12 | an-284 | 1C3677 | sp-11 | an-284 |
| 1A3678 | sp-10 | an-285 | 1U3678 | sp-12 | an-285 | 1C3678 | sp-11 | an-285 |
| 1A3679 | sp-10 | an-286 | 1U3679 | sp-12 | an-286 | 1C3679 | sp-11 | an-286 |
| 1A3680 | sp-10 | an-287 | 1U3680 | sp-12 | an-287 | 1C3680 | sp-11 | an-287 |
| 1A3681 | sp-10 | an-288 | 1U3681 | sp-12 | an-288 | 1C3681 | sp-11 | an-288 |
| 1A3682 | sp-10 | an-289 | 1U3682 | sp-12 | an-289 | 1C3682 | sp-11 | an-289 |
| 1A3683 | sp-10 | an-290 | 1U3683 | sp-12 | an-290 | 1C3683 | sp-11 | an-290 |
| 1A3684 | sp-10 | an-291 | 1U3684 | sp-12 | an-291 | 1C3684 | sp-11 | an-291 |
| 1A3685 | sp-10 | an-292 | 1U3685 | sp-12 | an-292 | 1C3685 | sp-11 | an-292 |
| 1A3686 | sp-10 | an-293 | 1U3686 | sp-12 | an-293 | 1C3686 | sp-11 | an-293 |
| 1A3687 | sp-10 | an-294 | 1U3687 | sp-12 | an-294 | 1C3687 | sp-11 | an-294 |
| 1A3688 | sp-10 | an-295 | 1U3688 | sp-12 | an-295 | 1C3688 | sp-11 | an-295 |
| 1A3689 | sp-10 | an-295 | 1U3689 | sp-12 | an-296 | 1C3689 | sp-11 | an-296 |
| 1A3690 | sp-10 | an-297 | 1U3690 | sp-12 | an-297 | 1C3690 | sp-11 | an-297 |
| 1A3691 | sp-10 | an-298 | 1U3691 | sp-12 | an-298 | 1C3691 | sp-11 | an-298 |
| 1A3692 | sp-10 | an-299 | 1U3692 | sp-12 | an-299 | 1C3692 | sp-11 | an-299 |
| 1A3693 | sp-10 | an-300 | 1U3693 | sp-12 | an-300 | 1C3693 | sp-11 | an-300 |
| 1A3694 | sp-10 | an-301 | 1U3694 | sp-12 | an-301 | 1C3694 | sp-11 | an-301 |
| 1A3695 | sp-10 | an-302 | 1U3695 | sp-12 | an-302 | 1C3695 | sp-11 | an-302 |
| 1A3696 | sp-10 | an-303 | 1U3696 | sp-12 | an-303 | 1C3696 | sp-11 | an-303 |
| 1A3697 | sp-10 | an-304 | 1U3697 | sp-12 | an-304 | 1C3697 | sp-11 | an-304 |
| 1A3698 | sp-10 | an-305 | 1U3698 | sp-12 | an-305 | 1C3698 | sp-11 | an-305 |
| 1A3699 | sp-10 | an-306 | 1U3699 | sp-12 | an-306 | 1C3699 | sp-11 | an-306 |
| 1A3700 | sp-10 | an-307 | 1U3700 | sp-12 | an-307 | 1C3700 | sp-11 | an-307 |
| 1A3701 | sp-10 | an-308 | 1U3701 | sp-12 | an-308 | 1C3701 | sp-11 | an-308 |
| 1A3702 | sp-10 | an-309 | 1U3702 | sp-12 | an-309 | 1C3702 | sp-11 | an-309 |
| 1A3703 | sp-10 | an-310 | 1U3703 | sp-12 | an-310 | 1C3703 | sp-11 | an-310 |
| 1A3704 | sp-10 | an-311 | 1U3704 | sp-12 | an-311 | 1C3704 | sp-11 | an-311 |
| 1A3705 | sp-10 | an-312 | 1U3705 | sp-12 | an-312 | 1C3705 | sp-11 | an-312 |
| 1A3706 | sp-10 | an-313 | 1U3706 | sp-12 | an-313 | 1C3706 | sp-11 | an-313 |
| 1A3707 | sp-10 | an-314 | 1U3707 | sp-12 | an-314 | 1C3707 | sp-11 | an-314 |
| 1A3708 | sp-10 | an-315 | 1U3708 | sp-12 | an-315 | 1C3708 | sp-11 | an-315 |
| 1A3709 | sp-10 | an-316 | 1U3709 | sp-12 | an-316 | 1C3709 | sp-11 | an-316 |
| 1A3710 | sp-10 | an-317 | 1U3710 | sp-12 | an-317 | 1C3710 | sp-11 | an-317 |
| 1A3711 | sp-10 | an-318 | 1U3711 | sp-12 | an-318 | 1C3711 | sp-11 | an-318 |
| 1A3712 | sp-10 | an-319 | 1U3712 | sp-12 | an-319 | 1C3712 | sp-11 | an-319 |
| 1A3713 | sp-10 | an-320 | 1U3713 | sp-12 | an-320 | 1C3713 | sp-11 | an-320 |
| 1A3714 | sp-10 | an-321 | 1U3714 | sp-12 | an-321 | 1C3714 | sp-11 | an-321 |
| 1A3715 | sp-10 | an-322 | 1U3715 | sp-12 | an-322 | 1C3715 | sp-11 | an-322 |
| 1A3716 | sp-10 | an-323 | 1U3716 | sp-12 | an-323 | 1C3716 | sp-11 | an-323 |
| 1A3717 | sp-10 | an-324 | 1U3717 | sp-12 | an-324 | 1C3717 | sp-11 | an-324 |
| 1A3718 | sp-10 | an-325 | 1U3718 | sp-12 | an-325 | 1C3718 | sp-11 | an-325 |
| 1A3719 | sp-10 | an-326 | 1U3719 | sp-12 | an-326 | 1C3719 | sp-11 | an-326 |
| 1A3720 | sp-10 | an-327 | 1U3720 | sp-12 | an-327 | 1C3720 | sp-11 | an-327 |
| 1A3721 | sp-10 | an-328 | 1U3721 | sp-12 | an-328 | 1C3721 | sp-11 | an-328 |
| 1A3722 | sp-10 | an-329 | 1U3722 | sp-12 | an-329 | 1C3722 | sp-11 | an-329 |
| 1A3723 | sp-10 | an-330 | 1U3723 | sp-12 | an-330 | 1C3723 | sp-11 | an-330 |
| 1A3724 | sp-10 | an-331 | 1U3724 | sp-12 | an-331 | 1C3724 | sp-11 | an-331 |
| 1A3725 | sp-10 | an-332 | 1U3725 | sp-12 | an-332 | 1C3725 | sp-11 | an-332 |
| 1A3726 | sp-10 | an-333 | 1U3726 | sp-12 | an-333 | 1C3726 | sp-11 | an-333 |
| 1A3727 | sp-10 | an-334 | 1U3727 | sp-12 | an-334 | 1C3727 | sp-11 | an-334 |
| 1A3728 | sp-10 | an-335 | 1U3728 | sp-12 | an-335 | 1C3728 | sp-11 | an-335 |
| 1A3729 | sp-10 | an-336 | 1U3729 | sp-12 | an-336 | 1C3729 | sp-11 | an-336 |
| 1A3730 | sp-10 | an-337 | 1U3730 | sp-12 | an-337 | 1C3730 | sp-11 | an-337 |

TABLE 1-continued

| | | | | | | | | |
|---|---|---|---|---|---|---|---|---|
| 1A3731 | sp-10 | an-338 | 1U3731 | sp-12 | an-338 | 1C3731 | sp-11 | an-338 |
| 1A3732 | sp-10 | an-339 | 1U3732 | sp-12 | an-339 | 1C3732 | sp-11 | an-339 |
| 1A3733 | sp-10 | an-340 | 1U3733 | sp-12 | an-340 | 1C3733 | sp-11 | an-340 |
| 1A3734 | sp-10 | an-341 | 1U3734 | sp-12 | an-341 | 1C3734 | sp-11 | an-341 |
| 1A3735 | sp-10 | an-342 | 1U3735 | sp-12 | an-342 | 1C3735 | sp-11 | an-342 |
| 1A3736 | sp-10 | an-343 | 1U3736 | sp-12 | an-343 | 1C3736 | sp-11 | an-343 |
| 1A3737 | sp-10 | an-344 | 1U3737 | sp-12 | an-344 | 1C3737 | sp-11 | an-344 |
| 1A3738 | sp-10 | an-345 | 1U3738 | sp-12 | an-345 | 1C3738 | sp-11 | an-345 |
| 1A3739 | sp-10 | an-346 | 1U3739 | sp-12 | an-346 | 1C3739 | sp-11 | an-346 |
| 1A3740 | sp-10 | an-347 | 1U3740 | sp-12 | an-347 | 1C3740 | sp-11 | an-347 |
| 1A3741 | sp-10 | an-348 | 1U3741 | sp-12 | an-348 | 1C3741 | sp-11 | an-348 |
| 1A3742 | sp-10 | an-349 | 1U3742 | sp-12 | an-349 | 1C3742 | sp-11 | an-349 |
| 1A3743 | sp-10 | an-350 | 1U3743 | sp-12 | an-350 | 1C3743 | sp-11 | an-350 |
| 1A3744 | sp-10 | an-351 | 1U3744 | sp-12 | an-351 | 1C3744 | sp-11 | an-351 |
| 1A3745 | sp-10 | an-352 | 1U3745 | sp-12 | an-352 | 1C3745 | sp-11 | an-352 |
| 1A3746 | sp-10 | an-353 | 1U3746 | sp-12 | an-353 | 1C3746 | sp-11 | an-353 |
| 1A3747 | sp-10 | an-354 | 1U3747 | sp-12 | an-354 | 1C3747 | sp-11 | an-354 |
| 1A3748 | sp-10 | an-355 | 1U3748 | sp-12 | an-355 | 1C3748 | sp-11 | an-355 |
| 1A3749 | sp-10 | an-356 | 1U3749 | sp-12 | an-356 | 1C3749 | sp-11 | an-356 |
| 1A3750 | sp-10 | an-357 | 1U3750 | sp-12 | an-357 | 1C3750 | sp-11 | an-357 |
| 1A3751 | sp-10 | an-358 | 1U3751 | sp-12 | an-358 | 1C3751 | sp-11 | an-358 |
| 1A3752 | sp-10 | an-359 | 1U3752 | sp-12 | an-359 | 1C3752 | sp-11 | an-359 |
| 1A3753 | sp-10 | an-360 | 1U3753 | sp-12 | an-360 | 1C3753 | sp-11 | an-360 |
| 1A3754 | sp-10 | an-361 | 1U3754 | sp-12 | an-361 | 1C3754 | sp-11 | an-361 |
| 1A3755 | sp-10 | an-362 | 1U3755 | sp-12 | an-362 | 1C3755 | sp-11 | an-362 |
| 1A3756 | sp-10 | an-363 | 1U3756 | sp-12 | an-363 | 1C3756 | sp-11 | an-363 |
| 1A3757 | sp-10 | an-364 | 1U3757 | sp-12 | an-364 | 1C3757 | sp-11 | an-364 |
| 1A3758 | sp-10 | an-365 | 1U3758 | sp-12 | an-365 | 1C3758 | sp-11 | an-365 |
| 1A3759 | sp-10 | an-366 | 1U3759 | sp-12 | an-366 | 1C3759 | sp-11 | an-366 |
| 1A3760 | sp-10 | an-367 | 1U3760 | sp-12 | an-367 | 1C3760 | sp-11 | an-367 |
| 1A3761 | sp-10 | an-368 | 1U3761 | sp-12 | an-368 | 1C3761 | sp-11 | an-368 |
| 1A3762 | sp-10 | an-369 | 1U3762 | sp-12 | an-369 | 1C3762 | sp-11 | an-369 |
| 1A3763 | sp-10 | an-370 | 1U3763 | sp-12 | an-370 | 1C3763 | sp-11 | an-370 |
| 1A3764 | sp-10 | an-371 | 1U3764 | sp-12 | an-371 | 1C3764 | sp-11 | an-371 |
| 1A3765 | sp-10 | an-372 | 1U3765 | sp-12 | an-372 | 1C3765 | sp-11 | an-372 |
| 1A3766 | sp-10 | an-373 | 1U3766 | sp-12 | an-373 | 1C3766 | sp-11 | an-373 |
| 1A3767 | sp-10 | an-374 | 1U3767 | sp-12 | an-374 | 1C3767 | sp-11 | an-374 |
| 1A3768 | sp-10 | an-375 | 1U3768 | sp-12 | an-375 | 1C3768 | sp-11 | an-375 |
| 1A3769 | sp-10 | an-376 | 1U3769 | sp-12 | an-376 | 1C3769 | sp-11 | an-376 |
| 1A3770 | sp-10 | an-377 | 1U3770 | sp-12 | an-377 | 1C3770 | sp-11 | an-377 |
| 1A3771 | sp-14 | an-1 | 1U3771 | sp-13 | an-1 | | | |
| 1A3772 | sp-14 | an-2 | 1U3772 | sp-13 | an-2 | | | |
| 1A3773 | sp-14 | an-3 | 1U3773 | sp-13 | an-3 | | | |
| 1A3774 | sp-14 | an-4 | 1U3774 | sp-13 | an-4 | | | |
| 1A3775 | sp-14 | an-5 | 1U3775 | sp-13 | an-5 | | | |
| 1A3776 | sp-14 | an-6 | 1U3776 | sp-13 | an-6 | | | |
| 1A3777 | sp-14 | an-7 | 1U3777 | sp-13 | an-7 | | | |
| 1A3778 | sp-14 | an-8 | 1U3778 | sp-13 | an-8 | | | |
| 1A3779 | sp-14 | an-9 | 1U3779 | sp-13 | an-9 | | | |
| 1A3780 | sp-14 | an-10 | 1U3780 | sp-13 | an-10 | | | |
| 1A3781 | sp-14 | an-11 | 1U3781 | sp-13 | an-11 | | | |
| 1A3782 | sp-14 | an-12 | 1U3782 | sp-13 | an-12 | | | |
| 1A3783 | sp-14 | an-13 | 1U3783 | sp-13 | an-13 | | | |
| 1A3784 | sp-14 | an-14 | 1U3784 | sp-13 | an-14 | | | |
| 1A3785 | sp-14 | an-15 | 1U3785 | sp-13 | an-15 | | | |
| 1A3786 | sp-14 | an-16 | 1U3786 | sp-13 | an-16 | | | |
| 1A3787 | sp-14 | an-17 | 1U3787 | sp-13 | an-17 | | | |
| 1A3788 | sp-14 | an-18 | 1U3788 | sp-13 | an-18 | | | |
| 1A3789 | sp-14 | an-19 | 1U3789 | sp-13 | an-19 | | | |
| 1A3790 | sp-14 | an-20 | 1U3790 | sp-13 | an-20 | | | |
| 1A3791 | sp-14 | an-21 | 1U3791 | sp-13 | an-21 | | | |
| 1A3792 | sp-14 | an-22 | 1U3792 | sp-13 | an-22 | | | |
| 1A3793 | sp-14 | an-23 | 1U3793 | sp-13 | an-23 | | | |
| 1A3794 | sp-14 | an-24 | 1U3794 | sp-13 | an-24 | | | |
| 1A3795 | sp-14 | an-25 | 1U3795 | sp-13 | an-25 | | | |
| 1A3796 | sp-14 | an-26 | 1U3796 | sp-13 | an-26 | | | |
| 1A3797 | sp-14 | an-27 | 1U3797 | sp-13 | an-27 | | | |
| 1A3798 | sp-14 | an-28 | 1U3798 | sp-13 | an-28 | | | |
| 1A3799 | sp-14 | an-29 | 1U3799 | sp-13 | an-29 | | | |
| 1A3800 | sp-14 | an-30 | 1U3800 | sp-13 | an-30 | | | |
| 1A3801 | sp-14 | an-31 | 1U3801 | sp-13 | an-31 | | | |
| 1A3802 | sp-14 | an-32 | 1U3802 | sp-13 | an-32 | | | |
| 1A3803 | sp-14 | an-33 | 1U3803 | sp-13 | an-33 | | | |
| 1A3804 | sp-14 | an-34 | 1U3804 | sp-13 | an-34 | | | |
| 1A3805 | sp-14 | an-35 | 1U3805 | sp-13 | an-35 | | | |
| 1A3806 | sp-14 | an-36 | 1U3806 | sp-13 | an-36 | | | |
| 1A3807 | sp-14 | an-37 | 1U3807 | sp-13 | an-37 | | | |
| 1A3808 | sp-14 | an-38 | 1U3808 | sp-13 | an-38 | | | |
| 1A3809 | sp-14 | an-39 | 1U3809 | sp-13 | an-39 | | | |

TABLE 1-continued

| | | | | | |
|---|---|---|---|---|---|
| 1A3810 | sp-14 | an-40 | 1U3810 | sp-13 | an-40 |
| 1A3811 | sp-14 | an-41 | 1U3811 | sp-13 | an-41 |
| 1A3812 | sp-14 | an-42 | 1U3812 | sp-13 | an-42 |
| 1A3813 | sp-14 | an-43 | 1U3813 | sp-13 | an-43 |
| 1A3814 | sp-14 | an-44 | 1U3814 | sp-13 | an-44 |
| 1A3815 | sp-14 | an-45 | 1U3815 | sp-13 | an-45 |
| 1A3816 | sp-14 | an-46 | 1U3816 | sp-13 | an-46 |
| 1A3817 | sp-14 | an-47 | 1U3817 | sp-13 | an-47 |
| 1A3818 | sp-14 | an-48 | 1U3818 | sp-13 | an-48 |
| 1A3819 | sp-14 | an-49 | 1U3819 | sp-13 | an-49 |
| 1A3820 | sp-14 | an-50 | 1U3820 | sp-13 | an-50 |
| 1A3821 | sp-14 | an-51 | 1U3821 | sp-13 | an-51 |
| 1A3822 | sp-14 | an-52 | 1U3822 | sp-13 | an-52 |
| 1A3823 | sp-14 | an-53 | 1U3823 | sp-13 | an-53 |
| 1A3824 | sp-14 | an-54 | 1U3824 | sp-13 | an-54 |
| 1A3825 | sp-14 | an-55 | 1U3825 | sp-13 | an-55 |
| 1A3826 | sp-14 | an-56 | 1U3826 | sp-13 | an-56 |
| 1A3827 | sp-14 | an-57 | 1U3827 | sp-13 | an-57 |
| 1A3828 | sp-14 | an-58 | 1U3828 | sp-13 | an-58 |
| 1A3829 | sp-14 | an-59 | 1U3829 | sp-13 | an-59 |
| 1A3830 | sp-14 | an-60 | 1U3830 | sp-13 | an-60 |
| 1A3831 | sp-14 | an-61 | 1U3831 | sp-13 | an-61 |
| 1A3832 | sp-14 | an-62 | 1U3832 | sp-13 | an-62 |
| 1A3833 | sp-14 | an-63 | 1U3833 | sp-13 | an-63 |
| 1A3834 | sp-14 | an-64 | 1U3834 | sp-13 | an-64 |
| 1A3835 | sp-14 | an-65 | 1U3835 | sp-13 | an-65 |
| 1A3836 | sp-14 | an-66 | 1U3836 | sp-13 | an-66 |
| 1A3837 | sp-14 | an-67 | 1U3837 | sp-13 | an-67 |
| 1A3838 | sp-14 | an-68 | 1U3838 | sp-13 | an-68 |
| 1A3839 | sp-14 | an-69 | 1U3839 | sp-13 | an-69 |
| 1A3840 | sp-14 | an-70 | 1U3840 | sp-13 | an-70 |
| 1A3841 | sp-14 | an-71 | 1U3841 | sp-13 | an-71 |
| 1A3842 | sp-14 | an-72 | 1U3842 | sp-13 | an-72 |
| 1A3843 | sp-14 | an-73 | 1U3843 | sp-13 | an-73 |
| 1A3844 | sp-14 | an-74 | 1U3844 | sp-13 | an-74 |
| 1A3845 | sp-14 | an-75 | 1U3845 | sp-13 | an-75 |
| 1A3846 | sp-14 | an-76 | 1U3846 | sp-13 | an-76 |
| 1A3847 | sp-14 | an-77 | 1U3847 | sp-13 | an-77 |
| 1A3848 | sp-14 | an-78 | 1U3848 | sp-13 | an-78 |
| 1A3849 | sp-14 | an-79 | 1U3849 | sp-13 | an-79 |
| 1A3850 | sp-14 | an-80 | 1U3850 | sp-13 | an-80 |
| 1A3851 | sp-14 | an-81 | 1U3851 | sp-13 | an-81 |
| 1A3852 | sp-14 | an-82 | 1U3852 | sp-13 | an-82 |
| 1A3853 | sp-14 | an-83 | 1U3853 | sp-13 | an-83 |
| 1A3854 | sp-14 | an-84 | 1U3854 | sp-13 | an-84 |
| 1A3855 | sp-14 | an-85 | 1U3855 | sp-13 | an-85 |
| 1A3856 | sp-14 | an-86 | 1U3856 | sp-13 | an-86 |
| 1A3857 | sp-14 | an-87 | 1U3857 | sp-13 | an-87 |
| 1A3858 | sp-14 | an-88 | 1U3858 | sp-13 | an-88 |
| 1A3859 | sp-14 | an-89 | 1U3859 | sp-13 | an-89 |
| 1A3860 | sp-14 | an-90 | 1U3860 | sp-13 | an-90 |
| 1A3861 | sp-14 | an-91 | 1U3861 | sp-13 | an-91 |
| 1A3862 | sp-14 | an-92 | 1U3862 | sp-13 | an-92 |
| 1A3863 | sp-14 | an-93 | 1U3863 | sp-13 | an-93 |
| 1A3864 | sp-14 | an-94 | 1U3864 | sp-13 | an-94 |
| 1A3865 | sp-14 | an-95 | 1U3865 | sp-13 | an-95 |
| 1A3866 | sp-14 | an-96 | 1U3866 | sp-13 | an-96 |
| 1A3867 | sp-14 | an-97 | 1U3867 | sp-13 | an-97 |
| 1A3868 | sp-14 | an-98 | 1U3868 | sp-13 | an-98 |
| 1A3869 | sp-14 | an-99 | 1U3869 | sp-13 | an-99 |
| 1A3870 | sp-14 | an-100 | 1U3870 | sp-13 | an-100 |
| 1A3871 | sp-14 | an-101 | 1U3871 | sp-13 | an-101 |
| 1A3872 | sp-14 | an-102 | 1U3872 | sp-13 | an-102 |
| 1A3873 | sp-14 | an-103 | 1U3873 | sp-13 | an-103 |
| 1A3874 | sp-14 | an-104 | 1U3874 | sp-13 | an-104 |
| 1A3875 | sp-14 | an-105 | 1U3875 | sp-13 | an-105 |
| 1A3876 | sp-14 | an-106 | 1U3876 | sp-13 | an-106 |
| 1A3877 | sp-14 | an-107 | 1U3877 | sp-13 | an-107 |
| 1A3878 | sp-14 | an-108 | 1U3878 | sp-13 | an-108 |
| 1A3879 | sp-14 | an-109 | 1U3879 | sp-13 | an-109 |
| 1A3880 | sp-14 | an-110 | 1U3880 | sp-13 | an-110 |
| 1A3881 | sp-14 | an-111 | 1U3881 | sp-13 | an-111 |
| 1A3882 | sp-14 | an-112 | 1U3882 | sp-13 | an-112 |
| 1A3883 | sp-14 | an-113 | 1U3883 | sp-13 | an-113 |
| 1A3884 | sp-14 | an-114 | 1U3884 | sp-13 | an-114 |
| 1A3885 | sp-14 | an-115 | 1U3885 | sp-13 | an-115 |
| 1A3886 | sp-14 | an-116 | 1U3886 | sp-13 | an-116 |
| 1A3887 | sp-14 | an-117 | 1U3887 | sp-13 | an-117 |
| 1A3888 | sp-14 | an-118 | 1U3888 | sp-13 | an-118 |

TABLE 1-continued

| | | | | | |
|---|---|---|---|---|---|
| 1A3889 | sp-14 | an-119 | 1U3889 | sp-13 | an-119 |
| 1A3890 | sp-14 | an-120 | 1U3890 | sp-13 | an-120 |
| 1A3891 | sp-14 | an-121 | 1U3891 | sp-13 | an-121 |
| 1A3892 | sp-14 | an-122 | 1U3892 | sp-13 | an-122 |
| 1A3893 | sp-14 | an-123 | 1U3893 | sp-13 | an-123 |
| 1A3894 | sp-14 | an-124 | 1U3894 | sp-13 | an-124 |
| 1A3895 | sp-14 | an-125 | 1U3895 | sp-13 | an-125 |
| 1A3896 | sp-14 | an-126 | 1U3896 | sp-13 | an-126 |
| 1A3897 | sp-14 | an-127 | 1U3897 | sp-13 | an-127 |
| 1A3898 | sp-14 | an-128 | 1U3898 | sp-13 | an-128 |
| 1A3899 | sp-14 | an-129 | 1U3899 | sp-13 | an-129 |
| 1A3900 | sp-14 | an-130 | 1U3900 | sp-13 | an-130 |
| 1A3901 | sp-14 | an-131 | 1U3901 | sp-13 | an-131 |
| 1A3902 | sp-14 | an-132 | 1U3902 | sp-13 | an-132 |
| 1A3903 | sp-14 | an-133 | 1U3903 | sp-13 | an-133 |
| 1A3904 | sp-14 | an-134 | 1U3904 | sp-13 | an-134 |
| 1A3905 | sp-14 | an-135 | 1U3905 | sp-13 | an-135 |
| 1A3906 | sp-14 | an-136 | 1U3906 | sp-13 | an-136 |
| 1A3907 | sp-14 | an-137 | 1U3907 | sp-13 | an-137 |
| 1A3908 | sp-14 | an-138 | 1U3908 | sp-13 | an-138 |
| 1A3909 | sp-14 | an-139 | 1U3909 | sp-13 | an-139 |
| 1A3910 | sp-14 | an-140 | 1U3910 | sp-13 | an-140 |
| 1A3911 | sp-14 | an-141 | 1U3911 | sp-13 | an-141 |
| 1A3912 | sp-14 | an-142 | 1U3912 | sp-13 | an-142 |
| 1A3913 | sp-14 | an-143 | 1U3913 | sp-13 | an-143 |
| 1A3914 | sp-14 | an-144 | 1U3914 | sp-13 | an-144 |
| 1A3915 | sp-14 | an-145 | 1U3915 | sp-13 | an-145 |
| 1A3916 | sp-14 | an-146 | 1U3916 | sp-13 | an-146 |
| 1A3917 | sp-14 | an-147 | 1U3917 | sp-13 | an-147 |
| 1A3918 | sp-14 | an-148 | 1U3918 | sp-13 | an-148 |
| 1A3919 | sp-14 | an-149 | 1U3919 | sp-13 | an-149 |
| 1A3920 | sp-14 | an-150 | 1U3920 | sp-13 | an-150 |
| 1A3921 | sp-14 | an-151 | 1U3921 | sp-13 | an-151 |
| 1A3922 | sp-14 | an-152 | 1U3922 | sp-13 | an-152 |
| 1A3923 | sp-14 | an-153 | 1U3923 | sp-13 | an-153 |
| 1A3924 | sp-14 | an-154 | 1U3924 | sp-13 | an-154 |
| 1A3925 | sp-14 | an-155 | 1U3925 | sp-13 | an-155 |
| 1A3926 | sp-14 | an-156 | 1U3926 | sp-13 | an-156 |
| 1A3927 | sp-14 | an-157 | 1U3927 | sp-13 | an-157 |
| 1A3928 | sp-14 | an-158 | 1U3928 | sp-13 | an-158 |
| 1A3929 | sp-14 | an-159 | 1U3929 | sp-13 | an-159 |
| 1A3930 | sp-14 | an-160 | 1U3930 | sp-13 | an-160 |
| 1A3931 | sp-14 | an-161 | 1U3931 | sp-13 | an-161 |
| 1A3932 | sp-14 | an-162 | 1U3932 | sp-13 | an-162 |
| 1A3933 | sp-14 | an-163 | 1U3933 | sp-13 | an-163 |
| 1A3934 | sp-14 | an-164 | 1U3934 | sp-13 | an-164 |
| 1A3935 | sp-14 | an-165 | 1U3935 | sp-13 | an-165 |
| 1A3936 | sp-14 | an-166 | 1U3936 | sp-13 | an-166 |
| 1A3937 | sp-14 | an-167 | 1U3937 | sp-13 | an-167 |
| 1A3938 | sp-14 | an-168 | 1U3938 | sp-13 | an-168 |
| 1A3939 | sp-14 | an-169 | 1U3939 | sp-13 | an-169 |
| 1A3940 | sp-14 | an-170 | 1U3940 | sp-13 | an-170 |
| 1A3941 | sp-14 | an-171 | 1U3941 | sp-13 | an-171 |
| 1A3942 | sp-14 | an-172 | 1U3942 | sp-13 | an-172 |
| 1A3943 | sp-14 | an-173 | 1U3943 | sp-13 | an-173 |
| 1A3944 | sp-14 | an-174 | 1U3944 | sp-13 | an-174 |
| 1A3945 | sp-14 | an-175 | 1U3945 | sp-13 | an-175 |
| 1A3946 | sp-14 | an-176 | 1U3946 | sp-13 | an-176 |
| 1A3947 | sp-14 | an-177 | 1U3947 | sp-13 | an-177 |
| 1A3948 | sp-14 | an-178 | 1U3948 | sp-13 | an-178 |
| 1A3949 | sp-14 | an-179 | 1U3949 | sp-13 | an-179 |
| 1A3950 | sp-14 | an-180 | 1U3950 | sp-13 | an-180 |
| 1A3951 | sp-14 | an-181 | 1U3951 | sp-13 | an-181 |
| 1A3952 | sp-14 | an-182 | 1U3952 | sp-13 | an-182 |
| 1A3953 | sp-14 | an-183 | 1U3953 | sp-13 | an-183 |
| 1A3954 | sp-14 | an-184 | 1U3954 | sp-13 | an-184 |
| 1A3955 | sp-14 | an-185 | 1U3955 | sp-13 | an-185 |
| 1A3956 | sp-14 | an-186 | 1U3956 | sp-13 | an-186 |
| 1A3957 | sp-14 | an-187 | 1U3957 | sp-13 | an-187 |
| 1A3958 | sp-14 | an-188 | 1U3958 | sp-13 | an-188 |
| 1A3959 | sp-14 | an-189 | 1U3959 | sp-13 | an-189 |
| 1A3960 | sp-14 | an-190 | 1U3960 | sp-13 | an-190 |
| 1A3961 | sp-14 | an-191 | 1U3961 | sp-13 | an-191 |
| 1A3962 | sp-14 | an-192 | 1U3962 | sp-13 | an-192 |
| 1A3963 | sp-14 | an-193 | 1U3963 | sp-13 | an-193 |
| 1A3964 | sp-14 | an-194 | 1U3964 | sp-13 | an-194 |
| 1A3965 | sp-14 | an-195 | 1U3965 | sp-13 | an-195 |
| 1A3966 | sp-14 | an-196 | 1U3966 | sp-13 | an-196 |
| 1A3967 | sp-14 | an-197 | 1U3967 | sp-13 | an-197 |

TABLE 1-continued

| | | | | | |
|---|---|---|---|---|---|
| 1A3968 | sp-14 | an-198 | 1U3968 | sp-13 | an-198 |
| 1A3969 | sp-14 | an-199 | 1U3969 | sp-13 | an-199 |
| 1A3970 | sp-14 | an-200 | 1U3970 | sp-13 | an-200 |
| 1A3971 | sp-14 | an-201 | 1U3971 | sp-13 | an-201 |
| 1A3972 | sp-14 | an-202 | 1U3972 | sp-13 | an-202 |
| 1A3973 | sp-14 | an-203 | 1U3973 | sp-13 | an-203 |
| 1A3974 | sp-14 | an-204 | 1U3974 | sp-13 | an-204 |
| 1A3975 | sp-14 | an-205 | 1U3975 | sp-13 | an-205 |
| 1A3976 | sp-14 | an-206 | 1U3976 | sp-13 | an-206 |
| 1A3977 | sp-14 | an-207 | 1U3977 | sp-13 | an-207 |
| 1A3978 | sp-14 | an-208 | 1U3978 | sp-13 | an-208 |
| 1A3979 | sp-14 | an-209 | 1U3979 | sp-13 | an-209 |
| 1A3980 | sp-14 | an-210 | 1U3980 | sp-13 | an-210 |
| 1A3981 | sp-14 | an-211 | 1U3981 | sp-13 | an-211 |
| 1A3982 | sp-14 | an-212 | 1U3982 | sp-13 | an-212 |
| 1A3983 | sp-14 | an-213 | 1U3983 | sp-13 | an-213 |
| 1A3984 | sp-14 | an-214 | 1U3984 | sp-13 | an-214 |
| 1A3985 | sp-14 | an-215 | 1U3985 | sp-13 | an-215 |
| 1A3986 | sp-14 | an-216 | 1U3986 | sp-13 | an-216 |
| 1A3987 | sp-14 | an-217 | 1U3987 | sp-13 | an-217 |
| 1A3988 | sp-14 | an-218 | 1U3988 | sp-13 | an-218 |
| 1A3989 | sp-14 | an-219 | 1U3989 | sp-13 | an-219 |
| 1A3990 | sp-14 | an-220 | 1U3990 | sp-13 | an-220 |
| 1A3991 | sp-14 | an-221 | 1U3991 | sp-13 | an-221 |
| 1A3992 | sp-14 | an-222 | 1U3992 | sp-13 | an-222 |
| 1A3993 | sp-14 | an-223 | 1U3993 | sp-13 | an-223 |
| 1A3994 | sp-14 | an-224 | 1U3994 | sp-13 | an-224 |
| 1A3995 | sp-14 | an-225 | 1U3995 | sp-13 | an-225 |
| 1A3996 | sp-14 | an-226 | 1U3996 | sp-13 | an-226 |
| 1A3997 | sp-14 | an-227 | 1U3997 | sp-13 | an-227 |
| 1A3998 | sp-14 | an-228 | 1U3998 | sp-13 | an-228 |
| 1A3999 | sp-14 | an-229 | 1U3999 | sp-13 | an-229 |
| 1A4000 | sp-14 | an-230 | 1U4000 | sp-13 | an-230 |
| 1A4001 | sp-14 | an-231 | 1U4001 | sp-13 | an-231 |
| 1A4002 | sp-14 | an-232 | 1U4002 | sp-13 | an-232 |
| 1A4003 | sp-14 | an-233 | 1U4003 | sp-13 | an-233 |
| 1A4004 | sp-14 | an-234 | 1U4004 | sp-13 | an-234 |
| 1A4005 | sp-14 | an-235 | 1U4005 | sp-13 | an-235 |
| 1A4006 | sp-14 | an-236 | 1U4006 | sp-13 | an-236 |
| 1A4007 | sp-14 | an-237 | 1U4007 | sp-13 | an-237 |
| 1A4008 | sp-14 | an-238 | 1U4008 | sp-13 | an-238 |
| 1A4009 | sp-14 | an-239 | 1U4009 | sp-13 | an-239 |
| 1A4010 | sp-14 | an-240 | 1U4010 | sp-13 | an-240 |
| 1A4011 | sp-14 | an-241 | 1U4011 | sp-13 | an-241 |
| 1A4012 | sp-14 | an-242 | 1U4012 | sp-13 | an-242 |
| 1A4013 | sp-14 | an-243 | 1U4013 | sp-13 | an-243 |
| 1A4014 | sp-14 | an-244 | 1U4014 | sp-13 | an-244 |
| 1A4015 | sp-14 | an-245 | 1U4015 | sp-13 | an-245 |
| 1A4016 | sp-14 | an-246 | 1U4016 | sp-13 | an-246 |
| 1A4017 | sp-14 | an-247 | 1U4017 | sp-13 | an-247 |
| 1A4018 | sp-14 | an-248 | 1U4018 | sp-13 | an-248 |
| 1A4019 | sp-14 | an-249 | 1U4019 | sp-13 | an-249 |
| 1A4020 | sp-14 | an-250 | 1U4020 | sp-13 | an-250 |
| 1A4021 | sp-14 | an-251 | 1U4021 | sp-13 | an-251 |
| 1A4022 | sp-14 | an-252 | 1U4022 | sp-13 | an-252 |
| 1A4023 | sp-14 | an-253 | 1U4023 | sp-13 | an-253 |
| 1A4024 | sp-14 | an-254 | 1U4024 | sp-13 | an-254 |
| 1A4025 | sp-14 | an-255 | 1U4025 | sp-13 | an-255 |
| 1A4026 | sp-14 | an-256 | 1U4026 | sp-13 | an-256 |
| 1A4027 | sp-14 | an-257 | 1U4027 | sp-13 | an-257 |
| 1A4028 | sp-14 | an-258 | 1U4028 | sp-13 | an-258 |
| 1A4029 | sp-14 | an-259 | 1U4029 | sp-13 | an-259 |
| 1A4030 | sp-14 | an-260 | 1U4030 | sp-13 | an-260 |
| 1A4031 | sp-14 | an-261 | 1U4031 | sp-13 | an-261 |
| 1A4032 | sp-14 | an-262 | 1U4032 | sp-13 | an-262 |
| 1A4033 | sp-14 | an-263 | 1U4033 | sp-13 | an-263 |
| 1A4034 | sp-14 | an-264 | 1U4034 | sp-13 | an-264 |
| 1A4035 | sp-14 | an-265 | 1U4035 | sp-13 | an-265 |
| 1A4036 | sp-14 | an-266 | 1U4036 | sp-13 | an-266 |
| 1A4037 | sp-14 | an-267 | 1U4037 | sp-13 | an-267 |
| 1A4038 | sp-14 | an-268 | 1U4038 | sp-13 | an-268 |
| 1A4039 | sp-14 | an-269 | 1U4039 | sp-13 | an-269 |
| 1A4040 | sp-14 | an-270 | 1U4040 | sp-13 | an-270 |
| 1A4041 | sp-14 | an-271 | 1U4041 | sp-13 | an-271 |
| 1A4042 | sp-14 | an-272 | 1U4042 | sp-13 | an-272 |
| 1A4043 | sp-14 | an-273 | 1U4043 | sp-13 | an-273 |
| 1A4044 | sp-14 | an-274 | 1U4044 | sp-13 | an-274 |
| 1A4045 | sp-14 | an-275 | 1U4045 | sp-13 | an-275 |
| 1A4046 | sp-14 | an-276 | 1U4046 | sp-13 | an-276 |

TABLE 1-continued

| | | | | | |
|---|---|---|---|---|---|
| 1A4047 | sp-14 | an-277 | 1U4047 | sp-13 | an-277 |
| 1A4048 | sp-14 | an-278 | 1U4048 | sp-13 | an-278 |
| 1A4049 | sp-14 | an-279 | 1U4049 | sp-13 | an-279 |
| 1A4050 | sp-14 | an-280 | 1U4050 | sp-13 | an-280 |
| 1A4051 | sp-14 | an-281 | 1U4051 | sp-13 | an-281 |
| 1A4052 | sp-14 | an-282 | 1U4052 | sp-13 | an-282 |
| 1A4053 | sp-14 | an-283 | 1U4053 | sp-13 | an-283 |
| 1A4054 | sp-14 | an-284 | 1U4054 | sp-13 | an-284 |
| 1A4055 | sp-14 | an-285 | 1U4055 | sp-13 | an-285 |
| 1A4056 | sp-14 | an-286 | 1U4056 | sp-13 | an-286 |
| 1A4057 | sp-14 | an-287 | 1U4057 | sp-13 | an-287 |
| 1A4058 | sp-14 | an-288 | 1U4058 | sp-13 | an-288 |
| 1A4059 | sp-14 | an-289 | 1U4059 | sp-13 | an-289 |
| 1A4060 | sp-14 | an-290 | 1U4060 | sp-13 | an-290 |
| 1A4061 | sp-14 | an-291 | 1U4061 | sp-13 | an-291 |
| 1A4062 | sp-14 | an-292 | 1U4062 | sp-13 | an-292 |
| 1A4063 | sp-14 | an-293 | 1U4063 | sp-13 | an-293 |
| 1A4064 | sp-14 | an-294 | 1U4064 | sp-13 | an-294 |
| 1A4065 | sp-14 | an-295 | 1U4065 | sp-13 | an-295 |
| 1A4066 | sp-14 | an-296 | 1U4066 | sp-13 | an-296 |
| 1A4067 | sp-14 | an-297 | 1U4067 | sp-13 | an-297 |
| 1A4068 | sp-14 | an-298 | 1U4068 | sp-13 | an-298 |
| 1A4069 | sp-14 | an-299 | 1U4069 | sp-13 | an-299 |
| 1A4070 | sp-14 | an-300 | 1U4070 | sp-13 | an-300 |
| 1A4071 | sp-14 | an-301 | 1U4071 | sp-13 | an-301 |
| 1A4072 | sp-14 | an-302 | 1U4072 | sp-13 | an-302 |
| 1A4073 | sp-14 | an-303 | 1U4073 | sp-13 | an-303 |
| 1A4074 | sp-14 | an-304 | 1U4074 | sp-13 | an-304 |
| 1A4075 | sp-14 | an-305 | 1U4075 | sp-13 | an-305 |
| 1A4076 | sp-14 | an-306 | 1U4076 | sp-13 | an-306 |
| 1A4077 | sp-14 | an-307 | 1U4077 | sp-13 | an-307 |
| 1A4078 | sp-14 | an-308 | 1U4078 | sp-13 | an-308 |
| 1A4079 | sp-14 | an-309 | 1U4079 | sp-13 | an-309 |
| 1A4080 | sp-14 | an-310 | 1U4080 | sp-13 | an-310 |
| 1A4081 | sp-14 | an-311 | 1U4081 | sp-13 | an-311 |
| 1A4082 | sp-14 | an-312 | 1U4082 | sp-13 | an-312 |
| 1A4083 | sp-14 | an-313 | 1U4083 | sp-13 | an-313 |
| 1A4084 | sp-14 | an-314 | 1U4084 | sp-13 | an-314 |
| 1A4085 | sp-14 | an-315 | 1U4085 | sp-13 | an-315 |
| 1A4086 | sp-14 | an-316 | 1U4086 | sp-13 | an-316 |
| 1A4087 | sp-14 | an-317 | 1U4087 | sp-13 | an-317 |
| 1A4088 | sp-14 | an-318 | 1U4088 | sp-13 | an-318 |
| 1A4089 | sp-14 | an-319 | 1U4089 | sp-13 | an-319 |
| 1A4090 | sp-14 | an-320 | 1U4090 | sp-13 | an-320 |
| 1A4091 | sp-14 | an-321 | 1U4091 | sp-13 | an-321 |
| 1A4092 | sp-14 | an-322 | 1U4092 | sp-13 | an-322 |
| 1A4093 | sp-14 | an-323 | 1U4093 | sp-13 | an-323 |
| 1A4094 | sp-14 | an-324 | 1U4094 | sp-13 | an-324 |
| 1A4095 | sp-14 | an-325 | 1U4095 | sp-13 | an-325 |
| 1A4096 | sp-14 | an-326 | 1U4096 | sp-13 | an-326 |
| 1A4097 | sp-14 | an-327 | 1U4097 | sp-13 | an-327 |
| 1A4098 | sp-14 | an-328 | 1U4098 | sp-13 | an-328 |
| 1A4099 | sp-14 | an-329 | 1U4099 | sp-13 | an-329 |
| 1A4100 | sp-14 | an-330 | 1U4100 | sp-13 | an-330 |
| 1A4101 | sp-14 | an-331 | 1U4101 | sp-13 | an-331 |
| 1A4102 | sp-14 | an-332 | 1U4102 | sp-13 | an-332 |
| 1A4103 | sp-14 | an-333 | 1U4103 | sp-13 | an-333 |
| 1A4104 | sp-14 | an-334 | 1U4104 | sp-13 | an-334 |
| 1A4105 | sp-14 | an-335 | 1U4105 | sp-13 | an-335 |
| 1A4106 | sp-14 | an-336 | 1U4106 | sp-13 | an-336 |
| 1A4107 | sp-14 | an-337 | 1U4107 | sp-13 | an-337 |
| 1A4108 | sp-14 | an-338 | 1U4108 | sp-13 | an-338 |
| 1A4109 | sp-14 | an-339 | 1U4109 | sp-13 | an-339 |
| 1A4110 | sp-14 | an-340 | 1U4110 | sp-13 | an-340 |
| 1A4111 | sp-14 | an-341 | 1U4111 | sp-13 | an-341 |
| 1A4112 | sp-14 | an-342 | 1U4112 | sp-13 | an-342 |
| 1A4113 | sp-14 | an-343 | 1U4113 | sp-13 | an-343 |
| 1A4114 | sp-14 | an-344 | 1U4114 | sp-13 | an-344 |
| 1A4115 | sp-14 | an-345 | 1U4115 | sp-13 | an-345 |
| 1A4116 | sp-14 | an-346 | 1U4116 | sp-13 | an-346 |
| 1A4117 | sp-14 | an-347 | 1U4117 | sp-13 | an-347 |
| 1A4118 | sp-14 | an-348 | 1U4118 | sp-13 | an-348 |
| 1A4119 | sp-14 | an-349 | 1U4119 | sp-13 | an-349 |
| 1A4120 | sp-14 | an-350 | 1U4120 | sp-13 | an-350 |
| 1A4121 | sp-14 | an-351 | 1U4121 | sp-13 | an-351 |
| 1A4122 | sp-14 | an-352 | 1U4122 | sp-13 | an-352 |
| 1A4123 | sp-14 | an-353 | 1U4123 | sp-13 | an-353 |
| 1A4124 | sp-14 | an-354 | 1U4124 | sp-13 | an-354 |
| 1A4125 | sp-14 | an-355 | 1U4125 | sp-13 | an-355 |

TABLE 1-continued

| | | | | | | | | |
|---|---|---|---|---|---|---|---|---|
| 1A4126 | sp-14 | an-356 | 1U4126 | sp-13 | an-356 | | | |
| 1A4127 | sp-14 | an-357 | 1U4127 | sp-13 | an-357 | | | |
| 1A4128 | sp-14 | an-358 | 1U4128 | sp-13 | an-358 | | | |
| 1A4129 | sp-14 | an-359 | 1U4129 | sp-13 | an-359 | | | |
| 1A4130 | sp-14 | an-360 | 1U4130 | sp-13 | an-360 | | | |
| 1A4131 | sp-14 | an-361 | 1U4131 | sp-13 | an-361 | | | |
| 1A4132 | sp-14 | an-362 | 1U4132 | sp-13 | an-362 | | | |
| 1A4133 | sp-14 | an-363 | 1U4133 | sp-13 | an-363 | | | |
| 1A4134 | sp-14 | an-364 | 1U4134 | sp-13 | an-364 | | | |
| 1A4135 | sp-14 | an-365 | 1U4135 | sp-13 | an-365 | | | |
| 1A4136 | sp-14 | an-366 | 1U4136 | sp-13 | an-366 | | | |
| 1A4137 | sp-14 | an-367 | 1U4137 | sp-13 | an-367 | | | |
| 1A4138 | sp-14 | an-368 | 1U4138 | sp-13 | an-368 | | | |
| 1A4139 | sp-14 | an-369 | 1U4139 | sp-13 | an-369 | | | |
| 1A4140 | sp-14 | an-370 | 1U4140 | sp-13 | an-370 | | | |
| 1A4141 | sp-14 | an-371 | 1U4141 | sp-13 | an-371 | | | |
| 1A4142 | sp-14 | an-372 | 1U4142 | sp-13 | an-372 | | | |
| 1A4143 | sp-14 | an-373 | 1U4143 | sp-13 | an-373 | | | |
| 1A4144 | sp-14 | an-374 | 1U4144 | sp-13 | an-374 | | | |
| 1A4145 | sp-14 | an-375 | 1U4145 | sp-13 | an-375 | | | |
| 1A4146 | sp-14 | an-376 | 1U4146 | sp-13 | an-376 | | | |
| 1A4147 | sp-14 | an-377 | 1U4147 | sp-13 | an-377 | | | |
| Y = NHCS | | | Y = NHCSNH | | | Y = NHCS | | |
| Exemplification | Z | $N^+R^5R^6R^7$ | Exemplification | Z | $N^+R^5R^6R^7$ | Exemplification | Z | $N^+R^5R^6R^7$ |
| 1A4148 | sp-15 | an-1 | 1U4148 | sp-14 | an-1 | 1A5279 | sp-19 | an-1 |
| 1A4149 | sp-15 | an-2 | 1U4149 | sp-14 | an-2 | 1A5280 | sp-19 | an-2 |
| 1A4150 | sp-15 | an-3 | 1U4150 | sp-14 | an-3 | 1A5281 | sp-19 | an-3 |
| 1A4151 | sp-15 | an-4 | 1U4151 | sp-14 | an-4 | 1A5282 | sp-19 | an-4 |
| 1A4152 | sp-15 | an-5 | 1U4152 | sp-14 | an-5 | 1A5283 | sp-19 | an-5 |
| 1A4153 | sp-15 | an-6 | 1U4153 | sp-14 | an-6 | 1A5284 | sp-19 | an-6 |
| 1A4154 | sp-15 | an-7 | 1U4154 | sp-14 | an-7 | 1A5285 | sp-19 | an-7 |
| 1A4155 | sp-15 | an-8 | 1U4155 | sp-14 | an-8 | 1A5286 | sp-19 | an-8 |
| 1A4156 | sp-15 | an-9 | 1U4156 | sp-14 | an-9 | 1A5287 | sp-19 | an-9 |
| 1A4157 | sp-15 | an-10 | 1U4157 | sp-14 | an-10 | 1A5288 | sp-19 | an-10 |
| 1A4158 | sp-15 | an-11 | 1U4158 | sp-14 | an-11 | 1A5289 | sp-19 | an-11 |
| 1A4159 | sp-15 | an-12 | 1U4159 | sp-14 | an-12 | 1A5290 | sp-19 | an-12 |
| 1A4160 | sp-15 | an-13 | 1U4160 | sp-14 | an-13 | 1A5291 | sp-19 | an-13 |
| 1A4161 | sp-15 | an-14 | 1U4161 | sp-14 | an-14 | 1A5292 | sp-19 | an-14 |
| 1A4162 | sp-15 | an-15 | 1U4162 | sp-14 | an-15 | 1A5293 | sp-19 | an-15 |
| 1A4163 | sp-15 | an-16 | 1U4163 | sp-14 | an-16 | 1A5294 | sp-19 | an-16 |
| 1A4164 | sp-15 | an-17 | 1U4164 | sp-14 | an-17 | 1A5295 | sp-19 | an-17 |
| 1A4165 | sp-15 | an-18 | 1U4165 | sp-14 | an-18 | 1A5296 | sp-19 | an-18 |
| 1A4166 | sp-15 | an-19 | 1U4166 | sp-14 | an-19 | 1A5297 | sp-19 | an-19 |
| 1A4167 | sp-15 | an-20 | 1U4167 | sp-14 | an-20 | 1A5298 | sp-19 | an-20 |
| 1A4168 | sp-15 | an-21 | 1U4168 | sp-14 | an-21 | 1A5299 | sp-19 | an-21 |
| 1A4169 | sp-15 | an-22 | 1U4169 | sp-14 | an-22 | 1A5300 | sp-19 | an-22 |
| 1A4170 | sp-15 | an-23 | 1U4170 | sp-14 | an-23 | 1A5301 | sp-19 | an-23 |
| 1A4171 | sp-15 | an-24 | 1U4171 | sp-14 | an-24 | 1A5302 | sp-19 | an-24 |
| 1A4172 | sp-15 | an-25 | 1U4172 | sp-14 | an-25 | 1A5303 | sp-19 | an-25 |
| 1A4173 | sp-15 | an-26 | 1U4173 | sp-14 | an-26 | 1A5304 | sp-19 | an-26 |
| 1A4174 | sp-15 | an-27 | 1U4174 | sp-14 | an-27 | 1A5305 | sp-19 | an-27 |
| 1A4175 | sp-15 | an-28 | 1U4175 | sp-14 | an-28 | 1A5306 | sp-19 | an-28 |
| 1A4176 | sp-15 | an-29 | 1U4176 | sp-14 | an-29 | 1A5307 | sp-19 | an-29 |
| 1A4177 | sp-15 | an-30 | 1U4177 | sp-14 | an-30 | 1A5308 | sp-19 | an-30 |
| 1A4178 | sp-15 | an-31 | 1U4178 | sp-14 | an-31 | 1A5309 | sp-19 | an-31 |
| 1A4179 | sp-15 | an-32 | 1U4179 | sp-14 | an-32 | 1A5310 | sp-19 | an-32 |
| 1A4180 | sp-15 | an-33 | 1U4180 | sp-14 | an-33 | 1A5311 | sp-19 | an-33 |
| 1A4181 | sp-15 | an-34 | 1U4181 | sp-14 | an-34 | 1A5312 | sp-19 | an-34 |
| 1A4182 | sp-15 | an-35 | 1U4182 | sp-14 | an-35 | 1A5313 | sp-19 | an-35 |
| 1A4183 | sp-15 | an-36 | 1U4183 | sp-14 | an-36 | 1A5314 | sp-19 | an-36 |
| 1A4184 | sp-15 | an-37 | 1U4184 | sp-14 | an-37 | 1A5315 | sp-19 | an-37 |
| 1A4185 | sp-15 | an-38 | 1U4185 | sp-14 | an-38 | 1A5316 | sp-19 | an-38 |
| 1A4186 | sp-15 | an-39 | 1U4186 | sp-14 | an-39 | 1A5317 | sp-19 | an-39 |
| 1A4187 | sp-15 | an-40 | 1U4187 | sp-14 | an-40 | 1A5318 | sp-19 | an-40 |
| 1A4188 | sp-15 | an-41 | 1U4188 | sp-14 | an-41 | 1A5319 | sp-19 | an-41 |
| 1A4189 | sp-15 | an-42 | 1U4189 | sp-14 | an-42 | 1A5320 | sp-19 | an-42 |
| 1A4190 | sp-15 | an-43 | 1U4190 | sp-14 | an-43 | 1A5321 | sp-19 | an-43 |
| 1A4191 | sp-15 | an-44 | 1U4191 | sp-14 | an-44 | 1A5322 | sp-19 | an-44 |
| 1A4192 | sp-15 | an-45 | 1U4192 | sp-14 | an-45 | 1A5323 | sp-19 | an-45 |
| 1A4193 | sp-15 | an-46 | 1U4193 | sp-14 | an-46 | 1A5324 | sp-19 | an-46 |
| 1A4194 | sp-15 | an-47 | 1U4194 | sp-14 | an-47 | 1A5325 | sp-19 | an-47 |
| 1A4195 | sp-15 | an-48 | 1U4195 | sp-14 | an-48 | 1A5326 | sp-19 | an-48 |
| 1A4196 | sp-15 | an-49 | 1U4196 | sp-14 | an-49 | 1A5327 | sp-19 | an-49 |

TABLE 1-continued

| 1A4197 | sp-15 | an-50 | 1U4197 | sp-14 | an-50 | 1A5328 | sp-19 | an-50 |
| 1A4198 | sp-15 | an-51 | 1U4198 | sp-14 | an-51 | 1A5329 | sp-19 | an-51 |

| Y = NHCS | | | Y = NHCSNH | | | Y = NHCSO | | |
| --- | --- | --- | --- | --- | --- | --- | --- | --- |
| Exemplification | Z | $N^+R^5R^6R^7$ | Exemplification | Z | $N^+R^5R^6R^7$ | Exemplification | Z | $N^+R^5R^6R^7$ |
| 1A4199 | sp-15 | an-52 | 1U4199 | sp-14 | an-52 | 1A5330 | sp-19 | an-52 |
| 1A4200 | sp-15 | an-53 | 1U4200 | sp-14 | an-53 | 1A5331 | sp-19 | an-53 |
| 1A4201 | sp-15 | an-54 | 1U4201 | sp-14 | an-54 | 1A5332 | sp-19 | an-54 |
| 1A4202 | sp-15 | an-55 | 1U4202 | sp-14 | an-55 | 1A5333 | sp-19 | an-55 |
| 1A4203 | sp-15 | an-56 | 1U4203 | sp-14 | an-56 | 1A5334 | sp-19 | an-56 |
| 1A4204 | sp-15 | an-57 | 1U4204 | sp-14 | an-57 | 1A5335 | sp-19 | an-57 |
| 1A4205 | sp-15 | an-58 | 1U4205 | sp-14 | an-58 | 1A5336 | sp-19 | an-58 |
| 1A4206 | sp-15 | an-59 | 1U4206 | sp-14 | an-59 | 1A5337 | sp-19 | an-59 |
| 1A4207 | sp-15 | an-60 | 1U4207 | sp-14 | an-60 | 1A5338 | sp-19 | an-60 |
| 1A4208 | sp-15 | an-61 | 1U4208 | sp-14 | an-61 | 1A5339 | sp-19 | an-61 |
| 1A4209 | sp-15 | an-62 | 1U4209 | sp-14 | an-62 | 1A5340 | sp-19 | an-62 |
| 1A4210 | sp-15 | an-63 | 1U4210 | sp-14 | an-63 | 1A5341 | sp-19 | an-63 |
| 1A4211 | sp-15 | an-64 | 1U4211 | sp-14 | an-64 | 1A5342 | sp-19 | an-64 |
| 1A4212 | sp-15 | an-65 | 1U4212 | sp-14 | an-65 | 1A5343 | sp-19 | an-65 |
| 1A4213 | sp-15 | an-66 | 1U4213 | sp-14 | an-66 | 1A5344 | sp-19 | an-66 |
| 1A4214 | sp-15 | an-67 | 1U4214 | sp-14 | an-67 | 1A5345 | sp-19 | an-67 |
| 1A4215 | sp-15 | an-68 | 1U4215 | sp-14 | an-68 | 1A5346 | sp-19 | an-68 |
| 1A4216 | sp-15 | an-69 | 1U4216 | sp-14 | an-69 | 1A5347 | sp-19 | an-69 |
| 1A4217 | sp-15 | an-70 | 1U4217 | sp-14 | an-70 | 1A5348 | sp-19 | an-70 |
| 1A4218 | sp-15 | an-71 | 1U4218 | sp-14 | an-71 | 1A5349 | sp-19 | an-71 |
| 1A4219 | sp-15 | an-72 | 1U4219 | sp-14 | an-72 | 1A5350 | sp-19 | an-72 |
| 1A4220 | sp-15 | an-73 | 1U4220 | sp-14 | an-73 | 1A5351 | sp-19 | an-73 |
| 1A4221 | sp-15 | an-74 | 1U4221 | sp-14 | an-74 | 1A5352 | sp-19 | an-74 |
| 1A4222 | sp-15 | an-75 | 1U4222 | sp-14 | an-75 | 1A5353 | sp-19 | an-75 |
| 1A4223 | sp-15 | an-76 | 1U4223 | sp-14 | an-76 | 1A5354 | sp-19 | an-76 |
| 1A4224 | sp-15 | an-77 | 1U4224 | sp-14 | an-77 | 1A5355 | sp-19 | an-77 |
| 1A4225 | sp-15 | an-78 | 1U4225 | sp-14 | an-78 | 1A5356 | sp-19 | an-78 |
| 1A4226 | sp-15 | an-79 | 1U4226 | sp-14 | an-79 | 1A5357 | sp-19 | an-79 |
| 1A4227 | sp-15 | an-80 | 1U4227 | sp-14 | an-80 | 1A5358 | sp-19 | an-80 |
| 1A4228 | sp-15 | an-81 | 1U4228 | sp-14 | an-81 | 1A5359 | sp-19 | an-81 |
| 1A4229 | sp-15 | an-82 | 1U4229 | sp-14 | an-82 | 1A5360 | sp-19 | an-82 |
| 1A4230 | sp-15 | an-83 | 1U4230 | sp-14 | an-83 | 1A5361 | sp-19 | an-83 |
| 1A4231 | sp-15 | an-84 | 1U4231 | sp-14 | an-84 | 1A5362 | sp-19 | an-84 |
| 1A4232 | sp-15 | an-85 | 1U4232 | sp-14 | an-85 | 1A5363 | sp-19 | an-85 |
| 1A4233 | sp-15 | an-86 | 1U4233 | sp-14 | an-86 | 1A5364 | sp-19 | an-86 |
| 1A4234 | sp-15 | an-87 | 1U4234 | sp-14 | an-87 | 1A5365 | sp-19 | an-87 |
| 1A4235 | sp-15 | an-88 | 1U4235 | sp-14 | an-88 | 1A5366 | sp-19 | an-88 |
| 1A4236 | sp-15 | an-89 | 1U4236 | sp-14 | an-89 | 1A5367 | sp-19 | an-89 |
| 1A4237 | sp-15 | an-90 | 1U4237 | sp-14 | an-90 | 1A5368 | sp-19 | an-90 |
| 1A4238 | sp-15 | an-91 | 1U4238 | sp-14 | an-91 | 1A5369 | sp-19 | an-91 |
| 1A4239 | sp-15 | an-92 | 1U4239 | sp-14 | an-92 | 1A5370 | sp-19 | an-92 |
| 1A4240 | sp-15 | an-93 | 1U4240 | sp-14 | an-93 | 1A5371 | sp-19 | an-93 |
| 1A4241 | sp-15 | an-94 | 1U4241 | sp-14 | an-94 | 1A5372 | sp-19 | an-94 |
| 1A4242 | sp-15 | an-95 | 1U4242 | sp-14 | an-95 | 1A5373 | sp-19 | an-95 |
| 1A4243 | sp-15 | an-96 | 1U4243 | sp-14 | an-96 | 1A5374 | sp-19 | an-96 |
| 1A4244 | sp-15 | an-97 | 1U4244 | sp-14 | an-97 | 1A5375 | sp-19 | an-97 |
| 1A4245 | sp-15 | an-98 | 1U4245 | sp-14 | an-98 | 1A5376 | sp-19 | an-98 |
| 1A4246 | sp-15 | an-99 | 1U4246 | sp-14 | an-99 | 1A5377 | sp-19 | an-99 |
| 1A4247 | sp-15 | an-100 | 1U4247 | sp-14 | an-100 | 1A5378 | sp-19 | an-100 |
| 1A4248 | sp-15 | an-101 | 1U4248 | sp-14 | an-101 | 1A5379 | sp-19 | an-101 |
| 1A4249 | sp-15 | an-102 | 1U4249 | sp-14 | an-102 | 1A5380 | sp-19 | an-102 |
| 1A4250 | sp-15 | an-103 | 1U4250 | sp-14 | an-103 | 1A5381 | sp-19 | an-103 |
| 1A4251 | sp-15 | an-104 | 1U4251 | sp-14 | an-104 | 1A5382 | sp-19 | an-104 |
| 1A4252 | sp-15 | an-105 | 1U4252 | sp-14 | an-105 | 1A5383 | sp-19 | an-105 |
| 1A4253 | sp-15 | an-106 | 1U4253 | sp-14 | an-106 | 1A5384 | sp-19 | an-106 |
| 1A4254 | sp-15 | an-107 | 1U4254 | sp-14 | an-107 | 1A5385 | sp-19 | an-107 |
| 1A4255 | sp-15 | an-108 | 1U4255 | sp-14 | an-108 | 1A5386 | sp-19 | an-108 |
| 1A4256 | sp-15 | an-109 | 1U4256 | sp-14 | an-109 | 1A5387 | sp-19 | an-109 |
| 1A4257 | sp-15 | an-110 | 1U4257 | sp-14 | an-110 | 1A5388 | sp-19 | an-110 |
| 1A4258 | sp-15 | an-111 | 1U4258 | sp-14 | an-111 | 1A5389 | sp-19 | an-111 |
| 1A4259 | sp-15 | an-112 | 1U4259 | sp-14 | an-112 | 1A5390 | sp-19 | an-112 |
| 1A4260 | sp-15 | an-113 | 1U4260 | sp-14 | an-113 | 1A5391 | sp-19 | an-113 |
| 1A4261 | sp-15 | an-114 | 1U4261 | sp-14 | an-114 | 1A5392 | sp-19 | an-114 |
| 1A4262 | sp-15 | an-115 | 1U4262 | sp-14 | an-115 | 1A5393 | sp-19 | an-115 |
| 1A4263 | sp-15 | an-116 | 1U4263 | sp-14 | an-116 | 1A5394 | sp-19 | an-116 |
| 1A4264 | sp-15 | an-117 | 1U4264 | sp-14 | an-117 | 1A5395 | sp-19 | an-117 |
| 1A4265 | sp-15 | an-118 | 1U4265 | sp-14 | an-118 | 1A5396 | sp-19 | an-118 |
| 1A4266 | sp-15 | an-119 | 1U4266 | sp-14 | an-119 | 1A5397 | sp-19 | an-119 |
| 1A4267 | sp-15 | an-120 | 1U4267 | sp-14 | an-120 | 1A5398 | sp-19 | an-120 |
| 1A4268 | sp-15 | an-121 | 1U4268 | sp-14 | an-121 | 1A5399 | sp-19 | an-121 |
| 1A4269 | sp-15 | an-122 | 1U4269 | sp-14 | an-122 | 1A5400 | sp-19 | an-122 |

TABLE 1-continued

| | | | | | | | | |
|---|---|---|---|---|---|---|---|---|
| 1A4270 | sp-15 | an-123 | 1U4270 | sp-14 | an-123 | 1A5401 | sp-19 | an-123 |
| 1A4271 | sp-15 | an-124 | 1U4271 | sp-14 | an-124 | 1A5402 | sp-19 | an-124 |
| 1A4272 | sp-15 | an-125 | 1U4272 | sp-14 | an-125 | 1A5403 | sp-19 | an-125 |
| 1A4273 | sp-15 | an-126 | 1U4273 | sp-14 | an-126 | 1A5404 | sp-19 | an-126 |
| 1A4274 | sp-15 | an-127 | 1U4274 | sp-14 | an-127 | 1A5405 | sp-19 | an-127 |
| 1A4275 | sp-15 | an-128 | 1U4275 | sp-14 | an-128 | 1A5406 | sp-19 | an-128 |
| 1A4276 | sp-15 | an-129 | 1U4276 | sp-14 | an-129 | 1A5407 | sp-19 | an-129 |
| 1A4277 | sp-15 | an-130 | 1U4277 | sp-14 | an-130 | 1A5408 | sp-19 | an-130 |
| 1A4278 | sp-15 | an-131 | 1U4278 | sp-14 | an-131 | 1A5409 | sp-19 | an-131 |
| 1A4279 | sp-15 | an-132 | 1U4279 | sp-14 | an-132 | 1A5410 | sp-19 | an-132 |
| 1A4280 | sp-15 | an-133 | 1U4280 | sp-14 | an-133 | 1A5411 | sp-19 | an-133 |
| 1A4281 | sp-15 | an-134 | 1U4281 | sp-14 | an-134 | 1A5412 | sp-19 | an-134 |
| 1A4282 | sp-15 | an-135 | 1U4282 | sp-14 | an-135 | 1A5413 | sp-19 | an-135 |
| 1A4283 | sp-15 | an-136 | 1U4283 | sp-14 | an-136 | 1A5414 | sp-19 | an-136 |
| 1A4284 | sp-15 | an-137 | 1U4284 | sp-14 | an-137 | 1A5415 | sp-19 | an-137 |
| 1A4285 | sp-15 | an-138 | 1U4285 | sp-14 | an-138 | 1A5416 | sp-19 | an-138 |
| 1A4286 | sp-15 | an-139 | 1U4286 | sp-14 | an-139 | 1A5417 | sp-19 | an-139 |
| 1A4287 | sp-15 | an-140 | 1U4287 | sp-14 | an-140 | 1A5418 | sp-19 | an-140 |
| 1A4288 | sp-15 | an-141 | 1U4288 | sp-14 | an-141 | 1A5419 | sp-19 | an-141 |
| 1A4289 | sp-15 | an-142 | 1U4289 | sp-14 | an-142 | 1A5420 | sp-19 | an-142 |
| 1A4290 | sp-15 | an-143 | 1U4290 | sp-14 | an-143 | 1A5421 | sp-19 | an-143 |
| 1A4291 | sp-15 | an-144 | 1U4291 | sp-14 | an-144 | 1A5422 | sp-19 | an-144 |
| 1A4292 | sp-15 | an-145 | 1U4292 | sp-14 | an-145 | 1A5423 | sp-19 | an-145 |
| 1A4293 | sp-15 | an-146 | 1U4293 | sp-14 | an-146 | 1A5424 | sp-19 | an-146 |
| 1A4294 | sp-15 | an-147 | 1U4294 | sp-14 | an-147 | 1A5425 | sp-19 | an-147 |
| 1A4295 | sp-15 | an-148 | 1U4295 | sp-14 | an-148 | 1A5426 | sp-19 | an-148 |
| 1A4296 | sp-15 | an-149 | 1U4296 | sp-14 | an-149 | 1A5427 | sp-19 | an-149 |
| 1A4297 | sp-15 | an-150 | 1U4297 | sp-14 | an-150 | 1A5428 | sp-19 | an-150 |
| 1A4298 | sp-15 | an-151 | 1U4298 | sp-14 | an-151 | 1A5429 | sp-19 | an-151 |
| 1A4299 | sp-15 | an-152 | 1U4299 | sp-14 | an-152 | 1A5430 | sp-19 | an-152 |
| 1A4300 | sp-15 | an-153 | 1U4300 | sp-14 | an-153 | 1A5431 | sp-19 | an-153 |
| 1A4301 | sp-15 | an-154 | 1U4301 | sp-14 | an-154 | 1A5432 | sp-19 | an-154 |
| 1A4302 | sp-15 | an-155 | 1U4302 | sp-14 | an-155 | 1A5433 | sp-19 | an-155 |
| 1A4303 | sp-15 | an-156 | 1U4303 | sp-14 | an-156 | 1A5434 | sp-19 | an-156 |
| 1A4304 | sp-15 | an-157 | 1U4304 | sp-14 | an-157 | 1A5435 | sp-19 | an-157 |
| 1A4305 | sp-15 | an-158 | 1U4305 | sp-14 | an-158 | 1A5436 | sp-19 | an-158 |
| 1A4306 | sp-15 | an-159 | 1U4306 | sp-14 | an-159 | 1A5437 | sp-19 | an-159 |
| 1A4307 | sp-15 | an-160 | 1U4307 | sp-14 | an-160 | 1A5438 | sp-19 | an-160 |
| 1A4308 | sp-15 | an-161 | 1U4308 | sp-14 | an-161 | 1A5439 | sp-19 | an-161 |
| 1A4309 | sp-15 | an-162 | 1U4309 | sp-14 | an-162 | 1A5440 | sp-19 | an-162 |
| 1A4310 | sp-15 | an-163 | 1U4310 | sp-14 | an-163 | 1A5441 | sp-19 | an-163 |
| 1A4311 | sp-15 | an-164 | 1U4311 | sp-14 | an-164 | 1A5442 | sp-19 | an-164 |
| 1A4312 | sp-15 | an-165 | 1U4312 | sp-14 | an-165 | 1A5443 | sp-19 | an-165 |
| 1A4313 | sp-15 | an-166 | 1U4313 | sp-14 | an-166 | 1A5444 | sp-19 | an-166 |
| 1A4314 | sp-15 | an-167 | 1U4314 | sp-14 | an-167 | 1A5445 | sp-19 | an-167 |
| 1A4315 | sp-15 | an-168 | 1U4315 | sp-14 | an-168 | 1A5446 | sp-19 | an-168 |
| 1A4316 | sp-15 | an-169 | 1U4316 | sp-14 | an-169 | 1A5447 | sp-19 | an-169 |
| 1A4317 | sp-15 | an-170 | 1U4317 | sp-14 | an-170 | 1A5448 | sp-19 | an-170 |
| 1A4318 | sp-15 | an-171 | 1U4318 | sp-14 | an-171 | 1A5449 | sp-19 | an-171 |
| 1A4319 | sp-15 | an-172 | 1U4319 | sp-14 | an-172 | 1A5450 | sp-19 | an-172 |
| 1A4320 | sp-15 | an-173 | 1U4320 | sp-14 | an-173 | 1A5451 | sp-19 | an-173 |
| 1A4321 | sp-15 | an-174 | 1U4321 | sp-14 | an-174 | 1A5452 | sp-19 | an-174 |
| 1A4322 | sp-15 | an-175 | 1U4322 | sp-14 | an-175 | 1A5453 | sp-19 | an-175 |
| 1A4323 | sp-15 | an-176 | 1U4323 | sp-14 | an-176 | 1A5454 | sp-19 | an-176 |
| 1A4324 | sp-15 | an-177 | 1U4324 | sp-14 | an-177 | 1A5455 | sp-19 | an-177 |
| 1A4325 | sp-15 | an-178 | 1U4325 | sp-14 | an-178 | 1A5456 | sp-19 | an-178 |
| 1A4326 | sp-15 | an-179 | 1U4326 | sp-14 | an-179 | 1A5457 | sp-19 | an-179 |
| 1A4327 | sp-15 | an-180 | 1U4327 | sp-14 | an-180 | 1A5458 | sp-19 | an-180 |
| 1A4328 | sp-15 | an-181 | 1U4328 | sp-14 | an-181 | 1A5459 | sp-19 | an-181 |
| 1A4329 | sp-15 | an-182 | 1U4329 | sp-14 | an-182 | 1A5460 | sp-19 | an-182 |
| 1A4330 | sp-15 | an-183 | 1U4330 | sp-14 | an-183 | 1A5461 | sp-19 | an-183 |
| 1A4331 | sp-15 | an-184 | 1U4331 | sp-14 | an-184 | 1A5462 | sp-19 | an-184 |
| 1A4332 | sp-15 | an-185 | 1U4332 | sp-14 | an-185 | 1A5463 | sp-19 | an-185 |
| 1A4333 | sp-15 | an-186 | 1U4333 | sp-14 | an-186 | 1A5464 | sp-19 | an-186 |
| 1A4334 | sp-15 | an-187 | 1U4334 | sp-14 | an-187 | 1A5465 | sp-19 | an-187 |
| 1A4335 | sp-15 | an-188 | 1U4335 | sp-14 | an-188 | 1A5466 | sp-19 | an-188 |
| 1A4336 | sp-15 | an-189 | 1U4336 | sp-14 | an-189 | 1A5467 | sp-19 | an-189 |
| 1A4337 | sp-15 | an-190 | 1U4337 | sp-14 | an-190 | 1A5468 | sp-19 | an-190 |
| 1A4338 | sp-15 | an-191 | 1U4338 | sp-14 | an-191 | 1A5469 | sp-19 | an-191 |
| 1A4339 | sp-15 | an-192 | 1U4339 | sp-14 | an-192 | 1A5470 | sp-19 | an-192 |
| 1A4340 | sp-15 | an-193 | 1U4340 | sp-14 | an-193 | 1A5471 | sp-19 | an-193 |
| 1A4341 | sp-15 | an-194 | 1U4341 | sp-14 | an-194 | 1A5472 | sp-19 | an-194 |
| 1A4342 | sp-15 | an-195 | 1U4342 | sp-14 | an-195 | 1A5473 | sp-19 | an-195 |
| 1A4343 | sp-15 | an-196 | 1U4343 | sp-14 | an-196 | 1A5474 | sp-19 | an-196 |
| 1A4344 | sp-15 | an-197 | 1U4344 | sp-14 | an-197 | 1A5475 | sp-19 | an-197 |
| 1A4345 | sp-15 | an-198 | 1U4345 | sp-14 | an-198 | 1A5476 | sp-19 | an-198 |
| 1A4346 | sp-15 | an-199 | 1U4346 | sp-14 | an-199 | 1A5477 | sp-19 | an-199 |
| 1A4347 | sp-15 | an-200 | 1U4347 | sp-14 | an-200 | 1A5478 | sp-19 | an-200 |
| 1A4348 | sp-15 | an-201 | 1U4348 | sp-14 | an-201 | 1A5479 | sp-19 | an-201 |

TABLE 1-continued

| | | | | | | | | |
|---|---|---|---|---|---|---|---|---|
| 1A4349 | sp-15 | an-202 | 1U4349 | sp-14 | an-202 | 1A5480 | sp-19 | an-202 |
| 1A4350 | sp-15 | an-203 | 1U4350 | sp-14 | an-203 | 1A5481 | sp-19 | an-203 |
| 1A4351 | sp-15 | an-204 | 1U4351 | sp-14 | an-204 | 1A5482 | sp-19 | an-204 |
| 1A4352 | sp-15 | an-205 | 1U4352 | sp-14 | an-205 | 1A5483 | sp-19 | an-205 |
| 1A4353 | sp-15 | an-206 | 1U4353 | sp-14 | an-206 | 1A5484 | sp-19 | an-206 |
| 1A4354 | sp-15 | an-207 | 1U4354 | sp-14 | an-207 | 1A5485 | sp-19 | an-207 |
| 1A4355 | sp-15 | an-208 | 1U4355 | sp-14 | an-208 | 1A5486 | sp-19 | an-208 |
| 1A4356 | sp-15 | an-209 | 1U4356 | sp-14 | an-209 | 1A5487 | sp-19 | an-209 |
| 1A4357 | sp-15 | an-210 | 1U4357 | sp-14 | an-210 | 1A5488 | sp-19 | an-210 |
| 1A4358 | sp-15 | an-211 | 1U4358 | sp-14 | an-211 | 1A5489 | sp-19 | an-211 |
| 1A4359 | sp-15 | an-212 | 1U4359 | sp-14 | an-212 | 1A5490 | sp-19 | an-212 |
| 1A4360 | sp-15 | an-213 | 1U4360 | sp-14 | an-213 | 1A5491 | sp-19 | an-213 |
| 1A4361 | sp-15 | an-214 | 1U4361 | sp-14 | an-214 | 1A5492 | sp-19 | an-214 |
| 1A4362 | sp-15 | an-215 | 1U4362 | sp-14 | an-215 | 1A5493 | sp-19 | an-215 |
| 1A4363 | sp-15 | an-216 | 1U4363 | sp-14 | an-216 | 1A5494 | sp-19 | an-216 |
| 1A4364 | sp-15 | an-217 | 1U4364 | sp-14 | an-217 | 1A5495 | sp-19 | an-217 |
| 1A4365 | sp-15 | an-218 | 1U4365 | sp-14 | an-218 | 1A5496 | sp-19 | an-218 |
| 1A4366 | sp-15 | an-219 | 1U4366 | sp-14 | an-219 | 1A5497 | sp-19 | an-219 |
| 1A4367 | sp-15 | an-220 | 1U4367 | sp-14 | an-220 | 1A5498 | sp-19 | an-220 |
| 1A4368 | sp-15 | an-221 | 1U4368 | sp-14 | an-221 | 1A5499 | sp-19 | an-221 |
| 1A4369 | sp-15 | an-222 | 1U4369 | sp-14 | an-222 | 1A5500 | sp-19 | an-222 |
| 1A4370 | sp-15 | an-223 | 1U4370 | sp-14 | an-223 | 1A5501 | sp-19 | an-223 |
| 1A4371 | sp-15 | an-224 | 1U4371 | sp-14 | an-224 | 1A5502 | sp-19 | an-224 |
| 1A4372 | sp-15 | an-225 | 1U4372 | sp-14 | an-225 | 1A5503 | sp-19 | an-225 |
| 1A4373 | sp-15 | an-226 | 1U4373 | sp-14 | an-226 | 1A5504 | sp-19 | an-226 |
| 1A4374 | sp-15 | an-227 | 1U4374 | sp-14 | an-227 | 1A5505 | sp-19 | an-227 |
| 1A4375 | sp-15 | an-228 | 1U4375 | sp-14 | an-228 | 1A5506 | sp-19 | an-228 |
| 1A4376 | sp-15 | an-229 | 1U4376 | sp-14 | an-229 | 1A5507 | sp-19 | an-229 |
| 1A4377 | sp-15 | an-230 | 1U4377 | sp-14 | an-230 | 1A5508 | sp-19 | an-230 |
| 1A4378 | sp-15 | an-231 | 1U4378 | sp-14 | an-231 | 1A5509 | sp-19 | an-231 |
| 1A4379 | sp-15 | an-232 | 1U4379 | sp-14 | an-232 | 1A5510 | sp-19 | an-232 |
| 1A4380 | sp-15 | an-233 | 1U4380 | sp-14 | an-233 | 1A5511 | sp-19 | an-233 |
| 1A4381 | sp-15 | an-234 | 1U4381 | sp-14 | an-234 | 1A5512 | sp-19 | an-234 |
| 1A4382 | sp-15 | an-235 | 1U4382 | sp-14 | an-235 | 1A5513 | sp-19 | an-235 |
| 1A4383 | sp-15 | an-236 | 1U4383 | sp-14 | an-236 | 1A5514 | sp-19 | an-236 |
| 1A4384 | sp-15 | an-237 | 1U4384 | sp-14 | an-237 | 1A5515 | sp-19 | an-237 |
| 1A4385 | sp-15 | an-238 | 1U4385 | sp-14 | an-238 | 1A5516 | sp-19 | an-238 |
| 1A4386 | sp-15 | an-239 | 1U4386 | sp-14 | an-239 | 1A5517 | sp-19 | an-239 |
| 1A4387 | sp-15 | an-240 | 1U4387 | sp-14 | an-240 | 1A5518 | sp-19 | an-240 |
| 1A4388 | sp-15 | an-241 | 1U4388 | sp-14 | an-241 | 1A5519 | sp-19 | an-241 |
| 1A4389 | sp-15 | an-242 | 1U4389 | sp-14 | an-242 | 1A5520 | sp-19 | an-242 |
| 1A4390 | sp-15 | an-243 | 1U4390 | sp-14 | an-243 | 1A5521 | sp-19 | an-243 |
| 1A4391 | sp-15 | an-244 | 1U4391 | sp-14 | an-244 | 1A5522 | sp-19 | an-244 |
| 1A4392 | sp-15 | an-245 | 1U4392 | sp-14 | an-245 | 1A5523 | sp-19 | an-245 |
| 1A4393 | sp-15 | an-246 | 1U4393 | sp-14 | an-246 | 1A5524 | sp-19 | an-246 |
| 1A4394 | sp-15 | an-247 | 1U4394 | sp-14 | an-247 | 1A5525 | sp-19 | an-247 |
| 1A4395 | sp-15 | an-248 | 1U4395 | sp-14 | an-248 | 1A5526 | sp-19 | an-248 |
| 1A4396 | sp-15 | an-249 | 1U4396 | sp-14 | an-249 | 1A5527 | sp-19 | an-249 |
| 1A4397 | sp-15 | an-250 | 1U4397 | sp-14 | an-250 | 1A5528 | sp-19 | an-250 |
| 1A4398 | sp-15 | an-251 | 1U4398 | sp-14 | an-251 | 1A5529 | sp-19 | an-251 |
| 1A4399 | sp-15 | an-252 | 1U4399 | sp-14 | an-252 | 1A5530 | sp-19 | an-252 |
| 1A4400 | sp-15 | an-253 | 1U4400 | sp-14 | an-253 | 1A5531 | sp-19 | an-253 |
| 1A4401 | sp-15 | an-254 | 1U4401 | sp-14 | an-254 | 1A5532 | sp-19 | an-254 |
| 1A4402 | sp-15 | an-255 | 1U4402 | sp-14 | an-255 | 1A5533 | sp-19 | an-255 |
| 1A4403 | sp-15 | an-256 | 1U4403 | sp-14 | an-256 | 1A5534 | sp-19 | an-256 |
| 1A4404 | sp-15 | an-257 | 1U4404 | sp-14 | an-257 | 1A5535 | sp-19 | an-257 |
| 1A4405 | sp-15 | an-258 | 1U4405 | sp-14 | an-258 | 1A5536 | sp-19 | an-258 |
| 1A4406 | sp-15 | an-259 | 1U4406 | sp-14 | an-259 | 1A5537 | sp-19 | an-259 |
| 1A4407 | sp-15 | an-260 | 1U4407 | sp-14 | an-260 | 1A5538 | sp-19 | an-260 |
| 1A4408 | sp-15 | an-261 | 1U4408 | sp-14 | an-261 | 1A5539 | sp-19 | an-261 |
| 1A4409 | sp-15 | an-262 | 1U4409 | sp-14 | an-262 | 1A5540 | sp-19 | an-262 |
| 1A4410 | sp-15 | an-263 | 1U4410 | sp-14 | an-263 | 1A5541 | sp-19 | an-263 |
| 1A4411 | sp-15 | an-264 | 1U4411 | sp-14 | an-264 | 1A5542 | sp-19 | an-264 |
| 1A4412 | sp-15 | an-265 | 1U4412 | sp-14 | an-265 | 1A5543 | sp-19 | an-265 |
| 1A4413 | sp-15 | an-266 | 1U4413 | sp-14 | an-266 | 1A5544 | sp-19 | an-266 |
| 1A4414 | sp-15 | an-267 | 1U4414 | sp-14 | an-267 | 1A5545 | sp-19 | an-267 |
| 1A4415 | sp-15 | an-268 | 1U4415 | sp-14 | an-268 | 1A5546 | sp-19 | an-268 |
| 1A4416 | sp-15 | an-269 | 1U4416 | sp-14 | an-269 | 1A5547 | sp-19 | an-269 |
| 1A4417 | sp-15 | an-270 | 1U4417 | sp-14 | an-270 | 1A5548 | sp-19 | an-270 |
| 1A4418 | sp-15 | an-271 | 1U4418 | sp-14 | an-271 | 1A5549 | sp-19 | an-271 |
| 1A4419 | sp-15 | an-272 | 1U4419 | sp-14 | an-272 | 1A5550 | sp-19 | an-272 |
| 1A4420 | sp-15 | an-273 | 1U4420 | sp-14 | an-273 | 1A5551 | sp-19 | an-273 |
| 1A4421 | sp-15 | an-274 | 1U4421 | sp-14 | an-274 | 1A5552 | sp-19 | an-274 |
| 1A4422 | sp-15 | an-275 | 1U4422 | sp-14 | an-275 | 1A5553 | sp-19 | an-275 |
| 1A4423 | sp-15 | an-276 | 1U4423 | sp-14 | an-276 | 1A5554 | sp-19 | an-276 |
| 1A4424 | sp-15 | an-277 | 1U4424 | sp-14 | an-277 | 1A5555 | sp-19 | an-277 |
| 1A4425 | sp-15 | an-278 | 1U4425 | sp-14 | an-278 | 1A5556 | sp-19 | an-278 |
| 1A4426 | sp-15 | an-279 | 1U4426 | sp-14 | an-279 | 1A5557 | sp-19 | an-279 |
| 1A4427 | sp-15 | an-280 | 1U4427 | sp-14 | an-280 | 1A5558 | sp-19 | an-280 |

TABLE 1-continued

| | | | | | | | | |
|---|---|---|---|---|---|---|---|---|
| 1A4428 | sp-15 | an-281 | 1U4428 | sp-14 | an-281 | 1A5559 | sp-19 | an-281 |
| 1A4429 | sp-15 | an-282 | 1U4429 | sp-14 | an-282 | 1A5560 | sp-19 | an-282 |
| 1A4430 | sp-15 | an-283 | 1U4430 | sp-14 | an-283 | 1A5561 | sp-19 | an-283 |
| 1A4431 | sp-15 | an-284 | 1U4431 | sp-14 | an-284 | 1A5562 | sp-19 | an-284 |
| 1A4432 | sp-15 | an-285 | 1U4432 | sp-14 | an-285 | 1A5563 | sp-19 | an-285 |
| 1A4433 | sp-15 | an-286 | 1U4433 | sp-14 | an-286 | 1A5564 | sp-19 | an-286 |
| 1A4434 | sp-15 | an-287 | 1U4434 | sp-14 | an-287 | 1A5565 | sp-19 | an-287 |
| 1A4435 | sp-15 | an-288 | 1U4435 | sp-14 | an-288 | 1A5566 | sp-19 | an-288 |
| 1A4436 | sp-15 | an-289 | 1U4436 | sp-14 | an-289 | 1A5567 | sp-19 | an-289 |
| 1A4437 | sp-15 | an-290 | 1U4437 | sp-14 | an-290 | 1A5568 | sp-19 | an-290 |
| 1A4438 | sp-15 | an-291 | 1U4438 | sp-14 | an-291 | 1A5569 | sp-19 | an-291 |
| 1A4439 | sp-15 | an-292 | 1U4439 | sp-14 | an-292 | 1A5570 | sp-19 | an-292 |
| 1A4440 | sp-15 | an-293 | 1U4440 | sp-14 | an-293 | 1A5571 | sp-19 | an-293 |
| 1A4441 | sp-15 | an-294 | 1U4441 | sp-14 | an-294 | 1A5572 | sp-19 | an-294 |
| 1A4442 | sp-15 | an-295 | 1U4442 | sp-14 | an-295 | 1A5573 | sp-19 | an-295 |
| 1A4443 | sp-15 | an-296 | 1U4443 | sp-14 | an-296 | 1A5574 | sp-19 | an-296 |
| 1A4444 | sp-15 | an-297 | 1U4444 | sp-14 | an-297 | 1A5575 | sp-19 | an-297 |
| 1A4445 | sp-15 | an-298 | 1U4445 | sp-14 | an-298 | 1A5576 | sp-19 | an-298 |
| 1A4446 | sp-15 | an-299 | 1U4446 | sp-14 | an-299 | 1A5577 | sp-19 | an-299 |
| 1A4447 | sp-15 | an-300 | 1U4447 | sp-14 | an-300 | 1A5578 | sp-19 | an-300 |
| 1A4448 | sp-15 | an-301 | 1U4448 | sp-14 | an-301 | 1A5579 | sp-19 | an-301 |
| 1A4449 | sp-15 | an-302 | 1U4449 | sp-14 | an-302 | 1A5580 | sp-19 | an-302 |
| 1A4450 | sp-15 | an-303 | 1U4450 | sp-14 | an-303 | 1A5581 | sp-19 | an-303 |
| 1A4451 | sp-15 | an-304 | 1U4451 | sp-14 | an-304 | 1A5582 | sp-19 | an-304 |
| 1A4452 | sp-15 | an-305 | 1U4452 | sp-14 | an-305 | 1A5583 | sp-19 | an-305 |
| 1A4453 | sp-15 | an-306 | 1U4453 | sp-14 | an-306 | 1A5584 | sp-19 | an-306 |
| 1A4454 | sp-15 | an-307 | 1U4454 | sp-14 | an-307 | 1A5585 | sp-19 | an-307 |
| 1A4455 | sp-15 | an-308 | 1U4455 | sp-14 | an-308 | 1A5586 | sp-19 | an-308 |
| 1A4456 | sp-15 | an-309 | 1U4456 | sp-14 | an-309 | 1A5587 | sp-19 | an-309 |
| 1A4457 | sp-15 | an-310 | 1U4457 | sp-14 | an-310 | 1A5588 | sp-19 | an-310 |
| 1A4458 | sp-15 | an-311 | 1U4458 | sp-14 | an-311 | 1A5589 | sp-19 | an-311 |
| 1A4459 | sp-15 | an-312 | 1U4459 | sp-14 | an-312 | 1A5590 | sp-19 | an-312 |
| 1A4460 | sp-15 | an-313 | 1U4460 | sp-14 | an-313 | 1A5591 | sp-19 | an-313 |
| 1A4461 | sp-15 | an-314 | 1U4461 | sp-14 | an-314 | 1A5592 | sp-19 | an-314 |
| 1A4462 | sp-15 | an-315 | 1U4462 | sp-14 | an-315 | 1A5593 | sp-19 | an-315 |
| 1A4463 | sp-15 | an-316 | 1U4463 | sp-14 | an-316 | 1A5594 | sp-19 | an-316 |
| 1A4464 | sp-15 | an-317 | 1U4464 | sp-14 | an-317 | 1A5595 | sp-19 | an-317 |
| 1A4465 | sp-15 | an-318 | 1U4465 | sp-14 | an-318 | 1A5596 | sp-19 | an-318 |
| 1A4466 | sp-15 | an-319 | 1U4466 | sp-14 | an-319 | 1A5597 | sp-19 | an-319 |
| 1A4467 | sp-15 | an-320 | 1U4467 | sp-14 | an-320 | 1A5598 | sp-19 | an-320 |
| 1A4468 | sp-15 | an-321 | 1U4468 | sp-14 | an-321 | 1A5599 | sp-19 | an-321 |
| 1A4469 | sp-15 | an-322 | 1U4469 | sp-14 | an-322 | 1A5600 | sp-19 | an-322 |
| 1A4470 | sp-15 | an-323 | 1U4470 | sp-14 | an-323 | 1A5601 | sp-19 | an-323 |
| 1A4471 | sp-15 | an-324 | 1U4471 | sp-14 | an-324 | 1A5602 | sp-19 | an-324 |
| 1A4472 | sp-15 | an-325 | 1U4472 | sp-14 | an-325 | 1A5603 | sp-19 | an-325 |
| 1A4473 | sp-15 | an-326 | 1U4473 | sp-14 | an-326 | 1A5604 | sp-19 | an-326 |
| 1A4474 | sp-15 | an-327 | 1U4474 | sp-14 | an-327 | 1A5605 | sp-19 | an-327 |
| 1A4475 | sp-15 | an-328 | 1U4475 | sp-14 | an-328 | 1A5606 | sp-19 | an-328 |
| 1A4476 | sp-15 | an-329 | 1U4476 | sp-14 | an-329 | 1A5607 | sp-19 | an-329 |
| 1A4477 | sp-15 | an-330 | 1U4477 | sp-14 | an-330 | 1A5608 | sp-19 | an-330 |
| 1A4478 | sp-15 | an-331 | 1U4478 | sp-14 | an-331 | 1A5609 | sp-19 | an-331 |
| 1A4479 | sp-15 | an-332 | 1U4479 | sp-14 | an-332 | 1A5610 | sp-19 | an-332 |
| 1A4480 | sp-15 | an-333 | 1U4480 | sp-14 | an-333 | 1A5611 | sp-19 | an-333 |
| 1A4481 | sp-15 | an-334 | 1U4481 | sp-14 | an-334 | 1A5612 | sp-19 | an-334 |
| 1A4482 | sp-15 | an-335 | 1U4482 | sp-14 | an-335 | 1A5613 | sp-19 | an-335 |
| 1A4483 | sp-15 | an-336 | 1U4483 | sp-14 | an-336 | 1A5614 | sp-19 | an-336 |
| 1A4484 | sp-15 | an-337 | 1U4484 | sp-14 | an-337 | 1A5615 | sp-19 | an-337 |
| 1A4485 | sp-15 | an-338 | 1U4485 | sp-14 | an-338 | 1A5616 | sp-19 | an-338 |
| 1A4486 | sp-15 | an-339 | 1U4486 | sp-14 | an-339 | 1A5617 | sp-19 | an-339 |
| 1A4487 | sp-15 | an-340 | 1U4487 | sp-14 | an-340 | 1A5618 | sp-19 | an-340 |
| 1A4488 | sp-15 | an-341 | 1U4488 | sp-14 | an-341 | 1A5619 | sp-19 | an-341 |
| 1A4489 | sp-15 | an-342 | 1U4489 | sp-14 | an-342 | 1A5620 | sp-19 | an-342 |
| 1A4490 | sp-15 | an-343 | 1U4490 | sp-14 | an-343 | 1A5621 | sp-19 | an-343 |
| 1A4491 | sp-15 | an-344 | 1U4491 | sp-14 | an-344 | 1A5622 | sp-19 | an-344 |
| 1A4492 | sp-15 | an-345 | 1U4492 | sp-14 | an-345 | 1A5623 | sp-19 | an-345 |
| 1A4493 | sp-15 | an-346 | 1U4493 | sp-14 | an-346 | 1A5624 | sp-19 | an-346 |
| 1A4494 | sp-15 | an-347 | 1U4494 | sp-14 | an-347 | 1A5625 | sp-19 | an-347 |
| 1A4495 | sp-15 | an-348 | 1U4495 | sp-14 | an-348 | 1A5626 | sp-19 | an-348 |
| 1A4496 | sp-15 | an-349 | 1U4496 | sp-14 | an-349 | 1A5627 | sp-19 | an-349 |
| 1A4497 | sp-15 | an-350 | 1U4497 | sp-14 | an-350 | 1A5628 | sp-19 | an-350 |
| 1A4498 | sp-15 | an-351 | 1U4498 | sp-14 | an-351 | 1A5629 | sp-19 | an-351 |
| 1A4499 | sp-15 | an-352 | 1U4499 | sp-14 | an-352 | 1A5630 | sp-19 | an-352 |
| 1A4500 | sp-15 | an-353 | 1U4500 | sp-14 | an-353 | 1A5631 | sp-19 | an-353 |
| 1A4501 | sp-15 | an-354 | 1U4501 | sp-14 | an-354 | 1A5632 | sp-19 | an-354 |
| 1A4502 | sp-15 | an-355 | 1U4502 | sp-14 | an-355 | 1A5633 | sp-19 | an-355 |
| 1A4503 | sp-15 | an-356 | 1U4503 | sp-14 | an-356 | 1A5634 | sp-19 | an-356 |
| 1A4504 | sp-15 | an-357 | 1U4504 | sp-14 | an-357 | 1A5635 | sp-19 | an-357 |
| 1A4505 | sp-15 | an-358 | 1U4505 | sp-14 | an-358 | 1A5636 | sp-19 | an-358 |
| 1A4506 | sp-15 | an-359 | 1U4506 | sp-14 | an-359 | 1A5637 | sp-19 | an-359 |

TABLE 1-continued

| | | | | | | | | |
|---|---|---|---|---|---|---|---|---|
| 1A4507 | sp-15 | an-360 | 1U4507 | sp-14 | an-360 | 1A5638 | sp-19 | an-360 |
| 1A4508 | sp-15 | an-361 | 1U4508 | sp-14 | an-361 | 1A5639 | sp-19 | an-361 |
| 1A4509 | sp-15 | an-362 | 1U4509 | sp-14 | an-362 | 1A5640 | sp-19 | an-362 |
| 1A4510 | sp-15 | an-363 | 1U4510 | sp-14 | an-363 | 1A5641 | sp-19 | an-363 |
| 1A4511 | sp-15 | an-364 | 1U4511 | sp-14 | an-364 | 1A5642 | sp-19 | an-364 |
| 1A4512 | sp-15 | an-365 | 1U4512 | sp-14 | an-365 | 1A5643 | sp-19 | an-365 |
| 1A4513 | sp-15 | an-366 | 1U4513 | sp-14 | an-366 | 1A5644 | sp-19 | an-366 |
| 1A4514 | sp-15 | an-367 | 1U4514 | sp-14 | an-367 | 1A5645 | sp-19 | an-367 |
| 1A4515 | sp-15 | an-368 | 1U4515 | sp-14 | an-368 | 1A5646 | sp-19 | an-368 |
| 1A4516 | sp-15 | an-369 | 1U4516 | sp-14 | an-369 | 1A5647 | sp-19 | an-369 |
| 1A4517 | sp-15 | an-370 | 1U4517 | sp-14 | an-370 | 1A5648 | sp-19 | an-370 |
| 1A4518 | sp-15 | an-371 | 1U4518 | sp-14 | an-371 | 1A5649 | sp-19 | an-371 |
| 1A4519 | sp-15 | an-372 | 1U4519 | sp-14 | an-372 | 1A5650 | sp-19 | an-372 |
| 1A4520 | sp-15 | an-373 | 1U4520 | sp-14 | an-373 | 1A5651 | sp-19 | an-373 |
| 1A4521 | sp-15 | an-374 | 1U4521 | sp-14 | an-374 | 1A5652 | sp-19 | an-374 |
| 1A4522 | sp-15 | an-375 | 1U4522 | sp-14 | an-375 | 1A5653 | sp-19 | an-375 |
| 1A4523 | sp-15 | an-376 | 1U4523 | sp-14 | an-376 | 1A5654 | sp-19 | an-376 |
| 1A4524 | sp-15 | an-377 | 1U4524 | sp-14 | an-377 | 1A5655 | sp-19 | an-377 |
| 1A4525 | sp-16 | an-1 | 1U4525 | sp-17 | an-1 | 1A5656 | sp-21 | an-1 |
| 1A4526 | sp-16 | an-2 | 1U4526 | sp-17 | an-2 | 1A5657 | sp-21 | an-2 |
| 1A4527 | sp-16 | an-3 | 1U4527 | sp-17 | an-3 | 1A5658 | sp-21 | an-3 |
| 1A4528 | sp-16 | an-4 | 1U4528 | sp-17 | an-4 | 1A5659 | sp-21 | an-4 |
| 1A4529 | sp-16 | an-5 | 1U4529 | sp-17 | an-5 | 1A5660 | sp-21 | an-5 |
| 1A4530 | sp-16 | an-6 | 1U4530 | sp-17 | an-6 | 1A5661 | sp-21 | an-6 |
| 1A4531 | sp-16 | an-7 | 1U4531 | sp-17 | an-7 | 1A5662 | sp-21 | an-7 |
| 1A4532 | sp-16 | an-8 | 1U4532 | sp-17 | an-8 | 1A5663 | sp-21 | an-8 |
| 1A4533 | sp-16 | an-9 | 1U4533 | sp-17 | an-9 | 1A5664 | sp-21 | an-9 |
| 1A4534 | sp-16 | an-10 | 1U4534 | sp-17 | an-10 | 1A5665 | sp-21 | an-10 |
| 1A4535 | sp-16 | an-11 | 1U4535 | sp-17 | an-11 | 1A5666 | sp-21 | an-11 |
| 1A4536 | sp-16 | an-12 | 1U4536 | sp-17 | an-12 | 1A5667 | sp-21 | an-12 |
| 1A4537 | sp-16 | an-13 | 1U4537 | sp-17 | an-13 | 1A5668 | sp-21 | an-13 |
| 1A4538 | sp-16 | an-14 | 1U4538 | sp-17 | an-14 | 1A5669 | sp-21 | an-14 |
| 1A4539 | sp-16 | an-15 | 1U4539 | sp-17 | an-15 | 1A5670 | sp-21 | an-15 |
| 1A4540 | sp-16 | an-16 | 1U4540 | sp-17 | an-16 | 1A5671 | sp-21 | an-16 |
| 1A4541 | sp-16 | an-17 | 1U4541 | sp-17 | an-17 | 1A5672 | sp-21 | an-17 |
| 1A4542 | sp-16 | an-18 | 1U4542 | sp-17 | an-18 | 1A5673 | sp-21 | an-18 |
| 1A4543 | sp-16 | an-19 | 1U4543 | sp-17 | an-19 | 1A5674 | sp-21 | an-19 |
| 1A4544 | sp-16 | an-20 | 1U4544 | sp-17 | an-20 | 1A5675 | sp-21 | an-20 |
| 1A4545 | sp-16 | an-21 | 1U4545 | sp-17 | an-21 | 1A5676 | sp-21 | an-21 |
| 1A4546 | sp-16 | an-22 | 1U4546 | sp-17 | an-22 | 1A5677 | sp-21 | an-22 |
| 1A4547 | sp-16 | an-23 | 1U4547 | sp-17 | an-23 | 1A5678 | sp-21 | an-23 |
| 1A4548 | sp-16 | an-24 | 1U4548 | sp-17 | an-24 | 1A5679 | sp-21 | an-24 |
| 1A4549 | sp-16 | an-25 | 1U4549 | sp-17 | an-25 | 1A5680 | sp-21 | an-25 |
| 1A4550 | sp-16 | an-26 | 1U4550 | sp-17 | an-26 | 1A5681 | sp-21 | an-26 |
| 1A4551 | sp-16 | an-27 | 1U4551 | sp-17 | an-27 | 1A5682 | sp-21 | an-27 |
| 1A4552 | sp-16 | an-28 | 1U4552 | sp-17 | an-28 | 1A5683 | sp-21 | an-28 |
| 1A4553 | sp-16 | an-29 | 1U4553 | sp-17 | an-29 | 1A5684 | sp-21 | an-29 |
| 1A4554 | sp-16 | an-30 | 1U4554 | sp-17 | an-30 | 1A5685 | sp-21 | an-30 |
| 1A4555 | sp-16 | an-31 | 1U4555 | sp-17 | an-31 | 1A5686 | sp-21 | an-31 |
| 1A4556 | sp-16 | an-32 | 1U4556 | sp-17 | an-32 | 1A5687 | sp-21 | an-32 |
| 1A4557 | sp-16 | an-33 | 1U4557 | sp-17 | an-33 | 1A5688 | sp-21 | an-33 |
| 1A4558 | sp-16 | an-34 | 1U4558 | sp-17 | an-34 | 1A5689 | sp-21 | an-34 |
| 1A4559 | sp-16 | an-35 | 1U4559 | sp-17 | an-35 | 1A5690 | sp-21 | an-35 |
| 1A4560 | sp-16 | an-36 | 1U4560 | sp-17 | an-36 | 1A5691 | sp-21 | an-36 |
| 1A4561 | sp-16 | an-37 | 1U4561 | sp-17 | an-37 | 1A5692 | sp-21 | an-37 |
| 1A4562 | sp-16 | an-38 | 1U4562 | sp-17 | an-38 | 1A5693 | sp-21 | an-38 |
| 1A4563 | sp-16 | an-39 | 1U4563 | sp-17 | an-39 | 1A5694 | sp-21 | an-39 |
| 1A4564 | sp-16 | an-40 | 1U4564 | sp-17 | an-40 | 1A5695 | sp-21 | an-40 |
| 1A4565 | sp-16 | an-41 | 1U4565 | sp-17 | an-41 | 1A5696 | sp-21 | an-41 |
| 1A4566 | sp-16 | an-42 | 1U4566 | sp-17 | an-42 | 1A5697 | sp-21 | an-42 |
| 1A4567 | sp-16 | an-43 | 1U4567 | sp-17 | an-43 | 1A5698 | sp-21 | an-43 |
| 1A4568 | sp-16 | an-44 | 1U4568 | sp-17 | an-44 | 1A5699 | sp-21 | an-44 |
| 1A4569 | sp-16 | an-45 | 1U4569 | sp-17 | an-45 | 1A5700 | sp-21 | an-45 |
| 1A4570 | sp-16 | an-46 | 1U4570 | sp-17 | an-45 | 1A5701 | sp-21 | an-46 |
| 1A4571 | sp-16 | an-47 | 1U4571 | sp-17 | an-47 | 1A5702 | sp-21 | an-47 |
| 1A4572 | sp-16 | an-48 | 1U4572 | sp-17 | an-48 | 1A5703 | sp-21 | an-48 |
| 1A4573 | sp-16 | an-49 | 1U4573 | sp-17 | an-49 | 1A5704 | sp-21 | an-49 |
| 1A4574 | sp-16 | an-50 | 1U4574 | sp-17 | an-50 | 1A5705 | sp-21 | an-50 |
| 1A4575 | sp-16 | an-51 | 1U4575 | sp-17 | an-51 | 1A5706 | sp-21 | an-51 |
| 1A4576 | sp-16 | an-52 | 1U4576 | sp-17 | an-52 | 1A5707 | sp-21 | an-52 |
| 1A4577 | sp-16 | an-53 | 1U4577 | sp-17 | an-53 | 1A5708 | sp-21 | an-53 |
| 1A4578 | sp-16 | an-54 | 1U4578 | sp-17 | an-54 | 1A5709 | sp-21 | an-54 |
| 1A4579 | sp-16 | an-55 | 1U4579 | sp-17 | an-55 | 1A5710 | sp-21 | an-55 |
| 1A4580 | sp-16 | an-56 | 1U4580 | sp-17 | an-56 | 1A5711 | sp-21 | an-56 |
| 1A4581 | sp-16 | an-57 | 1U4581 | sp-17 | an-57 | 1A5712 | sp-21 | an-57 |
| 1A4582 | sp-16 | an-58 | 1U4582 | sp-17 | an-58 | 1A5713 | sp-21 | an-58 |
| 1A4583 | sp-16 | an-59 | 1U4583 | sp-17 | an-59 | 1A5714 | sp-21 | an-59 |
| 1A4584 | sp-16 | an-60 | 1U4584 | sp-17 | an-60 | 1A5715 | sp-21 | an-60 |
| 1A4585 | sp-16 | an-61 | 1U4585 | sp-17 | an-61 | 1A5716 | sp-21 | an-61 |

TABLE 1-continued

| | | | | | | | | |
|---|---|---|---|---|---|---|---|---|
| 1A4586 | sp-16 | an-62 | 1U4586 | sp-17 | an-62 | 1A5717 | sp-21 | an-62 |
| 1A4587 | sp-16 | an-63 | 1U4587 | sp-17 | an-63 | 1A5718 | sp-21 | an-63 |
| 1A4588 | sp-16 | an-64 | 1U4588 | sp-17 | an-64 | 1A5719 | sp-21 | an-64 |
| 1A4589 | sp-16 | an-65 | 1U4589 | sp-17 | an-65 | 1A5720 | sp-21 | an-65 |
| 1A4590 | sp-16 | an-66 | 1U4590 | sp-17 | an-66 | 1A5721 | sp-21 | an-66 |
| 1A4591 | sp-16 | an-67 | 1U4591 | sp-17 | an-67 | 1A5722 | sp-21 | an-67 |
| 1A4592 | sp-16 | an-68 | 1U4592 | sp-17 | an-68 | 1A5723 | sp-21 | an-68 |
| 1A4593 | sp-16 | an-69 | 1U4593 | sp-17 | an-69 | 1A5724 | sp-21 | an-69 |
| 1A4594 | sp-16 | an-70 | 1U4594 | sp-17 | an-70 | 1A5725 | sp-21 | an-70 |
| 1A4595 | sp-16 | an-71 | 1U4595 | sp-17 | an-71 | 1A5726 | sp-21 | an-71 |
| 1A4596 | sp-16 | an-72 | 1U4596 | sp-17 | an-72 | 1A5727 | sp-21 | an-72 |
| 1A4597 | sp-16 | an-73 | 1U4597 | sp-17 | an-73 | 1A5728 | sp-21 | an-73 |
| 1A4598 | sp-16 | an-74 | 1U4598 | sp-17 | an-74 | 1A5729 | sp-21 | an-74 |
| 1A4599 | sp-16 | an-75 | 1U4599 | sp-17 | an-75 | 1A5730 | sp-21 | an-75 |
| 1A4600 | sp-16 | an-76 | 1U4600 | sp-17 | an-76 | 1A5731 | sp-21 | an-76 |
| 1A4601 | sp-16 | an-77 | 1U4601 | sp-17 | an-77 | 1A5732 | sp-21 | an-77 |
| 1A4602 | sp-16 | an-78 | 1U4602 | sp-17 | an-78 | 1A5733 | sp-21 | an-78 |
| 1A4603 | sp-16 | an-79 | 1U4603 | sp-17 | an-79 | 1A5734 | sp-21 | an-79 |
| 1A4604 | sp-16 | an-80 | 1U4604 | sp-17 | an-80 | 1A5735 | sp-21 | an-80 |
| 1A4605 | sp-16 | an-81 | 1U4605 | sp-17 | an-81 | 1A5736 | sp-21 | an-81 |
| 1A4606 | sp-16 | an-82 | 1U4606 | sp-17 | an-82 | 1A5737 | sp-21 | an-82 |
| 1A4607 | sp-16 | an-83 | 1U4607 | sp-17 | an-83 | 1A5738 | sp-21 | an-83 |
| 1A4608 | sp-16 | an-84 | 1U4608 | sp-17 | an-84 | 1A5739 | sp-21 | an-84 |
| 1A4609 | sp-16 | an-85 | 1U4609 | sp-17 | an-85 | 1A5740 | sp-21 | an-85 |
| 1A4610 | sp-16 | an-86 | 1U4610 | sp-17 | an-86 | 1A5741 | sp-21 | an-86 |
| 1A4611 | sp-16 | an-87 | 1U4611 | sp-17 | an-87 | 1A5742 | sp-21 | an-87 |
| 1A4612 | sp-16 | an-88 | 1U4612 | sp-17 | an-88 | 1A5743 | sp-21 | an-88 |
| 1A4613 | sp-16 | an-89 | 1U4613 | sp-17 | an-89 | 1A5744 | sp-21 | an-89 |
| 1A4614 | sp-16 | an-90 | 1U4614 | sp-17 | an-90 | 1A5745 | sp-21 | an-90 |
| 1A4615 | sp-16 | an-91 | 1U4615 | sp-17 | an-91 | 1A5746 | sp-21 | an-91 |
| 1A4616 | sp-16 | an-92 | 1U4616 | sp-17 | an-92 | 1A5747 | sp-21 | an-92 |
| 1A4617 | sp-16 | an-93 | 1U4617 | sp-17 | an-93 | 1A5748 | sp-21 | an-93 |
| 1A4618 | sp-16 | an-94 | 1U4618 | sp-17 | an-94 | 1A5749 | sp-21 | an-94 |
| 1A4619 | sp-16 | an-95 | 1U4619 | sp-17 | an-95 | 1A5750 | sp-21 | an-95 |
| 1A4620 | sp-16 | an-96 | 1U4620 | sp-17 | an-96 | 1A5751 | sp-21 | an-96 |
| 1A4621 | sp-16 | an-97 | 1U4621 | sp-17 | an-97 | 1A5752 | sp-21 | an-97 |
| 1A4622 | sp-16 | an-98 | 1U4622 | sp-17 | an-98 | 1A5753 | sp-21 | an-98 |
| 1A4623 | sp-16 | an-99 | 1U4623 | sp-17 | an-99 | 1A5754 | sp-21 | an-99 |
| 1A4624 | sp-16 | an-100 | 1U4624 | sp-17 | an-100 | 1A5755 | sp-21 | an-100 |
| 1A4625 | sp-16 | an-101 | 1U4625 | sp-17 | an-101 | 1A5756 | sp-21 | an-101 |
| 1A4626 | sp-16 | an-102 | 1U4626 | sp-17 | an-102 | 1A5757 | sp-21 | an-102 |
| 1A4627 | sp-16 | an-103 | 1U4627 | sp-17 | an-103 | 1A5758 | sp-21 | an-103 |
| 1A4628 | sp-16 | an-104 | 1U4628 | sp-17 | an-104 | 1A5759 | sp-21 | an-104 |
| 1A4629 | sp-16 | an-105 | 1U4629 | sp-17 | an-105 | 1A5760 | sp-21 | an-105 |
| 1A4630 | sp-16 | an-106 | 1U4630 | sp-17 | an-106 | 1A5761 | sp-21 | an-106 |
| 1A4631 | sp-16 | an-107 | 1U4631 | sp-17 | an-107 | 1A5762 | sp-21 | an-107 |
| 1A4632 | sp-16 | an-108 | 1U4632 | sp-17 | an-108 | 1A5763 | sp-21 | an-108 |
| 1A4633 | sp-16 | an-109 | 1U4633 | sp-17 | an-109 | 1A5764 | sp-21 | an-109 |
| 1A4634 | sp-16 | an-110 | 1U4634 | sp-17 | an-110 | 1A5765 | sp-21 | an-110 |
| 1A4635 | sp-16 | an-111 | 1U4635 | sp-17 | an-111 | 1A5766 | sp-21 | an-111 |
| 1A4636 | sp-16 | an-112 | 1U4636 | sp-17 | an-112 | 1A5767 | sp-21 | an-112 |
| 1A4637 | sp-16 | an-113 | 1U4637 | sp-17 | an-113 | 1A5768 | sp-21 | an-113 |
| 1A4638 | sp-16 | an-114 | 1U4638 | sp-17 | an-114 | 1A5769 | sp-21 | an-114 |
| 1A4639 | sp-16 | an-115 | 1U4639 | sp-17 | an-115 | 1A5770 | sp-21 | an-115 |
| 1A4640 | sp-16 | an-116 | 1U4640 | sp-17 | an-116 | 1A5771 | sp-21 | an-116 |
| 1A4641 | sp-16 | an-117 | 1U4641 | sp-17 | an-117 | 1A5772 | sp-21 | an-117 |
| 1A4642 | sp-16 | an-118 | 1U4642 | sp-17 | an-118 | 1A5773 | sp-21 | an-118 |
| 1A4643 | sp-16 | an-119 | 1U4643 | sp-17 | an-119 | 1A5774 | sp-21 | an-119 |
| 1A4644 | sp-16 | an-120 | 1U4644 | sp-17 | an-120 | 1A5775 | sp-21 | an-120 |
| 1A4645 | sp-16 | an-121 | 1U4645 | sp-17 | an-121 | 1A5776 | sp-21 | an-121 |
| 1A4646 | sp-16 | an-122 | 1U4646 | sp-17 | an-122 | 1A5777 | sp-21 | an-122 |
| 1A4647 | sp-16 | an-123 | 1U4647 | sp-17 | an-123 | 1A5778 | sp-21 | an-123 |
| 1A4648 | sp-16 | an-124 | 1U4648 | sp-17 | an-124 | 1A5779 | sp-21 | an-124 |
| 1A4649 | sp-16 | an-125 | 1U4649 | sp-17 | an-125 | 1A5780 | sp-21 | an-125 |
| 1A4650 | sp-16 | an-126 | 1U4650 | sp-17 | an-126 | 1A5781 | sp-21 | an-126 |
| 1A4651 | sp-16 | an-127 | 1U4651 | sp-17 | an-127 | 1A5782 | sp-21 | an-127 |
| 1A4652 | sp-16 | an-128 | 1U4652 | sp-17 | an-128 | 1A5783 | sp-21 | an-128 |
| 1A4653 | sp-16 | an-129 | 1U4653 | sp-17 | an-129 | 1A5784 | sp-21 | an-129 |
| 1A4654 | sp-16 | an-130 | 1U4654 | sp-17 | an-130 | 1A5785 | sp-21 | an-130 |
| 1A4655 | sp-16 | an-131 | 1U4655 | sp-17 | an-131 | 1A5786 | sp-21 | an-131 |
| 1A4656 | sp-16 | an-132 | 1U4656 | sp-17 | an-132 | 1A5787 | sp-21 | an-132 |
| 1A4657 | sp-16 | an-133 | 1U4657 | sp-17 | an-133 | 1A5788 | sp-21 | an-133 |
| 1A4658 | sp-16 | an-134 | 1U4658 | sp-17 | an-134 | 1A5789 | sp-21 | an-134 |
| 1A4659 | sp-16 | an-135 | 1U4659 | sp-17 | an-135 | 1A5790 | sp-21 | an-135 |
| 1A4660 | sp-16 | an-136 | 1U4660 | sp-17 | an-136 | 1A5791 | sp-21 | an-136 |
| 1A4661 | sp-16 | an-137 | 1U4661 | sp-17 | an-137 | 1A5792 | sp-21 | an-137 |
| 1A4662 | sp-16 | an-138 | 1U4662 | sp-17 | an-138 | 1A5793 | sp-21 | an-138 |
| 1A4663 | sp-16 | an-139 | 1U4663 | sp-17 | an-139 | 1A5794 | sp-21 | an-139 |
| 1A4664 | sp-16 | an-140 | 1U4664 | sp-17 | an-140 | 1A5795 | sp-21 | an-140 |

TABLE 1-continued

| | | | | | | | | |
|---|---|---|---|---|---|---|---|---|
| 1A4665 | sp-16 | an-141 | 1U4665 | sp-17 | an-141 | 1A5796 | sp-21 | an-141 |
| 1A4666 | sp-16 | an-142 | 1U4666 | sp-17 | an-142 | 1A5797 | sp-21 | an-142 |
| 1A4667 | sp-16 | an-143 | 1U4667 | sp-17 | an-143 | 1A5798 | sp-21 | an-143 |
| 1A4668 | sp-16 | an-144 | 1U4668 | sp-17 | an-144 | 1A5799 | sp-21 | an-144 |
| 1A4659 | sp-16 | an-145 | 1U4669 | sp-17 | an-145 | 1A5800 | sp-21 | an-145 |
| 1A4670 | sp-16 | an-146 | 1U4670 | sp-17 | an-146 | 1A5801 | sp-21 | an-146 |
| 1A4671 | sp-16 | an-147 | 1U4671 | sp-17 | an-147 | 1A5802 | sp-21 | an-147 |
| 1A4672 | sp-16 | an-148 | 1U4672 | sp-17 | an-148 | 1A5803 | sp-21 | an-148 |
| 1A4673 | sp-16 | an-149 | 1U4673 | sp-17 | an-149 | 1A5804 | sp-21 | an-149 |
| 1A4674 | sp-16 | an-150 | 1U4674 | sp-17 | an-150 | 1A5805 | sp-21 | an-150 |
| 1A4675 | sp-16 | an-151 | 1U4675 | sp-17 | an-151 | 1A5806 | sp-21 | an-151 |
| 1A4676 | sp-16 | an-152 | 1U4676 | sp-17 | an-152 | 1A5807 | sp-21 | an-152 |
| 1A4677 | sp-16 | an-153 | 1U4677 | sp-17 | an-153 | 1A5808 | sp-21 | an-153 |
| 1A4678 | sp-16 | an-154 | 1U4678 | sp-17 | an-154 | 1A5809 | sp-21 | an-154 |
| 1A4679 | sp-16 | an-155 | 1U4679 | sp-17 | an-155 | 1A5810 | sp-21 | an-155 |
| 1A4680 | sp-16 | an-156 | 1U4680 | sp-17 | an-156 | 1A5811 | sp-21 | an-156 |
| 1A4681 | sp-16 | an-157 | 1U4681 | sp-17 | an-157 | 1A5812 | sp-21 | an-157 |
| 1A4682 | sp-16 | an-158 | 1U4682 | sp-17 | an-158 | 1A5813 | sp-21 | an-158 |
| 1A4683 | sp-16 | an-159 | 1U4683 | sp-17 | an-159 | 1A5814 | sp-21 | an-159 |
| 1A4684 | sp-16 | an-160 | 1U4684 | sp-17 | an-160 | 1A5815 | sp-21 | an-160 |
| 1A4685 | sp-16 | an-161 | 1U4685 | sp-17 | an-161 | 1A5816 | sp-21 | an-161 |
| 1A4686 | sp-16 | an-162 | 1U4686 | sp-17 | an-162 | 1A5817 | sp-21 | an-162 |
| 1A4687 | sp-16 | an-163 | 1U4687 | sp-17 | an-163 | 1A5818 | sp-21 | an-163 |
| 1A4688 | sp-16 | an-164 | 1U4688 | sp-17 | an-164 | 1A5819 | sp-21 | an-164 |
| 1A4689 | sp-16 | an-165 | 1U4689 | sp-17 | an-165 | 1A5820 | sp-21 | an-165 |
| 1A4690 | sp-16 | an-166 | 1U4690 | sp-17 | an-166 | 1A5821 | sp-21 | an-166 |
| 1A4691 | sp-16 | an-167 | 1U4691 | sp-17 | an-167 | 1A5822 | sp-21 | an-167 |
| 1A4692 | sp-16 | an-168 | 1U4692 | sp-17 | an-168 | 1A5823 | sp-21 | an-168 |
| 1A4693 | sp-16 | an-169 | 1U4693 | sp-17 | an-169 | 1A5824 | sp-21 | an-169 |
| 1A4694 | sp-16 | an-170 | 1U4694 | sp-17 | an-170 | 1A5825 | sp-21 | an-170 |
| 1A4695 | sp-16 | an-171 | 1U4695 | sp-17 | an-171 | 1A5826 | sp-21 | an-171 |
| 1A4696 | sp-16 | an-172 | 1U4696 | sp-17 | an-172 | 1A5827 | sp-21 | an-172 |
| 1A4697 | sp-16 | an-173 | 1U4697 | sp-17 | an-173 | 1A5828 | sp-21 | an-173 |
| 1A4698 | sp-16 | an-174 | 1U4698 | sp-17 | an-174 | 1A5829 | sp-21 | an-174 |
| 1A4699 | sp-16 | an-175 | 1U4699 | sp-17 | an-175 | 1A5830 | sp-21 | an-175 |
| 1A4700 | sp-16 | an-176 | 1U4700 | sp-17 | an-176 | 1A5831 | sp-21 | an-176 |
| 1A4701 | sp-16 | an-177 | 1U4701 | sp-17 | an-177 | 1A5832 | sp-21 | an-177 |
| 1A4702 | sp-16 | an-178 | 1U4702 | sp-17 | an-178 | 1A5833 | sp-21 | an-178 |
| 1A4703 | sp-16 | an-179 | 1U4703 | sp-17 | an-179 | 1A5834 | sp-21 | an-179 |
| 1A4704 | sp-16 | an-180 | 1U4704 | sp-17 | an-180 | 1A5835 | sp-21 | an-180 |
| 1A4705 | sp-16 | an-181 | 1U4705 | sp-17 | an-181 | 1A5836 | sp-21 | an-181 |
| 1A4706 | sp-16 | an-182 | 1U4706 | sp-17 | an-182 | 1A5837 | sp-21 | an-182 |
| 1A4707 | sp-16 | an-183 | 1U4707 | sp-17 | an-183 | 1A5838 | sp-21 | an-183 |
| 1A4708 | sp-16 | an-184 | 1U4708 | sp-17 | an-184 | 1A5839 | sp-21 | an-184 |
| 1A4709 | sp-16 | an-185 | 1U4709 | sp-17 | an-185 | 1A5840 | sp-21 | an-185 |
| 1A4710 | sp-16 | an-186 | 1U4710 | sp-17 | an-186 | 1A5841 | sp-21 | an-186 |
| 1A4711 | sp-16 | an-187 | 1U4711 | sp-17 | an-187 | 1A5842 | sp-21 | an-187 |
| 1A4712 | sp-16 | an-188 | 1U4712 | sp-17 | an-188 | 1A5843 | sp-21 | an-188 |
| 1A4713 | sp-16 | an-189 | 1U4713 | sp-17 | an-189 | 1A5844 | sp-21 | an-189 |
| 1A4714 | sp-16 | an-190 | 1U4714 | sp-17 | an-190 | 1A5845 | sp-21 | an-190 |
| 1A4715 | sp-16 | an-191 | 1U4715 | sp-17 | an-191 | 1A5846 | sp-21 | an-191 |
| 1A4716 | sp-16 | an-192 | 1U4716 | sp-17 | an-192 | 1A5847 | sp-21 | an-192 |
| 1A4717 | sp-16 | an-193 | 1U4717 | sp-17 | an-193 | 1A5848 | sp-21 | an-193 |
| 1A4718 | sp-16 | an-194 | 1U4718 | sp-17 | an-194 | 1A5849 | sp-21 | an-194 |
| 1A4719 | sp-16 | an-195 | 1U4719 | sp-17 | an-195 | 1A5850 | sp-21 | an-195 |
| 1A4720 | sp-16 | an-196 | 1U4720 | sp-17 | an-196 | 1A5851 | sp-21 | an-196 |
| 1A4721 | sp-16 | an-197 | 1U4721 | sp-17 | an-197 | 1A5852 | sp-21 | an-197 |
| 1A4722 | sp-16 | an-198 | 1U4722 | sp-17 | an-198 | 1A5853 | sp-21 | an-198 |
| 1A4723 | sp-16 | an-199 | 1U4723 | sp-17 | an-199 | 1A5854 | sp-21 | an-199 |
| 1A4724 | sp-16 | an-200 | 1U4724 | sp-17 | an-200 | 1A5855 | sp-21 | an-200 |
| 1A4725 | sp-16 | an-201 | 1U4725 | sp-17 | an-201 | 1A5856 | sp-21 | an-201 |
| 1A4726 | sp-16 | an-202 | 1U4726 | sp-17 | an-202 | 1A5857 | sp-21 | an-202 |
| 1A4727 | sp-16 | an-203 | 1U4727 | sp-17 | an-203 | 1A5858 | sp-21 | an-203 |
| 1A4728 | sp-16 | an-204 | 1U4728 | sp-17 | an-204 | 1A5859 | sp-21 | an-204 |
| 1A4729 | sp-16 | an-205 | 1U4729 | sp-17 | an-205 | 1A5860 | sp-21 | an-205 |
| 1A4730 | sp-16 | an-206 | 1U4730 | sp-17 | an-206 | 1A5861 | sp-21 | an-206 |
| 1A4731 | sp-16 | an-207 | 1U4731 | sp-17 | an-207 | 1A5862 | sp-21 | an-207 |
| 1A4732 | sp-16 | an-208 | 1U4732 | sp-17 | an-208 | 1A5863 | sp-21 | an-208 |
| 1A4733 | sp-16 | an-209 | 1U4733 | sp-17 | an-209 | 1A5864 | sp-21 | an-209 |
| 1A4734 | sp-16 | an-210 | 1U4734 | sp-17 | an-210 | 1A5865 | sp-21 | an-210 |
| 1A4735 | sp-16 | an-211 | 1U4735 | sp-17 | an-211 | 1A5866 | sp-21 | an-211 |
| 1A4736 | sp-16 | an-212 | 1U4736 | sp-17 | an-212 | 1A5867 | sp-21 | an-212 |
| 1A4737 | sp-16 | an-213 | 1U4737 | sp-17 | an-213 | 1A5868 | sp-21 | an-213 |
| 1A4738 | sp-16 | an-214 | 1U4738 | sp-17 | an-214 | 1A5869 | sp-21 | an-214 |
| 1A4739 | sp-16 | an-215 | 1U4739 | sp-17 | an-215 | 1A5870 | sp-21 | an-215 |
| 1A4740 | sp-16 | an-216 | 1U4740 | sp-17 | an-216 | 1A5871 | sp-21 | an-216 |
| 1A4741 | sp-16 | an-217 | 1U4741 | sp-17 | an-217 | 1A5872 | sp-21 | an-217 |
| 1A4742 | sp-16 | an-218 | 1U4742 | sp-17 | an-218 | 1A5873 | sp-21 | an-218 |
| 1A4743 | sp-16 | an-219 | 1U4743 | sp-17 | an-219 | 1A5874 | sp-21 | an-219 |

TABLE 1-continued

| | | | | | | | | |
|---|---|---|---|---|---|---|---|---|
| 1A4744 | sp-16 | an-220 | 1U4744 | sp-17 | an-220 | 1A5875 | sp-21 | an-220 |
| 1A4745 | sp-16 | an-221 | 1U4745 | sp-17 | an-221 | 1A5876 | sp-21 | an-221 |
| 1A4746 | sp-16 | an-222 | 1U4746 | sp-17 | an-222 | 1A5877 | sp-21 | an-222 |
| 1A4747 | sp-16 | an-223 | 1U4747 | sp-17 | an-223 | 1A5878 | sp-21 | an-223 |
| 1A4748 | sp-16 | an-224 | 1U4748 | sp-17 | an-224 | 1A5879 | sp-21 | an-224 |
| 1A4749 | sp-16 | an-225 | 1U4749 | sp-17 | an-225 | 1A5880 | sp-21 | an-225 |
| 1A4750 | sp-16 | an-226 | 1U4750 | sp-17 | an-226 | 1A5881 | sp-21 | an-226 |
| 1A4751 | sp-16 | an-227 | 1U4751 | sp-17 | an-227 | 1A5882 | sp-21 | an-227 |
| 1A4752 | sp-16 | an-228 | 1U4752 | sp-17 | an-228 | 1A5883 | sp-21 | an-228 |
| 1A4753 | sp-16 | an-229 | 1U4753 | sp-17 | an-229 | 1A5884 | sp-21 | an-229 |
| 1A4754 | sp-16 | an-230 | 1U4754 | sp-17 | an-230 | 1A5885 | sp-21 | an-230 |
| 1A4755 | sp-16 | an-231 | 1U4755 | sp-17 | an-231 | 1A5886 | sp-21 | an-231 |
| 1A4756 | sp-16 | an-232 | 1U4756 | sp-17 | an-232 | 1A5887 | sp-21 | an-232 |
| 1A4757 | sp-16 | an-233 | 1U4757 | sp-17 | an-233 | 1A5888 | sp-21 | an-233 |
| 1A4758 | sp-16 | an-234 | 1U4758 | sp-17 | an-234 | 1A5889 | sp-21 | an-234 |
| 1A4759 | sp-16 | an-235 | 1U4759 | sp-17 | an-235 | 1A5890 | sp-21 | an-235 |
| 1A4760 | sp-16 | an-236 | 1U4760 | sp-17 | an-236 | 1A5891 | sp-21 | an-236 |
| 1A4761 | sp-16 | an-237 | 1U4761 | sp-17 | an-237 | 1A5892 | sp-21 | an-237 |
| 1A4762 | sp-16 | an-238 | 1U4762 | sp-17 | an-238 | 1A5893 | sp-21 | an-238 |
| 1A4763 | sp-16 | an-239 | 1U4763 | sp-17 | an-239 | 1A5894 | sp-21 | an-239 |
| 1A4764 | sp-16 | an-240 | 1U4764 | sp-17 | an-240 | 1A5895 | sp-21 | an-240 |
| 1A4765 | sp-16 | an-241 | 1U4765 | sp-17 | an-241 | 1A5896 | sp-21 | an-241 |
| 1A4766 | sp-16 | an-242 | 1U4766 | sp-17 | an-242 | 1A5897 | sp-21 | an-242 |
| 1A4767 | sp-16 | an-243 | 1U4767 | sp-17 | an-243 | 1A5898 | sp-21 | an-243 |
| 1A4768 | sp-16 | an-244 | 1U4768 | sp-17 | an-244 | 1A5899 | sp-21 | an-244 |
| 1A4769 | sp-16 | an-245 | 1U4769 | sp-17 | an-245 | 1A5900 | sp-21 | an-245 |
| 1A4770 | sp-16 | an-246 | 1U4770 | sp-17 | an-246 | 1A5901 | sp-21 | an-246 |
| 1A4771 | sp-16 | an-247 | 1U4771 | sp-17 | an-247 | 1A5902 | sp-21 | an-247 |
| 1A4772 | sp-16 | an-248 | 1U4772 | sp-17 | an-248 | 1A5903 | sp-21 | an-248 |
| 1A4773 | sp-16 | an-249 | 1U4773 | sp-17 | an-249 | 1A5904 | sp-21 | an-249 |
| 1A4774 | sp-16 | an-250 | 1U4774 | sp-17 | an-250 | 1A5905 | sp-21 | an-250 |
| 1A4775 | sp-16 | an-251 | 1U4775 | sp-17 | an-251 | 1A5906 | sp-21 | an-251 |
| 1A4776 | sp-16 | an-252 | 1U4776 | sp-17 | an-252 | 1A5907 | sp-21 | an-252 |
| 1A4777 | sp-16 | an-253 | 1U4777 | sp-17 | an-253 | 1A5908 | sp-21 | an-253 |
| 1A4778 | sp-16 | an-254 | 1U4778 | sp-17 | an-254 | 1A5909 | sp-21 | an-254 |
| 1A4779 | sp-16 | an-255 | 1U4779 | sp-17 | an-255 | 1A5910 | sp-21 | an-255 |
| 1A4780 | sp-16 | an-256 | 1U4780 | sp-17 | an-256 | 1A5911 | sp-21 | an-256 |
| 1A4781 | sp-16 | an-257 | 1U4781 | sp-17 | an-257 | 1A5912 | sp-21 | an-257 |
| 1A4782 | sp-16 | an-258 | 1U4782 | sp-17 | an-258 | 1A5913 | sp-21 | an-258 |
| 1A4783 | sp-16 | an-259 | 1U4783 | sp-17 | an-259 | 1A5914 | sp-21 | an-259 |
| 1A4784 | sp-16 | an-260 | 1U4784 | sp-17 | an-260 | 1A5915 | sp-21 | an-260 |
| 1A4785 | sp-16 | an-261 | 1U4785 | sp-17 | an-261 | 1A5916 | sp-21 | an-261 |
| 1A4786 | sp-16 | an-262 | 1U4786 | sp-17 | an-262 | 1A5917 | sp-21 | an-262 |
| 1A4787 | sp-16 | an-263 | 1U4787 | sp-17 | an-263 | 1A5918 | sp-21 | an-263 |
| 1A4788 | sp-16 | an-264 | 1U4788 | sp-17 | an-264 | 1A5919 | sp-21 | an-264 |
| 1A4789 | sp-16 | an-265 | 1U4789 | sp-17 | an-265 | 1A5920 | sp-21 | an-265 |
| 1A4790 | sp-16 | an-266 | 1U4790 | sp-17 | an-266 | 1A5921 | sp-21 | an-266 |
| 1A4791 | sp-16 | an-267 | 1U4791 | sp-17 | an-267 | 1A5922 | sp-21 | an-267 |
| 1A4792 | sp-16 | an-268 | 1U4792 | sp-17 | an-268 | 1A5923 | sp-21 | an-268 |
| 1A4793 | sp-16 | an-269 | 1U4793 | sp-17 | an-269 | 1A5924 | sp-21 | an-269 |
| 1A4794 | sp-16 | an-270 | 1U4794 | sp-17 | an-270 | 1A5925 | sp-21 | an-270 |
| 1A4795 | sp-16 | an-271 | 1U4795 | sp-17 | an-271 | 1A5926 | sp-21 | an-271 |
| 1A4796 | sp-16 | an-272 | 1U4796 | sp-17 | an-272 | 1A5927 | sp-21 | an-272 |
| 1A4797 | sp-16 | an-273 | 1U4797 | sp-17 | an-273 | 1A5928 | sp-21 | an-273 |
| 1A4798 | sp-16 | an-274 | 1U4798 | sp-17 | an-274 | 1A5929 | sp-21 | an-274 |
| 1A4799 | sp-16 | an-275 | 1U4799 | sp-17 | an-275 | 1A5930 | sp-21 | an-275 |
| 1A4800 | sp-16 | an-276 | 1U4800 | sp-17 | an-276 | 1A5931 | sp-21 | an-276 |
| 1A4801 | sp-16 | an-277 | 1U4801 | sp-17 | an-277 | 1A5932 | sp-21 | an-277 |
| 1A4802 | sp-16 | an-278 | 1U4802 | sp-17 | an-278 | 1A5933 | sp-21 | an-278 |
| 1A4803 | sp-16 | an-279 | 1U4803 | sp-17 | an-279 | 1A5934 | sp-21 | an-279 |
| 1A4804 | sp-16 | an-280 | 1U4804 | sp-17 | an-280 | 1A5935 | sp-21 | an-280 |
| 1A4805 | sp-16 | an-281 | 1U4805 | sp-17 | an-281 | 1A5936 | sp-21 | an-281 |
| 1A4806 | sp-16 | an-282 | 1U4806 | sp-17 | an-282 | 1A5937 | sp-21 | an-282 |
| 1A4807 | sp-16 | an-283 | 1U4807 | sp-17 | an-283 | 1A5938 | sp-21 | an-283 |
| 1A4808 | sp-16 | an-284 | 1U4808 | sp-17 | an-284 | 1A5939 | sp-21 | an-284 |
| 1A4809 | sp-16 | an-285 | 1U4809 | sp-17 | an-285 | 1A5940 | sp-21 | an-285 |
| 1A4810 | sp-16 | an-286 | 1U4810 | sp-17 | an-286 | 1A5941 | sp-21 | an-286 |
| 1A4811 | sp-16 | an-287 | 1U4811 | sp-17 | an-287 | 1A5942 | sp-21 | an-287 |
| 1A4812 | sp-16 | an-288 | 1U4812 | sp-17 | an-288 | 1A5943 | sp-21 | an-288 |
| 1A4813 | sp-16 | an-289 | 1U4813 | sp-17 | an-289 | 1A5944 | sp-21 | an-289 |
| 1A4814 | sp-16 | an-290 | 1U4814 | sp-17 | an-290 | 1A5945 | sp-21 | an-290 |
| 1A4815 | sp-16 | an-291 | 1U4815 | sp-17 | an-291 | 1A5946 | sp-21 | an-291 |
| 1A4816 | sp-16 | an-292 | 1U4816 | sp-17 | an-292 | 1A5947 | sp-21 | an-292 |
| 1A4817 | sp-16 | an-293 | 1U4817 | sp-17 | an-293 | 1A5948 | sp-21 | an-293 |
| 1A4818 | sp-16 | an-294 | 1U4818 | sp-17 | an-294 | 1A5949 | sp-21 | an-294 |
| 1A4819 | sp-16 | an-295 | 1U4819 | sp-17 | an-295 | 1A5950 | sp-21 | an-295 |
| 1A4820 | sp-16 | an-296 | 1U4820 | sp-17 | an-296 | 1A5951 | sp-21 | an-296 |
| 1A4821 | sp-16 | an-297 | 1U4821 | sp-17 | an-297 | 1A5952 | sp-21 | an-297 |
| 1A4822 | sp-16 | an-298 | 1U4822 | sp-17 | an-298 | 1A5953 | sp-21 | an-298 |

TABLE 1-continued

| | | | | | | | | |
|---|---|---|---|---|---|---|---|---|
| 1A4823 | sp-16 | an-299 | 1U4823 | sp-17 | an-299 | 1A5954 | sp-21 | an-299 |
| 1A4824 | sp-16 | an-300 | 1U4824 | sp-17 | an-300 | 1A5955 | sp-21 | an-300 |
| 1A4825 | sp-16 | an-301 | 1U4825 | sp-17 | an-301 | 1A5956 | sp-21 | an-301 |
| 1A4826 | sp-16 | an-302 | 1U4826 | sp-17 | an-302 | 1A5957 | sp-21 | an-302 |
| 1A4827 | sp-16 | an-303 | 1U4827 | sp-17 | an-303 | 1A5958 | sp-21 | an-303 |
| 1A4828 | sp-16 | an-304 | 1U4828 | sp-17 | an-304 | 1A5959 | sp-21 | an-304 |
| 1A4329 | sp-16 | an-305 | 1U4829 | sp-17 | an-305 | 1A5960 | sp-21 | an-305 |
| 1A4830 | sp-16 | an-306 | 1U4830 | sp-17 | an-306 | 1A5961 | sp-21 | an-306 |
| 1A4831 | sp-16 | an-307 | 1U4831 | sp-17 | an-307 | 1A5962 | sp-21 | an-307 |
| 1A4832 | sp-16 | an-308 | 1U4832 | sp-17 | an-308 | 1A5963 | sp-21 | an-308 |
| 1A4833 | sp-16 | an-309 | 1U4833 | sp-17 | an-309 | 1A5964 | sp-21 | an-309 |
| 1A4834 | sp-16 | an-310 | 1U4834 | sp-17 | an-310 | 1A5965 | sp-21 | an-310 |
| 1A4835 | sp-16 | an-311 | 1U4835 | sp-17 | an-311 | 1A5966 | sp-21 | an-311 |
| 1A4836 | sp-16 | an-312 | 1U4836 | sp-17 | an-312 | 1A5967 | sp-21 | an-312 |
| 1A4837 | sp-16 | an-313 | 1U4837 | sp-17 | an-313 | 1A5968 | sp-21 | an-313 |
| 1A4838 | sp-16 | an-314 | 1U4838 | sp-17 | an-314 | 1A5969 | sp-21 | an-314 |
| 1A4839 | sp-16 | an-315 | 1U4839 | sp-17 | an-315 | 1A5970 | sp-21 | an-315 |
| 1A4840 | sp-16 | an-316 | 1U4840 | sp-17 | an-316 | 1A5971 | sp-21 | an-316 |
| 1A4841 | sp-16 | an-317 | 1U4841 | sp-17 | an-317 | 1A5972 | sp-21 | an-317 |
| 1A4842 | sp-16 | an-318 | 1U4842 | sp-17 | an-318 | 1A5973 | sp-21 | an-318 |
| 1A4843 | sp-16 | an-319 | 1U4843 | sp-17 | an-319 | 1A5974 | sp-21 | an-319 |
| 1A4844 | sp-16 | an-320 | 1U4844 | sp-17 | an-320 | 1A5975 | sp-21 | an-320 |
| 1A4845 | sp-16 | an-321 | 1U4845 | sp-17 | an-321 | 1A5976 | sp-21 | an-321 |
| 1A4846 | sp-16 | an-322 | 1U4846 | sp-17 | an-322 | 1A5977 | sp-21 | an-322 |
| 1A4847 | sp-16 | an-323 | 1U4847 | sp-17 | an-323 | 1A5978 | sp-21 | an-323 |
| 1A4848 | sp-16 | an-324 | 1U4848 | sp-17 | an-324 | 1A5979 | sp-21 | an-324 |
| 1A4849 | sp-16 | an-325 | 1U4849 | sp-17 | an-325 | 1A5980 | sp-21 | an-325 |
| 1A4850 | sp-16 | an-326 | 1U4850 | sp-17 | an-326 | 1A5981 | sp-21 | an-326 |
| 1A4851 | sp-16 | an-327 | 1U4851 | sp-17 | an-327 | 1A5982 | sp-21 | an-327 |
| 1A4852 | sp-16 | an-328 | 1U4852 | sp-17 | an-328 | 1A5983 | sp-21 | an-328 |
| 1A4853 | sp-16 | an-329 | 1U4853 | sp-17 | an-329 | 1A5984 | sp-21 | an-329 |
| 1A4854 | sp-16 | an-330 | 1U4854 | sp-17 | an-330 | 1A5985 | sp-21 | an-330 |
| 1A4855 | sp-16 | an-331 | 1U4855 | sp-17 | an-331 | 1A5986 | sp-21 | an-331 |
| 1A4856 | sp-16 | an-332 | 1U4856 | sp-17 | an-332 | 1A5987 | sp-21 | an-332 |
| 1A4857 | sp-16 | an-333 | 1U4857 | sp-17 | an-333 | 1A5988 | sp-21 | an-333 |
| 1A4858 | sp-16 | an-334 | 1U4858 | sp-17 | an-334 | 1A5989 | sp-21 | an-334 |
| 1A4859 | sp-16 | an-335 | 1U4859 | sp-17 | an-335 | 1A5990 | sp-21 | an-335 |
| 1A4860 | sp-16 | an-336 | 1U4860 | sp-17 | an-336 | 1A5991 | sp-21 | an-336 |
| 1A4861 | sp-16 | an-337 | 1U4861 | sp-17 | an-337 | 1A5992 | sp-21 | an-337 |
| 1A4862 | sp-16 | an-338 | 1U4862 | sp-17 | an-338 | 1A5993 | sp-21 | an-338 |
| 1A4863 | sp-16 | an-339 | 1U4863 | sp-17 | an-339 | 1A5994 | sp-21 | an-339 |
| 1A4864 | sp-16 | an-340 | 1U4864 | sp-17 | an-340 | 1A5995 | sp-21 | an-340 |
| 1A4865 | sp-16 | an-341 | 1U4865 | sp-17 | an-341 | 1A5996 | sp-21 | an-341 |
| 1A4866 | sp-16 | an-342 | 1U4866 | sp-17 | an-342 | 1A5997 | sp-21 | an-342 |
| 1A4867 | sp-16 | an-343 | 1U4867 | sp-17 | an-343 | 1A5998 | sp-21 | an-343 |
| 1A4868 | sp-16 | an-344 | 1U4868 | sp-17 | an-344 | 1A5999 | sp-21 | an-344 |
| 1A4869 | sp-16 | an-345 | 1U4869 | sp-17 | an-345 | 1A6000 | sp-21 | an-345 |
| 1A4870 | sp-16 | an-346 | 1U4870 | sp-17 | an-346 | 1A6001 | sp-21 | an-346 |
| 1A4871 | sp-16 | an-347 | 1U4871 | sp-17 | an-347 | 1A6002 | sp-21 | an-347 |
| 1A4872 | sp-16 | an-348 | 1U4872 | sp-17 | an-348 | 1A6003 | sp-21 | an-348 |
| 1A4873 | sp-16 | an-349 | 1U4873 | sp-17 | an-349 | 1A6004 | sp-21 | an-349 |
| 1A4874 | sp-16 | an-350 | 1U4874 | sp-17 | an-350 | 1A6005 | sp-21 | an-350 |
| 1A4875 | sp-16 | an-351 | 1U4875 | sp-17 | an-351 | 1A6006 | sp-21 | an-351 |
| 1A4876 | sp-16 | an-352 | 1U4876 | sp-17 | an-352 | 1A6007 | sp-21 | an-352 |
| 1A4877 | sp-16 | an-353 | 1U4877 | sp-17 | an-353 | 1A6008 | sp-21 | an-353 |
| 1A4878 | sp-16 | an-354 | 1U4878 | sp-17 | an-354 | 1A6009 | sp-21 | an-354 |
| 1A4879 | sp-16 | an-355 | 1U4879 | sp-17 | an-355 | 1A6010 | sp-21 | an-355 |
| 1A4880 | sp-16 | an-356 | 1U4880 | sp-17 | an-356 | 1A6011 | sp-21 | an-356 |
| 1A4881 | sp-16 | an-357 | 1U4881 | sp-17 | an-357 | 1A6012 | sp-21 | an-357 |
| 1A4882 | sp-16 | an-358 | 1U4882 | sp-17 | an-358 | 1A6013 | sp-21 | an-358 |
| 1A4883 | sp-16 | an-359 | 1U4883 | sp-17 | an-359 | 1A6014 | sp-21 | an-359 |
| 1A4884 | sp-16 | an-360 | 1U4884 | sp-17 | an-360 | 1A6015 | sp-21 | an-360 |
| 1A4885 | sp-16 | an-361 | 1U4885 | sp-17 | an-361 | 1A6016 | sp-21 | an-361 |
| 1A4886 | sp-16 | an-362 | 1U4886 | sp-17 | an-362 | 1A6017 | sp-21 | an-362 |
| 1A4887 | sp-16 | an-363 | 1U4887 | sp-17 | an-363 | 1A6018 | sp-21 | an-363 |
| 1A4888 | sp-16 | an-364 | 1U4888 | sp-17 | an-364 | 1A6019 | sp-21 | an-364 |
| 1A4889 | sp-16 | an-365 | 1U4889 | sp-17 | an-365 | 1A6020 | sp-21 | an-365 |
| 1A4890 | sp-16 | an-366 | 1U4890 | sp-17 | an-366 | 1A6021 | sp-21 | an-366 |
| 1A4891 | sp-16 | an-367 | 1U4891 | sp-17 | an-367 | 1A6022 | sp-21 | an-367 |
| 1A4892 | sp-16 | an-368 | 1U4892 | sp-17 | an-368 | 1A6023 | sp-21 | an-368 |
| 1A4893 | sp-16 | an-369 | 1U4893 | sp-17 | an-369 | 1A6024 | sp-21 | an-369 |
| 1A4894 | sp-16 | an-370 | 1U4894 | sp-17 | an-370 | 1A6025 | sp-21 | an-370 |
| 1A4895 | sp-16 | an-371 | 1U4895 | sp-17 | an-371 | 1A6026 | sp-21 | an-371 |
| 1A4896 | sp-16 | an-372 | 1U4896 | sp-17 | an-372 | 1A6027 | sp-21 | an-372 |
| 1A4897 | sp-16 | an-373 | 1U4897 | sp-17 | an-373 | 1A6028 | sp-21 | an-373 |
| 1A4898 | sp-16 | an-374 | 1U4898 | sp-17 | an-374 | 1A6029 | sp-21 | an-374 |
| 1A4899 | sp-16 | an-375 | 1U4899 | sp-17 | an-375 | 1A6030 | sp-21 | an-375 |
| 1A4900 | sp-16 | an-376 | 1U4900 | sp-17 | an-376 | 1A6031 | sp-21 | an-376 |
| 1A4901 | sp-16 | an-377 | 1U4901 | sp-17 | an-377 | 1A6032 | sp-21 | an-377 |

TABLE 1-continued

| | | | | | | | | |
|---|---|---|---|---|---|---|---|---|
| 1A4902 | sp-18 | an-1 | 1U4902 | sp-20 | an-1 | 1A6033 | sp-22 | an-1 |
| 1A4903 | sp-18 | an-2 | 1U4903 | sp-20 | an-2 | 1A6034 | sp-22 | an-2 |
| 1A4904 | sp-18 | an-3 | 1U4904 | sp-20 | an-3 | 1A6035 | sp-22 | an-3 |
| 1A4905 | sp-18 | an-4 | 1U4905 | sp-20 | an-4 | 1A6036 | sp-22 | an-4 |
| 1A4906 | sp-18 | an-5 | 1U4906 | sp-20 | an-5 | 1A6037 | sp-22 | an-5 |
| 1A4907 | sp-18 | an-6 | 1U4907 | sp-20 | an-6 | 1A6038 | sp-22 | an-6 |
| 1A4908 | sp-18 | an-7 | 1U4908 | sp-20 | an-7 | 1A6039 | sp-22 | an-7 |
| 1A4909 | sp-18 | an-8 | 1U4909 | sp-20 | an-8 | 1A6040 | sp-22 | an-8 |
| 1A4910 | sp-18 | an-9 | 1U4910 | sp-20 | an-9 | 1A6041 | sp-22 | an-9 |
| 1A4911 | sp-18 | an-10 | 1U4911 | sp-20 | an-10 | 1A6042 | sp-22 | an-10 |
| 1A4912 | sp-18 | an-11 | 1U4912 | sp-20 | an-11 | 1A6043 | sp-22 | an-11 |
| 1A4913 | sp-18 | an-12 | 1U4913 | sp-20 | an-12 | 1A6044 | sp-22 | an-12 |
| 1A4914 | sp-18 | an-13 | 1U4914 | sp-20 | an-13 | 1A6045 | sp-22 | an-13 |
| 1A4915 | sp-18 | an-14 | 1U4915 | sp-20 | an-14 | 1A6046 | sp-22 | an-14 |
| 1A4916 | sp-18 | an-15 | 1U4916 | sp-20 | an-15 | 1A6047 | sp-22 | an-15 |
| 1A4917 | sp-18 | an-16 | 1U4917 | sp-20 | an-16 | 1A6048 | sp-22 | an-16 |
| 1A4918 | sp-18 | an-17 | 1U4918 | sp-20 | an-17 | 1A6049 | sp-22 | an-17 |
| 1A4919 | sp-18 | an-18 | 1U4919 | sp-20 | an-18 | 1A6050 | sp-22 | an-18 |
| 1A4920 | sp-18 | an-19 | 1U4920 | sp-20 | an-19 | 1A6051 | sp-22 | an-19 |
| 1A4921 | sp-18 | an-20 | 1U4921 | sp-20 | an-20 | 1A6052 | sp-22 | an-20 |
| 1A4922 | sp-18 | an-21 | 1U4922 | sp-20 | an-21 | 1A6053 | sp-22 | an-21 |
| 1A4923 | sp-18 | an-22 | 1U4923 | sp-20 | an-22 | 1A6054 | sp-22 | an-22 |
| 1A4924 | sp-18 | an-23 | 1U4924 | sp-20 | an-23 | 1A6055 | sp-22 | an-23 |
| 1A4925 | sp-18 | an-24 | 1U4925 | sp-20 | an-24 | 1A6056 | sp-22 | an-24 |
| 1A4926 | sp-18 | an-25 | 1U4926 | sp-20 | an-25 | 1A6057 | sp-22 | an-25 |
| 1A4927 | sp-18 | an-26 | 1U4927 | sp-20 | an-26 | 1A6058 | sp-22 | an-26 |
| 1A4928 | sp-18 | an-27 | 1U4928 | sp-20 | an-27 | 1A6059 | sp-22 | an-27 |
| 1A4929 | sp-18 | an-28 | 1U4929 | sp-20 | an-28 | 1A6060 | sp-22 | an-28 |
| 1A4930 | sp-18 | an-29 | 1U4930 | sp-20 | an-29 | 1A6061 | sp-22 | an-29 |
| 1A4931 | sp-18 | an-30 | 1U4931 | sp-20 | an-30 | 1A6062 | sp-22 | an-30 |
| 1A4932 | sp-18 | an-31 | 1U4932 | sp-20 | an-31 | 1A6063 | sp-22 | an-31 |
| 1A4933 | sp-18 | an-32 | 1U4933 | sp-20 | an-32 | 1A6064 | sp-22 | an-32 |
| 1A4934 | sp-18 | an-33 | 1U4934 | sp-20 | an-33 | 1A6065 | sp-22 | an-33 |
| 1A4935 | sp-18 | an-34 | 1U4935 | sp-20 | an-34 | 1A6066 | sp-22 | an-34 |
| 1A4936 | sp-18 | an-35 | 1U4936 | sp-20 | an-35 | 1A6067 | sp-22 | an-35 |
| 1A4937 | sp-18 | an-36 | 1U4937 | sp-20 | an-36 | 1A6068 | sp-22 | an-36 |
| 1A4938 | sp-18 | an-37 | 1U4938 | sp-20 | an-37 | 1A6069 | sp-22 | an-37 |
| 1A4939 | sp-18 | an-38 | 1U4939 | sp-20 | an-38 | 1A6070 | sp-22 | an-38 |
| 1A4940 | sp-18 | an-39 | 1U4940 | sp-20 | an-39 | 1A6071 | sp-22 | an-39 |
| 1A4941 | sp-18 | an-40 | 1U4941 | sp-20 | an-40 | 1A6072 | sp-22 | an-40 |
| 1A4942 | sp-18 | an-41 | 1U4942 | sp-20 | an-41 | 1A6073 | sp-22 | an-41 |
| 1A4943 | sp-18 | an-42 | 1U4943 | sp-20 | an-42 | 1A6074 | sp-22 | an-42 |
| 1A4944 | sp-18 | an-43 | 1U4944 | sp-20 | an-43 | 1A6075 | sp-22 | an-43 |
| 1A4945 | sp-18 | an-44 | 1U4945 | sp-20 | an-44 | 1A6076 | sp-22 | an-44 |
| 1A4946 | sp-18 | an-45 | 1U4946 | sp-20 | an-45 | 1A6077 | sp-22 | an-45 |
| 1A4947 | sp-18 | an-46 | 1U4947 | sp-20 | an-46 | 1A6078 | sp-22 | an-46 |
| 1A4948 | sp-18 | an-47 | 1U4948 | sp-20 | an-47 | 1A6079 | sp-22 | an-47 |
| 1A4949 | sp-18 | an-48 | 1U4949 | sp-20 | an-48 | 1A6080 | sp-22 | an-48 |
| 1A4950 | sp-18 | an-49 | 1U4950 | sp-20 | an-49 | 1A6081 | sp-22 | an-49 |
| 1A4951 | sp-18 | an-50 | 1U4951 | sp-20 | an-50 | 1A6082 | sp-22 | an-50 |
| 1A4952 | sp-18 | an-51 | 1U4952 | sp-20 | an-51 | 1A6083 | sp-22 | an-51 |
| 1A4953 | sp-18 | an-52 | 1U4953 | sp-20 | an-52 | 1A6084 | sp-22 | an-52 |
| 1A4954 | sp-18 | an-53 | 1U4954 | sp-20 | an-53 | 1A6085 | sp-22 | an-53 |
| 1A4955 | sp-18 | an-54 | 1U4955 | sp-20 | an-54 | 1A6086 | sp-22 | an-54 |
| 1A4956 | sp-18 | an-55 | 1U4956 | sp-20 | an-55 | 1A6087 | sp-22 | an-55 |
| 1A4957 | sp-18 | an-56 | 1U4957 | sp-20 | an-56 | 1A6088 | sp-22 | an-56 |
| 1A4958 | sp-18 | an-57 | 1U4958 | sp-20 | an-57 | 1A6089 | sp-22 | an-57 |
| 1A4959 | sp-18 | an-58 | 1U4959 | sp-20 | an-58 | 1A6090 | sp-22 | an-58 |
| 1A4960 | sp-18 | an-59 | 1U4960 | sp-20 | an-59 | 1A6091 | sp-22 | an-59 |
| 1A4961 | sp-18 | an-60 | 1U4961 | sp-20 | an-60 | 1A6092 | sp-22 | an-60 |
| 1A4962 | sp-18 | an-61 | 1U4962 | sp-20 | an-61 | 1A6093 | sp-22 | an-61 |
| 1A4963 | sp-18 | an-62 | 1U4963 | sp-20 | an-62 | 1A6094 | sp-22 | an-62 |
| 1A4964 | sp-18 | an-63 | 1U4964 | sp-20 | an-63 | 1A6095 | sp-22 | an-63 |
| 1A4965 | sp-18 | an-64 | 1U4965 | sp-20 | an-64 | 1A6096 | sp-22 | an-64 |
| 1A4966 | sp-18 | an-65 | 1U4966 | sp-20 | an-65 | 1A6097 | sp-22 | an-65 |
| 1A4967 | sp-18 | an-66 | 1U4967 | sp-20 | an-66 | 1A6098 | sp-22 | an-66 |
| 1A4968 | sp-18 | an-67 | 1U4968 | sp-20 | an-67 | 1A6099 | sp-22 | an-67 |
| 1A4969 | sp-18 | an-68 | 1U4969 | sp-20 | an-68 | 1A6100 | sp-22 | an-68 |
| 1A4970 | sp-18 | an-69 | 1U4970 | sp-20 | an-69 | 1A6101 | sp-22 | an-69 |
| 1A4971 | sp-18 | an-70 | 1U4971 | sp-20 | an-70 | 1A6102 | sp-22 | an-70 |
| 1A4972 | sp-18 | an-71 | 1U4972 | sp-20 | an-71 | 1A6103 | sp-22 | an-71 |
| 1A4973 | sp-18 | an-72 | 1U4973 | sp-20 | an-72 | 1A6104 | sp-22 | an-72 |
| 1A4974 | sp-18 | an-73 | 1U4974 | sp-20 | an-73 | 1A6105 | sp-22 | an-73 |
| 1A4975 | sp-18 | an-74 | 1U4975 | sp-20 | an-74 | 1A6106 | sp-22 | an-74 |
| 1A4976 | sp-18 | an-75 | 1U4976 | sp-20 | an-75 | 1A6107 | sp-22 | an-75 |
| 1A4977 | sp-18 | an-76 | 1U4977 | sp-20 | an-76 | 1A6108 | sp-22 | an-76 |
| 1A4978 | sp-18 | an-77 | 1U4978 | sp-20 | an-77 | 1A6109 | sp-22 | an-77 |
| 1A4979 | sp-18 | an-78 | 1U4979 | sp-20 | an-78 | 1A6110 | sp-22 | an-78 |
| 1A4980 | sp-18 | an-79 | 1U4980 | sp-20 | an-79 | 1A6111 | sp-22 | an-79 |

TABLE 1-continued

| | | | | | | | | |
|---|---|---|---|---|---|---|---|---|
| 1A4981 | sp-18 | an-80 | 1U4981 | sp-20 | an-80 | 1A6112 | sp-22 | an-80 |
| 1A4982 | sp-18 | an-81 | 1U4982 | sp-20 | an-81 | 1A6113 | sp-22 | an-81 |
| 1A4983 | sp-18 | an-82 | 1U4983 | sp-20 | an-82 | 1A6114 | sp-22 | an-82 |
| 1A4984 | sp-18 | an-83 | 1U4984 | sp-20 | an-83 | 1A6115 | sp-22 | an-83 |
| 1A4985 | sp-18 | an-84 | 1U4985 | sp-20 | an-84 | 1A6116 | sp-22 | an-84 |
| 1A4986 | sp-18 | an-85 | 1U4986 | sp-20 | an-85 | 1A6117 | sp-22 | an-85 |
| 1A4987 | sp-18 | an-86 | 1U4987 | sp-20 | an-86 | 1A6118 | sp-22 | an-86 |
| 1A4988 | sp-18 | an-87 | 1U4988 | sp-20 | an-87 | 1A6119 | sp-22 | an-87 |
| 1A4989 | sp-18 | an-88 | 1U4989 | sp-20 | an-88 | 1A6120 | sp-22 | an-88 |
| 1A4990 | sp-18 | an-89 | 1U4990 | sp-20 | an-89 | 1A6121 | sp-22 | an-89 |
| 1A4991 | sp-18 | an-90 | 1U4991 | sp-20 | an-90 | 1A6122 | sp-22 | an-90 |
| 1A4992 | sp-18 | an-91 | 1U4992 | sp-20 | an-91 | 1A6123 | sp-22 | an-91 |
| 1A4993 | sp-18 | an-92 | 1U4993 | sp-20 | an-92 | 1A6124 | sp-22 | an-92 |
| 1A4994 | sp-18 | an-93 | 1U4994 | sp-20 | an-93 | 1A6125 | sp-22 | an-93 |
| 1A4995 | sp-18 | an-94 | 1U4995 | sp-20 | an-94 | 1A6126 | sp-22 | an-94 |
| 1A4996 | sp-18 | an-95 | 1U4996 | sp-20 | an-95 | 1A6127 | sp-22 | an-95 |
| 1A4997 | sp-18 | an-96 | 1U4997 | sp-20 | an-96 | 1A6128 | sp-22 | an-96 |
| 1A4998 | sp-18 | an-97 | 1U4998 | sp-20 | an-97 | 1A6129 | sp-22 | an-97 |
| 1A4999 | sp-18 | an-98 | 1U4999 | sp-20 | an-98 | 1A6130 | sp-22 | an-98 |
| 1A5000 | sp-18 | an-99 | 1U5000 | sp-20 | an-99 | 1A6131 | sp-22 | an-99 |
| 1A5001 | sp-18 | an-100 | 1U5001 | sp-20 | an-100 | 1A6132 | sp-22 | an-100 |
| 1A5002 | sp-18 | an-101 | 1U5002 | sp-20 | an-101 | 1A6133 | sp-22 | an-101 |
| 1A5003 | sp-18 | an-102 | 1U5003 | sp-20 | an-102 | 1A6134 | sp-22 | an-102 |
| 1A5004 | sp-18 | an-103 | 1U5004 | sp-20 | an-103 | 1A6135 | sp-22 | an-103 |
| 1A5005 | sp-18 | an-104 | 1U5005 | sp-20 | an-104 | 1A6136 | sp-22 | an-104 |
| 1A5006 | sp-18 | an-105 | 1U5006 | sp-20 | an-105 | 1A6137 | sp-22 | an-105 |
| 1A5007 | sp-18 | an-106 | 1U5007 | sp-20 | an-106 | 1A6138 | sp-22 | an-106 |
| 1A5008 | sp-18 | an-107 | 1U5008 | sp-20 | an-107 | 1A6139 | sp-22 | an-107 |
| 1A5009 | sp-18 | an-108 | 1U5009 | sp-20 | an-108 | 1A6140 | sp-22 | an-108 |
| 1A5010 | sp-18 | an-109 | 1U5010 | sp-20 | an-109 | 1A6141 | sp-22 | an-109 |
| 1A5011 | sp-18 | an-110 | 1U5011 | sp-20 | an-110 | 1A6142 | sp-22 | an-110 |
| 1A5012 | sp-18 | an-111 | 1U5012 | sp-20 | an-111 | 1A6143 | sp-22 | an-111 |
| 1A5013 | sp-18 | an-112 | 1U5013 | sp-20 | an-112 | 1A6144 | sp-22 | an-112 |
| 1A5014 | sp-18 | an-113 | 1U5014 | sp-20 | an-113 | 1A6145 | sp-22 | an-113 |
| 1A5015 | 3P-18 | an-114 | 1U5015 | sp-20 | an-114 | 1A6146 | sp-22 | an-114 |
| 1A5016 | sp-18 | an-115 | 1U5016 | sp-20 | an-115 | 1A6147 | sp-22 | an-115 |
| 1A5017 | sp-18 | an-116 | 1U5017 | sp-20 | an-116 | 1A6148 | sp-22 | an-116 |
| 1A5018 | sp-18 | an-117 | 1U5018 | sp-20 | an-117 | 1A6149 | sp-22 | an-117 |
| 1A5019 | sp-18 | an-118 | 1U5019 | sp-20 | an-118 | 1A6150 | sp-22 | an-118 |
| 1A5020 | sp-18 | an-119 | 1U5020 | sp-20 | an-119 | 1A6151 | sp-22 | an-119 |
| 1A5021 | sp-18 | an-120 | 1U5021 | sp-20 | an-120 | 1A6152 | sp-22 | an-120 |
| 1A5022 | sp-18 | an-121 | 1U5022 | sp-20 | an-121 | 1A6153 | sp-22 | an-121 |
| 1A5023 | sp-18 | an-122 | 1U5023 | sp-20 | an-122 | 1A6154 | sp-22 | an-122 |
| 1A5024 | sp-18 | an-123 | 1U5024 | sp-20 | an-123 | 1A6155 | sp-22 | an-123 |
| 1A5025 | sp-18 | an-124 | 1U5025 | sp-20 | an-124 | 1A6156 | sp-22 | an-124 |
| 1A5026 | sp-18 | an-125 | 1U5026 | sp-20 | an-125 | 1A6157 | sp-22 | an-125 |
| 1A5027 | sp-18 | an-126 | 1U5027 | sp-20 | an-126 | 1A6158 | sp-22 | an-126 |
| 1A5028 | sp-18 | an-127 | 1U5028 | sp-20 | an-127 | 1A6159 | sp-22 | an-127 |
| 1A5029 | sp-18 | an-128 | 1U5029 | sp-20 | an-128 | 1A6160 | sp-22 | an-128 |
| 1A5030 | sp-18 | an-129 | 1U5030 | sp-20 | an-129 | 1A6161 | sp-22 | an-129 |
| 1A5031 | sp-18 | an-130 | 1U5031 | sp-20 | an-130 | 1A6162 | sp-22 | an-130 |
| 1A5032 | sp-18 | an-131 | 1U5032 | sp-20 | an-131 | 1A6163 | sp-22 | an-131 |
| 1A5033 | sp-18 | an-132 | 1U5033 | sp-20 | an-132 | 1A6164 | sp-22 | an-132 |
| 1A5034 | sp-18 | an-133 | 1U5034 | sp-20 | an-133 | 1A6165 | sp-22 | an-133 |
| 1A5035 | sp-18 | an-134 | 1U5035 | sp-20 | an-134 | 1A6166 | sp-22 | an-134 |
| 1A5036 | sp-18 | an-135 | 1U5036 | sp-20 | an-135 | 1A6167 | sp-22 | an-135 |
| 1A5037 | sp-18 | an-136 | 1U5037 | sp-20 | an-136 | 1A6168 | sp-22 | an-136 |
| 1A5038 | sp-18 | an-137 | 1U5038 | sp-20 | an-137 | 1A6169 | sp-22 | an-137 |
| 1A5039 | sp-18 | an-138 | 1U5039 | sp-20 | an-138 | 1A6170 | sp-22 | an-138 |
| 1A5040 | sp-18 | an-139 | 1U5040 | sp-20 | an-139 | 1A6171 | sp-22 | an-139 |
| 1A5041 | sp-18 | an-140 | 1U5041 | sp-20 | an-140 | 1A6172 | sp-22 | an-140 |
| 1A5042 | sp-18 | an-141 | 1U5042 | sp-20 | an-141 | 1A6173 | sp-22 | an-141 |
| 1A5043 | sp-18 | an-142 | 1U5043 | sp-20 | an-142 | 1A6174 | sp-22 | an-142 |
| 1A5044 | sp-18 | an-143 | 1U5044 | sp-20 | an-143 | 1A6175 | sp-22 | an-143 |
| 1A5045 | sp-18 | an-144 | 1U5045 | sp-20 | an-144 | 1A6176 | sp-22 | an-144 |
| 1A5046 | sp-18 | an-145 | 1U5046 | sp-20 | an-145 | 1A6177 | sp-22 | an-145 |
| 1A5047 | sp-18 | an-146 | 1U5047 | sp-20 | an-146 | 1A6178 | sp-22 | an-146 |
| 1A5048 | sp-18 | an-147 | 1U5048 | sp-20 | an-147 | 1A6179 | sp-22 | an-147 |
| 1A5049 | sp-18 | an-148 | 1U5049 | sp-20 | an-148 | 1A6180 | sp-22 | an-148 |
| 1A5050 | sp-18 | an-149 | 1U5050 | sp-20 | an-149 | 1A6181 | sp-22 | an-149 |
| 1A5051 | sp-18 | an-150 | 1U5051 | sp-20 | an-150 | 1A6182 | sp-22 | an-150 |
| 1A5052 | sp-18 | an-151 | 1U5052 | sp-20 | an-151 | 1A6183 | sp-22 | an-151 |
| 1A5053 | sp-18 | an-152 | 1U5053 | sp-20 | an-152 | 1A6184 | sp-22 | an-152 |
| 1A5054 | sp-18 | an-153 | 1U5054 | sp-20 | an-153 | 1A6185 | sp-22 | an-153 |
| 1A5055 | sp-18 | an-154 | 1U5055 | sp-20 | an-154 | 1A6186 | sp-22 | an-154 |
| 1A5056 | sp-18 | an-155 | 1U5056 | sp-20 | an-155 | 1A6187 | sp-22 | an-155 |
| 1A5057 | sp-18 | an-156 | 1U5057 | sp-20 | an-156 | 1A6188 | sp-22 | an-156 |
| 1A5058 | sp-18 | an-157 | 1U5058 | sp-20 | an-157 | 1A6189 | sp-22 | an-157 |
| 1A5059 | sp-18 | an-158 | 1U5059 | sp-20 | an-158 | 1A6190 | sp-22 | an-158 |

TABLE 1-continued

| | | | | | | | | |
|---|---|---|---|---|---|---|---|---|
| 1A5060 | sp-18 | an-159 | 1U5060 | sp-20 | an-159 | 1A6191 | sp-22 | an-159 |
| 1A5061 | sp-18 | an-160 | 1U5061 | sp-20 | an-160 | 1A6192 | sp-22 | an-160 |
| 1A5062 | sp-18 | an-161 | 1U5062 | sp-20 | an-161 | 1A6193 | sp-22 | an-161 |
| 1A5063 | sp-18 | an-162 | 1U5063 | sp-20 | an-162 | 1A6194 | sp-22 | an-162 |
| 1A5064 | sp-18 | an-163 | 1U5064 | sp-20 | an-163 | 1A6195 | sp-22 | an-163 |
| 1A5065 | sp-18 | an-164 | 1U5065 | sp-20 | an-164 | 1A6196 | sp-22 | an-164 |
| 1A5066 | sp-18 | an-165 | 1U5066 | sp-20 | an-165 | 1A6197 | sp-22 | an-165 |
| 1A5067 | sp-18 | an-166 | 1U5067 | sp-20 | an-166 | 1A6198 | sp-22 | an-166 |
| 1A5068 | sp-18 | an-167 | 1U5068 | sp-20 | an-167 | 1A5199 | sp-22 | an-167 |
| 1A5069 | sp-18 | an-168 | 1U5069 | sp-20 | an-168 | 1A6200 | sp-22 | an-168 |
| 1A5070 | sp-18 | an-169 | 1U5070 | sp-20 | an-169 | 1A6201 | sp-22 | an-169 |
| 1A5071 | sp-18 | an-170 | 1U5071 | sp-20 | an-170 | 1A6202 | sp-22 | an-170 |
| 1A5072 | sp-18 | an-171 | 1U5072 | sp-20 | an-171 | 1A6203 | sp-22 | an-171 |
| 1A5073 | sp-18 | an-172 | 1U5073 | sp-20 | an-172 | 1A6204 | sp-22 | an-172 |
| 1A5074 | sp-18 | an-173 | 1U5074 | sp-20 | an-173 | 1A6205 | sp-22 | an-173 |
| 1A5075 | sp-18 | an-174 | 1U5075 | sp-20 | an-174 | 1A6206 | sp-22 | an-174 |
| 1A5076 | sp-18 | an-175 | 1U5076 | sp-20 | an-175 | 1A6207 | sp-22 | an-175 |
| 1A5077 | sp-18 | an-176 | 1U5077 | sp-20 | an-176 | 1A6208 | sp-22 | an-176 |
| 1A5078 | sp-18 | an-177 | 1U5078 | sp-20 | an-177 | 1A6209 | sp-22 | an-177 |
| 1A5079 | sp-18 | an-178 | 1U5079 | sp-20 | an-178 | 1A6210 | sp-22 | an-178 |
| 1A5080 | sp-18 | an-179 | 1U5080 | sp-20 | an-179 | 1A6211 | sp-22 | an-179 |
| 1A5081 | sp-18 | an-180 | 1U5081 | sp-20 | an-180 | 1A6212 | sp-22 | an-180 |
| 1A5082 | sp-18 | an-181 | 1U5082 | sp-20 | an-181 | 1A6213 | sp-22 | an-181 |
| 1A5083 | sp-18 | an-182 | 1U5083 | sp-20 | an-182 | 1A6214 | sp-22 | an-182 |
| 1A5084 | sp-18 | an-183 | 1U5084 | sp-20 | an-183 | 1A6215 | sp-22 | an-183 |
| 1A5085 | sp-18 | an-184 | 1U5085 | sp-20 | an-184 | 1A6216 | sp-22 | an-184 |
| 1A5086 | sp-18 | an-185 | 1U5086 | sp-20 | an-185 | 1A6217 | sp-22 | an-185 |
| 1A5087 | sp-18 | an-186 | 1U5087 | sp-20 | an-186 | 1A6218 | sp-22 | an-186 |
| 1A5088 | sp-18 | an-187 | 1U5088 | sp-20 | an-187 | 1A6219 | sp-22 | an-187 |
| 1A5089 | sp-18 | an-188 | 1U5089 | sp-20 | an-188 | 1A6220 | sp-22 | an-188 |
| 1A5090 | sp-18 | an-189 | 1U5090 | sp-20 | an-189 | 1A6221 | sp-22 | an-189 |
| 1A5091 | sp-18 | an-190 | 1U5091 | sp-20 | an-190 | 1A6222 | sp-22 | an-190 |
| 1A5092 | sp-18 | an-191 | 1U5092 | sp-20 | an-191 | 1A6223 | sp-22 | an-191 |
| 1A5093 | sp-18 | an-192 | 1U5093 | sp-20 | an-192 | 1A6224 | sp-22 | an-192 |
| 1A5094 | sp-18 | an-193 | 1U5094 | sp-20 | an-193 | 1A6225 | sp-22 | an-193 |
| 1A5095 | sp-18 | an-194 | 1U5095 | sp-20 | an-194 | 1A6226 | sp-22 | an-194 |
| 1A5096 | sp-18 | an-195 | 1U5096 | sp-20 | an-195 | 1A6227 | sp-22 | an-195 |
| 1A5097 | sp-18 | an-196 | 1U5097 | sp-20 | an-196 | 1A6228 | sp-22 | an-196 |
| 1A5098 | sp-18 | an-197 | 1U5098 | sp-20 | an-197 | 1A6229 | sp-22 | an-197 |
| 1A5099 | sp-18 | an-198 | 1U5099 | sp-20 | an-198 | 1A6230 | sp-22 | an-198 |
| 1A5100 | sp-18 | an-199 | 1U5100 | sp-20 | an-199 | 1A6231 | sp-22 | an-199 |
| 1A5101 | sp-18 | an-200 | 1U5101 | sp-20 | an-200 | 1A6232 | sp-22 | an-200 |
| 1A5102 | sp-18 | an-201 | 1U5102 | sp-20 | an-201 | 1A6233 | sp-22 | an-201 |
| 1A5103 | sp-18 | an-202 | 1U5103 | sp-20 | an-202 | 1A6234 | sp-22 | an-202 |
| 1A5104 | sp-18 | an-203 | 1U5104 | sp-20 | an-203 | 1A6235 | sp-22 | an-203 |
| 1A5105 | sp-18 | an-204 | 1U5105 | sp-20 | an-204 | 1A6236 | sp-22 | an-204 |
| 1A5106 | sp-18 | an-205 | 1U5106 | sp-20 | an-205 | 1A6237 | sp-22 | an-205 |
| 1A5107 | sp-18 | an-206 | 1U5107 | sp-20 | an-206 | 1A6238 | sp-22 | an-206 |
| 1A5108 | sp-18 | an-207 | 1U5108 | sp-20 | an-207 | 1A6239 | sp-22 | an-207 |
| 1A5109 | sp-18 | an-208 | 1U5109 | sp-20 | an-208 | 1A6240 | sp-22 | an-208 |
| 1A5110 | sp-18 | an-209 | 1U5110 | sp-20 | an-209 | 1A6241 | sp-22 | an-209 |
| 1A5111 | sp-18 | an-210 | 1U5111 | sp-20 | an-210 | 1A6242 | sp-22 | an-210 |
| 1A5112 | sp-18 | an-211 | 1U5112 | sp-20 | an-211 | 1A6243 | sp-22 | an-211 |
| 1A5113 | sp-18 | an-212 | 1U5113 | sp-20 | an-212 | 1A6244 | sp-22 | an-212 |
| 1A5114 | sp-18 | an-213 | 1U5114 | sp-20 | an-213 | 1A6245 | sp-22 | an-213 |
| 1A5115 | sp-18 | an-214 | 1U5115 | sp-20 | an-214 | 1A6246 | sp-22 | an-214 |
| 1A5116 | sp-18 | an-215 | 1U5116 | sp-20 | an-215 | 1A6247 | sp-22 | an-215 |
| 1A5117 | sp-18 | an-216 | 1U5117 | sp-20 | an-216 | 1A6248 | sp-22 | an-216 |
| 1A5118 | sp-18 | an-217 | 1U5118 | sp-20 | an-217 | 1A6249 | sp-22 | an-217 |
| 1A5119 | sp-18 | an-218 | 1U5119 | sp-20 | an-218 | 1A6250 | sp-22 | an-218 |
| 1A5120 | sp-18 | an-219 | 1U5120 | sp-20 | an-219 | 1A6251 | sp-22 | an-219 |
| 1A5121 | sp-18 | an-220 | 1U5121 | sp-20 | an-220 | 1A6252 | sp-22 | an-220 |
| 1A5122 | sp-18 | an-221 | 1U5122 | sp-20 | an-221 | 1A6253 | sp-22 | an-221 |
| 1A5123 | sp-18 | an-222 | 1U5123 | sp-20 | an-222 | 1A6254 | sp-22 | an-222 |
| 1A5124 | sp-18 | an-223 | 1U5124 | sp-20 | an-223 | 1A6255 | sp-22 | an-223 |
| 1A5125 | sp-18 | an-224 | 1U5125 | sp-20 | an-224 | 1A6256 | sp-22 | an-224 |
| 1A5126 | sp-18 | an-225 | 1U5126 | sp-20 | an-225 | 1A6257 | sp-22 | an-225 |
| 1A5127 | sp-18 | an-226 | 1U5127 | sp-20 | an-226 | 1A6258 | sp-22 | an-226 |
| 1A5128 | sp-18 | an-227 | 1U5128 | sp-20 | an-227 | 1A6259 | sp-22 | an-227 |
| 1A5129 | sp-18 | an-228 | 1U5129 | sp-20 | an-228 | 1A6260 | sp-22 | an-228 |
| 1A5130 | sp-18 | an-229 | 1U5130 | sp-20 | an-229 | 1A6261 | sp-22 | an-229 |
| 1A5131 | sp-18 | an-230 | 1U5131 | sp-20 | an-230 | 1A6262 | sp-22 | an-230 |
| 1A5132 | sp-18 | an-231 | 1U5132 | sp-20 | an-231 | 1A6263 | sp-22 | an-231 |
| 1A5133 | sp-18 | an-232 | 1U5133 | sp-20 | an-232 | 1A6264 | sp-22 | an-232 |
| 1A5134 | sp-18 | an-233 | 1U5134 | sp-20 | an-233 | 1A6265 | sp-22 | an-233 |
| 1A5135 | sp-18 | an-234 | 1U5135 | sp-20 | an-234 | 1A6266 | sp-22 | an-234 |
| 1A5136 | sp-18 | an-235 | 1U5136 | sp-20 | an-235 | 1A6267 | sp-22 | an-235 |
| 1A5137 | sp-18 | an-236 | 1U5137 | sp-20 | an-236 | 1A6268 | sp-22 | an-236 |
| 1A5138 | sp-18 | an-237 | 1U5138 | sp-20 | an-237 | 1A6269 | sp-22 | an-237 |

TABLE 1-continued

| | | | | | | | | |
|---|---|---|---|---|---|---|---|---|
| 1A5139 | sp-18 | an-238 | 1U5139 | sp-20 | an-238 | 1A6270 | sp-22 | an-238 |
| 1A5140 | sp-18 | an-239 | 1U5140 | sp-20 | an-239 | 1A6271 | sp-22 | an-239 |
| 1A5141 | sp-18 | an-240 | 1U5141 | sp-20 | an-240 | 1A6272 | sp-22 | an-240 |
| 1A5142 | sp-18 | an-241 | 1U5142 | sp-20 | an-241 | 1A6273 | sp-22 | an-241 |
| 1A5143 | sp-18 | an-242 | 1U5143 | sp-20 | an-242 | 1A6274 | sp-22 | an-242 |
| 1A5144 | sp-18 | an-243 | 1U5144 | sp-20 | an-243 | 1A6275 | sp-22 | an-243 |
| 1A5145 | sp-18 | an-244 | 1U5145 | sp-20 | an-244 | 1A6276 | sp-22 | an-244 |
| 1A5146 | sp-18 | an-245 | 1U5146 | sp-20 | an-245 | 1A6277 | sp-22 | an-245 |
| 1A5147 | sp-18 | an-245 | 1U5147 | sp-20 | an-246 | 1A6278 | sp-22 | an-246 |
| 1A5148 | sp-18 | an-247 | 1U5148 | sp-20 | an-247 | 1A6279 | sp-22 | an-247 |
| 1A5149 | sp-18 | an-248 | 1U5149 | sp-20 | an-248 | 1A6280 | sp-22 | an-248 |
| 1A5150 | sp-18 | an-249 | 1U5150 | sp-20 | an-249 | 1A6281 | sp-22 | an-249 |
| 1A5151 | sp-18 | an-250 | 1U5151 | sp-20 | an-250 | 1A6282 | sp-22 | an-250 |
| 1A5152 | sp-18 | an-251 | 1U5152 | sp-20 | an-251 | 1A6283 | sp-22 | an-251 |
| 1A5153 | sp-18 | an-252 | 1U5153 | sp-20 | an-252 | 1A6284 | sp-22 | an-252 |
| 1A5154 | sp-18 | an-253 | 1U5154 | sp-20 | an-253 | 1A6285 | sp-22 | an-253 |
| 1A5155 | sp-18 | an-254 | 1U5155 | sp-20 | an-254 | 1A6286 | sp-22 | an-254 |
| 1A5156 | sp-18 | an-255 | 1U5156 | sp-20 | an-255 | 1A6287 | sp-22 | an-255 |
| 1A5157 | sp-18 | an-256 | 1U5157 | sp-20 | an-256 | 1A6288 | sp-22 | an-256 |
| 1A5158 | sp-18 | an-257 | 1U5158 | sp-20 | an-257 | 1A6289 | sp-22 | an-257 |
| 1A5159 | sp-18 | an-258 | 1U5159 | sp-20 | an-258 | 1A6290 | sp-22 | an-258 |
| 1A5160 | sp-18 | an-259 | 1U5160 | sp-20 | an-259 | 1A6291 | sp-22 | an-259 |
| 1A5161 | sp-18 | an-260 | 1U5161 | sp-20 | an-260 | 1A6292 | sp-22 | an-260 |
| 1A5162 | sp-18 | an-261 | 1U5162 | sp-20 | an-261 | 1A6293 | sp-22 | an-261 |
| 1A5163 | sp-18 | an-262 | 1U5163 | sp-20 | an-262 | 1A6294 | sp-22 | an-262 |
| 1A5164 | sp-18 | an-263 | 1U5164 | sp-20 | an-263 | 1A6295 | sp-22 | an-263 |
| 1A5165 | sp-18 | an-264 | 1U5165 | sp-20 | an-264 | 1A6296 | sp-22 | an-264 |
| 1A5166 | sp-18 | an-265 | 1U5166 | sp-20 | an-265 | 1A6297 | sp-22 | an-265 |
| 1A5167 | sp-18 | an-266 | 1U5167 | sp-20 | an-266 | 1A6298 | sp-22 | an-266 |
| 1A5168 | sp-18 | an-267 | 1U5168 | sp-20 | an-267 | 1A6299 | sp-22 | an-267 |
| 1A5169 | sp-18 | an-268 | 1U5169 | sp-20 | an-268 | 1A6300 | sp-22 | an-268 |
| 1A5170 | sp-18 | an-269 | 1U5170 | sp-20 | an-269 | 1A6301 | sp-22 | an-269 |
| 1A5171 | sp-18 | an-270 | 1U5171 | sp-20 | an-270 | 1A6302 | sp-22 | an-270 |
| 1A5172 | sp-18 | an-271 | 1U5172 | sp-20 | an-271 | 1A6303 | sp-22 | an-271 |
| 1A5173 | sp-18 | an-272 | 1U5173 | sp-20 | an-272 | 1A6304 | sp-22 | an-272 |
| 1A5174 | sp-18 | an-273 | 1U5174 | sp-20 | an-273 | 1A6305 | sp-22 | an-273 |
| 1A5175 | sp-18 | an-274 | 1U5175 | sp-20 | an-274 | 1A6306 | sp-22 | an-274 |
| 1A5176 | sp-18 | an-275 | 1U5176 | sp-20 | an-275 | 1A6307 | sp-22 | an-275 |
| 1A5177 | sp-18 | an-276 | 1U5177 | sp-20 | an-276 | 1A6308 | sp-22 | an-276 |
| 1A5178 | sp-18 | an-277 | 1U5178 | sp-20 | an-277 | 1A6309 | sp-22 | an-277 |
| 1A5179 | sp-18 | an-278 | 1U5179 | sp-20 | an-278 | 1A6310 | sp-22 | an-278 |
| 1A5180 | sp-18 | an-279 | 1U5180 | sp-20 | an-279 | 1A6311 | sp-22 | an-279 |
| 1A5181 | sp-18 | an-280 | 1U5181 | sp-20 | an-280 | 1A6312 | sp-22 | an-280 |
| 1A5182 | sp-18 | an-281 | 1U5182 | sp-20 | an-281 | 1A6313 | sp-22 | an-281 |
| 1A5183 | sp-18 | an-282 | 1U5183 | sp-20 | an-282 | 1A6314 | sp-22 | an-282 |
| 1A5184 | sp-18 | an-283 | 1U5184 | sp-20 | an-283 | 1A6315 | sp-22 | an-283 |
| 1A5185 | sp-18 | an-284 | 1U5185 | sp-20 | an-284 | 1A6316 | sp-22 | an-284 |
| 1A5186 | sp-18 | an-285 | 1U5186 | sp-20 | an-285 | 1A6317 | sp-22 | an-285 |
| 1A5187 | sp-18 | an-286 | 1U5187 | sp-20 | an-286 | 1A6318 | sp-22 | an-286 |
| 1A5188 | sp-18 | an-287 | 1U5188 | sp-20 | an-287 | 1A6319 | sp-22 | an-287 |
| 1A5189 | sp-18 | an-288 | 1U5189 | sp-20 | an-288 | 1A6320 | sp-22 | an-288 |
| 1A5190 | sp-18 | an-289 | 1U5190 | sp-20 | an-289 | 1A6321 | sp-22 | an-289 |
| 1A5191 | sp-18 | an-290 | 1U5191 | sp-20 | an-290 | 1A6322 | sp-22 | an-290 |
| 1A5192 | sp-18 | an-291 | 1U5192 | sp-20 | an-291 | 1A6323 | sp-22 | an-291 |
| 1A5193 | sp-18 | an-292 | 1U5193 | sp-20 | an-292 | 1A6324 | sp-22 | an-292 |
| 1A5194 | sp-18 | an-293 | 1U5194 | sp-20 | an-293 | 1A6325 | sp-22 | an-293 |
| 1A5195 | sp-18 | an-294 | 1U5195 | sp-20 | an-294 | 1A6326 | sp-22 | an-294 |
| 1A5196 | sp-18 | an-295 | 1U5196 | sp-20 | an-295 | 1A6327 | sp-22 | an-295 |
| 1A5197 | sp-18 | an-296 | 1U5197 | sp-20 | an-296 | 1A6328 | sp-22 | an-296 |
| 1A5198 | sp-18 | an-297 | 1U5198 | sp-20 | an-297 | 1A6329 | sp-22 | an-297 |
| 1A5199 | sp-18 | an-298 | 1U5199 | sp-20 | an-298 | 1A6330 | sp-22 | an-298 |
| 1A5200 | sp-18 | an-299 | 1U5200 | sp-20 | an-299 | 1A6331 | sp-22 | an-299 |
| 1A5201 | sp-18 | an-300 | 1U5201 | sp-20 | an-300 | 1A6332 | sp-22 | an-300 |
| 1A5202 | sp-18 | an-301 | 1U5202 | sp-20 | an-301 | 1A6333 | sp-22 | an-301 |
| 1A5203 | sp-18 | an-302 | 1U5203 | sp-20 | an-302 | 1A6334 | sp-22 | an-302 |
| 1A5204 | sp-18 | an-303 | 1U5204 | sp-20 | an-303 | 1A6335 | sp-22 | an-303 |
| 1A5205 | sp-18 | an-304 | 1U5205 | sp-20 | an-304 | 1A6336 | sp-22 | an-304 |
| 1A5206 | sp-18 | an-305 | 1U5206 | sp-20 | an-305 | 1A6337 | sp-22 | an-305 |
| 1A5207 | sp-18 | an-306 | 1U5207 | sp-20 | an-306 | 1A6338 | sp-22 | an-306 |
| 1A5208 | sp-18 | an-307 | 1U5208 | sp-20 | an-307 | 1A6339 | sp-22 | an-307 |
| 1A5209 | sp-18 | an-308 | 1U5209 | sp-20 | an-308 | 1A6340 | sp-22 | an-308 |
| 1A5210 | sp-18 | an-309 | 1U5210 | sp-20 | an-309 | 1A6341 | sp-22 | an-309 |
| 1A5211 | sp-18 | an-310 | 1U5211 | sp-20 | an-310 | 1A6342 | sp-22 | an-310 |
| 1A5212 | sp-18 | an-311 | 1U5212 | sp-20 | an-311 | 1A6343 | sp-22 | an-311 |
| 1A5213 | sp-18 | an-312 | 1U5213 | sp-20 | an-312 | 1A6344 | sp-22 | an-312 |
| 1A5214 | sp-18 | an-313 | 1U5214 | sp-20 | an-313 | 1A6345 | sp-22 | an-313 |
| 1A5215 | sp-18 | an-314 | 1U5215 | sp-20 | an-314 | 1A6346 | sp-22 | an-314 |
| 1A5216 | sp-18 | an-315 | 1U5216 | sp-20 | an-315 | 1A6347 | sp-22 | an-315 |
| 1A5217 | sp-18 | an-316 | 1U5217 | sp-20 | an-316 | 1A6348 | sp-22 | an-316 |

TABLE 1-continued

| | | | | | | | | |
|---|---|---|---|---|---|---|---|---|
| 1A5218 | sp-18 | an-317 | 1U5218 | sp-20 | an-317 | 1A6349 | sp-22 | an-317 |
| 1A5219 | sp-18 | an-318 | 1U5219 | sp-20 | an-318 | 1A6350 | sp-22 | an-318 |
| 1A5220 | sp-18 | an-319 | 1U5220 | sp-20 | an-319 | 1A6351 | sp-22 | an-319 |
| 1A5221 | sp-18 | an-320 | 1U5221 | sp-20 | an-320 | 1A6352 | sp-22 | an-320 |
| 1A5222 | sp-18 | an-321 | 1U5222 | sp-20 | an-321 | 1A6353 | sp-22 | an-321 |
| 1A5223 | sp-18 | an-322 | 1U5223 | sp-20 | an-322 | 1A6354 | sp-22 | an-322 |
| 1A5224 | sp-18 | an-323 | 1U5224 | sp-20 | an-323 | 1A6355 | sp-22 | an-323 |
| 1A5225 | sp-18 | an-324 | 1U5225 | sp-20 | an-324 | 1A6356 | sp-22 | an-324 |
| 1A5226 | sp-18 | an-325 | 1U5226 | sp-20 | an-325 | 1A6357 | sp-22 | an-325 |
| 1A5227 | sp-18 | an-326 | 1U5227 | sp-20 | an-326 | 1A6358 | sp-22 | an-326 |
| 1A5228 | sp-18 | an-327 | 1U5228 | sp-20 | an-327 | 1A6359 | sp-22 | an-327 |
| 1A5229 | sp-18 | an-328 | 1U5229 | sp-20 | an-328 | 1A6360 | sp-22 | an-328 |
| 1A5230 | sp-18 | an-329 | 1U5230 | sp-20 | an-329 | 1A6361 | sp-22 | an-329 |
| 1A5231 | sp-18 | an-330 | 1U5231 | sp-20 | an-330 | 1A6362 | sp-22 | an-330 |
| 1A5232 | sp-18 | an-331 | 1U5232 | sp-20 | an-331 | 1A6363 | sp-22 | an-331 |
| 1A5233 | sp-18 | an-332 | 1U5233 | sp-20 | an-332 | 1A6364 | sp-22 | an-332 |
| 1A5234 | sp-18 | an-333 | 1U5234 | sp-20 | an-333 | 1A6365 | sp-22 | an-333 |
| 1A5235 | sp-18 | an-334 | 1U5235 | sp-20 | an-334 | 1A6366 | sp-22 | an-334 |
| 1A5236 | sp-18 | an-335 | 1U5236 | sp-20 | an-335 | 1A6367 | sp-22 | an-335 |
| 1A5237 | sp-18 | an-336 | 1U5237 | sp-20 | an-336 | 1A6368 | sp-22 | an-336 |
| 1A5238 | sp-18 | an-337 | 1U5238 | sp-20 | an-337 | 1A6369 | sp-22 | an-337 |
| 1A5239 | sp-18 | an-338 | 1U5239 | sp-20 | an-338 | 1A6370 | sp-22 | an-338 |
| 1A5240 | sp-18 | an-339 | 1U5240 | sp-20 | an-339 | 1A6371 | sp-22 | an-339 |
| 1A5241 | sp-18 | an-340 | 1U5241 | sp-20 | an-340 | 1A6372 | sp-22 | an-340 |
| 1A5242 | sp-18 | an-341 | 1U5242 | sp-20 | an-341 | 1A6373 | sp-22 | an-341 |
| 1A5243 | sp-18 | an-342 | 1U5243 | sp-20 | an-342 | 1A6374 | sp-22 | an-342 |
| 1A5244 | sp-18 | an-343 | 1U5244 | sp-20 | an-343 | 1A6375 | sp-22 | an-343 |
| 1A5245 | sp-18 | an-344 | 1U5245 | sp-20 | an-344 | 1A6376 | sp-22 | an-344 |
| 1A5246 | sp-18 | an-345 | 1U5246 | sp-20 | an-345 | 1A6377 | sp-22 | an-345 |
| 1A5247 | sp-18 | an-346 | 1U5247 | sp-20 | an-346 | 1A6378 | sp-22 | an-346 |
| 1A5248 | sp-18 | an-347 | 1U5248 | sp-20 | an-347 | 1A6379 | sp-22 | an-347 |
| 1A5249 | sp-18 | an-348 | 1U5249 | sp-20 | an-348 | 1A6380 | sp-22 | an-348 |
| 1A5250 | sp-18 | an-349 | 1U5250 | sp-20 | an-349 | 1A6381 | sp-22 | an-349 |
| 1A5251 | sp-18 | an-350 | 1U5251 | sp-20 | an-350 | 1A6382 | sp-22 | an-350 |
| 1A5252 | sp-18 | an-351 | 1U5252 | sp-20 | an-351 | 1A6383 | sp-22 | an-351 |
| 1A5253 | sp-18 | an-352 | 1U5253 | sp-20 | an-352 | 1A6384 | sp-22 | an-352 |
| 1A5254 | sp-18 | an-353 | 1U5254 | sp-20 | an-353 | 1A6385 | sp-22 | an-353 |
| 1A5255 | sp-18 | an-354 | 1U5255 | sp-20 | an-354 | 1A6386 | sp-22 | an-354 |
| 1A5256 | sp-18 | an-355 | 1U5256 | sp-20 | an-355 | 1A6387 | sp-22 | an-355 |
| 1A5257 | sp-18 | an-356 | 1U5257 | sp-20 | an-356 | 1A6388 | sp-22 | an-356 |
| 1A5258 | sp-18 | an-357 | 1U5258 | sp-20 | an-357 | 1A6389 | sp-22 | an-357 |
| 1A5259 | sp-18 | an-358 | 1U5259 | sp-20 | an-358 | 1A6390 | sp-22 | an-358 |
| 1A5260 | sp-18 | an-359 | 1U5260 | sp-20 | an-359 | 1A6391 | sp-22 | an-359 |
| 1A5261 | sp-18 | an-360 | 1U5261 | sp-20 | an-360 | 1A6392 | sp-22 | an-360 |
| 1A5262 | sp-18 | an-361 | 1U5262 | sp-20 | an-361 | 1A6393 | sp-22 | an-361 |
| 1A5263 | sp-18 | an-362 | 1U5263 | sp-20 | an-362 | 1A6394 | sp-22 | an-362 |
| 1A5264 | sp-18 | an-363 | 1U5264 | sp-20 | an-363 | 1A6395 | sp-22 | an-363 |
| 1A5265 | sp-18 | an-364 | 1U5265 | sp-20 | an-364 | 1A6396 | sp-22 | an-364 |
| 1A5266 | sp-18 | an-365 | 1U5266 | sp-20 | an-365 | 1A6397 | sp-22 | an-365 |
| 1A5267 | sp-18 | an-366 | 1U5267 | sp-20 | an-366 | 1A6398 | sp-22 | an-366 |
| 1A5268 | sp-18 | an-367 | 1U5268 | sp-20 | an-367 | 1A6399 | sp-22 | an-367 |
| 1A5269 | sp-18 | an-368 | 1U5269 | sp-20 | an-368 | 1A6400 | sp-22 | an-368 |
| 1A5270 | sp-18 | an-369 | 1U5270 | sp-20 | an-369 | 1A6401 | sp-22 | an-369 |
| 1A5271 | sp-18 | an-370 | 1U5271 | sp-20 | an-370 | 1A6402 | sp-22 | an-370 |
| 1A5272 | sp-18 | an-371 | 1U5272 | sp-20 | an-371 | 1A6403 | sp-22 | an-371 |
| 1A5273 | sp-18 | an-372 | 1U5273 | sp-20 | an-372 | 1A6404 | sp-22 | an-372 |
| 1A5274 | sp-18 | an-373 | 1U5274 | sp-20 | an-373 | 1A6405 | sp-22 | an-373 |
| 1A5275 | sp-18 | an-374 | 1U5275 | sp-20 | an-374 | 1A6406 | sp-22 | an-374 |
| 1A5276 | sp-18 | an-375 | 1U5276 | sp-20 | an-375 | 1A6407 | sp-22 | an-375 |
| 1A5277 | sp-18 | an-376 | 1U5277 | sp-20 | an-376 | 1A6408 | sp-22 | an-376 |
| 1A5278 | sp-18 | an-377 | 1U5278 | sp-20 | an-377 | 1A6409 | sp-22 | an-377 |
| 1A6410 | sp-1 | an-378 | 1U5279 | sp-1 | an-378 | 1C3771 | sp-1 | an-378 |
| 1A6411 | sp-1 | an-379 | 1U5280 | sp-1 | an-379 | 1C3772 | sp-1 | an-379 |
| 1A6412 | sp-1 | an-380 | 1U5281 | sp-1 | an-380 | 1C3773 | sp-1 | an-380 |
| 1A6413 | sp-1 | an-381 | 1U5282 | sp-1 | an-381 | 1C3774 | sp-1 | an-381 |
| 1A6414 | sp-1 | an-382 | 1U5283 | sp-1 | an-382 | 1C3775 | sp-1 | an-382 |
| 1A6415 | sp-1 | an-383 | 1U5284 | sp-1 | an-383 | 1C3776 | sp-1 | an-383 |
| 1A6416 | sp-1 | an-384 | 1U5285 | sp-1 | an-384 | 1C3777 | sp-1 | an-384 |
| 1A6417 | sp-1 | an-385 | 1U5286 | sp-1 | an-385 | 1C3778 | sp-1 | an-385 |
| 1A6418 | sp-1 | an-386 | 1U5287 | sp-1 | an-386 | 1C3779 | sp-1 | an-386 |
| 1A6419 | sp-1 | an-387 | 1U5288 | sp-1 | an-387 | 1C3780 | sp-1 | an-387 |
| 1A6420 | sp-1 | an-388 | 1U5289 | sp-1 | an-388 | 1C3781 | sp-1 | an-388 |
| 1A6421 | sp-1 | an-389 | 1U5290 | sp-1 | an-389 | 1C3782 | sp-1 | an-389 |
| 1A6422 | sp-1 | an-390 | 1U5291 | sp-1 | an-390 | 1C3783 | sp-1 | an-390 |
| 1A6423 | sp-1 | an-391 | 1U5292 | sp-1 | an-391 | 1C3784 | sp-1 | an-391 |
| 1A6424 | sp-1 | an-392 | 1U5293 | sp-1 | an-392 | 1C3785 | sp-1 | an-392 |
| 1A6425 | sp-1 | an-393 | 1U5294 | sp-1 | an-393 | 1C3786 | sp-1 | an-393 |
| 1A6426 | sp-2 | an-378 | 1U5295 | sp-2 | an-378 | 1C3787 | sp-2 | an-378 |
| 1A6427 | sp-2 | an-379 | 1U5296 | sp-2 | an-379 | 1C3788 | sp-2 | an-379 |

TABLE 1-continued

| | | | | | | | | |
|---|---|---|---|---|---|---|---|---|
| 1A6428 | sp-2 | an-380 | 1U5297 | sp-2 | an-380 | 1C3789 | sp-2 | an-380 |
| 1A6429 | sp-2 | an-381 | 1U5298 | sp-2 | an-381 | 1C3790 | sp-2 | an-381 |
| 1A6430 | sp-2 | an-382 | 1U5299 | sp-2 | an-382 | 1C3791 | sp-2 | an-382 |
| 1A6431 | sp-2 | an-383 | 1U5300 | sp-2 | an-383 | 1C3792 | sp-2 | an-383 |
| 1A6432 | sp-2 | an-384 | 1U5301 | sp-2 | an-384 | 1C3793 | sp-2 | an-384 |
| 1A6433 | sp-2 | an-385 | 1U5302 | sp-2 | an-385 | 1C3794 | sp-2 | an-385 |
| 1A6434 | sp-2 | an-386 | 1U5303 | sp-2 | an-386 | 1C3795 | sp-2 | an-386 |
| 1A6435 | sp-2 | an-387 | 1U5304 | sp-2 | an-387 | 1C3796 | sp-2 | an-387 |
| 1A6436 | sp-2 | an-388 | 1U5305 | sp-2 | an-388 | 1C3797 | sp-2 | an-388 |
| 1A6437 | sp-2 | an-389 | 1U5306 | sp-2 | an-389 | 1C3798 | sp-2 | an-389 |
| 1A6438 | sp-2 | an-390 | 1U5307 | sp-2 | an-390 | 1C3799 | sp-2 | an-390 |
| 1A6439 | sp-2 | an-391 | 1U5308 | sp-2 | an-391 | 1C3800 | sp-2 | an-391 |
| 1A6440 | sp-2 | an-392 | 1U5309 | sp-2 | an-392 | 1C3801 | sp-2 | an-392 |
| 1A6441 | sp-2 | an-393 | 1U5310 | sp-2 | an-393 | 1C3802 | sp-2 | an-393 |
| 1A6442 | sp-3 | an-378 | 1U5311 | sp-3 | an-378 | 1C3803 | sp-3 | an-378 |
| 1A6443 | sp-3 | an-379 | 1U5312 | sp-3 | an-379 | 1C3804 | sp-3 | an-379 |
| 1A6444 | sp-3 | an-380 | 1U5313 | sp-3 | an-380 | 1C3805 | sp-3 | an-380 |
| 1A6445 | sp-3 | an-381 | 1U5314 | sp-3 | an-381 | 1C3806 | sp-3 | an-381 |
| 1A6446 | sp-3 | an-382 | 1U5315 | sp-3 | an-382 | 1C3807 | sp-3 | an-382 |
| 1A6447 | sp-3 | an-383 | 1U5316 | sp-3 | an-383 | 1C3808 | sp-3 | an-383 |
| 1A6448 | sp-3 | an-384 | 1U5317 | sp-3 | an-384 | 1C3809 | sp-3 | an-384 |
| 1A6449 | sp-3 | an-385 | 1U5318 | sp-3 | an-385 | 1C3810 | sp-3 | an-385 |
| 1A6450 | sp-3 | an-386 | 1U5319 | sp-3 | an-386 | 1C3811 | sp-3 | an-386 |
| 1A6451 | sp-3 | an-387 | 1U5320 | sp-3 | an-387 | 1C3812 | sp-3 | an-387 |
| 1A6452 | sp-3 | an-388 | 1U5321 | sp-3 | an-388 | 1C3813 | sp-3 | an-388 |
| 1A6453 | sp-3 | an-389 | 1U5322 | sp-3 | an-389 | 1C3814 | sp-3 | an-389 |
| 1A6454 | sp-3 | an-390 | 1U5323 | sp-3 | an-390 | 1C3815 | sp-3 | an-390 |
| 1A6455 | sp-3 | an-391 | 1U5324 | sp-3 | an-391 | 1C3816 | sp-3 | an-391 |
| 1A6456 | sp-3 | an-392 | 1U5325 | sp-3 | an-392 | 1C3817 | sp-3 | an-392 |
| 1A6457 | sp-3 | an-393 | 1U5326 | sp-3 | an-393 | 1C3818 | sp-3 | an-393 |
| 1A6458 | sp-4 | an-378 | 1U5327 | sp-4 | an-378 | 1C3819 | sp-4 | an-378 |
| 1A6459 | sp-4 | an-379 | 1U5328 | sp-4 | an-379 | 1C3820 | sp-4 | an-379 |
| 1A6460 | sp-4 | an-380 | 1U5329 | sp-4 | an-380 | 1C3821 | sp-4 | an-380 |
| 1A6461 | sp-4 | an-381 | 1U5330 | sp-4 | an-381 | 1C3822 | sp-4 | an-381 |
| 1A6462 | sp-4 | an-382 | 1U5331 | sp-4 | an-382 | 1C3823 | sp-4 | an-382 |
| 1A6463 | sp-4 | an-383 | 1U5332 | sp-4 | an-383 | 1C3824 | sp-4 | an-383 |
| 1A6464 | sp-4 | an-384 | 1U5333 | sp-4 | an-384 | 1C3825 | sp-4 | an-384 |
| 1A6465 | sp-4 | an-385 | 1U5334 | sp-4 | an-385 | 1C3826 | sp-4 | an-385 |
| 1A6466 | sp-4 | an-386 | 1U5335 | sp-4 | an-386 | 1C3827 | sp-4 | an-386 |
| 1A6467 | sp-4 | an-387 | 1U5336 | sp-4 | an-387 | 1C3828 | sp-4 | an-387 |
| 1A6468 | sp-4 | an-388 | 1U5337 | sp-4 | an-388 | 1C3829 | sp-4 | an-388 |
| 1A6469 | sp-4 | an-389 | 1U5338 | sp-4 | an-389 | 1C3830 | sp-4 | an-389 |
| 1A6470 | sp-4 | an-390 | 1U5339 | sp-4 | an-390 | 1C3831 | sp-4 | an-390 |
| 1A6471 | sp-4 | an-391 | 1U5340 | sp-4 | an-391 | 1C3832 | sp-4 | an-391 |
| 1A6472 | sp-4 | an-392 | 1U5341 | sp-4 | an-392 | 1C3833 | sp-4 | an-392 |
| 1A6473 | sp-4 | an-393 | 1U5342 | sp-4 | an-393 | 1C3834 | sp-4 | an-393 |
| 1A6474 | sp-5 | an-378 | 1U5343 | sp-5 | an-378 | 1C3835 | sp-5 | an-378 |
| 1A6475 | sp-5 | an-379 | 1U5344 | sp-5 | an-379 | 1C3836 | sp-5 | an-379 |
| 1A6476 | sp-5 | an-380 | 1U5345 | sp-5 | an-380 | 1C3837 | sp-5 | an-380 |
| 1A6477 | sp-5 | an-381 | 1U5346 | sp-5 | an-381 | 1C3838 | sp-5 | an-381 |
| 1A6478 | sp-5 | an-382 | 1U5347 | sp-5 | an-382 | 1C3839 | sp-5 | an-382 |
| 1A6479 | sp-5 | an-383 | 1U5348 | sp-5 | an-383 | 1C3840 | sp-5 | an-383 |
| 1A6480 | sp-5 | an-384 | 1U5349 | sp-5 | an-384 | 1C3841 | sp-5 | an-384 |
| 1A6481 | sp-5 | an-385 | 1U5350 | sp-5 | an-385 | 1C3842 | sp-5 | an-385 |
| 1A6482 | sp-5 | an-386 | 1U5351 | sp-5 | an-386 | 1C3843 | sp-5 | an-386 |
| 1A6483 | sp-5 | an-387 | 1U5352 | sp-5 | an-387 | 1C3844 | sp-5 | an-387 |
| 1A6484 | sp-5 | an-388 | 1U5353 | sp-5 | an-388 | 1C3845 | sp-5 | an-388 |
| 1A6485 | sp-5 | an-389 | 1U5354 | sp-5 | an-389 | 1C3846 | sp-5 | an-389 |
| 1A6486 | sp-5 | an-390 | 1U5355 | sp-5 | an-390 | 1C3847 | sp-5 | an-390 |
| 1A6487 | sp-5 | an-391 | 1U5356 | sp-5 | an-391 | 1C3848 | sp-5 | an-391 |
| 1A6488 | sp-5 | an-392 | 1U5357 | sp-5 | an-392 | 1C3849 | sp-5 | an-392 |
| 1A6489 | sp-5 | an-393 | 1U5358 | sp-5 | an-393 | 1C3850 | sp-5 | an-393 |
| 1A6490 | sp-6 | an-378 | 1U5359 | sp-6 | an-378 | 1C3851 | sp-6 | an-378 |
| 1A6491 | sp-6 | an-379 | 1U5360 | sp-6 | an-379 | 1C3852 | sp-6 | an-379 |
| 1A6492 | sp-6 | an-380 | 1U5361 | sp-6 | an-380 | 1C3853 | sp-6 | an-380 |
| 1A6493 | sp-6 | an-381 | 1U5362 | sp-6 | an-381 | 1C3854 | sp-6 | an-381 |
| 1A6494 | sp-6 | an-382 | 1U5363 | sp-6 | an-382 | 1C3855 | sp-6 | an-382 |
| 1A6495 | sp-6 | an-383 | 1U5364 | sp-6 | an-383 | 1C3856 | sp-6 | an-383 |
| 1A6496 | sp-6 | an-384 | 1U5365 | sp-6 | an-384 | 1C3857 | sp-6 | an-384 |
| 1A6497 | sp-6 | an-385 | 1U5366 | sp-6 | an-385 | 1C3858 | sp-6 | an-385 |
| 1A6498 | sp-6 | an-386 | 1U5367 | sp-6 | an-386 | 1C3859 | sp-6 | an-386 |
| 1A6499 | sp-6 | an-387 | 1U5368 | sp-6 | an-387 | 1C3860 | sp-6 | an-387 |
| 1A6500 | sp-6 | an-388 | 1U5369 | sp-6 | an-388 | 1C3861 | sp-6 | an-388 |
| 1A6501 | sp-6 | an-389 | 1U5370 | sp-6 | an-389 | 1C3862 | sp-6 | an-389 |
| 1A6502 | sp-6 | an-390 | 1U5371 | sp-6 | an-390 | 1C3863 | sp-6 | an-390 |
| 1A6503 | sp-6 | an-391 | 1U5372 | sp-6 | an-391 | 1C3864 | sp-6 | an-391 |
| 1A6504 | sp-6 | an-392 | 1U5373 | sp-6 | an-392 | 1C3865 | sp-6 | an-392 |
| 1A6505 | sp-6 | an-393 | 1U5374 | sp-6 | an-393 | 1C3866 | sp-6 | an-393 |
| 1A6506 | sp-7 | an-378 | 1U5375 | sp-7 | an-378 | 1C3867 | sp-7 | an-378 |

TABLE 1-continued

| | | | | | | | | |
|---|---|---|---|---|---|---|---|---|
| 1A6507 | sp-7 | an-379 | 1U5376 | sp-7 | an-379 | 1C3868 | sp-7 | an-379 |
| 1A6508 | sp-7 | an-380 | 1U5377 | sp-7 | an-380 | 1C3869 | sp-7 | an-380 |
| 1A6509 | sp-7 | an-381 | 1U5378 | sp-7 | an-381 | 1C3870 | sp-7 | an-381 |
| 1A6510 | sp-7 | an-382 | 1U5379 | sp-7 | an-382 | 1C3871 | sp-7 | an-382 |
| 1A6511 | sp-7 | an-383 | 1U5380 | sp-7 | an-383 | 1C3872 | sp-7 | an-383 |
| 1A6512 | sp-7 | an-384 | 1U5381 | sp-7 | an-384 | 1C3873 | sp-7 | an-384 |
| 1A6513 | sp-7 | an-385 | 1U5382 | sp-7 | an-385 | 1C3874 | sp-7 | an-385 |
| 1A6514 | sp-7 | an-386 | 1U5383 | sp-7 | an-386 | 1C3875 | sp-7 | an-386 |
| 1A6515 | sp-7 | an-387 | 1U5384 | sp-7 | an-387 | 1C3876 | sp-7 | an-387 |
| 1A6516 | sp-7 | an-388 | 1U5385 | sp-7 | an-388 | 1C3877 | sp-7 | an-388 |
| 1A6517 | sp-7 | an-389 | 1U5386 | sp-7 | an-389 | 1C3878 | sp-7 | an-389 |
| 1A6518 | sp-7 | an-390 | 1U5387 | sp-7 | an-390 | 1C3879 | sp-7 | an-390 |
| 1A6519 | sp-7 | an-391 | 1U5388 | sp-7 | an-391 | 1C3880 | sp-7 | an-391 |
| 1A6520 | sp-7 | an-392 | 1U5389 | sp-7 | an-392 | 1C3881 | sp-7 | an-392 |
| 1A6521 | sp-7 | an-393 | 1U5390 | sp-7 | an-393 | 1C3882 | sp-7 | an-393 |
| 1A6522 | sp-8 | an-378 | 1U5391 | sp-8 | an-378 | 1C3883 | sp-8 | an-378 |
| 1A6523 | sp-8 | an-379 | 1U5392 | sp-8 | an-379 | 1C3884 | sp-8 | an-379 |
| 1A6524 | sp-8 | an-380 | 1U5393 | sp-8 | an-380 | 1C3885 | sp-8 | an-380 |
| 1A6525 | sp-8 | an-381 | 1U5394 | sp-8 | an-381 | 1C3886 | sp-8 | an-381 |
| 1A6526 | sp-8 | an-382 | 1U5395 | sp-8 | an-382 | 1C3887 | sp-8 | an-382 |
| 1A6527 | sp-8 | an-383 | 1U5396 | sp-8 | an-383 | 1C3888 | sp-8 | an-383 |
| 1A6528 | sp-8 | an-384 | 1U5397 | sp-8 | an-384 | 1C3889 | sp-8 | an-384 |
| 1A6529 | sp-8 | an-385 | 1U5398 | sp-8 | an-385 | 1C3890 | sp-8 | an-385 |
| 1A6530 | sp-8 | an-386 | 1U5399 | sp-8 | an-386 | 1C3891 | sp-8 | an-386 |
| 1A6531 | sp-8 | an-387 | 1U5400 | sp-8 | an-387 | 1C3892 | sp-8 | an-387 |
| 1A6532 | sp-8 | an-388 | 1U5401 | sp-8 | an-388 | 1C3893 | sp-8 | an-388 |
| 1A6533 | sp-8 | an-389 | 1U5402 | sp-8 | an-389 | 1C3894 | sp-8 | an-389 |
| 1A6534 | sp-8 | an-390 | 1U5403 | sp-8 | an-390 | 1C3895 | sp-8 | an-390 |
| 1A6535 | sp-8 | an-391 | 1U5404 | sp-8 | an-391 | 1C3896 | sp-8 | an-391 |
| 1A6536 | sp-8 | an-392 | 1U5405 | sp-8 | an-392 | 1C3897 | sp-8 | an-392 |
| 1A6537 | sp-8 | an-393 | 1U5406 | sp-8 | an-393 | 1C3898 | sp-8 | an-393 |
| 1A6538 | sp-9 | an-378 | 1U5407 | sp-9 | an-378 | 1C3899 | sp-9 | an-378 |
| 1A6539 | sp-9 | an-379 | 1U5408 | sp-9 | an-379 | 1C3900 | sp-9 | an-379 |
| 1A6540 | sp-9 | an-380 | 1U5409 | sp-9 | an-380 | 1C3901 | sp-9 | an-380 |
| 1A6541 | sp-9 | an-381 | 1U5410 | sp-9 | an-381 | 1C3902 | sp-9 | an-381 |
| 1A6542 | sp-9 | an-382 | 1U5411 | sp-9 | an-382 | 1C3903 | sp-9 | an-382 |
| 1A6543 | sp-9 | an-383 | 1U5412 | sp-9 | an-383 | 1C3904 | sp-9 | an-383 |
| 1A6544 | sp-9 | an-384 | 1U5413 | sp-9 | an-384 | 1C3905 | sp-9 | an-384 |
| 1A6545 | sp-9 | an-385 | 1U5414 | sp-9 | an-385 | 1C3906 | sp-9 | an-385 |
| 1A6546 | sp-9 | an-386 | 1U5415 | sp-9 | an-386 | 1C3907 | sp-9 | an-386 |
| 1A6547 | sp-9 | an-387 | 1U5416 | sp-9 | an-387 | 1C3908 | sp-9 | an-387 |
| 1A6548 | sp-9 | an-388 | 1U5417 | sp-9 | an-388 | 1C3909 | sp-9 | an-388 |
| 1A6549 | sp-9 | an-389 | 1U5418 | sp-9 | an-389 | 1C3910 | sp-9 | an-389 |
| 1A6550 | sp-9 | an-390 | 1U5419 | sp-9 | an-390 | 1C3911 | sp-9 | an-390 |
| 1A6551 | sp-9 | an-391 | 1U5420 | sp-9 | an-391 | 1C3912 | sp-9 | an-391 |
| 1A6552 | sp-9 | an-392 | 1U5421 | sp-9 | an-392 | 1C3913 | sp-9 | an-392 |
| 1A6553 | sp-9 | an-393 | 1U5422 | sp-9 | an-393 | 1C3914 | sp-9 | an-393 |
| 1A6554 | sp-10 | an-378 | 1U5423 | sp-12 | an-378 | 1C3915 | sp-11 | an-378 |
| 1A6555 | sp-10 | an-379 | 1U5424 | sp-12 | an-379 | 1C3916 | sp-11 | an-379 |
| 1A6556 | sp-10 | an-380 | 1U5425 | sp-12 | an-380 | 1C3917 | sp-11 | an-380 |
| 1A6557 | sp-10 | an-381 | 1U5426 | sp-12 | an-381 | 1C3918 | sp-11 | an-381 |
| 1A6558 | sp-10 | an-382 | 1U5427 | sp-12 | an-382 | 1C3919 | sp-11 | an-382 |
| 1A6559 | sp-10 | an-383 | 1U5428 | sp-12 | an-383 | 1C3920 | sp-11 | an-383 |
| 1A6560 | sp-10 | an-384 | 1U5429 | sp-12 | an-384 | 1C3921 | sp-11 | an-384 |
| 1A6561 | sp-10 | an-385 | 1U5430 | sp-12 | an-385 | 1C3922 | sp-11 | an-385 |
| 1A6562 | sp-10 | an-386 | 1U5431 | sp-12 | an-386 | 1C3923 | sp-11 | an-386 |
| 1A6563 | sp-10 | an-387 | 1U5432 | sp-12 | an-387 | 1C3924 | sp-11 | an-387 |
| 1A6564 | sp-10 | an-388 | 1U5433 | sp-12 | an-388 | 1C3925 | sp-11 | an-388 |
| 1A6565 | sp-10 | an-389 | 1U5434 | sp-12 | an-389 | 1C3926 | sp-11 | an-389 |
| 1A6566 | sp-10 | an-390 | 1U5435 | sp-12 | an-390 | 1C3927 | sp-11 | an-390 |
| 1A6567 | sp-10 | an-391 | 1U5436 | sp-12 | an-391 | 1C3928 | sp-11 | an-391 |
| 1A6568 | sp-10 | an-392 | 1U5437 | sp-12 | an-392 | 1C3929 | sp-11 | an-392 |
| 1A6569 | sp-10 | an-393 | 1U5438 | sp-12 | an-393 | 1C3930 | sp-11 | an-393 |
| 1A6570 | sp-14 | an-378 | 1U5439 | sp-13 | an-378 | | | |
| 1A6571 | sp-14 | an-379 | 1U5440 | sp-13 | an-379 | | | |
| 1A6572 | sp-14 | an-380 | 1U5441 | sp-13 | an-380 | | | |
| 1A6573 | sp-14 | an-381 | 1U5442 | sp-13 | an-381 | | | |
| 1A6574 | sp-14 | an-382 | 1U5443 | sp-13 | an-382 | | | |
| 1A6575 | sp-14 | an-383 | 1U5444 | sp-13 | an-383 | | | |
| 1A6576 | sp-14 | an-384 | 1U5445 | sp-13 | an-384 | | | |
| 1A6577 | sp-14 | an-385 | 1U5446 | sp-13 | an-385 | | | |
| 1A6578 | sp-14 | an-386 | 1U5447 | sp-13 | an-386 | | | |
| 1A6579 | sp-14 | an-387 | 1U5448 | sp-13 | an-387 | | | |
| 1A6580 | sp-14 | an-388 | 1U5449 | sp-13 | an-388 | | | |
| 1A6581 | sp-14 | an-389 | 1U5450 | sp-13 | an-389 | | | |
| 1A6582 | sp-14 | an-390 | 1U5451 | sp-13 | an-390 | | | |
| 1A6583 | sp-14 | an-391 | 1U5452 | sp-13 | an-391 | | | |
| 1A6584 | sp-14 | an-392 | 1U5453 | sp-13 | an-392 | | | |
| 1A6585 | sp-14 | an-393 | 1U5454 | sp-13 | an-393 | | | |

TABLE 1-continued

| Y = NHCS | | | Y = NHCSNH | | | Y = NHCS | | |
|---|---|---|---|---|---|---|---|---|
| Exemplification | Z | N⁺R⁵R⁶R⁷ | Exemplification | Z | N⁺R⁵R⁶R⁷ | Exemplification | Z | N⁺R⁵R⁶R⁷ |
| 1A6586 | sp-15 | an-378 | 1U5455 | sp-14 | an-378 | 1A6634 | sp-19 | an-378 |
| 1A6587 | sp-15 | an-379 | 1U5456 | sp-14 | an-379 | 1A6635 | sp-19 | an-379 |
| 1A6588 | sp-15 | an-380 | 1U5457 | sp-14 | an-380 | 1A6636 | sp-19 | an-380 |
| 1A6589 | sp-15 | an-381 | 1U5458 | sp-14 | an-381 | 1A6637 | sp-19 | an-381 |
| 1A6590 | sp-15 | an-382 | 1U5459 | sp-14 | an-382 | 1A6638 | sp-19 | an-382 |
| 1A6591 | sp-15 | an-383 | 1U5460 | sp-14 | an-383 | 1A6639 | sp-19 | an-383 |
| 1A6592 | sp-15 | an-384 | 1U5461 | sp-14 | an-384 | 1A6640 | sp-19 | an-384 |
| 1A6593 | sp-15 | an-385 | 1U5462 | sp-14 | an-385 | 1A6641 | sp-19 | an-385 |
| 1A6594 | sp-15 | an-386 | 1U5463 | sp-14 | an-386 | 1A6642 | sp-19 | an-386 |
| 1A6595 | sp-15 | an-387 | 1U5464 | sp-14 | an-387 | 1A6643 | sp-19 | an-387 |
| 1A6596 | sp-15 | an-388 | 1U5465 | sp-14 | an-388 | 1A6644 | sp-19 | an-388 |
| 1A6597 | sp-15 | an-389 | 1U5466 | sp-14 | an-389 | 1A6645 | sp-19 | an-389 |
| 1A6598 | sp-15 | an-390 | 1U5467 | sp-14 | an-390 | 1A6646 | sp-19 | an-390 |
| 1A6599 | sp-15 | an-391 | 1U5468 | sp-14 | an-391 | 1A6647 | sp-19 | an-391 |
| 1A6600 | sp-15 | an-392 | 1U5469 | sp-14 | an-392 | 1A6648 | sp-19 | an-392 |
| 1A6601 | sp-15 | an-393 | 1U5470 | sp-14 | an-393 | 1A6649 | sp-19 | an-393 |
| 1A6602 | sp-16 | an-378 | 1U5471 | sp-17 | an-378 | 1A6650 | sp-21 | an-378 |
| 1A6603 | sp-16 | an-379 | 1U5472 | sp-17 | an-379 | 1A6651 | sp-21 | an-379 |
| 1A6604 | sp-16 | an-380 | 1U5473 | sp-17 | an-380 | 1A6652 | sp-21 | an-380 |
| 1A6605 | sp-16 | an-381 | 1U5474 | sp-17 | an-381 | 1A6653 | sp-21 | an-381 |
| 1A6606 | sp-16 | an-382 | 1U5475 | sp-17 | an-382 | 1A6654 | sp-21 | an-382 |
| 1A6607 | sp-16 | an-383 | 1U5476 | sp-17 | an-383 | 1A6655 | sp-21 | an-383 |
| 1A6608 | sp-16 | an-384 | 1U5477 | sp-17 | an-384 | 1A6656 | sp-21 | an-384 |
| 1A6609 | sp-16 | an-385 | 1U5478 | sp-17 | an-385 | 1A6657 | sp-21 | an-385 |
| 1A6610 | sp-16 | an-386 | 1U5479 | sp-17 | an-386 | 1A6658 | sp-21 | an-386 |
| 1A6611 | sp-16 | an-387 | 1U5480 | sp-17 | an-387 | 1A6659 | sp-21 | an-387 |
| 1A6612 | sp-16 | an-388 | 1U5481 | sp-17 | an-388 | 1A6660 | sp-21 | an-388 |
| 1A6613 | sp-16 | an-389 | 1U5482 | sp-17 | an-389 | 1A6661 | sp-21 | an-389 |

| Y = NHCS | | | Y = NHCSNH | | | Y = NHCSO | | |
|---|---|---|---|---|---|---|---|---|
| Exemplification | Z | N⁺R⁵R⁶R⁷ | Exemplification | Z | N⁺R⁵R⁶R⁷ | Exemplification | Z | N⁺R⁵R⁶R⁷ |
| 1A6614 | sp-16 | an-390 | 1U5483 | sp-17 | an-390 | 1A6662 | sp-21 | an-390 |
| 1A6615 | sp-16 | an-391 | 1U5484 | sp-17 | an-391 | 1A6663 | sp-21 | an-391 |
| 1A6616 | sp-16 | an-392 | 1U5485 | sp-17 | an-392 | 1A6664 | sp-21 | an-392 |
| 1A6617 | sp-16 | an-393 | 1U5486 | sp-17 | an-393 | 1A6665 | sp-21 | an-393 |
| 1A6618 | sp-18 | an-378 | 1U5487 | sp-20 | an-378 | 1A6666 | sp-22 | an-378 |
| 1A6619 | sp-18 | an-379 | 1U5488 | sp-20 | an-379 | 1A6667 | sp-22 | an-379 |
| 1A6620 | sp-18 | an-380 | 1U5489 | sp-20 | an-380 | 1A6668 | sp-22 | an-380 |
| 1A6621 | sp-18 | an-381 | 1U5490 | sp-20 | an-381 | 1A6669 | sp-22 | an-381 |
| 1A6622 | sp-18 | an-382 | 1U5491 | sp-20 | an-382 | 1A6670 | sp-22 | an-382 |
| 1A6623 | sp-18 | an-383 | 1U5492 | sp-20 | an-383 | 1A6671 | sp-22 | an-383 |
| 1A6624 | sp-18 | an-384 | 1U5493 | sp-20 | an-384 | 1A6672 | sp-22 | an-384 |
| 1A6625 | sp-18 | an-385 | 1U5494 | sp-20 | an-385 | 1A6673 | sp-22 | an-385 |
| 1A6626 | sp-18 | an-386 | 1U5495 | sp-20 | an-386 | 1A6674 | sp-22 | an-386 |
| 1A6627 | sp-18 | an-387 | 1U5496 | sp-20 | an-387 | 1A6675 | sp-22 | an-387 |
| 1A6628 | sp-18 | an-388 | 1U5497 | sp-20 | an-388 | 1A6676 | sp-22 | an-388 |
| 1A6629 | sp-18 | an-389 | 1U5498 | sp-20 | an-389 | 1A6677 | sp-22 | an-389 |
| 1A6630 | sp-18 | an-390 | 1U5499 | sp-20 | an-390 | 1A6678 | sp-22 | an-390 |
| 1A6631 | sp-18 | an-391 | 1U5500 | sp-20 | an-391 | 1A6679 | sp-22 | an-391 |
| 1A6632 | sp-18 | an-392 | 1U5501 | sp-20 | an-392 | 1A6680 | sp-22 | an-392 |
| 1A6633 | sp-18 | an-393 | 1U5502 | sp-20 | an-393 | 1A6681 | sp-22 | an-393 |

| Y = NHCSNH | | | Y = NHCSNH | | | Y = NHCNH | | |
|---|---|---|---|---|---|---|---|---|
| Exemplification | Z | N⁺R⁵R⁶R⁷ | Exemplification | Z | N⁺R⁵R⁶R⁷ | Exemplification | Z | N⁺R⁵R⁶R⁷ |
| 1U5503 | sp-23 | an-1 | 1U5896 | sp-24 | an-1 | 1U6289 | sp-25 | an-1 |
| 1U5504 | sp-23 | an-2 | 1U5897 | sp-24 | an-2 | 1U6290 | sp-25 | an-2 |
| 1U5505 | sp-23 | an-3 | 1U5898 | sp-24 | an-3 | 1U6291 | sp-25 | an-3 |
| 1U5506 | sp-23 | an-4 | 1U5899 | sp-24 | an-4 | 1U6292 | sp-25 | an-4 |
| 1U5507 | sp-23 | an-5 | 1U5900 | sp-24 | an-5 | 1U6293 | sp-25 | an-5 |
| 1U5508 | sp-23 | an-6 | 1U5901 | sp-24 | an-6 | 1U6294 | sp-25 | an-6 |
| 1U5509 | sp-23 | an-7 | 1U5902 | sp-24 | an-7 | 1U6295 | sp-25 | an-7 |
| 1U5510 | sp-23 | an-8 | 1U5903 | sp-24 | an-8 | 1U6296 | sp-25 | an-8 |
| 1U5511 | sp-23 | an-9 | 1U5904 | sp-24 | an-9 | 1U6297 | sp-25 | an-9 |
| 1U5512 | sp-23 | an-10 | 1U5905 | sp-24 | an-10 | 1U6298 | sp-25 | an-10 |
| 1U5513 | sp-23 | an-11 | 1U5906 | sp-24 | an-11 | 1U6299 | sp-25 | an-11 |
| 1U5514 | sp-23 | an-12 | 1U5907 | sp-24 | an-12 | 1U6300 | sp-25 | an-12 |
| 1U5515 | sp-23 | an-13 | 1U5908 | sp-24 | an-13 | 1U6301 | sp-25 | an-13 |
| 1U5516 | sp-23 | an-14 | 1U5909 | sp-24 | an-14 | 1U6302 | sp-25 | an-14 |
| 1U5517 | sp-23 | an-15 | 1U5910 | sp-24 | an-15 | 1U6303 | sp-25 | an-15 |
| 1U5518 | sp-23 | an-16 | 1U5911 | sp-24 | an-16 | 1U6304 | sp-25 | an-16 |

TABLE 1-continued

| Exemplification | Z | N⁺R⁵R⁶R⁷ | Exemplification | Z | N⁺R⁵R⁶R⁷ | Exemplification | Z | N⁺R⁵R⁶R⁷ |
|---|---|---|---|---|---|---|---|---|
| 1U5519 | sp-23 | an-17 | 1U5912 | sp-24 | an-17 | 1U6305 | sp-25 | an-17 |
| 1U5520 | sp-23 | an-18 | 1U5913 | sp-24 | an-18 | 1U6306 | sp-25 | an-18 |
| 1U5521 | sp-23 | an-19 | 1U5914 | sp-24 | an-19 | 1U6307 | sp-25 | an-19 |
| 1U5522 | sp-23 | an-20 | 1U5915 | sp-24 | an-20 | 1U6308 | sp-25 | an-20 |
| 1U5523 | sp-23 | an-21 | 1U5916 | sp-24 | an-21 | 1U6309 | sp-25 | an-21 |
| 1U5524 | sp-23 | an-22 | 1U5917 | sp-24 | an-22 | 1U6310 | sp-25 | an-22 |
| 1U5525 | sp-23 | an-23 | 1U5918 | sp-24 | an-23 | 1U6311 | sp-25 | an-23 |
| 1U5526 | sp-23 | an-24 | 1U5919 | sp-24 | an-24 | 1U6312 | sp-25 | an-24 |
| 1U5527 | sp-23 | an-25 | 1U5920 | sp-24 | an-25 | 1U6313 | sp-25 | an-25 |
| 1U5528 | sp-23 | an-26 | 1U5921 | sp-24 | an-26 | 1U6314 | sp-25 | an-26 |
| 1U5529 | sp-23 | an-27 | 1U5922 | sp-24 | an-27 | 1U6315 | sp-25 | an-27 |
| 1U5530 | sp-23 | an-28 | 1U5923 | sp-24 | an-28 | 1U6316 | sp-25 | an-28 |
| 1U5531 | sp-23 | an-29 | 1U5924 | sp-24 | an-29 | 1U6317 | sp-25 | an-29 |
| 1U5532 | sp-23 | an-30 | 1U5925 | sp-24 | an-30 | 1U6318 | sp-25 | an-30 |
| 1U5533 | sp-23 | an-31 | 1U5926 | sp-24 | an-31 | 1U6319 | sp-25 | an-31 |
| 1U5534 | sp-23 | an-32 | 1U5927 | sp-24 | an-32 | 1U6320 | sp-25 | an-32 |
| 1U5535 | sp-23 | an-33 | 1U5928 | sp-24 | an-33 | 1U6321 | sp-25 | an-33 |
| Y = NHCS | | | Y = NHCSNH | | | Y = NHCSO | | |
| 1U5536 | sp-23 | an-34 | 1U5929 | sp-24 | an-34 | 1U6322 | sp-25 | an-34 |
| 1U5537 | sp-23 | an-35 | 1U5930 | sp-24 | an-35 | 1U6323 | sp-25 | an-35 |
| 1U5538 | sp-23 | an-36 | 1U5931 | sp-24 | an-36 | 1U6324 | sp-25 | an-36 |
| 1U5539 | sp-23 | an-37 | 1U5932 | sp-24 | an-37 | 1U6325 | sp-25 | an-37 |
| 1U5540 | sp-23 | an-38 | 1U5933 | sp-24 | an-38 | 1U6326 | sp-25 | an-38 |
| 1U5541 | sp-23 | an-39 | 1U5934 | sp-24 | an-39 | 1U6327 | sp-25 | an-39 |
| 1U5542 | sp-23 | an-40 | 1U5935 | sp-24 | an-40 | 1U6328 | sp-25 | an-40 |
| 1U5543 | sp-23 | an-41 | 1U5936 | sp-24 | an-41 | 1U6329 | sp-25 | an-41 |
| 1U5544 | sp-23 | an-42 | 1U5937 | sp-24 | an-42 | 1U6330 | sp-25 | an-42 |
| 1U5545 | sp-23 | an-43 | 1U5938 | sp-24 | an-43 | 1U6331 | sp-25 | an-43 |
| 1U5546 | sp-23 | an-44 | 1U5939 | sp-24 | an-44 | 1U6332 | sp-25 | an-44 |
| 1U5547 | sp-23 | an-45 | 1U5940 | sp-24 | an-45 | 1U6333 | sp-25 | an-45 |
| 1U5548 | sp-23 | an-46 | 1U5941 | sp-24 | an-46 | 1U6334 | sp-25 | an-46 |
| 1U5549 | sp-23 | an-47 | 1U5942 | sp-24 | an-47 | 1U6335 | sp-25 | an-47 |
| 1U5550 | sp-23 | an-48 | 1U5943 | sp-24 | an-48 | 1U6336 | sp-25 | an-48 |
| 1U5551 | sp-23 | an-49 | 1U5944 | sp-24 | an-49 | 1U6337 | sp-25 | an-49 |
| 1U5552 | sp-23 | an-50 | 1U5945 | sp-24 | an-50 | 1U6338 | sp-25 | an-50 |
| 1U5553 | sp-23 | an-51 | 1U5946 | sp-24 | an-51 | 1U6339 | sp-25 | an-51 |
| 1U5554 | sp-23 | an-52 | 1U5947 | sp-24 | an-52 | 1U6340 | sp-25 | an-52 |
| 1U5555 | sp-23 | an-53 | 1U5948 | sp-24 | an-53 | 1U6341 | sp-25 | an-53 |
| 1U5556 | sp-23 | an-54 | 1U5949 | sp-24 | an-54 | 1U6342 | sp-25 | an-54 |
| 1U5557 | sp-23 | an-55 | 1U5950 | sp-24 | an-55 | 1U6343 | sp-25 | an-55 |
| 1U5558 | sp-23 | an-56 | 1U5951 | sp-24 | an-56 | 1U6344 | sp-25 | an-56 |
| 1U5559 | sp-23 | an-57 | 1U5952 | sp-24 | an-57 | 1U6345 | sp-25 | an-57 |
| 1U5560 | sp-23 | an-58 | 1U5953 | sp-24 | an-58 | 1U6346 | sp-25 | an-58 |
| 1U5561 | sp-23 | an-59 | 1U5954 | sp-24 | an-59 | 1U6347 | sp-25 | an-59 |
| 1U5562 | sp-23 | an-60 | 1U5955 | sp-24 | an-60 | 1U6348 | sp-25 | an-60 |
| 1U5563 | sp-23 | an-61 | 1U5956 | sp-24 | an-61 | 1U6349 | sp-25 | an-61 |
| 1U5564 | sp-23 | an-62 | 1U5957 | sp-24 | an-62 | 1U6350 | sp-25 | an-62 |
| 1U5565 | sp-23 | an-63 | 1U5958 | sp-24 | an-63 | 1U6351 | sp-25 | an-63 |
| 1U5566 | sp-23 | an-64 | 1U5959 | sp-24 | an-64 | 1U6352 | sp-25 | an-64 |
| 1U5567 | sp-23 | an-65 | 1U5960 | sp-24 | an-65 | 1U6353 | sp-25 | an-65 |
| 1U5568 | sp-23 | an-66 | 1U5961 | sp-24 | an-66 | 1U6354 | sp-25 | an-66 |
| 1U5569 | sp-23 | an-67 | 1U5962 | sp-24 | an-67 | 1U6355 | sp-25 | an-67 |
| 1U5570 | sp-23 | an-68 | 1U5963 | sp-24 | an-68 | 1U6356 | sp-25 | an-68 |
| 1U5571 | sp-23 | an-69 | 1U5964 | sp-24 | an-69 | 1U6357 | sp-25 | an-69 |
| 1U5572 | sp-23 | an-70 | 1U5965 | sp-24 | an-70 | 1U6358 | sp-25 | an-70 |
| 1U5573 | sp-23 | an-71 | 1U5966 | sp-24 | an-71 | 1U6359 | sp-25 | an-71 |
| 1U5574 | sp-23 | an-72 | 1U5967 | sp-24 | an-72 | 1U6360 | sp-25 | an-72 |
| 1U5575 | sp-23 | an-73 | 1U5968 | sp-24 | an-73 | 1U6361 | sp-25 | an-73 |
| 1U5576 | sp-23 | an-74 | 1U5969 | sp-24 | an-74 | 1U6362 | sp-25 | an-74 |
| 1U5577 | sp-23 | an-75 | 1U5970 | sp-24 | an-75 | 1U6363 | sp-25 | an-75 |
| 1U5578 | sp-23 | an-76 | 1U5971 | sp-24 | an-76 | 1U6364 | sp-25 | an-76 |
| 1U5579 | sp-23 | an-77 | 1U5972 | sp-24 | an-77 | 1U6365 | sp-25 | an-77 |
| 1U5580 | sp-23 | an-78 | 1U5973 | sp-24 | an-78 | 1U6366 | sp-25 | an-78 |
| 1U5581 | sp-23 | an-79 | 1U5974 | sp-24 | an-79 | 1U6367 | sp-25 | an-79 |
| 1U5582 | sp-23 | an-80 | 1U5975 | sp-24 | an-80 | 1U6368 | sp-25 | an-80 |
| 1U5583 | sp-23 | an-81 | 1U5976 | sp-24 | an-81 | 1U6369 | sp-25 | an-81 |
| 1U5584 | sp-23 | an-82 | 1U5977 | sp-24 | an-82 | 1U6370 | sp-25 | an-82 |
| 1U5585 | sp-23 | an-83 | 1U5978 | sp-24 | an-83 | 1U6371 | sp-25 | an-83 |
| 1U5586 | sp-23 | an-84 | 1U5979 | sp-24 | an-84 | 1U6372 | sp-25 | an-84 |
| 1U5587 | sp-23 | an-85 | 1U5980 | sp-24 | an-85 | 1U6373 | sp-25 | an-85 |
| 1U5588 | sp-23 | an-86 | 1U5981 | sp-24 | an-86 | 1U6374 | sp-25 | an-86 |
| 1U5589 | sp-23 | an-87 | 1U5982 | sp-24 | an-87 | 1U6375 | sp-25 | an-87 |
| 1U5590 | sp-23 | an-88 | 1U5983 | sp-24 | an-88 | 1U6376 | sp-25 | an-88 |
| 1U5591 | sp-23 | an-89 | 1U5984 | sp-24 | an-89 | 1U6377 | sp-25 | an-89 |
| 1U5592 | sp-23 | an-90 | 1U5985 | sp-24 | an-90 | 1U6378 | sp-25 | an-90 |

TABLE 1-continued

| | | | | | | | | |
|---|---|---|---|---|---|---|---|---|
| 1U5593 | sp-23 | an-91 | 1U5986 | sp-24 | an-91 | 1U6379 | sp-25 | an-91 |
| 1U5594 | sp-23 | an-92 | 1U5987 | sp-24 | an-92 | 1U6380 | sp-25 | an-92 |
| 1U5595 | sp-23 | an-93 | 1U5988 | sp-24 | an-93 | 1U6381 | sp-25 | an-93 |
| 1U5596 | sp-23 | an-94 | 1U5989 | sp-24 | an-94 | 1U6382 | sp-25 | an-94 |
| 1U5597 | sp-23 | an-95 | 1U5990 | sp-24 | an-95 | 1U6383 | sp-25 | an-95 |
| 1U5598 | sp-23 | an-96 | 1U5991 | sp-24 | an-96 | 1U6384 | sp-25 | an-96 |
| 1U5599 | sp-23 | an-97 | 1U5992 | sp-24 | an-97 | 1U6385 | sp-25 | an-97 |
| 1U5600 | sp-23 | an-98 | 1U5993 | sp-24 | an-98 | 1U6386 | sp-25 | an-98 |
| 1U5601 | sp-23 | an-99 | 1U5994 | sp-24 | an-99 | 1U6387 | sp-25 | an-99 |
| 1U5602 | sp-23 | an-100 | 1U5995 | sp-24 | an-100 | 1U6388 | sp-25 | an-100 |
| 1U5603 | sp-23 | an-101 | 1U5996 | sp-24 | an-101 | 1U6389 | sp-25 | an-101 |
| 1U5604 | sp-23 | an-102 | 1U5997 | sp-24 | an-102 | 1U6390 | sp-25 | an-102 |
| 1U5605 | sp-23 | an-103 | 1U5998 | sp-24 | an-103 | 1U6391 | sp-25 | an-103 |
| 1U5606 | sp-23 | an-104 | 1U5999 | sp-24 | an-104 | 1U6392 | sp-25 | an-104 |
| 1U5607 | sp-23 | an-105 | 1U6000 | sp-24 | an-105 | 1U6393 | sp-25 | an-105 |
| 1U5608 | sp-23 | an-106 | 1U6001 | sp-24 | an-106 | 1U6394 | sp-25 | an-106 |
| 1U5609 | sp-23 | an-107 | 1U6002 | sp-24 | an-107 | 1U6395 | sp-25 | an-107 |
| 1U5610 | sp-23 | an-108 | 1U6003 | sp-24 | an-108 | 1U6396 | sp-25 | an-108 |
| 1U5611 | sp-23 | an-109 | 1U6004 | sp-24 | an-109 | 1U6397 | sp-25 | an-109 |
| 1U5612 | sp-23 | an-110 | 1U6005 | sp-24 | an-110 | 1U6398 | sp-25 | an-110 |
| 1U5613 | sp-23 | an-111 | 1U6006 | sp-24 | an-111 | 1U6399 | sp-25 | an-111 |
| 1U5614 | sp-23 | an-112 | 1U6007 | sp-24 | an-112 | 1U6400 | sp-25 | an-112 |
| 1U5615 | sp-23 | an-113 | 1U6008 | sp-24 | an-113 | 1U6401 | sp-25 | an-113 |
| 1U5616 | sp-23 | an-114 | 1U6009 | sp-24 | an-114 | 1U6402 | sp-25 | an-114 |
| 1U5617 | sp-23 | an-115 | 1U6010 | sp-24 | an-115 | 1U6403 | sp-25 | an-115 |
| 1U5618 | sp-23 | an-116 | 1U6011 | sp-24 | an-116 | 1U6404 | sp-25 | an-116 |
| 1U5619 | sp-23 | an-117 | 1U6012 | sp-24 | an-117 | 1U6405 | sp-25 | an-117 |
| 1U5620 | sp-23 | an-118 | 1U6013 | sp-24 | an-118 | 1U6406 | sp-25 | an-118 |
| 1U5621 | sp-23 | an-119 | 1U6014 | sp-24 | an-119 | 1U6407 | sp-25 | an-119 |
| 1U5622 | sp-23 | an-120 | 1U6015 | sp-24 | an-120 | 1U6408 | sp-25 | an-120 |
| 1U5623 | sp-23 | an-121 | 1U6016 | sp-24 | an-121 | 1U6409 | sp-25 | an-121 |
| 1U5624 | sp-23 | an-122 | 1U6017 | sp-24 | an-122 | 1U6410 | sp-25 | an-122 |
| 1U5625 | sp-23 | an-123 | 1U6018 | sp-24 | an-123 | 1U6411 | sp-25 | an-123 |
| 1U5626 | sp-23 | an-124 | 1U6019 | sp-24 | an-124 | 1U6412 | sp-25 | an-124 |
| 1U5627 | sp-23 | an-125 | 1U6020 | sp-24 | an-125 | 1U6413 | sp-25 | an-125 |
| 1U5628 | sp-23 | an-126 | 1U6021 | sp-24 | an-126 | 1U6414 | sp-25 | an-126 |
| 1U5629 | sp-23 | an-127 | 1U6022 | sp-24 | an-127 | 1U6415 | sp-25 | an-127 |
| 1U5630 | sp-23 | an-128 | 1U6023 | sp-24 | an-128 | 1U6416 | sp-25 | an-128 |
| 1U5631 | sp-23 | an-129 | 1U6024 | sp-24 | an-129 | 1U6417 | sp-25 | an-129 |
| 1U5632 | sp-23 | an-130 | 1U6025 | sp-24 | an-130 | 1U6418 | sp-25 | an-130 |
| 1U5633 | sp-23 | an-131 | 1U6026 | sp-24 | an-131 | 1U6419 | sp-25 | an-131 |
| 1U5634 | sp-23 | an-132 | 1U6027 | sp-24 | an-132 | 1U6420 | sp-25 | an-132 |
| 1U5635 | sp-23 | an-133 | 1U6028 | sp-24 | an-133 | 1U6421 | sp-25 | an-133 |
| 1U5636 | sp-23 | an-134 | 1U6029 | sp-24 | an-134 | 1U6422 | sp-25 | an-134 |
| 1U5637 | sp-23 | an-135 | 1U6030 | sp-24 | an-135 | 1U6423 | sp-25 | an-135 |
| 1U5638 | sp-23 | an-136 | 1U6031 | sp-24 | an-136 | 1U6424 | sp-25 | an-136 |
| 1U5639 | sp-23 | an-137 | 1U6032 | sp-24 | an-137 | 1U6425 | sp-25 | an-137 |
| 1U5640 | sp-23 | an-138 | 1U6033 | sp-24 | an-138 | 1U6426 | sp-25 | an-138 |
| 1U5641 | sp-23 | an-139 | 1U6034 | sp-24 | an-139 | 1U6427 | sp-25 | an-139 |
| 1U5642 | sp-23 | an-140 | 1U6035 | sp-24 | an-140 | 1U6428 | sp-25 | an-140 |
| 1U5643 | sp-23 | an-141 | 1U6036 | sp-24 | an-141 | 1U6429 | sp-25 | an-141 |
| 1U5644 | sp-23 | an-142 | 1U6037 | sp-24 | an-142 | 1U6430 | sp-25 | an-142 |
| 1U5645 | sp-23 | an-143 | 1U6038 | sp-24 | an-143 | 1U6431 | sp-25 | an-143 |
| 1U5646 | sp-23 | an-144 | 1U6039 | sp-24 | an-144 | 1U6432 | sp-25 | an-144 |
| 1U5647 | sp-23 | an-145 | 1U6040 | sp-24 | an-145 | 1U6433 | sp-25 | an-145 |
| 1U5648 | sp-23 | an-146 | 1U6041 | sp-24 | an-146 | 1U6434 | sp-25 | an-146 |
| 1U5649 | sp-23 | an-147 | 1U6042 | sp-24 | an-147 | 1U6435 | sp-25 | an-147 |
| 1U5650 | sp-23 | an-148 | 1U6043 | sp-24 | an-148 | 1U6436 | sp-25 | an-148 |
| 1U5651 | sp-23 | an-149 | 1U6044 | sp-24 | an-149 | 1U6437 | sp-25 | an-149 |
| 1U5652 | sp-23 | an-150 | 1U6045 | sp-24 | an-150 | 1U6438 | sp-25 | an-150 |
| 1U5653 | sp-23 | an-151 | 1U6046 | sp-24 | an-151 | 1U6439 | sp-25 | an-151 |
| 1U5654 | sp-23 | an-152 | 1U6047 | sp-24 | an-152 | 1U6440 | sp-25 | an-152 |
| 1U5655 | sp-23 | an-153 | 1U6048 | sp-24 | an-153 | 1U6441 | sp-25 | an-153 |
| 1U5656 | sp-23 | an-154 | 1U6049 | sp-24 | an-154 | 1U6442 | sp-25 | an-154 |
| 1U5657 | sp-23 | an-155 | 1U6050 | sp-24 | an-155 | 1U6443 | sp-25 | an-155 |
| 1U5658 | sp-23 | an-156 | 1U6051 | sp-24 | an-156 | 1U6444 | sp-25 | an-156 |
| 1U5659 | sp-23 | an-157 | 1U6052 | sp-24 | an-157 | 1U6445 | sp-25 | an-157 |
| 1U5660 | sp-23 | an-158 | 1U6053 | sp-24 | an-158 | 1U6446 | sp-25 | an-158 |
| 1U5661 | sp-23 | an-159 | 1U6054 | sp-24 | an-159 | 1U6447 | sp-25 | an-159 |
| 1U5662 | sp-23 | an-160 | 1U6055 | sp-24 | an-160 | 1U6448 | sp-25 | an-160 |
| 1U5663 | sp-23 | an-161 | 1U6056 | sp-24 | an-161 | 1U6449 | sp-25 | an-161 |
| 1U5664 | sp-23 | an-162 | 1U6057 | sp-24 | an-162 | 1U6450 | sp-25 | an-162 |
| 1U5665 | sp-23 | an-163 | 1U6058 | sp-24 | an-163 | 1U6451 | sp-25 | an-163 |
| 1U5666 | sp-23 | an-164 | 1U6059 | sp-24 | an-164 | 1U6452 | sp-25 | an-164 |
| 1U5667 | sp-23 | an-165 | 1U6060 | sp-24 | an-165 | 1U6453 | sp-25 | an-165 |
| 1U5668 | sp-23 | an-166 | 1U6061 | sp-24 | an-166 | 1U6454 | sp-25 | an-166 |
| 1U5669 | sp-23 | an-167 | 1U6062 | sp-24 | an-167 | 1U6455 | sp-25 | an-167 |
| 1U5670 | sp-23 | an-168 | 1U6063 | sp-24 | an-168 | 1U6456 | sp-25 | an-168 |
| 1U5671 | sp-23 | an-169 | 1U6064 | sp-24 | an-169 | 1U6457 | sp-25 | an-169 |

TABLE 1-continued

| | | | | | | | | |
|---|---|---|---|---|---|---|---|---|
| 1U5672 | sp-23 | an-170 | 1U6065 | sp-24 | an-170 | 1U6458 | sp-25 | an-170 |
| 1U5673 | sp-23 | an-171 | 1U6066 | sp-24 | an-171 | 1U6459 | sp-25 | an-171 |
| 1U5674 | sp-23 | an-172 | 1U6067 | sp-24 | an-172 | 1U6460 | sp-25 | an-172 |
| 1U5675 | sp-23 | an-173 | 1U6068 | sp-24 | an-173 | 1U6461 | sp-25 | an-173 |
| 1U5676 | sp-23 | an-174 | 1U6069 | sp-24 | an-174 | 1U6462 | sp-25 | an-174 |
| 1U5677 | sp-23 | an-175 | 1U6070 | sp-24 | an-175 | 1U6463 | sp-25 | an-175 |
| 1U5678 | sp-23 | an-176 | 1U6071 | sp-24 | an-176 | 1U6464 | sp-25 | an-176 |
| 1U5679 | sp-23 | an-177 | 1U6072 | sp-24 | an-177 | 1U6465 | sp-25 | an-177 |
| 1U5680 | sp-23 | an-178 | 1U6073 | sp-24 | an-178 | 1U6466 | sp-25 | an-178 |
| 1U5681 | sp-23 | an-179 | 1U6074 | sp-24 | an-179 | 1U6467 | sp-25 | an-179 |
| 1U5682 | sp-23 | an-180 | 1U6075 | sp-24 | an-180 | 1U6468 | sp-25 | an-180 |
| 1U5683 | sp-23 | an-181 | 1U6076 | sp-24 | an-181 | 1U6469 | sp-25 | an-181 |
| 1U5684 | sp-23 | an-182 | 1U6077 | sp-24 | an-182 | 1U6470 | sp-25 | an-182 |
| 1U5685 | sp-23 | an-183 | 1U6078 | sp-24 | an-183 | 1U6471 | sp-25 | an-183 |
| 1U5686 | sp-23 | an-184 | 1U6079 | sp-24 | an-184 | 1U6472 | sp-25 | an-184 |
| 1U5687 | sp-23 | an-185 | 1U6080 | sp-24 | an-185 | 1U6473 | sp-25 | an-185 |
| 1U5688 | sp-23 | an-186 | 1U6081 | sp-24 | an-186 | 1U6474 | sp-25 | an-186 |
| 1U5689 | sp-23 | an-187 | 1U6082 | sp-24 | an-187 | 1U6475 | sp-25 | an-187 |
| 1U5690 | sp-23 | an-188 | 1U6083 | sp-24 | an-188 | 1U6476 | sp-25 | an-188 |
| 1U5691 | sp-23 | an-189 | 1U6084 | sp-24 | an-189 | 1U6477 | sp-25 | an-189 |
| 1U5692 | sp-23 | an-190 | 1U6085 | sp-24 | an-190 | 1U6478 | sp-25 | an-190 |
| 1U5693 | sp-23 | an-191 | 1U6086 | sp-24 | an-191 | 1U6479 | sp-25 | an-191 |
| 1U5694 | sp-23 | an-192 | 1U6087 | sp-24 | an-192 | 1U6480 | sp-25 | an-192 |
| 1U5695 | sp-23 | an-193 | 1U6088 | sp-24 | an-193 | 1U6481 | sp-25 | an-193 |
| 1U5696 | sp-23 | an-194 | 1U6089 | sp-24 | an-194 | 1U6482 | sp-25 | an-194 |
| 1U5697 | sp-23 | an-195 | 1U6090 | sp-24 | an-195 | 1U6483 | sp-25 | an-195 |
| 1U5698 | sp-23 | an-196 | 1U6091 | sp-24 | an-196 | 1U6484 | sp-25 | an-196 |
| 1U5699 | sp-23 | an-197 | 1U6092 | sp-24 | an-197 | 1U6485 | sp-25 | an-197 |
| 1U5700 | sp-23 | an-198 | 1U6093 | sp-24 | an-198 | 1U6486 | sp-25 | an-198 |
| 1U5701 | sp-23 | an-199 | 1U6094 | sp-24 | an-199 | 1U6487 | sp-25 | an-199 |
| 1U5702 | sp-23 | an-200 | 1U6095 | sp-24 | an-200 | 1U6488 | sp-25 | an-200 |
| 1U5703 | sp-23 | an-201 | 1U6096 | sp-24 | an-201 | 1U6489 | sp-25 | an-201 |
| 1U5704 | sp-23 | an-202 | 1U6097 | sp-24 | an-202 | 1U6490 | sp-25 | an-202 |
| 1U5705 | sp-23 | an-203 | 1U6098 | sp-24 | an-203 | 1U6491 | sp-25 | an-203 |
| 1U5706 | sp-23 | an-204 | 1U6099 | sp-24 | an-204 | 1U6492 | sp-25 | an-204 |
| 1U5707 | sp-23 | an-205 | 1U6100 | sp-24 | an-205 | 1U6493 | sp-25 | an-205 |
| 1U5708 | sp-23 | an-206 | 1U6101 | sp-24 | an-206 | 1U6494 | sp-25 | an-206 |
| 1U5709 | sp-23 | an-207 | 1U6102 | sp-24 | an-207 | 1U6495 | sp-25 | an-207 |
| 1U5710 | sp-23 | an-208 | 1U6103 | sp-24 | an-208 | 1U6496 | sp-25 | an-208 |
| 1U5711 | sp-23 | an-209 | 1U6104 | sp-24 | an-209 | 1U6497 | sp-25 | an-209 |
| 1U5712 | sp-23 | an-210 | 1U6105 | sp-24 | an-210 | 1U6498 | sp-25 | an-210 |
| 1U5713 | sp-23 | an-211 | 1U6106 | sp-24 | an-211 | 1U6499 | sp-25 | an-211 |
| 1U5714 | sp-23 | an-212 | 1U6107 | sp-24 | an-212 | 1U6500 | sp-25 | an-212 |
| 1U5715 | sp-23 | an-213 | 1U6108 | sp-24 | an-213 | 1U6501 | sp-25 | an-213 |
| 1U5716 | sp-23 | an-214 | 1U6109 | sp-24 | an-214 | 1U6502 | sp-25 | an-214 |
| 1U5717 | sp-23 | an-215 | 1U6110 | sp-24 | an-215 | 1U6503 | sp-25 | an-215 |
| 1U5718 | sp-23 | an-216 | 1U6111 | sp-24 | an-216 | 1U6504 | sp-25 | an-216 |
| 1U5719 | sp-23 | an-217 | 1U6112 | sp-24 | an-217 | 1U6505 | sp-25 | an-217 |
| 1U5720 | sp-23 | an-218 | 1U6113 | sp-24 | an-218 | 1U6506 | sp-25 | an-218 |
| 1U5721 | sp-23 | an-219 | 1U6114 | sp-24 | an-219 | 1U6507 | sp-25 | an-219 |
| 1U5722 | sp-23 | an-220 | 1U6115 | sp-24 | an-220 | 1U6508 | sp-25 | an-220 |
| 1U5723 | sp-23 | an-221 | 1U6116 | sp-24 | an-221 | 1U6509 | sp-25 | an-221 |
| 1U5724 | sp-23 | an-222 | 1U6117 | sp-24 | an-222 | 1U6510 | sp-25 | an-222 |
| 1U5725 | sp-23 | an-223 | 1U6118 | sp-24 | an-223 | 1U6511 | sp-25 | an-223 |
| 1U5726 | sp-23 | an-224 | 1U6119 | sp-24 | an-224 | 1U6512 | sp-25 | an-224 |
| 1U5727 | sp-23 | an-225 | 1U6120 | sp-24 | an-225 | 1U6513 | sp-25 | an-225 |
| 1U5728 | sp-23 | an-226 | 1U6121 | sp-24 | an-226 | 1U6514 | sp-25 | an-226 |
| 1U5729 | sp-23 | an-227 | 1U6122 | sp-24 | an-227 | 1U6515 | sp-25 | an-227 |
| 1U5730 | sp-23 | an-228 | 1U6123 | sp-24 | an-228 | 1U6516 | sp-25 | an-228 |
| 1U5731 | sp-23 | an-229 | 1U6124 | sp-24 | an-229 | 1U6517 | sp-25 | an-229 |
| 1U5732 | sp-23 | an-230 | 1U6125 | sp-24 | an-230 | 1U6518 | sp-25 | an-230 |
| 1U5733 | sp-23 | an-231 | 1U6126 | sp-24 | an-231 | 1U6519 | sp-25 | an-231 |
| 1U5734 | sp-23 | an-232 | 1U6127 | sp-24 | an-232 | 1U6520 | sp-25 | an-232 |
| 1U5735 | sp-23 | an-233 | 1U6128 | sp-24 | an-233 | 1U6521 | sp-25 | an-233 |
| 1U5736 | sp-23 | an-234 | 1U6129 | sp-24 | an-234 | 1U6522 | sp-25 | an-234 |
| 1U5737 | sp-23 | an-235 | 1U6130 | sp-24 | an-235 | 1U6523 | sp-25 | an-235 |
| 1U5738 | sp-23 | an-236 | 1U6131 | sp-24 | an-236 | 1U6524 | sp-25 | an-236 |
| 1U5739 | sp-23 | an-237 | 1U6132 | sp-24 | an-237 | 1U6525 | sp-25 | an-237 |
| 1U5740 | sp-23 | an-238 | 1U6133 | sp-24 | an-238 | 1U6526 | sp-25 | an-238 |
| 1U5741 | sp-23 | an-239 | 1U6134 | sp-24 | an-239 | 1U6527 | sp-25 | an-239 |
| 1U5742 | sp-23 | an-240 | 1U6135 | sp-24 | an-240 | 1U6528 | sp-25 | an-240 |
| 1U5743 | sp-23 | an-241 | 1U6136 | sp-24 | an-241 | 1U6529 | sp-25 | an-241 |
| 1U5744 | sp-23 | an-242 | 1U6137 | sp-24 | an-242 | 1U6530 | sp-25 | an-242 |
| 1U5745 | sp-23 | an-243 | 1U6138 | sp-24 | an-243 | 1U6531 | sp-25 | an-243 |
| 1U5746 | sp-23 | an-244 | 1U6139 | sp-24 | an-244 | 1U6532 | sp-25 | an-244 |
| 1U5747 | sp-23 | an-245 | 1U6140 | sp-24 | an-245 | 1U6533 | sp-25 | an-245 |
| 1U5748 | sp-23 | an-246 | 1U6141 | sp-24 | an-246 | 1U6534 | sp-25 | an-246 |
| 1U5749 | sp-23 | an-247 | 1U6142 | sp-24 | an-247 | 1U6535 | sp-25 | an-247 |
| 1U5750 | sp-23 | an-248 | 1U6143 | sp-24 | an-248 | 1U6536 | sp-25 | an-248 |

TABLE 1-continued

| | | | | | | | | |
|---|---|---|---|---|---|---|---|---|
| 1U5751 | sp-23 | an-249 | 1U6144 | sp-24 | an-249 | 1U6537 | sp-25 | an-249 |
| 1U5752 | sp-23 | an-250 | 1U6145 | sp-24 | an-250 | 1U6538 | sp-25 | an-250 |
| 1U5753 | sp-23 | an-251 | 1U6146 | sp-24 | an-251 | 1U6539 | sp-25 | an-251 |
| 1U5754 | sp-23 | an-252 | 1U6147 | sp-24 | an-252 | 1U6540 | sp-25 | an-252 |
| 1U5755 | sp-23 | an-253 | 1U6148 | sp-24 | an-253 | 1U6541 | sp-25 | an-253 |
| 1U5756 | sp-23 | an-254 | 1U6149 | sp-24 | an-254 | 1U6542 | sp-25 | an-254 |
| 1U5757 | sp-23 | an-255 | 1U6150 | sp-24 | an-255 | 1U6543 | sp-25 | an-255 |
| 1U5758 | sp-23 | an-256 | 1U6151 | sp-24 | an-256 | 1U6544 | sp-25 | an-256 |
| 1U5759 | sp-23 | an-257 | 1U6152 | sp-24 | an-257 | 1U6545 | sp-25 | an-257 |
| 1U5760 | sp-23 | an-258 | 1U6153 | sp-24 | an-258 | 1U6546 | sp-25 | an-258 |
| 1U5761 | sp-23 | an-259 | 1U6154 | sp-24 | an-259 | 1U6547 | sp-25 | an-259 |
| 1U5762 | sp-23 | an-260 | 1U6155 | sp-24 | an-260 | 1U6548 | sp-25 | an-260 |
| 1U5763 | sp-23 | an-261 | 1U6156 | sp-24 | an-261 | 1U6549 | sp-25 | an-261 |
| 1U5764 | sp-23 | an-262 | 1U6157 | sp-24 | an-262 | 1U6550 | sp-25 | an-262 |
| 1U5765 | sp-23 | an-263 | 1U6158 | sp-24 | an-263 | 1U6551 | sp-25 | an-263 |
| 1U5766 | sp-23 | an-264 | 1U6159 | sp-24 | an-264 | 1U6552 | sp-25 | an-264 |
| 1U5767 | sp-23 | an-265 | 1U6160 | sp-24 | an-265 | 1U6553 | sp-25 | an-265 |
| 1U5768 | sp-23 | an-266 | 1U6161 | sp-24 | an-266 | 1U6554 | sp-25 | an-266 |
| 1U5769 | sp-23 | an-267 | 1U6162 | sp-24 | an-267 | 1U6555 | sp-25 | an-267 |
| 1U5770 | sp-23 | an-268 | 1U6163 | sp-24 | an-268 | 1U6556 | sp-25 | an-268 |
| 1U5771 | sp-23 | an-269 | 1U6164 | sp-24 | an-269 | 1U6557 | sp-25 | an-269 |
| 1U5772 | sp-23 | an-270 | 1U6165 | sp-24 | an-270 | 1U6558 | sp-25 | an-270 |
| 1U5773 | sp-23 | an-271 | 1U6166 | sp-24 | an-271 | 1U6559 | sp-25 | an-271 |
| 1U5774 | sp-23 | an-272 | 1U6167 | sp-24 | an-272 | 1U6560 | sp-25 | an-272 |
| 1U5775 | sp-23 | an-273 | 1U6168 | sp-24 | an-273 | 1U6561 | sp-25 | an-273 |
| 1U5776 | sp-23 | an-274 | 1U6169 | sp-24 | an-274 | 1U6562 | sp-25 | an-274 |
| 1U5777 | sp-23 | an-275 | 1U6170 | sp-24 | an-275 | 1U6563 | sp-25 | an-275 |
| 1U5778 | sp-23 | an-276 | 1U6171 | sp-24 | an-276 | 1U6564 | sp-25 | an-276 |
| 1U5779 | sp-23 | an-277 | 1U6172 | sp-24 | an-277 | 1U6565 | sp-25 | an-277 |
| 1U5780 | sp-23 | an-278 | 1U6173 | sp-24 | an-278 | 1U6566 | sp-25 | an-278 |
| 1U5781 | sp-23 | an-279 | 1U6174 | sp-24 | an-279 | 1U6567 | sp-25 | an-279 |
| 1U5782 | sp-23 | an-280 | 1U6175 | sp-24 | an-280 | 1U6568 | sp-25 | an-280 |
| 1U5783 | sp-23 | an-281 | 1U6176 | sp-24 | an-281 | 1U6569 | sp-25 | an-281 |
| 1U5784 | sp-23 | an-282 | 1U6177 | sp-24 | an-282 | 1U6570 | sp-25 | an-282 |
| 1U5785 | sp-23 | an-283 | 1U6178 | sp-24 | an-283 | 1U6571 | sp-25 | an-283 |
| 1U5786 | sp-23 | an-284 | 1U6179 | sp-24 | an-284 | 1U6572 | sp-25 | an-284 |
| 1U5787 | sp-23 | an-285 | 1U6180 | sp-24 | an-285 | 1U6573 | sp-25 | an-285 |
| 1U5788 | sp-23 | an-286 | 1U6181 | sp-24 | an-286 | 1U6574 | sp-25 | an-286 |
| 1U5789 | sp-23 | an-287 | 1U6182 | sp-24 | an-287 | 1U6575 | sp-25 | an-287 |
| 1U5790 | sp-23 | an-288 | 1U6183 | sp-24 | an-288 | 1U6576 | sp-25 | an-288 |
| 1U5791 | sp-23 | an-289 | 1U6184 | sp-24 | an-289 | 1U6577 | sp-25 | an-289 |
| 1U5792 | sp-23 | an-290 | 1U6185 | sp-24 | an-290 | 1U6578 | sp-25 | an-290 |
| 1U5793 | sp-23 | an-291 | 1U6186 | sp-24 | an-291 | 1U6579 | sp-25 | an-291 |
| 1U5794 | sp-23 | an-292 | 1U6187 | sp-24 | an-292 | 1U6580 | sp-25 | an-292 |
| 1U5795 | sp-23 | an-293 | 1U6188 | sp-24 | an-293 | 1U6581 | sp-25 | an-293 |
| 1U5796 | sp-23 | an-294 | 1U6189 | sp-24 | an-294 | 1U6582 | sp-25 | an-294 |
| 1U5797 | sp-23 | an-295 | 1U6190 | sp-24 | an-295 | 1U6583 | sp-25 | an-295 |
| 1U5798 | sp-23 | an-296 | 1U6191 | sp-24 | an-296 | 1U6584 | sp-25 | an-296 |
| 1U5799 | sp-23 | an-297 | 1U6192 | sp-24 | an-297 | 1U6585 | sp-25 | an-297 |
| 1U5800 | sp-23 | an-298 | 1U6193 | sp-24 | an-298 | 1U6586 | sp-25 | an-298 |
| 1U5801 | sp-23 | an-299 | 1U6194 | sp-24 | an-299 | 1U6587 | sp-25 | an-299 |
| 1U5802 | sp-23 | an-300 | 1U6195 | sp-24 | an-300 | 1U6588 | sp-25 | an-300 |
| 1U5803 | sp-23 | an-301 | 1U6196 | sp-24 | an-301 | 1U6589 | sp-25 | an-301 |
| 1U5804 | sp-23 | an-302 | 1U6197 | sp-24 | an-302 | 1U6590 | sp-25 | an-302 |
| 1U5805 | sp-23 | an-303 | 1U6198 | sp-24 | an-303 | 1U6591 | sp-25 | an-303 |
| 1U5806 | sp-23 | an-304 | 1U6199 | sp-24 | an-304 | 1U6592 | sp-25 | an-304 |
| 1U5807 | sp-23 | an-305 | 1U6200 | sp-24 | an-305 | 1U6593 | sp-25 | an-305 |
| 1U5808 | sp-23 | an-306 | 1U6201 | sp-24 | an-306 | 1U6594 | sp-25 | an-306 |
| 1U5809 | sp-23 | an-307 | 1U6202 | sp-24 | an-307 | 1U6595 | sp-25 | an-307 |
| 1U5810 | sp-23 | an-308 | 1U6203 | sp-24 | an-308 | 1U6596 | sp-25 | an-308 |
| 1U5811 | sp-23 | an-309 | 1U6204 | sp-24 | an-309 | 1U6597 | sp-25 | an-309 |
| 1U5812 | sp-23 | an-310 | 1U6205 | sp-24 | an-310 | 1U6598 | sp-25 | an-310 |
| 1U5813 | sp-23 | an-311 | 1U6206 | sp-24 | an-311 | 1U6599 | sp-25 | an-311 |
| 1U5814 | sp-23 | an-312 | 1U6207 | sp-24 | an-312 | 1U6600 | sp-25 | an-312 |
| 1U5815 | sp-23 | an-313 | 1U6208 | sp-24 | an-313 | 1U6601 | sp-25 | an-313 |
| 1U5816 | sp-23 | an-314 | 1U6209 | sp-24 | an-314 | 1U6602 | sp-25 | an-314 |
| 1U5817 | sp-23 | an-315 | 1U6210 | sp-24 | an-315 | 1U6603 | sp-25 | an-315 |
| 1U5818 | sp-23 | an-316 | 1U6211 | sp-24 | an-316 | 1U6604 | sp-25 | an-316 |
| 1U5819 | sp-23 | an-317 | 1U6212 | sp-24 | an-317 | 1U6605 | sp-25 | an-317 |
| 1U5820 | sp-23 | an-318 | 1U6213 | sp-24 | an-318 | 1U6606 | sp-25 | an-318 |
| 1U5821 | sp-23 | an-319 | 1U6214 | sp-24 | an-319 | 1U6607 | sp-25 | an-319 |
| 1U5822 | sp-23 | an-320 | 1U6215 | sp-24 | an-320 | 1U6608 | sp-25 | an-320 |
| 1U5823 | sp-23 | an-321 | 1U6216 | sp-24 | an-321 | 1U6609 | sp-25 | an-321 |
| 1U5824 | sp-23 | an-322 | 1U6217 | sp-24 | an-322 | 1U6610 | sp-25 | an-322 |
| 1U5825 | sp-23 | an-323 | 1U6218 | sp-24 | an-323 | 1U6611 | sp-25 | an-323 |
| 1U5826 | sp-23 | an-324 | 1U6219 | sp-24 | an-324 | 1U6612 | sp-25 | an-324 |
| 1U5827 | sp-23 | an-325 | 1U6220 | sp-24 | an-325 | 1U6613 | sp-25 | an-325 |
| 1U5828 | sp-23 | an-326 | 1U6221 | sp-24 | an-326 | 1U6614 | sp-25 | an-326 |
| 1U5829 | sp-23 | an-327 | 1U6222 | sp-24 | an-327 | 1U6615 | sp-25 | an-327 |

TABLE 1-continued

| | | | | | | | | |
|---|---|---|---|---|---|---|---|---|
| 1U5830 | sp-23 | an-328 | 1U6223 | sp-24 | an-328 | 1U6616 | sp-25 | an-328 |
| 1U5831 | sp-23 | an-329 | 1U6224 | sp-24 | an-329 | 1U6617 | sp-25 | an-329 |
| 1U5832 | sp-23 | an-330 | 1U6225 | sp-24 | an-330 | 1U6618 | sp-25 | an-330 |
| 1U5833 | sp-23 | an-331 | 1U6226 | sp-24 | an-331 | 1U6619 | sp-25 | an-331 |
| 1U5834 | sp-23 | an-332 | 1U6227 | sp-24 | an-332 | 1U6620 | sp-25 | an-332 |
| 1U5835 | sp-23 | an-333 | 1U6228 | sp-24 | an-333 | 1U6621 | sp-25 | an-333 |
| 1U5836 | sp-23 | an-334 | 1U6229 | sp-24 | an-334 | 1U6622 | sp-25 | an-334 |
| 1U5837 | sp-23 | an-335 | 1U6230 | sp-24 | an-335 | 1U6623 | sp-25 | an-335 |
| 1U5838 | sp-23 | an-336 | 1U6231 | sp-24 | an-336 | 1U6624 | sp-25 | an-336 |
| 1U5839 | sp-23 | an-337 | 1U6232 | sp-24 | an-337 | 1U6625 | sp-25 | an-337 |
| 1U5840 | sp-23 | an-338 | 1U6233 | sp-24 | an-338 | 1U6626 | sp-25 | an-338 |
| 1U5841 | sp-23 | an-339 | 1U6234 | sp-24 | an-339 | 1U6627 | sp-25 | an-339 |
| 1U5842 | sp-23 | an-340 | 1U6235 | sp-24 | an-340 | 1U6628 | sp-25 | an-340 |
| 1U5843 | sp-23 | an-341 | 1U6236 | sp-24 | an-341 | 1U6629 | sp-25 | an-341 |
| 1U5844 | sp-23 | an-342 | 1U6237 | sp-24 | an-342 | 1U6630 | sp-25 | an-342 |
| 1U5845 | sp-23 | an-343 | 1U6238 | sp-24 | an-343 | 1U6631 | sp-25 | an-343 |
| 1U5846 | sp-23 | an-344 | 1U6239 | sp-24 | an-344 | 1U6632 | sp-25 | an-344 |
| 1U5847 | sp-23 | an-345 | 1U6240 | sp-24 | an-345 | 1U6633 | sp-25 | an-345 |
| 1U5848 | sp-23 | an-346 | 1U6241 | sp-24 | an-346 | 1U6634 | sp-25 | an-346 |
| 1U5849 | sp-23 | an-347 | 1U6242 | sp-24 | an-347 | 1U6635 | sp-25 | an-347 |
| 1U5850 | sp-23 | an-348 | 1U6243 | sp-24 | an-348 | 1U6636 | sp-25 | an-348 |
| 1U5851 | sp-23 | an-349 | 1U6244 | sp-24 | an-349 | 1U6637 | sp-25 | an-349 |
| 1U5852 | sp-23 | an-350 | 1U6245 | sp-24 | an-350 | 1U6638 | sp-25 | an-350 |
| 1U5853 | sp-23 | an-351 | 1U6246 | sp-24 | an-351 | 1U6639 | sp-25 | an-351 |
| 1U5854 | sp-23 | an-352 | 1U6247 | sp-24 | an-352 | 1U6640 | sp-25 | an-352 |
| 1U5855 | sp-23 | an-353 | 1U6248 | sp-24 | an-353 | 1U6641 | sp-25 | an-353 |
| 1U5856 | sp-23 | an-354 | 1U6249 | sp-24 | an-354 | 1U6642 | sp-25 | an-354 |
| 1U5857 | sp-23 | an-355 | 1U6250 | sp-24 | an-355 | 1U6643 | sp-25 | an-355 |
| 1U5858 | sp-23 | an-356 | 1U6251 | sp-24 | an-356 | 1U6644 | sp-25 | an-356 |
| 1U5859 | sp-23 | an-357 | 1U6252 | sp-24 | an-357 | 1U6645 | sp-25 | an-357 |
| 1U5860 | sp-23 | an-358 | 1U6253 | sp-24 | an-358 | 1U6646 | sp-25 | an-358 |
| 1U5861 | sp-23 | an-359 | 1U6254 | sp-24 | an-359 | 1U6647 | sp-25 | an-359 |
| 1U5862 | sp-23 | an-360 | 1U6255 | sp-24 | an-360 | 1U6648 | sp-25 | an-360 |
| 1U5863 | sp-23 | an-361 | 1U6256 | sp-24 | an-361 | 1U6649 | sp-25 | an-361 |
| 1U5864 | sp-23 | an-362 | 1U6257 | sp-24 | an-362 | 1U6650 | sp-25 | an-362 |
| 1U5865 | sp-23 | an-363 | 1U6258 | sp-24 | an-363 | 1U6651 | sp-25 | an-363 |
| 1U5866 | sp-23 | an-364 | 1U6259 | sp-24 | an-364 | 1U6652 | sp-25 | an-364 |
| 1U5867 | sp-23 | an-365 | 1U6260 | sp-24 | an-365 | 1U6653 | sp-25 | an-365 |
| 1U5868 | sp-23 | an-366 | 1U6261 | sp-24 | an-366 | 1U6654 | sp-25 | an-366 |
| 1U5869 | sp-23 | an-367 | 1U6262 | sp-24 | an-367 | 1U6655 | sp-25 | an-367 |
| 1U5870 | sp-23 | an-368 | 1U6263 | sp-24 | an-368 | 1U6656 | sp-25 | an-368 |
| 1U5871 | sp-23 | an-369 | 1U6264 | sp-24 | an-369 | 1U6657 | sp-25 | an-369 |
| 1U5872 | sp-23 | an-370 | 1U6265 | sp-24 | an-370 | 1U6658 | sp-25 | an-370 |
| 1U5873 | sp-23 | an-371 | 1U6266 | sp-24 | an-371 | 1U6659 | sp-25 | an-371 |
| 1U5874 | sp-23 | an-372 | 1U6267 | sp-24 | an-372 | 1U6660 | sp-25 | an-372 |
| 1U5875 | sp-23 | an-373 | 1U6268 | sp-24 | an-373 | 1U6661 | sp-25 | an-373 |
| 1U5876 | sp-23 | an-374 | 1U6269 | sp-24 | an-374 | 1U6662 | sp-25 | an-374 |
| 1U5877 | sp-23 | an-375 | 1U6270 | sp-24 | an-375 | 1U6663 | sp-25 | an-375 |
| 1U5878 | sp-23 | an-376 | 1U6271 | sp-24 | an-376 | 1U6664 | sp-25 | an-376 |
| 1U5879 | sp-23 | an-377 | 1U6272 | sp-24 | an-377 | 1U6665 | sp-25 | an-377 |
| 1U5880 | sp-23 | an-378 | 1U6273 | sp-24 | an-378 | 1U6666 | sp-25 | an-378 |
| 1U5881 | sp-23 | an-379 | 1U6274 | sp-24 | an-379 | 1U6667 | sp-25 | an-379 |
| 1U5882 | sp-23 | an-380 | 1U6275 | sp-24 | an-380 | 1U6668 | sp-25 | an-380 |
| 1U5883 | sp-23 | an-381 | 1U6276 | sp-24 | an-381 | 1U6669 | sp-25 | an-381 |
| 1U5884 | sp-23 | an-382 | 1U6277 | sp-24 | an-382 | 1U6670 | sp-25 | an-382 |
| 1U5885 | sp-23 | an-383 | 1U6278 | sp-24 | an-383 | 1U6671 | sp-25 | an-383 |
| 1U5886 | sp-23 | an-384 | 1U6279 | sp-24 | an-384 | 1U6672 | sp-25 | an-384 |
| 1U5887 | sp-23 | an-385 | 1U6280 | sp-24 | an-385 | 1U6673 | sp-25 | an-385 |
| 1U5888 | sp-23 | an-386 | 1U6281 | sp-24 | an-386 | 1U6674 | sp-25 | an-386 |
| 1U5889 | sp-23 | an-387 | 1U6282 | sp-24 | an-387 | 1U6675 | sp-25 | an-387 |
| 1U5890 | sp-23 | an-388 | 1U6283 | sp-24 | an-388 | 1U6676 | sp-25 | an-388 |
| 1U5891 | sp-23 | an-389 | 1U6284 | sp-24 | an-389 | 1U6677 | sp-25 | an-389 |
| 1U5892 | sp-23 | an-390 | 1U6285 | sp-24 | an-390 | 1U6678 | sp-25 | an-390 |
| 1U5893 | sp-23 | an-391 | 1U6286 | sp-24 | an-391 | 1U6679 | sp-25 | an-391 |
| 1U5894 | sp-23 | an-392 | 1U6287 | sp-24 | an-392 | 1U6680 | sp-25 | an-392 |
| 1U5895 | sp-23 | an-393 | 1U6288 | sp-24 | an-393 | 1U6681 | sp-25 | an-393 |

Moreover, mention may be made of compounds (from 2A0001 to 2A6681, from 2U0001 to 2U6681, and from 2C0001 to 2C3930) which are identical to the compounds described in Table 1 (from 1A0001 to 1A6681, from 1U0001 to 1U6681, and from 1C0001 to 1C3930) except that the bonding position of Y has been changed to the para-position. Here, it means that, for example, compound 1A0001 has been changed to compound 2A0001. The same is true for the following.

Moreover, mention may be made of compounds (from 3A0001 to 3A6681, from 3U0001 to 3U6681, and from 3C0001 to 3C3930) which are identical to the compounds described in Table 1 (from 1A0001 to 1A6681, from 1U0001 to 1U6681, and from 1C0001 to 1C3930) except that the $NR^3R^4$ has been replaced by a 7-diethylamino group.

Moreover, mention may be made of compounds (from 4A0001 to 4A6681, from 4U0001 to 4U6681, and from 4C0001 to 4C3930) which are identical to the compounds described in Table 1 (from 1A0001 to 1A6681, from 1U0001 to 1U6681, and from 1C0001 to 1C3930) except that the NR3R4 has been replaced by a 7-ethylmethylamino group.

Moreover, mention may be made of compounds (from 5A0001 to 5A6681, from 5U0001 to 5U6681, and from 5C0001 to 5C3930) which are identical to the compounds described in Table 1 (from 1A0001 to 1A6681, from 1U0001 to 1U6681, and from 1C0001 to 1C3930) except that the $NR^3R^4$ has been replaced by a 9-dimethylamino group.

Moreover, mention may be made of compounds (from 6A0001 to 6A6681, from 6U0001 to 6U6681, and from 6C0001 to 6C3930) which are identical to the compounds described in Table 1 (from 1A0001 to 1A6681, from 1U0001 to 1U6681, and from 1C0001 to 1C3930) except that the $NR^3R^4$ has been replaced by a 7,9-bis (dimethylamino) group.

Moreover, mention may be made of compounds (from 7A0001 to 7A6681, from 7U0001 to 7U6681, and from 7C0001 to 7C3930) which are identical to the compounds described in Table 1 (from 1A0001 to 1A6681, from 1U0001 to 1U6681, and from 1C0001 to 1C3930) except that both R1 and R2 have been replaced by propyl groups, respectively.

Moreover, mention may be made of compounds (from 8A0001 to 8A6681, from 8U0001 to 8U6681, and from 8C0001 to 8C3930) which are identical to the compounds described in Table 1 (from 1A0001 to 1A6681, from 1U0001 to 1U6681, and from 1C0001 to 1C3930) except that both $R^1$ and $R^2$ have been replaced by pentyl groups, respectively.

Moreover, mention may be made of compounds (from 9A0001 to 9A6681, from 9U0001 to 9U6681, and from 9C0001 to 9C3930) which are identical to the compounds described in Table 1 (from 1A0001 to 1A6681, from 1U0001 to 1U6681, and from 1C0001 to 1C3930) except that both $R^1$ and $R^2$ have been replaced by hexyl groups, respectively.

Moreover, mention may be made of compounds (from 10A0001 to 10A6681, from 10U0001 to 10U6681, and from 10C0001 to 10C3930) which are identical to the compounds (from 1A0001 to 1A6681, from 1U0001 to 1U6681, and from 10C0001 to 1C3930) except that the $R^1$ thereof has been replaced by an ethyl group.

The compounds represented by the formula (1) of the present invention can be produced by the following production method.

(Production Method)

Among the compounds represented by the formula (1), those compounds in which Y is —NHCS— can be obtained by allowing a compound represented by the following formula (2)

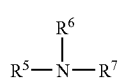

(2)

[wherein R5, R6, and R7 are as mentioned earlier, and the quaternary ammonium structure mentioned earlier has been changed to a tertiary amine structure] to react on a compound represented by the following formula (3)

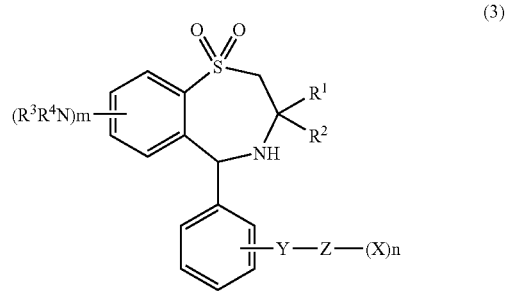

(3)

[wherein R1, R2, R3, R4, m, n, and Z are as mentioned earlier;

Y represents an —NHCS—; and

X represents a group which can become an anion].

The reaction is carried out, for example, at room temperature or 40 to 100° C optionally in a solvent such as acetonitrile or N,N-dimethylformamide (hereinafter, "DMF" for short) by allowing at least an equimolar amount, preferably 1 to 5 time molar amount of the compound represented by the formula (2) to react on the compound represented by the formula (3) for 1 to 48 hours.

X in the formula (3) is a group which undergoes nucleophilic substitution by the compound represented by the formula (2) and is released as an anion, preferably a group which is released as a pharmaceutically acceptable anion. Preferable examples thereof include F, Cl, Br, I, mesylate, and tosylate, and more preferably Cl, Br, and I.

Compounds represented by the formula (2) include compounds represented by formulae from (ta-1) to (ta-407). Letters next to the formula numbers indicate names of manufacturing companies as follows. "AC" stands for ACROSS ORGANICS, "AL" stands for ALDRICH CHEMICAL COMPANY "BO" stands for BIO-NET CHEMICAL CO. LTD., "FL" stands for FLUKA CHEMICAL CORPORATION "IC" stands for ICN-RF, "LN" stands for LANCASTER CHEMICAL CO. LTD., "MY" stands for MAYBRIDGE CHEMICALS, "NC" stands for NACALAI CO. LTD., "PF" stands for PFALZ & BAUER, "SG" stands for SIGMA CHEMICAL COMPANY "SL" stands for SALOR CHEMICAL COMPANY, "TK" stands for TOKYO CHEMICAL INDUSTRIES, LTD., "WK" stands for WAKO PURE CHEMICAL INDUSTRIES LTD., and "WT" stands for WATANABE CHEMICAL INDUSTRIES LTD. ta-37 is prepared by allowing benzyl bromide manufactured by TOKYO CHEMICAL INDUSTRIES, LTD. to react with dipropylamine manufactured by TOKYO CHEMICAL INDUSTRIES, LTD. in the presence of potassium carbonate. ta-56 is prepared by allowing 3-bromopropanol manufactured by TOKYO CHEMICAL INDUSTRIES, LTD. to react with dibutylamine manufactured by TOKYO CHEMICAL INDUSTRIES, LTD. in the presence of potassium carbonate. ta-57 is prepared by allowing 4-bromobutanol manufactured by TOKYO CHEMICAL INDUSTRIES, LTD. to react with dibutylamine in the presence of potassium carbonate. ta-117 is prepared by neutralizing its hydrochloride manufactured by SALOR CHEMICAL COMPANY. ta-137 is prepared by allowing benzyl bromide to react with N-ethyl ethanolamine manufactured by TOKYO CHEMICAL INDUSTRIES, LTD. in the presence of potassium carbonate. ta-138 is prepared by allowing benzyl bromide to react with N-propylethanolamine manufactured by ALDRICH CHEMICAL COMPANY in the presence of potassium carbonate. ta-139 is prepared by allowing benzyl bromide to react with N-butylethanolamine manufactured by TOKYO CHEMICAL INDUSTRIES, LTD. in the presence of potassium carbonate. ta-145 is prepared by neutralizing a hydrochloride manufactured by ALDRICH CHEMICAL COMPANY. ta-148 is prepared by neutralizing its hydrochloride manufactured by TOKYO CHEMICAL INDUSTRIES, LTD. ta-152 is prepared by allowing benzyl bromide to react with ta-99. ta-153 is prepared by allowing benzyl bromide to react with ta-100. ta-154 is prepared by allowing benzyl bromide to react with ta-101. ta-155 is prepared by allowing benzyl bromide to react with ta-105. ta-156 is prepared by allowing benzyl bromide to react with ta-106. ta-157 is prepared by allowing benzyl bromide to react with ta-108. ta-158 is prepared by allowing benzyl bromide to react with ta-112. ta-162 is prepared by allowing pentyl iodide manufactured by TOKYO CHEMICAL INDUSTRIES, LTD. to react with pyrrolidine manufactured by TOKYO CHEMICAL INDUSTRIES, LTD. in the presence of potassium carbonate. ta-172 is prepared by neutralizing its hydrochloride manufactured by MAYBRIDGE CHEMICALS. ta-178 is prepared by neutralizing its hydrochloride manufactured by NACALAI CO. LTD. ta-181 is prepared by allowing butyl iodide manufactured by TOKYO CHEMICAL INDUSTRIES, LTD. to react with piperidine manufactured by TOKYO CHEMICAL INDUSTRIES, LTD. in the presence of potassium carbonate. ta-182 is prepared by allowing pentyl iodide to react with piperidine in the presence of potassium carbonate. ta-185 is prepared by allowing benzyl bromide to react with piperidine in the presence of potassium carbonate. ta-193 is prepared by allowing sodium borohydride to react with ta-207. ta-212 is prepared by neutralizing its hydrochloride manufactured by TOKYO CHEMICAL INDUSTRIES, LTD.. ta-234 is prepared by allowing pentyl iodide to react with morpholine manufactured by TOKYO CHEMICAL INDUSTRIES, LTD. in the presence of potassium carbonate. ta.-237 is prepared by allowing benzyl bromide to react with morpholine in the presence of potassium carbonate. ta-255 is prepared by allowing ethyl iodide manufactured by TOKYO CHEMICAL INDUSTRIES, LTD. to react with piperazine manufactured by TOKYO CHEMICAL INDUSTRIES, LTD. in the presence of potassium carbonate. ta-256 is prepared by allowing butyl iodide to react with piperazine in the presence of potassium carbonate. ta-257 is manufactured by allowing pentyl iodide to react with piperazine in the presence of potassium carbonate. ta-259 is prepared by allowing benzyl bromide to react with piperazine in the presence of potassium carbonate. ta-264 is prepared by allowing benzyl bromide to react with ta-254. ta-265 is prepared by allowing benzyl bromide to react with ta-256. ta-266 is prepared by allowing benzyl bromide to react with ta-260. ta-279 is prepared by allowing butyl iodide to react with azepane manufactured by TOKYO CHEMICAL INDUSTRIES, LTD. in the presence of potassium carbonate. ta-280 is prepared by allowing pentyl iodide to react with azepane in the presence of potassium carbonate. ta-281 is prepared by allowing benzyl bromide to react with azepane in the presence of potassium carbonate. ta-290 is prepared by neutralizing its hydrochloride manufactured by TOKYO CHEMICAL INDUSTRIES, LTD.. ta-294 is prepared by allowing phenylacetyl chloride manufactured by ALDRICH CHEMICAL COMPANY to react with 3-aminoquinuclidine hydrochloride manufactured by TOKYO CHEMICAL INDUSTRIES, LTD. in the presence of potassium carbonate. ta-295 is prepared by allowing butyl chloride manufactured by ALDRICH CHEMICAL COMPANY to react with 3-aminoquinuclidine hydrochloride in the presence of potassium carbonate. ta-296 is prepared by allowing valeryl chloride manufactured by ALDRICH CHEMICAL COMPANY to react with 3-aminoquinuclidine hydrochloride in the presence of potassium carbonate. ta-298 is prepared by allowing butyl bromide manufactured by TOKYO CHEMICAL INDUSTRIES, LTD. to react with ta-297. ta-299 is prepared by allowing benzyl bromide to react with ta-297. (ta-1) to (ta-407) correspond to (an-1) to (an-407) mentioned earlier, respectively.

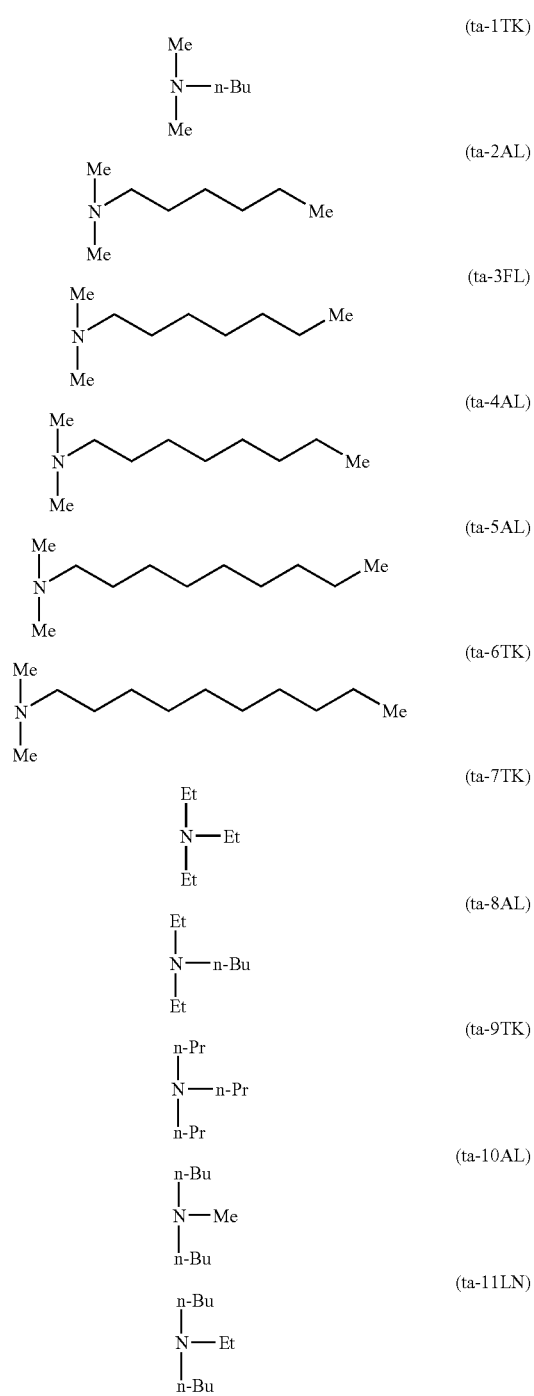

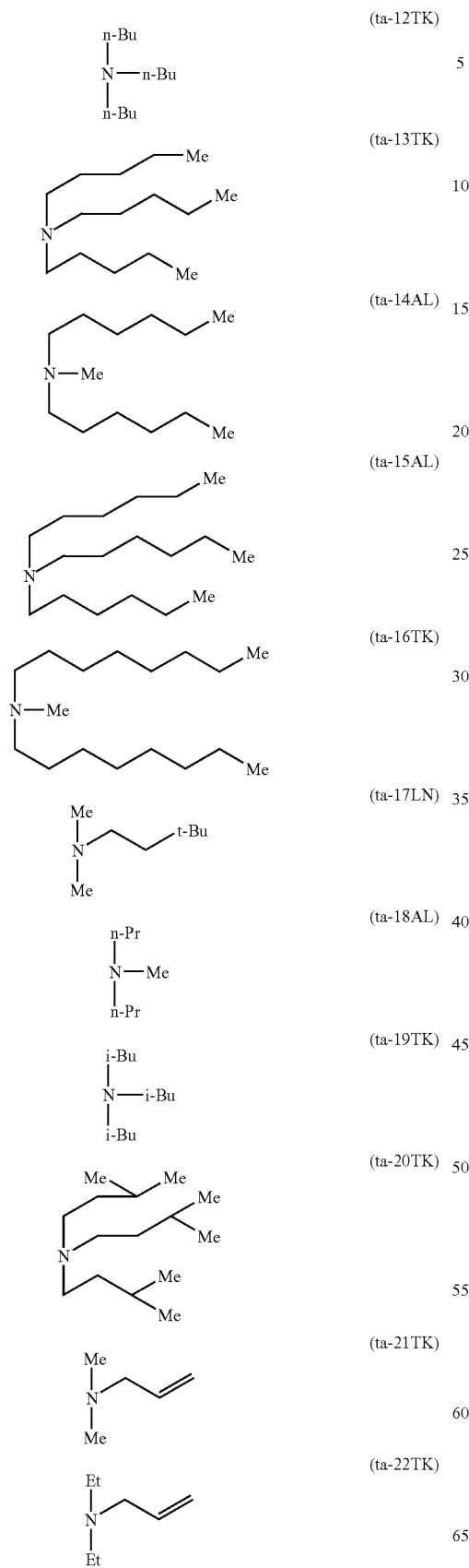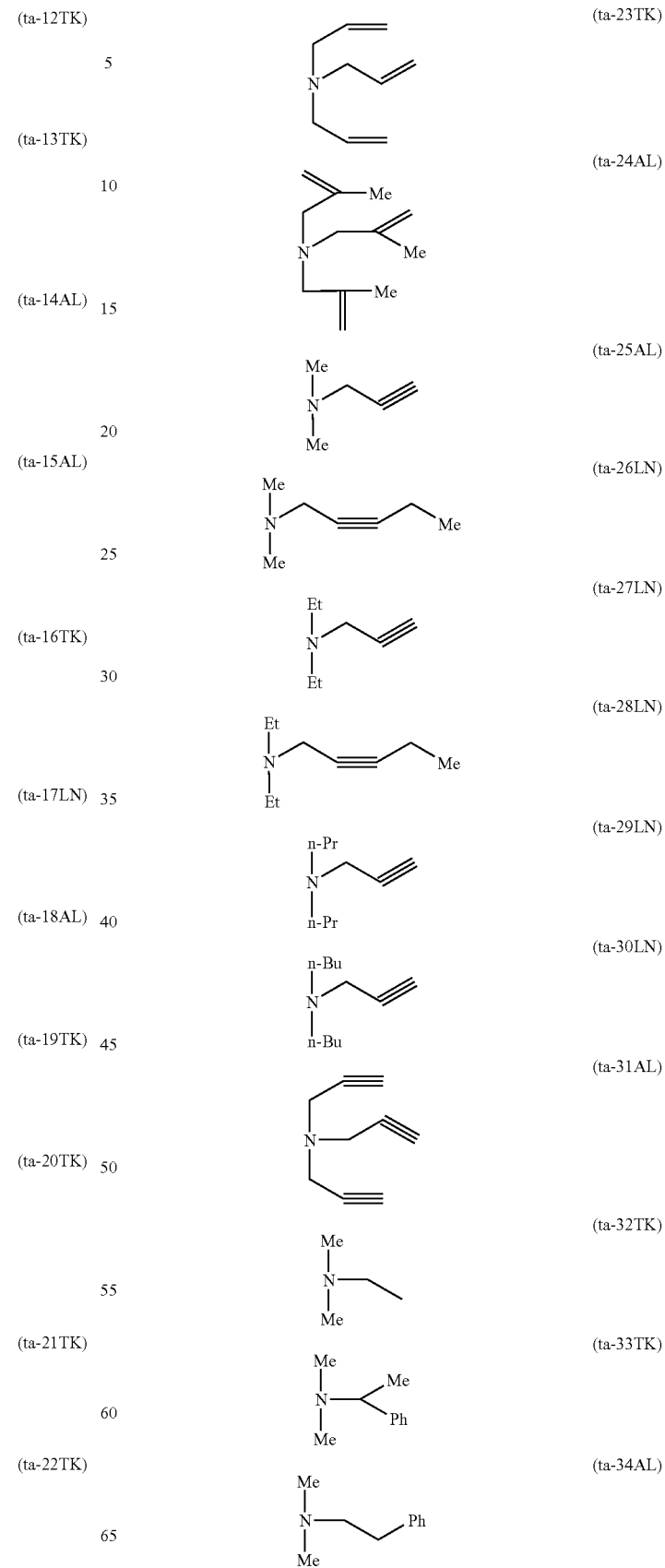

-continued
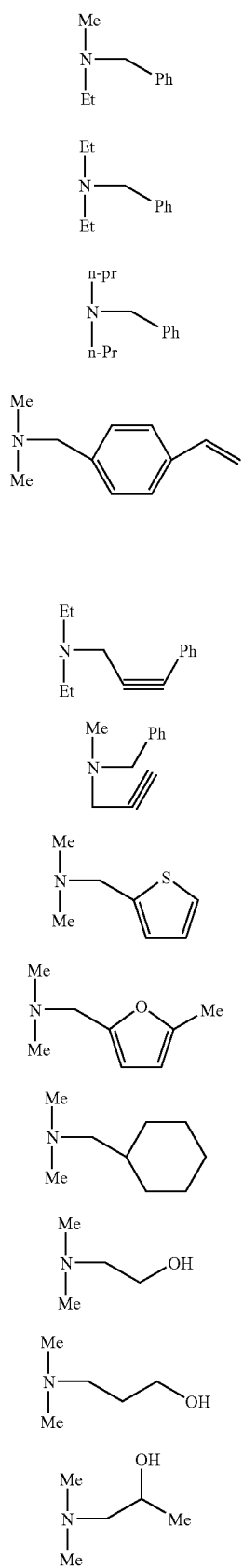
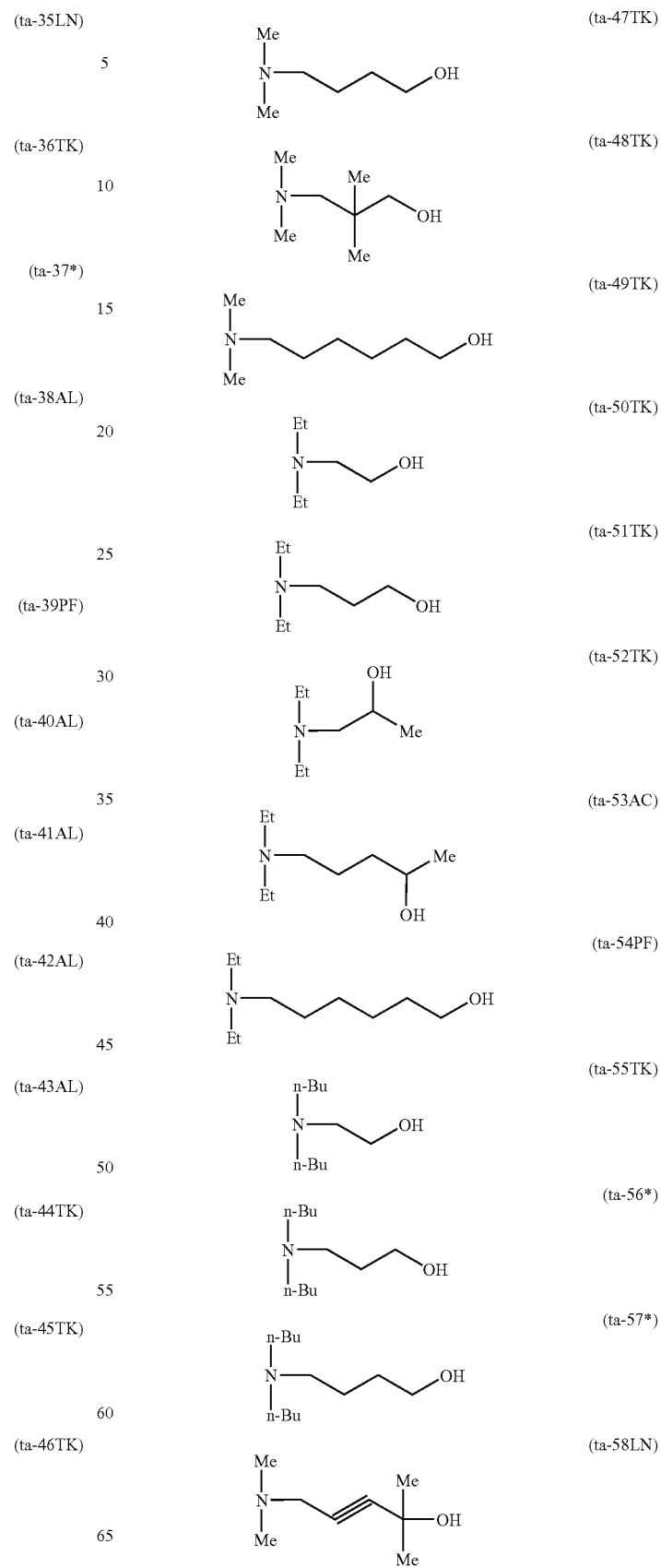

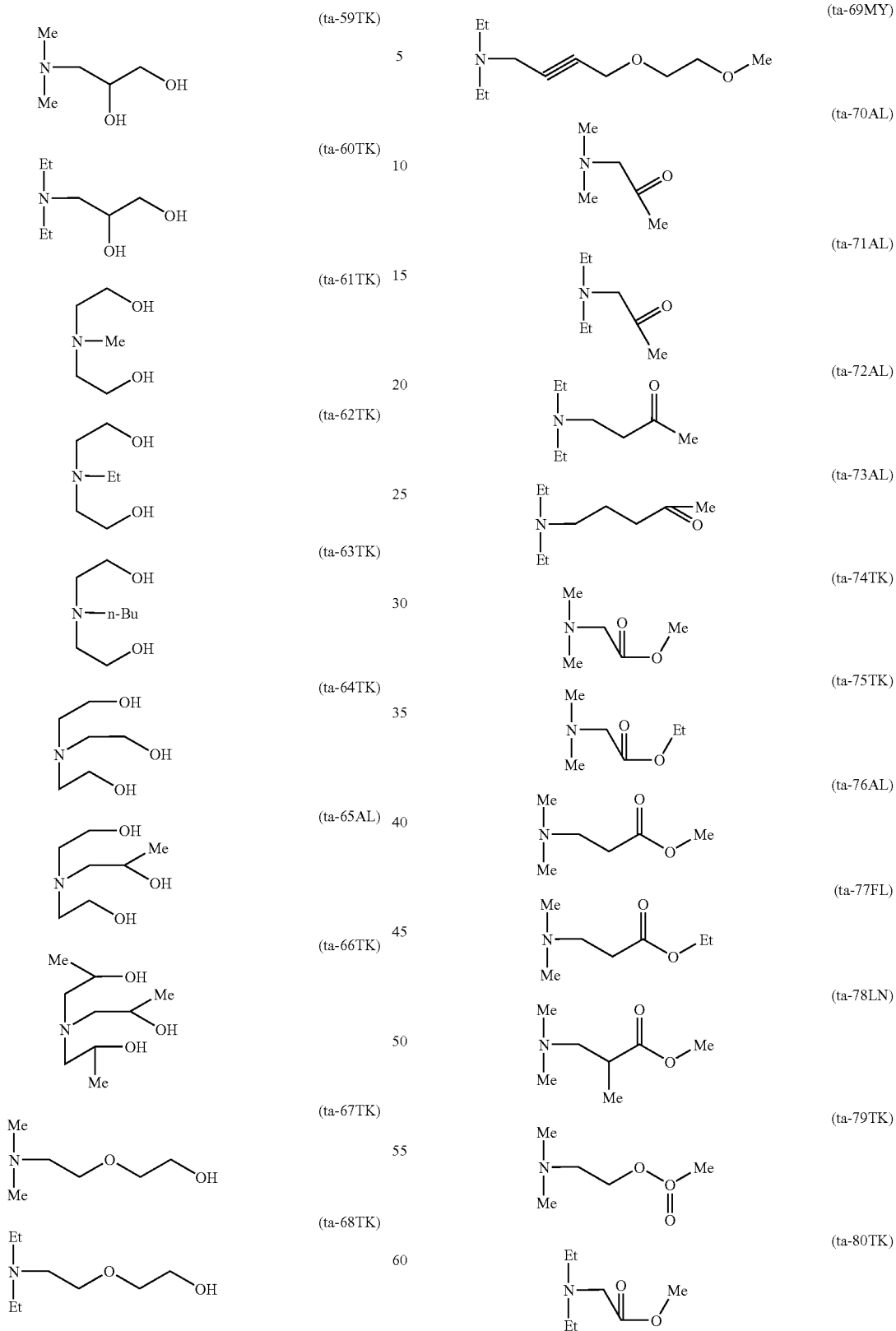

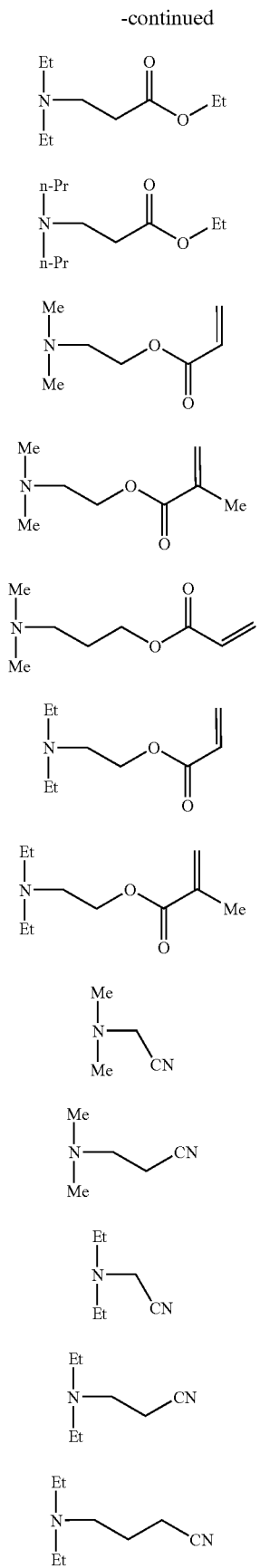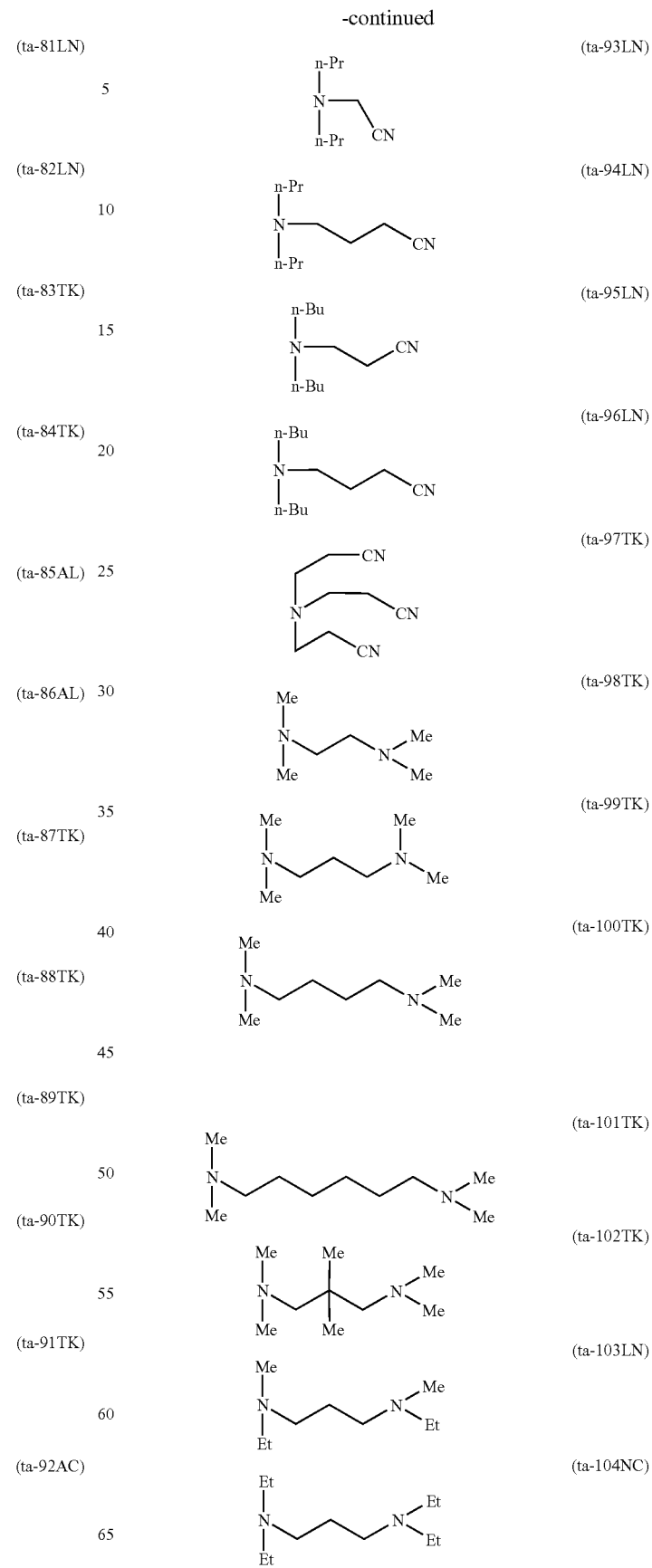

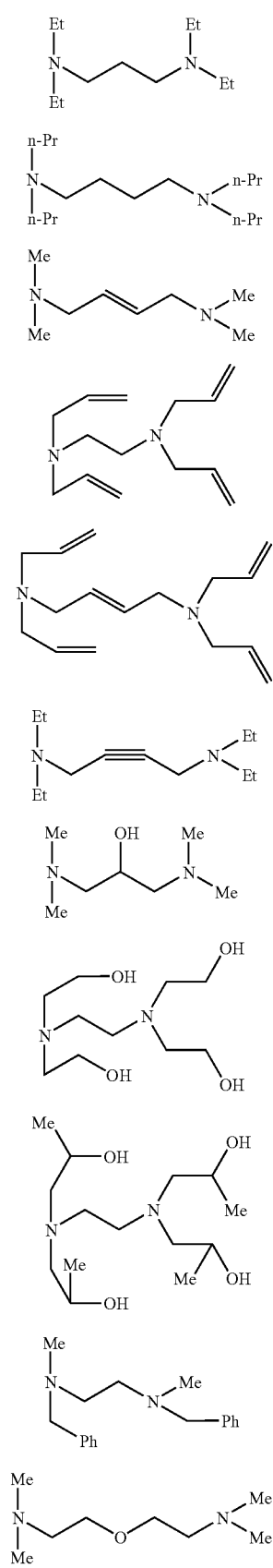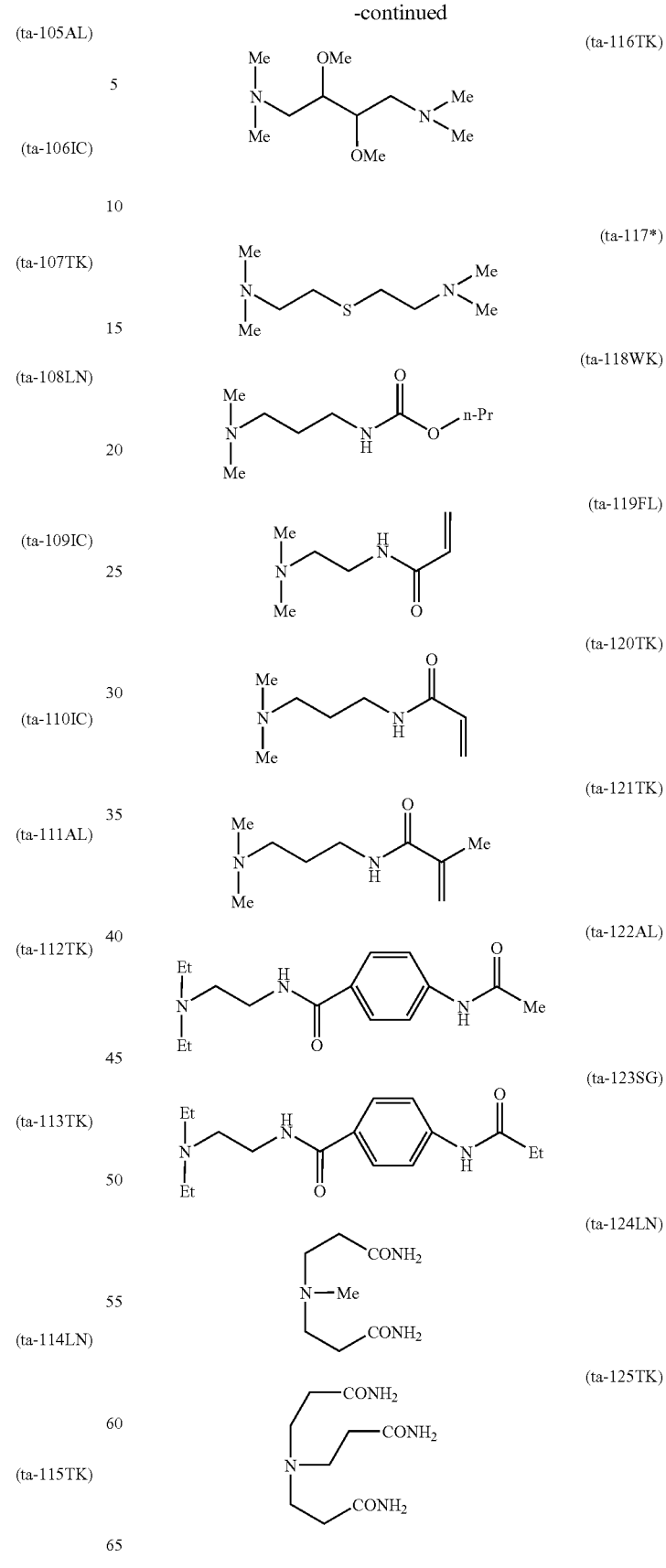

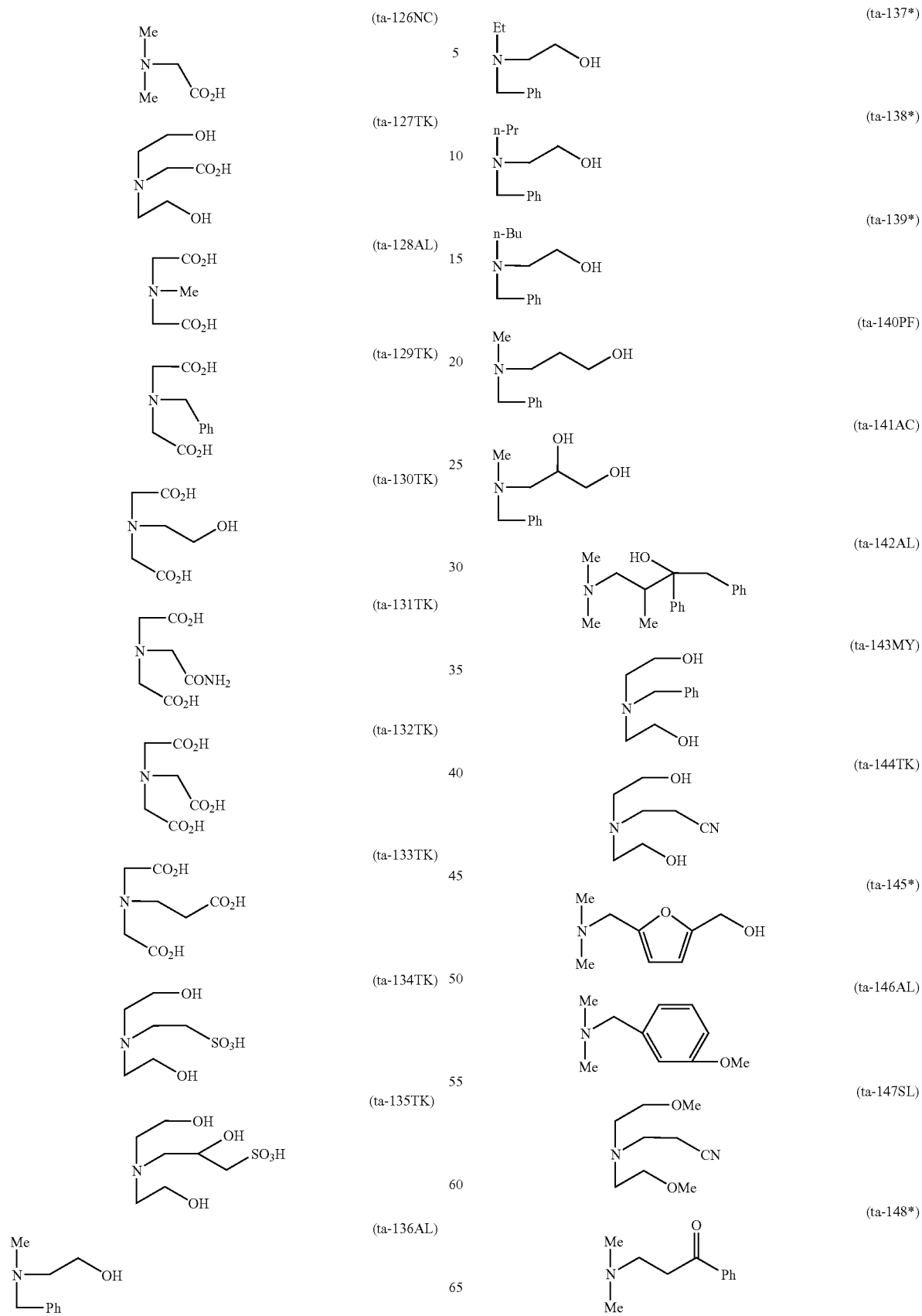

-continued
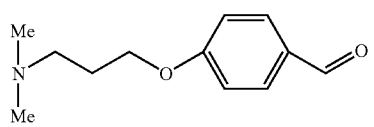 (ta-149AL)
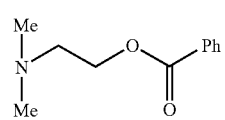 (ta-150TK)
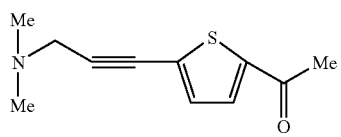 (ta-151MY)
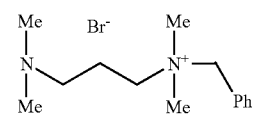 (ta-152*)
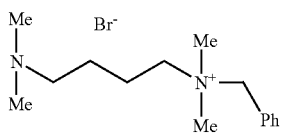 (ta-153*)
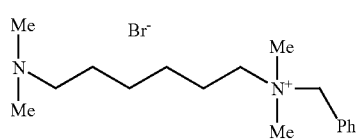 (ta-154*)
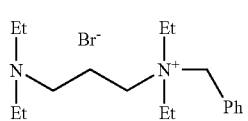 (ta-155*)
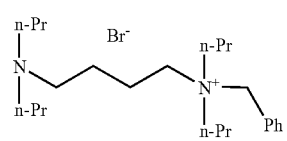 (ta-156*)
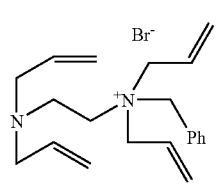 (ta-157*)
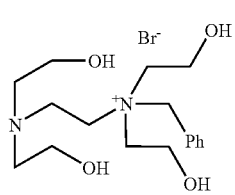 (ta-158*)
-continued
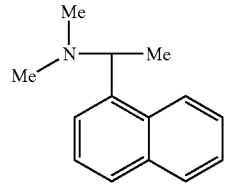 (ta-380AL)
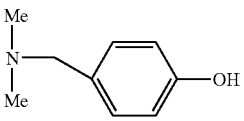 (ta-381SG)
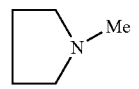 (ta-159TK)
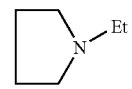 (ta-160TK)
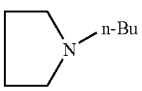 (ta-161AL)
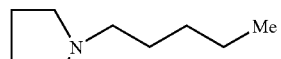 (ta-162*)
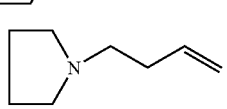 (ta-163IC)
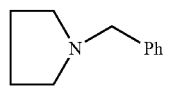 (ta-164AC)
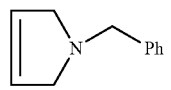 (ta-165AL)
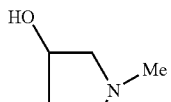 (ta-166AL)
 (ta-167TK)
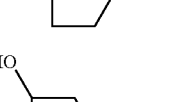 (ta-168TK)
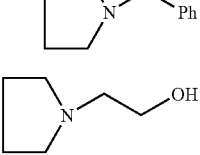 (ta-169TK)

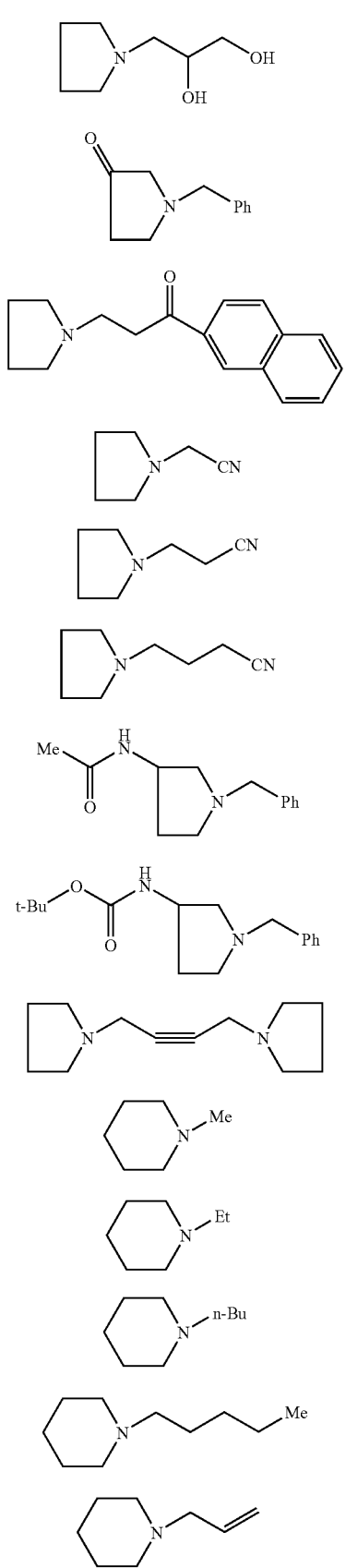
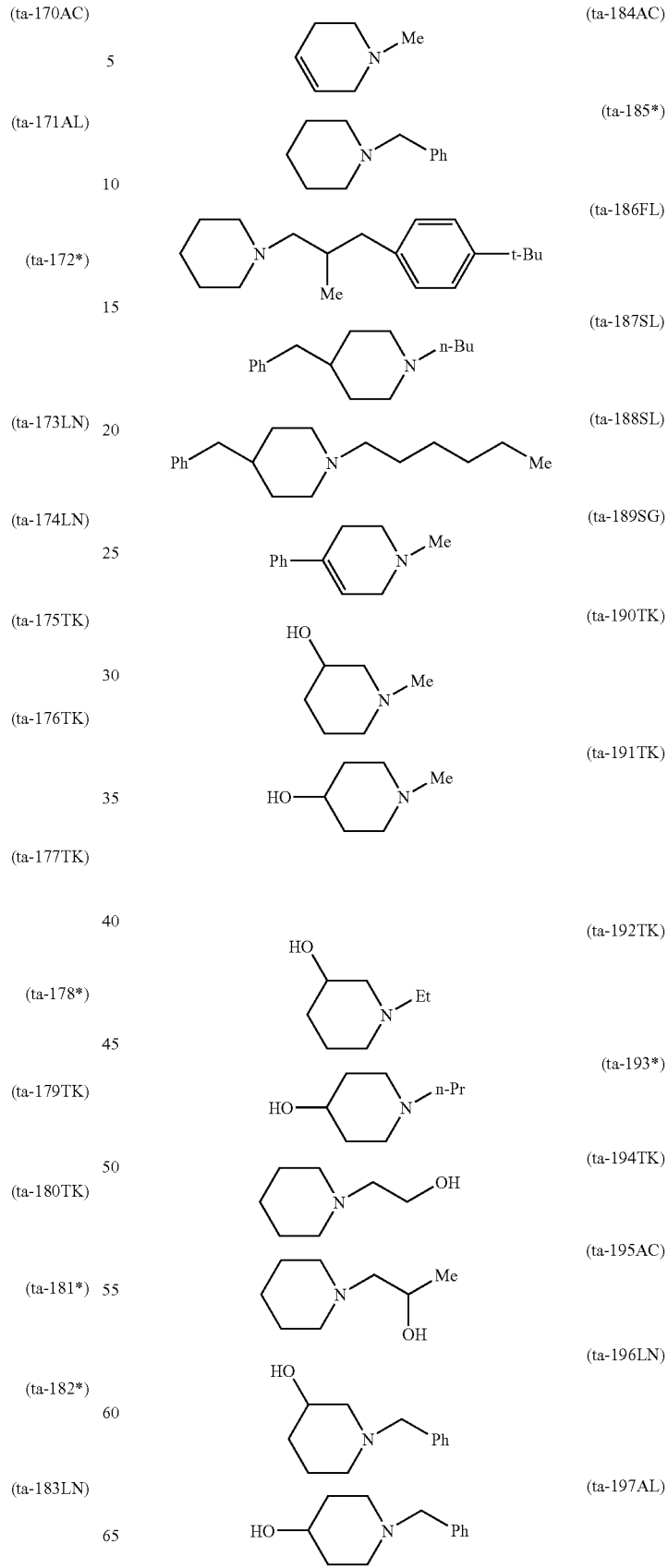

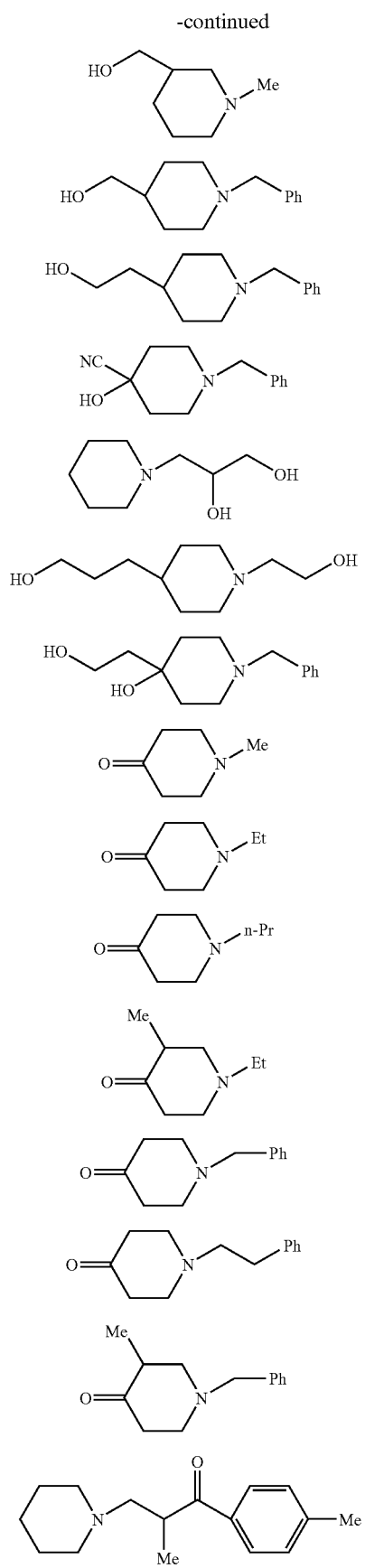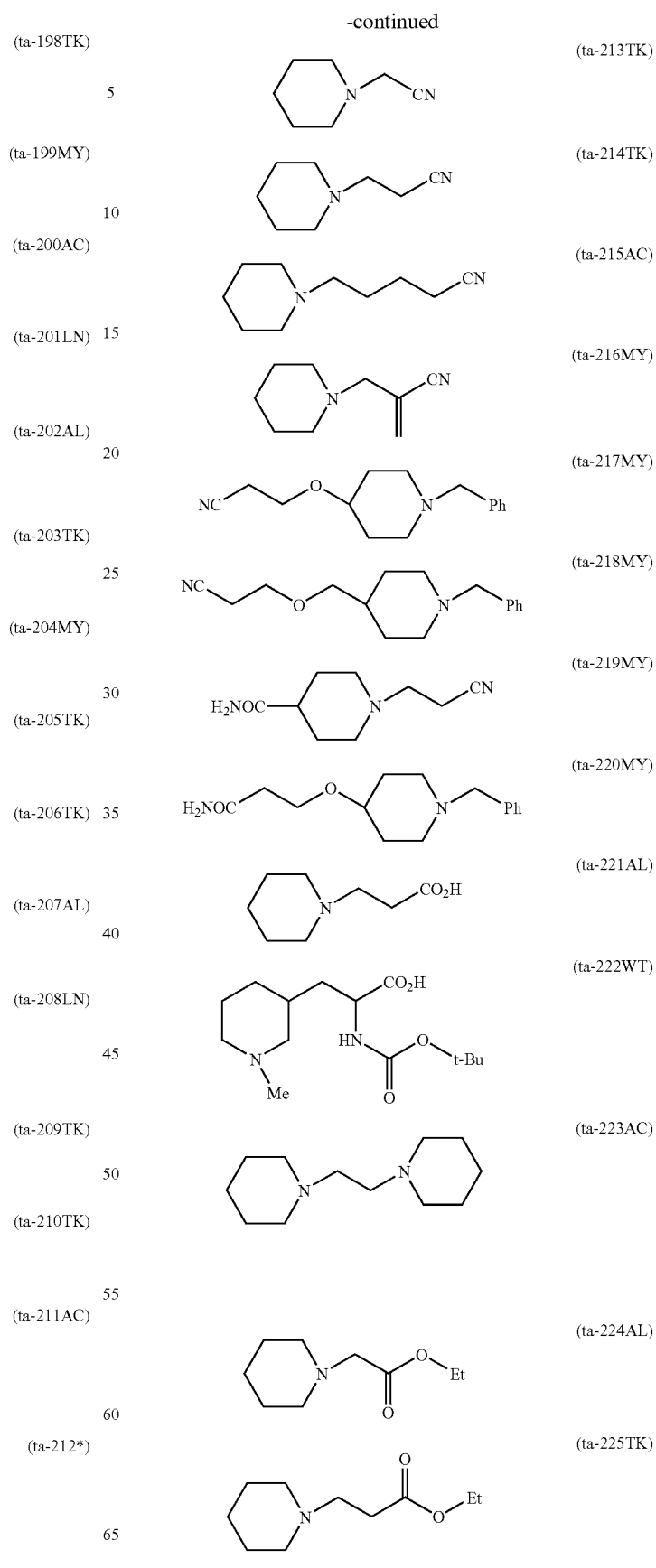

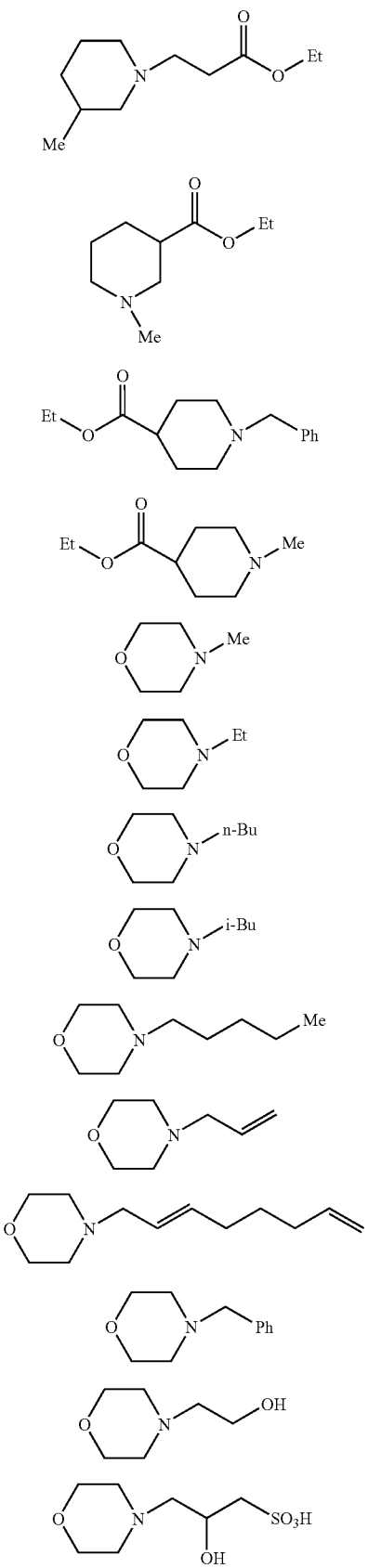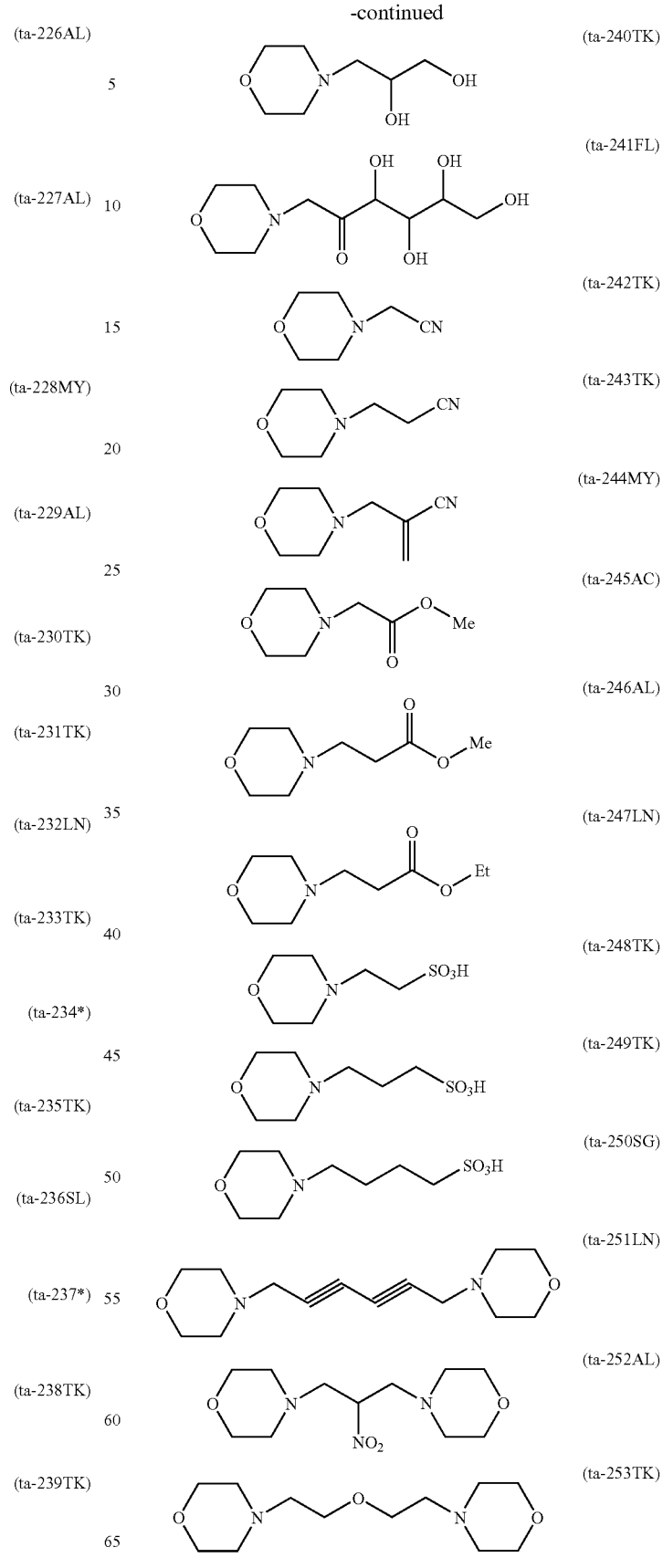

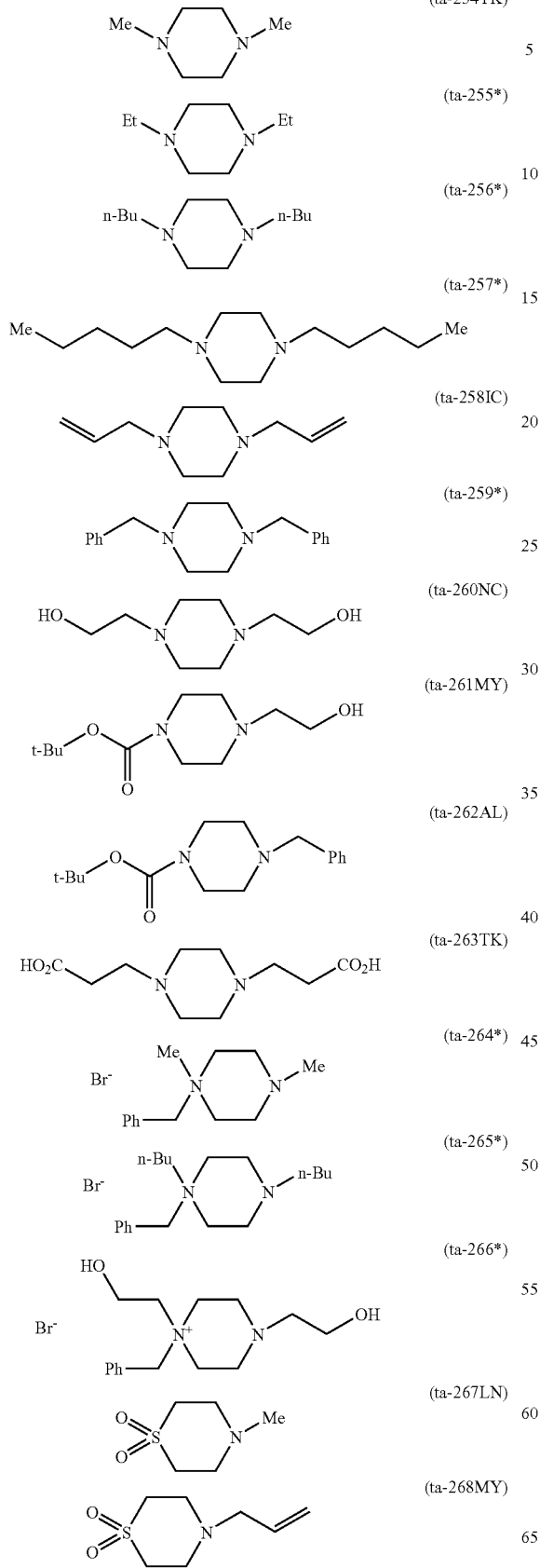
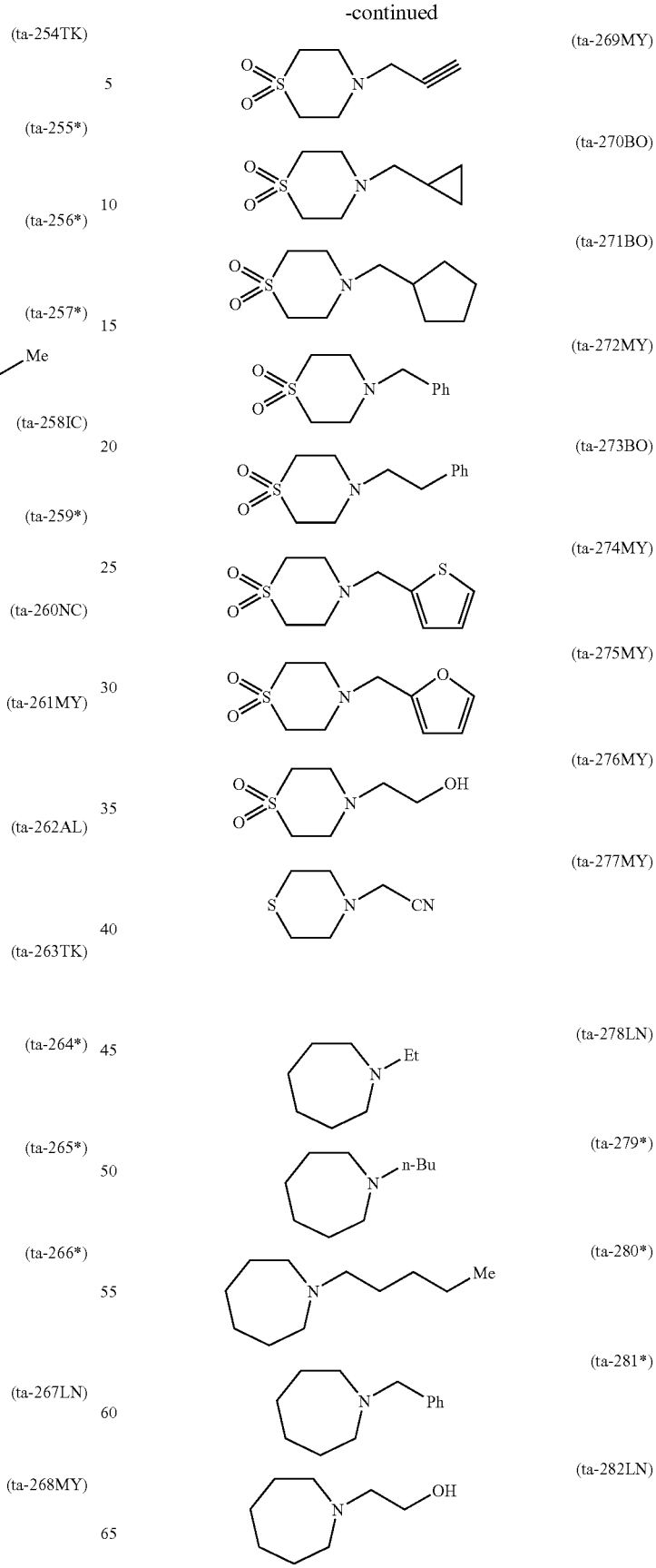

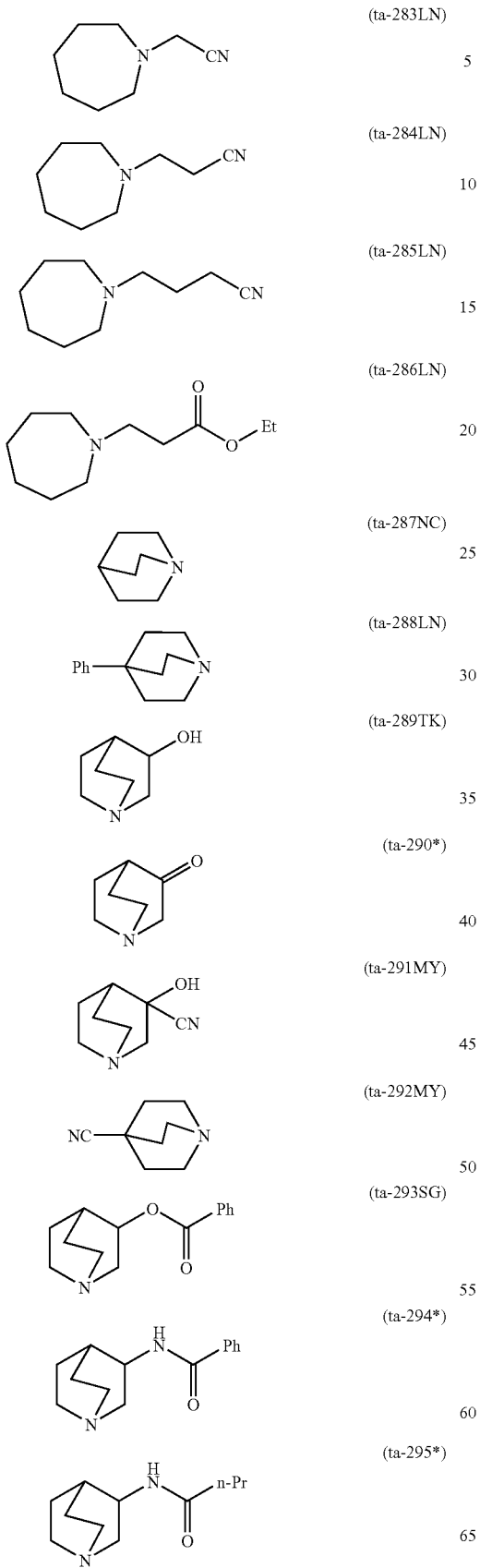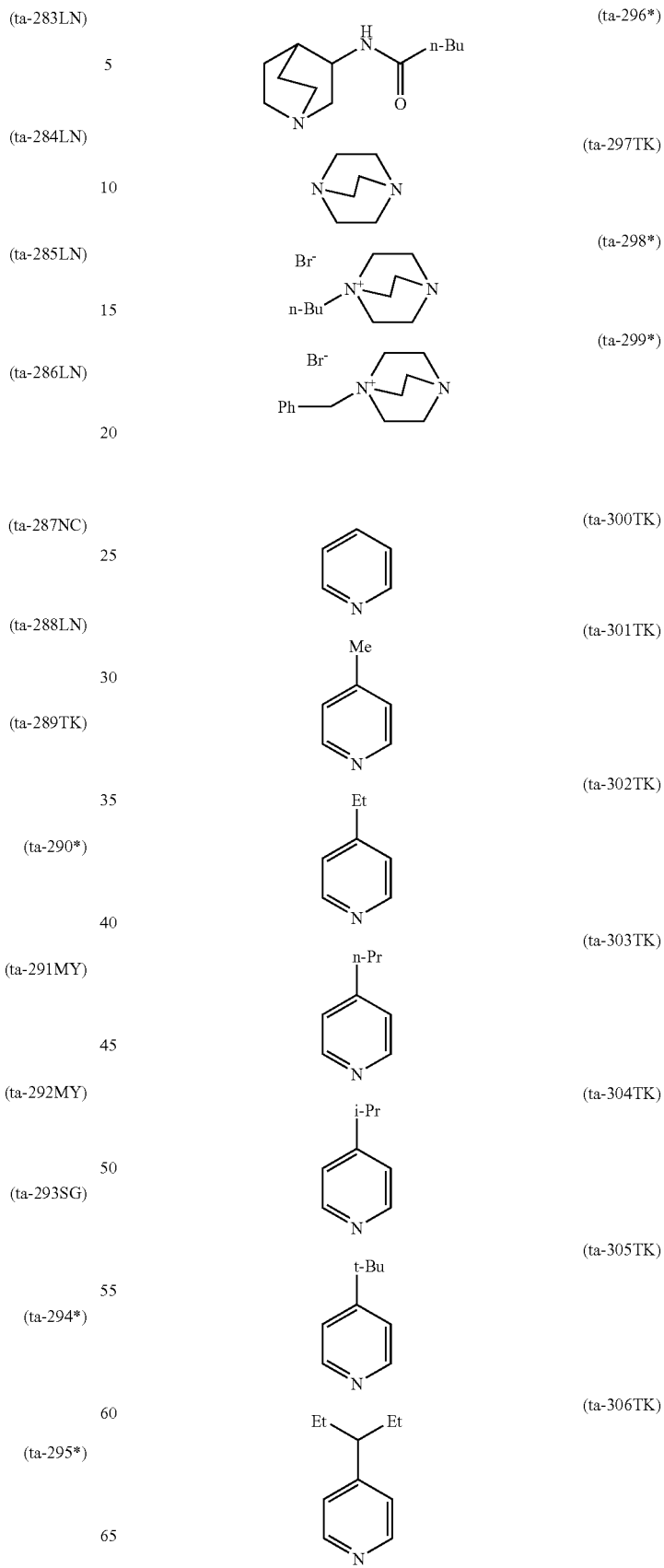

-continued
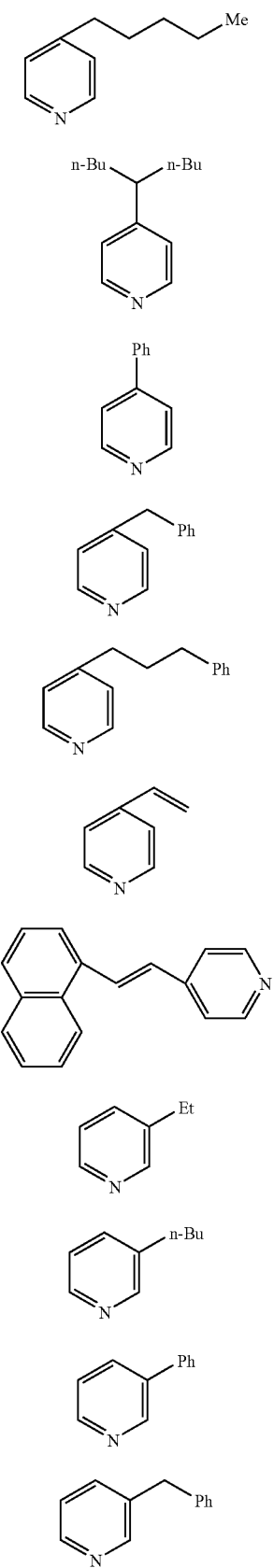
(ta-307TK)
(ta-308TK)
(ta-309TK)
(ta-310AL)
(ta-311TK)
(ta-312AL)
(ta-313TK)
(ta-314TK)
(ta-315TK)
(ta-316TK)
(ta-317TK)
-continued
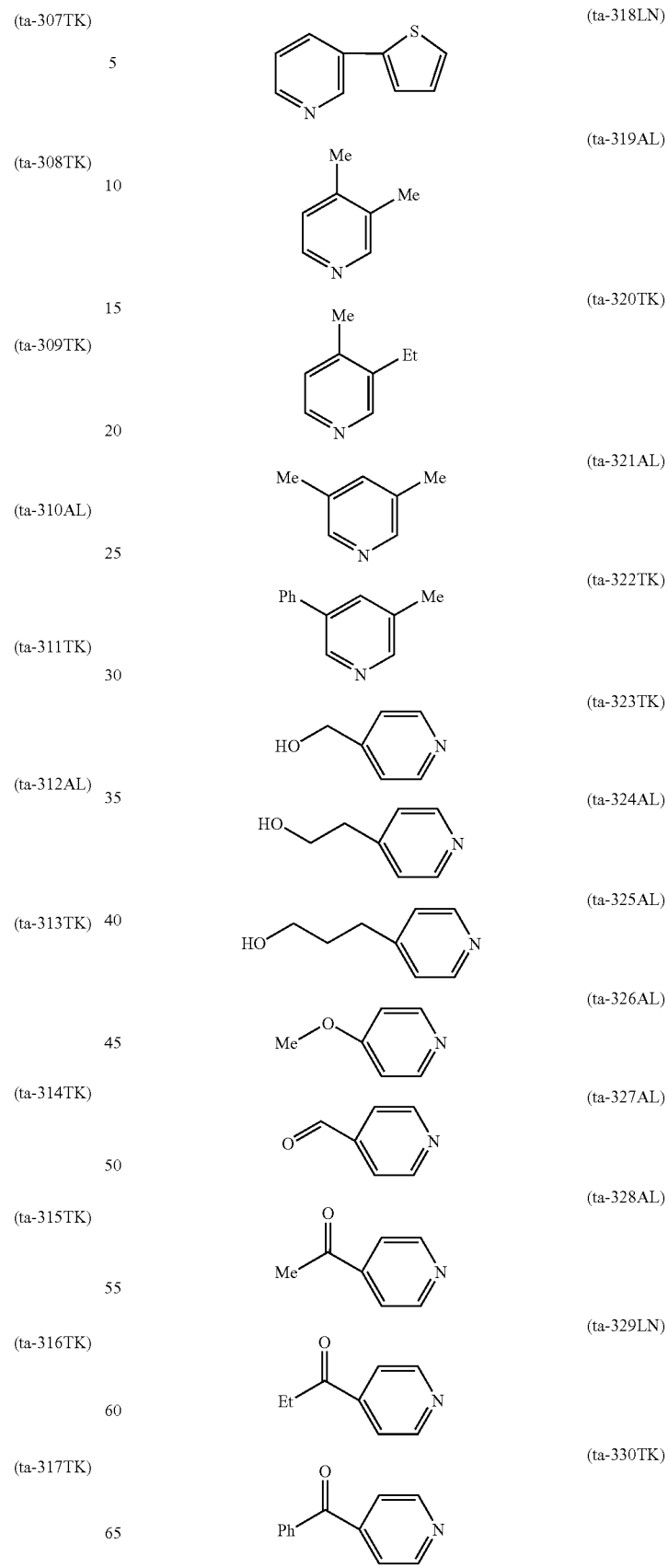
(ta-318LN)
(ta-319AL)
(ta-320TK)
(ta-321AL)
(ta-322TK)
(ta-323TK)
(ta-324AL)
(ta-325AL)
(ta-326AL)
(ta-327AL)
(ta-328AL)
(ta-329LN)
(ta-330TK)

-continued
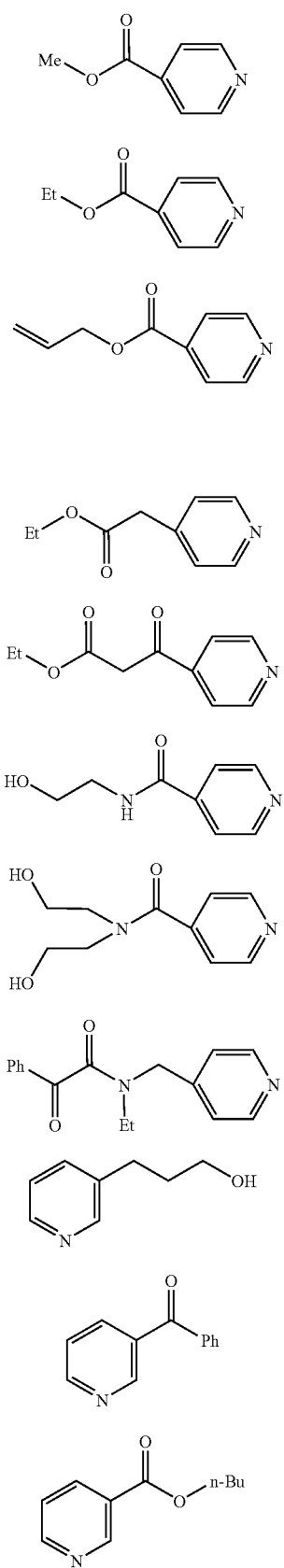
(ta-331TK)
(ta-332TK)
(ta-333TK)
(ta-334AL)
(ta-335AC)
(ta-336AL)
(ta-337AL)
(ta-338TK)
(ta-339TK)
(ta-340TK)
(ta-341TK)
-continued
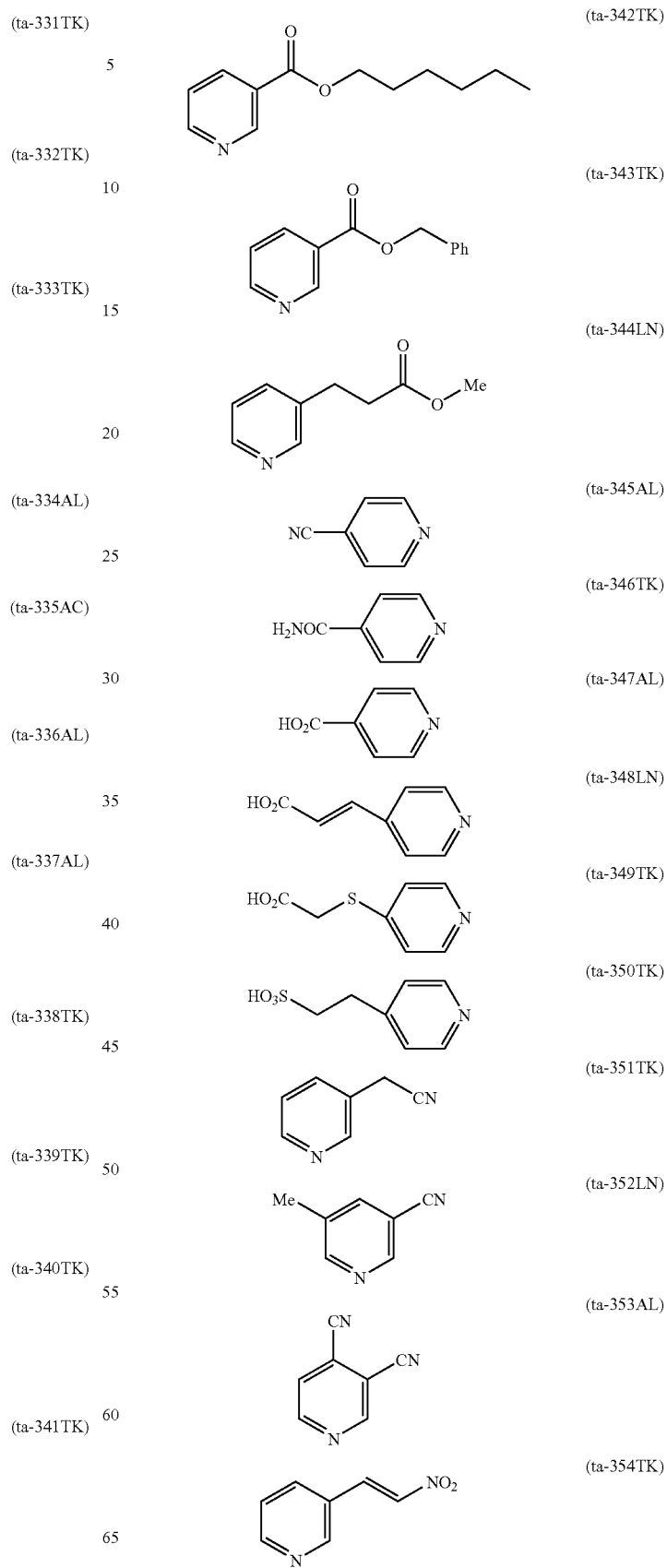
(ta-342TK)
(ta-343TK)
(ta-344LN)
(ta-345AL)
(ta-346TK)
(ta-347AL)
(ta-348LN)
(ta-349TK)
(ta-350TK)
(ta-351TK)
(ta-352LN)
(ta-353AL)
(ta-354TK)

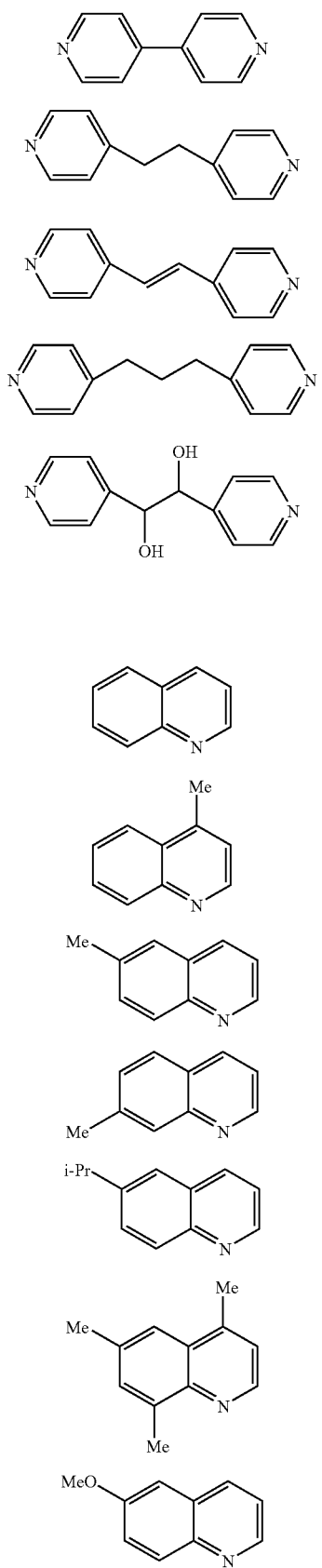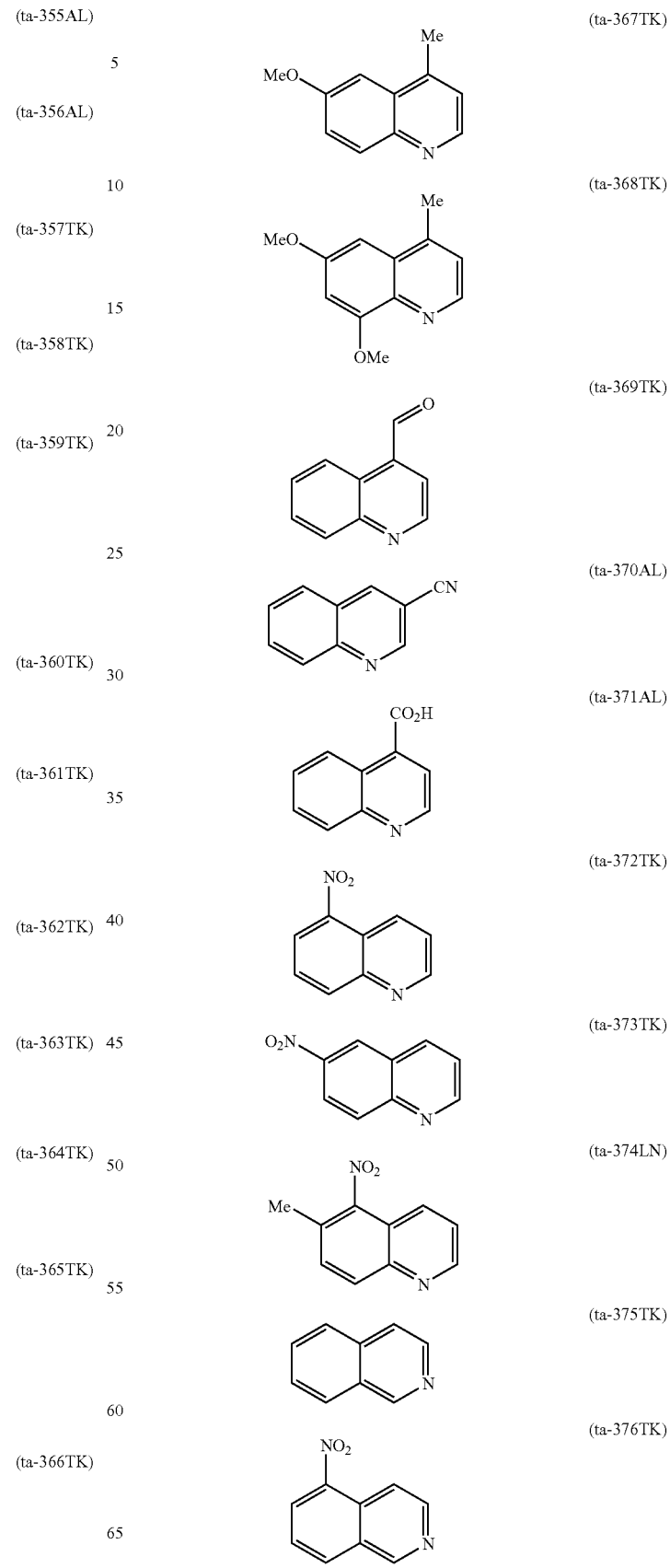

-continued (ta-377TK)

(ta-378TK)

(ta-379TK)

(ta-394TK)

(ta-395TK)

(ta-396TK)

(ta-397TK)

(ta-398AL)

(ta-399SL)

(ta-400TK)

-continued (ta-401TK)

(ta-402LN)

(ta-383SL)

(ta-384AL)

(ta-385TK)

(ta-386AL)

(ta-387TK)

(ta-388FL)

(ta-389TK)

(ta-390TK)

(ta-391TK)

(ta-392TK)

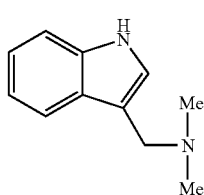 (ta-393TK)

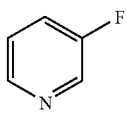 (ta-403TK)

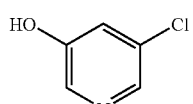 (ta-404TK)

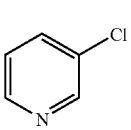 (ta-405TK)

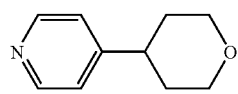 (ta-406SL)

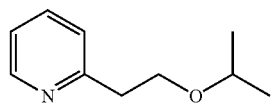 (ta-407AL)

The compounds represented by the formula (3) can be obtained by allowing compounds of the formula (4-1) below

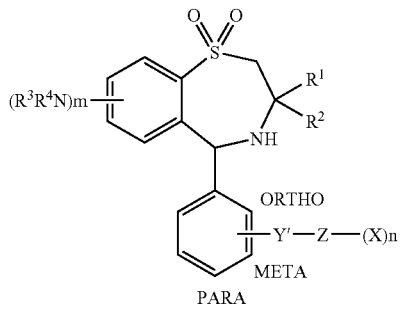

(4-1)

[wherein $R^1$, $R^2$, $R^3$, $R^4$, m, n, Z, and X are as mentioned earlier; Y' represents an —NHCO—, provided that the —NH in the —NHCO— represents a bond which links with an adjacent benzene ring and CO— represents a bond which links with an adjacent Z] to react with various sulfurizing agents.

The reaction is carried out, for example, at room temperature or 50 to 100° C in a solvent such as tetrahydrofuran (hereinafter, "THF" for short), 1,4-dioxane, or toluene, by allowing the compound represented by the formula (4-1) to react with at least an equimolar amount, preferably 1 to 10 time molar amount of a sulfurizing agent for 1 to 48 hours. Examples of preferable sulfurizing agent include Lawesson's reagent (manufactured by TOKYO CHEMICAL INDUSTRIES, LTD.) and diphosphorus pentasulfide (manufactured by WAKO PURE CHEMICAL INDUSTRIES LTD.).

The substituting position of Y in the formula (4-1) may be any one of an ortho-position, a meta-position, and a para-position, preferably a meta-position and a para-position, and most preferably a meta-position. The compound represented by the formula (4-1) can be obtained by allowing a compound represented by formula (5-1) below

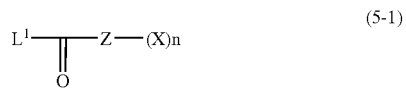

(5-1)

[where n, Z, and X are as mentioned earlier; and $L^1$ represents a leaving group] to react with a compound represented by the following formula (6-1)

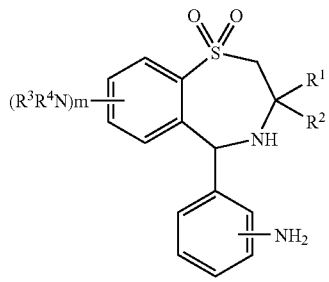

(6-1)

[where $R^1$, $R^2$, $R^3$, $R^4$, and m are as mentioned earlier].

The reaction is carried out, for example, by allowing at least an equimolar amount, preferably 1 to 1.2 time molar amount of the compound represented by the formula (5-1) to react with the compound represented by the formula (6-1), in a solvent such as dichloromethane or THF, in the presence of an excess amount, preferably 1.5 to 3 time molar amount of a base, preferably an organic base such as triethylamine or an inorganic base such as potassium carbonate, at room temperature to 60° C for 1 to 24 hours.

$L^1$ in the formula (5-1) is a group which undergoes nucleophilic substitution by the compound represented by the formula (6-1) and is released. Preferable examples of such a group include F, Cl, Br, I, mesylate and tosylate, with Cl and Br being more preferable. $L^1$ and X may be mutually different, but it is also preferable that $L^1$ and X are equal to each other. Examples of preferable compounds represented by the formula (5-1) include 3-bromopropionyl chloride (ac-1), 4-bromobutyryl chloride (ac-2), 5-bromovaleryl chloride (ac-3), 6-bromo-n-caproyl chloride (ac-4) (all the ac-1 to ac-4 are manufacture by TOKYO CHEMICAL INDUSTRIES, LTD.), 7-bromo-n-heptanoyl chloride (ac-5), (prepared by oxidizing 7-bromo-1-heptanol manufactured by TOKYO CHEMICAL INDUSTRIES, LTD. with chromium (VI) oxide in the presence of concentrated sulfuric acid and then allowing thionyl chloride to react with the resultant), 8-bromo-n-octanoyl chloride (ac-6) (prepared by allowing thionyl chloride to react with 8-bromooctanoic acid manufactured by TOKYO CHEMICAL INDUSTRIES, LTD.), 9-bromo-n-nonanoyl chloride (ac-7) (prepared by oxidizing 9-bromo-1-nonanol manufactured by TOKYO CHEMICAL INDUSTRIES, LTD. with chromium oxide (VI) in the presence of concentrated sulfuric acid and then allowing thionyl chloride to react with the resultant), 10-bromo-n-decanoyl chloride (ac-8) (prepared by allowing thionyl chloride to react with 10-bromodecanoic acid manufactured by PFALZ & BAUER), 11-bromo-n-undecanoyl chloride (ac-9) (prepared by allowing thionyl chloride to react with 11-bromoundecanoic acid manufactured by TOKYO CHEMICAL INDUSTRIES, LTD.), 3-bromo-2-methylpropionyl chloride (ac-10) (prepared by allowing thionyl chloride to react with 3-bromo-2-methylpropionic acid manufactured by FLUKA CHEMICAL CORPORATION), 4-(chloromethyl)benzoyl chloride (ac-11) (manufactured by ALDRICH CHEMICAL COMPANY), 4-(bromomethyl)phenylacetyl chloride (ac-12) (prepared by allowing thionyl chloride to react with 4-(bromomethyl) phenylacetic acid manufactured by TOKYO CHEMICAL INDUSTRIES, LTD.), 2-[4-(bromomethyl)phenyl] propionyl chloride (ac-13) (prepared by allowing thionyl chloride to react with 2-[4-(bromomethyl)phenyl] propionic acid manufactured by TOKYO CHEMICAL INDUSTRIES, LTD.), 3-(bromomethyl)phenoxyacetyl chloride (ac-14) (prepared by allowing thionyl chloride to react with 3-(bromomethyl)phenoxyacetic acid manufactured by LANCASTER), 3-bromo-2-(bromomethyl)propionyl chloride (ac-15) (prepared by allowing thionyl chloride to react with 3-bromo-2-(bromomethyl)propionic acid manufactured by ALDRICH CHEMICAL COMPANY), 3-bromoacryloyl chloride (ac-16) (prepared by allowing thionyl chloride to react with 3-bromoacrylic acid manufactured by MAYBRIDGE CHEMICALS), and 3-(bromomethyl)crotonyl chloride (ac-17) (prepared by allowing thionyl chloride to react with 3-(bromomethyl)crotonic acid manufactured by SALOR CHEMICAL COMPANY).

The substituting position of a primary amino group in the formula (6-1) may be any one of an ortho-position, a meta-position, and a para-position, preferably a meta-position and a para-position, and more preferably a meta-position.

Among the compounds represented by the formula (1), those compounds in which Y represents —NHCS— can be obtained by allowing various sulfurizing agents to react with compounds represented by the following formula (4-2)

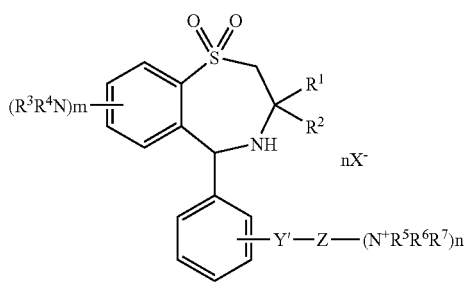

(4-2)

[wherein $R^1$, $R^2$, $R^3$, $R^4$, m, n, $R^5$, $R^6$, $R^7$, Y', Z, and $X^-$ are as mentioned earlier].

The reaction is carried out, for example, by allowing an equimolar amount or more, preferably 1 to 10 time molar amount of the sulfurizing agent to react with the compound represented by the formula (4-2) in a solvent such as ethanol, 1,4-dioxane, chloroform, or 1,2-dichloroethane, at room temperature or at 50° C to 100° C, for 1 to 48 hours. Examples of preferable sulfurizing agent include Lawesson's reagent and diphosphorus pentasulfide.

The compounds represented by the formula (4-2) are obtained by allowing the compound represented by the formula (2) to react with the compound represented by the formula (4-1).

The reaction is carried out, for example, by allowing an equimolar amount or more, preferably 1 to 5 time molar amount of the compound represented by the formula (2) to react with the compound represented by the formula (4-1) optionally in a solvent such as acetonitrile or DMF at room temperature or 40 to 100° C for 1 to 48 hours.

Among the compounds represented by the formula (1), those compounds in which Y represents —NHCSNH— can be obtained by allowing a compound represented by formula (5-2a)

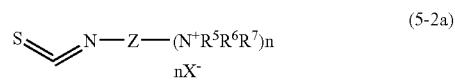

(5-2a)

[wherein n, $R^5$, $R^6$, $R^7$, Z, and $X^-$ are as mentioned earlier] to react with the compound represented by the formula (6-1).

The reaction is carried out, for example, by allowing an equimolar amount of the compound represented by the formula (5-2a) to react with the compound represented by the formula (6-1) in a solvent such as chloroform, acetonitrile, or DMF at room temperature or at 40° C to 100° C for 1 to 48 hours.

The compound represented by the formula (5-2a) can be obtained by allowing the compound represented by the formula (2) to react with a compound represented by formula (5-2b) below

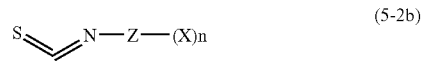

(5-2b)

[wherein n, Z, and X are as mentioned earlier].

The reaction is carried out, for example, by allowing at least equimolar amount, preferably 1 to 5 time molar amount of the compound represented by the formula (2) to react with the compound represented by the formula (5-2b) optionally in a solvent such as acetonitrile or DMF at room temperature or at 40° C to 100° C for 1 to 48 hours.

Examples of the compound represented by the formula (5-2b) include 2-bromoethyl isothiocyanate (is-1), 3-bromopropyl isothiocyanate (is-2), (both is-1and is-2 are manufactured by TRANS WORLD CHEMICAL CORPORATION), 4-bromobutyl isothiocyanate (is-3) (prepared by brominating 4-aminobutanol manufactured by TOKYO CHEMICAL INDUSTRIES, LTD. with hydrobromic acid and then allowing thiophosgene to react with the resultant according to the method described in Canadian Journal of Chemistry, Vol. 49, 971-974, 1971), 5-bromopentyl isothiocyanate (is-4) (prepared similarly from 5-aminopentanol manufactured by TOKYO CHEMICAL INDUSTRIES, LTD.), 6-bromohexyl isothiocyanate (is-5) (prepared similarly from 6-aminohexanol manufactured by TOKYO CHEMICAL INDUSTRIES, LTD.), 7-bromoheptyl isothiocyanate (is-6) (prepared similarly from 7-aminoheptanol manufactured by WATANABE CHEMICAL INDUSTRIES LTD.), 8-bromooctyl isothiocyanate (is-7) (prepared similarly from 8-aminooctanol manufactured by WATANABE CHEMICAL INDUSTRIES LTD.), 9-bromononyl isothiocyanate (is-8) (prepared similarly from 9-aminononanol manufactured by WATANABE CHEMICAL INDUSTRIES LTD.), 10-bromodecyl isothiocyanate (is-9) (prepared similarly from 10-aminodecanol manufactured by WATANABE CHEMICAL INDUSTRIES LTD.), 3-bromo-2,2-dimethylpropyl isothiocyanate (is-10) (prepared similarly from 3-amino-2,2-dimethylpropanol manufactured by TOKYO CHEMICAL INDUSTRIES, LTD.), 5-bromo-4,4-dimethylpentyl isothiocyanate (is-11) (prepared similarly from 5-amino-2,2-dimethylpentanol manufactured by ICN-RF, 2-(2-bromoethoxy)ethyl isothiocyanate (is-12) (prepared similarly from 2-(2-aminoethoxy)ethanol manufactured by TOKYO CHEMICAL INDUSTRIES, LTD.), 2,2-bis(bromomethyl)butyl isothiocyanate (is-13) (prepared similarly from 2-(aminoethyl)-2-ethyl-1,3-propanediol manufactured by SALOR CHEMICAL COMPANY), 4-(bromomethyl)phenyl isothiocyanate (is-14) (prepared from p-tolyl isothiocyanate manufactured by ALDRICH CHEMICAL COMPANY according to the method described in Journal of Heterocyclic Chemistry, Vol. 31, 457-480, 1994), 3-(bromomethyl)phenyl isothiocyanate (is-15) (prepared from m-tolyl isothiocyanate manufactured by ALDRICH CHEMICAL COMPANY according to the method described in the same document as above), 2-(bromomethyl)phenyl isothiocyanate (is-16) (prepared from 0-tolyl isothiocyanate manufactured by ALDRICH CHEMICAL COMPANY according to the method described in the same document as above), 4-(2-bromoethyl)phenyl isothiocyanate (is-17) (prepared by brominating 2-(4-aminophenyl)ethanol manufactured by TOKYO CHEMICAL INDUSTRIES, LTD. with hydrobromic acid and then allowing thiophosgene to react with the resultant according to the method described in Canadian Journal of Chemistry, Vol. 49, 971-974, 1971). Among the compounds represented by the formula (1), those compounds in which Y is —NHCSO— are obtained by allowing a compound represented by formula (5-3a) below

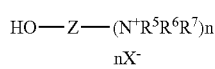

(5-3a)

[wherein n, $R^5$, $R^6$, $R^7$, Z, and $X^-$ are as mentioned earlier] to react with a compound represented by formula (6-2) below

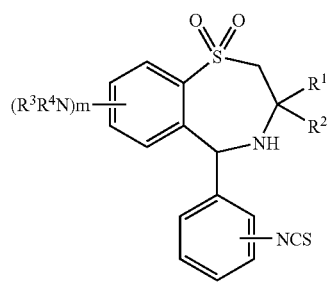

(6-2)

[wherein $R^1$, $R^2$, $R^3$, $R^4$, and m are as mentioned earlier].

The reaction is carried out, for example, by allowing an equimolar amount of the compound represented by the formula (5-3a) to react with the compound represented by the formula (6-2) in a solvent such as THF, 1,4-dioxane, or 2-ethoxyethyl ether in the presence of an equimolar amount or more, preferably 1 to 5 time molar amount of a base, preferably an inorganic base such as sodium hydride or metallic sodium at 50° C to 150° C, for 1 to 48 hours.

The substituting position of the —NCS in the formula (6-2) may be any one of an ortho-position, a meta-position, and a para-position, preferably a meta-position and a para-position, and most preferably a meta-position.

The compound represented by the formula (5-3a) are obtained by allowing the compound represented by the formula (2) to react on a compound represented by formula (5-3b)

(5-3 b)

[wherein n, Z, and X are as mentioned earlier].

The reaction is carried out, for example, by allowing an equimolar amount or more, preferably 1 to 5 time molar amount of the compound represented by the formula (2) to react with the compound represented by the formula (5-3b), optionally in a solvent such as acetonitrile or DMF, at room temperature or at 40° C to 100° C for 1 to 48 hours.

Examples of compounds represented by the formula (5-3b) include 2-bromoethanol (al-1), 3-bromopropanol (al-2), 4-bromobutanol (al-3), 5-bromopentanol (al-4), 6-bromohexanol (al-5), 7-bromoheptanol (al-6), 8-bromooctanol (al-7), 9-bromononanol (al-8), 10-bromodecanol (al-9) (all the compounds al-1to al-9 are manufactured by TOKYO CHEMICAL INDUSTRIES, LTD.), 3-bromo-2-methylpropanol (al-10), and 3-bromo-2,2-dimethylpropanol (al-11) (the compounds al-10 and al-11 are manufactured by ALDRICH CHEMICAL COMPANY).

The compound represented by the formula (6-2) is obtained by allowing thiophosgene to react with the compound represented by the formula (6-1).

The reaction is carried out, for example, by allowing an equimolar amount of thiophosgene (manufactured by ALDRICH CHEMICAL COMPANY) to react with the compound represented by the formula (6-1), optionally in a solvent such as THF or dichloromethane, in the presence of an equimolar amount or more, preferably 1 to 5 time molar amount of a base, preferably an organic base such as triethylamine, at room temperature or 0 to 100C for 1 to 24 hours.

The compound represented by the formula (6-1) is obtained by subjecting a compound represented by formula (7-2a) below

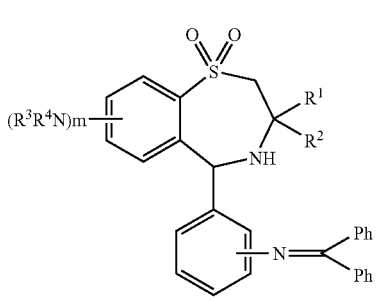

(7-2a)

[wherein $R^1$, $R^2$, $R^3$, $R^4$, and m are as mentioned earlier] to hydrogenation, reaction with hydroxylamine, or acid hydrolysis according to the method described in literature (Tetrahedron Letters, Vol. 38, 6367-6370, 1997).

In the case of the hydrogenation, the reaction is carried out, for example, by addition of hydrogen gas to the compound represented by the formula (7-2a) in a solvent such as methanol, ethyl acetate, or 1,4-dioxane in the presence of 1 mole % to 30 mole % of a catalytic reduction catalyst, at room temperature or at 40° C to 100 ° for 1 to 24 hours. Examples of a preferable catalytic reduction catalyst include palladium and platinum.

In the case of the reaction with hydroxylamine, the reaction is carried out, for example, by allowing an equimolar amount or more, preferably 1 to 3 time molar amount of hydroxylamine hydrochloride (manufactured by TOKYO CHEMICAL INDUSTRIES, LTD.) to react with the compound represented by the formula (7-2a) in a solvent such as methanol in the presence of an equimolar or more, preferably 1 to 5 time molar amount of a base such as sodium acetate at room temperature for 1 to 24 hours.

In the case of acid hydrolysis, the reaction is carried out, for example, by allowing an excess amount, preferably 30 to 300 time molar amount of an acid, preferably 1 N to 5 N hydrochloric acid to react with the compound represented by the formula (7-2a), optionally in a solvent such as THF or methanol, at room temperature for 1 to 24 hours.

The substituting position of the imino group in the formula (7-2a) may be any one of an ortho-position, a meta-position, and a para-position, preferably a meta-position and a para-position.

The compound represented by the formula (7-2a) is obtained by allowing benzophenonimine to react with a compound represented by formula (7-2b) below

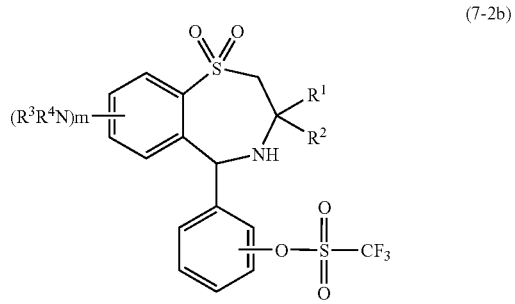

(7-2b)

[wherein $R^1$, $R^2$, $R^3$, $R^4$, and m are as mentioned earlier] according to the method described in literature (Tetrahedron Letters, Vol. 38, 6367-6370, 1997).

The reaction is carried out, for example, by allowing an equimolar amount or more, preferably 1 to 5 time molar amount of benzophenonimine (manufactured by ALDRICH CHEMICAL COMPANY) to react with the compound represented by the formula (7-2b) in a solvent such as THF, 1,4-dioxane, or toluene in the presence of an organic palladium compound such as 0.1 mole % to 10 mole % of palladium (II) acetate or an organic phosphorus compound such as 0.1 mole % to 10 mole % of 2,2'-bis(diphenylphosphenyl)-1,1-binaphthyl, and an inorganic base such as 1 to 3 time molar amount of cesium carbonate at room temperature or at 40 ° to 100 ° for 1 to 24 hours.

The substituting position of trifluoromesylate in the formula (7-2b) may be any one of an ortho-position, a meta-position, and a para-position, preferably a meta-position and para-position. Trifluoromesylate in the formula (7-2b) may be replaced by a mesylate or a tosylate.

The compound represented by the formula (7-2b) is obtained by allowing trifluoromethanesulfonic acid anhydride to react with a compound represented by formula (7-2c) below

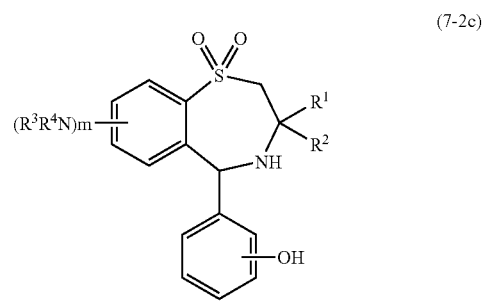

(7-2c)

[wherein $R^1$, $R^2$, $R^3$, $R^4$, and m are as mentioned earlier].

The reaction is carried out, for example, by allowing an equimolar amount or more, preferably 1 to 3 time molar amount of trifluoromethanesulfonic acid anhydride (manufactured by ALDRICH CHEMICAL COMPANY) to react with the compound represented by the formula (6-1), optionally in a solvent such as THF or dichioromethane, in the presence of an equimolar or more, preferably 1 to 20 time molar amount of a base, preferably an organic base such as triethylamine, at room temperature or at 0° C to 10° C for 1 to 24 hours. Compounds in which the trifluoromesylate in the formula (7-2b) is replaced by a mesylate or a tosylate, are obtained by allowing mesyl chloride (manufactured by TOKYO CHEMICAL INDUSTRIES, LTD.) or tosyl chloride (manufactured by ALDRICH CHEMICAL COMPANY), respectively, instead of the trifluoromethanesulfonic acid anhydride to react with the compound represented by the formula (6-1).

The substituting position of the hydroxyl group in the formula (7-2c) may be any one of an ortho-position, a meta-position, and a para-position, preferably a meta-position and a para-position. The compound represented by the formula (7-2c) is obtained by allowing Lewis acid, pyridine hydrochloride, or trimethylsilane iodide to react with a compound represented by the following formula (7-2d) below

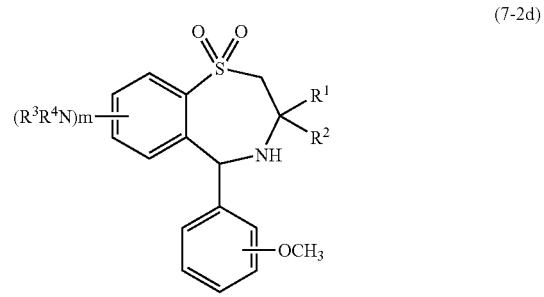

(7-2d)

[wherein $R^1$, $R^2$, $R^3$, $R^4$, and m are as mentioned earlier].

The reaction is carried out, for example, by allowing an equimolar amount or more of any one of various Lewis acids, such as aluminum chloride, boron trihalide, titanium tetrachloride, and tin tetrachloride, pyridine hydrochloride, or trimethylsilane iodide to react with the compound represented by the formula (7-2d) in a solvent such as dichloromethane at 0° C to 10° C, room temperature, or 50° C to 150° C, for 1 to 24 hours. Preferably, the reaction is carried out, for example, by allowing a 2 to 5 time molar amount of boron trihalide, preferably boron tribromide, in a solvent such as dichloromethane at room temperature or 0° C to 10° C for 1 to 5 hours.

The substituting position of the methoxy group in the formula (7-2d) may be any one of an ortho-position, a meta-position, and a para-position, preferably a meta-position and a para-position.

The compound represented by the formula (7-2d) is obtained by reducing a compound which is selected from compounds represented by formula (8) below

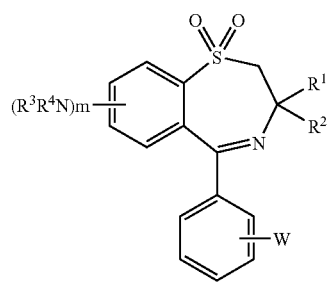

(8)

[wherein $R^1$, $R^2$, $R^3$, $R^4$, and m are as mentioned earlier; and W represents a methoxy group or a nitro group] and in which W is a methoxy group.

The reaction is carried out, for example, by allowing an equimolar amount or more of any one of various reducing agents such as sodium borohydride, sodium cyanohydride, borane, and lithium aluminum hydride, preferably sodium borohydride or borane to react with the compound represented by the formula (8) in which W is a methoxy group in a solvent such as methanol or THF at room temperature or while heating for 1 hour or more. In particular, it is preferable to allow a 20 to 50 time molar amount of borane to react in THF at room temperature for 1 to 5 hours.

When W in the formuia (8) is a methoxy group, the substituting position may be any one of an ortho-position, a meta-position, and a para-position, preferably a para-position. When W is a nitro group, the substituting position is a meta-position.

Among the compounds represented by the formula (6-1), a compound of which the substituting position of the primary amino group is the meta-position is also obtained by reducing a compound represented by the following formula (7-1) below

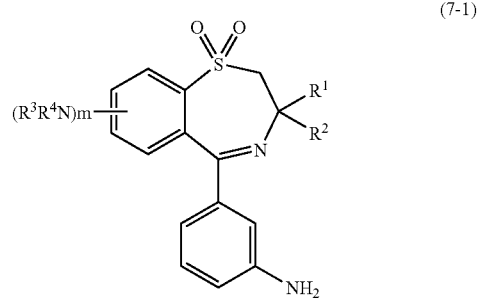

(7-1)

[wherein $R^1$, $R^2$, $R^3$, $R^4$, and m are as mentioned earlier].

The reaction is carried out, for example, by allowing an equimolar amount or more of any one of various reducing agents such as sodium borohydride, sodium cyanohydride, borane, or lithium aluminum hydride, preferably sodium borohydride or borane to react with the compound represented by the formula (7-1) in a solvent such as methanol or THF at room temperature or while heating for 1 hour or more. In particular, it is preferable to allow a 20 to 50 time molar amount of borane to react in THF at room temperature for 1 to 5 hours.

The compound represented by the formula (7-1) is obtained by reducing a compound represented by the formula (8) in which W is a nitro group at the meta-position.

The reaction is carried out, for example, by addition of hydrogen gas to the compound represented by the formula (8) in which W is a nitro group at the meta-position in a solvent such as methanol, ethyl acetate or 1,4-dioxane in the presence of 1 mole % to 30 mole % of a catalytic reduction catalyst at room temperature or at 40° C to 100° C for 1 to 24 hours. Examples of preferable catalytic reduction catalyst include palladium and platinum.

The compound represented by the formula (8) is obtained by allowing a compound represented by formula (9) below

(9)

[wherein $R^3$ and $R^4$ are as mentioned earlier] to react with a compound represented by formula (10-1) below

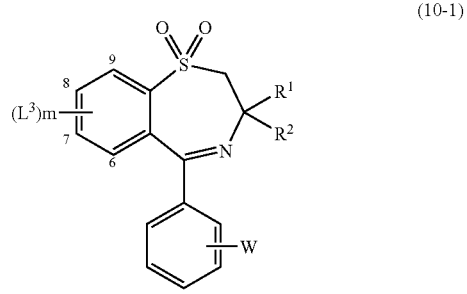

(10-1)

[where $R^1$, $R^2$, m, and W are as mentioned earlier; and $L^3$ represents a halogen].

The reaction is carried out, for example, by allowing an excess amount, preferably a 10 to 50 time molar amount of the compound represented by the formula (9) to react with the compound represented by the formula (10-1), optionally in a solvent such as THF, dioxane, or methanol, at 50° C to 150° C, for 5 to 72 hours.

Examples of the halogen represented by $L^3$ in the formula (10-1) include F, Cl, Br, and I, preferably F and Cl, with F being most preferable. $L^3$ may substitute at any one of the 6- to 9-positions. It is preferable that either the 7-position or the 9-position is mono-substituted or the 7- and 9-positions are di-substituted with $L^3$. It is more preferable that the 7-position is mono-substituted with $L^3$.

Examples of the compounds represented by the formula (9) include dimethylamine, diethylamine, and ethylmethylamine (all the three compounds are manufactured by ALDRICH CHEMICAL COMPANY).

Among the compounds represented by formula (10-1), a compound in which W is a methoxy group is obtained by oxidizing a compound represented by formula (11) below

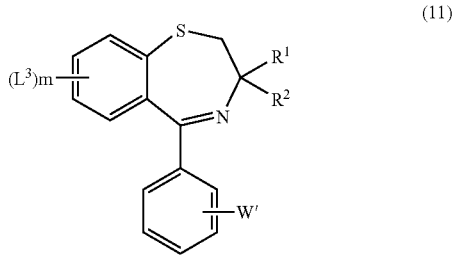

(11)

[wherein $R^1$, $R^2$, $R^3$, m, and W' are as mentioned earlier; and W' represents a methoxy group or a hydrogen atom] in which W' is a methoxy group.

The reaction is carried out, for example, by allowing an equimolar amount or more of any one of various oxidizing agents such as hydrogen peroxide, metachloroperbenzoic acid, and oxone, or an equimolar amount or more of sodium periodate in the presence of a catalytic amount of ruthenium trichloride to react with the compound represented by the formula (11) in which W⁻ is a methoxy group in a solvent such as trifluoroacetic acid, dichloromethane, methanol, acetonitrile or water under ice cooling or at room temperature for 1 hour or more. In particular, it is preferable to allow a 2 to 5 time molar amount of sodium periodate to react in a dichloromethane-acetonitrile-water mixed solvent in the presence of a 0.05 to 0.2 time molar amount of ruthenium trichloride at room temperature for 5 to 48 hours.

When W' in the formula (11) is a methoxy group, the substituting position thereof may be any one of an ortho-position, a meta-position, and a para-position, preferably a meta-position or a para-position.

Among the compounds represented by the formula (10-1), a compound in which W is a nitro group is obtained by nitration of a compound represented by formula (10-2) below

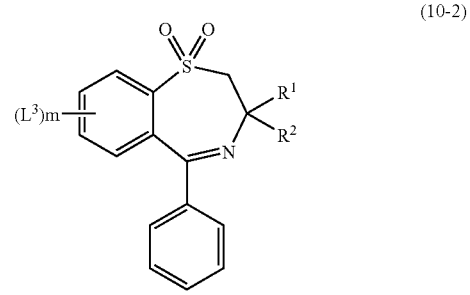

(10-2)

[where $R^1$, $R^2$, $R^3$, and m are as explained earlier].

The reaction is carried out, for example, by allowing an excess molar amount of nitric acid and sulfuric acid, preferably a 10 to 40 time molar amount of fuming nitric acid and a 10 to 20 time molar amount of concentrated sulfuric acid, to react with the compound represented by the formula (10-2) at 0° C to 10° C or at room temperature for 30 minutes to 3 hours.

The compound represented by the formula (10-2) is obtained by oxidizing the compound represented by the formula (11) in which W' is a hydrogen atom.

The reaction is carried out, for example, by allowing an equimolar amount or more of various oxidizing agents such as hydrogen peroxide, metachloroperbenzoic acid, or oxone, or an equimolar amount or more of sodium periodate in the presence of a catalytic amount of ruthenium trichloride to react with the compound of the formula (11) in which W' is a hydrogen atom, in a solvent such as trifluoroacetic acid, dichloromethane, methanol, acetonitrile, or water, under ice cooling or at room temperature for 1 hour or more. In particular, it is preferable to allow a 2 to 5 time molar amount of sodium periodate to react in a dichloromethane-acetonitrile-water mixed solvent, in the presence of a 0.05 to 0.2 time molar amount of ruthenium trichloride at room temperature for 5 to 48 hours.

The compound represented by the formula (11) is obtained by dehydrating a compound represented by formula (12) below

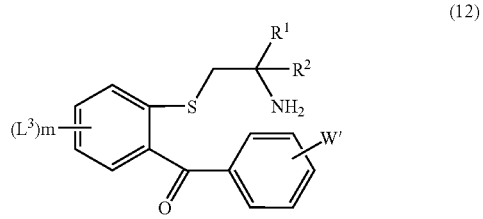

(12)

[wherein $R^1$, $R^2$, $L^3$, m, and W' are as mentioned earlier] according to the method described in literature (see WO93/16055).

The reaction is carried out, for example, in a solvent such as 2,6-lutidine, toluene, or xylene in the presence of a 0.1 to 1 time molar amount of an acid such as hydrochloric acid, toluenesulfonic acid, or camphorsulfonic acid, preferably toluenesulfonic acid, at 100° C to 150° C for 10 to 36 hours.

The compound represented by the formula (12) is obtained by allowing a compound represented by formula (13) below

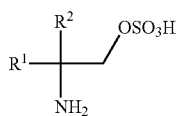

[where $R^1$ and $R^2$ are as mentioned earlier] to react with a compound represented by formula (14) below

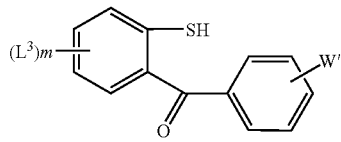

[where $L^3$, m, and W' are as mentioned earlier] according to the method described in literature (see WO93/16055).

The reaction is carried out, for example, by allowing an equimolar amount of the compound represented by the formula (13) to react with the compound represented by the formula (14) in a solvent such as a butyl acetate-water mixed solvent in the presence of an excess amount, preferably 3 to 5 time molar amount of inorganic base such as sodium hydroxide at 60° C to 120° C for 1 to 5 hours.

The compound represented by the formula (14) is obtained by allowing a base to react with a compound represented by formula (15-1) below

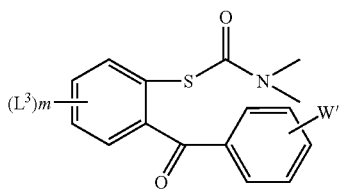

[wherein $L^3$, m, and W' are as mentioned earlier] according to the method described in literature (see WO93/16055).

The reaction is carried out, for example, by allowing an excess amount, preferably a 3 to 10 time molar amount of an inorganic base such as potassium hydroxide to react with the compound represented by the formula (15-1), in a solvent such as methanol, THF, or dioxane, at 50° C to 100° C for 1 to 24 hours.

Among the compounds represented by the formula (14), a compound in which W' is a hydrogen atom is also obtained by allowing a metal sulfide compound to react with a compound represented by formula (15-2) below

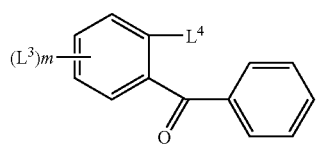

[wherein $L^3$ and m are as mentioned earlier; and $L^4$ represents a halogen].

The reaction is carried out, for example, by allowing an equimolar amount or more, preferably 1 to 1.5 time molar amount of a metal sulfide compound such as lithium sulfide or sodium sulfide to react with the compound represented by the formula (15-2) in a solvent such as dimethyl sulfoxide (hereinafter, "DMSO" for short) or DMF at 100° C to 150° C for 1 to 5 hours.

Examples of halogen represented by $L^4$ in the formula (15-2) include F, Cl, Br, and I, preferably F and Cl, with F being most preferable. $L^3$ and $L^4$ may be different; however, it is preferable that $L^3$ and $L^4$ are the same.

The compound represented by the formula (15-1) is obtained by heat treatment of a compound represented by formula (16) below

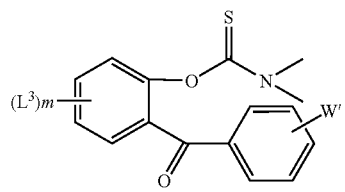

(wherein $L^3$, m, and W' are as mentioned earlier] according to the method described in literature (see WO93/16055).

The reaction is carried out, for example, by heat treatment optionally in a solvent such as tetradecane or diphenyl ether, at 200° C to 300° C for 1 to 24 hours.

The compound represented by the formula (16) is obtained by allowing N,N-dimethylthiocarbamoyl chloride to react with a compound represented by formula (17) below

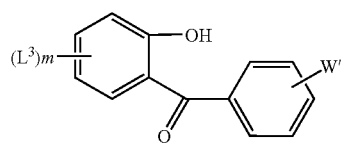

[wherein $L^3$, m, and W' are as mentioned earlier] according to the method described in literature (see WO93/16055).

The reaction is carried out, for example, by allowing an equimolar amount or more, preferably a 1 to 1.5 time molar amount of N,N-dimethylthiocarbamoyl chloride (manufactured by TOKYO CHEMICAL INDUSTRIES, LTD.) to react with the compound represented by the formula (16) in a solvent such as THF or dioxane in the presence of an excess amount, preferably a 1.5 to 3 time molar amount of an organic base such as triethylamine, and a catalytic amount, preferably a 0.1 to 0.2 time molar amount of a strong organic base such as dimethylaminopyridine or an equimolar amount or more, preferably a 1 to 1.5 time molar amount of an inorganic base such as sodium hydride at room temperature or at 50° C to 100° C for 1 to 24 hours.

The compound represented by the formula (17) is obtained by allowing a compound represented by formula (18) below

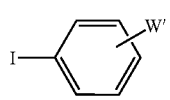
(18)

[where W' is as mentioned earlier] to react with a compound represented by formula (19) below

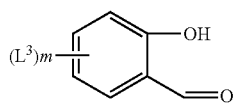
(19)

[wherein $L^3$ and m are as mentioned earlier] according to the method described in literature (see Chemistry Letters, 823-824, 1996). The reaction is carried out, for example, by allowing a 2 time molar amount of the compound represented by the formula (18) to react with the compound represented by the formula (19) in a solvent such as DMF in the presence of a 0.05 time molar amount of palladium chloride, a 0.2 time molar amount of lithium chloride, and a 2 time molar amount of sodium carbonate at 100° C to 150° C for 1 to 24 hours.

Examples of the compounds represented by the formula (18) include 4-iodoanisole, 3-iodoanisole, and iodobenzene (all the three are manufactured by TOKYO CHEMICAL INDUSTRIES, LTD.).

Examples of the compound represented by the formula (19) include 5-fluorosalicyl aldehyde (manufactured by APOLLO CHEMICAL COMPANY LTD.), and 3-fluorosalicyl aldehyde (manufactured by ALDRICH CHEMICAL COMPANY).

Furthermore, the compound represented by the formula (17) is also obtained by allowing a Lewis acid to react with a compound represented by formula (20) below

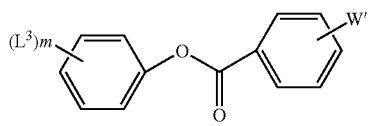
(20)

[where $L^3$, m, and W' are as mentioned earlier] according to the method described in literature (Journal of Compounds and Radiopharmaceuticals, Vol. 34, 643-652, 1994).

The reaction is carried out, for example, by allowing an excess amount, preferably a 1.5 to 5 time molar amount of a Lewis acid, preferably titanium tetrachloride or aluminum chloride, more preferably titanium tetrachloride to react with the compound represented by the formula (20), optionally in a solvent such as nitrobenzene at 120° C to 160° C, for 1 to 24 hours.

The compound represented by the formula (20) is obtained by allowing a compound represented by formula (21) below

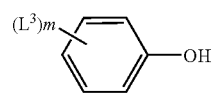
(21)

[where $L^3$ and m are as mentioned earlier] to react with a compound represented by formula (22) below

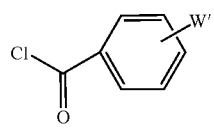
(22)

[where W' is as mentioned earlier] according to the method described in literature (see Journal of Compounds and Radiopharmaceuticals, Vol. 34, 643-652, 1994).

The reaction is carried out, for example, by allowing an equimolar amount of the compound represented by the formula (22) to react with the compound represented by the formula (21), in a solvent such as dichloromethane, chloroform or THF, in the presence of an equimolar amount, preferably a 1 to 1.5 time molar amount of an organic base such as triethylamine at 40° C to 60° C for 1 to 5 hours.

Examples of the compounds represented by the formula (21) include 4-fluorophenol, 2-fluorophenol, and 2,4-difluorophenol (all the three are manufactured by TOKYO CHEMICAL INDUSTRIES, LTD.).

Examples of the compounds represented by the formula (22) include 4-methoxybenzoyl chloride, 3-methoxybenzoyl chloride, and benzoyl chloride (all the three are manufactured by ALDRICH CHEMICAL COMPANY).

The compound represented by the formula (13) is obtained by allowing chlorosulfonic acid to react with a compound represented by formula (23) below

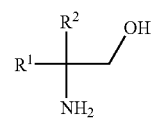
(23)

[wherein $R^1$ and $R^2$ are as mentioned earlier] according to the method described in literature (see WO93/16055).

The reaction is carried out, for example, by allowing an equimolar amount or more, preferably 1 to 2 time molar amount of chlorosulfonic acid to react with the compound represented by the formula (23) in a solvent such as dichloromethane at 0° to 10° C or at room temperature for 1 to 24 hours.

The compound represented by the formula (23) is obtained by reducing a compound represented by formula (24) below

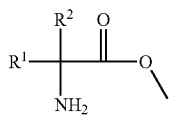

(24)

[where $R^1$ and $R^2$ are as mentioned earlier] according to the method described in literature (see WO93/16055).

The reaction is carried out, for example, by allowing an excess molar amount, preferably a 1.5 to 3 time molar amount of lithium aluminum hydride to react with the compound represented by the formula (23) in a solvent such as THE at room temperature or at 50° C to 60° C for 1 to 5 hours.

The compound represented by the formula (24) is obtained by hydrolyzing, with an acid, of a compound represented by formula (25) below

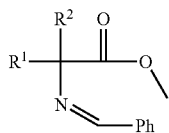

(25)

[where $R^1$ and $R^2$ are as mentioned earlier] according to the method described in literature (see WO93/16055).

The reaction is carried out, for example, by allowing an excess amount, preferably a 30 to 300 time molar amount of an acid, preferably 1 N to 5 N hydrochloric acid to react with the compound represented by the formula (25), optionally in a solvent such as THF or methanol, at room temperature for 1 to 24 hours.

The compound represented by the formula (25) is obtained by allowing a base to react with a compound represented by formula (26) below

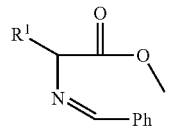

(26)

[where $R^1$ is as mentioned earlier] and then allowing a compound represented by formula (27) below $R^2$—$L^5$ (27)

[where $R^2$ is as mentioned earlier; and $L^5$ represents a halogen] to react with the resultant according to the method described in literature (see WO93/16055).

The reaction is carried out, for example, by allowing an equimolar amount or more, preferably 1 to 1.5 time molar amount of an inorganic base such as sodium hydride to react with the compound represented by the formula (26) in a solvent such as DMF at room temperature or at 0° C to 10° C for 1 to 3 hours and then allowing an equimolar amount or more, preferably 1 to 1.5 time molar amount of the compound represented by the formula (27) to react with the resultant at 0° C to 10° C or at room temperature for 1 to 24 hours.

Examples of the halogen represented by $L^5$ in the formula (27) include F, Cl, Br, and I, preferably Br and I, with I being more preferable.

Examples of the compounds represented by the formula (27) include iodoethane, 1-iodopropane, 1-iodobutane, 1-iodopentane, and 1-iodohexane (all are manufactured by TOKYO CHEMICAL INDUSTRIES, LTD.).

The compound represented by the formula (26) is obtained by allowing benzaldehyde to react with a compound represented by formula (28) below

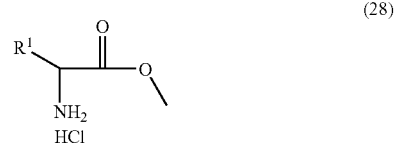

(28)

[where $R^1$ is as mentioned earlier] according to the method described in literature (see WO93/16055).

The reaction is carried out, for example, by allowing an equimolar amount or more, preferably 1 to 1.2 time molar amount of benzaldehyde (manufactured by WAKO PURE CHEMICAL INDUSTRIES LTD.) to react with the compound represented by the formula (28) in the presence of an excess amount, preferably 2 to 3 time molar amount of an organic base such as triethylamine and an excess amount, preferably a 1.5 to 2 time molar amount of a dehydrating agent such as anhydrous magnesium sulfate in a solvent such as dichloromethane at room temperature for 1 to 24 hours.

Examples of the compound represented by the formula (28) include methyl 2-aminobutyrate hydrochloride (manufactured by TOKYO CHEMICAL INDUSTRIES, LTD.), methyl 2-aminohexanoate hydrochloride (manufactured by BACH EM CHEMICAL COMPANY), methyl 2-aminopentanoate hydrochloride (prepared by allowing thionyl chloride to react with norvaline manufactured by TOKYO CHEMICAL INDUSTRIES, LTD. in methanol according to the method described in WO93/16055), methyl 2-aminoheptanoate hydrochloride, (prepared similarly from 2-aminoheptanoic acid manufactured by FLUKA CHEMICAL CORPORATION), and methyl 2-aminooctanoate hydrochloride (prepared similarly from 2-aminocaprylic acid manufactured by TOKYO CHEMICAL INDUSTRIES, LTD.).

The compounds represented by the formula (1) can have a plurality of stereoisomers depending on the number of asymmetric centers. Those isomers which are in a relationship of diastereomers can be separated by silica gel column chromatography or fractionating crystallization during the synthesis of any one of the compounds represented by the formulae (1), (3), (4-1), (4-2), (6-1), (6-2), and from (7-2a) to (7-2d). Moreover, those isomers which are in a relationship of enantiomers can be separated by column chromatography which uses an optically active carrier or separated by silica gel column chromatography or fractionating crystallization after they are derived to diastereomers, during the synthesis of any one of the compounds represented by the formulae (1), (3), (4-1), (4-2), (6-1), (6-2), and from (7-2a) to (7-2d). On the other hand, geometric isomers can be separated by silica gel column chromatography or fractionating crystallization during the synthesis of any one of the compounds represented by the formulae (1), (3), (4-1), and (4-2).

The compounds represented by the formula (1) of the present invention include the acid addition salts. The acid addition salts are preferably pharmaceutically acceptable salts that include, for example, various types of known salts, such as hydrochlorides, hydrobromides, sulfates, hydrogen sulfates, dihydrogen phosphates, citrates, maleates, tartarates, fumarates, gluconates, and methanesulfonates. When acid addition salts are to be made, addition of an equimolar amount or a few time molar amount of an acid component to the compounds represented by the formula (1) can provide acid addition salts thereof. Examples of the acid component which can be used include pharmaceutically acceptable mineral acids or organic acids, such as hydrochloric acid, hydrobromic acid, sulfuric acid, hydrogen sulfuric acid, dihydrogen phosphoric acid, citric acid, maleic acid, tartaric acid, fumaric acid gluconic acid, and methanesulfonic acid.

The compounds of the present invention have ileal bile acid transporter inhibiting activities and have blood cholesterol-lowering effects, and ameliorating effects for cholestasis-caused hepatopathy. Therefore, it has been verified that the compounds of the present invention can be used as cholesterol-lowering agents and as ameliorating agents for cholestasis-caused hepatopathy. No case of death has been observed when the compounds of the present invention were orally administered to rats in a dosage of 3 mg per kg of body weight twice a day for 3.5 days. Furthermore, the compounds of the present invention showed no microbe mutagenicity, which indicates that the compounds of the present invention can be used safely.

Specific examples of the cholesterol-lowering agent include pharmaceutical compositions for the treatment and prevention of any one of hyperlipidemia, arteriosclerosis, and syndrome X. Detailed explanation of these disorders is as follows.

That is, examples of hyperlipidemia include hyperchylomicronemia, low density lipoprotein (LDL) hyperlipoproteinemia, familial hypercholesterolemia, very low density lipoprotein (VLDL) hyperlipoproteinemia, hypertriglyceridemia, and disorders resulting from combinations of these. Ateriosclerosis may be mentioned as a preferable example of target arteriosclerosis which is subjected to treatment and prevention in the present invention. Syndrome X, as explained earlier, is a disorder which sometimes is one of the causes of hyperlipidemia and sometimes causes arteriosclerosis eventually.

The compounds of the present invention and pharmaceutical compositions containing the same are also useful as drugs for the treatment and prevention of cholestasis-caused hepatopathy and are particularly useful as drugs for the treatment and prevention of primary biliary cirrhosis and primary sclerosing cholangitis. Cholestasis means a state where eventually bile is not excreted from liver to duodenum for some reason. Once cholestasis occurs, it causes liver disorder, which is called as cholestasis-caused hepatopathy. Specific examples of hepatopathy caused by cholestasis include primary biliary cirrhosis, primary sclerosing cholangitis, and cholestatic hepatitis (cholangiolitic hepatitis) (Medical Encyclopedia published by Nanzando, 1333-1 334). Direct causes of cholestasis may include gallstones, etc. developed in bile duct or gall bladder. Primary biliary cirrhosis and primary sclerosing cholangitis are disorders which are not caused directly by gallstones.

The compounds of the present invention and pharmaceutical compositions containing the same are also useful as drugs for the treatment and prevention of obesity and fatty liver. Obesity means a state where fat is excessively accumulated in the body and specifically means a Body Mass Index (BMI) of more than 26 (Yoshio Ikeda et al., Nippon Rinsho (Japan Clinical), 53:229-236, 1995). Fatty liver means a state where usually, neutral fat is accumulated in large quantities in liver; in general, liver in which fat droplets are accumulated in approximately 30% or more of hepatic lobules is defined as fatty liver (Kyoichiro Tojima et al., Nippon Rinsho (Japan Clinical), 53:354-358, 1995).

Moreover, the compounds of the present invention and pharmaceutical compositions containing the same are also useful as drugs for the treatment and prevention of steatohepatitis. Steatohepatitis means a disease in which deposition of fat in the liver and inflammation and fibrillation of hepatic parenchyma are observed and steatohepatitis is a quite different disease from fatty liver in that steatohepatitis is accompanied by an image of inflammation (see Toshifumi Azuma et al., .KAN·TAN·SUI, 44:429-433, 2002). Among the steatohepatitis cases, those which show no causal relation to alcohol uptake are termed nonalcoholic steatohepatitis (NASH).

Upon manufacturing drugs of the present invention, it is preferable to make a pharmaceutical composition by optionally adding a pharmaceutically acceptable carrier to an effective amount of the compound represented by the formula (1) or its salts. Examples of the pharmaceutically acceptable carriers include an excipient, a binder such as carboxymethyl cellulose, a disintegrating agent, a lubricant, and an additive. The compounds of the present invention can be administered orally to humans in the form of a tablet, a powder, a granule, a capsule, a sugar coated tablet, a liquid, a syrup and so forth. Dosages may vary according to the age, weight, and symptom of a patient. Generally, in the case of an adult, a dosage of 0.1 mg to 500 mg is administered once a day or in a plural of times a day in portions. Administration period is as follows. Generally, the drug is administered everyday for a few weeks to a few months. However, the dosage and the administration period of the drug may be increased or decreased according to the symptom of the patient.

Moreover, the inventors of the present invention have studied on the pharmacological activity of various known ileal bile acid transporter (IBAT) inhibiting compounds. As a result, it has been verified that these IBAT inhibiting compounds have treating and preventing effects for cholestasis-caused hepatopathy and that these compounds can be used as drugs for the treatment and prevention of cholestasis-caused hepatopathy, particularly for the treatment and prevention of primary biliary cirrhosis and primary sclerosing cholangitis.

Thus, the present invention relates to a pharmaceutical composition which contains an IBAT inhibiting compound as an active ingredient and is effective for the treatment or prevention of cholestasis-ca used hepatopathy. Preferable examples of the pharmaceutical composition which is effective for the treatment or prevention of cholestasis-caused hepatopathy include pharmaceutical compositions for the treatment or prevention of primary biliary cirrhosis or primary sclerosing cholangitis.

As mentioned earlier, cholestasis means a state where eventually bile is not excreted from liver to duodenum for some reason. Once cholestasis occurs, it sometimes causes liver disorder, which is called as cholestasis-caused hepatopathy. Specific examples of cholestasis-caused hepatopathy include primary biliary cirrhosis, primary sclerosing cholangitis, and cholestatic hepatitis (cholangiolitic hepatitis) (see Medical Encyclopedia published by Nanzando, 1333-1334). Furthermore, direct causes of cholestasis may include gallstones developed in bile duct or gall bladder. Primary biliary cirrhosis and primary sclerosing cholangitis are disorders which are not caused directly by gallstones. Primary biliary cirrhosis is a disease in which cholestasis in liver caused by chronic nonsuppurutive destructive cholangitis of bile duct or loss of bile duct is a major pathological condition and symptoms observed based on cholestasis include fatigue, itching paraesthesia, jaundice and so forth. On the other hand, primary sclerosing cholangitis is a disease caused by inflammatory stricture of a bile duct and causes symptoms accompanying chronic cholestasis (such as fatigue and itching paraesthesia). Thus, the present invention provides drugs for diseases in which stasis of bile acids occurs in the liver due to lesion of the bile duct and which eventually leads to liver disorders.

The IBAT inhibiting compound which is used for the treatment of cholestasis-caused hepatopathy is not particularly restricted so far as it is a compound which is bonded to BAT and inhibits it. IBAT is a membrane protein which exists on the inner membrane of ileum and it recovers bile acids which are discharged in the inside of small intestine from liver through the bile duct. An inhibiting compound to IBAT is hoped as a drug for the treatment of hyperlipidemia (see The Journal of Biological Chemistry, 268, 18035-18046, 1993). IBAT inhibiting compounds are disclosed in literature such as International Patent Applications Gazette Nos. WO93/16055 and WO02/08211, and so forth. However, their effectiveness on cholestasis-caused hepatopathy, particularly their effectiveness on primary biliary cirrhosis and primary sclerosing cholangitis is not at all disclosed therein.

Examples of the IBAT inhibiting compound include 1,4-benzothiazepine derivatives, 1,5-benzothiazepine derivatives, 1,2-benzothiazepine derivatives, 1-benzothiepine derivatives, cholic acid derivatives, and lignan analogues.

Specific examples of the 1,4-benzothiazepine derivatives and 1,5-benzothiazepine derivatives as IBAT inhibiting compounds include those compounds described in International Patent Application Gazette No. WO02/08211, Published Translation of Japanese Patent Application No. Hei 10-504035, International Patent Application Gazette No. WO00/61568, and Japanese Patent Application Laid-open No. Hei 10-279568, and their salts, solvates, or derivatives having physiological functions.

Examples of the 1,2-benzothiazepine derivatives as IBAT inhibiting compounds include those compounds described in International Patent Application Gazette No. WO00/47568 and their salts, solvates, or derivatives having physiological functions. Moreover, examples of the IBAT inhibiting compounds include those compounds described in Japanese Patent No. 2839805, Japanese Patent Applications Nos. 4-277151, 5-310634, and 9-241206, International Patent Applications Gazette Nos. WO93-16055, WO94-18183, WO94-18184, WO98-38182, WO99-35135, WO99-64410, WO01-66533, WO96-16051, WO00-20437, European Patent Applications Nos. EP624593, EP624594, EP624595, EP624596, and EP489423, International Patent Application Gazette No. WO01-34570, Japanese Patent Application Laid-open No. Hei 6-321783, International Patent Applications Gazette Nos. WO00-20392, WO00-20393, WO00-20410, $WO_{02}$-08211, WO98-56757, WO00-35889, Japanese Patent Application Laid-open Nos. 2000-178188 and 2001-89429, and International Patent Applications Gazette Nos. $WO_{02}$-50051, WO03-22286, WO03-22825, WO03-22830, WO03-20710, WO03-43992, and WO03-40127, and their salts, solvates, or derivatives having physiological functions.

Further, examples of preferable IBAT inhibiting compounds include compounds described below. The compounds are merely exemplary and the present invention which relates to pharmaceutical compositions containing the IBAT inhibiting compounds which are drugs for the treatment or prevention of primary biliary cirrhosis or primary sclerosing cholangitis do not depend on specific IBAT inhibiting compounds.

1-{4-[4-(3,3-Dibutyl-7-dimethylamino-1,1-dioxo-2,3,4, 5-tetra- hydro-1,4-benzothiazepin-5-yl)phenoxymethyl] benzyl}-4aza-1- azoniabicyclo[2.2.2]octane chloride (compound A mentioned later);

Trans-3-butyl-3-ethyl-2 3,4,5-tetrahydro-7,8-dimethoxy-5-phenyl- 1,4-benzothiazepine-1,1-dioxide (compound B mentioned later);

Trans-3-butyl-3-ethyl-2,3,4,5-tetrahydro-5-phenyl-1,4-benzo- thiazepine-1,1-dioxide (compound C mentioned later);

Cis-[3-(3,3-dibutyl-7-dimethylamino-4-hydroxy-1,1-dioxo-2,3,4,5- tetrahydro-1-benzothiepin-5-yl)phenyl]trimethylammonium iodide (compound D mentioned later);

Cis-1-{4-[4-(3,3-dibutyl-7-dimethylamino-4-hydroxy-1, 1-dioxo- 2,3,4,5-tetrahydro-1-benzothiepin-5-yl)phenoxymethyl]benzyl}-4-aza-1- azoniabicyclo[2.2.2]octane chloride;

Cis-{4-[3-(3,3-dibutyl-7-dimethylamino-4-hydroxy-1,1-dioxo- 2,3,4,5-tetrahydro-1-benzothiepin-5-yl)phenylcarbamoyl]butyl}triethyl- ammonium trifluoroacetate;

2,3,4,5,6-Pentahydroxyhexanoic acid [3-(3,3-dibutyl-7-dimethylamino-4-hydroxy-1,1-dioxo-2,3,4,5-tetrahydro-1-benzothiepin- 5-yl)phenyl]amide;

2,3,4,5,6-Pentahydroxyhexanoic acid [3-(3-butyl-3-ethyl-7- dimethylamino-4-hydroxy-1,1-dioxo-2,3,4,5-tetrahydro-1-benzothiepin- 5-yl) phenyl]amide;

5-(2,3,4,5,6-Pentahydroxyhexylamino)pentanoic acid [3-(3,3- dibutyl-7-dimethylamino-4-hydroxy-1,1-dioxo-2,3,4, 5-tetrahydro-1- benzothiepin-5-yl)phenyl]amide;

5-(2,3,4,5,6-pentahydroxyhexylamino)pentanoic acid [3-(3-butyl-3-ethyl-7-dimethylamino-4-hydroxy-1,1-dioxo-2, 3,4,5- tetrahydro-1-benzothiepin-5-yl)phenyl]amide;

Methyl 1-(3,4-dimethoxyphenyl)-3-(3-ethylvaleryl)-4-hydroxy- 6,7,8-trimethoxy-2-naphthoate (compound E mentioned later);

{1-O-[4-(3,4-Dimethoxyphenyl)-2-(3-ethylpentanoyl)-5, 6,7- trimethoxy-3-(methoxycarbonyl)naphthalen-1-yl]-β-D-glucopyranosido}uronic acid (compound F mentioned later);

The IBAT inhibiting compounds also include respective salts, for example acid addition salts, of 1,4-benzothiazepine derivatives, 1,5-benzothiazepine derivatives, 1,2-benzothiazepine derivatives, or 1-benzothiepine derivatives, etc. The acid addition salts are preferably pharmaceutically acceptable salts and include various known salts, for example, hydrochlorides, hydrobromides, sulfates, hydrogen sulfates, dihydrogen phosphates, citrates, maleates, tartarates, fumarates, gluconates, and methanesulfonates. The acid addition salts of IBAT inhibiting compounds are obtained by adding an equimolar amount or a few times molar amount of an acid component to the IBAT inhibiting compounds. The acid component which can be used include pharmaceutically acceptable mineral acids or organic acids, such as hydrochloric acid, hydrobromic acid, sulfuric acid, hydrogen sulfuric acid, dihydrogen phosphoric acid, citric acid, maleic acid, tartaric acid, fumaric acid, gluconic acid, and methanesulfonic acid.

It is preferable to form salts of lignan derivatives. Examples of pharmaceutically acceptable salts include salts of alkali metals such as sodium salts and potassium salts, salts of alkaline earth metals such as calcium salts and magnesium salts, quaternary ammonium salts such as tetramethylammonium salts, organic amine salts (for example, diethylamine salts), inorganic acid addition salts such as hydrochlorides and sulfates, and organic acid addition salts such as acetates, oxalates, and benzenesulfonates.

To manufacture pharmaceutical compositions which are drugs for the treatment or prevention of cholestasis-caused hepatopathy, it is preferable to optionally add a pharmaceutically acceptable carrier to an effective amount of IBAT inhibiting compound. Examples of pharmaceutically acceptable carriers include an excipient, a binder such as carboxymethyl cellulose, a disintegrating agent, a lubricant, and an additive.

When the compounds of the present invention are administered to humans, they can be administered orally in the form of a tablet, a powder, a granule, a capsule, a sugar coated tablet, a liquid, a syrup and so forth. Dosages may vary according to the age, weight, and symptom of the patient. Normally, in the case of an adult, a dosage of 0.1 mg or more, preferably 1 mg or more and as upper limits, usually 5 g or less, preferably 1 g or less, particularly preferably 500 mg or less is exemplified. The aforementioned dosage is administered at a time or in portions in a plurality of times. Administration period is as follows. Generally, the drug is administered everyday for a few weeks to a few months. However, both the dosage and administration period of the drug may be increased or decreased according to the symptom of the patient.

EXAMPLES

The present invention is further explained based on the following examples. However, the present invention is not restricted to the following examples. Thin layer chromatography (TLC) was performed using Precoated Silica Gel 60 F254 (manufactured by MERCK COMPANY) and spots were confirmed by UV (254 nm) irradiation. Measurement of nuclear magnetic resonance spectra (NMR) was carried out with AL-300 (FT-NMR manufactured by JEOL COMPANY). Chemical shifts were indicated by δ (ppm) by use of tetramethylsilane (TMS) as an internal standard. Mass spectrum (MS) was measured by use of JMS-5X102 (manufactured by JEOL COMPANY) using fast atom bombardment mass spectrum (FAB-MS). Silica gel 60 of from 230 mesh to 400 mesh (manufactured by MERCK COMPANY) was used as a filler for silica gel column. In the operations carried out in the examples, "filtration" means filtration carried out by using a Kiriyama funnel and filter paper for the funnel (both the funnel and the filter paper are manufactured by NIPPON RIGAKU KIKAI CO., LTD.) and "concentration" means removal by evaporation of solvent or excess reagent under reduced pressure by using an evaporator (manufactured by TOKYO RIGAKU KIKAI CO., LTD.)

[Example 1] 1-{5-[3-(3,3-Dibutyl-7-dimethylamino-1,1-dioxo-2,3,4,5- tetrahydro-1,4-benzothiazepin-5-yl)phenylthiocarbamoyl]pentyl}-1- azoniabicyclo [2.2.2]octane bromide Step a: Synthesis of methyl 2-benzylideneaminohexanoate To a suspension of 7.79 g of methyl 2-aminohexanoate hydrochloride in 70 ml of dichloromethane were added 8.67 g of triethylamine (manufactured by WAKO PURE CHEMICAL INDUSTRIES LTD.), 7.74 g of anhydrous magnesium sulfate, and 4.55 g of benzaldehyde and the resultant was stirred overnight at room temperature. The reaction suspension was then filtered and the filtrate was concentrated. 280 ml of ether was added to the residue and the resultant suspension was filtered and the filtrate was concentrated. Again, 280 ml of ether was added to the residue and filtration and concentration were similarly repeated to obtain 10.0 g of the title compound.

Step b: Synthesis of methyl 2-benzylideneamino-2-butylhexanoate

To a solution of 8.06 g of the compound obtained in the step a in 25 ml of DMF was added 1.66 g of sodium hydride (60% dispersion in oil) (manufactured by WAKO PURE CHEMICAL INDUSTRIES LTD.) in an argon atmosphere under ice cooling, and the resultant was stirred for 2 hours at room temperature. To the reaction suspension was dropwise added a solution of 8.90 g of 1-1odobutane in 15 ml of DMF in an argon atmosphere under ice cooling, and the mixture was stirred at room temperature for 3 hours. Under ice cooling, a solution of 5.5 g of ammonium chloride in 50 ml of water was dropwise added to the reaction suspension and then the mixture was separated by adding to it 80 ml of ether and 30 ml of water. The organic layer was dried over anhydrous sodium sulfate and then concentrated to obtain 10.0 g of the title compound.

Step c: Synthesis of methyl 2-amino-2-butylhexanoate

To a solution of 15.46 g of the compound obtained in the step b in 70 ml of petroleum ether was added 30 ml of 1 N hydrochloric acid, and the mixture was stirred for 1 hour at room temperature. The reaction solution was separated by adding to it 60 ml of water. The water layer was washed twice with 80 ml of ether, an aqueous solution of 5N sodium hydroxide was added to it, and pH of the solution was adjusted to 9 to 10. The water layer was separated by adding to it 160 ml of ethyl acetate and the organic layer was washed with 160 ml of saturated saline. The organic layer was dried over anhydrous sodium sulfate and then concentrated to obtain 10.0 g of the title compound.

Step d: Synthesis of 2-amino-2-butylhexanol

To a suspension of 7.52 g of lithium aluminum hydride (manufactured by WAKO PURE CHEMICAL INDUSTRIES LTD.) in 50 ml of THF was dropwise added a solution of 17.34 g of the compound obtained in the step c in 120 ml of THE under ice cooling and the mixture was stirred at 60° C for 1 hour. To the reaction suspension was dropwise added 25 ml of water under ice cooling. Then, 600 ml of ethyl acetate was added to the resultant at room temperature. The mixture was filtered through Celite and washed with 900 ml of ethyl acetate. The filtrate was concentrated to obtain 10.0 g of the title compound.

Step e: Synthesis of 2-amino-2-butylhexyl hydrogen sulfate

To a solution of 7.97 g of the compound obtained in the step d in 90 ml of dichioromethane was dropwise added 8.04 g of chiorosulfonic acid under ice cooling and the mixture was stirred overnight at room temperature. The reaction solution was concentrated and 90 ml of acetone-ether (1:1)

Step f: Synthesis of 4-fluoro-2-benzoylthiophenol

To a solution of 10.1 g of 2,5-difluorobenzophenone in 200 ml of DMSO was added 3.5 g of lithium sulfide (manufactured by ALDRICH CHEMICAL COMPANY) and the mixture was stirred in a nitrogen atmosphere at 1200C for 3 hours. To the reaction solution was added 200 ml of 1N hydrochloric acid under ice cooling, and further 400 ml of ethyl acetate and 200 ml of water were added to the mixture to separate it. The organic layer was washed with 400 ml of water and then with 200 ml of saturated saline. The organic layer was dried over anhydrous sodium sulfate and then concentrated to obtain 10.54 g of the title compound.

Step g: Synthesis of 2-(2-amino-2-butylhexylthio)-5-fluoro- benzophenone

To a solution of 10.54 g of the compound obtained in the step f in 100 ml of butyl acetate were added 11.50 g of the compound obtained in the step e and a solution of 7.25 g of sodium hydroxide in 100 ml of water and the mixture was stirred at 90° C for 1 hour. The reaction mixture was separated by adding to it 300 ml of ethyl acetate and 300 ml of water. The organic layer was dried over anhydrous sodium sulfate and then concentrated. The residue was charged in a silica gel column and eluted with chloroform-methanol-28% aqueous ammonia (50:1 :0.1) to obtain 10.09 g of the title compound.

Step h: Synthesis of 3,3-dibutyl-2,3-dihydro-7-fluoro-5-phenyl-1 4- benzothiazepine To a solution of 10.08 g of the compound obtained in the step g in 40m1 of 2,6-lutidine (manufactured by WAKO PURE CHEMICAL INDUSTRIES LTD.) was added 0.60 g of p-toluenesulfonic acid monohydrate (manufactured by WAKO PURE CHEMICAL INDUSTRIES LTD.), and the mixture was stirred at 130° C for 34 hours. The reaction solution was separated by adding to it 400 ml of ethyl acetate and 400 ml of water. The organic layer was dried over anhydrous sodium sulfate and concentrated. The residue was charged in a silica gel column and eluted with hexane-ethyl acetate (30:1) to obtain 7.87 g of the title compound.

Step i: Synthesis of 3,3-dibutyl-2,3-dihydro-7-fluoro-5-phenyl-1,4- benzothiazepine-1,1-dioxide To a solution of 7.86 g of the compound obtained in the step h in 50 ml of dichloromethane were added 150 ml of acetonitrile, a solution of 13.3 g of sodium periodate (manufactured by WAKO PURE CHEMICAL INDUSTRIES LTD.) in 70 ml of water, and 0.42 g of ruthenium trichloride (manufactured by WAKO PURE CHEMICAL INDUSTRIES LTD.), and the mixture was stirred at room temperature for 24 hours. The reaction suspension was separated by adding to it 300 ml of dichloromethane and 300 ml of water. The organic layer was dried over anhydrous sodium sulfate and then concentrated. The residue was charged in a silica gel column and eluted with hexane-ethyl acetate (6:1) to obtain 5.72 g of the title compound.

Step j: Synthesis of 3,3-dibutyl-2,3-dihydro-7-fluoro-5-(3-nitrophenyl)- 1,4-benzothiazepine-1,1-dioxide To 5.32 g of the compound obtained in the step i was added a mixed solution composed of 20 ml of fuming nitric acid and 15 ml of concentrated sulfuric acid under ice cooling and the mixture was stirred at room temperature for 1 hour. The reaction mixture was dropwise added to a SN sodium hydroxide solution under ice cooling, and the mixture was separated by adding to it iSOml of dichloromethane and 50 ml of water at room temperature. The organic layer was washed with 150 ml of saturated saline, dried over anhydrous sodium sulfate, and then concentrated. The residue was charged in a silica gel column and eluted with hexane-ethyl acetate (5:1) to obtain 5.48 g of the title compound.

Step k: Synthesis of 3,3-dibutyl-2,3-dihydro-7-dimethylamino-5- (3-nitrophenyl)-1,4-benzothiazepine-1,1-dioxide To 5.48 g of the compound obtained in the step j was added 200 ml of a THF solution of 2 mol/l dimethylamine (manufactured by ALDRICH CHEMICAL COMPANY) and the mixture was heated at 55° C for 14 hours. The reaction solution was concentrated. The residue was charged in a silica gel column and eluted with hexane-ethyl acetate (2:1). The eluate was washed with 50 ml of ether to obtain 5.69 g of the title compound.

Step l: Synthesis of 3,3-dibutyl-2,3-dihydro-7-dimethylamino-5- (3-aminophenyl) -1,4-benzothiazepine-1,1-dioxide To a solution of 5.9 g of the compound obtained in the step k in 100 ml of chloroform were added 100 ml of methanol and 1.2 g of 10% palladium-carbon (manufactured by MERCK COMPANY), and the mixture was stirred in a hydrogen atmosphere at room temperature for 4 hours. The catalyst in the reaction suspension was removed by filtering and the filtrate was concentrated. The residue was charged in a silica gel column and then eluted with chloroform-methanol (30:1) to obtain 4.38 g of the title compound.

Step m: Synthesis of 3,3-dibutyl-2,3,4,5-tetrahydro-7-dimethylamino-5- (3-aminophenyl)-1,4-benzothiazepine-1,1-dioxide To 4.38 g of the compound obtained in the step l was added 150 ml of a THF solution of 1 mol/l borane-THF complex (manufactured by KANTO CHEMICAL COMPANY), and the mixture was stirred at room temperature for 1 hour. To the reaction mixture was dropwise added 10 ml of water under ice cooling until foaming stopped and then the reaction solution was stirred at room temperature for 1.5 hours. The mixture was then separated by adding to it 150 ml of ethyl acetate, 50 ml of water, and 100 ml of aqueous solution of 1N sodium hydroxide at room temperature. The organic layer was washed with 150 ml of water and allowed to stand at room temperature for 1.5 hours. The organic layer was dried over anhydroussodium sulfate and then concentrated. The residue was charged in a silica gel column and eluted with hexane-ethyl acetate (1:1) to obtain 3.83 g of the title compound.

was added to the residue. The mixture was allowed to stand at −20° C for 3 hours. The precipitate was filtered, washed with 300 ml of acetone-ether (1:1) to obtain 10.0 g of the title compound.

Step n: Synthesis of 3,3-dibutyl-2,3,4,5-tetrahydro-7-dimethylamino-5-[3-(6-bromohexanoyl)aminophenyl]-1,4-benzothiazepine-1,1-dioxide To a solution of 0.73 g of the compound obtained in the step m in 15 ml of dichloromethane was added 0.27 g of potassium carbonate and then 0.37 g of 6-bromo-n-caproyl chloride, and the mixture was stirred at room temperature for 20 minutes. The reaction solution was separated by adding to it 35 ml of dichloromethane and 50 ml of water. The organic layer was dried over anhydrous sodium sulfate and then concentrated. The residue was charged in a silica gel column and eluted with hexane-ethyl acetate (1:1) to obtain 1.00 g of the title compound.

Step o: Synthesis of 3,3-dibutyl-2,3,4,5-tetrahydro-7-dimethylamino-5-[3-(6-bromothiohexanoyl)aminophenyl]-1,4-benzothiazepine-1,1-dioxide To a solution of 50 mg of the compound obtained in the step n in 1.5 ml of THF was added 90 mg of Lawesson's reagent, and the mixture was stirred at room temperature for 40 hours. The reaction solution was then separated by adding to it 6 ml of ethyl acetate and 8 ml of water. The organic layer was dried over anhydrous sodium sulfate and then concentrated. The residue was charged in a silica gel column and eluted with hexane-ethyl acetate (2:1) to obtain 37 mg of the title compound. Rf value 0.41 (developed with hexane:ethyl acetate=3:1).

Step p: Synthesis of 1-{5-[3-(3,3-dibutyl-7-dimethylamino-1,1-dioxo-2,3,4,5-tetrahydro-1,4-benzothiazepin-5-yl)phenylthiocarbamoyl]-pentyl}-1-azoniabicyclo[2.2.2]octane bromide To a solution of 36 mg of the compound obtained in the step o in 1 ml of acetonitrile was added 7 mg of quinuclidine (ta-287 mentioned earlier), and the mixture was heated at 50° C for 22 hours. The reaction solution was concentrated and the residue was dissolved in 0.2 ml of dichloromethane. 2 ml of ether was added to the solution and the precipitate formed was washed with 2 ml of ether to obtain 32 mg of the title compound. $^1$H-NMR (CDCl$_3$) δ: 0.84 (3H, t); 0.90 (3H, t); 1.18-1.51 (8H, m); 1.60-2.23 (17H, m); 2.84 (6H, s); 2.95-3.12 (3H, m); 3.26-3.43 (3H, m); 3.58 (6H, t); 6.03-6.07 (2H, m); 6.47 (1H, dd); 7.34-7.39 (2H, m); 7.72-7.76 (1H, m); 7.84 (1H, d); 7.98 (1H, s); 11.56 (1H, s). MS (m/z): 667 (M+).

[Example 2] 1-{5-[3-(3-Butyl-3-ethyl-7-dimethylamino-1,1-dioxo-2,3,4,5-tetrahydro-1,4-benzothiazepin-5-yl)phenylthiocarbamoyl]pentyl}-1-azoniabicyclo[2.2.2]octane bromide

Step a: Synthesis of 3-butyl-3-ethyl-2,3,4,5-tetrahydro-7-dimethylamino-5-(3-aminophenyl)-1,4-benzothiazepine-1,1-dioxide The procedure in the steps a to m in Example 1 was followed except that methyl 2-aminobutyrate hydrochloride was used instead of the methyl 2-aminohexanoate hydrochloride used in the step a of Example 1 to obtain the title compound.

Step b: Synthesis of 1-{5-[3-(3-butyl-3-ethyl-7-dimethylamino-1,1-dioxo-2,3,4,5-tetrahydro-1,4-benzothiazepin-5-yl)phenylthiocarbamoyl]pentyl}-1-azoniabicyclo[2.2.2]octane bromide The procedure in the steps n to p in Example 1 was followed except that the compound obtained in the step a in this example was used to obtain the title compound.

[Example 3] 1-{5-[3-(3,3-Dipropyl-7-dimethylamino-1,1-dioxo-2,3,4,5-tetrahydro-1,4-benzothiazepin-5-yl)phenylthiocarbanmoyl]pentyl}-1-azoniabicyclo-[2.2.2]octane bromide

Step a: Synthesis of 3,3-dipropyl-2,3,4,5-tetrahydro-7-dimethylamino-5-(3-aminophenyl)-1,4-benzothiazepine-1,1-dioxide The procedure in the steps d to m in Example 1 was followed except that 2-amino-2-propylpentanoic acid (manufactured by ADVANCED CHEMTECH COMPANY) was used instead of the compound obtained in the step c in Example 1 to obtain the title compound.

Step b: Synthesis of 1-{5-[3-(3,3-dipropyl-7-dimethylamino-1,1-dioxo-2,3,4,5-tetrahydro-1,4-benzothiazepin-5-yl)phenylthiocarbanmoyl]-pentyl}-1-azoniabicyclo[2.2.2]octane bromide The procedure in the steps n to p in Example 1 was followed except that the compound obtained in the step a in this example was used to obtain the title compound.

[Example 4] 1-{5-[3-(3,3-Dipentyl-7-dimethylamino-1,1-dioxo-2,3,4,5-tetrahydro-1,4-benzothiazepin-5-yl)phenylthiocarbamoyl]-pentyl}-1-azoniabicyclo[2.2.2]octane bromide

Step a: Synthesis of methyl 2-aminoheptanoate hydrochloride

To a suspension of 2.18 g of 2-aminoheptanoic acid in 50 ml of methanol was dropwise added 2.19 g of thionyl chloride (manufactured by WAKO PURE CHEMICAL INDUSTRIES LTD.), and the mixture was stirred overnight at 60° C. Methanol and thionyl chloride were removed by evaporation and the residue was washed with 20 ml of ether to obtain 2.84 g of the title compound.

Step b: Synthesis of 3,3-dipentyl-2,3,4,5-tetrahydro-7-dimethylamino-5-(3-aminophenyl)-1,4-benzothiazepine-1,1-dioxide The procedure in the steps a to m in Example 1 was followed except that the compound obtained in the step a in this example was used and that in the step b, 1-1odopentane instead of 1-1odobutane was allowed to react to obtain the title compound.

Step c: Synthesis of 1-{5-[3-(3,3-dipentyl-7-dimethylamino-1,1-dioxo-2,3,4,5-tetrahydro-1,4-benzothiazepin-5-yl)phenylthiocarbamoyl]pentyl}-1-azoniabicyclo[2.2.2]octane bromide The procedure in the steps n to p in Example 1 was followed except that the compound obtained in the step b in this example was used to obtain the title compound.

[Example 5] 1-{5-[3-(3,3-Dihexyl-7-dimethylamino-1,1-dioxo-2,3,4,5-tetrahydro-1,4-benzothiazepin-5-yl)phenylthiocarbamoyl]pentyl}-1-azoniabicyclo[2.2.2]octane bromide Step a: Synthesis of methyl 2-aminooctanoate hydrochloride Instead of 2-aminoheptanoic acid used in the step a in Example 4,2-aminocaprylic acid was used to obtain the title compound.

Step b: Synthesis of 3,3-dihexyl-2,3,4,5-tetrahydro-7-dimethylamino-5-(3-aminophenyl)-1,4-benzothiazepine-1,1-dioxide The procedure in the steps a to m in Example 1 was followed except that the compound obtained in the step a in this example was used and that in the step b, 1-odohexane instead of 1-odobutane was allowed to react to obtain the title compound.

Step c: Synthesis of 1-{5-[3-(3,3-dihexyl-7-dimethylamino-1,1-dioxo-2,3,4,5-tetrahydro-1,4-benzothiazepin-5-yl)phenylthiocarbamoyl]pentyl}-1-azoniabicyclo[2.2.2]octane bromide The procedure in the steps n to p in Example 1 was followed except that the compound obtained in the step b in this example was used to obtain the title compound.

[Example 6] 1-{5-[3-(3,3-Dibutyl-7-diethylamino-1,1-dioxo-2,3,4,5-tetrahydro-1,4-benzothiazepin-5-yl)phenylthiocarbamoyl]pentyl}1-azoniabicyclo[2.2.2]octane bromide Step a: Synthesis of 3,3-dibutyl-2,3,4,5-tetrahydro-7-diethylamino-5-(3-aminophenyl)-1,4-benzothiazepine-1,1-dioxide The procedure in the steps a to m in Example 1 was followed except that in the step k, diethylamine instead of dimethylamine was allowed to react to obtain the title compound.

Step b: Synthesis of 1-{5-[3-(3,3-dibutyl-7-diethylamino-1,1-dioxo-2,3,4,5-tetrahydro-1,4-benzothiazepin-5-yl)phenylthiocarbamoyl]pentyl}-1-azoniabicyclo[2.2.2]octane bromide The procedure in the steps n to p in Example 1 was followed except that the compound obtained in the step a in this example was used to obtain the title compound.

[Example 7] 1-{5-[3-(3,3-Dibutyl-7-ethylmethylamino-1,1-dioxo-2,3,4,5-tetrahydro-1,4-benzothiazepin-5-yl)phenylthiocarbamoyl]pentyl}1-azoniabicyclo[2.2.2]octane bromide Step a: Synthesis of 3,3-dibutyl-2,3,4,5-tetrahydro-7-ethylmethyl-amino-5-(3-aminophenyl)-1,4-benzothiazepine-1,1-dioxide The procedure in the steps a to m in Example 1 was followed except that in the step k, ethylmethylamine instead of dimethylamine was allowed to react to obtain the title compound.

Step b: Synthesis of 1-{5-[3-(3,3-dibutyl-7-ethylmethylamino-1,1-dioxo-2,3,4,5-tetrahydro-1,4-benzothiazepin-5-yl)phenylthiocarbamoyl]pentyl}-1-azoniabicyclo[2.2.2]octane bromide The procedure in the steps n to p in Example 1 was followed except that the compound obtained in the step a in this example was used to obtain the title compound.

[Example 8] 1-{5-[3-(3,3-Dibutyl-7-dimethylamino-1,1-dioxo-2,3,4,5-tetrahydro-1,4-benzothiazepin-5-yl)phenylthiocarbamoyl]-pentyl}-1-azoniabicyclo[2.2.2]octane bromide (an optically active form)

Step a: Synthesis of 3,3-dibutyl-2,3,4,5-tetrahydro-7-dimethylamino-5-(3-aminophenyl)-1,4-benzothiazepine-1,1-dioxide (an optically active form)

The compound obtained in the step m in Example 1 was charged in an optical column CHIRALCEL-OJ for preparatory chromatography (manufactured by DAICEL CHEMICAL INDUSTRIES LTD., having a particle size of 10 μm, a diameter of 2 cm, and a length of 25 cm) at a flow rate of 18.9 ml/mm, and then eluted with methanol to separate the compounds into compounds of S form and R form. The retention times of the obtained optically active forms in the optical column for analysis were 7 minutes and 14 minutes, respectively. Column; CHIRALPAK-OJ (manufactured by DAICEL CHEMICAL INDUSTRIES LTD., having a particle size of 10 μm, a diameter of 0.46 cm, and a length of 25 cm), mobile phase; methanol, flow rate; 0.5 ml/mm, UV wavelength detected; 288 nm.

Step b: Synthesis of 1-{5-[3-(3,3-dibutyl-7-dimethylamino-1,1-dioxo-2,3,4,5-tetrahydro-1,4-benzothiazepin-5-yl)phenylthiocarbamoyl]-pentyl}-1-azoniabicyclo[2.2.2]octane bromide (an optically active form)

The procedure in the steps n to p in Example 1 was followed except that the optically active synthetic intermediate obtained in the step a in this example was used to obtain the title compound.

[Example 9] 1-(3-{3-[3,3-Dibutyl-7-dimethylamino-1,1-dioxo-2,3,4,5-tetrahydro-1,4-benzothiazepin-5-yl)phenyl]thioureido}-propyl)-1-azoniabicyclo[2.2.2]octane bromide Step a: Synthesis of 1-(3-isothiocyanatopropyl)-1-azoniabicyclo-[2.2.2]octane bromide To a solution of 55 mg of 3-bromopropyl isothiocyanate in 1 ml of acetonitrile was added 33 mg of quinuclidine, and the mixture was heated at 50° C for 19 hours. The reaction solution was concentrated and the residue was washed 3 times with 1 ml of ether to obtain the title compound.

Step b: Synthesis of 1-(3-{3-[3-(3,3-dibutyl-7-dimethylamino-1,1-dioxo-2,3,4,5-tetrahydro-1,4-benzothiazepin-5-yl)phenyl]thioureido}propyl)-1-azoniabicyclo[2.2.2]octane bromide To a solution of 60 mg of the compound obtained in the step m in Example 1 in 1.5 ml of chloroform was added a solution of 43 mg of the compound obtained in the step a in this example in 0.5 ml of acetonitrile, and the mixture was heated at 55° C overnight. The reaction solution was concentrated and the residue was dissolved in 0.3 ml of dichloromethane. To the resultant was added 1.5 ml of ether, and the precipitate formed was washed with 2 ml of ether to obtain 77 mg of the title compound. $^1$H -NMR (ODCl$_3$) δ: 0.84 (3H, t); 0.90 (3H, t); 1.13-1.49 (8H, m); 1.68-2.23 (13H, in); 2.84 (6H, s); 2.99 (1H, d); 3.40 (1H, d); 3.52 (6H, t); 3.59-3.75 (4H, m); 6.00 (1H, s); 6.02 (1H, d); 6.48 (1H, dd); 7.24-7.34 (2H, m); 7.46 (1H, d); 7.62 (1H, s); 7.85 (1H, d); 8.58 (1H, s), 940 (1H, s). MS (m/z) 654 (M+).

[Example 10] 1-(3-{3-[3-(3-Butyl-3-ethyl-7-dimethylamino-1,1-dioxo- 2,3,4,5-tetrahydro-1,4-benzothiazepin-5-yl)phenyl] thioureido}propyl)- 1-azoniabicyclo[2.2.2]octane bromide The procedure in the step b in Example 9 was followed except that instead of the compound obtained in the step m in Example 1, the compound obtained in the step a in Example 2 was used to obtain the title compound. [Example 11] 1-(3-{3-[3-(3,3-Dipropyl-7-dimethylamino-1,1-dioxo-2,3,4,5-tetrahydro-1,4-benzothiazepin-5-yl)phenyl] thioureido}propyl)-1- azoniabicyclo[2.2.2]octafle bromide The procedure in the step b in Example 9 was followed except that instead of the compound obtained in the step m in Example 1, the compound obtained in the step a in Example 3 was used to obtain the title compound.

[Example 12] 1-(3-{3-[3-(3,3-Dipentyl-7-dimethylamino-1,1-dioxo- 2,3,4,5-tetrahydro-1,4-benzothiazepin-5-yl)phenyl]thioureido}propyl)-1- azoniabicyclo[2.2.2]octane bromide The procedure in the step b in Example 9 was followed except that instead of the compound obtained in the step m in Example 1, the compound obtained in the step b in Example 4 was used to obtain the title compound.

[Example 13] 1-(3-{3-[3-(3,3-Dihexyl-7-dimethylamino-1,1-dioxo- 2,3,4,5-tetrahydro-1,4-benzothiazepin-5-yl)phenyl]thioureido}propyl)-1- azoniabicyclo[2.2.2]octane bromide The procedure in the step b in Example 9 was followed except that instead of the compound obtained in the step m in Example 1, the compound obtained in the step b in Example 5 was used to obtain the title compound.

[Example 14] 1-(3-{3-[3-(3,3-Dibutyl-7-diethylamino-1,1-dioxo- 2,3,4,5-tetrahydro-1,4-benzothiazepin-5-yl)phenyl]thioureido}propyl)-1- azoniabicyclo[2.2.2]octane bromide The procedure in the step b in Example 9 was followed except that instead of the compound obtained in the step m in Example 1, the compound obtained in the step a in Example 6 was used to obtain the title compound.

[Example 15] 1-(3-{3-[3-(3,3-Dibutyl-7-ethylmethylamino-1,1-dioxo- 2,3,4,5-tetrahydro-1,4-benzothiazepin-5-yl)phenyl]thioureido}propyl)-1- azoniabicyclo[2.2.2]octane bromide The procedure in the step b in Example 9 was followed except that instead of the compound obtained in the step m in Example 1, the compound obtained in the step a in Example 7 was used to obtain the title compound.

[Example 16] 1-(3-{3-[3-(3,3-Dibutyl-7-dimethylamino-1,1-dioxo- 2,3,4,5-tetrahydro-1,4-benzothiazepin-5-yl)phenyl]thioureido}propyl)-1- azoniabicyclo[2.2.2]octane bromide (an optically active form)

The procedure in the step b in Example 9 was followed except that instead of the compound obtained in the step m in Example 1, the compound obtained in the step a in Example 8 was used to obtain the title compound.

[Examples 17 to 3785, 4067 to 5404, and 5407 to 5448]

As shown in the following formulae,

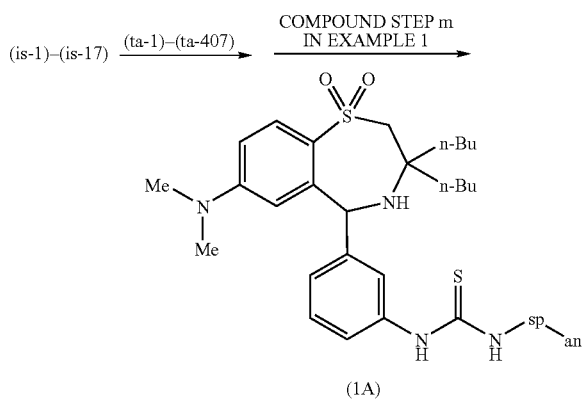

the procedure in the steps a and b in Example 9 is followed except that any one of the various isothiocyanate (is-1) to (is-17) represented by the formula (5-2b), any one of various tertiary amines (ta-1) to (ta-407) represented by the formula (2), and the compound obtained in the step m in Example 1 are used to obtain compounds of Examples 17 to 3785, 4067 to 5404, and 5407 to 5448 as represented by the formula (1A) as shown in Table 2. In the formula (1A), "-sp-" indicates any one of the (sp-1) to (sp-25) and "-an" indicates any one of the (an-1) to (an-407).

TABLE 2

| Example No. | Reaction reagent | | Compound of Example | |
|---|---|---|---|---|
| | is | ta | sp | an |
| 17 | is-1 | ta-1 | sp-1 | an-1 |
| 18 | is-1 | ta-2 | sp-1 | an-2 |
| 19 | is-1 | ta-3 | sp-1 | an-3 |
| 20 | is-1 | ta-4 | sp-1 | an-4 |
| 21 | is-1 | ta-5 | sp-1 | an-5 |
| 22 | is-1 | ta-6 | sp-1 | an-6 |
| 23 | is-1 | ta-7 | sp-1 | an-7 |
| 24 | is-1 | ta-8 | sp-1 | an-8 |
| 25 | is-1 | ta-9 | sp-1 | an-9 |
| 26 | is-1 | ta-10 | sp-1 | an-10 |
| 27 | is-1 | ta-11 | sp-1 | an-11 |
| 28 | is-1 | ta-12 | sp-1 | an-12 |
| 29 | is-1 | ta-13 | sp-1 | an-13 |
| 30 | is-1 | ta-14 | sp-1 | an-14 |
| 31 | is-1 | ta-15 | sp-1 | an-15 |

TABLE 2-continued

| Example No. | Reaction reagent is | Reaction reagent ta | Compound of Example sp | Compound of Example an |
|---|---|---|---|---|
| 32 | is-1 | ta-16 | sp-1 | an-16 |
| 33 | is-1 | ta-17 | sp-1 | an-17 |
| 34 | is-1 | ta-18 | sp-1 | an-18 |
| 35 | is-1 | ta-19 | sp-1 | an-19 |
| 36 | is-1 | ta-20 | sp-1 | an-20 |
| 37 | is-1 | ta-21 | sp-1 | an-21 |
| 38 | is-1 | ta-22 | sp-1 | an-22 |
| 39 | is-1 | ta-23 | sp-1 | an-23 |
| 40 | is-1 | ta-24 | sp-1 | an-24 |
| 41 | is-1 | ta-25 | sp-1 | an-25 |
| 42 | is-1 | ta-26 | sp-1 | an-26 |
| 43 | is-1 | ta-27 | sp-1 | an-27 |
| 44 | is-1 | ta-28 | sp-1 | an-28 |
| 45 | is-1 | ta-29 | sp-1 | an-29 |
| 46 | is-1 | ta-30 | sp-1 | an-30 |
| 47 | is-1 | ta-31 | sp-1 | an-31 |
| 48 | is-1 | ta-32 | sp-1 | an-32 |
| 49 | is-1 | ta-33 | sp-1 | an-33 |
| 50 | is-1 | ta-34 | sp-1 | an-34 |
| 51 | is-1 | ta-35 | sp-1 | an-35 |
| 52 | is-1 | ta-36 | sp-1 | an-36 |
| 53 | is-1 | ta-37 | sp-1 | an-37 |
| 54 | is-1 | ta-38 | sp-1 | an-38 |
| 55 | is-1 | ta-39 | sp-1 | an-39 |
| 56 | is-1 | ta-40 | sp-1 | an-40 |
| 57 | is-1 | ta-41 | sp-1 | an-41 |
| 58 | is-1 | ta-42 | sp-1 | an-42 |
| 59 | is-1 | ta-43 | sp-1 | an-43 |
| 60 | is-1 | ta-44 | sp-1 | an-44 |
| 61 | is-1 | ta-45 | sp-1 | an-45 |
| 62 | is-1 | ta-46 | sp-1 | an-46 |
| 63 | is-1 | ta-47 | sp-1 | an-47 |
| 64 | is-1 | ta-48 | sp-1 | an-48 |
| 65 | is-1 | ta-49 | sp-1 | an-49 |
| 66 | is-1 | ta-50 | sp-1 | an-50 |
| 67 | is-1 | ta-51 | sp-1 | an-51 |
| 68 | is-1 | ta-52 | sp-1 | an-52 |
| 69 | is-1 | ta-53 | sp-1 | an-53 |
| 70 | is-1 | ta-54 | sp-1 | an-54 |
| 71 | is-1 | ta-55 | sp-1 | an-55 |
| 72 | is-1 | ta-56 | sp-1 | an-56 |
| 73 | is-1 | ta-57 | sp-1 | an-57 |
| 74 | is-1 | ta-58 | sp-1 | an-58 |
| 75 | is-1 | ta-59 | sp-1 | an-59 |
| 76 | is-1 | ta-60 | sp-1 | an-60 |
| 77 | is-1 | ta-61 | sp-1 | an-61 |
| 78 | is-1 | ta-62 | sp-1 | an-62 |
| 79 | is-1 | ta-63 | sp-1 | an-63 |
| 80 | is-1 | ta-64 | sp-1 | an-64 |
| 81 | is-1 | ta-65 | sp-1 | an-65 |
| 82 | is-1 | ta-66 | sp-1 | an-66 |
| 83 | is-1 | ta-67 | sp-1 | an-67 |
| 84 | is-1 | ta-68 | sp-1 | an-68 |
| 85 | is-1 | ta-69 | sp-1 | an-69 |
| 86 | is-1 | ta-70 | sp-1 | an-70 |
| 87 | is-1 | ta-71 | sp-1 | an-71 |
| 88 | is-1 | ta-72 | sp-1 | an-72 |
| 89 | is-1 | ta-73 | sp-1 | an-73 |
| 90 | is-1 | ta-74 | sp-1 | an-74 |
| 91 | is-1 | ta-75 | sp-1 | an-75 |
| 92 | is-1 | ta-76 | sp-1 | an-76 |
| 93 | is-1 | ta-77 | sp-1 | an-77 |
| 94 | is-1 | ta-78 | sp-1 | an-78 |
| 95 | is-1 | ta-79 | sp-1 | an-79 |
| 96 | is-1 | ta-80 | sp-1 | an-80 |
| 97 | is-1 | ta-81 | sp-1 | an-81 |
| 98 | is-1 | ta-82 | sp-1 | an-82 |
| 99 | is-1 | ta-83 | sp-1 | an-83 |
| 100 | is-1 | ta-84 | sp-1 | an-84 |
| 101 | is-1 | ta-85 | sp-1 | an-85 |
| 102 | is-1 | ta-86 | sp-1 | an-86 |
| 103 | is-1 | ta-87 | sp-1 | an-87 |
| 104 | is-1 | ta-88 | sp-1 | an-88 |
| 105 | is-1 | ta-89 | sp-1 | an-89 |
| 106 | is-1 | ta-90 | sp-1 | an-90 |
| 107 | is-1 | ta-91 | sp-1 | an-91 |
| 108 | is-1 | ta-92 | sp-1 | an-92 |
| 109 | is-1 | ta-93 | sp-1 | an-93 |
| 110 | is-1 | ta-94 | sp-1 | an-94 |
| 111 | is-1 | ta-95 | sp-1 | an-95 |
| 112 | is-1 | ta-96 | sp-1 | an-96 |
| 113 | is-1 | ta-97 | sp-1 | an-97 |
| 114 | is-1 | ta-98 | sp-1 | an-98 |
| 115 | is-1 | ta-99 | sp-1 | an-99 |
| 116 | is-1 | ta-100 | sp-1 | an-100 |
| 117 | is-1 | ta-101 | sp-1 | an-101 |
| 118 | is-1 | ta-102 | sp-1 | an-102 |
| 119 | is-1 | ta-103 | sp-1 | an-103 |
| 120 | is-1 | ta-104 | sp-1 | an-104 |
| 121 | is-1 | ta-105 | sp-1 | an-105 |
| 122 | is-1 | ta-106 | sp-1 | an-106 |
| 123 | is-1 | ta-107 | sp-1 | an-107 |
| 124 | is-1 | ta-108 | sp-1 | an-108 |
| 125 | is-1 | ta-109 | sp-1 | an-109 |
| 126 | is-1 | ta-110 | sp-1 | an-110 |
| 127 | is-1 | ta-111 | sp-1 | an-111 |
| 128 | is-1 | ta-112 | sp-1 | an-112 |
| 129 | is-1 | ta-113 | sp-1 | an-113 |
| 130 | is-1 | ta-114 | sp-1 | an-114 |
| 131 | is-1 | ta-115 | sp-1 | an-115 |
| 132 | is-1 | ta-116 | sp-1 | an-116 |
| 133 | is-1 | ta-117 | sp-1 | an-117 |
| 134 | is-1 | ta-118 | sp-1 | an-118 |
| 135 | is-1 | ta-119 | sp-1 | an-119 |
| 136 | is-1 | ta-120 | sp-1 | an-120 |
| 137 | is-1 | ta-121 | sp-1 | an-121 |
| 138 | is-1 | ta-122 | sp-1 | an-122 |
| 139 | is-1 | ta-123 | sp-1 | an-123 |
| 140 | is-1 | ta-124 | sp-1 | an-124 |
| 141 | is-1 | ta-125 | sp-1 | an-125 |
| 142 | is-1 | ta-126 | sp-1 | an-126 |
| 143 | is-1 | ta-127 | sp-1 | an-127 |
| 144 | is-1 | ta-128 | sp-1 | an-128 |
| 145 | is-1 | ta-129 | sp-1 | an-129 |
| 146 | is-1 | ta-130 | sp-1 | an-130 |
| 147 | is-1 | ta-131 | sp-1 | an-131 |
| 148 | is-1 | ta-132 | sp-1 | an-132 |
| 149 | is-1 | ta-133 | sp-1 | an-133 |
| 150 | is-1 | ta-134 | sp-1 | an-134 |
| 151 | is-1 | ta-135 | sp-1 | an-135 |
| 152 | is-1 | ta-136 | sp-1 | an-136 |
| 153 | is-1 | ta-137 | sp-1 | an-137 |
| 154 | is-1 | ta-138 | sp-1 | an-138 |
| 155 | is-1 | ta-139 | sp-1 | an-139 |
| 156 | is-1 | ta-140 | sp-1 | an-140 |
| 157 | is-1 | ta-141 | sp-1 | an-141 |
| 158 | is-1 | ta-142 | sp-1 | an-142 |
| 159 | is-1 | ta-143 | sp-1 | an-143 |
| 160 | is-1 | ta-144 | sp-1 | an-144 |
| 161 | is-1 | ta-145 | sp-1 | an-145 |
| 162 | is-1 | ta-146 | sp-1 | an-146 |
| 163 | is-1 | ta-147 | sp-1 | an-147 |
| 164 | is-1 | ta-148 | sp-1 | an-148 |
| 165 | is-1 | ta-149 | sp-1 | an-149 |
| 166 | is-1 | ta-150 | sp-1 | an-150 |
| 167 | is-1 | ta-151 | sp-1 | an-151 |
| 168 | is-1 | ta-152 | sp-1 | an-152 |
| 169 | is-1 | ta-153 | sp-1 | an-153 |
| 170 | is-1 | ta-154 | sp-1 | an-154 |
| 171 | is-1 | ta-155 | sp-1 | an-155 |
| 172 | is-1 | ta-156 | sp-1 | an-156 |
| 173 | is-1 | ta-157 | sp-1 | an-157 |
| 174 | is-1 | ta-158 | sp-1 | an-158 |
| 175 | is-1 | ta-159 | sp-1 | an-159 |
| 176 | is-1 | ta-160 | sp-1 | an-160 |
| 177 | is-1 | ta-161 | sp-1 | an-161 |
| 178 | is-1 | ta-162 | sp-1 | an-162 |
| 179 | is-1 | ta-163 | sp-1 | an-163 |

TABLE 2-continued

| Example No. | Reaction reagent is | Reaction reagent ta | Compound of Example sp | Compound of Example an |
|---|---|---|---|---|
| 180 | is-1 | ta-164 | sp-1 | an-164 |
| 181 | is-1 | ta-165 | sp-1 | an-165 |
| 182 | is-1 | ta-166 | sp-1 | an-166 |
| 183 | is-1 | ta-167 | sp-1 | an-167 |
| 184 | is-1 | ta-168 | sp-1 | an-168 |
| 185 | is-1 | ta-169 | sp-1 | an-169 |
| 186 | is-1 | ta-170 | sp-1 | an-170 |
| 187 | is-1 | ta-171 | sp-1 | an-171 |
| 188 | is-1 | ta-172 | sp-1 | an-172 |
| 189 | is-1 | ta-173 | sp-1 | an-173 |
| 190 | is-1 | ta-174 | sp-1 | an-174 |
| 191 | is-1 | ta-175 | sp-1 | an-175 |
| 192 | is-1 | ta-176 | sp-1 | an-176 |
| 193 | is-1 | ta-177 | sp-1 | an-177 |
| 194 | is-1 | ta-178 | sp-1 | an-178 |
| 195 | is-1 | ta-179 | sp-1 | an-179 |
| 196 | is-1 | ta-180 | sp-1 | an-180 |
| 197 | is-1 | ta-181 | sp-1 | an-181 |
| 198 | is-1 | ta-182 | sp-1 | an-182 |
| 199 | is-1 | ta-183 | sp-1 | an-183 |
| 200 | is-1 | ta-184 | sp-1 | an-184 |
| 201 | is-1 | ta-185 | sp-1 | an-185 |
| 202 | is-1 | ta-186 | sp-1 | an-186 |
| 203 | is-1 | ta-187 | sp-1 | an-187 |
| 204 | is-1 | ta-188 | sp-1 | an-188 |
| 205 | is-1 | ta-189 | sp-1 | an-189 |
| 206 | is-1 | ta-190 | sp-1 | an-190 |
| 207 | is-1 | ta-191 | sp-1 | an-191 |
| 208 | is-1 | ta-192 | sp-1 | an-192 |
| 209 | is-1 | ta-193 | sp-1 | an-193 |
| 210 | is-1 | ta-194 | sp-1 | an-194 |
| 211 | is-1 | ta-195 | sp-1 | an-195 |
| 212 | is-1 | ta-196 | sp-1 | an-196 |
| 213 | is-1 | ta-197 | sp-1 | an-197 |
| 214 | is-1 | ta-198 | sp-1 | an-198 |
| 215 | is-1 | ta-199 | sp-1 | an-199 |
| 216 | is-1 | ta-200 | sp-1 | an-200 |
| 217 | is-1 | ta-201 | sp-1 | an-201 |
| 218 | is-1 | ta-202 | sp-1 | an-202 |
| 219 | is-1 | ta-203 | sp-1 | an-203 |
| 220 | is-1 | ta-204 | sp-1 | an-204 |
| 221 | is-1 | ta-205 | sp-1 | an-205 |
| 222 | is-1 | ta-206 | sp-1 | an-206 |
| 223 | is-1 | ta-207 | sp-1 | an-207 |
| 224 | is-1 | ta-208 | sp-1 | an-208 |
| 225 | is-1 | ta-209 | sp-1 | an-209 |
| 226 | is-1 | ta-210 | sp-1 | an-210 |
| 227 | is-1 | ta-211 | sp-1 | an-211 |
| 228 | is-1 | ta-212 | sp-1 | an-212 |
| 229 | is-1 | ta-213 | sp-1 | an-213 |
| 230 | is-1 | ta-214 | sp-1 | an-214 |
| 231 | is-1 | ta-215 | sp-1 | an-215 |
| 232 | is-1 | ta-216 | sp-1 | an-216 |
| 233 | is-1 | ta-217 | sp-1 | an-217 |
| 234 | is-1 | ta-218 | sp-1 | an-218 |
| 235 | is-1 | ta-219 | sp-1 | an-219 |
| 236 | is-1 | ta-220 | sp-1 | an-220 |
| 237 | is-1 | ta-221 | sp-1 | an-221 |
| 238 | is-1 | ta-222 | sp-1 | an-222 |
| 239 | is-1 | ta-223 | sp-1 | an-223 |
| 240 | is-1 | ta-224 | sp-1 | an-224 |
| 241 | is-1 | ta-225 | sp-1 | an-225 |
| 242 | is-1 | ta-226 | sp-1 | an-226 |
| 243 | is-1 | ta-227 | sp-1 | an-227 |
| 244 | is-1 | ta-228 | sp-1 | an-228 |
| 245 | is-1 | ta-229 | sp-1 | an-229 |
| 246 | is-1 | ta-230 | sp-1 | an-230 |
| 247 | is-1 | ta-231 | sp-1 | an-231 |
| 248 | is-1 | ta-232 | sp-1 | an-232 |
| 249 | is-1 | ta-233 | sp-1 | an-233 |
| 250 | is-1 | ta-234 | sp-1 | an-234 |
| 251 | is-1 | ta-235 | sp-1 | an-235 |
| 252 | is-1 | ta-236 | sp-1 | an-236 |
| 253 | is-1 | ta-237 | sp-1 | an-237 |
| 254 | is-1 | ta-238 | sp-1 | an-238 |
| 255 | is-1 | ta-239 | sp-1 | an-239 |
| 256 | is-1 | ta-240 | sp-1 | an-240 |
| 257 | is-1 | ta-241 | sp-1 | an-241 |
| 258 | is-1 | ta-242 | sp-1 | an-242 |
| 259 | is-1 | ta-243 | sp-1 | an-243 |
| 260 | is-1 | ta-244 | sp-1 | an-244 |
| 261 | is-1 | ta-245 | sp-1 | an-245 |
| 262 | is-1 | ta-246 | sp-1 | an-246 |
| 263 | is-1 | ta-247 | sp-1 | an-247 |
| 264 | is-1 | ta-248 | sp-1 | an-248 |
| 265 | is-1 | ta-249 | sp-1 | an-249 |
| 266 | is-1 | ta-250 | sp-1 | an-250 |
| 267 | is-1 | ta-251 | sp-1 | an-251 |
| 268 | is-1 | ta-252 | sp-1 | an-252 |
| 269 | is-1 | ta-253 | sp-1 | an-253 |
| 270 | is-1 | ta-254 | sp-1 | an-254 |
| 271 | is-1 | ta-255 | sp-1 | an-255 |
| 272 | is-1 | ta-256 | sp-1 | an-256 |
| 273 | is-1 | ta-257 | sp-1 | an-257 |
| 274 | is-1 | ta-258 | sp-1 | an-258 |
| 275 | is-1 | ta-259 | sp-1 | an-259 |
| 276 | is-1 | ta-260 | sp-1 | an-260 |
| 277 | is-1 | ta-261 | sp-1 | an-261 |
| 278 | is-1 | ta-262 | sp-1 | an-262 |
| 279 | is-1 | ta-263 | sp-1 | an-263 |
| 280 | is-1 | ta-264 | sp-1 | an-264 |
| 281 | is-1 | ta-265 | sp-1 | an-265 |
| 282 | is-1 | ta-266 | sp-1 | an-266 |
| 283 | is-1 | ta-267 | sp-1 | an-267 |
| 284 | is-1 | ta-268 | sp-1 | an-268 |
| 285 | is-1 | ta-269 | sp-1 | an-269 |
| 286 | is-1 | ta-270 | sp-1 | an-270 |
| 287 | is-1 | ta-271 | sp-1 | an-271 |
| 288 | is-1 | ta-272 | sp-1 | an-272 |
| 289 | is-1 | ta-273 | sp-1 | an-273 |
| 290 | is-1 | ta-274 | sp-1 | an-274 |
| 291 | is-1 | ta-275 | sp-1 | an-275 |
| 292 | is-1 | ta-276 | sp-1 | an-276 |
| 293 | is-1 | ta-277 | sp-1 | an-277 |
| 294 | is-1 | ta-278 | sp-1 | an-278 |
| 295 | is-1 | ta-279 | sp-1 | an-279 |
| 296 | is-1 | ta-280 | sp-1 | an-280 |
| 297 | is-1 | ta-281 | sp-1 | an-281 |
| 298 | is-1 | ta-282 | sp-1 | an-282 |
| 299 | is-1 | ta-283 | sp-1 | an-283 |
| 300 | is-1 | ta-284 | sp-1 | an-284 |
| 301 | is-1 | ta-285 | sp-1 | an-285 |
| 302 | is-1 | ta-286 | sp-1 | an-286 |
| 303 | is-1 | ta-287 | sp-1 | an-287 |
| 304 | is-1 | ta-288 | sp-1 | an-288 |
| 305 | is-1 | ta-289 | sp-1 | an-289 |
| 306 | is-1 | ta-290 | sp-1 | an-290 |
| 307 | is-1 | ta-291 | sp-1 | an-291 |
| 308 | is-1 | ta-292 | sp-1 | an-292 |
| 309 | is-1 | ta-293 | sp-1 | an-293 |
| 310 | is-1 | ta-294 | sp-1 | an-294 |
| 311 | is-1 | ta-295 | sp-1 | an-295 |
| 312 | is-1 | ta-296 | sp-1 | an-296 |
| 313 | is-1 | ta-297 | sp-1 | an-297 |
| 314 | is-1 | ta-298 | sp-1 | an-298 |
| 315 | is-1 | ta-299 | sp-1 | an-299 |
| 316 | is-1 | ta-300 | sp-1 | an-300 |
| 317 | is-1 | ta-301 | sp-1 | an-301 |
| 318 | is-1 | ta-302 | sp-1 | an-302 |
| 319 | is-1 | ta-303 | sp-1 | an-303 |
| 320 | is-1 | ta-304 | sp-1 | an-304 |
| 321 | is-1 | ta-305 | sp-1 | an-305 |
| 322 | is-1 | ta-306 | sp-1 | an-306 |
| 323 | is-1 | ta-307 | sp-1 | an-307 |
| 324 | is-1 | ta-308 | sp-1 | an-308 |
| 325 | is-1 | ta-309 | sp-1 | an-309 |
| 326 | is-1 | ta-310 | sp-1 | an-310 |
| 327 | is-1 | ta-311 | sp-1 | an-311 |

TABLE 2-continued

| Example No. | Reaction reagent is | Reaction reagent ta | Compound of Example sp | Compound of Example an |
|---|---|---|---|---|
| 328 | is-1 | ta-312 | sp-1 | an-312 |
| 329 | is-1 | ta-313 | sp-1 | an-313 |
| 330 | is-1 | ta-314 | sp-1 | an-314 |
| 331 | is-1 | ta-315 | sp-1 | an-315 |
| 332 | is-1 | ta-316 | sp-1 | an-316 |
| 333 | is-1 | ta-317 | sp-1 | an-317 |
| 334 | is-1 | ta-318 | sp-1 | an-318 |
| 335 | is-1 | ta-319 | sp-1 | an-319 |
| 336 | is-1 | ta-320 | sp-1 | an-320 |
| 337 | is-1 | ta-321 | sp-1 | an-321 |
| 338 | is-1 | ta-322 | sp-1 | an-322 |
| 339 | is-1 | ta-323 | sp-1 | an-323 |
| 340 | is-1 | ta-324 | sp-1 | an-324 |
| 341 | is-1 | ta-325 | sp-1 | an-325 |
| 342 | is-1 | ta-326 | sp-1 | an-326 |
| 343 | is-1 | ta-327 | sp-1 | an-327 |
| 344 | is-1 | ta-328 | sp-1 | an-328 |
| 345 | is-1 | ta-329 | sp-1 | an-329 |
| 346 | is-1 | ta-330 | sp-1 | an-330 |
| 347 | is-1 | ta-331 | sp-1 | an-331 |
| 348 | is-1 | ta-332 | sp-1 | an-332 |
| 349 | is-1 | ta-333 | sp-1 | an-333 |
| 350 | is-1 | ta-334 | sp-1 | an-334 |
| 351 | is-1 | ta-335 | sp-1 | an-335 |
| 352 | is-1 | ta-336 | sp-1 | an-336 |
| 353 | is-1 | ta-337 | sp-1 | an-337 |
| 354 | is-1 | ta-338 | sp-1 | an-338 |
| 355 | is-1 | ta-339 | sp-1 | an-339 |
| 356 | is-1 | ta-340 | sp-1 | an-340 |
| 357 | is-1 | ta-341 | sp-1 | an-341 |
| 358 | is-1 | ta-342 | sp-1 | an-342 |
| 359 | is-1 | ta-343 | sp-1 | an-343 |
| 360 | is-1 | ta-344 | sp-1 | an-344 |
| 361 | is-1 | ta-345 | sp-1 | an-345 |
| 362 | is-1 | ta-346 | sp-1 | an-346 |
| 363 | is-1 | ta-347 | sp-1 | an-347 |
| 364 | is-1 | ta-348 | sp-1 | an-348 |
| 365 | is-1 | ta-349 | sp-1 | an-349 |
| 366 | is-1 | ta-350 | sp-1 | an-350 |
| 367 | is-1 | ta-351 | sp-1 | an-351 |
| 368 | is-1 | ta-352 | sp-1 | an-352 |
| 369 | is-1 | ta-353 | sp-1 | an-353 |
| 370 | is-1 | ta-354 | sp-1 | an-354 |
| 371 | is-1 | ta-355 | sp-1 | an-355 |
| 372 | is-1 | ta-356 | sp-1 | an-356 |
| 373 | is-1 | ta-357 | sp-1 | an-357 |
| 374 | is-1 | ta-358 | sp-1 | an-358 |
| 375 | is-1 | ta-359 | sp-1 | an-359 |
| 376 | is-1 | ta-360 | sp-1 | an-360 |
| 377 | is-1 | ta-361 | sp-1 | an-361 |
| 378 | is-1 | ta-362 | sp-1 | an-362 |
| 379 | is-1 | ta-363 | sp-1 | an-363 |
| 380 | is-1 | ta-364 | sp-1 | an-364 |
| 381 | is-1 | ta-365 | sp-1 | an-365 |
| 382 | is-1 | ta-366 | sp-1 | an-366 |
| 383 | is-1 | ta-367 | sp-1 | an-367 |
| 384 | is-1 | ta-368 | sp-1 | an-368 |
| 385 | is-1 | ta-369 | sp-1 | an-369 |
| 386 | is-1 | ta-370 | sp-1 | an-370 |
| 387 | is-1 | ta-371 | sp-1 | an-371 |
| 388 | is-1 | ta-372 | sp-1 | an-372 |
| 389 | is-1 | ta-373 | sp-1 | an-373 |
| 390 | is-1 | ta-374 | sp-1 | an-374 |
| 391 | is-1 | ta-375 | sp-1 | an-375 |
| 392 | is-1 | ta-376 | sp-1 | an-376 |
| 393 | is-1 | ta-377 | sp-1 | an-377 |
| 394 | is-2 | ta-1 | sp-2 | an-1 |
| 395 | is-2 | ta-2 | sp-2 | an-2 |
| 396 | is-2 | ta-3 | sp-2 | an-3 |
| 397 | is-2 | ta-4 | sp-2 | an-4 |
| 398 | is-2 | ta-5 | sp-2 | an-5 |
| 399 | is-2 | ta-6 | sp-2 | an-6 |
| 400 | is-2 | ta-7 | sp-2 | an-7 |
| 401 | is-2 | ta-8 | sp-2 | an-8 |
| 402 | is-2 | ta-9 | sp-2 | an-9 |
| 403 | is-2 | ta-10 | sp-2 | an-10 |
| 404 | is-2 | ta-11 | sp-2 | an-11 |
| 405 | is-2 | ta-12 | sp-2 | an-12 |
| 406 | is-2 | ta-13 | sp-2 | an-13 |
| 407 | is-2 | ta-14 | sp-2 | an-14 |
| 408 | is-2 | ta-15 | sp-2 | an-15 |
| 409 | is-2 | ta-16 | sp-2 | an-16 |
| 410 | is-2 | ta-17 | sp-2 | an-17 |
| 411 | is-2 | ta-18 | sp-2 | an-18 |
| 412 | is-2 | ta-19 | sp-2 | an-19 |
| 413 | is-2 | ta-20 | sp-2 | an-20 |
| 414 | is-2 | ta-21 | sp-2 | an-21 |
| 415 | is-2 | ta-22 | sp-2 | an-22 |
| 416 | is-2 | ta-23 | sp-2 | an-23 |
| 417 | is-2 | ta-24 | sp-2 | an-24 |
| 418 | is-2 | ta-25 | sp-2 | an-25 |
| 419 | is-2 | ta-26 | sp-2 | an-26 |
| 420 | is-2 | ta-27 | sp-2 | an-27 |
| 421 | is-2 | ta-28 | sp-2 | an-28 |
| 422 | is-2 | ta-29 | sp-2 | an-29 |
| 423 | is-2 | ta-30 | sp-2 | an-30 |
| 424 | is-2 | ta-31 | sp-2 | an-31 |
| 425 | is-2 | ta-32 | sp-2 | an-32 |
| 426 | is-2 | ta-33 | sp-2 | an-33 |
| 427 | is-2 | ta-34 | sp-2 | an-34 |
| 428 | is-2 | ta-35 | sp-2 | an-35 |
| 429 | is-2 | ta-36 | sp-2 | an-36 |
| 430 | is-2 | ta-37 | sp-2 | an-37 |
| 431 | is-2 | ta-38 | sp-2 | an-38 |
| 432 | is-2 | ta-39 | sp-2 | an-39 |
| 433 | is-2 | ta-40 | sp-2 | an-40 |
| 434 | is-2 | ta-41 | sp-2 | an-41 |
| 435 | is-2 | ta-42 | sp-2 | an-42 |
| 436 | is-2 | ta-43 | sp-2 | an-43 |
| 437 | is-2 | ta-44 | sp-2 | an-44 |
| 438 | is-2 | ta-45 | sp-2 | an-45 |
| 439 | is-2 | ta-46 | sp-2 | an-46 |
| 440 | is-2 | ta-47 | sp-2 | an-47 |
| 441 | is-2 | ta-48 | sp-2 | an-48 |
| 442 | is-2 | ta-49 | sp-2 | an-49 |
| 443 | is-2 | ta-50 | sp-2 | an-50 |
| 444 | is-2 | ta-51 | sp-2 | an-51 |
| 445 | is-2 | ta-52 | sp-2 | an-52 |
| 446 | is-2 | ta-53 | sp-2 | an-53 |
| 447 | is-2 | ta-54 | sp-2 | an-54 |
| 448 | is-2 | ta-55 | sp-2 | an-55 |
| 449 | is-2 | ta-56 | sp-2 | an-56 |
| 450 | is-2 | ta-57 | sp-2 | an-57 |
| 451 | is-2 | ta-58 | sp-2 | an-58 |
| 452 | is-2 | ta-59 | sp-2 | an-59 |
| 453 | is-2 | ta-60 | sp-2 | an-60 |
| 454 | is-2 | ta-61 | sp-2 | an-61 |
| 455 | is-2 | ta-62 | sp-2 | an-62 |
| 456 | is-2 | ta-63 | sp-2 | an-63 |
| 457 | is-2 | ta-64 | sp-2 | an-64 |
| 458 | is-2 | ta-65 | sp-2 | an-65 |
| 459 | is-2 | ta-66 | sp-2 | an-66 |
| 460 | is-2 | ta-67 | sp-2 | an-67 |
| 461 | is-2 | ta-68 | sp-2 | an-68 |
| 462 | is-2 | ta-69 | sp-2 | an-69 |
| 463 | is-2 | ta-70 | sp-2 | an-70 |
| 464 | is-2 | ta-71 | sp-2 | an-71 |
| 465 | is-2 | ta-72 | sp-2 | an-72 |
| 466 | is-2 | ta-73 | sp-2 | an-73 |
| 467 | is-2 | ta-74 | sp-2 | an-74 |
| 468 | is-2 | ta-75 | sp-2 | an-75 |
| 469 | is-2 | ta-76 | sp-2 | an-76 |
| 470 | is-2 | ta-77 | sp-2 | an-77 |
| 471 | is-2 | ta-78 | sp-2 | an-78 |
| 472 | is-2 | ta-79 | sp-2 | an-79 |
| 473 | is-2 | ta-80 | sp-2 | an-80 |
| 474 | is-2 | ta-81 | sp-2 | an-81 |
| 475 | is-2 | ta-82 | sp-2 | an-82 |

TABLE 2-continued

| Example No. | Reaction reagent | | Compound of Example | |
|---|---|---|---|---|
| | is | ta | sp | an |
| 476 | is-2 | ta-83 | sp-2 | an-83 |
| 477 | is-2 | ta-84 | sp-2 | an-84 |
| 478 | is-2 | ta-85 | sp-2 | an-85 |
| 479 | is-2 | ta-86 | sp-2 | an-86 |
| 480 | is-2 | ta-87 | sp-2 | an-87 |
| 481 | is-2 | ta-88 | sp-2 | an-88 |
| 482 | is-2 | ta-89 | sp-2 | an-89 |
| 483 | is-2 | ta-90 | sp-2 | an-90 |
| 484 | is-2 | ta-91 | sp-2 | an-91 |
| 485 | is-2 | ta-92 | sp-2 | an-92 |
| 486 | is-2 | ta-93 | sp-2 | an-93 |
| 487 | is-2 | ta-94 | sp-2 | an-94 |
| 488 | is-2 | ta-95 | sp-2 | an-95 |
| 489 | is-2 | ta-96 | sp-2 | an-96 |
| 490 | is-2 | ta-97 | sp-2 | an-97 |
| 491 | is-2 | ta-98 | sp-2 | an-98 |
| 492 | is-2 | ta-99 | sp-2 | an-99 |
| 493 | is-2 | ta-100 | sp-2 | an-100 |
| 494 | is-2 | ta-101 | sp-2 | an-101 |
| 495 | is-2 | ta-102 | sp-2 | an-102 |
| 496 | is-2 | ta-103 | sp-2 | an-103 |
| 497 | is-2 | ta-104 | sp-2 | an-104 |
| 498 | is-2 | ta-105 | sp-2 | an-105 |
| 499 | is-2 | ta-106 | sp-2 | an-106 |
| 500 | is-2 | ta-107 | sp-2 | an-107 |
| 501 | is-2 | ta-108 | sp-2 | an-108 |
| 502 | is-2 | ta-109 | sp-2 | an-109 |
| 503 | is-2 | ta-110 | sp-2 | an-110 |
| 504 | is-2 | ta-111 | sp-2 | an-111 |
| 505 | is-2 | ta-112 | sp-2 | an-112 |
| 506 | is-2 | ta-113 | sp-2 | an-113 |
| 507 | is-2 | ta-114 | sp-2 | an-114 |
| 508 | is-2 | ta-115 | sp-2 | an-115 |
| 509 | is-2 | ta-116 | sp-2 | an-116 |
| 510 | is-2 | ta-117 | sp-2 | an-117 |
| 511 | is-2 | ta-118 | sp-2 | an-118 |
| 512 | is-2 | ta-119 | sp-2 | an-119 |
| 513 | is-2 | ta-120 | sp-2 | an-120 |
| 514 | is-2 | ta-121 | sp-2 | an-121 |
| 515 | is-2 | ta-122 | sp-2 | an-122 |
| 516 | is-2 | ta-123 | sp-2 | an-123 |
| 517 | is-2 | ta-124 | sp-2 | an-124 |
| 518 | is-2 | ta-125 | sp-2 | an-125 |
| 519 | is-2 | ta-126 | sp-2 | an-126 |
| 520 | is-2 | ta-127 | sp-2 | an-127 |
| 521 | is-2 | ta-128 | sp-2 | an-128 |
| 522 | is-2 | ta-129 | sp-2 | an-129 |
| 523 | is-2 | ta-130 | sp-2 | an-130 |
| 524 | is-2 | ta-131 | sp-2 | an-131 |
| 525 | is-2 | ta-132 | sp-2 | an-132 |
| 526 | is-2 | ta-133 | sp-2 | an-133 |
| 527 | is-2 | ta-134 | sp-2 | an-134 |
| 528 | is-2 | ta-135 | sp-2 | an-135 |
| 529 | is-2 | ta-136 | sp-2 | an-136 |
| 530 | is-2 | ta-137 | sp-2 | an-137 |
| 531 | is-2 | ta-138 | sp-2 | an-138 |
| 532 | is-2 | ta-139 | sp-2 | an-139 |
| 533 | is-2 | ta-140 | sp-2 | an-140 |
| 534 | is-2 | ta-141 | sp-2 | an-141 |
| 535 | is-2 | ta-142 | sp-2 | an-142 |
| 536 | is-2 | ta-143 | sp-2 | an-143 |
| 537 | is-2 | ta-144 | sp-2 | an-144 |
| 538 | is-2 | ta-145 | sp-2 | an-145 |
| 539 | is-2 | ta-146 | sp-2 | an-146 |
| 540 | is-2 | ta-147 | sp-2 | an-147 |
| 541 | is-2 | ta-148 | sp-2 | an-148 |
| 542 | is-2 | ta-149 | sp-2 | an-149 |
| 543 | is-2 | ta-150 | sp-2 | an-150 |
| 544 | is-2 | ta-151 | sp-2 | an-151 |
| 545 | is-2 | ta-152 | sp-2 | an-152 |
| 546 | is-2 | ta-153 | sp-2 | an-153 |
| 547 | is-2 | ta-154 | sp-2 | an-154 |
| 548 | is-2 | ta-155 | sp-2 | an-155 |
| 549 | is-2 | ta-156 | sp-2 | an-156 |
| 550 | is-2 | ta-157 | sp-2 | an-157 |
| 551 | is-2 | ta-158 | sp-2 | an-158 |
| 552 | is-2 | ta-159 | sp-2 | an-159 |
| 553 | is-2 | ta-160 | sp-2 | an-160 |
| 554 | is-2 | ta-161 | sp-2 | an-161 |
| 555 | is-2 | ta-162 | sp-2 | an-162 |
| 556 | is-2 | ta-163 | sp-2 | an-163 |
| 557 | is-2 | ta-164 | sp-2 | an-164 |
| 558 | is-2 | ta-165 | sp-2 | an-165 |
| 559 | is-2 | ta-166 | sp-2 | an-166 |
| 560 | is-2 | ta-167 | sp-2 | an-167 |
| 561 | is-2 | ta-168 | sp-2 | an-168 |
| 562 | is-2 | ta-169 | sp-2 | an-169 |
| 563 | is-2 | ta-170 | sp-2 | an-170 |
| 564 | is-2 | ta-171 | sp-2 | an-171 |
| 565 | is-2 | ta-172 | sp-2 | an-172 |
| 566 | is-2 | ta-173 | sp-2 | an-173 |
| 567 | is-2 | ta-174 | sp-2 | an-174 |
| 568 | is-2 | ta-175 | sp-2 | an-175 |
| 569 | is-2 | ta-176 | sp-2 | an-176 |
| 570 | is-2 | ta-177 | sp-2 | an-177 |
| 571 | is-2 | ta-178 | sp-2 | an-178 |
| 572 | is-2 | ta-179 | sp-2 | an-179 |
| 573 | is-2 | ta-180 | sp-2 | an-180 |
| 574 | is-2 | ta-181 | sp-2 | an-181 |
| 575 | is-2 | ta-182 | sp-2 | an-182 |
| 576 | is-2 | ta-183 | sp-2 | an-183 |
| 577 | is-2 | ta-184 | sp-2 | an-184 |
| 578 | is-2 | ta-185 | sp-2 | an-185 |
| 579 | is-2 | ta-186 | sp-2 | an-186 |
| 580 | is-2 | ta-187 | sp-2 | an-187 |
| 581 | is-2 | ta-188 | sp-2 | an-188 |
| 582 | is-2 | ta-189 | sp-2 | an-189 |
| 583 | is-2 | ta-190 | sp-2 | an-190 |
| 584 | is-2 | ta-191 | sp-2 | an-191 |
| 585 | is-2 | ta-192 | sp-2 | an-192 |
| 586 | is-2 | ta-193 | sp-2 | an-193 |
| 587 | is-2 | ta-194 | sp-2 | an-194 |
| 588 | is-2 | ta-195 | sp-2 | an-195 |
| 589 | is-2 | ta-196 | sp-2 | an-196 |
| 590 | is-2 | ta-197 | sp-2 | an-197 |
| 591 | is-2 | ta-198 | sp-2 | an-198 |
| 592 | is-2 | ta-199 | sp-2 | an-199 |
| 593 | is-2 | ta-200 | sp-2 | an-200 |
| 594 | is-2 | ta-201 | sp-2 | an-201 |
| 595 | is-2 | ta-202 | sp-2 | an-202 |
| 596 | is-2 | ta-203 | sp-2 | an-203 |
| 597 | is-2 | ta-204 | sp-2 | an-204 |
| 598 | is-2 | ta-205 | sp-2 | an-205 |
| 599 | is-2 | ta-206 | sp-2 | an-206 |
| 600 | is-2 | ta-207 | sp-2 | an-207 |
| 601 | is-2 | ta-208 | sp-2 | an-208 |
| 602 | is-2 | ta-209 | sp-2 | an-209 |
| 603 | is-2 | ta-210 | sp-2 | an-210 |
| 604 | is-2 | ta-211 | sp-2 | an-211 |
| 605 | is-2 | ta-212 | sp-2 | an-212 |
| 606 | is-2 | ta-213 | sp-2 | an-213 |
| 607 | is-2 | ta-214 | sp-2 | an-214 |
| 608 | is-2 | ta-215 | sp-2 | an-215 |
| 609 | is-2 | ta-216 | sp-2 | an-216 |
| 610 | is-2 | ta-217 | sp-2 | an-217 |
| 611 | is-2 | ta-218 | sp-2 | an-218 |
| 612 | is-2 | ta-219 | sp-2 | an-219 |
| 613 | is-2 | ta-220 | sp-2 | an-220 |
| 614 | is-2 | ta-221 | sp-2 | an-221 |
| 615 | is-2 | ta-222 | sp-2 | an-222 |
| 616 | is-2 | ta-223 | sp-2 | an-223 |
| 617 | is-2 | ta-224 | sp-2 | an-224 |
| 618 | is-2 | ta-225 | sp-2 | an-225 |
| 619 | is-2 | ta-226 | sp-2 | an-226 |
| 620 | is-2 | ta-227 | sp-2 | an-227 |
| 621 | is-2 | ta-228 | sp-2 | an-228 |
| 622 | is-2 | ta-229 | sp-2 | an-229 |
| 623 | is-2 | ta-230 | sp-2 | an-230 |

TABLE 2-continued

| Example No. | Reaction reagent is | Reaction reagent ta | Compound of Example sp | Compound of Example an |
|---|---|---|---|---|
| 624 | is-2 | ta-231 | sp-2 | an-231 |
| 625 | is-2 | ta-232 | sp-2 | an-232 |
| 626 | is-2 | ta-233 | sp-2 | an-233 |
| 627 | is-2 | ta-234 | sp-2 | an-234 |
| 628 | is-2 | ta-235 | sp-2 | an-235 |
| 629 | is-2 | ta-236 | sp-2 | an-236 |
| 630 | is-2 | ta-237 | sp-2 | an-237 |
| 631 | is-2 | ta-238 | sp-2 | an-238 |
| 632 | is-2 | ta-239 | sp-2 | an-239 |
| 633 | is-2 | ta-240 | sp-2 | an-240 |
| 634 | is-2 | ta-241 | sp-2 | an-241 |
| 635 | is-2 | ta-242 | sp-2 | an-242 |
| 636 | is-2 | ta-243 | sp-2 | an-243 |
| 637 | is-2 | ta-244 | sp-2 | an-244 |
| 638 | is-2 | ta-245 | sp-2 | an-245 |
| 639 | is-2 | ta-246 | sp-2 | an-246 |
| 640 | is-2 | ta-247 | sp-2 | an-247 |
| 641 | is-2 | ta-248 | sp-2 | an-248 |
| 642 | is-2 | ta-249 | sp-2 | an-249 |
| 643 | is-2 | ta-250 | sp-2 | an-250 |
| 644 | is-2 | ta-251 | sp-2 | an-251 |
| 645 | is-2 | ta-252 | sp-2 | an-252 |
| 646 | is-2 | ta-253 | sp-2 | an-253 |
| 647 | is-2 | ta-254 | sp-2 | an-254 |
| 648 | is-2 | ta-255 | sp-2 | an-255 |
| 649 | is-2 | ta-256 | sp-2 | an-256 |
| 650 | is-2 | ta-257 | sp-2 | an-257 |
| 651 | is-2 | ta-258 | sp-2 | an-258 |
| 652 | is-2 | ta-259 | sp-2 | an-259 |
| 653 | is-2 | ta-260 | sp-2 | an-260 |
| 654 | is-2 | ta-261 | sp-2 | an-261 |
| 655 | is-2 | ta-262 | sp-2 | an-262 |
| 656 | is-2 | ta-263 | sp-2 | an-263 |
| 657 | is-2 | ta-264 | sp-2 | an-264 |
| 658 | is-2 | ta-265 | sp-2 | an-265 |
| 659 | is-2 | ta-266 | sp-2 | an-266 |
| 660 | is-2 | ta-267 | sp-2 | an-267 |
| 661 | is-2 | ta-268 | sp-2 | an-268 |
| 662 | is-2 | ta-269 | sp-2 | an-269 |
| 663 | is-2 | ta-270 | sp-2 | an-270 |
| 664 | is-2 | ta-271 | sp-2 | an-271 |
| 665 | is-2 | ta-272 | sp-2 | an-272 |
| 666 | is-2 | ta-273 | sp-2 | an-273 |
| 667 | is-2 | ta-274 | sp-2 | an-274 |
| 668 | is-2 | ta-275 | sp-2 | an-275 |
| 669 | is-2 | ta-276 | sp-2 | an-276 |
| 670 | is-2 | ta-277 | sp-2 | an-277 |
| 671 | is-2 | ta-278 | sp-2 | an-278 |
| 672 | is-2 | ta-279 | sp-2 | an-279 |
| 673 | is-2 | ta-280 | sp-2 | an-280 |
| 674 | is-2 | ta-281 | sp-2 | an-281 |
| 675 | is-2 | ta-282 | sp-2 | an-282 |
| 676 | is-2 | ta-283 | sp-2 | an-283 |
| 677 | is-2 | ta-284 | sp-2 | an-284 |
| 678 | is-2 | ta-285 | sp-2 | an-285 |
| 679 | is-2 | ta-286 | sp-2 | an-286 |
| 9 | is-2 | ta-287 | sp-2 | an-287 |
| 680 | is-2 | ta-288 | sp-2 | an-288 |
| 681 | is-2 | ta-289 | sp-2 | an-289 |
| 682 | is-2 | ta-290 | sp-2 | an-290 |
| 683 | is-2 | ta-291 | sp-2 | an-291 |
| 684 | is-2 | ta-292 | sp-2 | an-292 |
| 685 | is-2 | ta-293 | sp-2 | an-293 |
| 686 | is-2 | ta-294 | sp-2 | an-294 |
| 687 | is-2 | ta-295 | sp-2 | an-295 |
| 688 | is-2 | ta-296 | sp-2 | an-296 |
| 689 | is-2 | ta-297 | sp-2 | an-297 |
| 690 | is-2 | ta-298 | sp-2 | an-298 |
| 691 | is-2 | ta-299 | sp-2 | an-299 |
| 692 | is-2 | ta-300 | sp-2 | an-300 |
| 693 | is-2 | ta-301 | sp-2 | an-301 |
| 694 | is-2 | ta-302 | sp-2 | an-302 |
| 695 | is-2 | ta-303 | sp-2 | an-303 |
| 696 | is-2 | ta-304 | sp-2 | an-304 |
| 697 | is-2 | ta-305 | sp-2 | an-305 |
| 698 | is-2 | ta-306 | sp-2 | an-306 |
| 699 | is-2 | ta-307 | sp-2 | an-307 |
| 700 | is-2 | ta-308 | sp-2 | an-308 |
| 701 | is-2 | ta-309 | sp-2 | an-309 |
| 702 | is-2 | ta-310 | sp-2 | an-310 |
| 703 | is-2 | ta-311 | sp-2 | an-311 |
| 704 | is-2 | ta-312 | sp-2 | an-312 |
| 705 | is-2 | ta-313 | sp-2 | an-313 |
| 706 | is-2 | ta-314 | sp-2 | an-314 |
| 707 | is-2 | ta-315 | sp-2 | an-315 |
| 708 | is-2 | ta-316 | sp-2 | an-316 |
| 709 | is-2 | ta-317 | sp-2 | an-317 |
| 710 | is-2 | ta-318 | sp-2 | an-318 |
| 711 | is-2 | ta-319 | sp-2 | an-319 |
| 712 | is-2 | ta-320 | sp-2 | an-320 |
| 713 | is-2 | ta-321 | sp-2 | an-321 |
| 714 | is-2 | ta-322 | sp-2 | an-322 |
| 715 | is-2 | ta-323 | sp-2 | an-323 |
| 716 | is-2 | ta-324 | sp-2 | an-324 |
| 717 | is-2 | ta-325 | sp-2 | an-325 |
| 718 | is-2 | ta-326 | sp-2 | an-326 |
| 719 | is-2 | ta-327 | sp-2 | an-327 |
| 720 | is-2 | ta-328 | sp-2 | an-328 |
| 721 | is-2 | ta-329 | sp-2 | an-329 |
| 722 | is-2 | ta-330 | sp-2 | an-330 |
| 723 | is-2 | ta-331 | sp-2 | an-331 |
| 724 | is-2 | ta-332 | sp-2 | an-332 |
| 725 | is-2 | ta-333 | sp-2 | an-333 |
| 726 | is-2 | ta-334 | sp-2 | an-334 |
| 727 | is-2 | ta-335 | sp-2 | an-335 |
| 728 | is-2 | ta-336 | sp-2 | an-336 |
| 729 | is-2 | ta-337 | sp-2 | an-337 |
| 730 | is-2 | ta-338 | sp-2 | an-338 |
| 731 | is-2 | ta-339 | sp-2 | an-339 |
| 732 | is-2 | ta-340 | sp-2 | an-340 |
| 733 | is-2 | ta-341 | sp-2 | an-341 |
| 734 | is-2 | ta-342 | sp-2 | an-342 |
| 735 | is-2 | ta-343 | sp-2 | an-343 |
| 736 | is-2 | ta-344 | sp-2 | an-344 |
| 737 | is-2 | ta-345 | sp-2 | an-345 |
| 738 | is-2 | ta-346 | sp-2 | an-346 |
| 739 | is-2 | ta-347 | sp-2 | an-347 |
| 740 | is-2 | ta-348 | sp-2 | an-348 |
| 741 | is-2 | ta-349 | sp-2 | an-349 |
| 742 | is-2 | ta-350 | sp-2 | an-350 |
| 743 | is-2 | ta-351 | sp-2 | an-351 |
| 744 | is-2 | ta-352 | sp-2 | an-352 |
| 745 | is-2 | ta-353 | sp-2 | an-353 |
| 746 | is-2 | ta-354 | sp-2 | an-354 |
| 747 | is-2 | ta-355 | sp-2 | an-355 |
| 748 | is-2 | ta-356 | sp-2 | an-356 |
| 749 | is-2 | ta-357 | sp-2 | an-357 |
| 750 | is-2 | ta-358 | sp-2 | an-358 |
| 751 | is-2 | ta-359 | sp-2 | an-359 |
| 752 | is-2 | ta-360 | sp-2 | an-360 |
| 753 | is-2 | ta-361 | sp-2 | an-361 |
| 754 | is-2 | ta-362 | sp-2 | an-362 |
| 755 | is-2 | ta-363 | sp-2 | an-363 |
| 756 | is-2 | ta-364 | sp-2 | an-364 |
| 757 | is-2 | ta-365 | sp-2 | an-365 |
| 758 | is-2 | ta-366 | sp-2 | an-366 |
| 759 | is-2 | ta-367 | sp-2 | an-367 |
| 760 | is-2 | ta-368 | sp-2 | an-368 |
| 761 | is-2 | ta-369 | sp-2 | an-369 |
| 762 | is-2 | ta-370 | sp-2 | an-370 |
| 763 | is-2 | ta-371 | sp-2 | an-371 |
| 764 | is-2 | ta-372 | sp-2 | an-372 |
| 765 | is-2 | ta-373 | sp-2 | an-373 |
| 766 | is-2 | ta-374 | sp-2 | an-374 |
| 767 | is-2 | ta-375 | sp-2 | an-375 |
| 768 | is-2 | ta-376 | sp-2 | an-376 |
| 769 | is-2 | ta-377 | sp-2 | an-377 |
| 770 | is-3 | ta-1 | sp-3 | an-1 |

TABLE 2-continued

| Example No. | Reaction reagent is | Reaction reagent ta | Compound of Example sp | Compound of Example an |
|---|---|---|---|---|
| 771 | is-3 | ta-2 | sp-3 | an-2 |
| 772 | is-3 | ta-3 | sp-3 | an-3 |
| 773 | is-3 | ta-4 | sp-3 | an-4 |
| 774 | is-3 | ta-5 | sp-3 | an-5 |
| 775 | is-3 | ta-6 | sp-3 | an-6 |
| 776 | is-3 | ta-7 | sp-3 | an-7 |
| 777 | is-3 | ta-8 | sp-3 | an-8 |
| 778 | is-3 | ta-9 | sp-3 | an-9 |
| 779 | is-3 | ta-10 | sp-3 | an-10 |
| 780 | is-3 | ta-11 | sp-3 | an-11 |
| 781 | is-3 | ta-12 | sp-3 | an-12 |
| 782 | is-3 | ta-13 | sp-3 | an-13 |
| 783 | is-3 | ta-14 | sp-3 | an-14 |
| 784 | is-3 | ta-15 | sp-3 | an-15 |
| 785 | is-3 | ta-16 | sp-3 | an-16 |
| 786 | is-3 | ta-17 | sp-3 | an-17 |
| 787 | is-3 | ta-18 | sp-3 | an-18 |
| 788 | is-3 | ta-19 | sp-3 | an-19 |
| 789 | is-3 | ta-20 | sp-3 | an-20 |
| 790 | is-3 | ta-21 | sp-3 | an-21 |
| 791 | is-3 | ta-22 | sp-3 | an-22 |
| 792 | is-3 | ta-23 | sp-3 | an-23 |
| 793 | is-3 | ta-24 | sp-3 | an-24 |
| 794 | is-3 | ta-25 | sp-3 | an-25 |
| 795 | is-3 | ta-26 | sp-3 | an-26 |
| 796 | is-3 | ta-27 | sp-3 | an-27 |
| 797 | is-3 | ta-28 | sp-3 | an-28 |
| 798 | is-3 | ta-29 | sp-3 | an-29 |
| 799 | is-3 | ta-30 | sp-3 | an-30 |
| 800 | is-3 | ta-31 | sp-3 | an-31 |
| 801 | is-3 | ta-32 | sp-3 | an-32 |
| 802 | is-3 | ta-33 | sp-3 | an-33 |
| 803 | is-3 | ta-34 | sp-3 | an-34 |
| 804 | is-3 | ta-35 | sp-3 | an-35 |
| 805 | is-3 | ta-36 | sp-3 | an-36 |
| 806 | is-3 | ta-37 | sp-3 | an-37 |
| 807 | is-3 | ta-38 | sp-3 | an-38 |
| 808 | is-3 | ta-39 | sp-3 | an-39 |
| 809 | is-3 | ta-40 | sp-3 | an-40 |
| 810 | is-3 | ta-41 | sp-3 | an-41 |
| 811 | is-3 | ta-42 | sp-3 | an-42 |
| 812 | is-3 | ta-43 | sp-3 | an-43 |
| 813 | is-3 | ta-44 | sp-3 | an-44 |
| 814 | is-3 | ta-45 | sp-3 | an-45 |
| 815 | is-3 | ta-46 | sp-3 | an-46 |
| 816 | is-3 | ta-47 | sp-3 | an-47 |
| 817 | is-3 | ta-48 | sp-3 | an-48 |
| 818 | is-3 | ta-49 | sp-3 | an-49 |
| 819 | is-3 | ta-50 | sp-3 | an-50 |
| 820 | is-3 | ta-51 | sp-3 | an-51 |
| 821 | is-3 | ta-52 | sp-3 | an-52 |
| 822 | is-3 | ta-53 | sp-3 | an-53 |
| 823 | is-3 | ta-54 | sp-3 | an-54 |
| 824 | is-3 | ta-55 | sp-3 | an-55 |
| 825 | is-3 | ta-56 | sp-3 | an-56 |
| 826 | is-3 | ta-57 | sp-3 | an-57 |
| 827 | is-3 | ta-58 | sp-3 | an-58 |
| 828 | is-3 | ta-59 | sp-3 | an-59 |
| 829 | is-3 | ta-60 | sp-3 | an-60 |
| 830 | is-3 | ta-61 | sp-3 | an-61 |
| 831 | is-3 | ta-62 | sp-3 | an-62 |
| 832 | is-3 | ta-63 | sp-3 | an-63 |
| 833 | is-3 | ta-64 | sp-3 | an-64 |
| 834 | is-3 | ta-65 | sp-3 | an-65 |
| 835 | is-3 | ta-66 | sp-3 | an-66 |
| 836 | is-3 | ta-67 | sp-3 | an-67 |
| 837 | is-3 | ta-68 | sp-3 | an-68 |
| 838 | is-3 | ta-69 | sp-3 | an-69 |
| 839 | is-3 | ta-70 | sp-3 | an-70 |
| 840 | is-3 | ta-71 | sp-3 | an-71 |
| 841 | is-3 | ta-72 | sp-3 | an-72 |
| 842 | is-3 | ta-73 | sp-3 | an-73 |
| 843 | is-3 | ta-74 | sp-3 | an-74 |
| 844 | is-3 | ta-75 | sp-3 | an-75 |
| 845 | is-3 | ta-76 | sp-3 | an-76 |
| 846 | is-3 | ta-77 | sp-3 | an-77 |
| 847 | is-3 | ta-78 | sp-3 | an-78 |
| 848 | is-3 | ta-79 | sp-3 | an-79 |
| 849 | is-3 | ta-80 | sp-3 | an-80 |
| 850 | is-3 | ta-81 | sp-3 | an-81 |
| 851 | is-3 | ta-82 | sp-3 | an-82 |
| 852 | is-3 | ta-83 | sp-3 | an-83 |
| 853 | is-3 | ta-84 | sp-3 | an-84 |
| 854 | is-3 | ta-85 | sp-3 | an-85 |
| 855 | is-3 | ta-86 | sp-3 | an-86 |
| 856 | is-3 | ta-87 | sp-3 | an-87 |
| 857 | is-3 | ta-88 | sp-3 | an-88 |
| 858 | is-3 | ta-89 | sp-3 | an-89 |
| 859 | is-3 | ta-90 | sp-3 | an-90 |
| 860 | is-3 | ta-91 | sp-3 | an-91 |
| 861 | is-3 | ta-92 | sp-3 | an-92 |
| 862 | is-3 | ta-93 | sp-3 | an-93 |
| 863 | is-3 | ta-94 | sp-3 | an-94 |
| 864 | is-3 | ta-95 | sp-3 | an-95 |
| 865 | is-3 | ta-96 | sp-3 | an-96 |
| 866 | is-3 | ta-97 | sp-3 | an-97 |
| 867 | is-3 | ta-98 | sp-3 | an-98 |
| 868 | is-3 | ta-99 | sp-3 | an-99 |
| 869 | is-3 | ta-100 | sp-3 | an-100 |
| 870 | is-3 | ta-101 | sp-3 | an-101 |
| 871 | is-3 | ta-102 | sp-3 | an-102 |
| 872 | is-3 | ta-103 | sp-3 | an-103 |
| 873 | is-3 | ta-104 | sp-3 | an-104 |
| 874 | is-3 | ta-105 | sp-3 | an-105 |
| 875 | is-3 | ta-106 | sp-3 | an-106 |
| 876 | is-3 | ta-107 | sp-3 | an-107 |
| 877 | is-3 | ta-108 | sp-3 | an-108 |
| 878 | is-3 | ta-109 | sp-3 | an-109 |
| 879 | is-3 | ta-110 | sp-3 | an-110 |
| 880 | is-3 | ta-111 | sp-3 | an-111 |
| 881 | is-3 | ta-112 | sp-3 | an-112 |
| 882 | is-3 | ta-113 | sp-3 | an-113 |
| 883 | is-3 | ta-114 | sp-3 | an-114 |
| 884 | is-3 | ta-115 | sp-3 | an-115 |
| 885 | is-3 | ta-116 | sp-3 | an-116 |
| 886 | is-3 | ta-117 | sp-3 | an-117 |
| 887 | is-3 | ta-118 | sp-3 | an-118 |
| 888 | is-3 | ta-119 | sp-3 | an-119 |
| 889 | is-3 | ta-120 | sp-3 | an-120 |
| 890 | is-3 | ta-121 | sp-3 | an-121 |
| 891 | is-3 | ta-122 | sp-3 | an-122 |
| 892 | is-3 | ta-123 | sp-3 | an-123 |
| 893 | is-3 | ta-124 | sp-3 | an-124 |
| 894 | is-3 | ta-125 | sp-3 | an-125 |
| 895 | is-3 | ta-126 | sp-3 | an-126 |
| 896 | is-3 | ta-127 | sp-3 | an-127 |
| 897 | is-3 | ta-128 | sp-3 | an-128 |
| 898 | is-3 | ta-129 | sp-3 | an-129 |
| 899 | is-3 | ta-130 | sp-3 | an-130 |
| 900 | is-3 | ta-131 | sp-3 | an-131 |
| 901 | is-3 | ta-132 | sp-3 | an-132 |
| 902 | is-3 | ta-133 | sp-3 | an-133 |
| 903 | is-3 | ta-134 | sp-3 | an-134 |
| 904 | is-3 | ta-135 | sp-3 | an-135 |
| 905 | is-3 | ta-136 | sp-3 | an-136 |
| 906 | is-3 | ta-137 | sp-3 | an-137 |
| 907 | is-3 | ta-138 | sp-3 | an-138 |
| 908 | is-3 | ta-139 | sp-3 | an-139 |
| 909 | is-3 | ta-140 | sp-3 | an-140 |
| 910 | is-3 | ta-141 | sp-3 | an-141 |
| 911 | is-3 | ta-142 | sp-3 | an-142 |
| 912 | is-3 | ta-143 | sp-3 | an-143 |
| 913 | is-3 | ta-144 | sp-3 | an-144 |
| 914 | is-3 | ta-145 | sp-3 | an-145 |
| 915 | is-3 | ta-146 | sp-3 | an-146 |
| 916 | is-3 | ta-147 | sp-3 | an-147 |
| 917 | is-3 | ta-148 | sp-3 | an-148 |
| 918 | is-3 | ta-149 | sp-3 | an-149 |

TABLE 2-continued

| Example No. | Reaction reagent is | Reaction reagent ta | Compound of Example sp | Compound of Example an |
|---|---|---|---|---|
| 919 | is-3 | ta-150 | sp-3 | an-150 |
| 920 | is-3 | ta-151 | sp-3 | an-151 |
| 921 | is-3 | ta-152 | sp-3 | an-152 |
| 922 | is-3 | ta-153 | sp-3 | an-153 |
| 923 | is-3 | ta-154 | sp-3 | an-154 |
| 924 | is-3 | ta-155 | sp-3 | an-155 |
| 925 | is-3 | ta-156 | sp-3 | an-156 |
| 926 | is-3 | ta-157 | sp-3 | an-157 |
| 927 | is-3 | ta-158 | sp-3 | an-158 |
| 928 | is-3 | ta-159 | sp-3 | an-159 |
| 929 | is-3 | ta-160 | sp-3 | an-160 |
| 930 | is-3 | ta-161 | sp-3 | an-161 |
| 931 | is-3 | ta-162 | sp-3 | an-162 |
| 932 | is-3 | ta-163 | sp-3 | an-163 |
| 933 | is-3 | ta-164 | sp-3 | an-164 |
| 934 | is-3 | ta-165 | sp-3 | an-165 |
| 935 | is-3 | ta-166 | sp-3 | an-166 |
| 936 | is-3 | ta-167 | sp-3 | an-167 |
| 937 | is-3 | ta-168 | sp-3 | an-168 |
| 938 | is-3 | ta-169 | sp-3 | an-169 |
| 939 | is-3 | ta-170 | sp-3 | an-170 |
| 940 | is-3 | ta-171 | sp-3 | an-171 |
| 941 | is-3 | ta-172 | sp-3 | an-172 |
| 942 | is-3 | ta-173 | sp-3 | an-173 |
| 943 | is-3 | ta-174 | sp-3 | an-174 |
| 944 | is-3 | ta-175 | sp-3 | an-175 |
| 945 | is-3 | ta-176 | sp-3 | an-176 |
| 946 | is-3 | ta-177 | sp-3 | an-177 |
| 947 | is-3 | ta-178 | sp-3 | an-178 |
| 948 | is-3 | ta-179 | sp-3 | an-179 |
| 949 | is-3 | ta-180 | sp-3 | an-180 |
| 950 | is-3 | ta-181 | sp-3 | an-181 |
| 951 | is-3 | ta-182 | sp-3 | an-182 |
| 952 | is-3 | ta-183 | sp-3 | an-183 |
| 953 | is-3 | ta-184 | sp-3 | an-184 |
| 954 | is-3 | ta-185 | sp-3 | an-185 |
| 955 | is-3 | ta-186 | sp-3 | an-186 |
| 956 | is-3 | ta-187 | sp-3 | an-187 |
| 957 | is-3 | ta-188 | sp-3 | an-188 |
| 958 | is-3 | ta-189 | sp-3 | an-189 |
| 959 | is-3 | ta-190 | sp-3 | an-190 |
| 960 | is-3 | ta-191 | sp-3 | an-191 |
| 961 | is-3 | ta-192 | sp-3 | an-192 |
| 962 | is-3 | ta-193 | sp-3 | an-193 |
| 963 | is-3 | ta-194 | sp-3 | an-194 |
| 964 | is-3 | ta-195 | sp-3 | an-195 |
| 965 | is-3 | ta-196 | sp-3 | an-196 |
| 966 | is-3 | ta-197 | sp-3 | an-197 |
| 967 | is-3 | ta-198 | sp-3 | an-198 |
| 968 | is-3 | ta-199 | sp-3 | an-199 |
| 969 | is-3 | ta-200 | sp-3 | an-200 |
| 970 | is-3 | ta-201 | sp-3 | an-201 |
| 971 | is-3 | ta-202 | sp-3 | an-202 |
| 972 | is-3 | ta-203 | sp-3 | an-203 |
| 973 | is-3 | ta-204 | sp-3 | an-204 |
| 974 | is-3 | ta-205 | sp-3 | an-205 |
| 975 | is-3 | ta-206 | sp-3 | an-206 |
| 976 | is-3 | ta-207 | sp-3 | an-207 |
| 977 | is-3 | ta-208 | sp-3 | an-208 |
| 978 | is-3 | ta-209 | sp-3 | an-209 |
| 979 | is-3 | ta-210 | sp-3 | an-210 |
| 980 | is-3 | ta-211 | sp-3 | an-211 |
| 981 | is-3 | ta-212 | sp-3 | an-212 |
| 982 | is-3 | ta-213 | sp-3 | an-213 |
| 983 | is-3 | ta-214 | sp-3 | an-214 |
| 984 | is-3 | ta-215 | sp-3 | an-215 |
| 985 | is-3 | ta-216 | sp-3 | an-216 |
| 986 | is-3 | ta-217 | sp-3 | an-217 |
| 987 | is-3 | ta-218 | sp-3 | an-218 |
| 988 | is-3 | ta-219 | sp-3 | an-219 |
| 989 | is-3 | ta-220 | sp-3 | an-220 |
| 990 | is-3 | ta-221 | sp-3 | an-221 |
| 991 | is-3 | ta-222 | sp-3 | an-222 |
| 992 | is-3 | ta-223 | sp-3 | an-223 |
| 993 | is-3 | ta-224 | sp-3 | an-224 |
| 994 | is-3 | ta-225 | sp-3 | an-225 |
| 995 | is-3 | ta-226 | sp-3 | an-226 |
| 996 | is-3 | ta-227 | sp-3 | an-227 |
| 997 | is-3 | ta-228 | sp-3 | an-228 |
| 998 | is-3 | ta-229 | sp-3 | an-229 |
| 999 | is-3 | ta-230 | sp-3 | an-230 |
| 1000 | is-3 | ta-231 | sp-3 | an-231 |
| 1001 | is-3 | ta-232 | sp-3 | an-232 |
| 1002 | is-3 | ta-233 | sp-3 | an-233 |
| 1003 | is-3 | ta-234 | sp-3 | an-234 |
| 1004 | is-3 | ta-235 | sp-3 | an-235 |
| 1005 | is-3 | ta-236 | sp-3 | an-236 |
| 1006 | is-3 | ta-237 | sp-3 | an-237 |
| 1007 | is-3 | ta-238 | sp-3 | an-238 |
| 1008 | is-3 | ta-239 | sp-3 | an-239 |
| 1009 | is-3 | ta-240 | sp-3 | an-240 |
| 1010 | is-3 | ta-241 | sp-3 | an-241 |
| 1011 | is-3 | ta-242 | sp-3 | an-242 |
| 1012 | is-3 | ta-243 | sp-3 | an-243 |
| 1013 | is-3 | ta-244 | sp-3 | an-244 |
| 1014 | is-3 | ta-245 | sp-3 | an-245 |
| 1015 | is-3 | ta-246 | sp-3 | an-246 |
| 1016 | is-3 | ta-247 | sp-3 | an-247 |
| 1017 | is-3 | ta-248 | sp-3 | an-248 |
| 1018 | is-3 | ta-249 | sp-3 | an-249 |
| 1019 | is-3 | ta-250 | sp-3 | an-250 |
| 1020 | is-3 | ta-251 | sp-3 | an-251 |
| 1021 | is-3 | ta-252 | sp-3 | an-252 |
| 1022 | is-3 | ta-253 | sp-3 | an-253 |
| 1023 | is-3 | ta-254 | sp-3 | an-254 |
| 1024 | is-3 | ta-255 | sp-3 | an-255 |
| 1025 | is-3 | ta-256 | sp-3 | an-256 |
| 1026 | is-3 | ta-257 | sp-3 | an-257 |
| 1027 | is-3 | ta-258 | sp-3 | an-258 |
| 1028 | is-3 | ta-259 | sp-3 | an-259 |
| 1029 | is-3 | ta-260 | sp-3 | an-260 |
| 1030 | is-3 | ta-261 | sp-3 | an-261 |
| 1031 | is-3 | ta-262 | sp-3 | an-262 |
| 1032 | is-3 | ta-263 | sp-3 | an-263 |
| 1033 | is-3 | ta-264 | sp-3 | an-264 |
| 1034 | is-3 | ta-265 | sp-3 | an-265 |
| 1035 | is-3 | ta-266 | sp-3 | an-266 |
| 1036 | is-3 | ta-267 | sp-3 | an-267 |
| 1037 | is-3 | ta-268 | sp-3 | an-268 |
| 1038 | is-3 | ta-269 | sp-3 | an-269 |
| 1039 | is-3 | ta-270 | sp-3 | an-270 |
| 1040 | is-3 | ta-271 | sp-3 | an-271 |
| 1041 | is-3 | ta-272 | sp-3 | an-272 |
| 1042 | is-3 | ta-273 | sp-3 | an-273 |
| 1043 | is-3 | ta-274 | sp-3 | an-274 |
| 1044 | is-3 | ta-275 | sp-3 | an-275 |
| 1045 | is-3 | ta-276 | sp-3 | an-276 |
| 1046 | is-3 | ta-277 | sp-3 | an-277 |
| 1047 | is-3 | ta-278 | sp-3 | an-278 |
| 1048 | is-3 | ta-279 | sp-3 | an-279 |
| 1049 | is-3 | ta-280 | sp-3 | an-280 |
| 1050 | is-3 | ta-281 | sp-3 | an-281 |
| 1051 | is-3 | ta-282 | sp-3 | an-282 |
| 1052 | is-3 | ta-283 | sp-3 | an-283 |
| 1053 | is-3 | ta-284 | sp-3 | an-284 |
| 1054 | is-3 | ta-285 | sp-3 | an-285 |
| 1055 | is-3 | ta-286 | sp-3 | an-286 |
| 1056 | is-3 | ta-287 | sp-3 | an-287 |
| 1057 | is-3 | ta-288 | sp-3 | an-288 |
| 1058 | is-3 | ta-289 | sp-3 | an-289 |
| 1059 | is-3 | ta-290 | sp-3 | an-290 |
| 1060 | is-3 | ta-291 | sp-3 | an-291 |
| 1061 | is-3 | ta-292 | sp-3 | an-292 |
| 1062 | is-3 | ta-293 | sp-3 | an-293 |
| 1063 | is-3 | ta-294 | sp-3 | an-294 |
| 1064 | is-3 | ta-295 | sp-3 | an-295 |
| 1065 | is-3 | ta-296 | sp-3 | an-296 |
| 1066 | is-3 | ta-297 | sp-3 | an-297 |

TABLE 2-continued

| Example No. | Reaction reagent is | Reaction reagent ta | Compound of Example sp | Compound of Example an |
|---|---|---|---|---|
| 1067 | is-3 | ta-298 | sp-3 | an-298 |
| 1068 | is-3 | ta-299 | sp-3 | an-299 |
| 1069 | is-3 | ta-300 | sp-3 | an-300 |
| 1070 | is-3 | ta-301 | sp-3 | an-301 |
| 1071 | is-3 | ta-302 | sp-3 | an-302 |
| 1072 | is-3 | ta-303 | sp-3 | an-303 |
| 1073 | is-3 | ta-304 | sp-3 | an-304 |
| 1074 | is-3 | ta-305 | sp-3 | an-305 |
| 1075 | is-3 | ta-306 | sp-3 | an-306 |
| 1076 | is-3 | ta-307 | sp-3 | an-307 |
| 1077 | is-3 | ta-308 | sp-3 | an-308 |
| 1078 | is-3 | ta-309 | sp-3 | an-309 |
| 1079 | is-3 | ta-310 | sp-3 | an-310 |
| 1080 | is-3 | ta-311 | sp-3 | an-311 |
| 1081 | is-3 | ta-312 | sp-3 | an-312 |
| 1082 | is-3 | ta-313 | sp-3 | an-313 |
| 1083 | is-3 | ta-314 | sp-3 | an-314 |
| 1084 | is-3 | ta-315 | sp-3 | an-315 |
| 1085 | is-3 | ta-316 | sp-3 | an-316 |
| 1086 | is-3 | ta-317 | sp-3 | an-317 |
| 1087 | is-3 | ta-318 | sp-3 | an-318 |
| 1088 | is-3 | ta-319 | sp-3 | an-319 |
| 1089 | is-3 | ta-320 | sp-3 | an-320 |
| 1090 | is-3 | ta-321 | sp-3 | an-321 |
| 1091 | is-3 | ta-322 | sp-3 | an-322 |
| 1092 | is-3 | ta-323 | sp-3 | an-323 |
| 1093 | is-3 | ta-324 | sp-3 | an-324 |
| 1094 | is-3 | ta-325 | sp-3 | an-325 |
| 1095 | is-3 | ta-326 | sp-3 | an-326 |
| 1096 | is-3 | ta-327 | sp-3 | an-327 |
| 1097 | is-3 | ta-328 | sp-3 | an-328 |
| 1098 | is-3 | ta-329 | sp-3 | an-329 |
| 1099 | is-3 | ta-330 | sp-3 | an-330 |
| 1100 | is-3 | ta-331 | sp-3 | an-331 |
| 1101 | is-3 | ta-332 | sp-3 | an-332 |
| 1102 | is-3 | ta-333 | sp-3 | an-333 |
| 1103 | is-3 | ta-334 | sp-3 | an-334 |
| 1104 | is-3 | ta-335 | sp-3 | an-335 |
| 1105 | is-3 | ta-336 | sp-3 | an-336 |
| 1106 | is-3 | ta-337 | sp-3 | an-337 |
| 1107 | is-3 | ta-338 | sp-3 | an-338 |
| 1108 | is-3 | ta-339 | sp-3 | an-339 |
| 1109 | is-3 | ta-340 | sp-3 | an-340 |
| 1110 | is-3 | ta-341 | sp-3 | an-341 |
| 1111 | is-3 | ta-342 | sp-3 | an-342 |
| 1112 | is-3 | ta-343 | sp-3 | an-343 |
| 1113 | is-3 | ta-344 | sp-3 | an-344 |
| 1114 | is-3 | ta-345 | sp-3 | an-345 |
| 1115 | is-3 | ta-346 | sp-3 | an-346 |
| 1116 | is-3 | ta-347 | sp-3 | an-347 |
| 1117 | is-3 | ta-348 | sp-3 | an-348 |
| 1118 | is-3 | ta-349 | sp-3 | an-349 |
| 1119 | is-3 | ta-350 | sp-3 | an-350 |
| 1120 | is-3 | ta-351 | sp-3 | an-351 |
| 1121 | is-3 | ta-352 | sp-3 | an-352 |
| 1122 | is-3 | ta-353 | sp-3 | an-353 |
| 1123 | is-3 | ta-354 | sp-3 | an-354 |
| 1124 | is-3 | ta-355 | sp-3 | an-355 |
| 1125 | is-3 | ta-356 | sp-3 | an-356 |
| 1126 | is-3 | ta-357 | sp-3 | an-357 |
| 1127 | is-3 | ta-358 | sp-3 | an-358 |
| 1128 | is-3 | ta-359 | sp-3 | an-359 |
| 1129 | is-3 | ta-360 | sp-3 | an-360 |
| 1130 | is-3 | ta-361 | sp-3 | an-361 |
| 1131 | is-3 | ta-362 | sp-3 | an-362 |
| 1132 | is-3 | ta-363 | sp-3 | an-363 |
| 1133 | is-3 | ta-364 | sp-3 | an-364 |
| 1134 | is-3 | ta-365 | sp-3 | an-365 |
| 1135 | is-3 | ta-366 | sp-3 | an-366 |
| 1136 | is-3 | ta-367 | sp-3 | an-367 |
| 1137 | is-3 | ta-368 | sp-3 | an-368 |
| 1138 | is-3 | ta-369 | sp-3 | an-369 |
| 1139 | is-3 | ta-370 | sp-3 | an-370 |
| 1140 | is-3 | ta-371 | sp-3 | an-371 |
| 1141 | is-3 | ta-372 | sp-3 | an-372 |
| 1142 | is-3 | ta-373 | sp-3 | an-373 |
| 1143 | is-3 | ta-374 | sp-3 | an-374 |
| 1144 | is-3 | ta-375 | sp-3 | an-375 |
| 1145 | is-3 | ta-376 | sp-3 | an-376 |
| 1146 | is-3 | ta-377 | sp-3 | an-377 |
| 1147 | is-4 | ta-1 | sp-4 | an-1 |
| 1148 | is-4 | ta-2 | sp-4 | an-2 |
| 1149 | is-4 | ta-3 | sp-4 | an-3 |
| 1150 | is-4 | ta-4 | sp-4 | an-4 |
| 1151 | is-4 | ta-5 | sp-4 | an-5 |
| 1152 | is-4 | ta-6 | sp-4 | an-6 |
| 1153 | is-4 | ta-7 | sp-4 | an-7 |
| 1154 | is-4 | ta-8 | sp-4 | an-8 |
| 1155 | is-4 | ta-9 | sp-4 | an-9 |
| 1156 | is-4 | ta-10 | sp-4 | an-10 |
| 1157 | is-4 | ta-11 | sp-4 | an-11 |
| 1158 | is-4 | ta-12 | sp-4 | an-12 |
| 1159 | is-4 | ta-13 | sp-4 | an-13 |
| 1160 | is-4 | ta-14 | sp-4 | an-14 |
| 1161 | is-4 | ta-15 | sp-4 | an-15 |
| 1162 | is-4 | ta-16 | sp-4 | an-16 |
| 1163 | is-4 | ta-17 | sp-4 | an-17 |
| 1164 | is-4 | ta-18 | sp-4 | an-18 |
| 1165 | is-4 | ta-19 | sp-4 | an-19 |
| 1166 | is-4 | ta-20 | sp-4 | an-20 |
| 1167 | is-4 | ta-21 | sp-4 | an-21 |
| 1168 | is-4 | ta-22 | sp-4 | an-22 |
| 1169 | is-4 | ta-23 | sp-4 | an-23 |
| 1170 | is-4 | ta-24 | sp-4 | an-24 |
| 1171 | is-4 | ta-25 | sp-4 | an-25 |
| 1172 | is-4 | ta-26 | sp-4 | an-26 |
| 1173 | is-4 | ta-27 | sp-4 | an-27 |
| 1174 | is-4 | ta-28 | sp-4 | an-28 |
| 1175 | is-4 | ta-29 | sp-4 | an-29 |
| 1176 | is-4 | ta-30 | sp-4 | an-30 |
| 1177 | is-4 | ta-31 | sp-4 | an-31 |
| 1178 | is-4 | ta-32 | sp-4 | an-32 |
| 1179 | is-4 | ta-33 | sp-4 | an-33 |
| 1180 | is-4 | ta-34 | sp-4 | an-34 |
| 1181 | is-4 | ta-35 | sp-4 | an-35 |
| 1182 | is-4 | ta-36 | sp-4 | an-36 |
| 1183 | is-4 | ta-37 | sp-4 | an-37 |
| 1184 | is-4 | ta-38 | sp-4 | an-38 |
| 1185 | is-4 | ta-39 | sp-4 | an-39 |
| 1186 | is-4 | ta-40 | sp-4 | an-40 |
| 1187 | is-4 | ta-41 | sp-4 | an-41 |
| 1188 | is-4 | ta-42 | sp-4 | an-42 |
| 1189 | is-4 | ta-43 | sp-4 | an-43 |
| 1190 | is-4 | ta-44 | sp-4 | an-44 |
| 1191 | is-4 | ta-45 | sp-4 | an-45 |
| 1192 | is-4 | ta-46 | sp-4 | an-46 |
| 1193 | is-4 | ta-47 | sp-4 | an-47 |
| 1194 | is-4 | ta-48 | sp-4 | an-48 |
| 1195 | is-4 | ta-49 | sp-4 | an-49 |
| 1196 | is-4 | ta-50 | sp-4 | an-50 |
| 1197 | is-4 | ta-51 | sp-4 | an-51 |
| 1198 | is-4 | ta-52 | sp-4 | an-52 |
| 1199 | is-4 | ta-53 | sp-4 | an-53 |
| 1200 | is-4 | ta-54 | sp-4 | an-54 |
| 1201 | is-4 | ta-55 | sp-4 | an-55 |
| 1202 | is-4 | ta-56 | sp-4 | an-56 |
| 1203 | is-4 | ta-57 | sp-4 | an-57 |
| 1204 | is-4 | ta-58 | sp-4 | an-58 |
| 1205 | is-4 | ta-59 | sp-4 | an-59 |
| 1206 | is-4 | ta-60 | sp-4 | an-60 |
| 1207 | is-4 | ta-61 | sp-4 | an-61 |
| 1208 | is-4 | ta-62 | sp-4 | an-62 |
| 1209 | is-4 | ta-63 | sp-4 | an-63 |
| 1210 | is-4 | ta-64 | sp-4 | an-64 |
| 1211 | is-4 | ta-65 | sp-4 | an-65 |
| 1212 | is-4 | ta-66 | sp-4 | an-66 |
| 1213 | is-4 | ta-67 | sp-4 | an-67 |
| 1214 | is-4 | ta-68 | sp-4 | an-68 |

TABLE 2-continued

| Example No. | Reaction reagent is | Reaction reagent ta | Compound of Example sp | Compound of Example an |
|---|---|---|---|---|
| 1215 | is-4 | ta-69 | sp-4 | an-69 |
| 1216 | is-4 | ta-70 | sp-4 | an-70 |
| 1217 | is-4 | ta-71 | sp-4 | an-71 |
| 1218 | is-4 | ta-72 | sp-4 | an-72 |
| 1219 | is-4 | ta-73 | sp-4 | an-73 |
| 1220 | is-4 | ta-74 | sp-4 | an-74 |
| 1221 | is-4 | ta-75 | sp-4 | an-75 |
| 1222 | is-4 | ta-76 | sp-4 | an-76 |
| 1223 | is-4 | ta-77 | sp-4 | an-77 |
| 1224 | is-4 | ta-78 | sp-4 | an-78 |
| 1225 | is-4 | ta-79 | sp-4 | an-79 |
| 1226 | is-4 | ta-80 | sp-4 | an-80 |
| 1227 | is-4 | ta-81 | sp-4 | an-81 |
| 1228 | is-4 | ta-82 | sp-4 | an-82 |
| 1229 | is-4 | ta-83 | sp-4 | an-83 |
| 1230 | is-4 | ta-84 | sp-4 | an-84 |
| 1231 | is-4 | ta-85 | sp-4 | an-85 |
| 1232 | is-4 | ta-86 | sp-4 | an-86 |
| 1233 | is-4 | ta-87 | sp-4 | an-87 |
| 1234 | is-4 | ta-88 | sp-4 | an-88 |
| 1235 | is-4 | ta-89 | sp-4 | an-89 |
| 1236 | is-4 | ta-90 | sp-4 | an-90 |
| 1237 | is-4 | ta-91 | sp-4 | an-91 |
| 1238 | is-4 | ta-92 | sp-4 | an-92 |
| 1239 | is-4 | ta-93 | sp-4 | an-93 |
| 1240 | is-4 | ta-94 | sp-4 | an-94 |
| 1241 | is-4 | ta-95 | sp-4 | an-95 |
| 1242 | is-4 | ta-96 | sp-4 | an-96 |
| 1243 | is-4 | ta-97 | sp-4 | an-97 |
| 1244 | is-4 | ta-98 | sp-4 | an-98 |
| 1245 | is-4 | ta-99 | sp-4 | an-99 |
| 1246 | is-4 | ta-100 | sp-4 | an-100 |
| 1247 | is-4 | ta-101 | sp-4 | an-101 |
| 1248 | is-4 | ta-102 | sp-4 | an-102 |
| 1249 | is-4 | ta-103 | sp-4 | an-103 |
| 1250 | is-4 | ta-104 | sp-4 | an-104 |
| 1251 | is-4 | ta-105 | sp-4 | an-105 |
| 1252 | is-4 | ta-106 | sp-4 | an-106 |
| 1253 | is-4 | ta-107 | sp-4 | an-107 |
| 1254 | is-4 | ta-108 | sp-4 | an-108 |
| 1255 | is-4 | ta-109 | sp-4 | an-109 |
| 1256 | is-4 | ta-110 | sp-4 | an-110 |
| 1257 | is-4 | ta-111 | sp-4 | an-111 |
| 1258 | is-4 | ta-112 | sp-4 | an-112 |
| 1259 | is-4 | ta-113 | sp-4 | an-113 |
| 1260 | is-4 | ta-114 | sp-4 | an-114 |
| 1261 | is-4 | ta-115 | sp-4 | an-115 |
| 1262 | is-4 | ta-116 | sp-4 | an-116 |
| 1263 | is-4 | ta-117 | sp-4 | an-117 |
| 1264 | is-4 | ta-118 | sp-4 | an-118 |
| 1265 | is-4 | ta-119 | sp-4 | an-119 |
| 1266 | is-4 | ta-120 | sp-4 | an-120 |
| 1267 | is-4 | ta-121 | sp-4 | an-121 |
| 1268 | is-4 | ta-122 | sp-4 | an-122 |
| 1269 | is-4 | ta-123 | sp-4 | an-123 |
| 1270 | is-4 | ta-124 | sp-4 | an-124 |
| 1271 | is-4 | ta-125 | sp-4 | an-125 |
| 1272 | is-4 | ta-126 | sp-4 | an-126 |
| 1273 | is-4 | ta-127 | sp-4 | an-127 |
| 1274 | is-4 | ta-128 | sp-4 | an-128 |
| 1275 | is-4 | ta-129 | sp-4 | an-129 |
| 1276 | is-4 | ta-130 | sp-4 | an-130 |
| 1277 | is-4 | ta-131 | sp-4 | an-131 |
| 1278 | is-4 | ta-132 | sp-4 | an-132 |
| 1279 | is-4 | ta-133 | sp-4 | an-133 |
| 1280 | is-4 | ta-134 | sp-4 | an-134 |
| 1281 | is-4 | ta-135 | sp-4 | an-135 |
| 1282 | is-4 | ta-136 | sp-4 | an-136 |
| 1283 | is-4 | ta-137 | sp-4 | an-137 |
| 1284 | is-4 | ta-138 | sp-4 | an-138 |
| 1285 | is-4 | ta-139 | sp-4 | an-139 |
| 1286 | is-4 | ta-140 | sp-4 | an-140 |
| 1287 | is-4 | ta-141 | sp-4 | an-141 |
| 1288 | is-4 | ta-142 | sp-4 | an-142 |
| 1289 | is-4 | ta-143 | sp-4 | an-143 |
| 1290 | is-4 | ta-144 | sp-4 | an-144 |
| 1291 | is-4 | ta-145 | sp-4 | an-145 |
| 1292 | is-4 | ta-146 | sp-4 | an-146 |
| 1293 | is-4 | ta-147 | sp-4 | an-147 |
| 1294 | is-4 | ta-148 | sp-4 | an-148 |
| 1295 | is-4 | ta-149 | sp-4 | an-149 |
| 1296 | is-4 | ta-150 | sp-4 | an-150 |
| 1297 | is-4 | ta-151 | sp-4 | an-151 |
| 1298 | is-4 | ta-152 | sp-4 | an-152 |
| 1299 | is-4 | ta-153 | sp-4 | an-153 |
| 1300 | is-4 | ta-154 | sp-4 | an-154 |
| 1301 | is-4 | ta-155 | sp-4 | an-155 |
| 1302 | is-4 | ta-156 | sp-4 | an-156 |
| 1303 | is-4 | ta-157 | sp-4 | an-157 |
| 1304 | is-4 | ta-158 | sp-4 | an-158 |
| 1305 | is-4 | ta-159 | sp-4 | an-159 |
| 1306 | is-4 | ta-160 | sp-4 | an-160 |
| 1307 | is-4 | ta-161 | sp-4 | an-161 |
| 1308 | is-4 | ta-162 | sp-4 | an-162 |
| 1309 | is-4 | ta-163 | sp-4 | an-163 |
| 1310 | is-4 | ta-164 | sp-4 | an-164 |
| 1311 | is-4 | ta-165 | sp-4 | an-165 |
| 1312 | is-4 | ta-166 | sp-4 | an-166 |
| 1313 | is-4 | ta-167 | sp-4 | an-167 |
| 1314 | is-4 | ta-168 | sp-4 | an-168 |
| 1315 | is-4 | ta-169 | sp-4 | an-169 |
| 1316 | is-4 | ta-170 | sp-4 | an-170 |
| 1317 | is-4 | ta-171 | sp-4 | an-171 |
| 1318 | is-4 | ta-172 | sp-4 | an-172 |
| 1319 | is-4 | ta-173 | sp-4 | an-173 |
| 1320 | is-4 | ta-174 | sp-4 | an-174 |
| 1321 | is-4 | ta-175 | sp-4 | an-175 |
| 1322 | is-4 | ta-176 | sp-4 | an-176 |
| 1323 | is-4 | ta-177 | sp-4 | an-177 |
| 1324 | is-4 | ta-178 | sp-4 | an-178 |
| 1325 | is-4 | ta-179 | sp-4 | an-179 |
| 1326 | is-4 | ta-180 | sp-4 | an-180 |
| 1327 | is-4 | ta-181 | sp-4 | an-181 |
| 1328 | is-4 | ta-182 | sp-4 | an-182 |
| 1329 | is-4 | ta-183 | sp-4 | an-183 |
| 1330 | is-4 | ta-184 | sp-4 | an-184 |
| 1331 | is-4 | ta-185 | sp-4 | an-185 |
| 1332 | is-4 | ta-186 | sp-4 | an-186 |
| 1333 | is-4 | ta-187 | sp-4 | an-187 |
| 1334 | is-4 | ta-188 | sp-4 | an-188 |
| 1335 | is-4 | ta-189 | sp-4 | an-189 |
| 1336 | is-4 | ta-190 | sp-4 | an-190 |
| 1337 | is-4 | ta-191 | sp-4 | an-191 |
| 1338 | is-4 | ta-192 | sp-4 | an-192 |
| 1339 | is-4 | ta-193 | sp-4 | an-193 |
| 1340 | is-4 | ta-194 | sp-4 | an-194 |
| 1341 | is-4 | ta-195 | sp-4 | an-195 |
| 1342 | is-4 | ta-196 | sp-4 | an-196 |
| 1343 | is-4 | ta-197 | sp-4 | an-197 |
| 1344 | is-4 | ta-198 | sp-4 | an-198 |
| 1345 | is-4 | ta-199 | sp-4 | an-199 |
| 1346 | is-4 | ta-200 | sp-4 | an-200 |
| 1347 | is-4 | ta-201 | sp-4 | an-201 |
| 1348 | is-4 | ta-202 | sp-4 | an-202 |
| 1349 | is-4 | ta-203 | sp-4 | an-203 |
| 1350 | is-4 | ta-204 | sp-4 | an-204 |
| 1351 | is-4 | ta-205 | sp-4 | an-205 |
| 1352 | is-4 | ta-206 | sp-4 | an-206 |
| 1353 | is-4 | ta-207 | sp-4 | an-207 |
| 1354 | is-4 | ta-208 | sp-4 | an-208 |
| 1355 | is-4 | ta-209 | sp-4 | an-209 |
| 1356 | is-4 | ta-210 | sp-4 | an-210 |
| 1357 | is-4 | ta-211 | sp-4 | an-211 |
| 1358 | is-4 | ta-212 | sp-4 | an-212 |
| 1359 | is-4 | ta-213 | sp-4 | an-213 |
| 1360 | is-4 | ta-214 | sp-4 | an-214 |
| 1361 | is-4 | ta-215 | sp-4 | an-215 |
| 1362 | is-4 | ta-216 | sp-4 | an-216 |

TABLE 2-continued

| Example No. | Reaction reagent is | Reaction reagent ta | Compound of Example sp | Compound of Example an |
|---|---|---|---|---|
| 1363 | is-4 | ta-217 | sp-4 | an-217 |
| 1364 | is-4 | ta-218 | sp-4 | an-218 |
| 1365 | is-4 | ta-219 | sp-4 | an-219 |
| 1366 | is-4 | ta-220 | sp-4 | an-220 |
| 1367 | is-4 | ta-221 | sp-4 | an-221 |
| 1368 | is-4 | ta-222 | sp-4 | an-222 |
| 1369 | is-4 | ta-223 | sp-4 | an-223 |
| 1370 | is-4 | ta-224 | sp-4 | an-224 |
| 1371 | is-4 | ta-225 | sp-4 | an-225 |
| 1372 | is-4 | ta-226 | sp-4 | an-226 |
| 1373 | is-4 | ta-227 | sp-4 | an-227 |
| 1374 | is-4 | ta-228 | sp-4 | an-228 |
| 1375 | is-4 | ta-229 | sp-4 | an-229 |
| 1376 | is-4 | ta-230 | sp-4 | an-230 |
| 1377 | is-4 | ta-231 | sp-4 | an-231 |
| 1378 | is-4 | ta-232 | sp-4 | an-232 |
| 1379 | is-4 | ta-233 | sp-4 | an-233 |
| 1380 | is-4 | ta-234 | sp-4 | an-234 |
| 1381 | is-4 | ta-235 | sp-4 | an-235 |
| 1382 | is-4 | ta-236 | sp-4 | an-236 |
| 1383 | is-4 | ta-237 | sp-4 | an-237 |
| 1384 | is-4 | ta-238 | sp-4 | an-238 |
| 1385 | is-4 | ta-239 | sp-4 | an-239 |
| 1386 | is-4 | ta-240 | sp-4 | an-240 |
| 1387 | is-4 | ta-241 | sp-4 | an-241 |
| 1388 | is-4 | ta-242 | sp-4 | an-242 |
| 1389 | is-4 | ta-243 | sp-4 | an-243 |
| 1390 | is-4 | ta-244 | sp-4 | an-244 |
| 1391 | is-4 | ta-245 | sp-4 | an-245 |
| 1392 | is-4 | ta-246 | sp-4 | an-246 |
| 1393 | is-4 | ta-247 | sp-4 | an-247 |
| 1394 | is-4 | ta-248 | sp-4 | an-248 |
| 1395 | is-4 | ta-249 | sp-4 | an-249 |
| 1396 | is-4 | ta-250 | sp-4 | an-250 |
| 1397 | is-4 | ta-251 | sp-4 | an-251 |
| 1398 | is-4 | ta-252 | sp-4 | an-252 |
| 1399 | is-4 | ta-253 | sp-4 | an-253 |
| 1400 | is-4 | ta-254 | sp-4 | an-254 |
| 1401 | is-4 | ta-255 | sp-4 | an-255 |
| 1402 | is-4 | ta-256 | sp-4 | an-256 |
| 1403 | is-4 | ta-257 | sp-4 | an-257 |
| 1404 | is-4 | ta-258 | sp-4 | an-258 |
| 1405 | is-4 | ta-259 | sp-4 | an-259 |
| 1406 | is-4 | ta-260 | sp-4 | an-260 |
| 1407 | is-4 | ta-261 | sp-4 | an-261 |
| 1408 | is-4 | ta-262 | sp-4 | an-262 |
| 1409 | is-4 | ta-263 | sp-4 | an-263 |
| 1410 | is-4 | ta-264 | sp-4 | an-264 |
| 1411 | is-4 | ta-265 | sp-4 | an-265 |
| 1412 | is-4 | ta-266 | sp-4 | an-266 |
| 1413 | is-4 | ta-267 | sp-4 | an-267 |
| 1414 | is-4 | ta-268 | sp-4 | an-268 |
| 1415 | is-4 | ta-269 | sp-4 | an-269 |
| 1416 | is-4 | ta-270 | sp-4 | an-270 |
| 1417 | is-4 | ta-271 | sp-4 | an-271 |
| 1418 | is-4 | ta-272 | sp-4 | an-272 |
| 1419 | is-4 | ta-273 | sp-4 | an-273 |
| 1420 | is-4 | ta-274 | sp-4 | an-274 |
| 1421 | is-4 | ta-275 | sp-4 | an-275 |
| 1422 | is-4 | ta-276 | sp-4 | an-276 |
| 1423 | is-4 | ta-277 | sp-4 | an-277 |
| 1424 | is-4 | ta-278 | sp-4 | an-278 |
| 1425 | is-4 | ta-279 | sp-4 | an-279 |
| 1426 | is-4 | ta-280 | sp-4 | an-280 |
| 1427 | is-4 | ta-281 | sp-4 | an-281 |
| 1428 | is-4 | ta-282 | sp-4 | an-282 |
| 1429 | is-4 | ta-283 | sp-4 | an-283 |
| 1430 | is-4 | ta-284 | sp-4 | an-284 |
| 1431 | is-4 | ta-285 | sp-4 | an-285 |
| 1432 | is-4 | ta-286 | sp-4 | an-286 |
| 1433 | is-4 | ta-287 | sp-4 | an-287 |
| 1434 | is-4 | ta-288 | sp-4 | an-288 |
| 1435 | is-4 | ta-289 | sp-4 | an-289 |
| 1436 | is-4 | ta-290 | sp-4 | an-290 |
| 1437 | is-4 | ta-291 | sp-4 | an-291 |
| 1438 | is-4 | ta-292 | sp-4 | an-292 |
| 1439 | is-4 | ta-293 | sp-4 | an-293 |
| 1440 | is-4 | ta-294 | sp-4 | an-294 |
| 1441 | is-4 | ta-295 | sp-4 | an-295 |
| 1442 | is-4 | ta-296 | sp-4 | an-296 |
| 1443 | is-4 | ta-297 | sp-4 | an-297 |
| 1444 | is-4 | ta-298 | sp-4 | an-298 |
| 1445 | is-4 | ta-299 | sp-4 | an-299 |
| 1446 | is-4 | ta-300 | sp-4 | an-300 |
| 1447 | is-4 | ta-301 | sp-4 | an-301 |
| 1448 | is-4 | ta-302 | sp-4 | an-302 |
| 1449 | is-4 | ta-303 | sp-4 | an-303 |
| 1450 | is-4 | ta-304 | sp-4 | an-304 |
| 1451 | is-4 | ta-305 | sp-4 | an-305 |
| 1452 | is-4 | ta-306 | sp-4 | an-306 |
| 1453 | is-4 | ta-307 | sp-4 | an-307 |
| 1454 | is-4 | ta-308 | sp-4 | an-308 |
| 1455 | is-4 | ta-309 | sp-4 | an-309 |
| 1456 | is-4 | ta-310 | sp-4 | an-310 |
| 1457 | is-4 | ta-311 | sp-4 | an-311 |
| 1458 | is-4 | ta-312 | sp-4 | an-312 |
| 1459 | is-4 | ta-313 | sp-4 | an-313 |
| 1460 | is-4 | ta-314 | sp-4 | an-314 |
| 1461 | is-4 | ta-315 | sp-4 | an-315 |
| 1462 | is-4 | ta-316 | sp-4 | an-316 |
| 1463 | is-4 | ta-317 | sp-4 | an-317 |
| 1464 | is-4 | ta-318 | sp-4 | an-318 |
| 1465 | is-4 | ta-319 | sp-4 | an-319 |
| 1466 | is-4 | ta-320 | sp-4 | an-320 |
| 1467 | is-4 | ta-321 | sp-4 | an-321 |
| 1468 | is-4 | ta-322 | sp-4 | an-322 |
| 1469 | is-4 | ta-323 | sp-4 | an-323 |
| 1470 | is-4 | ta-324 | sp-4 | an-324 |
| 1471 | is-4 | ta-325 | sp-4 | an-325 |
| 1472 | is-4 | ta-326 | sp-4 | an-326 |
| 1473 | is-4 | ta-327 | sp-4 | an-327 |
| 1474 | is-4 | ta-328 | sp-4 | an-328 |
| 1475 | is-4 | ta-329 | sp-4 | an-329 |
| 1476 | is-4 | ta-330 | sp-4 | an-330 |
| 1477 | is-4 | ta-331 | sp-4 | an-331 |
| 1478 | is-4 | ta-332 | sp-4 | an-332 |
| 1479 | is-4 | ta-333 | sp-4 | an-333 |
| 1480 | is-4 | ta-334 | sp-4 | an-334 |
| 1481 | is-4 | ta-335 | sp-4 | an-335 |
| 1482 | is-4 | ta-336 | sp-4 | an-336 |
| 1483 | is-4 | ta-337 | sp-4 | an-337 |
| 1484 | is-4 | ta-338 | sp-4 | an-338 |
| 1485 | is-4 | ta-339 | sp-4 | an-339 |
| 1486 | is-4 | ta-340 | sp-4 | an-340 |
| 1487 | is-4 | ta-341 | sp-4 | an-341 |
| 1488 | is-4 | ta-342 | sp-4 | an-342 |
| 1489 | is-4 | ta-343 | sp-4 | an-343 |
| 1490 | is-4 | ta-344 | sp-4 | an-344 |
| 1491 | is-4 | ta-345 | sp-4 | an-345 |
| 1492 | is-4 | ta-346 | sp-4 | an-346 |
| 1493 | is-4 | ta-347 | sp-4 | an-347 |
| 1494 | is-4 | ta-348 | sp-4 | an-348 |
| 1495 | is-4 | ta-349 | sp-4 | an-349 |
| 1496 | is-4 | ta-350 | sp-4 | an-350 |
| 1497 | is-4 | ta-351 | sp-4 | an-351 |
| 1498 | is-4 | ta-352 | sp-4 | an-352 |
| 1499 | is-4 | ta-353 | sp-4 | an-353 |
| 1500 | is-4 | ta-354 | sp-4 | an-354 |
| 1501 | is-4 | ta-355 | sp-4 | an-355 |
| 1502 | is-4 | ta-356 | sp-4 | an-356 |
| 1503 | is-4 | ta-357 | sp-4 | an-357 |
| 1504 | is-4 | ta-358 | sp-4 | an-358 |
| 1505 | is-4 | ta-359 | sp-4 | an-359 |
| 1506 | is-4 | ta-360 | sp-4 | an-360 |
| 1507 | is-4 | ta-361 | sp-4 | an-361 |
| 1508 | is-4 | ta-362 | sp-4 | an-362 |
| 1509 | is-4 | ta-363 | sp-4 | an-363 |
| 1510 | is-4 | ta-364 | sp-4 | an-364 |

TABLE 2-continued

| Example No. | Reaction reagent is | Reaction reagent ta | Compound of Example sp | Compound of Example an |
|---|---|---|---|---|
| 1511 | is-4 | ta-365 | sp-4 | an-365 |
| 1512 | is-4 | ta-366 | sp-4 | an-366 |
| 1513 | is-4 | ta-367 | sp-4 | an-367 |
| 1514 | is-4 | ta-368 | sp-4 | an-368 |
| 1515 | is-4 | ta-369 | sp-4 | an-369 |
| 1516 | is-4 | ta-370 | sp-4 | an-370 |
| 1517 | is-4 | ta-371 | sp-4 | an-371 |
| 1518 | is-4 | ta-372 | sp-4 | an-372 |
| 1519 | is-4 | ta-373 | sp-4 | an-373 |
| 1520 | is-4 | ta-374 | sp-4 | an-374 |
| 1521 | is-4 | ta-375 | sp-4 | an-375 |
| 1522 | is-4 | ta-376 | sp-4 | an-376 |
| 1523 | is-4 | ta-377 | sp-4 | an-377 |
| 1524 | is-5 | ta-1 | sp-5 | an-1 |
| 1525 | is-5 | ta-2 | sp-5 | an-2 |
| 1526 | is-5 | ta-3 | sp-5 | an-3 |
| 1527 | is-5 | ta-4 | sp-5 | an-4 |
| 1528 | is-5 | ta-5 | sp-5 | an-5 |
| 1529 | is-5 | ta-6 | sp-5 | an-6 |
| 1530 | is-5 | ta-7 | sp-5 | an-7 |
| 1531 | is-5 | ta-8 | sp-5 | an-8 |
| 1532 | is-5 | ta-9 | sp-5 | an-9 |
| 1533 | is-5 | ta-10 | sp-5 | an-10 |
| 1534 | is-5 | ta-11 | sp-5 | an-11 |
| 1535 | is-5 | ta-12 | sp-5 | an-12 |
| 1536 | is-5 | ta-13 | sp-5 | an-13 |
| 1537 | is-5 | ta-14 | sp-5 | an-14 |
| 1538 | is-5 | ta-15 | sp-5 | an-15 |
| 1539 | is-5 | ta-16 | sp-5 | an-16 |
| 1540 | is-5 | ta-17 | sp-5 | an-17 |
| 1541 | is-5 | ta-18 | sp-5 | an-18 |
| 1542 | is-5 | ta-19 | sp-5 | an-19 |
| 1543 | is-5 | ta-20 | sp-5 | an-20 |
| 1544 | is-5 | ta-21 | sp-5 | an-21 |
| 1545 | is-5 | ta-22 | sp-5 | an-22 |
| 1546 | is-5 | ta-23 | sp-5 | an-23 |
| 1547 | is-5 | ta-24 | sp-5 | an-24 |
| 1548 | is-5 | ta-25 | sp-5 | an-25 |
| 1549 | is-5 | ta-26 | sp-5 | an-26 |
| 1550 | is-5 | ta-27 | sp-5 | an-27 |
| 1551 | is-5 | ta-28 | sp-5 | an-28 |
| 1552 | is-5 | ta-29 | sp-5 | an-29 |
| 1553 | is-5 | ta-30 | sp-5 | an-30 |
| 1554 | is-5 | ta-31 | sp-5 | an-31 |
| 1555 | is-5 | ta-32 | sp-5 | an-32 |
| 1556 | is-5 | ta-33 | sp-5 | an-33 |
| 1557 | is-5 | ta-34 | sp-5 | an-34 |
| 1558 | is-5 | ta-35 | sp-5 | an-35 |
| 1559 | is-5 | ta-36 | sp-5 | an-36 |
| 1560 | is-5 | ta-37 | sp-5 | an-37 |
| 1561 | is-5 | ta-38 | sp-5 | an-38 |
| 1562 | is-5 | ta-39 | sp-5 | an-39 |
| 1563 | is-5 | ta-40 | sp-5 | an-40 |
| 1564 | is-5 | ta-41 | sp-5 | an-41 |
| 1565 | is-5 | ta-42 | sp-5 | an-42 |
| 1566 | is-5 | ta-43 | sp-5 | an-43 |
| 1567 | is-5 | ta-44 | sp-5 | an-44 |
| 1568 | is-5 | ta-45 | sp-5 | an-45 |
| 1569 | is-5 | ta-46 | sp-5 | an-46 |
| 1570 | is-5 | ta-47 | sp-5 | an-47 |
| 1571 | is-5 | ta-48 | sp-5 | an-48 |
| 1572 | is-5 | ta-49 | sp-5 | an-49 |
| 1573 | is-5 | ta-50 | sp-5 | an-50 |
| 1574 | is-5 | ta-51 | sp-5 | an-51 |
| 1575 | is-5 | ta-52 | sp-5 | an-52 |
| 1576 | is-5 | ta-53 | sp-5 | an-53 |
| 1577 | is-5 | ta-54 | sp-5 | an-54 |
| 1578 | is-5 | ta-55 | sp-5 | an-55 |
| 1579 | is-5 | ta-56 | sp-5 | an-56 |
| 1580 | is-5 | ta-57 | sp-5 | an-57 |
| 1581 | is-5 | ta-58 | sp-5 | an-58 |
| 1582 | is-5 | ta-59 | sp-5 | an-59 |
| 1583 | is-5 | ta-60 | sp-5 | an-60 |
| 1584 | is-5 | ta-61 | sp-5 | an-61 |
| 1585 | is-5 | ta-62 | sp-5 | an-62 |
| 1586 | is-5 | ta-63 | sp-5 | an-63 |
| 1587 | is-5 | ta-64 | sp-5 | an-64 |
| 1588 | is-5 | ta-65 | sp-5 | an-65 |
| 1589 | is-5 | ta-66 | sp-5 | an-66 |
| 1590 | is-5 | ta-67 | sp-5 | an-67 |
| 1591 | is-5 | ta-68 | sp-5 | an-68 |
| 1592 | is-5 | ta-69 | sp-5 | an-69 |
| 1593 | is-5 | ta-70 | sp-5 | an-70 |
| 1594 | is-5 | ta-71 | sp-5 | an-71 |
| 1595 | is-5 | ta-72 | sp-5 | an-72 |
| 1596 | is-5 | ta-73 | sp-5 | an-73 |
| 1597 | is-5 | ta-74 | sp-5 | an-74 |
| 1598 | is-5 | ta-75 | sp-5 | an-75 |
| 1599 | is-5 | ta-76 | sp-5 | an-76 |
| 1600 | is-5 | ta-77 | sp-5 | an-77 |
| 1601 | is-5 | ta-78 | sp-5 | an-78 |
| 1602 | is-5 | ta-79 | sp-5 | an-79 |
| 1603 | is-5 | ta-80 | sp-5 | an-80 |
| 1604 | is-5 | ta-81 | sp-5 | an-81 |
| 1605 | is-5 | ta-82 | sp-5 | an-82 |
| 1606 | is-5 | ta-83 | sp-5 | an-83 |
| 1607 | is-5 | ta-84 | sp-5 | an-84 |
| 1608 | is-5 | ta-85 | sp-5 | an-85 |
| 1609 | is-5 | ta-86 | sp-5 | an-86 |
| 1610 | is-5 | ta-87 | sp-5 | an-87 |
| 1611 | is-5 | ta-88 | sp-5 | an-88 |
| 1612 | is-5 | ta-89 | sp-5 | an-89 |
| 1613 | is-5 | ta-90 | sp-5 | an-90 |
| 1614 | is-5 | ta-91 | sp-5 | an-91 |
| 1615 | is-5 | ta-92 | sp-5 | an-92 |
| 1616 | is-5 | ta-93 | sp-5 | an-93 |
| 1617 | is-5 | ta-94 | sp-5 | an-94 |
| 1618 | is-5 | ta-95 | sp-5 | an-95 |
| 1619 | is-5 | ta-96 | sp-5 | an-96 |
| 1620 | is-5 | ta-97 | sp-5 | an-97 |
| 1621 | is-5 | ta-98 | sp-5 | an-98 |
| 1622 | is-5 | ta-99 | sp-5 | an-99 |
| 1623 | is-5 | ta-100 | sp-5 | an-100 |
| 1624 | is-5 | ta-101 | sp-5 | an-101 |
| 1625 | is-5 | ta-102 | sp-5 | an-102 |
| 1626 | is-5 | ta-103 | sp-5 | an-103 |
| 1627 | is-5 | ta-104 | sp-5 | an-104 |
| 1628 | is-5 | ta-105 | sp-5 | an-105 |
| 1629 | is-5 | ta-106 | sp-5 | an-106 |
| 1630 | is-5 | ta-107 | sp-5 | an-107 |
| 1631 | is-5 | ta-108 | sp-5 | an-108 |
| 1632 | is-5 | ta-109 | sp-5 | an-109 |
| 1633 | is-5 | ta-110 | sp-5 | an-110 |
| 1634 | is-5 | ta-111 | sp-5 | an-111 |
| 1635 | is-5 | ta-112 | sp-5 | an-112 |
| 1636 | is-5 | ta-113 | sp-5 | an-113 |
| 1637 | is-5 | ta-114 | sp-5 | an-114 |
| 1638 | is-5 | ta-115 | sp-5 | an-115 |
| 1639 | is-5 | ta-116 | sp-5 | an-116 |
| 1640 | is-5 | ta-117 | sp-5 | an-117 |
| 1641 | is-5 | ta-118 | sp-5 | an-118 |
| 1642 | is-5 | ta-119 | sp-5 | an-119 |
| 1643 | is-5 | ta-120 | sp-5 | an-120 |
| 1644 | is-5 | ta-121 | sp-5 | an-121 |
| 1645 | is-5 | ta-122 | sp-5 | an-122 |
| 1646 | is-5 | ta-123 | sp-5 | an-123 |
| 1647 | is-5 | ta-124 | sp-5 | an-124 |
| 1648 | is-5 | ta-125 | sp-5 | an-125 |
| 1649 | is-5 | ta-126 | sp-5 | an-126 |
| 1650 | is-5 | ta-127 | sp-5 | an-127 |
| 1651 | is-5 | ta-128 | sp-5 | an-128 |
| 1652 | is-5 | ta-129 | sp-5 | an-129 |
| 1653 | is-5 | ta-130 | sp-5 | an-130 |
| 1654 | is-5 | ta-131 | sp-5 | an-131 |
| 1655 | is-5 | ta-132 | sp-5 | an-132 |
| 1656 | is-5 | ta-133 | sp-5 | an-133 |
| 1657 | is-5 | ta-134 | sp-5 | an-134 |
| 1658 | is-5 | ta-135 | sp-5 | an-135 |

TABLE 2-continued

| Example No. | Reaction reagent is | Reaction reagent ta | Compound of Example sp | Compound of Example an |
|---|---|---|---|---|
| 1659 | is-5 | ta-136 | sp-5 | an-136 |
| 1660 | is-5 | ta-137 | sp-5 | an-137 |
| 1661 | is-5 | ta-138 | sp-5 | an-138 |
| 1662 | is-5 | ta-139 | sp-5 | an-139 |
| 1663 | is-5 | ta-140 | sp-5 | an-140 |
| 1664 | is-5 | ta-141 | sp-5 | an-141 |
| 1665 | is-5 | ta-142 | sp-5 | an-142 |
| 1666 | is-5 | ta-143 | sp-5 | an-143 |
| 1667 | is-5 | ta-144 | sp-5 | an-144 |
| 1668 | is-5 | ta-145 | sp-5 | an-145 |
| 1669 | is-5 | ta-146 | sp-5 | an-146 |
| 1670 | is-5 | ta-147 | sp-5 | an-147 |
| 1671 | is-5 | ta-148 | sp-5 | an-148 |
| 1672 | is-5 | ta-149 | sp-5 | an-149 |
| 1673 | is-5 | ta-150 | sp-5 | an-150 |
| 1674 | is-5 | ta-151 | sp-5 | an-151 |
| 1675 | is-5 | ta-152 | sp-5 | an-152 |
| 1676 | is-5 | ta-153 | sp-5 | an-153 |
| 1677 | is-5 | ta-154 | sp-5 | an-154 |
| 1678 | is-5 | ta-155 | sp-5 | an-155 |
| 1679 | is-5 | ta-156 | sp-5 | an-156 |
| 1680 | is-5 | ta-157 | sp-5 | an-157 |
| 1681 | is-5 | ta-158 | sp-5 | an-158 |
| 1682 | is-5 | ta-159 | sp-5 | an-159 |
| 1683 | is-5 | ta-160 | sp-5 | an-160 |
| 1684 | is-5 | ta-161 | sp-5 | an-161 |
| 1685 | is-5 | ta-162 | sp-5 | an-162 |
| 1686 | is-5 | ta-163 | sp-5 | an-163 |
| 1687 | is-5 | ta-164 | sp-5 | an-164 |
| 1688 | is-5 | ta-165 | sp-5 | an-165 |
| 1689 | is-5 | ta-166 | sp-5 | an-166 |
| 1690 | is-5 | ta-167 | sp-5 | an-167 |
| 1691 | is-5 | ta-168 | sp-5 | an-168 |
| 1692 | is-5 | ta-169 | sp-5 | an-169 |
| 1693 | is-5 | ta-170 | sp-5 | an-170 |
| 1694 | is-5 | ta-171 | sp-5 | an-171 |
| 1695 | is-5 | ta-172 | sp-5 | an-172 |
| 1696 | is-5 | ta-173 | sp-5 | an-173 |
| 1697 | is-5 | ta-174 | sp-5 | an-174 |
| 1698 | is-5 | ta-175 | sp-5 | an-175 |
| 1699 | is-5 | ta-176 | sp-5 | an-176 |
| 1700 | is-5 | ta-177 | sp-5 | an-177 |
| 1701 | is-5 | ta-178 | sp-5 | an-178 |
| 1702 | is-5 | ta-179 | sp-5 | an-179 |
| 1703 | is-5 | ta-180 | sp-5 | an-180 |
| 1704 | is-5 | ta-181 | sp-5 | an-181 |
| 1705 | is-5 | ta-182 | sp-5 | an-182 |
| 1706 | is-5 | ta-183 | sp-5 | an-183 |
| 1707 | is-5 | ta-184 | sp-5 | an-184 |
| 1708 | is-5 | ta-185 | sp-5 | an-185 |
| 1709 | is-5 | ta-186 | sp-5 | an-186 |
| 1710 | is-5 | ta-187 | sp-5 | an-187 |
| 1711 | is-5 | ta-188 | sp-5 | an-188 |
| 1712 | is-5 | ta-189 | sp-5 | an-189 |
| 1713 | is-5 | ta-190 | sp-5 | an-190 |
| 1714 | is-5 | ta-191 | sp-5 | an-191 |
| 1715 | is-5 | ta-192 | sp-5 | an-192 |
| 1716 | is-5 | ta-193 | sp-5 | an-193 |
| 1717 | is-5 | ta-194 | sp-5 | an-194 |
| 1718 | is-5 | ta-195 | sp-5 | an-195 |
| 1719 | is-5 | ta-196 | sp-5 | an-196 |
| 1720 | is-5 | ta-197 | sp-5 | an-197 |
| 1721 | is-5 | ta-198 | sp-5 | an-198 |
| 1722 | is-5 | ta-199 | sp-5 | an-199 |
| 1723 | is-5 | ta-200 | sp-5 | an-200 |
| 1724 | is-5 | ta-201 | sp-5 | an-201 |
| 1725 | is-5 | ta-202 | sp-5 | an-202 |
| 1726 | is-5 | ta-203 | sp-5 | an-203 |
| 1727 | is-5 | ta-204 | sp-5 | an-204 |
| 1728 | is-5 | ta-205 | sp-5 | an-205 |
| 1729 | is-5 | ta-206 | sp-5 | an-206 |
| 1730 | is-5 | ta-207 | sp-5 | an-207 |
| 1731 | is-5 | ta-208 | sp-5 | an-208 |
| 1732 | is-5 | ta-209 | sp-5 | an-209 |
| 1733 | is-5 | ta-210 | sp-5 | an-210 |
| 1734 | is-5 | ta-211 | sp-5 | an-211 |
| 1735 | is-5 | ta-212 | sp-5 | an-212 |
| 1736 | is-5 | ta-213 | sp-5 | an-213 |
| 1737 | is-5 | ta-214 | sp-5 | an-214 |
| 1738 | is-5 | ta-215 | sp-5 | an-215 |
| 1739 | is-5 | ta-216 | sp-5 | an-216 |
| 1740 | is-5 | ta-217 | sp-5 | an-217 |
| 1741 | is-5 | ta-218 | sp-5 | an-218 |
| 1742 | is-5 | ta-219 | sp-5 | an-219 |
| 1743 | is-5 | ta-220 | sp-5 | an-220 |
| 1744 | is-5 | ta-221 | sp-5 | an-221 |
| 1745 | is-5 | ta-222 | sp-5 | an-222 |
| 1746 | is-5 | ta-223 | sp-5 | an-223 |
| 1747 | is-5 | ta-224 | sp-5 | an-224 |
| 1748 | is-5 | ta-225 | sp-5 | an-225 |
| 1749 | is-5 | ta-226 | sp-5 | an-226 |
| 1750 | is-5 | ta-227 | sp-5 | an-227 |
| 1751 | is-5 | ta-228 | sp-5 | an-228 |
| 1752 | is-5 | ta-229 | sp-5 | an-229 |
| 1753 | is-5 | ta-230 | sp-5 | an-230 |
| 1754 | is-5 | ta-231 | sp-5 | an-231 |
| 1755 | is-5 | ta-232 | sp-5 | an-232 |
| 1756 | is-5 | ta-233 | sp-5 | an-233 |
| 1757 | is-5 | ta-234 | sp-5 | an-234 |
| 1758 | is-5 | ta-235 | sp-5 | an-235 |
| 1759 | is-5 | ta-236 | sp-5 | an-236 |
| 1760 | is-5 | ta-237 | sp-5 | an-237 |
| 1761 | is-5 | ta-238 | sp-5 | an-238 |
| 1762 | is-5 | ta-239 | sp-5 | an-239 |
| 1763 | is-5 | ta-240 | sp-5 | an-240 |
| 1764 | is-5 | ta-241 | sp-5 | an-241 |
| 1765 | is-5 | ta-242 | sp-5 | an-242 |
| 1766 | is-5 | ta-243 | sp-5 | an-243 |
| 1767 | is-5 | ta-244 | sp-5 | an-244 |
| 1768 | is-5 | ta-245 | sp-5 | an-245 |
| 1769 | is-5 | ta-246 | sp-5 | an-246 |
| 1770 | is-5 | ta-247 | sp-5 | an-247 |
| 1771 | is-5 | ta-248 | sp-5 | an-248 |
| 1772 | is-5 | ta-249 | sp-5 | an-249 |
| 1773 | is-5 | ta-250 | sp-5 | an-250 |
| 1774 | is-5 | ta-251 | sp-5 | an-251 |
| 1775 | is-5 | ta-252 | sp-5 | an-252 |
| 1776 | is-5 | ta-253 | sp-5 | an-253 |
| 1777 | is-5 | ta-254 | sp-5 | an-254 |
| 1778 | is-5 | ta-255 | sp-5 | an-255 |
| 1779 | is-5 | ta-256 | sp-5 | an-256 |
| 1780 | is-5 | ta-257 | sp-5 | an-257 |
| 1781 | is-5 | ta-258 | sp-5 | an-258 |
| 1782 | is-5 | ta-259 | sp-5 | an-259 |
| 1783 | is-5 | ta-260 | sp-5 | an-260 |
| 1784 | is-5 | ta-261 | sp-5 | an-261 |
| 1785 | is-5 | ta-262 | sp-5 | an-262 |
| 1786 | is-5 | ta-263 | sp-5 | an-263 |
| 1787 | is-5 | ta-264 | sp-5 | an-264 |
| 1788 | is-5 | ta-265 | sp-5 | an-265 |
| 1789 | is-5 | ta-266 | sp-5 | an-266 |
| 1790 | is-5 | ta-267 | sp-5 | an-267 |
| 1791 | is-5 | ta-268 | sp-5 | an-268 |
| 1792 | is-5 | ta-269 | sp-5 | an-269 |
| 1793 | is-5 | ta-270 | sp-5 | an-270 |
| 1794 | is-5 | ta-271 | sp-5 | an-271 |
| 1795 | is-5 | ta-272 | sp-5 | an-272 |
| 1796 | is-5 | ta-273 | sp-5 | an-273 |
| 1797 | is-5 | ta-274 | sp-5 | an-274 |
| 1798 | is-5 | ta-275 | sp-5 | an-275 |
| 1799 | is-5 | ta-276 | sp-5 | an-276 |
| 1800 | is-5 | ta-277 | sp-5 | an-277 |
| 1801 | is-5 | ta-278 | sp-5 | an-278 |
| 1802 | is-5 | ta-279 | sp-5 | an-279 |
| 1803 | is-5 | ta-280 | sp-5 | an-280 |
| 1804 | is-5 | ta-281 | sp-5 | an-281 |
| 1805 | is-5 | ta-282 | sp-5 | an-282 |
| 1806 | is-5 | ta-283 | sp-5 | an-283 |

TABLE 2-continued

| Example No. | Reaction reagent is | Reaction reagent ta | Compound of Example sp | Compound of Example an |
|---|---|---|---|---|
| 1807 | is-5 | ta-284 | sp-5 | an-284 |
| 1808 | is-5 | ta-285 | sp-5 | an-285 |
| 1809 | is-5 | ta-286 | sp-5 | an-286 |
| 1810 | is-5 | ta-287 | sp-5 | an-287 |
| 1811 | is-5 | ta-288 | sp-5 | an-288 |
| 1812 | is-5 | ta-289 | sp-5 | an-289 |
| 1813 | is-5 | ta-290 | sp-5 | an-290 |
| 1814 | is-5 | ta-291 | sp-5 | an-291 |
| 1815 | is-5 | ta-292 | sp-5 | an-292 |
| 1816 | is-5 | ta-293 | sp-5 | an-293 |
| 1817 | is-5 | ta-294 | sp-5 | an-294 |
| 1818 | is-5 | ta-295 | sp-5 | an-295 |
| 1819 | is-5 | ta-296 | sp-5 | an-296 |
| 1820 | is-5 | ta-297 | sp-5 | an-297 |
| 1821 | is-5 | ta-298 | sp-5 | an-298 |
| 1822 | is-5 | ta-299 | sp-5 | an-299 |
| 1823 | is-5 | ta-300 | sp-5 | an-300 |
| 1824 | is-5 | ta-301 | sp-5 | an-301 |
| 1825 | is-5 | ta-302 | sp-5 | an-302 |
| 1826 | is-5 | ta-303 | sp-5 | an-303 |
| 1827 | is-5 | ta-304 | sp-5 | an-304 |
| 1828 | is-5 | ta-305 | sp-5 | an-305 |
| 1829 | is-5 | ta-306 | sp-5 | an-306 |
| 1830 | is-5 | ta-307 | sp-5 | an-307 |
| 1831 | is-5 | ta-308 | sp-5 | an-308 |
| 1832 | is-5 | ta-309 | sp-5 | an-309 |
| 1833 | is-5 | ta-310 | sp-5 | an-310 |
| 1834 | is-5 | ta-311 | sp-5 | an-311 |
| 1835 | is-5 | ta-312 | sp-5 | an-312 |
| 1836 | is-5 | ta-313 | sp-5 | an-313 |
| 1837 | is-5 | ta-314 | sp-5 | an-314 |
| 1838 | is-5 | ta-315 | sp-5 | an-315 |
| 1839 | is-5 | ta-316 | sp-5 | an-316 |
| 1840 | is-5 | ta-317 | sp-5 | an-317 |
| 1841 | is-5 | ta-318 | sp-5 | an-318 |
| 1842 | is-5 | ta-319 | sp-5 | an-319 |
| 1843 | is-5 | ta-320 | sp-5 | an-320 |
| 1844 | is-5 | ta-321 | sp-5 | an-321 |
| 1845 | is-5 | ta-322 | sp-5 | an-322 |
| 1846 | is-5 | ta-323 | sp-5 | an-323 |
| 1847 | is-5 | ta-324 | sp-5 | an-324 |
| 1848 | is-5 | ta-325 | sp-5 | an-325 |
| 1849 | is-5 | ta-326 | sp-5 | an-326 |
| 1850 | is-5 | ta-327 | sp-5 | an-327 |
| 1851 | is-5 | ta-328 | sp-5 | an-328 |
| 1852 | is-5 | ta-329 | sp-5 | an-329 |
| 1853 | is-5 | ta-330 | sp-5 | an-330 |
| 1854 | is-5 | ta-331 | sp-5 | an-331 |
| 1855 | is-5 | ta-332 | sp-5 | an-332 |
| 1856 | is-5 | ta-333 | sp-5 | an-333 |
| 1857 | is-5 | ta-334 | sp-5 | an-334 |
| 1858 | is-5 | ta-335 | sp-5 | an-335 |
| 1859 | is-5 | ta-336 | sp-5 | an-336 |
| 1860 | is-5 | ta-337 | sp-5 | an-337 |
| 1861 | is-5 | ta-338 | sp-5 | an-338 |
| 1862 | is-5 | ta-339 | sp-5 | an-339 |
| 1863 | is-5 | ta-340 | sp-5 | an-340 |
| 1864 | is-5 | ta-341 | sp-5 | an-341 |
| 1865 | is-5 | ta-342 | sp-5 | an-342 |
| 1866 | is-5 | ta-343 | sp-5 | an-343 |
| 1867 | is-5 | ta-344 | sp-5 | an-344 |
| 1868 | is-5 | ta-345 | sp-5 | an-345 |
| 1869 | is-5 | ta-346 | sp-5 | an-346 |
| 1870 | is-5 | ta-347 | sp-5 | an-347 |
| 1871 | is-5 | ta-348 | sp-5 | an-348 |
| 1872 | is-5 | ta-349 | sp-5 | an-349 |
| 1873 | is-5 | ta-350 | sp-5 | an-350 |
| 1874 | is-5 | ta-351 | sp-5 | an-351 |
| 1875 | is-5 | ta-352 | sp-5 | an-352 |
| 1876 | is-5 | ta-353 | sp-5 | an-353 |
| 1877 | is-5 | ta-354 | sp-5 | an-354 |
| 1878 | is-5 | ta-355 | sp-5 | an-355 |
| 1879 | is-5 | ta-356 | sp-5 | an-356 |
| 1880 | is-5 | ta-357 | sp-5 | an-357 |
| 1881 | is-5 | ta-358 | sp-5 | an-358 |
| 1882 | is-5 | ta-359 | sp-5 | an-359 |
| 1883 | is-5 | ta-360 | sp-5 | an-360 |
| 1884 | is-5 | ta-361 | sp-5 | an-361 |
| 1885 | is-5 | ta-362 | sp-5 | an-362 |
| 1886 | is-5 | ta-363 | sp-5 | an-363 |
| 1887 | is-5 | ta-364 | sp-5 | an-364 |
| 1888 | is-5 | ta-365 | sp-5 | an-365 |
| 1889 | is-5 | ta-366 | sp-5 | an-366 |
| 1890 | is-5 | ta-367 | sp-5 | an-367 |
| 1891 | is-5 | ta-368 | sp-5 | an-368 |
| 1892 | is-5 | ta-369 | sp-5 | an-369 |
| 1893 | is-5 | ta-370 | sp-5 | an-370 |
| 1894 | is-5 | ta-371 | sp-5 | an-371 |
| 1895 | is-5 | ta-372 | sp-5 | an-372 |
| 1896 | is-5 | ta-373 | sp-5 | an-373 |
| 1897 | is-5 | ta-374 | sp-5 | an-374 |
| 1898 | is-5 | ta-375 | sp-5 | an-375 |
| 1899 | is-5 | ta-376 | sp-5 | an-376 |
| 1900 | is-5 | ta-377 | sp-5 | an-377 |
| 1901 | is-6 | ta-1 | sp-6 | an-1 |
| 1902 | is-6 | ta-2 | sp-6 | an-2 |
| 1903 | is-6 | ta-3 | sp-6 | an-3 |
| 1904 | is-6 | ta-4 | sp-6 | an-4 |
| 1905 | is-6 | ta-5 | sp-6 | an-5 |
| 1906 | is-6 | ta-6 | sp-6 | an-6 |
| 1907 | is-6 | ta-7 | sp-6 | an-7 |
| 1908 | is-6 | ta-8 | sp-6 | an-8 |
| 1909 | is-6 | ta-9 | sp-6 | an-9 |
| 1910 | is-6 | ta-10 | sp-6 | an-10 |
| 1911 | is-6 | ta-11 | sp-6 | an-11 |
| 1912 | is-6 | ta-12 | sp-6 | an-12 |
| 1913 | is-6 | ta-13 | sp-6 | an-13 |
| 1914 | is-6 | ta-14 | sp-6 | an-14 |
| 1915 | is-6 | ta-15 | sp-6 | an-15 |
| 1916 | is-6 | ta-16 | sp-6 | an-16 |
| 1917 | is-6 | ta-17 | sp-6 | an-17 |
| 1918 | is-6 | ta-18 | sp-6 | an-18 |
| 1919 | is-6 | ta-19 | sp-6 | an-19 |
| 1920 | is-6 | ta-20 | sp-6 | an-20 |
| 1921 | is-6 | ta-21 | sp-6 | an-21 |
| 1922 | is-6 | ta-22 | sp-6 | an-22 |
| 1923 | is-6 | ta-23 | sp-6 | an-23 |
| 1924 | is-6 | ta-24 | sp-6 | an-24 |
| 1925 | is-6 | ta-25 | sp-6 | an-25 |
| 1926 | is-6 | ta-26 | sp-6 | an-26 |
| 1927 | is-6 | ta-27 | sp-6 | an-27 |
| 1928 | is-6 | ta-28 | sp-6 | an-28 |
| 1929 | is-6 | ta-29 | sp-6 | an-29 |
| 1930 | is-6 | ta-30 | sp-6 | an-30 |
| 1931 | is-6 | ta-31 | sp-6 | an-31 |
| 1932 | is-6 | ta-32 | sp-6 | an-32 |
| 1933 | is-6 | ta-33 | sp-6 | an-33 |
| 1934 | is-6 | ta-34 | sp-6 | an-34 |
| 1935 | is-6 | ta-35 | sp-6 | an-35 |
| 1936 | is-6 | ta-36 | sp-6 | an-36 |
| 1937 | is-6 | ta-37 | sp-6 | an-37 |
| 1938 | is-6 | ta-38 | sp-6 | an-38 |
| 1939 | is-6 | ta-39 | sp-6 | an-39 |
| 1940 | is-6 | ta-40 | sp-6 | an-40 |
| 1941 | is-6 | ta-41 | sp-6 | an-41 |
| 1942 | is-6 | ta-42 | sp-6 | an-42 |
| 1943 | is-6 | ta-43 | sp-6 | an-43 |
| 1944 | is-6 | ta-44 | sp-6 | an-44 |
| 1945 | is-6 | ta-45 | sp-6 | an-45 |
| 1946 | is-6 | ta-46 | sp-6 | an-46 |
| 1947 | is-6 | ta-47 | sp-6 | an-47 |
| 1948 | is-6 | ta-48 | sp-6 | an-48 |
| 1949 | is-6 | ta-49 | sp-6 | an-49 |
| 1950 | is-6 | ta-50 | sp-6 | an-50 |
| 1951 | is-6 | ta-51 | sp-6 | an-51 |
| 1952 | is-6 | ta-52 | sp-6 | an-52 |
| 1953 | is-6 | ta-53 | sp-6 | an-53 |
| 1954 | is-6 | ta-54 | sp-6 | an-54 |

TABLE 2-continued

| Example | Reaction reagent | | Compound of Example | |
|---|---|---|---|---|
| No. | is | ta | sp | an |
| 1955 | is-6 | ta-55 | sp-6 | an-55 |
| 1956 | is-6 | ta-56 | sp-6 | an-56 |
| 1957 | is-6 | ta-57 | sp-6 | an-57 |
| 1958 | is-6 | ta-58 | sp-6 | an-58 |
| 1959 | is-6 | ta-59 | sp-6 | an-59 |
| 1960 | is-6 | ta-60 | sp-6 | an-60 |
| 1961 | is-6 | ta-61 | sp-6 | an-61 |
| 1962 | is-6 | ta-62 | sp-6 | an-62 |
| 1963 | is-6 | ta-63 | sp-6 | an-63 |
| 1964 | is-6 | ta-64 | sp-6 | an-64 |
| 1965 | is-6 | ta-65 | sp-6 | an-65 |
| 1966 | is-6 | ta-66 | sp-6 | an-66 |
| 1967 | is-6 | ta-67 | sp-6 | an-67 |
| 1968 | is-6 | ta-68 | sp-6 | an-68 |
| 1969 | is-6 | ta-69 | sp-6 | an-69 |
| 1970 | is-6 | ta-70 | sp-6 | an-70 |
| 1971 | is-6 | ta-71 | sp-6 | an-71 |
| 1972 | is-6 | ta-72 | sp-6 | an-72 |
| 1973 | is-6 | ta-73 | sp-6 | an-73 |
| 1974 | is-6 | ta-74 | sp-6 | an-74 |
| 1975 | is-6 | ta-75 | sp-6 | an-75 |
| 1976 | is-6 | ta-76 | sp-6 | an-76 |
| 1977 | is-6 | ta-77 | sp-6 | an-77 |
| 1978 | is-6 | ta-78 | sp-6 | an-78 |
| 1979 | is-6 | ta-79 | sp-6 | an-79 |
| 1980 | is-6 | ta-80 | sp-6 | an-80 |
| 1981 | is-6 | ta-81 | sp-6 | an-81 |
| 1982 | is-6 | ta-82 | sp-6 | an-82 |
| 1983 | is-6 | ta-83 | sp-6 | an-83 |
| 1984 | is-6 | ta-84 | sp-6 | an-84 |
| 1985 | is-6 | ta-85 | sp-6 | an-85 |
| 1986 | is-6 | ta-86 | sp-6 | an-86 |
| 1987 | is-6 | ta-87 | sp-6 | an-87 |
| 1988 | is-6 | ta-88 | sp-6 | an-88 |
| 1989 | is-6 | ta-89 | sp-6 | an-89 |
| 1990 | is-6 | ta-90 | sp-6 | an-90 |
| 1991 | is-6 | ta-91 | sp-6 | an-91 |
| 1992 | is-6 | ta-92 | sp-6 | an-92 |
| 1993 | is-6 | ta-93 | sp-6 | an-93 |
| 1994 | is-6 | ta-94 | sp-6 | an-94 |
| 1995 | is-6 | ta-95 | sp-6 | an-95 |
| 1996 | is-6 | ta-96 | sp-6 | an-96 |
| 1997 | is-6 | ta-97 | sp-6 | an-97 |
| 1998 | is-6 | ta-98 | sp-6 | an-98 |
| 1999 | is-6 | ta-99 | sp-6 | an-99 |
| 2000 | is-6 | ta-100 | sp-6 | an-100 |
| 2001 | is-6 | ta-101 | sp-6 | an-101 |
| 2002 | is-6 | ta-102 | sp-6 | an-102 |
| 2003 | is-6 | ta-103 | sp-6 | an-103 |
| 2004 | is-6 | ta-104 | sp-6 | an-104 |
| 2005 | is-6 | ta-105 | sp-6 | an-105 |
| 2006 | is-6 | ta-106 | sp-6 | an-106 |
| 2007 | is-6 | ta-107 | sp-6 | an-107 |
| 2008 | is-6 | ta-108 | sp-6 | an-108 |
| 2009 | is-6 | ta-109 | sp-6 | an-109 |
| 2010 | is-6 | ta-110 | sp-6 | an-110 |
| 2011 | is-6 | ta-111 | sp-6 | an-111 |
| 2012 | is-6 | ta-112 | sp-6 | an-112 |
| 2013 | is-6 | ta-113 | sp-6 | an-113 |
| 2014 | is-6 | ta-114 | sp-6 | an-114 |
| 2015 | is-6 | ta-115 | sp-6 | an-115 |
| 2016 | is-6 | ta-116 | sp-6 | an-116 |
| 2017 | is-6 | ta-117 | sp-6 | an-117 |
| 2018 | is-6 | ta-118 | sp-6 | an-118 |
| 2019 | is-6 | ta-119 | sp-6 | an-119 |
| 2020 | is-6 | ta-120 | sp-6 | an-120 |
| 2021 | is-6 | ta-121 | sp-6 | an-121 |
| 2022 | is-6 | ta-122 | sp-6 | an-122 |
| 2023 | is-6 | ta-123 | sp-6 | an-123 |
| 2024 | is-6 | ta-124 | sp-6 | an-124 |
| 2025 | is-6 | ta-125 | sp-6 | an-125 |
| 2026 | is-6 | ta-126 | sp-6 | an-126 |
| 2027 | is-6 | ta-127 | sp-6 | an-127 |
| 2028 | is-6 | ta-128 | sp-6 | an-128 |
| 2029 | is-6 | ta-129 | sp-6 | an-129 |
| 2030 | is-6 | ta-130 | sp-6 | an-130 |
| 2031 | is-6 | ta-131 | sp-6 | an-131 |
| 2032 | is-6 | ta-132 | sp-6 | an-132 |
| 2033 | is-6 | ta-133 | sp-6 | an-133 |
| 2034 | is-6 | ta-134 | sp-6 | an-134 |
| 2035 | is-6 | ta-135 | sp-6 | an-135 |
| 2036 | is-6 | ta-136 | sp-6 | an-136 |
| 2037 | is-6 | ta-137 | sp-6 | an-137 |
| 2038 | is-6 | ta-138 | sp-6 | an-138 |
| 2039 | is-6 | ta-139 | sp-6 | an-139 |
| 2040 | is-6 | ta-140 | sp-6 | an-140 |
| 2041 | is-6 | ta-141 | sp-6 | an-141 |
| 2042 | is-6 | ta-142 | sp-6 | an-142 |
| 2043 | is-6 | ta-143 | sp-6 | an-143 |
| 2044 | is-6 | ta-144 | sp-6 | an-144 |
| 2045 | is-6 | ta-145 | sp-6 | an-145 |
| 2046 | is-6 | ta-146 | sp-6 | an-146 |
| 2047 | is-6 | ta-147 | sp-6 | an-147 |
| 2048 | is-6 | ta-148 | sp-6 | an-148 |
| 2049 | is-6 | ta-149 | sp-6 | an-149 |
| 2050 | is-6 | ta-150 | sp-6 | an-150 |
| 2051 | is-6 | ta-151 | sp-6 | an-151 |
| 2052 | is-6 | ta-152 | sp-6 | an-152 |
| 2053 | is-6 | ta-153 | sp-6 | an-153 |
| 2054 | is-6 | ta-154 | sp-6 | an-154 |
| 2055 | is-6 | ta-155 | sp-6 | an-155 |
| 2056 | is-6 | ta-156 | sp-6 | an-156 |
| 2057 | is-6 | ta-157 | sp-6 | an-157 |
| 2058 | is-6 | ta-158 | sp-6 | an-158 |
| 2059 | is-6 | ta-159 | sp-6 | an-159 |
| 2060 | is-6 | ta-160 | sp-6 | an-160 |
| 2061 | is-6 | ta-161 | sp-6 | an-161 |
| 2062 | is-6 | ta-162 | sp-6 | an-162 |
| 2063 | is-6 | ta-163 | sp-6 | an-163 |
| 2064 | is-6 | ta-164 | sp-6 | an-164 |
| 2065 | is-6 | ta-165 | sp-6 | an-165 |
| 2066 | is-6 | ta-166 | sp-6 | an-166 |
| 2067 | is-6 | ta-167 | sp-6 | an-167 |
| 2068 | is-6 | ta-168 | sp-6 | an-168 |
| 2069 | is-6 | ta-169 | sp-6 | an-169 |
| 2070 | is-6 | ta-170 | sp-6 | an-170 |
| 2071 | is-6 | ta-171 | sp-6 | an-171 |
| 2072 | is-6 | ta-172 | sp-6 | an-172 |
| 2073 | is-6 | ta-173 | sp-6 | an-173 |
| 2074 | is-6 | ta-174 | sp-6 | an-174 |
| 2075 | is-6 | ta-175 | sp-6 | an-175 |
| 2076 | is-6 | ta-176 | sp-6 | an-176 |
| 2077 | is-6 | ta-177 | sp-6 | an-177 |
| 2078 | is-6 | ta-178 | sp-6 | an-178 |
| 2079 | is-6 | ta-179 | sp-6 | an-179 |
| 2080 | is-6 | ta-180 | sp-6 | an-180 |
| 2081 | is-6 | ta-181 | sp-6 | an-181 |
| 2082 | is-6 | ta-182 | sp-6 | an-182 |
| 2083 | is-6 | ta-183 | sp-6 | an-183 |
| 2084 | is-6 | ta-184 | sp-6 | an-184 |
| 2085 | is-6 | ta-185 | sp-6 | an-185 |
| 2086 | is-6 | ta-186 | sp-6 | an-186 |
| 2087 | is-6 | ta-187 | sp-6 | an-187 |
| 2088 | is-6 | ta-188 | sp-6 | an-188 |
| 2089 | is-6 | ta-189 | sp-6 | an-189 |
| 2090 | is-6 | ta-190 | sp-6 | an-190 |
| 2091 | is-6 | ta-191 | sp-6 | an-191 |
| 2092 | is-6 | ta-192 | sp-6 | an-192 |
| 2093 | is-6 | ta-193 | sp-6 | an-193 |
| 2094 | is-6 | ta-194 | sp-6 | an-194 |
| 2095 | is-6 | ta-195 | sp-6 | an-195 |
| 2096 | is-6 | ta-196 | sp-6 | an-196 |
| 2097 | is-6 | ta-197 | sp-6 | an-197 |
| 2098 | is-6 | ta-198 | sp-6 | an-198 |
| 2099 | is-6 | ta-199 | sp-6 | an-199 |
| 2100 | is-6 | ta-200 | sp-6 | an-200 |
| 2101 | is-6 | ta-201 | sp-6 | an-201 |
| 2102 | is-6 | ta-202 | sp-6 | an-202 |

TABLE 2-continued

| Example No. | Reaction reagent is | Reaction reagent ta | Compound of Example sp | Compound of Example an |
|---|---|---|---|---|
| 2103 | is-6 | ta-203 | sp-6 | an-203 |
| 2104 | is-6 | ta-204 | sp-6 | an-204 |
| 2105 | is-6 | ta-205 | sp-6 | an-205 |
| 2106 | is-6 | ta-206 | sp-6 | an-206 |
| 2107 | is-6 | ta-207 | sp-6 | an-207 |
| 2108 | is-6 | ta-208 | sp-6 | an-208 |
| 2109 | is-6 | ta-209 | sp-6 | an-209 |
| 2110 | is-6 | ta-210 | sp-6 | an-210 |
| 2111 | is-6 | ta-211 | sp-6 | an-211 |
| 2112 | is-6 | ta-212 | sp-6 | an-212 |
| 2113 | is-6 | ta-213 | sp-6 | an-213 |
| 2114 | is-6 | ta-214 | sp-6 | an-214 |
| 2115 | is-6 | ta-215 | sp-6 | an-215 |
| 2116 | is-6 | ta-216 | sp-6 | an-216 |
| 2117 | is-6 | ta-217 | sp-6 | an-217 |
| 2118 | is-6 | ta-218 | sp-6 | an-218 |
| 2119 | is-6 | ta-219 | sp-6 | an-219 |
| 2120 | is-6 | ta-220 | sp-6 | an-220 |
| 2121 | is-6 | ta-221 | sp-6 | an-221 |
| 2122 | is-6 | ta-222 | sp-6 | an-222 |
| 2123 | is-6 | ta-223 | sp-6 | an-223 |
| 2124 | is-6 | ta-224 | sp-6 | an-224 |
| 2125 | is-6 | ta-225 | sp-6 | an-225 |
| 2126 | is-6 | ta-226 | sp-6 | an-226 |
| 2127 | is-6 | ta-227 | sp-6 | an-227 |
| 2128 | is-6 | ta-228 | sp-6 | an-228 |
| 2129 | is-6 | ta-229 | sp-6 | an-229 |
| 2130 | is-6 | ta-230 | sp-6 | an-230 |
| 2131 | is-6 | ta-231 | sp-6 | an-231 |
| 2132 | is-6 | ta-232 | sp-6 | an-232 |
| 2133 | is-6 | ta-233 | sp-6 | an-233 |
| 2134 | is-6 | ta-234 | sp-6 | an-234 |
| 2135 | is-6 | ta-235 | sp-6 | an-235 |
| 2136 | is-6 | ta-236 | sp-6 | an-236 |
| 2137 | is-6 | ta-237 | sp-6 | an-237 |
| 2138 | is-6 | ta-238 | sp-6 | an-238 |
| 2139 | is-6 | ta-239 | sp-6 | an-239 |
| 2140 | is-6 | ta-240 | sp-6 | an-240 |
| 2141 | is-6 | ta-241 | sp-6 | an-241 |
| 2142 | is-6 | ta-242 | sp-6 | an-242 |
| 2143 | is-6 | ta-243 | sp-6 | an-243 |
| 2144 | is-6 | ta-244 | sp-6 | an-244 |
| 2145 | is-6 | ta-245 | sp-6 | an-245 |
| 2146 | is-6 | ta-246 | sp-6 | an-246 |
| 2147 | is-6 | ta-247 | sp-6 | an-247 |
| 2148 | is-6 | ta-248 | sp-6 | an-248 |
| 2149 | is-6 | ta-249 | sp-6 | an-249 |
| 2150 | is-6 | ta-250 | sp-6 | an-250 |
| 2151 | is-6 | ta-251 | sp-6 | an-251 |
| 2152 | is-6 | ta-252 | sp-6 | an-252 |
| 2153 | is-6 | ta-253 | sp-6 | an-253 |
| 2154 | is-6 | ta-254 | sp-6 | an-254 |
| 2155 | is-6 | ta-255 | sp-6 | an-255 |
| 2156 | is-6 | ta-256 | sp-6 | an-256 |
| 2157 | is-6 | ta-257 | sp-6 | an-257 |
| 2158 | is-6 | ta-258 | sp-6 | an-258 |
| 2159 | is-6 | ta-259 | sp-6 | an-259 |
| 2160 | is-6 | ta-260 | sp-6 | an-260 |
| 2161 | is-6 | ta-261 | sp-6 | an-261 |
| 2162 | is-6 | ta-262 | sp-6 | an-262 |
| 2163 | is-6 | ta-263 | sp-6 | an-263 |
| 2164 | is-6 | ta-264 | sp-6 | an-264 |
| 2165 | is-6 | ta-265 | sp-6 | an-265 |
| 2166 | is-6 | ta-266 | sp-6 | an-266 |
| 2167 | is-6 | ta-267 | sp-6 | an-267 |
| 2168 | is-6 | ta-268 | sp-6 | an-268 |
| 2169 | is-6 | ta-269 | sp-6 | an-269 |
| 2170 | is-6 | ta-270 | sp-6 | an-270 |
| 2171 | is-6 | ta-271 | sp-6 | an-271 |
| 2172 | is-6 | ta-272 | sp-6 | an-272 |
| 2173 | is-6 | ta-273 | sp-6 | an-273 |
| 2174 | is-6 | ta-274 | sp-6 | an-274 |
| 2175 | is-6 | ta-275 | sp-6 | an-275 |
| 2176 | is-6 | ta-276 | sp-6 | an-276 |
| 2177 | is-6 | ta-277 | sp-6 | an-277 |
| 2178 | is-6 | ta-278 | sp-6 | an-278 |
| 2179 | is-6 | ta-279 | sp-6 | an-279 |
| 2180 | is-6 | ta-280 | sp-6 | an-280 |
| 2181 | is-6 | ta-281 | sp-6 | an-281 |
| 2182 | is-6 | ta-282 | sp-6 | an-282 |
| 2183 | is-6 | ta-283 | sp-6 | an-283 |
| 2184 | is-6 | ta-284 | sp-6 | an-284 |
| 2185 | is-6 | ta-285 | sp-6 | an-285 |
| 2186 | is-6 | ta-286 | sp-6 | an-286 |
| 2187 | is-6 | ta-287 | sp-6 | an-287 |
| 2188 | is-6 | ta-288 | sp-6 | an-288 |
| 2189 | is-6 | ta-289 | sp-6 | an-289 |
| 2190 | is-6 | ta-290 | sp-6 | an-290 |
| 2191 | is-6 | ta-291 | sp-6 | an-291 |
| 2192 | is-6 | ta-292 | sp-6 | an-292 |
| 2193 | is-6 | ta-293 | sp-6 | an-293 |
| 2194 | is-6 | ta-294 | sp-6 | an-294 |
| 2195 | is-6 | ta-295 | sp-6 | an-295 |
| 2196 | is-6 | ta-296 | sp-6 | an-296 |
| 2197 | is-6 | ta-297 | sp-6 | an-297 |
| 2198 | is-6 | ta-298 | sp-6 | an-298 |
| 2199 | is-6 | ta-299 | sp-6 | an-299 |
| 2200 | is-6 | ta-300 | sp-6 | an-300 |
| 2201 | is-6 | ta-301 | sp-6 | an-301 |
| 2202 | is-6 | ta-302 | sp-6 | an-302 |
| 2203 | is-6 | ta-303 | sp-6 | an-303 |
| 2204 | is-6 | ta-304 | sp-6 | an-304 |
| 2205 | is-6 | ta-305 | sp-6 | an-305 |
| 2206 | is-6 | ta-306 | sp-6 | an-306 |
| 2207 | is-6 | ta-307 | sp-6 | an-307 |
| 2208 | is-6 | ta-308 | sp-6 | an-308 |
| 2209 | is-6 | ta-309 | sp-6 | an-309 |
| 2210 | is-6 | ta-310 | sp-6 | an-310 |
| 2211 | is-6 | ta-311 | sp-6 | an-311 |
| 2212 | is-6 | ta-312 | sp-6 | an-312 |
| 2213 | is-6 | ta-313 | sp-6 | an-313 |
| 2214 | is-6 | ta-314 | sp-6 | an-314 |
| 2215 | is-6 | ta-315 | sp-6 | an-315 |
| 2216 | is-6 | ta-316 | sp-6 | an-316 |
| 2217 | is-6 | ta-317 | sp-6 | an-317 |
| 2218 | is-6 | ta-318 | sp-6 | an-318 |
| 2219 | is-6 | ta-319 | sp-6 | an-319 |
| 2220 | is-6 | ta-320 | sp-6 | an-320 |
| 2221 | is-6 | ta-321 | sp-6 | an-321 |
| 2222 | is-6 | ta-322 | sp-6 | an-322 |
| 2223 | is-6 | ta-323 | sp-6 | an-323 |
| 2224 | is-6 | ta-324 | sp-6 | an-324 |
| 2225 | is-6 | ta-325 | sp-6 | an-325 |
| 2226 | is-6 | ta-326 | sp-6 | an-326 |
| 2227 | is-6 | ta-327 | sp-6 | an-327 |
| 2228 | is-6 | ta-328 | sp-6 | an-328 |
| 2229 | is-6 | ta-329 | sp-6 | an-329 |
| 2230 | is-6 | ta-330 | sp-6 | an-330 |
| 2231 | is-6 | ta-331 | sp-6 | an-331 |
| 2232 | is-6 | ta-332 | sp-6 | an-332 |
| 2233 | is-6 | ta-333 | sp-6 | an-333 |
| 2234 | is-6 | ta-334 | sp-6 | an-334 |
| 2235 | is-6 | ta-335 | sp-6 | an-335 |
| 2236 | is-6 | ta-336 | sp-6 | an-336 |
| 2237 | is-6 | ta-337 | sp-6 | an-337 |
| 2238 | is-6 | ta-338 | sp-6 | an-338 |
| 2239 | is-6 | ta-339 | sp-6 | an-339 |
| 2240 | is-6 | ta-340 | sp-6 | an-340 |
| 2241 | is-6 | ta-341 | sp-6 | an-341 |
| 2242 | is-6 | ta-342 | sp-6 | an-342 |
| 2243 | is-6 | ta-343 | sp-6 | an-343 |
| 2244 | is-6 | ta-344 | sp-6 | an-344 |
| 2245 | is-6 | ta-345 | sp-6 | an-345 |
| 2246 | is-6 | ta-346 | sp-6 | an-346 |
| 2247 | is-6 | ta-347 | sp-6 | an-347 |
| 2248 | is-6 | ta-348 | sp-6 | an-348 |
| 2249 | is-6 | ta-349 | sp-6 | an-349 |
| 2250 | is-6 | ta-350 | sp-6 | an-350 |

TABLE 2-continued

| Example No. | Reaction reagent is | Reaction reagent ta | Compound of Example sp | Compound of Example an |
|---|---|---|---|---|
| 2251 | is-6 | ta-351 | sp-6 | an-351 |
| 2252 | is-6 | ta-352 | sp-6 | an-352 |
| 2253 | is-6 | ta-353 | sp-6 | an-353 |
| 2254 | is-6 | ta-354 | sp-6 | an-354 |
| 2255 | is-6 | ta-355 | sp-6 | an-355 |
| 2256 | is-6 | ta-356 | sp-6 | an-356 |
| 2257 | is-6 | ta-357 | sp-6 | an-357 |
| 2258 | is-6 | ta-358 | sp-6 | an-358 |
| 2259 | is-6 | ta-359 | sp-6 | an-359 |
| 2260 | is-6 | ta-360 | sp-6 | an-360 |
| 2261 | is-6 | ta-361 | sp-6 | an-361 |
| 2262 | is-6 | ta-362 | sp-6 | an-362 |
| 2263 | is-6 | ta-363 | sp-6 | an-363 |
| 2264 | is-6 | ta-364 | sp-6 | an-364 |
| 2265 | is-6 | ta-365 | sp-6 | an-365 |
| 2266 | is-6 | ta-366 | sp-6 | an-366 |
| 2267 | is-6 | ta-367 | sp-6 | an-367 |
| 2268 | is-6 | ta-368 | sp-6 | an-368 |
| 2269 | is-6 | ta-369 | sp-6 | an-369 |
| 2270 | is-6 | ta-370 | sp-6 | an-370 |
| 2271 | is-6 | ta-371 | sp-6 | an-371 |
| 2272 | is-6 | ta-372 | sp-6 | an-372 |
| 2273 | is-6 | ta-373 | sp-6 | an-373 |
| 2274 | is-6 | ta-374 | sp-6 | an-374 |
| 2275 | is-6 | ta-375 | sp-6 | an-375 |
| 2276 | is-6 | ta-376 | sp-6 | an-376 |
| 2277 | is-6 | ta-377 | sp-6 | an-377 |
| 2278 | is-7 | ta-1 | sp-7 | an-1 |
| 2279 | is-7 | ta-2 | sp-7 | an-2 |
| 2280 | is-7 | ta-3 | sp-7 | an-3 |
| 2281 | is-7 | ta-4 | sp-7 | an-4 |
| 2282 | is-7 | ta-5 | sp-7 | an-5 |
| 2283 | is-7 | ta-6 | sp-7 | an-6 |
| 2284 | is-7 | ta-7 | sp-7 | an-7 |
| 2285 | is-7 | ta-8 | sp-7 | an-8 |
| 2286 | is-7 | ta-9 | sp-7 | an-9 |
| 2287 | is-7 | ta-10 | sp-7 | an-10 |
| 2288 | is-7 | ta-11 | sp-7 | an-11 |
| 2289 | is-7 | ta-12 | sp-7 | an-12 |
| 2290 | is-7 | ta-13 | sp-7 | an-13 |
| 2291 | is-7 | ta-14 | sp-7 | an-14 |
| 2292 | is-7 | ta-15 | sp-7 | an-15 |
| 2293 | is-7 | ta-16 | sp-7 | an-16 |
| 2294 | is-7 | ta-17 | sp-7 | an-17 |
| 2295 | is-7 | ta-18 | sp-7 | an-18 |
| 2296 | is-7 | ta-19 | sp-7 | an-19 |
| 2297 | is-7 | ta-20 | sp-7 | an-20 |
| 2298 | is-7 | ta-21 | sp-7 | an-21 |
| 2299 | is-7 | ta-22 | sp-7 | an-22 |
| 2300 | is-7 | ta-23 | sp-7 | an-23 |
| 2301 | is-7 | ta-24 | sp-7 | an-24 |
| 2302 | is-7 | ta-25 | sp-7 | an-25 |
| 2303 | is-7 | ta-26 | sp-7 | an-26 |
| 2304 | is-7 | ta-27 | sp-7 | an-27 |
| 2305 | is-7 | ta-28 | sp-7 | an-28 |
| 2306 | is-7 | ta-29 | sp-7 | an-29 |
| 2307 | is-7 | ta-30 | sp-7 | an-30 |
| 2308 | is-7 | ta-31 | sp-7 | an-31 |
| 2309 | is-7 | ta-32 | sp-7 | an-32 |
| 2310 | is-7 | ta-33 | sp-7 | an-33 |
| 2311 | is-7 | ta-34 | sp-7 | an-34 |
| 2312 | is-7 | ta-35 | sp-7 | an-35 |
| 2313 | is-7 | ta-36 | sp-7 | an-36 |
| 2314 | is-7 | ta-37 | sp-7 | an-37 |
| 2315 | is-7 | ta-38 | sp-7 | an-38 |
| 2316 | is-7 | ta-39 | sp-7 | an-39 |
| 2317 | is-7 | ta-40 | sp-7 | an-40 |
| 2318 | is-7 | ta-41 | sp-7 | an-41 |
| 2319 | is-7 | ta-42 | sp-7 | an-42 |
| 2320 | is-7 | ta-43 | sp-7 | an-43 |
| 2321 | is-7 | ta-44 | sp-7 | an-44 |
| 2322 | is-7 | ta-45 | sp-7 | an-45 |
| 2323 | is-7 | ta-46 | sp-7 | an-46 |
| 2324 | is-7 | ta-47 | sp-7 | an-47 |
| 2325 | is-7 | ta-48 | sp-7 | an-48 |
| 2326 | is-7 | ta-49 | sp-7 | an-49 |
| 2327 | is-7 | ta-50 | sp-7 | an-50 |
| 2328 | is-7 | ta-51 | sp-7 | an-51 |
| 2329 | is-7 | ta-52 | sp-7 | an-52 |
| 2330 | is-7 | ta-53 | sp-7 | an-53 |
| 2331 | is-7 | ta-54 | sp-7 | an-54 |
| 2332 | is-7 | ta-55 | sp-7 | an-55 |
| 2333 | is-7 | ta-56 | sp-7 | an-56 |
| 2334 | is-7 | ta-57 | sp-7 | an-57 |
| 2335 | is-7 | ta-58 | sp-7 | an-58 |
| 2336 | is-7 | ta-59 | sp-7 | an-59 |
| 2337 | is-7 | ta-60 | sp-7 | an-60 |
| 2338 | is-7 | ta-61 | sp-7 | an-61 |
| 2339 | is-7 | ta-62 | sp-7 | an-62 |
| 2340 | is-7 | ta-63 | sp-7 | an-63 |
| 2341 | is-7 | ta-64 | sp-7 | an-64 |
| 2342 | is-7 | ta-65 | sp-7 | an-65 |
| 2343 | is-7 | ta-66 | sp-7 | an-66 |
| 2344 | is-7 | ta-67 | sp-7 | an-67 |
| 2345 | is-7 | ta-68 | sp-7 | an-68 |
| 2346 | is-7 | ta-69 | sp-7 | an-69 |
| 2347 | is-7 | ta-70 | sp-7 | an-70 |
| 2348 | is-7 | ta-71 | sp-7 | an-71 |
| 2349 | is-7 | ta-72 | sp-7 | an-72 |
| 2350 | is-7 | ta-73 | sp-7 | an-73 |
| 2351 | is-7 | ta-74 | sp-7 | an-74 |
| 2352 | is-7 | ta-75 | sp-7 | an-75 |
| 2353 | is-7 | ta-76 | sp-7 | an-76 |
| 2354 | is-7 | ta-77 | sp-7 | an-77 |
| 2355 | is-7 | ta-78 | sp-7 | an-78 |
| 2356 | is-7 | ta-79 | sp-7 | an-79 |
| 2357 | is-7 | ta-80 | sp-7 | an-80 |
| 2358 | is-7 | ta-81 | sp-7 | an-81 |
| 2359 | is-7 | ta-82 | sp-7 | an-82 |
| 2360 | is-7 | ta-83 | sp-7 | an-83 |
| 2361 | is-7 | ta-84 | sp-7 | an-84 |
| 2362 | is-7 | ta-85 | sp-7 | an-85 |
| 2363 | is-7 | ta-86 | sp-7 | an-86 |
| 2364 | is-7 | ta-87 | sp-7 | an-87 |
| 2365 | is-7 | ta-88 | sp-7 | an-88 |
| 2366 | is-7 | ta-89 | sp-7 | an-89 |
| 2367 | is-7 | ta-90 | sp-7 | an-90 |
| 2368 | is-7 | ta-91 | sp-7 | an-91 |
| 2369 | is-7 | ta-92 | sp-7 | an-92 |
| 2370 | is-7 | ta-93 | sp-7 | an-93 |
| 2371 | is-7 | ta-94 | sp-7 | an-94 |
| 2372 | is-7 | ta-95 | sp-7 | an-95 |
| 2373 | is-7 | ta-96 | sp-7 | an-96 |
| 2374 | is-7 | ta-97 | sp-7 | an-97 |
| 2375 | is-7 | ta-98 | sp-7 | an-98 |
| 2376 | is-7 | ta-99 | sp-7 | an-99 |
| 2377 | is-7 | ta-100 | sp-7 | an-100 |
| 2378 | is-7 | ta-101 | sp-7 | an-101 |
| 2379 | is-7 | ta-102 | sp-7 | an-102 |
| 2380 | is-7 | ta-103 | sp-7 | an-103 |
| 2381 | is-7 | ta-104 | sp-7 | an-104 |
| 2382 | is-7 | ta-105 | sp-7 | an-105 |
| 2383 | is-7 | ta-106 | sp-7 | an-106 |
| 2384 | is-7 | ta-107 | sp-7 | an-107 |
| 2385 | is-7 | ta-108 | sp-7 | an-108 |
| 2386 | is-7 | ta-109 | sp-7 | an-109 |
| 2387 | is-7 | ta-110 | sp-7 | an-110 |
| 2388 | is-7 | ta-111 | sp-7 | an-111 |
| 2389 | is-7 | ta-112 | sp-7 | an-112 |
| 2390 | is-7 | ta-113 | sp-7 | an-113 |
| 2391 | is-7 | ta-114 | sp-7 | an-114 |
| 2392 | is-7 | ta-115 | sp-7 | an-115 |
| 2393 | is-7 | ta-116 | sp-7 | an-116 |
| 2394 | is-7 | ta-117 | sp-7 | an-117 |
| 2395 | is-7 | ta-118 | sp-7 | an-118 |
| 2396 | is-7 | ta-119 | sp-7 | an-119 |
| 2397 | is-7 | ta-120 | sp-7 | an-120 |
| 2398 | is-7 | ta-121 | sp-7 | an-121 |

TABLE 2-continued

| Example No. | Reaction reagent | | Compound of Example | |
|---|---|---|---|---|
| | is | ta | sp | an |
| 2399 | is-7 | ta-122 | sp-7 | an-122 |
| 2400 | is-7 | ta-123 | sp-7 | an-123 |
| 2401 | is-7 | ta-124 | sp-7 | an-124 |
| 2402 | is-7 | ta-125 | sp-7 | an-125 |
| 2403 | is-7 | ta-126 | sp-7 | an-126 |
| 2404 | is-7 | ta-127 | sp-7 | an-127 |
| 2405 | is-7 | ta-128 | sp-7 | an-128 |
| 2406 | is-7 | ta-129 | sp-7 | an-129 |
| 2407 | is-7 | ta-130 | sp-7 | an-130 |
| 2408 | is-7 | ta-131 | sp-7 | an-131 |
| 2409 | is-7 | ta-132 | sp-7 | an-132 |
| 2410 | is-7 | ta-133 | sp-7 | an-133 |
| 2411 | is-7 | ta-134 | sp-7 | an-134 |
| 2412 | is-7 | ta-135 | sp-7 | an-135 |
| 2413 | is-7 | ta-136 | sp-7 | an-136 |
| 2414 | is-7 | ta-137 | sp-7 | an-137 |
| 2415 | is-7 | ta-138 | sp-7 | an-138 |
| 2416 | is-7 | ta-139 | sp-7 | an-139 |
| 2417 | is-7 | ta-140 | sp-7 | an-140 |
| 2418 | is-7 | ta-141 | sp-7 | an-141 |
| 2419 | is-7 | ta-142 | sp-7 | an-142 |
| 2420 | is-7 | ta-143 | sp-7 | an-143 |
| 2421 | is-7 | ta-144 | sp-7 | an-144 |
| 2422 | is-7 | ta-145 | sp-7 | an-145 |
| 2423 | is-7 | ta-146 | sp-7 | an-146 |
| 2424 | is-7 | ta-147 | sp-7 | an-147 |
| 2425 | is-7 | ta-148 | sp-7 | an-148 |
| 2426 | is-7 | ta-149 | sp-7 | an-149 |
| 2427 | is-7 | ta-150 | sp-7 | an-150 |
| 2428 | is-7 | ta-151 | sp-7 | an-151 |
| 2429 | is-7 | ta-152 | sp-7 | an-152 |
| 2430 | is-7 | ta-153 | sp-7 | an-153 |
| 2431 | is-7 | ta-154 | sp-7 | an-154 |
| 2432 | is-7 | ta-155 | sp-7 | an-155 |
| 2433 | is-7 | ta-156 | sp-7 | an-156 |
| 2434 | is-7 | ta-157 | sp-7 | an-157 |
| 2435 | is-7 | ta-158 | sp-7 | an-158 |
| 2436 | is-7 | ta-159 | sp-7 | an-159 |
| 2437 | is-7 | ta-160 | sp-7 | an-160 |
| 2438 | is-7 | ta-161 | sp-7 | an-161 |
| 2439 | is-7 | ta-162 | sp-7 | an-162 |
| 2440 | is-7 | ta-163 | sp-7 | an-163 |
| 2441 | is-7 | ta-164 | sp-7 | an-164 |
| 2442 | is-7 | ta-165 | sp-7 | an-165 |
| 2443 | is-7 | ta-166 | sp-7 | an-166 |
| 2444 | is-7 | ta-167 | sp-7 | an-167 |
| 2445 | is-7 | ta-168 | sp-7 | an-168 |
| 2446 | is-7 | ta-169 | sp-7 | an-169 |
| 2447 | is-7 | ta-170 | sp-7 | an-170 |
| 2448 | is-7 | ta-171 | sp-7 | an-171 |
| 2449 | is-7 | ta-172 | sp-7 | an-172 |
| 2450 | is-7 | ta-173 | sp-7 | an-173 |
| 2451 | is-7 | ta-174 | sp-7 | an-174 |
| 2452 | is-7 | ta-175 | sp-7 | an-175 |
| 2453 | is-7 | ta-176 | sp-7 | an-176 |
| 2454 | is-7 | ta-177 | sp-7 | an-177 |
| 2455 | is-7 | ta-178 | sp-7 | an-178 |
| 2456 | is-7 | ta-179 | sp-7 | an-179 |
| 2457 | is-7 | ta-180 | sp-7 | an-180 |
| 2458 | is-7 | ta-181 | sp-7 | an-181 |
| 2459 | is-7 | ta-182 | sp-7 | an-182 |
| 2460 | is-7 | ta-183 | sp-7 | an-183 |
| 2461 | is-7 | ta-184 | sp-7 | an-184 |
| 2462 | is-7 | ta-185 | sp-7 | an-185 |
| 2463 | is-7 | ta-186 | sp-7 | an-186 |
| 2464 | is-7 | ta-187 | sp-7 | an-187 |
| 2465 | is-7 | ta-188 | sp-7 | an-188 |
| 2466 | is-7 | ta-189 | sp-7 | an-189 |
| 2467 | is-7 | ta-190 | sp-7 | an-190 |
| 2468 | is-7 | ta-191 | sp-7 | an-191 |
| 2469 | is-7 | ta-192 | sp-7 | an-192 |
| 2470 | is-7 | ta-193 | sp-7 | an-193 |
| 2471 | is-7 | ta-194 | sp-7 | an-194 |
| 2472 | is-7 | ta-195 | sp-7 | an-195 |
| 2473 | is-7 | ta-196 | sp-7 | an-196 |
| 2474 | is-7 | ta-197 | sp-7 | an-197 |
| 2475 | is-7 | ta-198 | sp-7 | an-198 |
| 2476 | is-7 | ta-199 | sp-7 | an-199 |
| 2477 | is-7 | ta-200 | sp-7 | an-200 |
| 2478 | is-7 | ta-201 | sp-7 | an-201 |
| 2479 | is-7 | ta-202 | sp-7 | an-202 |
| 2480 | is-7 | ta-203 | sp-7 | an-203 |
| 2481 | is-7 | ta-204 | sp-7 | an-204 |
| 2482 | is-7 | ta-205 | sp-7 | an-205 |
| 2483 | is-7 | ta-206 | sp-7 | an-206 |
| 2484 | is-7 | ta-207 | sp-7 | an-207 |
| 2485 | is-7 | ta-208 | sp-7 | an-208 |
| 2486 | is-7 | ta-209 | sp-7 | an-209 |
| 2487 | is-7 | ta-210 | sp-7 | an-210 |
| 2488 | is-7 | ta-211 | sp-7 | an-211 |
| 2489 | is-7 | ta-212 | sp-7 | an-212 |
| 2490 | is-7 | ta-213 | sp-7 | an-213 |
| 2491 | is-7 | ta-214 | sp-7 | an-214 |
| 2492 | is-7 | ta-215 | sp-7 | an-215 |
| 2493 | is-7 | ta-216 | sp-7 | an-216 |
| 2494 | is-7 | ta-217 | sp-7 | an-217 |
| 2495 | is-7 | ta-218 | sp-7 | an-218 |
| 2496 | is-7 | ta-219 | sp-7 | an-219 |
| 2497 | is-7 | ta-220 | sp-7 | an-220 |
| 2498 | is-7 | ta-221 | sp-7 | an-221 |
| 2499 | is-7 | ta-222 | sp-7 | an-222 |
| 2500 | is-7 | ta-223 | sp-7 | an-223 |
| 2501 | is-7 | ta-224 | sp-7 | an-224 |
| 2502 | is-7 | ta-225 | sp-7 | an-225 |
| 2503 | is-7 | ta-226 | sp-7 | an-226 |
| 2504 | is-7 | ta-227 | sp-7 | an-227 |
| 2505 | is-7 | ta-228 | sp-7 | an-228 |
| 2506 | is-7 | ta-229 | sp-7 | an-229 |
| 2507 | is-7 | ta-230 | sp-7 | an-230 |
| 2508 | is-7 | ta-231 | sp-7 | an-231 |
| 2509 | is-7 | ta-232 | sp-7 | an-232 |
| 2510 | is-7 | ta-233 | sp-7 | an-233 |
| 2511 | is-7 | ta-234 | sp-7 | an-234 |
| 2512 | is-7 | ta-235 | sp-7 | an-235 |
| 2513 | is-7 | ta-236 | sp-7 | an-236 |
| 2514 | is-7 | ta-237 | sp-7 | an-237 |
| 2515 | is-7 | ta-238 | sp-7 | an-238 |
| 2516 | is-7 | ta-239 | sp-7 | an-239 |
| 2517 | is-7 | ta-240 | sp-7 | an-240 |
| 2518 | is-7 | ta-241 | sp-7 | an-241 |
| 2519 | is-7 | ta-242 | sp-7 | an-242 |
| 2520 | is-7 | ta-243 | sp-7 | an-243 |
| 2521 | is-7 | ta-244 | sp-7 | an-244 |
| 2522 | is-7 | ta-245 | sp-7 | an-245 |
| 2523 | is-7 | ta-246 | sp-7 | an-246 |
| 2524 | is-7 | ta-247 | sp-7 | an-247 |
| 2525 | is-7 | ta-248 | sp-7 | an-248 |
| 2526 | is-7 | ta-249 | sp-7 | an-249 |
| 2527 | is-7 | ta-250 | sp-7 | an-250 |
| 2528 | is-7 | ta-251 | sp-7 | an-251 |
| 2529 | is-7 | ta-252 | sp-7 | an-252 |
| 2530 | is-7 | ta-253 | sp-7 | an-253 |
| 2531 | is-7 | ta-254 | sp-7 | an-254 |
| 2532 | is-7 | ta-255 | sp-7 | an-255 |
| 2533 | is-7 | ta-256 | sp-7 | an-256 |
| 2534 | is-7 | ta-257 | sp-7 | an-257 |
| 2535 | is-7 | ta-258 | sp-7 | an-258 |
| 2536 | is-7 | ta-259 | sp-7 | an-259 |
| 2537 | is-7 | ta-260 | sp-7 | an-260 |
| 2538 | is-7 | ta-261 | sp-7 | an-261 |
| 2539 | is-7 | ta-262 | sp-7 | an-262 |
| 2540 | is-7 | ta-263 | sp-7 | an-263 |
| 2541 | is-7 | ta-264 | sp-7 | an-264 |
| 2542 | is-7 | ta-265 | sp-7 | an-265 |
| 2543 | is-7 | ta-266 | sp-7 | an-266 |
| 2544 | is-7 | ta-267 | sp-7 | an-267 |
| 2545 | is-7 | ta-268 | sp-7 | an-268 |
| 2546 | is-7 | ta-269 | sp-7 | an-269 |

TABLE 2-continued

| Example No. | Reaction reagent is | Reaction reagent ta | Compound of Example sp | Compound of Example an |
|---|---|---|---|---|
| 2547 | is-7 | ta-270 | sp-7 | an-270 |
| 2548 | is-7 | ta-271 | sp-7 | an-271 |
| 2549 | is-7 | ta-272 | sp-7 | an-272 |
| 2550 | is-7 | ta-273 | sp-7 | an-273 |
| 2551 | is-7 | ta-274 | sp-7 | an-274 |
| 2552 | is-7 | ta-275 | sp-7 | an-275 |
| 2553 | is-7 | ta-276 | sp-7 | an-276 |
| 2554 | is-7 | ta-277 | sp-7 | an-277 |
| 2555 | is-7 | ta-278 | sp-7 | an-278 |
| 2556 | is-7 | ta-279 | sp-7 | an-279 |
| 2557 | is-7 | ta-280 | sp-7 | an-280 |
| 2558 | is-7 | ta-281 | sp-7 | an-281 |
| 2559 | is-7 | ta-282 | sp-7 | an-282 |
| 2560 | is-7 | ta-283 | sp-7 | an-283 |
| 2561 | is-7 | ta-284 | sp-7 | an-284 |
| 2562 | is-7 | ta-285 | sp-7 | an-285 |
| 2563 | is-7 | ta-286 | sp-7 | an-286 |
| 2564 | is-7 | ta-287 | sp-7 | an-287 |
| 2565 | is-7 | ta-288 | sp-7 | an-288 |
| 2566 | is-7 | ta-289 | sp-7 | an-289 |
| 2567 | is-7 | ta-290 | sp-7 | an-290 |
| 2568 | is-7 | ta-291 | sp-7 | an-291 |
| 2569 | is-7 | ta-292 | sp-7 | an-292 |
| 2570 | is-7 | ta-293 | sp-7 | an-293 |
| 2571 | is-7 | ta-294 | sp-7 | an-294 |
| 2572 | is-7 | ta-295 | sp-7 | an-295 |
| 2573 | is-7 | ta-296 | sp-7 | an-296 |
| 2574 | is-7 | ta-297 | sp-7 | an-297 |
| 2575 | is-7 | ta-298 | sp-7 | an-298 |
| 2576 | is-7 | ta-299 | sp-7 | an-299 |
| 2577 | is-7 | ta-300 | sp-7 | an-300 |
| 2578 | is-7 | ta-301 | sp-7 | an-301 |
| 2579 | is-7 | ta-302 | sp-7 | an-302 |
| 2580 | is-7 | ta-303 | sp-7 | an-303 |
| 2581 | is-7 | ta-304 | sp-7 | an-304 |
| 2582 | is-7 | ta-305 | sp-7 | an-305 |
| 2583 | is-7 | ta-306 | sp-7 | an-306 |
| 2584 | is-7 | ta-307 | sp-7 | an-307 |
| 2585 | is-7 | ta-308 | sp-7 | an-308 |
| 2586 | is-7 | ta-309 | sp-7 | an-309 |
| 2587 | is-7 | ta-310 | sp-7 | an-310 |
| 2588 | is-7 | ta-311 | sp-7 | an-311 |
| 2589 | is-7 | ta-312 | sp-7 | an-312 |
| 2590 | is-7 | ta-313 | sp-7 | an-313 |
| 2591 | is-7 | ta-314 | sp-7 | an-314 |
| 2592 | is-7 | ta-315 | sp-7 | an-315 |
| 2593 | is-7 | ta-316 | sp-7 | an-316 |
| 2594 | is-7 | ta-317 | sp-7 | an-317 |
| 2595 | is-7 | ta-318 | sp-7 | an-318 |
| 2596 | is-7 | ta-319 | sp-7 | an-319 |
| 2597 | is-7 | ta-320 | sp-7 | an-320 |
| 2598 | is-7 | ta-321 | sp-7 | an-321 |
| 2599 | is-7 | ta-322 | sp-7 | an-322 |
| 2600 | is-7 | ta-323 | sp-7 | an-323 |
| 2601 | is-7 | ta-324 | sp-7 | an-324 |
| 2602 | is-7 | ta-325 | sp-7 | an-325 |
| 2603 | is-7 | ta-326 | sp-7 | an-326 |
| 2604 | is-7 | ta-327 | sp-7 | an-327 |
| 2605 | is-7 | ta-328 | sp-7 | an-328 |
| 2606 | is-7 | ta-329 | sp-7 | an-329 |
| 2607 | is-7 | ta-330 | sp-7 | an-330 |
| 2608 | is-7 | ta-331 | sp-7 | an-331 |
| 2609 | is-7 | ta-332 | sp-7 | an-332 |
| 2610 | is-7 | ta-333 | sp-7 | an-333 |
| 2611 | is-7 | ta-334 | sp-7 | an-334 |
| 2612 | is-7 | ta-335 | sp-7 | an-335 |
| 2613 | is-7 | ta-336 | sp-7 | an-336 |
| 2614 | is-7 | ta-337 | sp-7 | an-337 |
| 2615 | is-7 | ta-338 | sp-7 | an-338 |
| 2616 | is-7 | ta-339 | sp-7 | an-339 |
| 2617 | is-7 | ta-340 | sp-7 | an-340 |
| 2618 | is-7 | ta-341 | sp-7 | an-341 |
| 2619 | is-7 | ta-342 | sp-7 | an-342 |
| 2620 | is-7 | ta-343 | sp-7 | an-343 |
| 2621 | is-7 | ta-344 | sp-7 | an-344 |
| 2622 | is-7 | ta-345 | sp-7 | an-345 |
| 2623 | is-7 | ta-346 | sp-7 | an-346 |
| 2624 | is-7 | ta-347 | sp-7 | an-347 |
| 2625 | is-7 | ta-348 | sp-7 | an-348 |
| 2626 | is-7 | ta-349 | sp-7 | an-349 |
| 2627 | is-7 | ta-350 | sp-7 | an-350 |
| 2628 | is-7 | ta-351 | sp-7 | an-351 |
| 2629 | is-7 | ta-352 | sp-7 | an-352 |
| 2630 | is-7 | ta-353 | sp-7 | an-353 |
| 2631 | is-7 | ta-354 | sp-7 | an-354 |
| 2632 | is-7 | ta-355 | sp-7 | an-355 |
| 2633 | is-7 | ta-356 | sp-7 | an-356 |
| 2634 | is-7 | ta-357 | sp-7 | an-357 |
| 2635 | is-7 | ta-358 | sp-7 | an-358 |
| 2636 | is-7 | ta-359 | sp-7 | an-359 |
| 2637 | is-7 | ta-360 | sp-7 | an-360 |
| 2638 | is-7 | ta-361 | sp-7 | an-361 |
| 2639 | is-7 | ta-362 | sp-7 | an-362 |
| 2640 | is-7 | ta-363 | sp-7 | an-363 |
| 2641 | is-7 | ta-364 | sp-7 | an-364 |
| 2642 | is-7 | ta-365 | sp-7 | an-365 |
| 2643 | is-7 | ta-366 | sp-7 | an-366 |
| 2644 | is-7 | ta-367 | sp-7 | an-367 |
| 2645 | is-7 | ta-368 | sp-7 | an-368 |
| 2646 | is-7 | ta-369 | sp-7 | an-369 |
| 2647 | is-7 | ta-370 | sp-7 | an-370 |
| 2648 | is-7 | ta-371 | sp-7 | an-371 |
| 2649 | is-7 | ta-372 | sp-7 | an-372 |
| 2650 | is-7 | ta-373 | sp-7 | an-373 |
| 2651 | is-7 | ta-374 | sp-7 | an-374 |
| 2652 | is-7 | ta-375 | sp-7 | an-375 |
| 2653 | is-7 | ta-376 | sp-7 | an-376 |
| 2654 | is-7 | ta-377 | sp-7 | an-377 |
| 2655 | is-8 | ta-1 | sp-8 | an-1 |
| 2656 | is-8 | ta-2 | sp-8 | an-2 |
| 2657 | is-8 | ta-3 | sp-8 | an-3 |
| 2658 | is-8 | ta-4 | sp-8 | an-4 |
| 2659 | is-8 | ta-5 | sp-8 | an-5 |
| 2660 | is-8 | ta-6 | sp-8 | an-6 |
| 2661 | is-8 | ta-7 | sp-8 | an-7 |
| 2662 | is-8 | ta-8 | sp-8 | an-8 |
| 2663 | is-8 | ta-9 | sp-8 | an-9 |
| 2664 | is-8 | ta-10 | sp-8 | an-10 |
| 2665 | is-8 | ta-11 | sp-8 | an-11 |
| 2666 | is-8 | ta-12 | sp-8 | an-12 |
| 2667 | is-8 | ta-13 | sp-8 | an-13 |
| 2668 | is-8 | ta-14 | sp-8 | an-14 |
| 2669 | is-8 | ta-15 | sp-8 | an-15 |
| 2670 | is-8 | ta-16 | sp-8 | an-16 |
| 2671 | is-8 | ta-17 | sp-8 | an-17 |
| 2672 | is-8 | ta-18 | sp-8 | an-18 |
| 2673 | is-8 | ta-19 | sp-8 | an-19 |
| 2674 | is-8 | ta-20 | sp-8 | an-20 |
| 2675 | is-8 | ta-21 | sp-8 | an-21 |
| 2676 | is-8 | ta-22 | sp-8 | an-22 |
| 2677 | is-8 | ta-23 | sp-8 | an-23 |
| 2678 | is-8 | ta-24 | sp-8 | an-24 |
| 2679 | is-8 | ta-25 | sp-8 | an-25 |
| 2680 | is-8 | ta-26 | sp-8 | an-26 |
| 2681 | is-8 | ta-27 | sp-8 | an-27 |
| 2682 | is-8 | ta-28 | sp-8 | an-28 |
| 2683 | is-8 | ta-29 | sp-8 | an-29 |
| 2684 | is-8 | ta-30 | sp-8 | an-30 |
| 2685 | is-8 | ta-31 | sp-8 | an-31 |
| 2686 | is-8 | ta-32 | sp-8 | an-32 |
| 2687 | is-8 | ta-33 | sp-8 | an-33 |
| 2688 | is-8 | ta-34 | sp-8 | an-34 |
| 2689 | is-8 | ta-35 | sp-8 | an-35 |
| 2690 | is-8 | ta-36 | sp-8 | an-36 |
| 2691 | is-8 | ta-37 | sp-8 | an-37 |
| 2692 | is-8 | ta-38 | sp-8 | an-38 |
| 2693 | is-8 | ta-39 | sp-8 | an-39 |
| 2694 | is-8 | ta-40 | sp-8 | an-40 |

TABLE 2-continued

| Example No. | Reaction reagent is | Reaction reagent ta | Compound of Example sp | Compound of Example an |
|---|---|---|---|---|
| 2695 | is-8 | ta-41 | sp-8 | an-41 |
| 2696 | is-8 | ta-42 | sp-8 | an-42 |
| 2697 | is-8 | ta-43 | sp-8 | an-43 |
| 2698 | is-8 | ta-44 | sp-8 | an-44 |
| 2699 | is-8 | ta-45 | sp-8 | an-45 |
| 2700 | is-8 | ta-46 | sp-8 | an-46 |
| 2701 | is-8 | ta-47 | sp-8 | an-47 |
| 2702 | is-8 | ta-48 | sp-8 | an-48 |
| 2703 | is-8 | ta-49 | sp-8 | an-49 |
| 2704 | is-8 | ta-50 | sp-8 | an-50 |
| 2705 | is-8 | ta-51 | sp-8 | an-51 |
| 2706 | is-8 | ta-52 | sp-8 | an-52 |
| 2707 | is-8 | ta-53 | sp-8 | an-53 |
| 2708 | is-8 | ta-54 | sp-8 | an-54 |
| 2709 | is-8 | ta-55 | sp-8 | an-55 |
| 2710 | is-8 | ta-56 | sp-8 | an-56 |
| 2711 | is-8 | ta-57 | sp-8 | an-57 |
| 2712 | is-8 | ta-58 | sp-8 | an-58 |
| 2713 | is-8 | ta-59 | sp-8 | an-59 |
| 2714 | is-8 | ta-60 | sp-8 | an-60 |
| 2715 | is-8 | ta-61 | sp-8 | an-61 |
| 2716 | is-8 | ta-62 | sp-8 | an-62 |
| 2717 | is-8 | ta-63 | sp-8 | an-63 |
| 2718 | is-8 | ta-64 | sp-8 | an-64 |
| 2719 | is-8 | ta-65 | sp-8 | an-65 |
| 2720 | is-8 | ta-66 | sp-8 | an-66 |
| 2721 | is-8 | ta-67 | sp-8 | an-67 |
| 2722 | is-8 | ta-68 | sp-8 | an-68 |
| 2723 | is-8 | ta-69 | sp-8 | an-69 |
| 2724 | is-8 | ta-70 | sp-8 | an-70 |
| 2725 | is-8 | ta-71 | sp-8 | an-71 |
| 2726 | is-8 | ta-72 | sp-8 | an-72 |
| 2727 | is-8 | ta-73 | sp-8 | an-73 |
| 2728 | is-8 | ta-74 | sp-8 | an-74 |
| 2729 | is-8 | ta-75 | sp-8 | an-75 |
| 2730 | is-8 | ta-76 | sp-8 | an-76 |
| 2731 | is-8 | ta-77 | sp-8 | an-77 |
| 2732 | is-8 | ta-78 | sp-8 | an-78 |
| 2733 | is-8 | ta-79 | sp-8 | an-79 |
| 2734 | is-8 | ta-80 | sp-8 | an-80 |
| 2735 | is-8 | ta-81 | sp-8 | an-81 |
| 2736 | is-8 | ta-82 | sp-8 | an-82 |
| 2737 | is-8 | ta-83 | sp-8 | an-83 |
| 2738 | is-8 | ta-84 | sp-8 | an-84 |
| 2739 | is-8 | ta-85 | sp-8 | an-85 |
| 2740 | is-8 | ta-86 | sp-8 | an-86 |
| 2741 | is-8 | ta-87 | sp-8 | an-87 |
| 2742 | is-8 | ta-88 | sp-8 | an-88 |
| 2743 | is-8 | ta-89 | sp-8 | an-89 |
| 2744 | is-8 | ta-90 | sp-8 | an-90 |
| 2745 | is-8 | ta-91 | sp-8 | an-91 |
| 2746 | is-8 | ta-92 | sp-8 | an-92 |
| 2747 | is-8 | ta-93 | sp-8 | an-93 |
| 2748 | is-8 | ta-94 | sp-8 | an-94 |
| 2749 | is-8 | ta-95 | sp-8 | an-95 |
| 2750 | is-8 | ta-96 | sp-8 | an-96 |
| 2751 | is-8 | ta-97 | sp-8 | an-97 |
| 2752 | is-8 | ta-98 | sp-8 | an-98 |
| 2753 | is-8 | ta-99 | sp-8 | an-99 |
| 2754 | is-8 | ta-100 | sp-8 | an-100 |
| 2755 | is-8 | ta-101 | sp-8 | an-101 |
| 2756 | is-8 | ta-102 | sp-8 | an-102 |
| 2757 | is-8 | ta-103 | sp-8 | an-103 |
| 2758 | is-8 | ta-104 | sp-8 | an-104 |
| 2759 | is-8 | ta-105 | sp-8 | an-105 |
| 2760 | is-8 | ta-106 | sp-8 | an-106 |
| 2761 | is-8 | ta-107 | sp-8 | an-107 |
| 2762 | is-8 | ta-108 | sp-8 | an-108 |
| 2763 | is-8 | ta-109 | sp-8 | an-109 |
| 2764 | is-8 | ta-110 | sp-8 | an-110 |
| 2765 | is-8 | ta-111 | sp-8 | an-111 |
| 2766 | is-8 | ta-112 | sp-8 | an-112 |
| 2767 | is-8 | ta-113 | sp-8 | an-113 |
| 2768 | is-8 | ta-114 | sp-8 | an-114 |
| 2769 | is-8 | ta-115 | sp-8 | an-115 |
| 2770 | is-8 | ta-116 | sp-8 | an-116 |
| 2771 | is-8 | ta-117 | sp-8 | an-117 |
| 2772 | is-8 | ta-118 | sp-8 | an-118 |
| 2773 | is-8 | ta-119 | sp-8 | an-119 |
| 2774 | is-8 | ta-120 | sp-8 | an-120 |
| 2775 | is-8 | ta-121 | sp-8 | an-121 |
| 2776 | is-8 | ta-122 | sp-8 | an-122 |
| 2777 | ia-8 | ta-123 | sp-8 | an-123 |
| 2778 | is-8 | ta-124 | sp-8 | an-124 |
| 2779 | is-8 | ta-125 | sp-8 | an-125 |
| 2780 | is-8 | ta-126 | sp-8 | an-126 |
| 2781 | is-8 | ta-127 | sp-8 | an-127 |
| 2782 | is-8 | ta-128 | sp-8 | an-128 |
| 2783 | is-8 | ta-129 | sp-8 | an-129 |
| 2784 | is-8 | ta-130 | sp-8 | an-130 |
| 2785 | is-8 | ta-131 | sp-8 | an-131 |
| 2786 | is-8 | ta-132 | sp-8 | an-132 |
| 2787 | is-8 | ta-133 | sp-8 | an-133 |
| 2788 | is-8 | ta-134 | sp-8 | an-134 |
| 2789 | is-8 | ta-135 | sp-8 | an-135 |
| 2790 | is-8 | ta-136 | sp-8 | an-136 |
| 2791 | is-8 | ta-137 | sp-8 | an-137 |
| 2792 | is-8 | ta-138 | sp-8 | an-138 |
| 2793 | is-8 | ta-139 | sp-8 | an-139 |
| 2794 | is-8 | ta-140 | sp-8 | an-140 |
| 2795 | is-8 | ta-141 | sp-8 | an-141 |
| 2796 | is-8 | ta-142 | sp-8 | an-142 |
| 2797 | is-8 | ta-143 | sp-8 | an-143 |
| 2798 | is-8 | ta-144 | sp-8 | an-144 |
| 2799 | is-8 | ta-145 | sp-8 | an-145 |
| 2800 | is-8 | ta-146 | sp-8 | an-146 |
| 2801 | is-8 | ta-147 | sp-8 | an-147 |
| 2802 | is-8 | ta-148 | sp-8 | an-148 |
| 2803 | is-8 | ta-149 | sp-8 | an-149 |
| 2804 | is-8 | ta-150 | sp-8 | an-150 |
| 2805 | is-8 | ta-151 | sp-8 | an-151 |
| 2806 | is-8 | ta-152 | sp-8 | an-152 |
| 2807 | is-8 | ta-153 | sp-8 | an-153 |
| 2808 | is-8 | ta-154 | sp-8 | an-154 |
| 2809 | is-8 | ta-155 | sp-8 | an-155 |
| 2810 | is-8 | ta-156 | sp-8 | an-156 |
| 2811 | is-8 | ta-157 | sp-8 | an-157 |
| 2812 | is-8 | ta-158 | sp-8 | an-158 |
| 2813 | is-8 | ta-159 | sp-8 | an-159 |
| 2814 | is-8 | ta-160 | sp-8 | an-160 |
| 2815 | is-8 | ta-161 | sp-8 | an-161 |
| 2816 | is-8 | ta-162 | sp-8 | an-162 |
| 2817 | is-8 | ta-163 | sp-8 | an-163 |
| 2818 | is-8 | ta-164 | sp-8 | an-164 |
| 2819 | is-8 | ta-165 | sp-8 | an-165 |
| 2820 | is-8 | ta-166 | sp-8 | an-166 |
| 2821 | is-8 | ta-167 | sp-8 | an-167 |
| 2822 | is-8 | ta-168 | sp-8 | an-168 |
| 2823 | is-8 | ta-169 | sp-8 | an-169 |
| 2824 | is-8 | ta-170 | sp-8 | an-170 |
| 2825 | is-8 | ta-171 | sp-8 | an-171 |
| 2826 | is-8 | ta-172 | sp-8 | an-172 |
| 2827 | is-8 | ta-173 | sp-8 | an-173 |
| 2828 | is-8 | ta-174 | sp-8 | an-174 |
| 2829 | is-8 | ta-175 | sp-8 | an-175 |
| 2830 | is-8 | ta-176 | sp-8 | an-176 |
| 2831 | is-8 | ta-177 | sp-8 | an-177 |
| 2832 | is-8 | ta-178 | sp-8 | an-178 |
| 2833 | is-8 | ta-179 | sp-8 | an-179 |
| 2834 | is-8 | ta-180 | sp-8 | an-180 |
| 2835 | is-8 | ta-181 | sp-8 | an-181 |
| 2836 | is-8 | ta-182 | sp-8 | an-182 |
| 2837 | is-8 | ta-183 | sp-8 | an-183 |
| 2838 | is-8 | ta-184 | sp-8 | an-184 |
| 2839 | is-8 | ta-185 | sp-8 | an-185 |
| 2840 | is-8 | ta-186 | sp-8 | an-186 |
| 2841 | is-8 | ta-187 | sp-8 | an-187 |
| 2842 | is-8 | ta-188 | sp-8 | an-188 |

TABLE 2-continued

| Example No. | Reaction reagent is | Reaction reagent ta | Compound of Example sp | Compound of Example an |
|---|---|---|---|---|
| 2843 | is-8 | ta-189 | sp-8 | an-189 |
| 2844 | is-8 | ta-190 | sp-8 | an-190 |
| 2845 | is-8 | ta-191 | sp-8 | an-191 |
| 2846 | is-8 | ta-192 | sp-8 | an-192 |
| 2847 | is-8 | ta-193 | sp-8 | an-193 |
| 2848 | is-8 | ta-194 | sp-8 | an-194 |
| 2849 | is-8 | ta-195 | sp-8 | an-195 |
| 2850 | is-8 | ta-196 | sp-8 | an-196 |
| 2851 | is-8 | ta-197 | sp-8 | an-197 |
| 2852 | is-8 | ta-198 | sp-8 | an-198 |
| 2853 | is-8 | ta-199 | sp-8 | an-199 |
| 2854 | is-8 | ta-200 | sp-8 | an-200 |
| 2855 | is-8 | ta-201 | sp-8 | an-201 |
| 2856 | is-8 | ta-202 | sp-8 | an-202 |
| 2857 | is-8 | ta-203 | sp-8 | an-203 |
| 2858 | is-8 | ta-204 | sp-8 | an-204 |
| 2859 | is-8 | ta-205 | sp-8 | an-205 |
| 2860 | is-8 | ta-206 | sp-8 | an-206 |
| 2861 | is-8 | ta-207 | sp-8 | an-207 |
| 2862 | is-8 | ta-208 | sp-8 | an-208 |
| 2863 | is-8 | ta-209 | sp-8 | an-209 |
| 2864 | is-8 | ta-210 | sp-8 | an-210 |
| 2865 | is-8 | ta-211 | sp-8 | an-211 |
| 2866 | is-8 | ta-212 | sp-8 | an-212 |
| 2867 | is-8 | ta-213 | sp-8 | an-213 |
| 2868 | is-8 | ta-214 | sp-8 | an-214 |
| 2869 | is-8 | ta-215 | sp-8 | an-215 |
| 2870 | is-8 | ta-216 | sp-8 | an-216 |
| 2871 | is-8 | ta-217 | sp-8 | an-217 |
| 2872 | is-8 | ta-218 | sp-8 | an-218 |
| 2873 | is-8 | ta-219 | sp-8 | an-219 |
| 2874 | is-8 | ta-220 | sp-8 | an-220 |
| 2875 | is-8 | ta-221 | sp-8 | an-221 |
| 2876 | is-8 | ta-222 | sp-8 | an-222 |
| 2877 | is-8 | ta-223 | sp-8 | an-223 |
| 2878 | is-8 | ta-224 | sp-8 | an-224 |
| 2879 | is-8 | ta-225 | sp-8 | an-225 |
| 2880 | is-8 | ta-226 | sp-8 | an-226 |
| 2881 | is-8 | ta-227 | sp-8 | an-227 |
| 2882 | is-8 | ta-228 | sp-8 | an-228 |
| 2833 | is-8 | ta-229 | sp-8 | an-229 |
| 2884 | is-8 | ta-230 | sp-8 | an-230 |
| 2885 | is-8 | ta-231 | sp-8 | an-231 |
| 2886 | is-8 | ta-232 | sp-8 | an-232 |
| 2887 | is-8 | ta-233 | sp-8 | an-233 |
| 2888 | is-8 | ta-234 | sp-8 | an-234 |
| 2889 | is-8 | ta-235 | sp-8 | an-235 |
| 2890 | is-8 | ta-236 | sp-8 | an-236 |
| 2891 | is-8 | ta-237 | sp-8 | an-237 |
| 2892 | is-8 | ta-238 | sp-8 | an-238 |
| 2893 | is-8 | ta-239 | sp-8 | an-239 |
| 2894 | is-8 | ta-240 | sp-8 | an-240 |
| 2895 | is-8 | ta-241 | sp-8 | an-241 |
| 2896 | is-8 | ta-242 | sp-8 | an-242 |
| 2897 | is-8 | ta-243 | sp-8 | an-243 |
| 2898 | is-8 | ta-244 | sp-8 | an-244 |
| 2899 | is-8 | ta-245 | sp-8 | an-245 |
| 2900 | is-8 | ta-246 | sp-8 | an-246 |
| 2901 | is-8 | ta-247 | sp-8 | an-247 |
| 2902 | is-8 | ta-248 | sp-8 | an-248 |
| 2903 | is-8 | ta-249 | sp-8 | an-249 |
| 2904 | is-8 | ta-250 | sp-8 | an-250 |
| 2905 | is-8 | ta-251 | sp-8 | an-251 |
| 2906 | is-8 | ta-252 | sp-8 | an-252 |
| 2907 | is-8 | ta-253 | sp-8 | an-253 |
| 2908 | is-8 | ta-254 | sp-8 | an-254 |
| 2909 | is-8 | ta-255 | sp-8 | an-255 |
| 2910 | is-8 | ta-256 | sp-8 | an-256 |
| 2911 | is-8 | ta-257 | sp-8 | an-257 |
| 2912 | is-8 | ta-258 | sp-8 | an-258 |
| 2913 | is-8 | ta-259 | sp-8 | an-259 |
| 2914 | is-8 | ta-260 | sp-8 | an-260 |
| 2915 | is-8 | ta-261 | sp-8 | an-261 |
| 2916 | is-8 | ta-262 | sp-8 | an-262 |
| 2917 | is-8 | ta-263 | sp-8 | an-263 |
| 2918 | is-8 | ta-264 | sp-8 | an-264 |
| 2919 | is-8 | ta-265 | sp-8 | an-265 |
| 2920 | is-8 | ta-266 | sp-8 | an-266 |
| 2921 | is-8 | ta-267 | sp-8 | an-267 |
| 2922 | is-8 | ta-268 | sp-8 | an-268 |
| 2923 | is-8 | ta-269 | sp-8 | an-269 |
| 2924 | is-8 | ta-270 | sp-8 | an-270 |
| 2925 | is-8 | ta-271 | sp-8 | an-271 |
| 2926 | is-8 | ta-272 | sp-8 | an-272 |
| 2927 | is-8 | ta-273 | sp-8 | an-273 |
| 2928 | is-8 | ta-274 | sp-8 | an-274 |
| 2929 | is-8 | ta-275 | sp-8 | an-275 |
| 2930 | is-8 | ta-276 | sp-8 | an-276 |
| 2931 | is-8 | ta-277 | sp-8 | an-277 |
| 2932 | is-8 | ta-278 | sp-8 | an-278 |
| 2933 | is-8 | ta-279 | sp-8 | an-279 |
| 2934 | is-8 | ta-280 | sp-8 | an-280 |
| 2935 | is-8 | ta-281 | sp-8 | an-281 |
| 2936 | is-8 | ta-282 | sp-8 | an-282 |
| 2937 | is-8 | ta-283 | sp-8 | an-283 |
| 2938 | is-8 | ta-284 | sp-8 | an-284 |
| 2939 | is-8 | ta-285 | sp-8 | an-285 |
| 2940 | is-8 | ta-286 | sp-8 | an-286 |
| 2941 | is-8 | ta-287 | sp-8 | an-287 |
| 2942 | is-8 | ta-288 | sp-8 | an-288 |
| 2943 | is-8 | ta-289 | sp-8 | an-289 |
| 2944 | is-8 | ta-290 | sp-8 | an-290 |
| 2945 | is-8 | ta-291 | sp-8 | an-291 |
| 2946 | is-8 | ta-292 | sp-8 | an-292 |
| 2947 | is-8 | ta-293 | sp-8 | an-293 |
| 2948 | is-8 | ta-294 | sp-8 | an-294 |
| 2949 | is-8 | ta-295 | sp-8 | an-295 |
| 2950 | is-8 | ta-296 | sp-8 | an-296 |
| 2951 | is-8 | ta-297 | sp-8 | an-297 |
| 2952 | is-8 | ta-298 | sp-8 | an-298 |
| 2953 | is-8 | ta-299 | sp-8 | an-299 |
| 2954 | is-8 | ta-300 | sp-8 | an-300 |
| 2955 | is-8 | ta-301 | sp-8 | an-301 |
| 2956 | is-8 | ta-302 | sp-8 | an-302 |
| 2957 | is-8 | ta-303 | sp-8 | an-303 |
| 2958 | is-8 | ta-304 | sp-8 | an-304 |
| 2959 | is-8 | ta-305 | sp-8 | an-305 |
| 2960 | is-8 | ta-306 | sp-8 | an-306 |
| 2961 | is-8 | ta-307 | sp-8 | an-307 |
| 2962 | is-8 | ta-308 | sp-8 | an-308 |
| 2963 | is-8 | ta-309 | sp-8 | an-309 |
| 2964 | is-8 | ta-310 | sp-8 | an-310 |
| 2965 | is-8 | ta-311 | sp-8 | an-311 |
| 2966 | is-8 | ta-312 | sp-8 | an-312 |
| 2967 | is-8 | ta-313 | sp-8 | an-313 |
| 2968 | is-8 | ta-314 | sp-8 | an-314 |
| 2969 | is-8 | ta-315 | sp-8 | an-315 |
| 2970 | is-8 | ta-316 | sp-8 | an-316 |
| 2971 | is-8 | ta-317 | sp-8 | an-317 |
| 2972 | is-8 | ta-318 | sp-8 | an-318 |
| 2973 | is-8 | ta-319 | sp-8 | an-319 |
| 2974 | is-8 | ta-320 | sp-8 | an-320 |
| 2975 | is-8 | ta-321 | sp-8 | an-321 |
| 2976 | is-8 | ta-322 | sp-8 | an-322 |
| 2977 | is-8 | ta-323 | sp-8 | an-323 |
| 2978 | is-8 | ta-324 | sp-8 | an-324 |
| 2979 | is-8 | ta-325 | sp-8 | an-325 |
| 2980 | is-8 | ta-326 | sp-8 | an-326 |
| 2981 | is-8 | ta-327 | sp-8 | an-327 |
| 2982 | is-8 | ta-328 | sp-8 | an-328 |
| 2983 | is-8 | ta-329 | sp-8 | an-329 |
| 2984 | is-8 | ta-330 | sp-8 | an-330 |
| 2985 | is-8 | ta-331 | sp-8 | an-331 |
| 2986 | is-8 | ta-332 | sp-8 | an-332 |
| 2987 | is-8 | ta-333 | sp-8 | an-333 |
| 2988 | is-8 | ta-334 | sp-8 | an-334 |
| 2989 | is-8 | ta-335 | sp-8 | an-335 |
| 2990 | is-8 | ta-336 | sp-8 | an-336 |

TABLE 2-continued

| Example No. | Reaction reagent is | Reaction reagent ta | Compound of Example sp | Compound of Example an |
|---|---|---|---|---|
| 2991 | is-8 | ta-337 | sp-8 | an-337 |
| 2992 | is-8 | ta-338 | sp-8 | an-338 |
| 2993 | is-8 | ta-339 | sp-8 | an-339 |
| 2994 | is-8 | ta-340 | sp-8 | an-340 |
| 2995 | is-8 | ta-341 | sp-8 | an-341 |
| 2996 | is-8 | ta-342 | sp-8 | an-342 |
| 2997 | is-8 | ta-343 | sp-8 | an-343 |
| 2998 | is-8 | ta-344 | sp-8 | an-344 |
| 2999 | is-8 | ta-345 | sp-8 | an-345 |
| 3000 | is-8 | ta-346 | sp-8 | an-346 |
| 3001 | is-8 | ta-347 | sp-8 | an-347 |
| 3002 | is-8 | ta-348 | sp-8 | an-348 |
| 3003 | is-8 | ta-349 | sp-8 | an-349 |
| 3004 | is-8 | ta-350 | sp-8 | an-350 |
| 3005 | is-8 | ta-351 | sp-8 | an-351 |
| 3006 | is-8 | ta-352 | sp-8 | an-352 |
| 3007 | is-8 | ta-353 | sp-8 | an-353 |
| 3008 | is-8 | ta-354 | sp-8 | an-354 |
| 3009 | is-8 | ta-355 | sp-8 | an-355 |
| 3010 | is-8 | ta-356 | sp-8 | an-356 |
| 3011 | is-8 | ta-357 | sp-8 | an-357 |
| 3012 | is-8 | ta-358 | sp-8 | an-358 |
| 3013 | is-8 | ta-359 | sp-8 | an-359 |
| 3014 | is-8 | ta-360 | sp-8 | an-360 |
| 3015 | is-8 | ta-361 | sp-8 | an-361 |
| 3016 | is-8 | ta-362 | sp-8 | an-362 |
| 3017 | is-8 | ta-363 | sp-8 | an-363 |
| 3018 | is-8 | ta-364 | sp-8 | an-364 |
| 3019 | is-8 | ta-365 | sp-8 | an-365 |
| 3020 | is-8 | ta-366 | sp-8 | an-366 |
| 3021 | is-8 | ta-367 | sp-8 | an-367 |
| 3022 | is-8 | ta-368 | sp-8 | an-368 |
| 3023 | is-8 | ta-369 | sp-8 | an-369 |
| 3024 | is-8 | ta-370 | sp-8 | an-370 |
| 3025 | is-8 | ta-371 | sp-8 | an-371 |
| 3026 | is-3 | ta-372 | sp-8 | an-372 |
| 3027 | is-8 | ta-373 | sp-8 | an-373 |
| 3028 | is-8 | ta-374 | sp-8 | an-374 |
| 3029 | is-8 | ta-375 | sp-8 | an-375 |
| 3030 | is-8 | ta-376 | sp-8 | an-376 |
| 3031 | is-8 | ta-377 | sp-8 | an-377 |
| 3032 | is-9 | ta-1 | sp-9 | an-1 |
| 3033 | is-9 | ta-2 | sp-9 | an-2 |
| 3034 | is-9 | ta-3 | sp-9 | an-3 |
| 3035 | is-9 | ta-4 | sp-9 | an-4 |
| 3036 | is-9 | ta-5 | sp-9 | an-5 |
| 3037 | is-9 | ta-6 | sp-9 | an-6 |
| 3038 | is-9 | ta-7 | sp-9 | an-7 |
| 3039 | is-9 | ta-8 | sp-9 | an-8 |
| 3040 | is-9 | ta-9 | sp-9 | an-9 |
| 3041 | is-9 | ta-10 | sp-9 | an-10 |
| 3042 | is-9 | ta-11 | sp-9 | an-11 |
| 3043 | is-9 | ta-12 | sp-9 | an-12 |
| 3044 | is-9 | ta-13 | sp-9 | an-13 |
| 3045 | is-9 | ta-14 | sp-9 | an-14 |
| 3046 | is-9 | ta-15 | sp-9 | an-15 |
| 3047 | is-9 | ta-16 | sp-9 | an-16 |
| 3048 | is-9 | ta-17 | sp-9 | an-17 |
| 3049 | is-9 | ta-18 | sp-9 | an-18 |
| 3050 | is-9 | ta-19 | sp-9 | an-19 |
| 3051 | is-9 | ta-20 | sp-9 | an-20 |
| 3052 | is-9 | ta-21 | sp-9 | an-21 |
| 3053 | is-9 | ta-22 | sp-9 | an-22 |
| 3054 | is-9 | ta-23 | sp-9 | an-23 |
| 3055 | is-9 | ta-24 | sp-9 | an-24 |
| 3056 | is-9 | ta-25 | sp-9 | an-25 |
| 3057 | is-9 | ta-26 | sp-9 | an-26 |
| 3058 | is-9 | ta-27 | sp-9 | an-27 |
| 3059 | is-9 | ta-28 | sp-9 | an-28 |
| 3060 | is-9 | ta-29 | sp-9 | an-29 |
| 3061 | is-9 | ta-30 | sp-9 | an-30 |
| 3062 | is-9 | ta-31 | sp-9 | an-31 |
| 3063 | is-9 | ta-32 | sp-9 | an-32 |
| 3064 | is-9 | ta-33 | sp-9 | an-33 |
| 3065 | is-9 | ta-34 | sp-9 | an-34 |
| 3066 | is-9 | ta-35 | sp-9 | an-35 |
| 3067 | is-9 | ta-36 | sp-9 | an-36 |
| 3068 | is-9 | ta-37 | sp-9 | an-37 |
| 3069 | is-9 | ta-38 | sp-9 | an-38 |
| 3070 | is-9 | ta-39 | sp-9 | an-39 |
| 3071 | is-9 | ta-40 | sp-9 | an-40 |
| 3072 | is-9 | ta-41 | sp-9 | an-41 |
| 3073 | is-9 | ta-42 | sp-9 | an-42 |
| 3074 | is-9 | ta-43 | sp-9 | an-43 |
| 3075 | is-9 | ta-44 | sp-9 | an-44 |
| 3076 | is-9 | ta-45 | sp-9 | an-45 |
| 3077 | is-9 | ta-46 | sp-9 | an-46 |
| 3078 | is-9 | ta-47 | sp-9 | an-47 |
| 3079 | is-9 | ta-48 | sp-9 | an-48 |
| 3080 | is-9 | ta-49 | sp-9 | an-49 |
| 3081 | is-9 | ta-50 | sp-9 | an-50 |
| 3082 | is-9 | ta-51 | sp-9 | an-51 |
| 3083 | is-9 | ta-52 | sp-9 | an-52 |
| 3084 | is-9 | ta-53 | sp-9 | an-53 |
| 3085 | is-9 | ta-54 | sp-9 | an-54 |
| 3086 | is-9 | ta-55 | sp-9 | an-55 |
| 3087 | is-9 | ta-56 | sp-9 | an-56 |
| 3088 | is-9 | ta-57 | sp-9 | an-57 |
| 3089 | is-9 | ta-58 | sp-9 | an-58 |
| 3090 | is-9 | ta-59 | sp-9 | an-59 |
| 3091 | is-9 | ta-60 | sp-9 | an-60 |
| 3092 | is-9 | ta-61 | sp-9 | an-61 |
| 3093 | is-9 | ta-62 | sp-9 | an-62 |
| 3094 | is-9 | ta-63 | sp-9 | an-63 |
| 3095 | is-9 | ta-64 | sp-9 | an-64 |
| 3096 | is-9 | ta-65 | sp-9 | an-65 |
| 3097 | is-9 | ta-66 | sp-9 | an-66 |
| 3098 | is-9 | ta-67 | sp-9 | an-67 |
| 3099 | is-9 | ta-68 | sp-9 | an-68 |
| 3100 | is-9 | ta-69 | sp-9 | an-69 |
| 3101 | is-9 | ta-70 | sp-9 | an-70 |
| 3102 | is-9 | ta-71 | sp-9 | an-71 |
| 3103 | is-9 | ta-72 | sp-9 | an-72 |
| 3104 | is-9 | ta-73 | sp-9 | an-73 |
| 3105 | is-9 | ta-74 | sp-9 | an-74 |
| 3106 | is-9 | ta-75 | sp-9 | an-75 |
| 3107 | is-9 | ta-76 | sp-9 | an-76 |
| 3108 | is-9 | ta-77 | sp-9 | an-77 |
| 3109 | is-9 | ta-78 | sp-9 | an-78 |
| 3110 | is-9 | ta-79 | sp-9 | an-79 |
| 3111 | is-9 | ta-80 | sp-9 | an-80 |
| 3112 | is-9 | ta-81 | sp-9 | an-81 |
| 3113 | is-9 | ta-82 | sp-9 | an-82 |
| 3114 | is-9 | ta-83 | sp-9 | an-83 |
| 3115 | is-9 | ta-84 | sp-9 | an-84 |
| 3116 | is-9 | ta-85 | sp-9 | an-85 |
| 3117 | is-9 | ta-86 | sp-9 | an-86 |
| 3118 | is-9 | ta-87 | sp-9 | an-87 |
| 3119 | is-9 | ta-88 | sp-9 | an-88 |
| 3120 | is-9 | ta-89 | sp-9 | an-89 |
| 3121 | is-9 | ta-90 | sp-9 | an-90 |
| 3122 | is-9 | ta-91 | sp-9 | an-91 |
| 3123 | is-9 | ta-92 | sp-9 | an-92 |
| 3124 | is-9 | ta-93 | sp-9 | an-93 |
| 3125 | is-9 | ta-94 | sp-9 | an-94 |
| 3126 | is-9 | ta-95 | sp-9 | an-95 |
| 3127 | is-9 | ta-96 | sp-9 | an-96 |
| 3128 | is-9 | ta-97 | sp-9 | an-97 |
| 3129 | is-9 | ta-98 | sp-9 | an-98 |
| 3130 | is-9 | ta-99 | sp-9 | an-99 |
| 3131 | is-9 | ta-100 | sp-9 | an-100 |
| 3132 | is-9 | ta-101 | sp-9 | an-101 |
| 3133 | is-9 | ta-102 | sp-9 | an-102 |
| 3134 | is-9 | ta-103 | sp-9 | an-103 |
| 3135 | is-9 | ta-104 | sp-9 | an-104 |
| 3136 | is-9 | ta-105 | sp-9 | an-105 |
| 3137 | is-9 | ta-106 | sp-9 | an-106 |
| 3138 | is-9 | ta-107 | sp-9 | an-107 |

TABLE 2-continued

| Example No. | Reaction reagent is | Reaction reagent ta | Compound of Example sp | Compound of Example an |
|---|---|---|---|---|
| 3139 | is-9 | ta-108 | sp-9 | an-108 |
| 3140 | is-9 | ta-109 | sp-9 | an-109 |
| 3141 | is-9 | ta-110 | sp-9 | an-110 |
| 3142 | is-9 | ta-111 | sp-9 | an-111 |
| 3143 | is-9 | ta-112 | sp-9 | an-112 |
| 3144 | is-9 | ta-113 | sp-9 | an-113 |
| 3145 | is-9 | ta-114 | sp-9 | an-114 |
| 3146 | is-9 | ta-115 | sp-9 | an-115 |
| 3147 | is-9 | ta-116 | sp-9 | an-116 |
| 3148 | is-9 | ta-117 | sp-9 | an-117 |
| 3149 | is-9 | ta-118 | sp-9 | an-118 |
| 3150 | is-9 | ta-119 | sp-9 | an-119 |
| 3151 | is-9 | ta-120 | sp-9 | an-120 |
| 3152 | is-9 | ta-121 | sp-9 | an-121 |
| 3153 | is-9 | ta-122 | sp-9 | an-122 |
| 3154 | is-9 | ta-123 | sp-9 | an-123 |
| 3155 | is-9 | ta-124 | sp-9 | an-124 |
| 3156 | is-9 | ta-125 | sp-9 | an-125 |
| 3157 | is-9 | ta-126 | sp-9 | an-126 |
| 3158 | is-9 | ta-127 | sp-9 | an-127 |
| 3159 | is-9 | ta-128 | sp-9 | an-128 |
| 3160 | is-9 | ta-129 | sp-9 | an-129 |
| 3161 | is-9 | ta-130 | sp-9 | an-130 |
| 3162 | is-9 | ta-131 | sp-9 | an-131 |
| 3163 | is-9 | ta-132 | sp-9 | an-132 |
| 3164 | is-9 | ta-133 | sp-9 | an-133 |
| 3165 | is-9 | ta-134 | sp-9 | an-134 |
| 3166 | is-9 | ta-135 | sp-9 | an-135 |
| 3167 | is-9 | ta-136 | sp-9 | an-136 |
| 3168 | is-9 | ta-137 | sp-9 | an-137 |
| 3169 | is-9 | ta-138 | sp-9 | an-138 |
| 3170 | is-9 | ta-139 | sp-9 | an-139 |
| 3171 | is-9 | ta-140 | sp-9 | an-140 |
| 3172 | is-9 | ta-141 | sp-9 | an-141 |
| 3173 | is-9 | ta-142 | sp-9 | an-142 |
| 3174 | is-9 | ta-143 | sp-9 | an-143 |
| 3175 | is-9 | ta-144 | sp-9 | an-144 |
| 3176 | is-9 | ta-145 | sp-9 | an-145 |
| 3177 | is-9 | ta-146 | sp-9 | an-146 |
| 3178 | is-9 | ta-147 | sp-9 | an-147 |
| 3179 | is-9 | ta-148 | sp-9 | an-148 |
| 3180 | is-9 | ta-149 | sp-9 | an-149 |
| 3181 | is-9 | ta-150 | sp-9 | an-150 |
| 3182 | is-9 | ta-151 | sp-9 | an-151 |
| 3183 | is-9 | ta-152 | sp-9 | an-152 |
| 3184 | is-9 | ta-153 | sp-9 | an-153 |
| 3185 | is-9 | ta-154 | sp-9 | an-154 |
| 3186 | is-9 | ta-155 | sp-9 | an-155 |
| 3187 | is-9 | ta-156 | sp-9 | an-156 |
| 3188 | is-9 | ta-157 | sp-9 | an-157 |
| 3189 | is-9 | ta-158 | sp-9 | an-158 |
| 3190 | is-9 | ta-159 | sp-9 | an-159 |
| 3191 | is-9 | ta-160 | sp-9 | an-160 |
| 3192 | is-9 | ta-161 | sp-9 | an-161 |
| 3193 | is-9 | ta-162 | sp-9 | an-162 |
| 3194 | is-9 | ta-163 | sp-9 | an-163 |
| 3195 | is-9 | ta-164 | sp-9 | an-164 |
| 3196 | is-9 | ta-165 | sp-9 | an-165 |
| 3197 | is-9 | ta-166 | sp-9 | an-166 |
| 3198 | is-9 | ta-167 | sp-9 | an-167 |
| 3199 | is-9 | ta-168 | sp-9 | an-168 |
| 3200 | is-9 | ta-169 | sp-9 | an-169 |
| 3201 | is-9 | ta-170 | sp-9 | an-170 |
| 3202 | is-9 | ta-171 | sp-9 | an-171 |
| 3203 | is-9 | ta-172 | sp-9 | an-172 |
| 3204 | is-9 | ta-173 | sp-9 | an-173 |
| 3205 | is-9 | ta-174 | sp-9 | an-174 |
| 3206 | is-9 | ta-175 | sp-9 | an-175 |
| 3207 | is-9 | ta-176 | sp-9 | an-176 |
| 3208 | is-9 | ta-177 | sp-9 | an-177 |
| 3209 | is-9 | ta-178 | sp-9 | an-178 |
| 3210 | is-9 | ta-179 | sp-9 | an-179 |
| 3211 | is-9 | ta-180 | sp-9 | an-180 |
| 3212 | is-9 | ta-181 | sp-9 | an-181 |
| 3213 | is-9 | ta-182 | sp-9 | an-182 |
| 3214 | is-9 | ta-183 | sp-9 | an-183 |
| 3215 | is-9 | ta-184 | sp-9 | an-184 |
| 3216 | is-9 | ta-185 | sp-9 | an-185 |
| 3217 | is-9 | ta-186 | sp-9 | an-186 |
| 3218 | is-9 | ta-187 | sp-9 | an-187 |
| 3219 | is-9 | ta-188 | sp-9 | an-188 |
| 3220 | is-9 | ta-189 | sp-9 | an-189 |
| 3221 | is-9 | ta-190 | sp-9 | an-190 |
| 3222 | is-9 | ta-191 | sp-9 | an-191 |
| 3223 | is-9 | ta-192 | sp-9 | an-192 |
| 3224 | is-9 | ta-193 | sp-9 | an-193 |
| 3225 | is-9 | ta-194 | sp-9 | an-194 |
| 3226 | is-9 | ta-195 | sp-9 | an-195 |
| 3227 | is-9 | ta-196 | sp-9 | an-196 |
| 3228 | is-9 | ta-197 | sp-9 | an-197 |
| 3229 | is-9 | ta-198 | sp-9 | an-198 |
| 3230 | is-9 | ta-199 | sp-9 | an-199 |
| 3231 | is-9 | ta-200 | sp-9 | an-200 |
| 3232 | is-9 | ta-201 | sp-9 | an-201 |
| 3233 | is-9 | ta-202 | sp-9 | an-202 |
| 3234 | is-9 | ta-203 | sp-9 | an-203 |
| 3235 | is-9 | ta-204 | sp-9 | an-204 |
| 3236 | is-9 | ta-205 | sp-9 | an-205 |
| 3237 | is-9 | ta-206 | sp-9 | an-206 |
| 3238 | is-9 | ta-207 | sp-9 | an-207 |
| 3239 | is-9 | ta-208 | sp-9 | an-208 |
| 3240 | is-9 | ta-209 | sp-9 | an-209 |
| 3241 | is-9 | ta-210 | sp-9 | an-210 |
| 3242 | is-9 | ta-211 | sp-9 | an-211 |
| 3243 | is-9 | ta-212 | sp-9 | an-212 |
| 3244 | is-9 | ta-213 | sp-9 | an-213 |
| 3245 | is-9 | ta-214 | sp-9 | an-214 |
| 3246 | is-9 | ta-215 | sp-9 | an-215 |
| 3247 | is-9 | ta-216 | sp-9 | an-216 |
| 3248 | is-9 | ta-217 | sp-9 | an-217 |
| 3249 | is-9 | ta-218 | sp-9 | an-218 |
| 3250 | is-9 | ta-219 | sp-9 | an-219 |
| 3251 | is-9 | ta-220 | sp-9 | an-220 |
| 3252 | is-9 | ta-221 | sp-9 | an-221 |
| 3253 | is-9 | ta-222 | sp-9 | an-222 |
| 3254 | is-9 | ta-223 | sp-9 | an-223 |
| 3255 | is-9 | ta-224 | sp-9 | an-224 |
| 3256 | is-9 | ta-225 | sp-9 | an-225 |
| 3257 | is-9 | ta-226 | sp-9 | an-226 |
| 3258 | is-9 | ta-227 | sp-9 | an-227 |
| 3259 | is-9 | ta-228 | sp-9 | an-228 |
| 3260 | is-9 | ta-229 | sp-9 | an-229 |
| 3261 | is-9 | ta-230 | sp-9 | an-230 |
| 3262 | is-9 | ta-231 | sp-9 | an-231 |
| 3263 | is-9 | ta-232 | sp-9 | an-232 |
| 3264 | is-9 | ta-233 | sp-9 | an-233 |
| 3265 | is-9 | ta-234 | sp-9 | an-234 |
| 3266 | is-9 | ta-235 | sp-9 | an-235 |
| 3267 | is-9 | ta-236 | sp-9 | an-236 |
| 3268 | is-9 | ta-237 | sp-9 | an-237 |
| 3269 | is-9 | ta-238 | sp-9 | an-238 |
| 3270 | is-9 | ta-239 | sp-9 | an-239 |
| 3271 | is-9 | ta-240 | sp-9 | an-240 |
| 3272 | is-9 | ta-241 | sp-9 | an-241 |
| 3273 | is-9 | ta-242 | sp-9 | an-242 |
| 3274 | is-9 | ta-243 | sp-9 | an-243 |
| 3275 | is-9 | ta-244 | sp-9 | an-244 |
| 3276 | is-9 | ta-245 | sp-9 | an-245 |
| 3277 | is-9 | ta-246 | sp-9 | an-246 |
| 3278 | is-9 | ta-247 | sp-9 | an-247 |
| 3279 | is-9 | ta-248 | sp-9 | an-248 |
| 3280 | is-9 | ta-249 | sp-9 | an-249 |
| 3281 | is-9 | ta-250 | sp-9 | an-250 |
| 3282 | is-9 | ta-251 | sp-9 | an-251 |
| 3283 | is-9 | ta-252 | sp-9 | an-252 |
| 3284 | is-9 | ta-253 | sp-9 | an-253 |
| 3285 | is-9 | ta-254 | sp-9 | an-254 |
| 3286 | is-9 | ta-255 | sp-9 | an-255 |

TABLE 2-continued

| Example No. | Reaction reagent is | Reaction reagent ta | Compound of Example sp | Compound of Example an |
|---|---|---|---|---|
| 3287 | is-9 | ta-256 | sp-9 | an-256 |
| 3288 | is-9 | ta-257 | sp-9 | an-257 |
| 3289 | is-9 | ta-258 | sp-9 | an-258 |
| 3290 | is-9 | ta-259 | sp-9 | an-259 |
| 3291 | is-9 | ta-260 | sp-9 | an-260 |
| 3292 | is-9 | ta-261 | sp-9 | an-261 |
| 3293 | is-9 | ta-262 | sp-9 | an-262 |
| 3294 | is-9 | ta-263 | sp-9 | an-263 |
| 3295 | is-9 | ta-264 | sp-9 | an-264 |
| 3296 | is-9 | ta-265 | sp-9 | an-265 |
| 3297 | is-9 | ta-266 | sp-9 | an-266 |
| 3298 | is-9 | ta-267 | sp-9 | an-267 |
| 3299 | is-9 | ta-268 | sp-9 | an-268 |
| 3300 | is-9 | ta-269 | sp-9 | an-269 |
| 3301 | is-9 | ta-270 | sp-9 | an-270 |
| 3302 | is-9 | ta-271 | sp-9 | an-271 |
| 3303 | is-9 | ta-272 | sp-9 | an-272 |
| 3304 | is-9 | ta-273 | sp-9 | an-273 |
| 3305 | is-9 | ta-274 | sp-9 | an-274 |
| 3306 | is-9 | ta-275 | sp-9 | an-275 |
| 3307 | is-9 | ta-276 | sp-9 | an-276 |
| 3308 | is-9 | ta-277 | sp-9 | an-277 |
| 3309 | is-9 | ta-278 | sp-9 | an-273 |
| 3310 | is-9 | ta-279 | sp-9 | an-279 |
| 3311 | is-9 | ta-280 | sp-9 | an-280 |
| 3312 | is-9 | ta-281 | sp-9 | an-281 |
| 3313 | is-9 | ta-282 | sp-9 | an-282 |
| 3314 | is-9 | ta-283 | sp-9 | an-283 |
| 3315 | is-9 | ta-284 | sp-9 | an-284 |
| 3316 | is-9 | ta-285 | sp-9 | an-285 |
| 3317 | is-9 | ta-286 | sp-9 | an-286 |
| 3318 | is-9 | ta-287 | sp-9 | an-287 |
| 3319 | is-9 | ta-288 | sp-9 | an-288 |
| 3320 | is-9 | ta-289 | sp-9 | an-289 |
| 3321 | is-9 | ta-290 | sp-9 | an-290 |
| 3322 | is-9 | ta-291 | sp-9 | an-291 |
| 3323 | is-9 | ta-292 | sp-9 | an-292 |
| 3324 | is-9 | ta-293 | sp-9 | an-293 |
| 3325 | is-9 | ta-294 | sp-9 | an-294 |
| 3326 | is-9 | ta-295 | sp-9 | an-295 |
| 3327 | is-9 | ta-296 | sp-9 | an-296 |
| 3328 | is-9 | ta-297 | sp-9 | an-297 |
| 3329 | is-9 | ta-298 | sp-9 | an-298 |
| 3330 | is-9 | ta-299 | sp-9 | an-299 |
| 3331 | is-9 | ta-300 | sp-9 | an-300 |
| 3332 | is-9 | ta-301 | sp-9 | an-301 |
| 3333 | is-9 | ta-302 | sp-9 | an-302 |
| 3334 | is-9 | ta-303 | sp-9 | an-303 |
| 3335 | is-9 | ta-304 | sp-9 | an-304 |
| 3336 | is-9 | ta-305 | sp-9 | an-305 |
| 3337 | is-9 | ta-306 | sp-9 | an-306 |
| 3338 | is-9 | ta-307 | sp-9 | an-307 |
| 3339 | is-9 | ta-308 | sp-9 | an-308 |
| 3340 | is-9 | ta-309 | sp-9 | an-309 |
| 3341 | is-9 | ta-310 | sp-9 | an-310 |
| 3342 | is-9 | ta-311 | sp-9 | an-311 |
| 3343 | is-9 | ta-312 | sp-9 | an-312 |
| 3344 | is-9 | ta-313 | sp-9 | an-313 |
| 3345 | is-9 | ta-314 | sp-9 | an-314 |
| 3346 | is-9 | ta-315 | sp-9 | an-315 |
| 3347 | is-9 | ta-316 | sp-9 | an-316 |
| 3348 | is-9 | ta-317 | sp-9 | an-317 |
| 3349 | is-9 | ta-318 | sp-9 | an-318 |
| 3350 | is-9 | ta-319 | sp-9 | an-319 |
| 3351 | is-9 | ta-320 | sp-9 | an-320 |
| 3352 | is-9 | ta-321 | sp-9 | an-321 |
| 3353 | is-9 | ta-322 | sp-9 | an-322 |
| 3354 | is-9 | ta-323 | sp-9 | an-323 |
| 3355 | is-9 | ta-324 | sp-9 | an-324 |
| 3356 | is-9 | ta-325 | sp-9 | an-325 |
| 3357 | is-9 | ta-326 | sp-9 | an-326 |
| 3358 | is-9 | ta-327 | sp-9 | an-327 |
| 3359 | is-9 | ta-328 | sp-9 | an-328 |
| 3360 | is-9 | ta-329 | sp-9 | an-329 |
| 3361 | is-9 | ta-330 | sp-9 | an-330 |
| 3362 | is-9 | ta-331 | sp-9 | an-331 |
| 3363 | is-9 | ta-332 | sp-9 | an-332 |
| 3364 | is-9 | ta-333 | sp-9 | an-333 |
| 3365 | is-9 | ta-334 | sp-9 | an-334 |
| 3366 | is-9 | ta-335 | sp-9 | an-335 |
| 3367 | is-9 | ta-336 | sp-9 | an-336 |
| 3368 | is-9 | ta-337 | sp-9 | an-337 |
| 3369 | is-9 | ta-338 | sp-9 | an-338 |
| 3370 | is-9 | ta-339 | sp-9 | an-339 |
| 3371 | is-9 | ta-340 | sp-9 | an-340 |
| 3372 | is-9 | ta-341 | sp-9 | an-341 |
| 3373 | is-9 | ta-342 | sp-9 | an-342 |
| 3374 | is-9 | ta-343 | sp-9 | an-343 |
| 3375 | is-9 | ta-344 | sp-9 | an-344 |
| 3376 | is-9 | ta-345 | sp-9 | an-345 |
| 3377 | is-9 | ta-346 | sp-9 | an-346 |
| 3378 | is-9 | ta-347 | sp-9 | an-347 |
| 3379 | is-9 | ta-348 | sp-9 | an-348 |
| 3380 | is-9 | ta-349 | sp-9 | an-349 |
| 3381 | is-9 | ta-350 | sp-9 | an-350 |
| 3382 | is-9 | ta-351 | sp-9 | an-351 |
| 3383 | is-9 | ta-352 | sp-9 | an-352 |
| 3384 | is-9 | ta-353 | sp-9 | an-353 |
| 3385 | is-9 | ta-354 | sp-9 | an-354 |
| 3386 | is-9 | ta-355 | sp-9 | an-355 |
| 3387 | is-9 | ta-356 | sp-9 | an-356 |
| 3388 | is-9 | ta-357 | sp-9 | an-357 |
| 3389 | is-9 | ta-358 | sp-9 | an-358 |
| 3390 | is-9 | ta-359 | sp-9 | an-359 |
| 3391 | is-9 | ta-360 | sp-9 | an-360 |
| 3392 | is-9 | ta-361 | sp-9 | an-361 |
| 3393 | is-9 | ta-362 | sp-9 | an-362 |
| 3394 | is-9 | ta-363 | sp-9 | an-363 |
| 3395 | is-9 | ta-364 | sp-9 | an-364 |
| 3396 | is-9 | ta-365 | sp-9 | an-365 |
| 3397 | is-9 | ta-366 | sp-9 | an-366 |
| 3398 | is-9 | ta-367 | sp-9 | an-367 |
| 3399 | is-9 | ta-368 | sp-9 | an-368 |
| 3400 | is-9 | ta-369 | sp-9 | an-369 |
| 3401 | is-9 | ta-370 | sp-9 | an-370 |
| 3402 | is-9 | ta-371 | sp-9 | an-371 |
| 3403 | is-9 | ta-372 | sp-9 | an-372 |
| 3404 | is-9 | ta-373 | sp-9 | an-373 |
| 3405 | is-9 | ta-374 | sp-9 | an-374 |
| 3406 | is-9 | ta-375 | sp-9 | an-375 |
| 3407 | is-9 | ta-376 | sp-9 | an-376 |
| 3408 | is-9 | ta-377 | sp-9 | an-377 |
| 3409 | is-14 | ta-1 | sp-14 | an-1 |
| 3410 | is-14 | ta-2 | sp-14 | an-2 |
| 3411 | is-14 | ta-3 | sp-14 | an-3 |
| 3412 | is-14 | ta-4 | sp-14 | an-4 |
| 3413 | is-14 | ta-5 | sp-14 | an-5 |
| 3414 | is-14 | ta-6 | sp-14 | an-6 |
| 3415 | is-14 | ta-7 | sp-14 | an-7 |
| 3416 | is-14 | ta-8 | sp-14 | an-8 |
| 3417 | is-14 | ta-9 | sp-14 | an-9 |
| 3418 | is-14 | ta-10 | sp-14 | an-10 |
| 3419 | is-14 | ta-11 | sp-14 | an-11 |
| 3420 | is-14 | ta-12 | sp-14 | an-12 |
| 3421 | is-14 | ta-13 | sp-14 | an-13 |
| 3422 | is-14 | ta-14 | sp-14 | an-14 |
| 3423 | is-14 | ta-15 | sp-14 | an-15 |
| 3424 | is-14 | ta-16 | sp-14 | an-16 |
| 3425 | is-14 | ta-17 | sp-14 | an-17 |
| 3426 | is-14 | ta-18 | sp-14 | an-18 |
| 3427 | is-14 | ta-19 | sp-14 | an-19 |
| 3428 | is-14 | ta-20 | sp-14 | an-20 |
| 3429 | is-14 | ta-21 | sp-14 | an-21 |
| 3430 | is-14 | ta-22 | sp-14 | an-22 |
| 3431 | is-14 | ta-23 | sp-14 | an-23 |
| 3432 | is-14 | ta-24 | sp-14 | an-24 |
| 3433 | is-14 | ta-25 | sp-14 | an-25 |
| 3434 | is-14 | ta-26 | sp-14 | an-26 |

TABLE 2-continued

| Example No. | Reaction reagent | | Compound of Example | |
|---|---|---|---|---|
| | is | ta | sp | an |
| 3435 | is-14 | ta-27 | sp-14 | an-27 |
| 3436 | is-14 | ta-28 | sp-14 | an-28 |
| 3437 | is-14 | ta-29 | sp-14 | an-29 |
| 3438 | is-14 | ta-30 | sp-14 | an-30 |
| 3439 | is-14 | ta-31 | sp-14 | an-31 |
| 3440 | is-14 | ta-32 | sp-14 | an-32 |
| 3441 | is-14 | ta-33 | sp-14 | an-33 |
| 3442 | is-14 | ta-34 | sp-14 | an-34 |
| 3443 | is-14 | ta-35 | sp-14 | an-35 |
| 3444 | is-14 | ta-36 | sp-14 | an-36 |
| 3445 | is-14 | ta-37 | sp-14 | an-37 |
| 3446 | is-14 | ta-38 | sp-14 | an-38 |
| 3447 | is-14 | ta-39 | sp-14 | an-39 |
| 3448 | is-14 | ta-40 | sp-14 | an-40 |
| 3449 | is-14 | ta-41 | sp-14 | an-41 |
| 3450 | is-14 | ta-42 | sp-14 | an-42 |
| 3451 | is-14 | ta-43 | sp-14 | an-43 |
| 3452 | is-14 | ta-44 | sp-14 | an-44 |
| 3453 | is-14 | ta-45 | sp-14 | an-45 |
| 3454 | is-14 | ta-46 | sp-14 | an-46 |
| 3455 | is-14 | ta-47 | sp-14 | an-47 |
| 3456 | is-14 | ta-48 | sp-14 | an-48 |
| 3457 | is-14 | ta-49 | sp-14 | an-49 |
| 3458 | is-14 | ta-50 | sp-14 | an-50 |
| 3459 | is-14 | ta-51 | sp-14 | an-51 |
| 3460 | is-14 | ta-52 | sp-14 | an-52 |
| 3461 | is-14 | ta-53 | sp-14 | an-53 |
| 3462 | is-14 | ta-54 | sp-14 | an-54 |
| 3463 | is-14 | ta-55 | sp-14 | an-55 |
| 3464 | is-14 | ta-56 | sp-14 | an-56 |
| 3465 | is-14 | ta-57 | sp-14 | an-57 |
| 3466 | is-14 | ta-58 | sp-14 | an-58 |
| 3467 | is-14 | ta-59 | sp-14 | an-59 |
| 3468 | is-14 | ta-60 | sp-14 | an-60 |
| 3469 | is-14 | ta-61 | sp-14 | an-61 |
| 3470 | is-14 | ta-62 | sp-14 | an-62 |
| 3471 | is-14 | ta-63 | sp-14 | an-63 |
| 3472 | is-14 | ta-64 | sp-14 | an-64 |
| 3473 | is-14 | ta-65 | sp-14 | an-65 |
| 3474 | is-14 | ta-66 | sp-14 | an-66 |
| 3475 | is-14 | ta-67 | sp-14 | an-67 |
| 3476 | is-14 | ta-68 | sp-14 | an-68 |
| 3477 | is-14 | ta-69 | sp-14 | an-69 |
| 3478 | is-14 | ta-70 | sp-14 | an-70 |
| 3479 | is-14 | ta-71 | sp-14 | an-71 |
| 3480 | is-14 | ta-72 | sp-14 | an-72 |
| 3481 | is-14 | ta-73 | sp-14 | an-73 |
| 3482 | is-14 | ta-74 | sp-14 | an-74 |
| 3483 | is-14 | ta-75 | sp-14 | an-75 |
| 3484 | is-14 | ta-76 | sp-14 | an-76 |
| 3485 | is-14 | ta-77 | sp-14 | an-77 |
| 3486 | is-14 | ta-78 | sp-14 | an-78 |
| 3487 | is-14 | ta-79 | sp-14 | an-79 |
| 3488 | is-14 | ta-80 | sp-14 | an-80 |
| 3489 | is-14 | ta-81 | sp-14 | an-81 |
| 3490 | is-14 | ta-82 | sp-14 | an-82 |
| 3491 | is-14 | ta-83 | sp-14 | an-83 |
| 3492 | is-14 | ta-84 | sp-14 | an-84 |
| 3493 | is-14 | ta-85 | sp-14 | an-85 |
| 3494 | is-14 | ta-86 | sp-14 | an-86 |
| 3495 | is-14 | ta-87 | sp-14 | an-87 |
| 3496 | is-14 | ta-88 | sp-14 | an-88 |
| 3497 | is-14 | ta-89 | sp-14 | an-89 |
| 3498 | is-14 | ta-90 | sp-14 | an-90 |
| 3499 | is-14 | ta-91 | sp-14 | an-91 |
| 3500 | is-14 | ta-92 | sp-14 | an-92 |
| 3501 | is-14 | ta-93 | sp-14 | an-93 |
| 3502 | is-14 | ta-94 | sp-14 | an-94 |
| 3503 | is-14 | ta-95 | sp-14 | an-95 |
| 3504 | is-14 | ta-96 | sp-14 | an-96 |
| 3505 | is-14 | ta-97 | sp-14 | an-97 |
| 3506 | is-14 | ta-98 | sp-14 | an-98 |
| 3507 | is-14 | ta-99 | sp-14 | an-99 |
| 3508 | is-14 | ta-100 | sp-14 | an-100 |
| 3509 | is-14 | ta-101 | sp-14 | an-101 |
| 3510 | is-14 | ta-102 | sp-14 | an-102 |
| 3511 | is-14 | ta-103 | sp-14 | an-103 |
| 3512 | is-14 | ta-104 | sp-14 | an-104 |
| 3513 | is-14 | ta-105 | sp-14 | an-105 |
| 3514 | is-14 | ta-106 | sp-14 | an-106 |
| 3515 | is-14 | ta-107 | sp-14 | an-107 |
| 3516 | is-14 | ta-108 | sp-14 | an-108 |
| 3517 | is-14 | ta-109 | sp-14 | an-109 |
| 3518 | is-14 | ta-110 | sp-14 | an-110 |
| 3519 | is-14 | ta-111 | sp-14 | an-111 |
| 3520 | is-14 | ta-112 | sp-14 | an-112 |
| 3521 | is-14 | ta-113 | sp-14 | an-113 |
| 3522 | is-14 | ta-114 | sp-14 | an-114 |
| 3523 | is-14 | ta-115 | sp-14 | an-115 |
| 3524 | is-14 | ta-116 | sp-14 | an-116 |
| 3525 | is-14 | ta-117 | sp-14 | an-117 |
| 3526 | is-14 | ta-118 | sp-14 | an-118 |
| 3527 | is-14 | ta-119 | sp-14 | an-119 |
| 3528 | is-14 | ta-120 | sp-14 | an-120 |
| 3529 | is-14 | ta-121 | sp-14 | an-121 |
| 3530 | is-14 | ta-122 | sp-14 | an-122 |
| 3531 | is-14 | ta-123 | sp-14 | an-123 |
| 3532 | is-14 | ta-124 | sp-14 | an-124 |
| 3533 | is-14 | ta-125 | sp-14 | an-125 |
| 3534 | is-14 | ta-126 | sp-14 | an-126 |
| 3535 | is-14 | ta-127 | sp-14 | an-127 |
| 3536 | is-14 | ta-128 | sp-14 | an-128 |
| 3537 | is-14 | ta-129 | sp-14 | an-129 |
| 3538 | is-14 | ta-130 | sp-14 | an-130 |
| 3539 | is-14 | ta-131 | sp-14 | an-131 |
| 3540 | is-14 | ta-132 | sp-14 | an-132 |
| 3541 | is-14 | ta-133 | sp-14 | an-133 |
| 3542 | is-14 | ta-134 | sp-14 | an-134 |
| 3543 | is-14 | ta-135 | sp-14 | an-135 |
| 3544 | is-14 | ta-136 | sp-14 | an-136 |
| 3545 | is-14 | ta-137 | sp-14 | an-137 |
| 3546 | is-14 | ta-138 | sp-14 | an-138 |
| 3547 | is-14 | ta-139 | sp-14 | an-139 |
| 3548 | is-14 | ta-140 | sp-14 | an-140 |
| 3549 | is-14 | ta-141 | sp-14 | an-141 |
| 3550 | is-14 | ta-142 | sp-14 | an-142 |
| 3551 | is-14 | ta-143 | sp-14 | an-143 |
| 3552 | is-14 | ta-144 | sp-14 | an-144 |
| 3553 | is-14 | ta-145 | sp-14 | an-145 |
| 3554 | is-14 | ta-146 | sp-14 | an-146 |
| 3555 | is-14 | ta-147 | sp-14 | an-147 |
| 3556 | is-14 | ta-148 | sp-14 | an-148 |
| 3557 | is-14 | ta-149 | sp-14 | an-149 |
| 3558 | is-14 | ta-150 | sp-14 | an-150 |
| 3559 | is-14 | ta-151 | sp-14 | an-151 |
| 3560 | is-14 | ta-152 | sp-14 | an-152 |
| 3561 | is-14 | ta-153 | sp-14 | an-153 |
| 3562 | is-14 | ta-154 | sp-14 | an-154 |
| 3563 | is-14 | ta-155 | sp-14 | an-155 |
| 3564 | is-14 | ta-156 | sp-14 | an-156 |
| 3565 | is-14 | ta-157 | sp-14 | an-157 |
| 3566 | is-14 | ta-158 | sp-14 | an-158 |
| 3567 | is-14 | ta-159 | sp-14 | an-159 |
| 3568 | is-14 | ta-160 | sp-14 | an-160 |
| 3569 | is-14 | ta-161 | sp-14 | an-161 |
| 3570 | is-14 | ta-162 | sp-14 | an-162 |
| 3571 | is-14 | ta-163 | sp-14 | an-163 |
| 3572 | is-14 | ta-164 | sp-14 | an-164 |
| 3573 | is-14 | ta-165 | sp-14 | an-165 |
| 3574 | is-14 | ta-166 | sp-14 | an-166 |
| 3575 | is-14 | ta-167 | sp-14 | an-167 |
| 3576 | is-14 | ta-168 | sp-14 | an-168 |
| 3577 | is-14 | ta-169 | sp-14 | an-169 |
| 3578 | is-14 | ta-170 | sp-14 | an-170 |
| 3579 | is-14 | ta-171 | sp-14 | an-171 |
| 3580 | is-14 | ta-172 | sp-14 | an-172 |
| 3581 | is-14 | ta-173 | sp-14 | an-173 |
| 3582 | is-14 | ta-174 | sp-14 | an-174 |

TABLE 2-continued

| Example No. | Reaction reagent is | Reaction reagent ta | Compound of Example sp | Compound of Example an |
|---|---|---|---|---|
| 3583 | is-14 | ta-175 | sp-14 | an-175 |
| 3584 | is-14 | ta-176 | sp-14 | an-176 |
| 3585 | is-14 | ta-177 | sp-14 | an-177 |
| 3586 | is-14 | ta-178 | sp-14 | an-178 |
| 3587 | is-14 | ta-179 | sp-14 | an-179 |
| 3588 | is-14 | ta-180 | sp-14 | an-180 |
| 3589 | is-14 | ta-181 | sp-14 | an-181 |
| 3590 | is-14 | ta-182 | sp-14 | an-182 |
| 3591 | is-14 | ta-183 | sp-14 | an-183 |
| 3592 | is-14 | ta-184 | sp-14 | an-184 |
| 3593 | is-14 | ta-185 | sp-14 | an-185 |
| 3594 | is-14 | ta-186 | sp-14 | an-186 |
| 3595 | is-14 | ta-187 | sp-14 | an-187 |
| 3596 | is-14 | ta-188 | sp-14 | an-188 |
| 3597 | is-14 | ta-189 | sp-14 | an-189 |
| 3598 | is-14 | ta-190 | sp-14 | an-190 |
| 3599 | is-14 | ta-191 | sp-14 | an-191 |
| 3600 | is-14 | ta-192 | sp-14 | an-192 |
| 3601 | is-14 | ta-193 | sp-14 | an-193 |
| 3602 | is-14 | ta-194 | sp-14 | an-194 |
| 3603 | is-14 | ta-195 | sp-14 | an-195 |
| 3604 | is-14 | ta-196 | sp-14 | an-196 |
| 3605 | is-14 | ta-197 | sp-14 | an-197 |
| 3606 | is-14 | ta-198 | sp-14 | an-198 |
| 3607 | is-14 | ta-199 | sp-14 | an-199 |
| 3608 | is-14 | ta-200 | sp-14 | an-200 |
| 3609 | is-14 | ta-201 | sp-14 | an-201 |
| 3610 | is-14 | ta-202 | sp-14 | an-202 |
| 3611 | is-14 | ta-203 | sp-14 | an-203 |
| 3612 | is-14 | ta-204 | sp-14 | an-204 |
| 3613 | is-14 | ta-205 | sp-14 | an-205 |
| 3614 | is-14 | ta-206 | sp-14 | an-206 |
| 3615 | is-14 | ta-207 | sp-14 | an-207 |
| 3616 | is-14 | ta-208 | sp-14 | an-208 |
| 3617 | is-14 | ta-209 | sp-14 | an-209 |
| 3618 | is-14 | ta-210 | sp-14 | an-210 |
| 3619 | is-14 | ta-211 | sp-14 | an-211 |
| 3620 | is-14 | ta-212 | sp-14 | an-212 |
| 3621 | is-14 | ta-213 | sp-14 | an-213 |
| 3622 | is-14 | ta-214 | sp-14 | an-214 |
| 3623 | is-14 | ta-215 | sp-14 | an-215 |
| 3624 | is-14 | ta-216 | sp-14 | an-216 |
| 3625 | is-14 | ta-217 | sp-14 | an-217 |
| 3626 | is-14 | ta-218 | sp-14 | an-218 |
| 3627 | is-14 | ta-219 | sp-14 | an-219 |
| 3628 | is-14 | ta-220 | sp-14 | an-220 |
| 3629 | is-14 | ta-221 | sp-14 | an-221 |
| 3630 | is-14 | ta-222 | sp-14 | an-222 |
| 3631 | is-14 | ta-223 | sp-14 | an-223 |
| 3632 | is-14 | ta-224 | sp-14 | an-224 |
| 3633 | is-14 | ta-225 | sp-14 | an-225 |
| 3634 | is-14 | ta-226 | sp-14 | an-226 |
| 3635 | is-14 | ta-227 | sp-14 | an-227 |
| 3636 | is-14 | ta-228 | sp-14 | an-228 |
| 3637 | is-14 | ta-229 | sp-14 | an-229 |
| 3638 | is-14 | ta-230 | sp-14 | an-230 |
| 3639 | is-14 | ta-231 | sp-14 | an-231 |
| 3640 | is-14 | ta-232 | sp-14 | an-232 |
| 3641 | is-14 | ta-233 | sp-14 | an-233 |
| 3642 | is-14 | ta-234 | sp-14 | an-234 |
| 3643 | is-14 | ta-235 | sp-14 | an-235 |
| 3644 | is-14 | ta-236 | sp-14 | an-236 |
| 3645 | is-14 | ta-237 | sp-14 | an-237 |
| 3646 | is-14 | ta-238 | sp-14 | an-238 |
| 3647 | is-14 | ta-239 | sp-14 | an-239 |
| 3648 | is-14 | ta-240 | sp-14 | an-240 |
| 3649 | is-14 | ta-241 | sp-14 | an-241 |
| 3650 | is-14 | ta-242 | sp-14 | an-242 |
| 3651 | is-14 | ta-243 | sp-14 | an-243 |
| 3652 | is-14 | ta-244 | sp-14 | an-244 |
| 3653 | is-14 | ta-245 | sp-14 | an-245 |
| 3654 | is-14 | ta-246 | sp-14 | an-246 |
| 3655 | is-14 | ta-247 | sp-14 | an-247 |
| 3656 | is-14 | ta-248 | sp-14 | an-248 |
| 3657 | is-14 | ta-249 | sp-14 | an-249 |
| 3658 | is-14 | ta-250 | sp-14 | an-250 |
| 3659 | is-14 | ta-251 | sp-14 | an-251 |
| 3660 | is-14 | ta-252 | sp-14 | an-252 |
| 3661 | is-14 | ta-253 | sp-14 | an-253 |
| 3662 | is-14 | ta-254 | sp-14 | an-254 |
| 3663 | is-14 | ta-255 | sp-14 | an-255 |
| 3664 | is-14 | ta-256 | sp-14 | an-256 |
| 3665 | is-14 | ta-257 | sp-14 | an-257 |
| 3666 | is-14 | ta-258 | sp-14 | an-258 |
| 3667 | is-14 | ta-259 | sp-14 | an-259 |
| 3668 | is-14 | ta-260 | sp-14 | an-260 |
| 3669 | is-14 | ta-261 | sp-14 | an-261 |
| 3670 | is-14 | ta-262 | sp-14 | an-262 |
| 3671 | is-14 | ta-263 | sp-14 | an-263 |
| 3672 | is-14 | ta-264 | sp-14 | an-264 |
| 3673 | is-14 | ta-265 | sp-14 | an-265 |
| 3674 | is-14 | ta-266 | sp-14 | an-266 |
| 3675 | is-14 | ta-267 | sp-14 | an-267 |
| 3676 | is-14 | ta-268 | sp-14 | an-268 |
| 3677 | is-14 | ta-269 | sp-14 | an-269 |
| 3678 | is-14 | ta-270 | sp-14 | an-270 |
| 3679 | is-14 | ta-271 | sp-14 | an-271 |
| 3680 | is-14 | ta-272 | sp-14 | an-272 |
| 3681 | is-14 | ta-273 | sp-14 | an-273 |
| 3682 | is-14 | ta-274 | sp-14 | an-274 |
| 3683 | is-14 | ta-275 | sp-14 | an-275 |
| 3684 | is-14 | ta-276 | sp-14 | an-276 |
| 3685 | is-14 | ta-277 | sp-14 | an-277 |
| 3686 | is-14 | ta-278 | sp-14 | an-278 |
| 3687 | is-14 | ta-279 | sp-14 | an-279 |
| 3688 | is-14 | ta-280 | sp-14 | an-280 |
| 3689 | is-14 | ta-281 | sp-14 | an-281 |
| 3690 | is-14 | ta-282 | sp-14 | an-282 |
| 3691 | is-14 | ta-283 | sp-14 | an-283 |
| 3692 | is-14 | ta-284 | sp-14 | an-284 |
| 3693 | is-14 | ta-285 | sp-14 | an-285 |
| 3694 | is-14 | ta-286 | sp-14 | an-286 |
| 3695 | is-14 | ta-287 | sp-14 | an-287 |
| 3696 | is-14 | ta-288 | sp-14 | an-288 |
| 3697 | is-14 | ta-289 | sp-14 | an-289 |
| 3698 | is-14 | ta-290 | sp-14 | an-290 |
| 3699 | is-14 | ta-291 | sp-14 | an-291 |
| 3700 | is-14 | ta-292 | sp-14 | an-292 |
| 3701 | is-14 | ta-293 | sp-14 | an-293 |
| 3702 | is-14 | ta-294 | sp-14 | an-294 |
| 3703 | is-14 | ta-295 | sp-14 | an-295 |
| 3704 | is-14 | ta-296 | sp-14 | an-296 |
| 3705 | is-14 | ta-297 | sp-14 | an-297 |
| 3706 | is-14 | ta-298 | sp-14 | an-298 |
| 3707 | is-14 | ta-299 | sp-14 | an-299 |
| 3708 | is-14 | ta-300 | sp-14 | an-300 |
| 3709 | is-14 | ta-301 | sp-14 | an-301 |
| 3710 | is-14 | ta-302 | sp-14 | an-302 |
| 3711 | is-14 | ta-303 | sp-14 | an-303 |
| 3712 | is-14 | ta-304 | sp-14 | an-304 |
| 3713 | is-14 | ta-305 | sp-14 | an-305 |
| 3714 | is-14 | ta-306 | sp-14 | an-306 |
| 3715 | is-14 | ta-307 | sp-14 | an-307 |
| 3716 | is-14 | ta-308 | sp-14 | an-308 |
| 3717 | is-14 | ta-309 | sp-14 | an-309 |
| 3718 | is-14 | ta-310 | sp-14 | an-310 |
| 3719 | is-14 | ta-311 | sp-14 | an-311 |
| 3720 | is-14 | ta-312 | sp-14 | an-312 |
| 3721 | is-14 | ta-313 | sp-14 | an-313 |
| 3722 | is-14 | ta-314 | sp-14 | an-314 |
| 3723 | is-14 | ta-315 | sp-14 | an-315 |
| 3724 | is-14 | ta-316 | sp-14 | an-316 |
| 3725 | is-14 | ta-317 | sp-14 | an-317 |
| 3726 | is-14 | ta-318 | sp-14 | an-318 |
| 3727 | is-14 | ta-319 | sp-14 | an-319 |
| 3728 | is-14 | ta-320 | sp-14 | an-320 |
| 3729 | is-14 | ta-321 | sp-14 | an-321 |
| 3730 | is-14 | ta-322 | sp-14 | an-322 |

TABLE 2-continued

| Example No. | Reaction reagent is | Reaction reagent ta | Compound of Example sp | Compound of Example an |
|---|---|---|---|---|
| 3731 | is-14 | ta-323 | sp-14 | an-323 |
| 3732 | is-14 | ta-324 | sp-14 | an-324 |
| 3733 | is-14 | ta-325 | sp-14 | an-325 |
| 3734 | is-14 | ta-326 | sp-14 | an-326 |
| 3735 | is-14 | ta-327 | sp-14 | an-327 |
| 3736 | is-14 | ta-328 | sp-14 | an-328 |
| 3737 | is-14 | ta-329 | sp-14 | an-329 |
| 3738 | is-14 | ta-330 | sp-14 | an-330 |
| 3739 | is-14 | ta-331 | sp-14 | an-331 |
| 3740 | is-14 | ta-332 | sp-14 | an-332 |
| 3741 | is-14 | ta-333 | sp-14 | an-333 |
| 3742 | is-14 | ta-334 | sp-14 | an-334 |
| 3743 | is-14 | ta-335 | sp-14 | an-335 |
| 3744 | is-14 | ta-336 | sp-14 | an-336 |
| 3745 | is-14 | ta-337 | sp-14 | an-337 |
| 3746 | is-14 | ta-338 | sp-14 | an-338 |
| 3747 | is-14 | ta-339 | sp-14 | an-339 |
| 3748 | is-14 | ta-340 | sp-14 | an-340 |
| 3749 | is-14 | ta-341 | sp-14 | an-341 |
| 3750 | is-14 | ta-342 | sp-14 | an-342 |
| 3751 | is-14 | ta-343 | sp-14 | an-343 |
| 3752 | is-14 | ta-344 | sp-14 | an-344 |
| 3753 | is-14 | ta-345 | sp-14 | an-345 |
| 3754 | is-14 | ta-346 | sp-14 | an-346 |
| 3755 | is-14 | ta-347 | sp-14 | an-347 |
| 3756 | is-14 | ta-348 | sp-14 | an-348 |
| 3757 | is-14 | ta-349 | sp-14 | an-349 |
| 3758 | is-14 | ta-350 | sp-14 | an-350 |
| 3759 | is-14 | ta-351 | sp-14 | an-351 |
| 3760 | is-14 | ta-352 | sp-14 | an-352 |
| 3761 | is-14 | ta-353 | sp-14 | an-353 |
| 3762 | is-14 | ta-354 | sp-14 | an-354 |
| 3763 | is-14 | ta-355 | sp-14 | an-355 |
| 3764 | is-14 | ta-356 | sp-14 | an-356 |
| 3765 | is-14 | ta-357 | sp-14 | an-357 |
| 3766 | is-14 | ta-358 | sp-14 | an-358 |
| 3767 | is-14 | ta-359 | sp-14 | an-359 |
| 3768 | is-14 | ta-360 | sp-14 | an-360 |
| 3769 | is-14 | ta-361 | sp-14 | an-361 |
| 3770 | is-14 | ta-362 | sp-14 | an-362 |
| 3771 | is-14 | ta-363 | sp-14 | an-363 |
| 3772 | is-14 | ta-364 | sp-14 | an-364 |
| 3773 | is-14 | ta-365 | sp-14 | an-365 |
| 3774 | is-14 | ta-366 | sp-14 | an-366 |
| 3775 | is-14 | ta-367 | sp-14 | an-367 |
| 3776 | is-14 | ta-368 | sp-14 | an-368 |
| 3777 | is-14 | ta-369 | sp-14 | an-369 |
| 3778 | is-14 | ta-370 | sp-14 | an-370 |
| 3779 | is-14 | ta-371 | sp-14 | an-371 |
| 3780 | is-14 | ta-372 | sp-14 | an-372 |
| 3781 | is-14 | ta-373 | sp-14 | an-373 |
| 3782 | is-14 | ta-374 | sp-14 | an-374 |
| 3783 | is-14 | ta-375 | sp-14 | an-375 |
| 3784 | is-14 | ta-376 | sp-14 | an-376 |
| 3785 | is-14 | ta-377 | sp-14 | an-377 |
| 4067 | is-1 | ta-378 | sp-1 | an-378 |
| 4068 | is-1 | ta-379 | sp-1 | an-379 |
| 4069 | is-1 | ta-380 | sp-1 | an-380 |
| 4070 | is-1 | ta-381 | sp-1 | an-381 |
| 4071 | is-1 | ta-382 | sp-1 | an-382 |
| 4072 | is-1 | ta-383 | sp-1 | an-383 |
| 4073 | is-1 | ta-384 | sp-1 | an-384 |
| 4074 | is-1 | ta-385 | sp-1 | an-385 |
| 4075 | is-1 | ta-386 | sp-1 | an-386 |
| 4076 | is-1 | ta-387 | sp-1 | an-387 |
| 4077 | is-1 | ta-388 | sp-1 | an-388 |
| 4078 | is-1 | ta-389 | sp-1 | an-389 |
| 4079 | is-1 | ta-390 | sp-1 | an-390 |
| 4080 | is-1 | ta-391 | sp-1 | an-391 |
| 4081 | is-1 | ta-392 | sp-1 | an-392 |
| 4082 | is-1 | ta-393 | sp-1 | an-393 |
| 4083 | is-2 | ta-378 | sp-2 | an-378 |
| 4084 | is-2 | ta-379 | sp-2 | an-379 |
| 4085 | is-2 | ta-380 | sp-2 | an-380 |
| 4086 | is-2 | ta-381 | sp-2 | an-381 |
| 4087 | is-2 | ta-382 | sp-2 | an-382 |
| 4088 | is-2 | ta-383 | sp-2 | an-383 |
| 4089 | is-2 | ta-384 | sp-2 | an-384 |
| 4090 | is-2 | ta-385 | sp-2 | an-385 |
| 4091 | is-2 | ta-386 | sp-2 | an-386 |
| 4092 | is-2 | ta-387 | sp-2 | an-387 |
| 4093 | is-2 | ta-388 | sp-2 | an-388 |
| 4094 | is-2 | ta-389 | sp-2 | an-389 |
| 4095 | is-2 | ta-390 | sp-2 | an-390 |
| 4096 | is-2 | ta-391 | sp-2 | an-391 |
| 4097 | is-2 | ta-392 | sp-2 | an-392 |
| 4098 | is-2 | ta-393 | sp-2 | an-393 |
| 4099 | is-3 | ta-378 | sp-3 | an-378 |
| 4100 | is-3 | ta-379 | sp-3 | an-379 |
| 4101 | is-3 | ta-380 | sp-3 | an-380 |
| 4102 | is-3 | ta-381 | sp-3 | an-381 |
| 4103 | is-3 | ta-382 | sp-3 | an-382 |
| 4104 | is-3 | ta-383 | sp-3 | an-383 |
| 4105 | is-3 | ta-384 | sp-3 | an-384 |
| 4106 | is-3 | ta-385 | sp-3 | an-385 |
| 4107 | is-3 | ta-386 | sp-3 | an-386 |
| 4108 | is-3 | ta-387 | sp-3 | an-387 |
| 4109 | is-3 | ta-388 | sp-3 | an-388 |
| 4110 | is-3 | ta-389 | sp-3 | an-389 |
| 4111 | is-3 | ta-390 | sp-3 | an-390 |
| 4112 | is-3 | ta-391 | sp-3 | an-391 |
| 4113 | is-3 | ta-392 | sp-3 | an-392 |
| 4114 | is-3 | ta-393 | sp-3 | an-393 |
| 4115 | is-4 | ta-378 | sp-4 | an-378 |
| 4116 | is-4 | ta-379 | sp-4 | an-379 |
| 4117 | is-4 | ta-380 | sp-4 | an-380 |
| 4118 | is-4 | ta-381 | sp-4 | an-381 |
| 4119 | is-4 | ta-382 | sp-4 | an-382 |
| 4120 | is-4 | ta-383 | sp-4 | an-383 |
| 4121 | is-4 | ta-384 | sp-4 | an-384 |
| 4122 | is-4 | ta-385 | sp-4 | an-385 |
| 4123 | is-4 | ta-386 | sp-4 | an-386 |
| 4124 | is-4 | ta-387 | sp-4 | an-387 |
| 4125 | is-4 | ta-388 | sp-4 | an-388 |
| 4126 | is-4 | ta-389 | sp-4 | an-389 |
| 4127 | is-4 | ta-390 | sp-4 | an-390 |
| 4128 | is-4 | ta-391 | sp-4 | an-391 |
| 4129 | is-4 | ta-392 | sp-4 | an-392 |
| 4130 | is-4 | ta-393 | sp-4 | an-393 |
| 4131 | is-5 | ta-378 | sp-5 | an-378 |
| 4132 | is-5 | ta-379 | sp-5 | an-379 |
| 4133 | is-5 | ta-380 | sp-5 | an-380 |
| 4134 | is-5 | ta-381 | sp-5 | an-381 |
| 4135 | is-5 | ta-382 | sp-5 | an-382 |
| 4136 | is-5 | ta-383 | sp-5 | an-383 |
| 4137 | is-5 | ta-384 | sp-5 | an-384 |
| 4138 | is-5 | ta-385 | sp-5 | an-385 |
| 4139 | is-5 | ta-386 | sp-5 | an-386 |
| 4140 | is-5 | ta-387 | sp-5 | an-387 |
| 4141 | is-5 | ta-388 | sp-5 | an-388 |
| 4142 | is-5 | ta-389 | sp-5 | an-389 |
| 4143 | is-5 | ta-390 | sp-5 | an-390 |
| 4144 | is-5 | ta-391 | sp-5 | an-391 |
| 4145 | is-5 | ta-392 | sp-5 | an-392 |
| 4146 | is-5 | ta-393 | sp-5 | an-393 |
| 4146 | is-6 | ta-378 | sp-6 | an-378 |
| 4147 | is-6 | ta-379 | sp-6 | an-379 |
| 4148 | is-6 | ta-380 | sp-6 | an-380 |
| 4149 | is-6 | ta-381 | sp-6 | an-381 |
| 4150 | is-6 | ta-382 | sp-6 | an-382 |
| 4151 | is-6 | ta-383 | sp-6 | an-383 |
| 4152 | is-6 | ta-384 | sp-6 | an-384 |
| 4153 | is-6 | ta-385 | sp-6 | an-385 |
| 4154 | is-6 | ta-386 | sp-6 | an-386 |
| 4155 | is-6 | ta-387 | sp-6 | an-387 |
| 4156 | is-6 | ta-388 | sp-6 | an-388 |
| 4157 | is-6 | ta-389 | sp-6 | an-389 |
| 4158 | is-6 | ta-390 | sp-6 | an-390 |

TABLE 2-continued

| Example No. | Reaction reagent is | Reaction reagent ta | Compound of Example sp | Compound of Example an |
|---|---|---|---|---|
| 4159 | is-6 | ta-391 | sp-6 | an-391 |
| 4160 | is-6 | ta-392 | sp-6 | an-392 |
| 4161 | is-6 | ta-393 | sp-6 | an-393 |
| 4162 | is-7 | ta-378 | sp-7 | an-378 |
| 4163 | is-7 | ta-379 | sp-7 | an-379 |
| 4164 | is-7 | ta-380 | sp-7 | an-380 |
| 4165 | is-7 | ta-381 | sp-7 | an-381 |
| 4166 | is-7 | ta-382 | sp-7 | an-382 |
| 4167 | is-7 | ta-383 | sp-7 | an-383 |
| 4168 | is-7 | ta-384 | sp-7 | an-384 |
| 4169 | is-7 | ta-385 | sp-7 | an-385 |
| 4170 | is-7 | ta-386 | sp-7 | an-386 |
| 4171 | is-7 | ta-387 | sp-7 | an-387 |
| 4172 | is-7 | ta-388 | sp-7 | an-388 |
| 4173 | is-7 | ta-389 | sp-7 | an-389 |
| 4174 | is-7 | ta-390 | sp-7 | an-390 |
| 4175 | is-7 | ta-391 | sp-7 | an-391 |
| 4176 | is-7 | ta-392 | sp-7 | an-392 |
| 4177 | is-7 | ta-393 | sp-7 | an-393 |
| 4178 | is-8 | ta-378 | sp-8 | an-378 |
| 4179 | is-8 | ta-379 | sp-8 | an-379 |
| 4180 | is-8 | ta-380 | sp-8 | an-380 |
| 4181 | is-8 | ta-381 | sp-8 | an-381 |
| 4182 | is-8 | ta-382 | sp-8 | an-382 |
| 4183 | is-8 | ta-383 | sp-8 | an-383 |
| 4184 | is-8 | ta-384 | sp-8 | an-384 |
| 4185 | is-8 | ta-385 | sp-8 | an-385 |
| 4186 | is-8 | ta-386 | sp-8 | an-386 |
| 4187 | is-8 | ta-387 | sp-8 | an-387 |
| 4188 | is-8 | ta-388 | sp-8 | an-388 |
| 4189 | is-8 | ta-389 | sp-8 | an-389 |
| 4190 | is-8 | ta-390 | sp-8 | an-390 |
| 4191 | is-8 | ta-391 | sp-8 | an-391 |
| 4192 | is-8 | ta-392 | sp-8 | an-392 |
| 4193 | is-8 | ta-393 | sp-8 | an-393 |
| 4194 | is-9 | ta-378 | sp-9 | an-378 |
| 4195 | is-9 | ta-379 | sp-9 | an-379 |
| 4196 | is-9 | ta-380 | sp-9 | an-380 |
| 4197 | is-9 | ta-381 | sp-9 | an-381 |
| 4198 | is-9 | ta-382 | sp-9 | an-382 |
| 4199 | is-9 | ta-383 | sp-9 | an-383 |
| 4200 | is-9 | ta-384 | sp-9 | an-384 |
| 4201 | is-9 | ta-385 | sp-9 | an-385 |
| 4202 | is-9 | ta-386 | sp-9 | an-386 |
| 4203 | is-9 | ta-387 | sp-9 | an-387 |
| 4204 | is-9 | ta-388 | sp-9 | an-388 |
| 4205 | is-9 | ta-389 | sp-9 | an-389 |
| 4206 | is-9 | ta-390 | sp-9 | an-390 |
| 4207 | is-9 | ta-391 | sp-9 | an-391 |
| 4208 | is-9 | ta-392 | sp-9 | an-392 |
| 4209 | is-9 | ta-393 | sp-9 | an-393 |
| 4210 | is-14 | ta-378 | sp-14 | an-378 |
| 4211 | is-14 | ta-379 | sp-14 | an-379 |
| 4212 | is-14 | ta-380 | sp-14 | an-380 |
| 4213 | is-14 | ta-381 | sp-14 | an-381 |
| 4214 | is-14 | ta-382 | sp-14 | an-382 |
| 4215 | is-14 | ta-383 | sp-14 | an-383 |
| 4216 | is-14 | ta-384 | sp-14 | an-384 |
| 4217 | is-14 | ta-385 | sp-14 | an-385 |
| 4218 | is-14 | ta-386 | sp-14 | an-386 |
| 4219 | is-14 | ta-387 | sp-14 | an-387 |
| 4220 | is-14 | ta-388 | sp-14 | an-388 |
| 4221 | is-14 | ta-389 | sp-14 | an-389 |
| 4222 | is-14 | ta-390 | sp-14 | an-390 |
| 4223 | is-14 | ta-391 | sp-14 | an-391 |
| 4224 | is-14 | ta-392 | sp-14 | an-392 |
| 4225 | is-14 | ta-393 | sp-14 | an-393 |
| 4226 | is-15 | ta-1 | sp-23 | an-1 |
| 4227 | is-15 | ta-2 | sp-23 | an-2 |
| 4228 | is-15 | ta-3 | sp-23 | an-3 |
| 4229 | is-15 | ta-4 | sp-23 | an-4 |
| 4230 | is-15 | ta-5 | sp-23 | an-5 |
| 4231 | is-15 | ta-6 | sp-23 | an-6 |
| 4232 | is-15 | ta-7 | sp-23 | an-7 |
| 4233 | is-15 | ta-8 | sp-23 | an-8 |
| 4234 | is-15 | ta-9 | sp-23 | an-9 |
| 4235 | is-15 | ta-10 | sp-23 | an-10 |
| 4236 | is-15 | ta-11 | sp-23 | an-11 |
| 4237 | is-15 | ta-12 | sp-23 | an-12 |
| 4238 | is-15 | ta-13 | sp-23 | an-13 |
| 4239 | is-15 | ta-14 | sp-23 | an-14 |
| 4240 | is-15 | ta-15 | sp-23 | an-15 |
| 4241 | is-15 | ta-16 | sp-23 | an-16 |
| 4242 | is-15 | ta-17 | sp-23 | an-17 |
| 4243 | is-15 | ta-18 | sp-23 | an-18 |
| 4244 | is-15 | ta-19 | sp-23 | an-19 |
| 4245 | is-15 | ta-20 | sp-23 | an-20 |
| 4246 | is-15 | ta-21 | sp-23 | an-21 |
| 4247 | is-15 | ta-22 | sp-23 | an-22 |
| 4248 | is-15 | ta-23 | sp-23 | an-23 |
| 4249 | is-15 | ta-24 | sp-23 | an-24 |
| 4250 | is-15 | ta-25 | sp-23 | an-25 |
| 4251 | is-15 | ta-26 | sp-23 | an-26 |
| 4252 | is-15 | ta-27 | sp-23 | an-27 |
| 4253 | is-15 | ta-28 | sp-23 | an-28 |
| 4254 | is-15 | ta-29 | sp-23 | an-29 |
| 4255 | is-15 | ta-30 | sp-23 | an-30 |
| 4256 | is-15 | ta-31 | sp-23 | an-31 |
| 4257 | is-15 | ta-32 | sp-23 | an-32 |
| 4258 | is-15 | ta-33 | sp-23 | an-33 |
| 4259 | is-15 | ta-34 | sp-23 | an-34 |
| 4260 | is-15 | ta-35 | sp-23 | an-35 |
| 4261 | is-15 | ta-36 | sp-23 | an-36 |
| 4262 | is-15 | ta-37 | sp-23 | an-37 |
| 4263 | is-15 | ta-38 | sp-23 | an-38 |
| 4264 | is-15 | ta-39 | sp-23 | an-39 |
| 4265 | is-15 | ta-40 | sp-23 | an-40 |
| 4266 | is-15 | ta-41 | sp-23 | an-41 |
| 4267 | is-15 | ta-42 | sp-23 | an-42 |
| 4268 | is-15 | ta-43 | sp-23 | an-43 |
| 4269 | is-15 | ta-44 | sp-23 | an-44 |
| 4270 | is-15 | ta-45 | sp-23 | an-45 |
| 4271 | is-15 | ta-46 | sp-23 | an-46 |
| 4272 | is-15 | ta-47 | sp-23 | an-47 |
| 4273 | is-15 | ta-48 | sp-23 | an-48 |
| 4274 | is-15 | ta-49 | sp-23 | an-49 |
| 4275 | is-15 | ta-50 | sp-23 | an-50 |
| 4276 | is-15 | ta-51 | sp-23 | an-51 |
| 4277 | is-15 | ta-52 | sp-23 | an-52 |
| 4278 | is-15 | ta-53 | sp-23 | an-53 |
| 4279 | is-15 | ta-54 | sp-23 | an-54 |
| 4280 | is-15 | ta-55 | sp-23 | an-55 |
| 4281 | is-15 | ta-56 | sp-23 | an-56 |
| 4282 | is-15 | ta-57 | sp-23 | an-57 |
| 4283 | is-15 | ta-58 | sp-23 | an-58 |
| 4284 | is-15 | ta-59 | sp-23 | an-59 |
| 4285 | is-15 | ta-60 | sp-23 | an-60 |
| 4286 | is-15 | ta-61 | sp-23 | an-61 |
| 4287 | is-15 | ta-62 | sp-23 | an-62 |
| 4288 | is-15 | ta-63 | sp-23 | an-63 |
| 4289 | is-15 | ta-64 | sp-23 | an-64 |
| 4290 | is-15 | ta-65 | sp-23 | an-65 |
| 4291 | is-15 | ta-66 | sp-23 | an-66 |
| 4292 | is-15 | ta-67 | sp-23 | an-67 |
| 4293 | is-15 | ta-68 | sp-23 | an-68 |
| 4294 | is-15 | ta-69 | sp-23 | an-69 |
| 4295 | is-15 | ta-70 | sp-23 | an-70 |
| 4296 | is-15 | ta-71 | sp-23 | an-71 |
| 4297 | is-15 | ta-72 | sp-23 | an-72 |
| 4298 | is-15 | ta-73 | sp-23 | an-73 |
| 4299 | is-15 | ta-74 | sp-23 | an-74 |
| 4300 | is-15 | ta-75 | sp-23 | an-75 |
| 4301 | is-15 | ta-76 | sp-23 | an-76 |
| 4302 | is-15 | ta-77 | sp-23 | an-77 |
| 4303 | is-15 | ta-78 | sp-23 | an-78 |
| 4304 | is-15 | ta-79 | sp-23 | an-79 |
| 4305 | is-15 | ta-80 | sp-23 | an-80 |
| 4306 | is-15 | ta-81 | sp-23 | an-81 |

TABLE 2-continued

| Example No. | Reaction reagent | | Compound of Example | |
|---|---|---|---|---|
| | is | ta | sp | an |
| 4307 | is-15 | ta-82 | sp-23 | an-82 |
| 4308 | is-15 | ta-83 | sp-23 | an-83 |
| 4309 | is-15 | ta-84 | sp-23 | an-84 |
| 4310 | is-15 | ta-85 | sp-23 | an-85 |
| 4311 | is-15 | ta-86 | sp-23 | an-86 |
| 4312 | is-15 | ta-87 | sp-23 | an-87 |
| 4313 | is-15 | ta-88 | sp-23 | an-88 |
| 4314 | is-15 | ta-89 | sp-23 | an-89 |
| 4315 | is-15 | ta-90 | sp-23 | an-90 |
| 4316 | is-15 | ta-91 | sp-23 | an-91 |
| 4317 | is-15 | ta-92 | sp-23 | an-92 |
| 4318 | is-15 | ta-93 | sp-23 | an-93 |
| 4319 | is-15 | ta-94 | sp-23 | an-94 |
| 4320 | is-15 | ta-95 | sp-23 | an-95 |
| 4321 | is-15 | ta-96 | sp-23 | an-96 |
| 4322 | is-15 | ta-97 | sp-23 | an-97 |
| 4323 | is-15 | ta-98 | sp-23 | an-98 |
| 4324 | is-15 | ta-99 | sp-23 | an-99 |
| 4325 | is-15 | ta-100 | sp-23 | an-100 |
| 4326 | is-15 | ta-101 | sp-23 | an-101 |
| 4327 | is-15 | ta-102 | sp-23 | an-102 |
| 4328 | is-15 | ta-103 | sp-23 | an-103 |
| 4329 | is-15 | ta-104 | sp-23 | an-104 |
| 4330 | is-15 | ta-105 | sp-23 | an-105 |
| 4331 | is-15 | ta-106 | sp-23 | an-106 |
| 4332 | is-15 | ta-107 | sp-23 | an-107 |
| 4333 | is-15 | ta-108 | sp-23 | an-108 |
| 4334 | is-15 | ta-109 | sp-23 | an-109 |
| 4335 | is-15 | ta-110 | sp-23 | an-110 |
| 4336 | is-15 | ta-111 | sp-23 | an-111 |
| 4337 | is-15 | ta-112 | sp-23 | an-112 |
| 4338 | is-15 | ta-113 | sp-23 | an-113 |
| 4339 | is-15 | ta-114 | sp-23 | an-114 |
| 4340 | is-15 | ta-115 | sp-23 | an-115 |
| 4341 | is-15 | ta-116 | sp-23 | an-116 |
| 4342 | is-15 | ta-117 | sp-23 | an-117 |
| 4343 | is-15 | ta-118 | sp-23 | an-118 |
| 4344 | is-15 | ta-119 | sp-23 | an-119 |
| 4345 | is-15 | ta-120 | sp-23 | an-120 |
| 4346 | is-15 | ta-121 | sp-23 | an-121 |
| 4347 | is-15 | ta-122 | sp-23 | an-122 |
| 4348 | is-15 | ta-123 | sp-23 | an-123 |
| 4349 | is-15 | ta-124 | sp-23 | an-124 |
| 4350 | is-15 | ta-125 | sp-23 | an-125 |
| 4351 | is-15 | ta-126 | sp-23 | an-126 |
| 4352 | is-15 | ta-127 | sp-23 | an-127 |
| 4353 | is-15 | ta-128 | sp-23 | an-128 |
| 4354 | is-15 | ta-129 | sp-23 | an-129 |
| 4355 | is-15 | ta-130 | sp-23 | an-130 |
| 4356 | is-15 | ta-131 | sp-23 | an-131 |
| 4357 | is-15 | ta-132 | sp-23 | an-132 |
| 4358 | is-15 | ta-133 | sp-23 | an-133 |
| 4359 | is-15 | ta-134 | sp-23 | an-134 |
| 4360 | is-15 | ta-135 | sp-23 | an-135 |
| 4361 | is-15 | ta-136 | sp-23 | an-136 |
| 4362 | is-15 | ta-137 | sp-23 | an-137 |
| 4363 | is-15 | ta-138 | sp-23 | an-138 |
| 4364 | is-15 | ta-139 | sp-23 | an-139 |
| 4365 | is-15 | ta-140 | sp-23 | an-140 |
| 4366 | is-15 | ta-141 | sp-23 | an-141 |
| 4367 | is-15 | ta-142 | sp-23 | an-142 |
| 4368 | is-15 | ta-143 | sp-23 | an-143 |
| 4369 | is-15 | ta-144 | sp-23 | an-144 |
| 4370 | is-15 | ta-145 | sp-23 | an-145 |
| 4371 | is-15 | ta-146 | sp-23 | an-146 |
| 4372 | is-15 | ta-147 | sp-23 | an-147 |
| 4373 | is-15 | ta-148 | sp-23 | an-148 |
| 4374 | is-15 | ta-149 | sp-23 | an-149 |
| 4375 | is-15 | ta-150 | sp-23 | an-150 |
| 4376 | is-15 | ta-151 | sp-23 | an-151 |
| 4377 | is-15 | ta-152 | sp-23 | an-152 |
| 4378 | is-15 | ta-153 | sp-23 | an-153 |
| 4379 | is-15 | ta-154 | sp-23 | an-154 |
| 4380 | is-15 | ta-155 | sp-23 | an-155 |
| 4381 | is-15 | ta-156 | sp-23 | an-156 |
| 4382 | is-15 | ta-157 | sp-23 | an-157 |
| 4383 | is-15 | ta-158 | sp-23 | an-158 |
| 4384 | is-15 | ta-159 | sp-23 | an-159 |
| 4385 | is-15 | ta-160 | sp-23 | an-160 |
| 4386 | is-15 | ta-161 | sp-23 | an-161 |
| 4387 | is-15 | ta-162 | sp-23 | an-162 |
| 4388 | is-15 | ta-163 | sp-23 | an-163 |
| 4389 | is-15 | ta-164 | sp-23 | an-164 |
| 4390 | is-15 | ta-165 | sp-23 | an-165 |
| 4391 | is-15 | ta-166 | sp-23 | an-166 |
| 4392 | is-15 | ta-167 | sp-23 | an-167 |
| 4393 | is-15 | ta-168 | sp-23 | an-168 |
| 4394 | is-15 | ta-169 | sp-23 | an-169 |
| 4395 | is-15 | ta-170 | sp-23 | an-170 |
| 4396 | is-15 | ta-171 | sp-23 | an-171 |
| 4397 | is-15 | ta-172 | sp-23 | an-172 |
| 4398 | is-15 | ta-173 | sp-23 | an-173 |
| 4399 | is-15 | ta-174 | sp-23 | an-174 |
| 4400 | is-15 | ta-175 | sp-23 | an-175 |
| 4401 | is-15 | ta-176 | sp-23 | an-176 |
| 4402 | is-15 | ta-177 | sp-23 | an-177 |
| 4403 | is-15 | ta-178 | sp-23 | an-178 |
| 4404 | is-15 | ta-179 | sp-23 | an-179 |
| 4405 | is-15 | ta-180 | sp-23 | an-180 |
| 4406 | is-15 | ta-181 | sp-23 | an-181 |
| 4407 | is-15 | ta-182 | sp-23 | an-182 |
| 4408 | is-15 | ta-183 | sp-23 | an-183 |
| 4409 | is-15 | ta-184 | sp-23 | an-184 |
| 4410 | is-15 | ta-185 | sp-23 | an-185 |
| 4411 | is-15 | ta-186 | sp-23 | an-186 |
| 4412 | is-15 | ta-187 | sp-23 | an-187 |
| 4413 | is-15 | ta-188 | sp-23 | an-188 |
| 4414 | is-15 | ta-189 | sp-23 | an-189 |
| 4415 | is-15 | ta-190 | sp-23 | an-190 |
| 4416 | is-15 | ta-191 | sp-23 | an-191 |
| 4417 | is-15 | ta-192 | sp-23 | an-192 |
| 4418 | is-15 | ta-193 | sp-23 | an-193 |
| 4419 | is-15 | ta-194 | sp-23 | an-194 |
| 4420 | is-15 | ta-195 | sp-23 | an-195 |
| 4421 | is-15 | ta-196 | sp-23 | an-196 |
| 4422 | is-15 | ta-197 | sp-23 | an-197 |
| 4423 | is-15 | ta-198 | sp-23 | an-198 |
| 4424 | is-15 | ta-199 | sp-23 | an-199 |
| 4425 | is-15 | ta-200 | sp-23 | an-200 |
| 4426 | is-15 | ta-201 | sp-23 | an-201 |
| 4427 | is-15 | ta-202 | sp-23 | an-202 |
| 4428 | is-15 | ta-203 | sp-23 | an-203 |
| 4429 | is-15 | ta-204 | sp-23 | an-204 |
| 4430 | is-15 | ta-205 | sp-23 | an-205 |
| 4431 | is-15 | ta-206 | sp-23 | an-206 |
| 4432 | is-15 | ta-207 | sp-23 | an-207 |
| 4433 | is-15 | ta-208 | sp-23 | an-208 |
| 4434 | is-15 | ta-209 | sp-23 | an-209 |
| 4435 | is-15 | ta-210 | sp-23 | an-210 |
| 4436 | is-15 | ta-211 | sp-23 | an-211 |
| 4437 | is-15 | ta-212 | sp-23 | an-212 |
| 4438 | is-15 | ta-213 | sp-23 | an-213 |
| 4439 | is-15 | ta-214 | sp-23 | an-214 |
| 4440 | is-15 | ta-215 | sp-23 | an-215 |
| 4441 | is-15 | ta-216 | sp-23 | an-216 |
| 4442 | is-15 | ta-217 | sp-23 | an-217 |
| 4443 | is-15 | ta-218 | sp-23 | an-218 |
| 4444 | is-15 | ta-219 | sp-23 | an-219 |
| 4445 | is-15 | ta-220 | sp-23 | an-220 |
| 4446 | is-15 | ta-221 | sp-23 | an-221 |
| 4447 | is-15 | ta-222 | sp-23 | an-222 |
| 4448 | is-15 | ta-223 | sp-23 | an-223 |
| 4449 | is-15 | ta-224 | sp-23 | an-224 |
| 4450 | is-15 | ta-225 | sp-23 | an-225 |
| 4451 | is-15 | ta-226 | sp-23 | an-226 |
| 4452 | is-15 | ta-227 | sp-23 | an-227 |
| 4453 | is-15 | ta-228 | sp-23 | an-228 |
| 4454 | is-15 | ta-229 | sp-23 | an-229 |

TABLE 2-continued

| Example No. | Reaction reagent is | Reaction reagent ta | Compound of Example sp | Compound of Example an |
|---|---|---|---|---|
| 4455 | is-15 | ta-230 | sp-23 | an-230 |
| 4456 | is-15 | ta-231 | sp-23 | an-231 |
| 4457 | is-15 | ta-232 | sp-23 | an-232 |
| 4458 | is-15 | ta-233 | sp-23 | an-233 |
| 4459 | is-15 | ta-234 | sp-23 | an-234 |
| 4460 | is-15 | ta-235 | sp-23 | an-235 |
| 4461 | is-15 | ta-236 | sp-23 | an-236 |
| 4462 | is-15 | ta-237 | sp-23 | an-237 |
| 4463 | is-15 | ta-238 | sp-23 | an-238 |
| 4464 | is-15 | ta-239 | sp-23 | an-239 |
| 4465 | is-15 | ta-240 | sp-23 | an-240 |
| 4466 | is-15 | ta-241 | sp-23 | an-241 |
| 4467 | is-15 | ta-242 | sp-23 | an-242 |
| 4468 | is-15 | ta-243 | sp-23 | an-243 |
| 4469 | is-15 | ta-244 | sp-23 | an-244 |
| 4470 | is-15 | ta-245 | sp-23 | an-245 |
| 4471 | is-15 | ta-246 | sp-23 | an-246 |
| 4472 | is-15 | ta-247 | sp-23 | an-247 |
| 4473 | is-15 | ta-248 | sp-23 | an-248 |
| 4474 | is-15 | ta-249 | sp-23 | an-249 |
| 4475 | is-15 | ta-250 | sp-23 | an-250 |
| 4476 | is-15 | ta-251 | sp-23 | an-251 |
| 4477 | is-15 | ta-252 | sp-23 | an-252 |
| 4478 | is-15 | ta-253 | sp-23 | an-253 |
| 4479 | is-15 | ta-254 | sp-23 | an-254 |
| 4480 | is-15 | ta-255 | sp-23 | an-255 |
| 4481 | is-15 | ta-256 | sp-23 | an-256 |
| 4482 | is-15 | ta-257 | sp-23 | an-257 |
| 4483 | is-15 | ta-258 | sp-23 | an-258 |
| 4484 | is-15 | ta-259 | sp-23 | an-259 |
| 4485 | is-15 | ta-260 | sp-23 | an-260 |
| 4486 | is-15 | ta-261 | sp-23 | an-261 |
| 4487 | is-15 | ta-262 | sp-23 | an-262 |
| 4488 | is-15 | ta-263 | sp-23 | an-263 |
| 4489 | is-15 | ta-264 | sp-23 | an-264 |
| 4490 | is-15 | ta-265 | sp-23 | an-265 |
| 4491 | is-15 | ta-266 | sp-23 | an-266 |
| 4492 | is-15 | ta-267 | sp-23 | an-267 |
| 4493 | is-15 | ta-268 | sp-23 | an-268 |
| 4494 | is-15 | ta-269 | sp-23 | an-269 |
| 4495 | is-15 | ta-270 | sp-23 | an-270 |
| 4496 | is-15 | ta-271 | sp-23 | an-271 |
| 4497 | is-15 | ta-272 | sp-23 | an-272 |
| 4498 | is-15 | ta-273 | sp-23 | an-273 |
| 4499 | is-15 | ta-274 | sp-23 | an-274 |
| 4500 | is-15 | ta-275 | sp-23 | an-275 |
| 4501 | is-15 | ta-276 | sp-23 | an-276 |
| 4502 | is-15 | ta-277 | sp-23 | an-277 |
| 4503 | is-15 | ta-278 | sp-23 | an-278 |
| 4504 | is-15 | ta-279 | sp-23 | an-279 |
| 4505 | is-15 | ta-280 | sp-23 | an-280 |
| 4506 | is-15 | ta-281 | sp-23 | an-281 |
| 4507 | is-15 | ta-282 | sp-23 | an-282 |
| 4508 | is-15 | ta-283 | sp-23 | an-283 |
| 4509 | is-15 | ta-284 | sp-23 | an-284 |
| 4510 | is-15 | ta-285 | sp-23 | an-285 |
| 4511 | is-15 | ta-286 | sp-23 | an-286 |
| 4512 | is-15 | ta-287 | sp-23 | an-287 |
| 4513 | is-15 | ta-288 | sp-23 | an-288 |
| 4514 | is-15 | ta-289 | sp-23 | an-289 |
| 4515 | is-15 | ta-290 | sp-23 | an-290 |
| 4516 | is-15 | ta-291 | sp-23 | an-291 |
| 4517 | is-15 | ta-292 | sp-23 | an-292 |
| 4518 | is-15 | ta-293 | sp-23 | an-293 |
| 4519 | is-15 | ta-294 | sp-23 | an-294 |
| 4520 | is-15 | ta-295 | sp-23 | an-295 |
| 4521 | is-15 | ta-296 | sp-23 | an-296 |
| 4522 | is-15 | ta-297 | sp-23 | an-297 |
| 4523 | is-15 | ta-298 | sp-23 | an-298 |
| 4524 | is-15 | ta-299 | sp-23 | an-299 |
| 4525 | is-15 | ta-300 | sp-23 | an-300 |
| 4526 | is-15 | ta-301 | sp-23 | an-301 |
| 4527 | is-15 | ta-302 | sp-23 | an-302 |
| 4528 | is-15 | ta-303 | sp-23 | an-303 |
| 4529 | is-15 | ta-304 | sp-23 | an-304 |
| 4530 | is-15 | ta-305 | sp-23 | an-305 |
| 4531 | is-15 | ta-306 | sp-23 | an-306 |
| 4532 | is-15 | ta-307 | sp-23 | an-307 |
| 4533 | is-15 | ta-308 | sp-23 | an-308 |
| 4534 | is-15 | ta-309 | sp-23 | an-309 |
| 4535 | is-15 | ta-310 | sp-23 | an-310 |
| 4536 | is-15 | ta-311 | sp-23 | an-311 |
| 4537 | is-15 | ta-312 | sp-23 | an-312 |
| 4538 | is-15 | ta-313 | sp-23 | an-313 |
| 4539 | is-15 | ta-314 | sp-23 | an-314 |
| 4540 | is-15 | ta-315 | sp-23 | an-315 |
| 4541 | is-15 | ta-316 | sp-23 | an-316 |
| 4542 | is-15 | ta-317 | sp-23 | an-317 |
| 4543 | is-15 | ta-318 | sp-23 | an-318 |
| 4544 | is-15 | ta-319 | sp-23 | an-319 |
| 4545 | is-15 | ta-320 | sp-23 | an-320 |
| 4546 | is-15 | ta-321 | sp-23 | an-321 |
| 4547 | is-15 | ta-322 | sp-23 | an-322 |
| 4548 | is-15 | ta-323 | sp-23 | an-323 |
| 4549 | is-15 | ta-324 | sp-23 | an-324 |
| 4550 | is-15 | ta-325 | sp-23 | an-325 |
| 4551 | is-15 | ta-326 | sp-23 | an-326 |
| 4552 | is-15 | ta-327 | sp-23 | an-327 |
| 4553 | is-15 | ta-328 | sp-23 | an-328 |
| 4554 | is-15 | ta-329 | sp-23 | an-329 |
| 4555 | is-15 | ta-330 | sp-23 | an-330 |
| 4556 | is-15 | ta-331 | sp-23 | an-331 |
| 4557 | is-15 | ta-332 | sp-23 | an-332 |
| 4558 | is-15 | ta-333 | sp-23 | an-333 |
| 4559 | is-15 | ta-334 | sp-23 | an-334 |
| 4560 | is-15 | ta-335 | sp-23 | an-335 |
| 4561 | is-15 | ta-336 | sp-23 | an-336 |
| 4562 | is-15 | ta-337 | sp-23 | an-337 |
| 4563 | is-15 | ta-338 | sp-23 | an-338 |
| 4564 | is-15 | ta-339 | sp-23 | an-339 |
| 4565 | is-15 | ta-340 | sp-23 | an-340 |
| 4566 | is-15 | ta-341 | sp-23 | an-341 |
| 4567 | is-15 | ta-342 | sp-23 | an-342 |
| 4568 | is-15 | ta-343 | sp-23 | an-343 |
| 4569 | is-15 | ta-344 | sp-23 | an-344 |
| 4570 | is-15 | ta-345 | sp-23 | an-345 |
| 4571 | is-15 | ta-346 | sp-23 | an-346 |
| 4572 | is-15 | ta-347 | sp-23 | an-347 |
| 4573 | is-15 | ta-348 | sp-23 | an-348 |
| 4574 | is-15 | ta-349 | sp-23 | an-349 |
| 4575 | is-15 | ta-350 | sp-23 | an-350 |
| 4576 | is-15 | ta-351 | sp-23 | an-351 |
| 4577 | is-15 | ta-352 | sp-23 | an-352 |
| 4578 | is-15 | ta-353 | sp-23 | an-353 |
| 4579 | is-15 | ta-354 | sp-23 | an-354 |
| 4580 | is-15 | ta-355 | sp-23 | an-355 |
| 4581 | is-15 | ta-356 | sp-23 | an-356 |
| 4582 | is-15 | ta-357 | sp-23 | an-357 |
| 4583 | is-15 | ta-358 | sp-23 | an-358 |
| 4584 | is-15 | ta-359 | sp-23 | an-359 |
| 4585 | is-15 | ta-360 | sp-23 | an-360 |
| 4586 | is-15 | ta-361 | sp-23 | an-361 |
| 4587 | is-15 | ta-362 | sp-23 | an-362 |
| 4588 | is-15 | ta-363 | sp-23 | an-363 |
| 4589 | is-15 | ta-364 | sp-23 | an-364 |
| 4590 | is-15 | ta-365 | sp-23 | an-365 |
| 4591 | is-15 | ta-366 | sp-23 | an-366 |
| 4592 | is-15 | ta-367 | sp-23 | an-367 |
| 4593 | is-15 | ta-368 | sp-23 | an-368 |
| 4594 | is-15 | ta-369 | sp-23 | an-369 |
| 4595 | is-15 | ta-370 | sp-23 | an-370 |
| 4596 | is-15 | ta-371 | sp-23 | an-371 |
| 4597 | is-15 | ta-372 | sp-23 | an-372 |
| 4598 | is-15 | ta-373 | sp-23 | an-373 |
| 4599 | is-15 | ta-374 | sp-23 | an-374 |
| 4600 | is-15 | ta-375 | sp-23 | an-375 |
| 4601 | is-15 | ta-376 | sp-23 | an-376 |
| 4602 | is-15 | ta-377 | sp-23 | an-377 |

TABLE 2-continued

| Example No. | Reaction reagent is | Reaction reagent ta | Compound of Example sp | Compound of Example an |
|---|---|---|---|---|
| 4603 | is-15 | ta-378 | sp-23 | an-378 |
| 4604 | is-15 | ta-379 | sp-23 | an-379 |
| 4605 | is-15 | ta-380 | sp-23 | an-380 |
| 4606 | is-15 | ta-381 | sp-23 | an-381 |
| 4607 | is-15 | ta-382 | sp-23 | an-382 |
| 4608 | is-15 | ta-383 | sp-23 | an-383 |
| 4609 | is-15 | ta-384 | sp-23 | an-384 |
| 4610 | is-15 | ta-385 | sp-23 | an-385 |
| 4611 | is-15 | ta-386 | sp-23 | an-386 |
| 4612 | is-15 | ta-387 | sp-23 | an-387 |
| 4613 | is-15 | ta-388 | sp-23 | an-388 |
| 4614 | is-15 | ta-389 | sp-23 | an-389 |
| 4615 | is-15 | ta-390 | sp-23 | an-390 |
| 4616 | is-15 | ta-391 | sp-23 | an-391 |
| 4617 | is-15 | ta-392 | sp-23 | an-392 |
| 4618 | is-15 | ta-393 | sp-23 | an-393 |
| 4619 | is-16 | ta-1 | sp-24 | an-1 |
| 4620 | is-16 | ta-2 | sp-24 | an-2 |
| 4621 | is-16 | ta-3 | sp-24 | an-3 |
| 4622 | is-16 | ta-4 | sp-24 | an-4 |
| 4623 | is-16 | ta-5 | sp-24 | an-5 |
| 4624 | is-16 | ta-6 | sp-24 | an-6 |
| 4625 | is-16 | ta-7 | sp-24 | an-7 |
| 4626 | is-16 | ta-8 | sp-24 | an-8 |
| 4627 | is-16 | ta-9 | sp-24 | an-9 |
| 4628 | is-16 | ta-10 | sp-24 | an-10 |
| 4629 | is-16 | ta-11 | sp-24 | an-11 |
| 4630 | is-16 | ta-12 | sp-24 | an-12 |
| 4631 | is-16 | ta-13 | sp-24 | an-13 |
| 4632 | is-16 | ta-14 | sp-24 | an-14 |
| 4633 | is-16 | ta-15 | sp-24 | an-15 |
| 4634 | is-16 | ta-16 | sp-24 | an-16 |
| 4635 | is-16 | ta-17 | sp-24 | an-17 |
| 4636 | is-16 | ta-18 | sp-24 | an-18 |
| 4637 | is-16 | ta-19 | sp-24 | an-19 |
| 4638 | is-16 | ta-20 | sp-24 | an-20 |
| 4639 | is-16 | ta-21 | sp-24 | an-21 |
| 4640 | is-16 | ta-22 | sp-24 | an-22 |
| 4641 | is-16 | ta-23 | sp-24 | an-23 |
| 4642 | is-16 | ta-24 | sp-24 | an-24 |
| 4643 | is-16 | ta-25 | sp-24 | an-25 |
| 4644 | is-16 | ta-26 | sp-24 | an-26 |
| 4645 | is-16 | ta-27 | sp-24 | an-27 |
| 4646 | is-16 | ta-28 | sp-24 | an-28 |
| 4647 | is-16 | ta-29 | sp-24 | an-29 |
| 4648 | is-16 | ta-30 | sp-24 | an-30 |
| 4649 | is-16 | ta-31 | sp-24 | an-31 |
| 4650 | is-16 | ta-32 | sp-24 | an-32 |
| 4651 | is-16 | ta-33 | sp-24 | an-33 |
| 4652 | is-16 | ta-34 | sp-24 | an-34 |
| 4653 | is-16 | ta-35 | sp-24 | an-35 |
| 4654 | is-16 | ta-36 | sp-24 | an-36 |
| 4655 | is-16 | ta-37 | sp-24 | an-37 |
| 4656 | is-16 | ta-38 | sp-24 | an-38 |
| 4657 | is-16 | ta-39 | sp-24 | an-39 |
| 4658 | is-16 | ta-40 | sp-24 | an-40 |
| 4659 | is-16 | ta-41 | sp-24 | an-41 |
| 4660 | is-16 | ta-42 | sp-24 | an-42 |
| 4661 | is-16 | ta-43 | sp-24 | an-43 |
| 4662 | is-16 | ta-44 | sp-24 | an-44 |
| 4663 | is-16 | ta-45 | sp-24 | an-45 |
| 4664 | is-16 | ta-46 | sp-24 | an-46 |
| 4665 | is-16 | ta-47 | sp-24 | an-47 |
| 4666 | is-16 | ta-48 | sp-24 | an-48 |
| 4667 | is-16 | ta-49 | sp-24 | an-49 |
| 4668 | is-16 | ta-50 | sp-24 | an-50 |
| 4669 | is-16 | ta-51 | sp-24 | an-51 |
| 4670 | is-16 | ta-52 | sp-24 | an-52 |
| 4671 | is-16 | ta-53 | sp-24 | an-53 |
| 4672 | is-16 | ta-54 | sp-24 | an-54 |
| 4673 | is-16 | ta-55 | sp-24 | an-55 |
| 4674 | is-16 | ta-56 | sp-24 | an-56 |
| 4675 | is-16 | ta-57 | sp-24 | an-57 |
| 4676 | is-16 | ta-58 | sp-24 | an-58 |
| 4677 | is-16 | ta-59 | sp-24 | an-59 |
| 4678 | is-16 | ta-60 | sp-24 | an-60 |
| 4679 | is-16 | ta-61 | sp-24 | an-61 |
| 4680 | is-16 | ta-62 | sp-24 | an-62 |
| 4681 | is-16 | ta-63 | sp-24 | an-63 |
| 4682 | is-16 | ta-64 | sp-24 | an-64 |
| 4683 | is-16 | ta-65 | sp-24 | an-65 |
| 4684 | is-16 | ta-66 | sp-24 | an-66 |
| 4685 | is-16 | ta-67 | sp-24 | an-67 |
| 4686 | is-16 | ta-68 | sp-24 | an-68 |
| 4687 | is-16 | ta-69 | sp-24 | an-69 |
| 4688 | is-16 | ta-70 | sp-24 | an-70 |
| 4689 | is-16 | ta-71 | sp-24 | an-71 |
| 4690 | is-16 | ta-72 | sp-24 | an-72 |
| 4691 | is-16 | ta-73 | sp-24 | an-73 |
| 4692 | is-16 | ta-74 | sp-24 | an-74 |
| 4693 | is-16 | ta-75 | sp-24 | an-75 |
| 4694 | is-16 | ta-76 | sp-24 | an-76 |
| 4695 | is-16 | ta-77 | sp-24 | an-77 |
| 4696 | is-16 | ta-78 | sp-24 | an-78 |
| 4697 | is-16 | ta-79 | sp-24 | an-79 |
| 4698 | is-16 | ta-80 | sp-24 | an-80 |
| 4699 | is-16 | ta-81 | sp-24 | an-81 |
| 4700 | is-16 | ta-82 | sp-24 | an-82 |
| 4701 | is-16 | ta-83 | sp-24 | an-83 |
| 4702 | is-16 | ta-84 | sp-24 | an-84 |
| 4703 | is-16 | ta-85 | sp-24 | an-85 |
| 4704 | is-16 | ta-86 | sp-24 | an-86 |
| 4705 | is-16 | ta-87 | sp-24 | an-87 |
| 4706 | is-16 | ta-88 | sp-24 | an-88 |
| 4707 | is-16 | ta-89 | sp-24 | an-89 |
| 4708 | is-16 | ta-90 | sp-24 | an-90 |
| 4709 | is-16 | ta-91 | sp-24 | an-91 |
| 4710 | is-16 | ta-92 | sp-24 | an-92 |
| 4711 | is-16 | ta-93 | sp-24 | an-93 |
| 4712 | is-16 | ta-94 | sp-24 | an-94 |
| 4713 | is-16 | ta-95 | sp-24 | an-95 |
| 4714 | is-16 | ta-96 | sp-24 | an-96 |
| 4715 | is-16 | ta-97 | sp-24 | an-97 |
| 4716 | is-16 | ta-98 | sp-24 | an-98 |
| 4717 | is-16 | ta-99 | sp-24 | an-99 |
| 4718 | is-16 | ta-100 | sp-24 | an-100 |
| 4719 | is-16 | ta-101 | sp-24 | an-101 |
| 4720 | is-16 | ta-102 | sp-24 | an-102 |
| 4721 | is-16 | ta-103 | sp-24 | an-103 |
| 4722 | is-16 | ta-104 | sp-24 | an-104 |
| 4723 | is-16 | ta-105 | sp-24 | an-105 |
| 4724 | is-16 | ta-106 | sp-24 | an-106 |
| 4725 | is-16 | ta-107 | sp-24 | an-107 |
| 4726 | is-16 | ta-108 | sp-24 | an-108 |
| 4727 | is-16 | ta-109 | sp-24 | an-109 |
| 4728 | is-16 | ta-110 | sp-24 | an-110 |
| 4729 | is-16 | ta-111 | sp-24 | an-111 |
| 4730 | is-16 | ta-112 | sp-24 | an-112 |
| 4731 | is-16 | ta-113 | sp-24 | an-113 |
| 4732 | is-16 | ta-114 | sp-24 | an-114 |
| 4733 | is-16 | ta-115 | sp-24 | an-115 |
| 4734 | is-16 | ta-116 | sp-24 | an-116 |
| 4735 | is-16 | ta-117 | sp-24 | an-117 |
| 4736 | is-16 | ta-118 | sp-24 | an-118 |
| 4737 | is-16 | ta-119 | sp-24 | an-119 |
| 4738 | is-16 | ta-120 | sp-24 | an-120 |
| 4739 | is-16 | ta-121 | sp-24 | an-121 |
| 4740 | is-16 | ta-122 | sp-24 | an-122 |
| 4741 | is-16 | ta-123 | sp-24 | an-123 |
| 4742 | is-16 | ta-124 | sp-24 | an-124 |
| 4743 | is-16 | ta-125 | sp-24 | an-125 |
| 4744 | is-16 | ta-126 | sp-24 | an-126 |
| 4745 | is-16 | ta-127 | sp-24 | an-127 |
| 4746 | is-16 | ta-128 | sp-24 | an-128 |
| 4747 | is-16 | ta-129 | sp-24 | an-129 |
| 4748 | is-16 | ta-130 | sp-24 | an-130 |
| 4749 | is-16 | ta-131 | sp-24 | an-131 |
| 4750 | is-16 | ta-132 | sp-24 | an-132 |

TABLE 2-continued

| Example | Reaction reagent | | Compound of Example | |
|---|---|---|---|---|
| No. | is | ta | sp | an |
| 4751 | is-16 | ta-133 | sp-24 | an-133 |
| 4752 | is-16 | ta-134 | sp-24 | an-134 |
| 4753 | is-16 | ta-135 | sp-24 | an-135 |
| 4754 | is-16 | ta-136 | sp-24 | an-136 |
| 4755 | is-16 | ta-137 | sp-24 | an-137 |
| 4756 | is-16 | ta-138 | sp-24 | an-138 |
| 4757 | is-16 | ta-139 | sp-24 | an-139 |
| 4758 | is-16 | ta-140 | sp-24 | an-140 |
| 4759 | is-16 | ta-141 | sp-24 | an-141 |
| 4760 | is-16 | ta-142 | sp-24 | an-142 |
| 4761 | is-16 | ta-143 | sp-24 | an-143 |
| 4762 | is-16 | ta-144 | sp-24 | an-144 |
| 4763 | is-16 | ta-145 | sp-24 | an-145 |
| 4764 | is-16 | ta-146 | sp-24 | an-146 |
| 4765 | is-16 | ta-147 | sp-24 | an-147 |
| 4766 | is-16 | ta-148 | sp-24 | an-148 |
| 4767 | is-16 | ta-149 | sp-24 | an-149 |
| 4768 | is-16 | ta-150 | sp-24 | an-150 |
| 4769 | is-16 | ta-151 | sp-24 | an-151 |
| 4770 | is-16 | ta-152 | sp-24 | an-152 |
| 4771 | is-16 | ta-153 | sp-24 | an-153 |
| 4772 | is-16 | ta-154 | sp-24 | an-154 |
| 4773 | is-16 | ta-155 | sp-24 | an-155 |
| 4774 | is-16 | ta-156 | sp-24 | an-156 |
| 4775 | is-16 | ta-157 | sp-24 | an-157 |
| 4776 | is-16 | ta-158 | sp-24 | an-158 |
| 4777 | is-16 | ta-159 | sp-24 | an-159 |
| 4778 | is-16 | ta-160 | sp-24 | an-160 |
| 4779 | is-16 | ta-161 | sp-24 | an-161 |
| 4780 | is-16 | ta-162 | sp-24 | an-162 |
| 4781 | is-16 | ta-163 | sp-24 | an-163 |
| 4782 | is-16 | ta-164 | sp-24 | an-164 |
| 4783 | is-16 | ta-165 | sp-24 | an-165 |
| 4784 | is-16 | ta-166 | sp-24 | an-166 |
| 4785 | is-16 | ta-167 | sp-24 | an-167 |
| 4786 | is-16 | ta-168 | sp-24 | an-168 |
| 4787 | is-16 | ta-169 | sp-24 | an-169 |
| 4788 | is-16 | ta-170 | sp-24 | an-170 |
| 4789 | is-16 | ta-171 | sp-24 | an-171 |
| 4790 | is-16 | ta-172 | sp-24 | an-172 |
| 4791 | is-16 | ta-173 | sp-24 | an-173 |
| 4792 | is-16 | ta-174 | sp-24 | an-174 |
| 4793 | is-16 | ta-175 | sp-24 | an-175 |
| 4794 | is-16 | ta-176 | sp-24 | an-176 |
| 4795 | is-16 | ta-177 | sp-24 | an-177 |
| 4796 | is-16 | ta-178 | sp-24 | an-178 |
| 4797 | is-16 | ta-179 | sp-24 | an-179 |
| 4798 | is-16 | ta-180 | sp-24 | an-180 |
| 4799 | is-16 | ta-181 | sp-24 | an-181 |
| 4800 | is-16 | ta-182 | sp-24 | an-182 |
| 4801 | is-16 | ta-183 | sp-24 | an-183 |
| 4802 | is-16 | ta-184 | sp-24 | an-184 |
| 4803 | is-16 | ta-185 | sp-24 | an-185 |
| 4804 | is-16 | ta-186 | sp-24 | an-186 |
| 4805 | is-16 | ta-187 | sp-24 | an-187 |
| 4806 | is-16 | ta-188 | sp-24 | an-188 |
| 4807 | is-16 | ta-189 | sp-24 | an-189 |
| 4808 | is-16 | ta-190 | sp-24 | an-190 |
| 4809 | is-16 | ta-191 | sp-24 | an-191 |
| 4810 | is-16 | ta-192 | sp-24 | an-192 |
| 4811 | is-16 | ta-193 | sp-24 | an-193 |
| 4812 | is-16 | ta-194 | sp-24 | an-194 |
| 4813 | is-16 | ta-195 | sp-24 | an-195 |
| 4814 | is-16 | ta-196 | sp-24 | an-196 |
| 4815 | is-16 | ta-197 | sp-24 | an-197 |
| 4816 | is-16 | ta-198 | sp-24 | an-198 |
| 4817 | is-16 | ta-199 | sp-24 | an-199 |
| 4818 | is-16 | ta-200 | sp-24 | an-200 |
| 4819 | is-16 | ta-201 | sp-24 | an-201 |
| 4820 | is-16 | ta-202 | sp-24 | an-202 |
| 4821 | is-16 | ta-203 | sp-24 | an-203 |
| 4822 | is-16 | ta-204 | sp-24 | an-204 |
| 4823 | is-16 | ta-205 | sp-24 | an-205 |
| 4824 | is-16 | ta-206 | sp-24 | an-206 |
| 4825 | is-16 | ta-207 | sp-24 | an-207 |
| 4826 | is-16 | ta-208 | sp-24 | an-208 |
| 4827 | is-16 | ta-209 | sp-24 | an-209 |
| 4828 | is-16 | ta-210 | sp-24 | an-210 |
| 4829 | is-16 | ta-211 | sp-24 | an-211 |
| 4830 | is-16 | ta-212 | sp-24 | an-212 |
| 4831 | is-16 | ta-213 | sp-24 | an-213 |
| 4832 | is-16 | ta-214 | sp-24 | an-214 |
| 4833 | is-16 | ta-215 | sp-24 | an-215 |
| 4834 | is-16 | ta-216 | sp-24 | an-216 |
| 4835 | is-16 | ta-217 | sp-24 | an-217 |
| 4836 | is-16 | ta-218 | sp-24 | an-218 |
| 4837 | is-16 | ta-219 | sp-24 | an-219 |
| 4838 | is-16 | ta-220 | sp-24 | an-220 |
| 4839 | is-16 | ta-221 | sp-24 | an-221 |
| 4840 | is-16 | ta-222 | sp-24 | an-222 |
| 4841 | is-16 | ta-223 | sp-24 | an-223 |
| 4842 | is-16 | ta-224 | sp-24 | an-224 |
| 4843 | is-16 | ta-225 | sp-24 | an-225 |
| 4844 | is-16 | ta-226 | sp-24 | an-226 |
| 4845 | is-16 | ta-227 | sp-24 | an-227 |
| 4846 | is-16 | ta-228 | sp-24 | an-228 |
| 4847 | is-16 | ta-229 | sp-24 | an-229 |
| 4848 | is-16 | ta-230 | sp-24 | an-230 |
| 4849 | is-16 | ta-231 | sp-24 | an-231 |
| 4850 | is-16 | ta-232 | sp-24 | an-232 |
| 4851 | is-16 | ta-233 | sp-24 | an-233 |
| 4852 | is-16 | ta-234 | sp-24 | an-234 |
| 4853 | is-16 | ta-235 | sp-24 | an-235 |
| 4854 | is-16 | ta-236 | sp-24 | an-236 |
| 4855 | is-16 | ta-237 | sp-24 | an-237 |
| 4856 | is-16 | ta-238 | sp-24 | an-238 |
| 4857 | is-16 | ta-239 | sp-24 | an-239 |
| 4858 | is-16 | ta-240 | sp-24 | an-240 |
| 4859 | is-16 | ta-241 | sp-24 | an-241 |
| 4860 | is-16 | ta-242 | sp-24 | an-242 |
| 4861 | is-16 | ta-243 | sp-24 | an-243 |
| 4862 | is-16 | ta-244 | sp-24 | an-244 |
| 4863 | is-16 | ta-245 | sp-24 | an-245 |
| 4864 | is-16 | ta-246 | sp-24 | an-246 |
| 4865 | is-16 | ta-247 | sp-24 | an-247 |
| 4866 | is-16 | ta-248 | sp-24 | an-248 |
| 4867 | is-16 | ta-249 | sp-24 | an-249 |
| 4868 | is-16 | ta-250 | sp-24 | an-250 |
| 4869 | is-16 | ta-251 | sp-24 | an-251 |
| 4870 | is-16 | ta-252 | sp-24 | an-252 |
| 4871 | is-16 | ta-253 | sp-24 | an-253 |
| 4872 | is-16 | ta-254 | sp-24 | an-254 |
| 4873 | is-16 | ta-255 | sp-24 | an-255 |
| 4874 | is-16 | ta-256 | sp-24 | an-256 |
| 4875 | is-16 | ta-257 | sp-24 | an-257 |
| 4876 | is-16 | ta-258 | sp-24 | an-258 |
| 4877 | is-16 | ta-259 | sp-24 | an-259 |
| 4878 | is-16 | ta-260 | sp-24 | an-260 |
| 4879 | is-16 | ta-261 | sp-24 | an-261 |
| 4880 | is-16 | ta-262 | sp-24 | an-262 |
| 4881 | is-16 | ta-263 | sp-24 | an-263 |
| 4882 | is-16 | ta-264 | sp-24 | an-264 |
| 4883 | is-16 | ta-265 | sp-24 | an-265 |
| 4884 | is-16 | ta-266 | sp-24 | an-266 |
| 4885 | is-16 | ta-267 | sp-24 | an-267 |
| 4886 | is-16 | ta-268 | sp-24 | an-268 |
| 4887 | is-16 | ta-269 | sp-24 | an-269 |
| 4888 | is-16 | ta-270 | sp-24 | an-270 |
| 4889 | is-16 | ta-271 | sp-24 | an-271 |
| 4890 | is-16 | ta-272 | sp-24 | an-272 |
| 4891 | is-16 | ta-273 | sp-24 | an-273 |
| 4892 | is-16 | ta-274 | sp-24 | an-274 |
| 4893 | is-16 | ta-275 | sp-24 | an-275 |
| 4894 | is-16 | ta-276 | sp-24 | an-276 |
| 4895 | is-16 | ta-277 | sp-24 | an-277 |
| 4896 | is-16 | ta-278 | sp-24 | an-278 |
| 4897 | is-16 | ta-279 | sp-24 | an-279 |
| 4898 | is-16 | ta-280 | sp-24 | an-280 |

TABLE 2-continued

| Example No. | Reaction reagent is | Reaction reagent ta | Compound of Example sp | Compound of Example an |
|---|---|---|---|---|
| 4899 | is-16 | ta-281 | sp-24 | an-281 |
| 4900 | is-16 | ta-282 | sp-24 | an-282 |
| 4901 | is-16 | ta-283 | sp-24 | an-283 |
| 4902 | is-16 | ta-284 | sp-24 | an-284 |
| 4903 | is-16 | ta-285 | sp-24 | an-285 |
| 4904 | is-16 | ta-286 | sp-24 | an-286 |
| 4905 | is-16 | ta-287 | sp-24 | an-287 |
| 4906 | is-16 | ta-288 | sp-24 | an-288 |
| 4907 | is-16 | ta-289 | sp-24 | an-289 |
| 4908 | is-16 | ta-290 | sp-24 | an-290 |
| 4909 | is-16 | ta-291 | sp-24 | an-291 |
| 4910 | is-16 | ta-292 | sp-24 | an-292 |
| 4911 | is-16 | ta-293 | sp-24 | an-293 |
| 4912 | is-16 | ta-294 | sp-24 | an-294 |
| 4913 | is-16 | ta-295 | sp-24 | an-295 |
| 4914 | is-16 | ta-296 | sp-24 | an-296 |
| 4915 | is-16 | ta-297 | sp-24 | an-297 |
| 4916 | is-16 | ta-298 | sp-24 | an-298 |
| 4917 | is-16 | ta-299 | sp-24 | an-299 |
| 4918 | is-16 | ta-300 | sp-24 | an-300 |
| 4919 | is-16 | ta-301 | sp-24 | an-301 |
| 4920 | is-16 | ta-302 | sp-24 | an-302 |
| 4921 | is-16 | ta-303 | sp-24 | an-303 |
| 4922 | is-16 | ta-304 | sp-24 | an-304 |
| 4923 | is-16 | ta-305 | sp-24 | an-305 |
| 4924 | is-16 | ta-306 | sp-24 | an-306 |
| 4925 | is-16 | ta-307 | sp-24 | an-307 |
| 4926 | is-16 | ta-308 | sp-24 | an-308 |
| 4927 | is-16 | ta-309 | sp-24 | an-309 |
| 4928 | is-16 | ta-310 | sp-24 | an-310 |
| 4929 | is-16 | ta-311 | sp-24 | an-311 |
| 4930 | is-16 | ta-312 | sp-24 | an-312 |
| 4931 | is-16 | ta-313 | sp-24 | an-313 |
| 4932 | is-16 | ta-314 | sp-24 | an-314 |
| 4933 | is-16 | ta-315 | sp-24 | an-315 |
| 4934 | is-16 | ta-316 | sp-24 | an-316 |
| 4935 | is-16 | ta-317 | sp-24 | an-317 |
| 4936 | is-16 | ta-318 | sp-24 | an-318 |
| 4937 | is-16 | ta-319 | sp-24 | an-319 |
| 4938 | is-16 | ta-320 | sp-24 | an-320 |
| 4939 | is-16 | ta-321 | sp-24 | an-321 |
| 4940 | is-16 | ta-322 | sp-24 | an-322 |
| 4941 | is-16 | ta-323 | sp-24 | an-323 |
| 4942 | is-16 | ta-324 | sp-24 | an-324 |
| 4943 | is-16 | ta-325 | sp-24 | an-325 |
| 4944 | is-16 | ta-326 | sp-24 | an-326 |
| 4945 | is-16 | ta-327 | sp-24 | an-327 |
| 4946 | is-16 | ta-328 | sp-24 | an-328 |
| 4947 | is-16 | ta-329 | sp-24 | an-329 |
| 4948 | is-16 | ta-330 | sp-24 | an-330 |
| 4949 | is-16 | ta-331 | sp-24 | an-331 |
| 4950 | is-16 | ta-332 | sp-24 | an-332 |
| 4951 | is-16 | ta-333 | sp-24 | an-333 |
| 4952 | is-16 | ta-334 | sp-24 | an-334 |
| 4953 | is-16 | ta-335 | sp-24 | an-335 |
| 4954 | is-16 | ta-336 | sp-24 | an-336 |
| 4955 | is-16 | ta-337 | sp-24 | an-337 |
| 4956 | is-16 | ta-338 | sp-24 | an-338 |
| 4957 | is-16 | ta-339 | sp-24 | an-339 |
| 4958 | is-16 | ta-340 | sp-24 | an-340 |
| 4959 | is-16 | ta-341 | sp-24 | an-341 |
| 4960 | is-16 | ta-342 | sp-24 | an-342 |
| 4961 | is-16 | ta-343 | sp-24 | an-343 |
| 4962 | is-16 | ta-344 | sp-24 | an-344 |
| 4963 | is-16 | ta-345 | sp-24 | an-345 |
| 4964 | is-16 | ta-346 | sp-24 | an-346 |
| 4965 | is-16 | ta-347 | sp-24 | an-347 |
| 4966 | is-16 | ta-348 | sp-24 | an-348 |
| 4967 | is-16 | ta-349 | sp-24 | an-349 |
| 4968 | is-16 | ta-350 | sp-24 | an-350 |
| 4969 | is-16 | ta-351 | sp-24 | an-351 |
| 4970 | is-16 | ta-352 | sp-24 | an-352 |
| 4971 | is-16 | ta-353 | sp-24 | an-353 |
| 4972 | is-16 | ta-354 | sp-24 | an-354 |
| 4973 | is-16 | ta-355 | sp-24 | an-355 |
| 4974 | is-16 | ta-356 | sp-24 | an-356 |
| 4975 | is-16 | ta-357 | sp-24 | an-357 |
| 4976 | is-16 | ta-358 | sp-24 | an-358 |
| 4977 | is-16 | ta-359 | sp-24 | an-359 |
| 4978 | is-16 | ta-360 | sp-24 | an-360 |
| 4979 | is-16 | ta-361 | sp-24 | an-361 |
| 4980 | is-16 | ta-362 | sp-24 | an-362 |
| 4981 | is-16 | ta-363 | sp-24 | an-363 |
| 4982 | is-16 | ta-364 | sp-24 | an-364 |
| 4983 | is-16 | ta-365 | sp-24 | an-365 |
| 4984 | is-16 | ta-366 | sp-24 | an-366 |
| 4985 | is-16 | ta-367 | sp-24 | an-367 |
| 4986 | is-16 | ta-368 | sp-24 | an-368 |
| 4987 | is-16 | ta-369 | sp-24 | an-369 |
| 4988 | is-16 | ta-370 | sp-24 | an-370 |
| 4989 | is-16 | ta-371 | sp-24 | an-371 |
| 4990 | is-16 | ta-372 | sp-24 | an-372 |
| 4991 | is-16 | ta-373 | sp-24 | an-373 |
| 4992 | is-16 | ta-374 | sp-24 | an-374 |
| 4993 | is-16 | ta-375 | sp-24 | an-375 |
| 4994 | is-16 | ta-376 | sp-24 | an-376 |
| 4995 | is-16 | ta-377 | sp-24 | an-377 |
| 4996 | is-16 | ta-378 | sp-24 | an-378 |
| 4997 | is-16 | ta-379 | sp-24 | an-379 |
| 4998 | is-16 | ta-380 | sp-24 | an-380 |
| 4999 | is-16 | ta-381 | sp-24 | an-381 |
| 5000 | is-16 | ta-382 | sp-24 | an-382 |
| 5001 | is-16 | ta-383 | sp-24 | an-383 |
| 5002 | is-16 | ta-384 | sp-24 | an-384 |
| 5003 | is-16 | ta-385 | sp-24 | an-385 |
| 5004 | is-16 | ta-386 | sp-24 | an-386 |
| 5005 | is-16 | ta-387 | sp-24 | an-387 |
| 5006 | is-16 | ta-388 | sp-24 | an-388 |
| 5007 | is-16 | ta-389 | sp-24 | an-389 |
| 5008 | is-16 | ta-390 | sp-24 | an-390 |
| 5009 | is-16 | ta-391 | sp-24 | an-391 |
| 5010 | is-16 | ta-392 | sp-24 | an-392 |
| 5011 | is-16 | ta-393 | sp-24 | an-393 |
| 5012 | is-17 | ta-1 | sp-25 | an-1 |
| 5013 | is-17 | ta-2 | sp-25 | an-2 |
| 5014 | is-17 | ta-3 | sp-25 | an-3 |
| 5015 | is-17 | ta-4 | sp-25 | an-4 |
| 5016 | is-17 | ta-5 | sp-25 | an-5 |
| 5017 | is-17 | ta-6 | sp-25 | an-6 |
| 5018 | is-17 | ta-7 | sp-25 | an-7 |
| 5019 | is-17 | ta-8 | sp-25 | an-8 |
| 5020 | is-17 | ta-9 | sp-25 | an-9 |
| 5021 | is-17 | ta-10 | sp-25 | an-10 |
| 5022 | is-17 | ta-11 | sp-25 | an-11 |
| 5023 | is-17 | ta-12 | sp-25 | an-12 |
| 5024 | is-17 | ta-13 | sp-25 | an-13 |
| 5025 | is-17 | ta-14 | sp-25 | an-14 |
| 5026 | is-17 | ta-15 | sp-25 | an-15 |
| 5027 | is-17 | ta-16 | sp-25 | an-16 |
| 5028 | is-17 | ta-17 | sp-25 | an-17 |
| 5029 | is-17 | ta-18 | sp-25 | an-18 |
| 5030 | is-17 | ta-19 | sp-25 | an-19 |
| 5031 | is-17 | ta-20 | sp-25 | an-20 |
| 5032 | is-17 | ta-21 | sp-25 | an-21 |
| 5033 | is-17 | ta-22 | sp-25 | an-22 |
| 5034 | is-17 | ta-23 | sp-25 | an-23 |
| 5035 | is-17 | ta-24 | sp-25 | an-24 |
| 5036 | is-17 | ta-25 | sp-25 | an-25 |
| 5037 | is-17 | ta-26 | sp-25 | an-26 |
| 5038 | is-17 | ta-27 | sp-25 | an-27 |
| 5039 | is-17 | ta-28 | sp-25 | an-28 |
| 5040 | is-17 | ta-29 | sp-25 | an-29 |
| 5041 | is-17 | ta-30 | sp-25 | an-30 |
| 5042 | is-17 | ta-31 | sp-25 | an-31 |
| 5043 | is-17 | ta-32 | sp-25 | an-32 |
| 5044 | is-17 | ta-33 | sp-25 | an-33 |
| 5045 | is-17 | ta-34 | sp-25 | an-34 |
| 5046 | is-17 | ta-35 | sp-25 | an-35 |

TABLE 2-continued

| Example No. | Reaction reagent is | Reaction reagent ta | Compound of Example sp | Compound of Example an |
|---|---|---|---|---|
| 5047 | is-17 | ta-36 | sp-25 | an-36 |
| 5048 | is-17 | ta-37 | sp-25 | an-37 |
| 5049 | is-17 | ta-38 | sp-25 | an-38 |
| 5050 | is-17 | ta-39 | sp-25 | an-39 |
| 5051 | is-17 | ta-40 | sp-25 | an-40 |
| 5052 | is-17 | ta-41 | sp-25 | an-41 |
| 5053 | is-17 | ta-42 | sp-25 | an-42 |
| 5054 | is-17 | ta-43 | sp-25 | an-43 |
| 5055 | is-17 | ta-44 | sp-25 | an-44 |
| 5056 | is-17 | ta-45 | sp-25 | an-45 |
| 5057 | is-17 | ta-46 | sp-25 | an-46 |
| 5058 | is-17 | ta-47 | sp-25 | an-47 |
| 5059 | is-17 | ta-48 | sp-25 | an-48 |
| 5060 | is-17 | ta-49 | sp-25 | an-49 |
| 5061 | is-17 | ta-50 | sp-25 | an-50 |
| 5062 | is-17 | ta-51 | sp-25 | an-51 |
| 5063 | is-17 | ta-52 | sp-25 | an-52 |
| 5064 | is-17 | ta-53 | sp-25 | an-53 |
| 5065 | is-17 | ta-54 | sp-25 | an-54 |
| 5066 | is-17 | ta-55 | sp-25 | an-55 |
| 5067 | is-17 | ta-56 | sp-25 | an-56 |
| 5068 | is-17 | ta-57 | sp-25 | an-57 |
| 5069 | is-17 | ta-58 | sp-25 | an-58 |
| 5070 | is-17 | ta-59 | sp-25 | an-59 |
| 5071 | is-17 | ta-60 | sp-25 | an-60 |
| 5072 | is-17 | ta-61 | sp-25 | an-61 |
| 5073 | is-17 | ta-62 | sp-25 | an-62 |
| 5074 | is-17 | ta-63 | sp-25 | an-63 |
| 5075 | is-17 | ta-64 | sp-25 | an-64 |
| 5076 | is-17 | ta-65 | sp-25 | an-65 |
| 5077 | is-17 | ta-66 | sp-25 | an-66 |
| 5078 | is-17 | ta-67 | sp-25 | an-67 |
| 5079 | is-17 | ta-68 | sp-25 | an-68 |
| 5080 | is-17 | ta-69 | sp-25 | an-69 |
| 5081 | is-17 | ta-70 | sp-25 | an-70 |
| 5082 | is-17 | ta-71 | sp-25 | an-71 |
| 5083 | is-17 | ta-72 | sp-25 | an-72 |
| 5084 | is-17 | ta-73 | sp-25 | an-73 |
| 5085 | is-17 | ta-74 | sp-25 | an-74 |
| 5086 | is-17 | ta-75 | sp-25 | an-75 |
| 5087 | is-17 | ta-76 | sp-25 | an-76 |
| 5088 | is-17 | ta-77 | sp-25 | an-77 |
| 5089 | is-17 | ta-78 | sp-25 | an-78 |
| 5090 | is-17 | ta-79 | sp-25 | an-79 |
| 5091 | is-17 | ta-80 | sp-25 | an-80 |
| 5092 | is-17 | ta-81 | sp-25 | an-81 |
| 5093 | is-17 | ta-82 | sp-25 | an-82 |
| 5094 | is-17 | ta-83 | sp-25 | an-83 |
| 5095 | is-17 | ta-84 | sp-25 | an-84 |
| 5096 | is-17 | ta-85 | sp-25 | an-85 |
| 5097 | is-17 | ta-86 | sp-25 | an-86 |
| 5098 | is-17 | ta-87 | sp-25 | an-87 |
| 5099 | is-17 | ta-88 | sp-25 | an-88 |
| 5100 | is-17 | ta-89 | sp-25 | an-89 |
| 5101 | is-17 | ta-90 | sp-25 | an-90 |
| 5102 | is-17 | ta-91 | sp-25 | an-91 |
| 5103 | is-17 | ta-92 | sp-25 | an-92 |
| 5104 | is-17 | ta-93 | sp-25 | an-93 |
| 5105 | is-17 | ta-94 | sp-25 | an-94 |
| 5106 | is-17 | ta-95 | sp-25 | an-95 |
| 5107 | is-17 | ta-96 | sp-25 | an-96 |
| 5108 | is-17 | ta-97 | sp-25 | an-97 |
| 5109 | is-17 | ta-98 | sp-25 | an-98 |
| 5110 | is-17 | ta-99 | sp-25 | an-99 |
| 5111 | is-17 | ta-100 | sp-25 | an-100 |
| 5112 | is-17 | ta-101 | sp-25 | an-101 |
| 5113 | is-17 | ta-102 | sp-25 | an-102 |
| 5114 | is-17 | ta-103 | sp-25 | an-103 |
| 5115 | is-17 | ta-104 | sp-25 | an-104 |
| 5116 | is-17 | ta-105 | sp-25 | an-105 |
| 5117 | is-17 | ta-106 | sp-25 | an-106 |
| 5118 | is-17 | ta-107 | sp-25 | an-107 |
| 5119 | is-17 | ta-108 | sp-25 | an-108 |
| 5120 | is-17 | ta-109 | sp-25 | an-109 |
| 5121 | is-17 | ta-110 | sp-25 | an-110 |
| 5122 | is-17 | ta-111 | sp-25 | an-111 |
| 5123 | is-17 | ta-112 | sp-25 | an-112 |
| 5124 | is-17 | ta-113 | sp-25 | an-113 |
| 5125 | is-17 | ta-114 | sp-25 | an-114 |
| 5126 | is-17 | ta-115 | sp-25 | an-115 |
| 5127 | is-17 | ta-116 | sp-25 | an-116 |
| 5128 | is-17 | ta-117 | sp-25 | an-117 |
| 5129 | is-17 | ta-118 | sp-25 | an-118 |
| 5130 | is-17 | ta-119 | sp-25 | an-119 |
| 5131 | is-17 | ta-120 | sp-25 | an-120 |
| 5132 | is-17 | ta-121 | sp-25 | an-121 |
| 5133 | is-17 | ta-122 | sp-25 | an-122 |
| 5134 | is-17 | ta-123 | sp-25 | an-123 |
| 5135 | is-17 | ta-124 | sp-25 | an-124 |
| 5136 | is-17 | ta-125 | sp-25 | an-125 |
| 5137 | is-17 | ta-126 | sp-25 | an-126 |
| 5138 | is-17 | ta-127 | sp-25 | an-127 |
| 5139 | is-17 | ta-128 | sp-25 | an-128 |
| 5140 | is-17 | ta-129 | sp-25 | an-129 |
| 5141 | is-17 | ta-130 | sp-25 | an-130 |
| 5142 | is-17 | ta-131 | sp-25 | an-131 |
| 5143 | is-17 | ta-132 | sp-25 | an-132 |
| 5144 | is-17 | ta-133 | sp-25 | an-133 |
| 5145 | is-17 | ta-134 | sp-25 | an-134 |
| 5146 | is-17 | ta-135 | sp-25 | an-135 |
| 5147 | is-17 | ta-136 | sp-25 | an-136 |
| 5148 | is-17 | ta-137 | sp-25 | an-137 |
| 5149 | is-17 | ta-138 | sp-25 | an-138 |
| 5150 | is-17 | ta-139 | sp-25 | an-139 |
| 5151 | is-17 | ta-140 | sp-25 | an-140 |
| 5152 | is-17 | ta-141 | sp-25 | an-141 |
| 5153 | is-17 | ta-142 | sp-25 | an-142 |
| 5154 | is-17 | ta-143 | sp-25 | an-143 |
| 5155 | is-17 | ta-144 | sp-25 | an-144 |
| 5156 | is-17 | ta-145 | sp-25 | an-145 |
| 5157 | is-17 | ta-146 | sp-25 | an-146 |
| 5158 | is-17 | ta-147 | sp-25 | an-147 |
| 5159 | is-17 | ta-148 | sp-25 | an-148 |
| 5160 | is-17 | ta-149 | sp-25 | an-149 |
| 5161 | is-17 | ta-150 | sp-25 | an-150 |
| 5162 | is-17 | ta-151 | sp-25 | an-151 |
| 5163 | is-17 | ta-152 | sp-25 | an-152 |
| 5164 | is-17 | ta-153 | sp-25 | an-153 |
| 5165 | is-17 | ta-154 | sp-25 | an-154 |
| 5166 | is-17 | ta-155 | sp-25 | an-155 |
| 5167 | is-17 | ta-156 | sp-25 | an-156 |
| 5168 | is-17 | ta-157 | sp-25 | an-157 |
| 5169 | is-17 | ta-158 | sp-25 | an-158 |
| 5170 | is-17 | ta-159 | sp-25 | an-159 |
| 5171 | is-17 | ta-160 | sp-25 | an-160 |
| 5172 | is-17 | ta-161 | sp-25 | an-161 |
| 5173 | is-17 | ta-162 | sp-25 | an-162 |
| 5174 | is-17 | ta-163 | sp-25 | an-163 |
| 5175 | is-17 | ta-164 | sp-25 | an-164 |
| 5176 | is-17 | ta-165 | sp-25 | an-165 |
| 5177 | is-17 | ta-166 | sp-25 | an-166 |
| 5178 | is-17 | ta-167 | sp-25 | an-167 |
| 5179 | is-17 | ta-168 | sp-25 | an-168 |
| 5180 | is-17 | ta-169 | sp-25 | an-169 |
| 5181 | is-17 | ta-170 | sp-25 | an-170 |
| 5182 | is-17 | ta-171 | sp-25 | an-171 |
| 5183 | is-17 | ta-172 | sp-25 | an-172 |
| 5184 | is-17 | ta-173 | sp-25 | an-173 |
| 5185 | is-17 | ta-174 | sp-25 | an-174 |
| 5186 | is-17 | ta-175 | sp-25 | an-175 |
| 5187 | is-17 | ta-176 | sp-25 | an-176 |
| 5188 | is-17 | ta-177 | sp-25 | an-177 |
| 5189 | is-17 | ta-178 | sp-25 | an-178 |
| 5190 | is-17 | ta-179 | sp-25 | an-179 |
| 5191 | is-17 | ta-180 | sp-25 | an-180 |
| 5192 | is-17 | ta-181 | sp-25 | an-181 |
| 5193 | is-17 | ta-182 | sp-25 | an-182 |
| 5194 | is-17 | ta-183 | sp-25 | an-183 |

TABLE 2-continued

| Example No. | Reaction reagent is | Reaction reagent ta | Compound of Example sp | Compound of Example an |
|---|---|---|---|---|
| 5195 | is-17 | ta-184 | sp-25 | an-184 |
| 5196 | is-17 | ta-185 | sp-25 | an-185 |
| 5197 | is-17 | ta-186 | sp-25 | an-186 |
| 5198 | is-17 | ta-187 | sp-25 | an-187 |
| 5199 | is-17 | ta-188 | sp-25 | an-188 |
| 5200 | is-17 | ta-189 | sp-25 | an-189 |
| 5201 | is-17 | ta-190 | sp-25 | an-190 |
| 5202 | is-17 | ta-191 | sp-25 | an-191 |
| 5203 | is-17 | ta-192 | sp-25 | an-192 |
| 5204 | is-17 | ta-193 | sp-25 | an-193 |
| 5205 | is-17 | ta-194 | sp-25 | an-194 |
| 5206 | is-17 | ta-195 | sp-25 | an-195 |
| 5207 | is-17 | ta-196 | sp-25 | an-196 |
| 5208 | is-17 | ta-197 | sp-25 | an-197 |
| 5209 | is-17 | ta-198 | sp-25 | an-198 |
| 5210 | is-17 | ta-199 | sp-25 | an-199 |
| 5211 | is-17 | ta-200 | sp-25 | an-200 |
| 5212 | is-17 | ta-201 | sp-25 | an-201 |
| 5213 | is-17 | ta-202 | sp-25 | an-202 |
| 5214 | is-17 | ta-203 | sp-25 | an-203 |
| 5215 | is-17 | ta-204 | sp-25 | an-204 |
| 5216 | is-17 | ta-205 | sp-25 | an-205 |
| 5217 | is-17 | ta-206 | sp-25 | an-206 |
| 5218 | is-17 | ta-207 | sp-25 | an-207 |
| 5219 | is-17 | ta-208 | sp-25 | an-208 |
| 5220 | is-17 | ta-209 | sp-25 | an-209 |
| 5221 | is-17 | ta-210 | sp-25 | an-210 |
| 5222 | is-17 | ta-211 | sp-25 | an-211 |
| 5223 | is-17 | ta-212 | sp-25 | an-212 |
| 5224 | is-17 | ta-213 | sp-25 | an-213 |
| 5225 | is-17 | ta-214 | sp-25 | an-214 |
| 5226 | is-17 | ta-215 | sp-25 | an-215 |
| 5227 | is-17 | ta-216 | sp-25 | an-216 |
| 5228 | is-17 | ta-217 | sp-25 | an-217 |
| 5229 | is-17 | ta-218 | sp-25 | an-218 |
| 5230 | is-17 | ta-219 | sp-25 | an-219 |
| 5231 | is-17 | ta-220 | sp-25 | an-220 |
| 5232 | is-17 | ta-221 | sp-25 | an-221 |
| 5233 | is-17 | ta-222 | sp-25 | an-222 |
| 5234 | is-17 | ta-223 | sp-25 | an-223 |
| 5235 | is-17 | ta-224 | sp-25 | an-224 |
| 5236 | is-17 | ta-225 | sp-25 | an-225 |
| 5237 | is-17 | ta-226 | sp-25 | an-226 |
| 5238 | is-17 | ta-227 | sp-25 | an-227 |
| 5239 | is-17 | ta-228 | sp-25 | an-228 |
| 5240 | is-17 | ta-229 | sp-25 | an-229 |
| 5241 | is-17 | ta-230 | sp-25 | an-230 |
| 5242 | is-17 | ta-231 | sp-25 | an-231 |
| 5243 | is-17 | ta-232 | sp-25 | an-232 |
| 5244 | is-17 | ta-233 | sp-25 | an-233 |
| 5245 | is-17 | ta-234 | sp-25 | an-234 |
| 5246 | is-17 | ta-235 | sp-25 | an-235 |
| 5247 | is-17 | ta-236 | sp-25 | an-236 |
| 5248 | is-17 | ta-237 | sp-25 | an-237 |
| 5249 | is-17 | ta-238 | sp-25 | an-238 |
| 5250 | is-17 | ta-239 | sp-25 | an-239 |
| 5251 | is-17 | ta-240 | sp-25 | an-240 |
| 5252 | is-17 | ta-241 | sp-25 | an-241 |
| 5253 | is-17 | ta-242 | sp-25 | an-242 |
| 5254 | is-17 | ta-243 | sp-25 | an-243 |
| 5255 | is-17 | ta-244 | sp-25 | an-244 |
| 5256 | is-17 | ta-245 | sp-25 | an-245 |
| 5257 | is-17 | ta-246 | sp-25 | an-246 |
| 5258 | is-17 | ta-247 | sp-25 | an-247 |
| 5259 | is-17 | ta-248 | sp-25 | an-248 |
| 5260 | is-17 | ta-249 | sp-25 | an-249 |
| 5261 | is-17 | ta-250 | sp-25 | an-250 |
| 5262 | is-17 | ta-251 | sp-25 | an-251 |
| 5263 | is-17 | ta-252 | sp-25 | an-252 |
| 5264 | is-17 | ta-253 | sp-25 | an-253 |
| 5265 | is-17 | ta-254 | sp-25 | an-254 |
| 5266 | is-17 | ta-255 | sp-25 | an-255 |
| 5267 | is-17 | ta-256 | sp-25 | an-256 |
| 5268 | is-17 | ta-257 | sp-25 | an-257 |
| 5269 | is-17 | ta-258 | sp-25 | an-258 |
| 5270 | is-17 | ta-259 | sp-25 | an-259 |
| 5271 | is-17 | ta-260 | sp-25 | an-260 |
| 5272 | is-17 | ta-261 | sp-25 | an-261 |
| 5273 | is-17 | ta-262 | sp-25 | an-262 |
| 5274 | is-17 | ta-263 | sp-25 | an-263 |
| 5275 | is-17 | ta-264 | sp-25 | an-264 |
| 5276 | is-17 | ta-265 | sp-25 | an-265 |
| 5277 | is-17 | ta-266 | sp-25 | an-266 |
| 5278 | is-17 | ta-267 | sp-25 | an-267 |
| 5279 | is-17 | ta-268 | sp-25 | an-268 |
| 5280 | is-17 | ta-269 | sp-25 | an-269 |
| 5281 | is-17 | ta-270 | sp-25 | an-270 |
| 5282 | is-17 | ta-271 | sp-25 | an-271 |
| 5283 | is-17 | ta-272 | sp-25 | an-272 |
| 5284 | is-17 | ta-273 | sp-25 | an-273 |
| 5285 | is-17 | ta-274 | sp-25 | an-274 |
| 5286 | is-17 | ta-275 | sp-25 | an-275 |
| 5287 | is-17 | ta-276 | sp-25 | an-276 |
| 5288 | is-17 | ta-277 | sp-25 | an-277 |
| 5289 | is-17 | ta-278 | sp-25 | an-278 |
| 5290 | is-17 | ta-279 | sp-25 | an-279 |
| 5291 | is-17 | ta-280 | sp-25 | an-280 |
| 5292 | is-17 | ta-281 | sp-25 | an-281 |
| 5293 | is-17 | ta-282 | sp-25 | an-282 |
| 5294 | is-17 | ta-283 | sp-25 | an-283 |
| 5295 | is-17 | ta-284 | sp-25 | an-284 |
| 5296 | is-17 | ta-285 | sp-25 | an-285 |
| 5297 | is-17 | ta-286 | sp-25 | an-286 |
| 5298 | is-17 | ta-287 | sp-25 | an-287 |
| 5299 | is-17 | ta-288 | sp-25 | an-288 |
| 5300 | is-17 | ta-289 | sp-25 | an-289 |
| 5301 | is-17 | ta-290 | sp-25 | an-290 |
| 5302 | is-17 | ta-291 | sp-25 | an-291 |
| 5303 | is-17 | ta-292 | sp-25 | an-292 |
| 5304 | is-17 | ta-293 | sp-25 | an-293 |
| 5305 | is-17 | ta-294 | sp-25 | an-294 |
| 5306 | is-17 | ta-295 | sp-25 | an-295 |
| 5307 | is-17 | ta-296 | sp-25 | an-296 |
| 5308 | is-17 | ta-297 | sp-25 | an-297 |
| 5309 | is-17 | ta-298 | sp-25 | an-298 |
| 5310 | is-17 | ta-299 | sp-25 | an-299 |
| 5311 | is-17 | ta-300 | sp-25 | an-300 |
| 5312 | is-17 | ta-301 | sp-25 | an-301 |
| 5313 | is-17 | ta-302 | sp-25 | an-302 |
| 5314 | is-17 | ta-303 | sp-25 | an-303 |
| 5315 | is-17 | ta-304 | sp-25 | an-304 |
| 5316 | is-17 | ta-305 | sp-25 | an-305 |
| 5317 | is-17 | ta-306 | sp-25 | an-306 |
| 5318 | is-17 | ta-307 | sp-25 | an-307 |
| 5319 | is-17 | ta-308 | sp-25 | an-308 |
| 5320 | is-17 | ta-309 | sp-25 | an-309 |
| 5321 | is-17 | ta-310 | sp-25 | an-310 |
| 5322 | is-17 | ta-311 | sp-25 | an-311 |
| 5323 | is-17 | ta-312 | sp-25 | an-312 |
| 5324 | is-17 | ta-313 | sp-25 | an-313 |
| 5325 | is-17 | ta-314 | sp-25 | an-314 |
| 5326 | is-17 | ta-315 | sp-25 | an-315 |
| 5327 | is-17 | ta-316 | sp-25 | an-316 |
| 5328 | is-17 | ta-317 | sp-25 | an-317 |
| 5329 | is-17 | ta-318 | sp-25 | an-318 |
| 5330 | is-17 | ta-319 | sp-25 | an-319 |
| 5331 | is-17 | ta-320 | sp-25 | an-320 |
| 5332 | is-17 | ta-321 | sp-25 | an-321 |
| 5333 | is-17 | ta-322 | sp-25 | an-322 |
| 5334 | is-17 | ta-323 | sp-25 | an-323 |
| 5335 | is-17 | ta-324 | sp-25 | an-324 |
| 5336 | is-17 | ta-325 | sp-25 | an-325 |
| 5337 | is-17 | ta-326 | sp-25 | an-326 |
| 5338 | is-17 | ta-327 | sp-25 | an-327 |
| 5339 | is-17 | ta-328 | sp-25 | an-328 |
| 5340 | is-17 | ta-329 | sp-25 | an-329 |
| 5341 | is-17 | ta-330 | sp-25 | an-330 |
| 5342 | is-17 | ta-331 | sp-25 | an-331 |

TABLE 2-continued

| Example No. | Reaction reagent is | Reaction reagent ta | Compound of Example sp | Compound of Example an |
|---|---|---|---|---|
| 5343 | is-17 | ta-332 | sp-25 | an-332 |
| 5344 | is-17 | ta-333 | sp-25 | an-333 |
| 5345 | is-17 | ta-334 | sp-25 | an-334 |
| 5346 | is-17 | ta-335 | sp-25 | an-335 |
| 5347 | is-17 | ta-336 | sp-25 | an-336 |
| 5348 | is-17 | ta-337 | sp-25 | an-337 |
| 5349 | is-17 | ta-338 | sp-25 | an-338 |
| 5350 | is-17 | ta-339 | sp-25 | an-339 |
| 5351 | is-17 | ta-340 | sp-25 | an-340 |
| 5352 | is-17 | ta-341 | sp-25 | an-341 |
| 5353 | is-17 | ta-342 | sp-25 | an-342 |
| 5354 | is-17 | ta-343 | sp-25 | an-343 |
| 5355 | is-17 | ta-344 | sp-25 | an-344 |
| 5356 | is-17 | ta-345 | sp-25 | an-345 |
| 5357 | is-17 | ta-346 | sp-25 | an-346 |
| 5358 | is-17 | ta-347 | sp-25 | an-347 |
| 5359 | is-17 | ta-348 | sp-25 | an-348 |
| 5360 | is-17 | ta-349 | sp-25 | an-349 |
| 5361 | is-17 | ta-350 | sp-25 | an-350 |
| 5362 | is-17 | ta-351 | sp-25 | an-351 |
| 5363 | is-17 | ta-352 | sp-25 | an-352 |
| 5364 | is-17 | ta-353 | sp-25 | an-353 |
| 5365 | is-17 | ta-354 | sp-25 | an-354 |
| 5366 | is-17 | ta-355 | sp-25 | an-355 |
| 5367 | is-17 | ta-356 | sp-25 | an-356 |
| 5368 | is-17 | ta-357 | sp-25 | an-357 |
| 5369 | is-17 | ta-358 | sp-25 | an-358 |
| 5370 | is-17 | ta-359 | sp-25 | an-359 |
| 5371 | is-17 | ta-360 | sp-25 | an-360 |
| 5372 | is-17 | ta-361 | sp-25 | an-361 |
| 5373 | is-17 | ta-362 | sp-25 | an-362 |
| 5374 | is-17 | ta-363 | sp-25 | an-363 |
| 5375 | is-17 | ta-364 | sp-25 | an-364 |
| 5376 | is-17 | ta-365 | sp-25 | an-365 |
| 5377 | is-17 | ta-366 | sp-25 | an-366 |
| 5378 | is-17 | ta-367 | sp-25 | an-367 |
| 5379 | is-17 | ta-368 | sp-25 | an-368 |
| 5380 | is-17 | ta-369 | sp-25 | an-369 |
| 5381 | is-17 | ta-370 | sp-25 | an-370 |
| 5382 | is-17 | ta-371 | sp-25 | an-371 |
| 5383 | is-17 | ta-372 | sp-25 | an-372 |
| 5384 | is-17 | ta-373 | sp-25 | an-373 |
| 5385 | is-17 | ta-374 | sp-25 | an-374 |
| 5386 | is-17 | ta-375 | sp-25 | an-375 |
| 5387 | is-17 | ta-376 | sp-25 | an-376 |
| 5388 | is-17 | ta-377 | sp-25 | an-377 |
| 5389 | is-17 | ta-378 | sp-25 | an-378 |
| 5390 | is-17 | ta-379 | sp-25 | an-379 |
| 5391 | is-17 | ta-380 | sp-25 | an-380 |
| 5392 | is-17 | ta-381 | sp-25 | an-381 |
| 5393 | is-17 | ta-382 | sp-25 | an-382 |
| 5394 | is-17 | ta-383 | sp-25 | an-383 |
| 5395 | is-17 | ta-384 | sp-25 | an-384 |
| 5396 | is-17 | ta-385 | sp-25 | an-385 |
| 5397 | is-17 | ta-386 | sp-25 | an-386 |
| 5398 | is-17 | ta-387 | sp-25 | an-387 |
| 5399 | is-17 | ta-388 | sp-25 | an-388 |
| 5400 | is-17 | ta-389 | sp-25 | an-389 |
| 5401 | is-17 | ta-390 | sp-25 | an-390 |
| 5402 | is-17 | ta-391 | sp-25 | an-391 |
| 5403 | is-17 | ta-392 | sp-25 | an-392 |
| 5404 | is-17 | ta-393 | sp-25 | an-393 |
| 5407 | is-14 | ta-394 | sp-14 | an-394 |
| 5408 | is-14 | ta-395 | sp-14 | an-395 |
| 5409 | is-14 | ta-396 | sp-14 | an-396 |
| 5410 | is-14 | ta-397 | sp-14 | an-397 |
| 5411 | is-14 | ta-398 | sp-14 | an-398 |
| 5412 | is-14 | ta-399 | sp-14 | an-399 |
| 5413 | is-14 | ta-400 | sp-14 | an-400 |
| 5414 | is-14 | ta-401 | sp-14 | an-401 |
| 5415 | is-14 | ta-402 | sp-14 | an-402 |
| 5416 | is-14 | ta-403 | sp-14 | an-403 |
| 5417 | is-14 | ta-404 | sp-14 | an-404 |
| 5418 | is-14 | ta-405 | sp-14 | an-405 |
| 5419 | is-14 | ta-406 | sp-14 | an-406 |
| 5420 | is-14 | ta-407 | sp-14 | an-407 |
| 5421 | is-15 | ta-394 | sp-23 | an-394 |
| 5422 | is-15 | ta-395 | sp-23 | an-395 |
| 5423 | is-15 | ta-396 | sp-23 | an-396 |
| 5424 | is-15 | ta-397 | sp-23 | an-397 |
| 5425 | is-15 | ta-398 | sp-23 | an-398 |
| 5426 | is-15 | ta-399 | sp-23 | an-399 |
| 5427 | is-15 | ta-400 | sp-23 | an-400 |
| 5428 | is-15 | ta-401 | sp-23 | an-401 |
| 5429 | is-15 | ta-402 | sp-23 | an-402 |
| 5430 | is-15 | ta-403 | sp-23 | an-403 |
| 5431 | is-15 | ta-404 | sp-23 | an-404 |
| 5432 | is-15 | ta-405 | sp-23 | an-405 |
| 5433 | is-15 | ta-406 | sp-23 | an-406 |
| 5434 | is-15 | ta-407 | sp-23 | an-407 |
| 5435 | is-17 | ta-394 | sp-25 | an-394 |
| 5436 | is-17 | ta-395 | sp-25 | an-395 |
| 5437 | is-17 | ta-396 | sp-25 | an-396 |
| 5438 | is-17 | ta-397 | sp-25 | an-397 |
| 5439 | is-17 | ta-398 | sp-25 | an-398 |
| 5440 | is-17 | ta-399 | sp-25 | an-399 |
| 5441 | is-17 | ta-400 | sp-25 | an-400 |
| 5442 | is-17 | ta-401 | sp-25 | an-401 |
| 5443 | is-17 | ta-402 | sp-25 | an-402 |
| 5444 | is-17 | ta-403 | sp-25 | an-403 |
| 5445 | is-17 | ta-404 | sp-25 | an-404 |
| 5446 | is-17 | ta-405 | sp-25 | an-405 |
| 5447 | is-17 | ta-406 | sp-25 | an-406 |
| 5448 | is-17 | ta-407 | sp-25 | an-407 |

[Examples 3786 to 4064]

As shown in the following formulae,

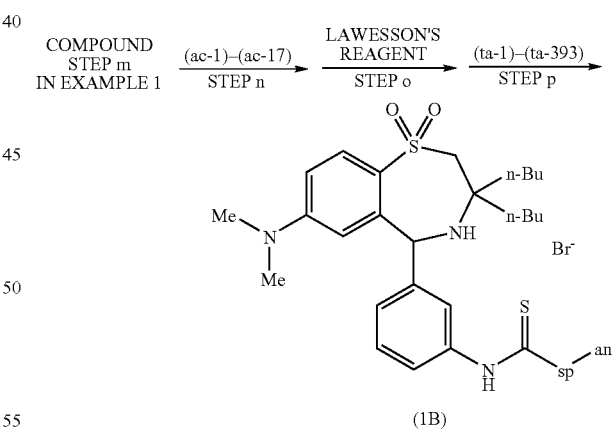

the procedure in the steps n to p in Example 1 is followed except that the compound obtained in the step m in Example 1, any one of the various acyl halides (ac-1) to (ac-17) represented by the formula (5-1), and any one of the various tertiary amines (ta-1) to (ta-393) represented by the formula (2) are used to obtain compounds of Examples 3786 to 4064 as represented by the formula (1B) as shown in Table 3. In the formula (1B), "-sp-" indicates any one of the (sp-1) to (sp-25) and "-an" indicates any one of the (an-1) to (an-393).

TABLE 3

| EX. No. | REACTION REAGENT ac | REACTION REAGENT ta | COMPOUND OF EXAMPLE sp | COMPOUND OF EXAMPLE an |
|---|---|---|---|---|
| 3786 | ac-3 | ta-1 | sp-3 | an-1 |
| 3787 | ac-3 | ta-2 | sp-3 | an-2 |
| 3788 | ac-3 | ta-3 | sp-3 | an-3 |
| 3789 | ac-3 | ta-4 | sp-3 | an-4 |
| 3790 | ac-3 | ta-5 | sp-3 | an-5 |
| 3791 | ac-3 | ta-6 | sp-3 | an-6 |
| 3792 | ac-3 | ta-21 | sp-3 | an-21 |
| 3793 | ac-3 | ta-25 | sp-3 | an-25 |
| 3794 | ac-3 | ta-26 | sp-3 | an-26 |
| 3795 | ac-3 | ta-32 | sp-3 | an-32 |
| 3796 | ac-3 | ta-34 | sp-3 | an-34 |
| 3797 | ac-3 | ta-38 | sp-3 | an-38 |
| 3798 | ac-3 | ta-41 | sp-3 | an-41 |
| 3799 | ac-3 | ta-42 | sp-3 | an-42 |
| 3800 | ac-3 | ta-44 | sp-3 | an-44 |
| 3801 | ac-3 | ta-45 | sp-3 | an-45 |
| 3802 | ac-3 | ta-47 | sp-3 | an-47 |
| 3803 | ac-3 | ta-49 | sp-3 | an-49 |
| 3804 | ac-3 | ta-67 | sp-3 | an-67 |
| 3805 | ac-3 | ta-88 | sp-3 | an-88 |
| 3806 | ac-3 | ta-89 | sp-3 | an-89 |
| 3807 | ac-3 | ta-98 | sp-3 | an-98 |
| 3808 | ac-3 | ta-99 | sp-3 | an-99 |
| 3809 | ac-3 | ta-100 | sp-3 | an-100 |
| 3810 | ac-3 | ta-101 | sp-3 | an-101 |
| 3811 | ac-3 | ta-107 | sp-3 | an-107 |
| 3812 | ac-3 | ta-115 | sp-3 | an-115 |
| 3813 | ac-3 | ta-287 | sp-3 | an-287 |
| 3814 | ac-3 | ta-288 | sp-3 | an-288 |
| 3815 | ac-3 | ta-289 | sp-3 | an-289 |
| 3816 | ac-3 | ta-290 | sp-3 | an-290 |
| 3817 | ac-3 | ta-291 | sp-3 | an-291 |
| 3818 | ac-3 | ta-292 | sp-3 | an-292 |
| 3819 | ac-3 | ta-293 | sp-3 | an-293 |
| 3820 | ac-3 | ta-294 | sp-3 | an-294 |
| 3821 | ac-3 | ta-295 | sp-3 | an-295 |
| 3822 | ac-3 | ta-296 | sp-3 | an-296 |
| 3823 | ac-3 | ta-297 | sp-3 | an-297 |
| 3824 | ac-3 | ta-298 | sp-3 | an-298 |
| 3825 | ac-3 | ta-299 | sp-3 | an-299 |
| 3826 | ac-4 | ta-1 | sp-4 | an-1 |
| 3827 | ac-4 | ta-2 | sp-4 | an-2 |
| 3828 | ac-4 | ta-3 | sp-4 | an-3 |
| 3829 | ac-4 | ta-4 | sp-4 | an-4 |
| 3830 | ac-4 | ta-5 | sp-4 | an-5 |
| 3831 | ac-4 | ta-6 | sp-4 | an-6 |
| 3832 | ac-4 | ta-21 | sp-4 | an-21 |
| 3833 | ac-4 | ta-25 | sp-4 | an-25 |
| 3834 | ac-4 | ta-26 | sp-4 | an-26 |
| 3835 | ac-4 | ta-32 | sp-4 | an-32 |
| 3836 | ac-4 | ta-34 | sp-4 | an-34 |
| 3837 | ac-4 | ta-38 | sp-4 | an-38 |
| 3838 | ac-4 | ta-41 | sp-4 | an-41 |
| 3839 | ac-4 | ta-42 | sp-4 | an-42 |
| 3840 | ac-4 | ta-44 | sp-4 | an-44 |
| 3841 | ac-4 | ta-45 | sp-4 | an-45 |
| 3842 | ac-4 | ta-47 | sp-4 | an-47 |
| 3843 | ac-4 | ta-49 | sp-4 | an-49 |
| 3844 | ac-4 | ta-67 | sp-4 | an-67 |
| 3845 | ac-4 | ta-88 | sp-4 | an-88 |
| 3846 | ac-4 | ta-89 | sp-4 | an-89 |
| 3847 | ac-4 | ta-98 | sp-4 | an-98 |
| 3848 | ac-4 | ta-99 | sp-4 | an-99 |
| 3849 | ac-4 | ta-100 | sp-4 | an-100 |
| 3850 | ac-4 | ta-101 | sp-4 | an-101 |
| 3851 | ac-4 | ta-107 | sp-4 | an-107 |
| 3852 | ac-4 | ta-115 | sp-4 | an-115 |
| 1 | ac-4 | ta-287 | sp-4 | an-287 |
| 3853 | ac-4 | ta-288 | sp-4 | an-288 |
| 3854 | ac-4 | ta-289 | sp-4 | an-289 |
| 3855 | ac-4 | ta-290 | sp-4 | an-290 |
| 3856 | ac-4 | ta-291 | sp-4 | an-291 |
| 3857 | ac-4 | ta-292 | sp-4 | an-292 |
| 3858 | ac-4 | ta-293 | sp-4 | an-293 |
| 3859 | ac-4 | ta-294 | sp-4 | an-294 |
| 3860 | ac-4 | ta-295 | sp-4 | an-295 |
| 3861 | ac-4 | ta-296 | sp-4 | an-296 |
| 3862 | ac-4 | ta-297 | sp-4 | an-297 |
| 3863 | ac-4 | ta-298 | sp-4 | an-298 |
| 3864 | ac-4 | ta-299 | sp-4 | an-299 |
| 3865 | ac-5 | ta-1 | sp-5 | an-1 |
| 3866 | ac-5 | ta-2 | sp-5 | an-2 |
| 3867 | ac-5 | ta-3 | sp-5 | an-3 |
| 3868 | ac-5 | ta-4 | sp-5 | an-4 |
| 3869 | ac-5 | ta-5 | sp-5 | an-5 |
| 3870 | ac-5 | ta-6 | sp-5 | an-6 |
| 3871 | ac-5 | ta-21 | sp-5 | an-21 |
| 3872 | ac-5 | ta-25 | sp-5 | an-25 |
| 3873 | ac-5 | ta-26 | sp-5 | an-26 |
| 3874 | ac-5 | ta-32 | sp-5 | an-32 |
| 3875 | ac-5 | ta-34 | sp-5 | an-34 |
| 3876 | ac-5 | ta-38 | sp-5 | an-38 |
| 3877 | ac-5 | ta-41 | sp-5 | an-41 |
| 3878 | ac-5 | ta-42 | sp-5 | an-42 |
| 3879 | ac-5 | ta-44 | sp-5 | an-44 |
| 3880 | ac-5 | ta-45 | sp-5 | an-45 |
| 3881 | ac-5 | ta-47 | sp-5 | an-47 |
| 3882 | ac-5 | ta-49 | sp-5 | an-49 |
| 3883 | ac-5 | ta-67 | sp-5 | an-67 |
| 3884 | ac-5 | ta-88 | sp-5 | an-88 |
| 3885 | ac-5 | ta-89 | sp-5 | an-89 |
| 3886 | ac-5 | ta-98 | sp-5 | an-98 |
| 3887 | ac-5 | ta-99 | sp-5 | an-99 |
| 3888 | ac-5 | ta-100 | sp-5 | an-100 |
| 3889 | ac-5 | ta-101 | sp-5 | an-101 |
| 3890 | ac-5 | ta-107 | sp-5 | an-107 |
| 3891 | ac-5 | ta-115 | sp-5 | an-115 |
| 3892 | ac-5 | ta-287 | sp-5 | an-287 |
| 3893 | ac-5 | ta-288 | sp-5 | an-288 |
| 3894 | ac-5 | ta-289 | sp-5 | an-289 |
| 3895 | ac-5 | ta-290 | sp-5 | an-290 |
| 3896 | ac-5 | ta-291 | sp-5 | an-291 |
| 3897 | ac-5 | ta-292 | sp-5 | an-292 |
| 3898 | ac-5 | ta-293 | sp-5 | an-293 |
| 3899 | ac-5 | ta-294 | sp-5 | an-294 |
| 3900 | ac-5 | ta-295 | sp-5 | an-295 |
| 3901 | ac-5 | ta-296 | sp-5 | an-296 |
| 3902 | ac-5 | ta-297 | sp-5 | an-297 |
| 3903 | ac-5 | ta-298 | sp-5 | an-298 |
| 3904 | ac-5 | ta-299 | sp-5 | an-299 |
| 3905 | ac-6 | ta-1 | sp-6 | an-1 |
| 3906 | ac-6 | ta-2 | sp-6 | an-2 |
| 3907 | ac-6 | ta-3 | sp-6 | an-3 |
| 3908 | ac-6 | ta-4 | sp-6 | an-4 |
| 3909 | ac-6 | ta-5 | sp-6 | an-5 |
| 3910 | ac-6 | ta-6 | sp-6 | an-6 |
| 3911 | ac-6 | ta-21 | sp-6 | an-21 |
| 3912 | ac-6 | ta-25 | sp-6 | an-25 |
| 3913 | ac-6 | ta-26 | sp-6 | an-26 |
| 3914 | ac-6 | ta-32 | sp-6 | an-32 |
| 3915 | ac-6 | ta-34 | sp-6 | an-34 |
| 3916 | ac-6 | ta-38 | sp-6 | an-38 |
| 3917 | ac-6 | ta-41 | sp-6 | an-41 |
| 3918 | ac-6 | ta-42 | sp-6 | an-42 |
| 3919 | ac-6 | ta-44 | sp-6 | an-44 |
| 3920 | ac-6 | ta-45 | sp-6 | an-45 |
| 3921 | ac-6 | ta-47 | sp-6 | an-47 |
| 3922 | ac-6 | ta-49 | sp-6 | an-49 |
| 3923 | ac-6 | ta-67 | sp-6 | an-67 |
| 3924 | ac-6 | ta-88 | sp-6 | an-88 |
| 3925 | ac-6 | ta-89 | sp-6 | an-89 |
| 3926 | ac-6 | ta-98 | sp-6 | an-98 |
| 3927 | ac-6 | ta-99 | sp-6 | an-99 |
| 3928 | ac-6 | ta-100 | sp-6 | an-100 |
| 3929 | ac-6 | ta-101 | sp-6 | an-101 |
| 3930 | ac-6 | ta-107 | sp-6 | an-107 |
| 3931 | ac-6 | ta-115 | sp-6 | an-115 |
| 3932 | ac-6 | ta-287 | sp-6 | an-287 |

TABLE 3-continued

| EX. No. | REACTION REAGENT ac | REACTION REAGENT ta | COMPOUND OF EXAMPLE sp | COMPOUND OF EXAMPLE an |
|---|---|---|---|---|
| 3933 | ac-6 | ta-288 | sp-6 | an-288 |
| 3934 | ac-6 | ta-289 | sp-6 | an-289 |
| 3935 | ac-6 | ta-290 | sp-6 | an-290 |
| 3936 | ac-6 | ta-291 | sp-6 | an-291 |
| 3937 | ac-6 | ta-292 | sp-6 | an-292 |
| 3938 | ac-6 | ta-293 | sp-6 | an-293 |
| 3939 | ac-6 | ta-294 | sp-6 | an-294 |
| 3940 | ac-6 | ta-295 | sp-6 | an-295 |
| 3941 | ac-6 | ta-296 | sp-6 | an-296 |
| 3942 | ac-6 | ta-297 | sp-6 | an-297 |
| 3943 | ac-6 | ta-298 | sp-6 | an-298 |
| 3944 | ac-6 | ta-299 | sp-6 | an-299 |
| 3945 | ac-7 | ta-1 | sp-7 | an-1 |
| 3946 | ac-7 | ta-2 | sp-7 | an-2 |
| 3947 | ac-7 | ta-3 | sp-7 | an-3 |
| 3948 | ac-7 | ta-4 | sp-7 | an-4 |
| 3949 | ac-7 | ta-5 | sp-7 | an-5 |
| 3950 | ac-7 | ta-6 | sp-7 | an-6 |
| 3951 | ac-7 | ta-21 | sp-7 | an-21 |
| 3952 | ac-7 | ta-25 | sp-7 | an-25 |
| 3953 | ac-7 | ta-26 | sp-7 | an-26 |
| 3954 | ac-7 | ta-32 | sp-7 | an-32 |
| 3955 | ac-7 | ta-34 | sp-7 | an-34 |
| 3956 | ac-7 | ta-38 | sp-7 | an-38 |
| 3957 | ac-7 | ta-41 | sp-7 | an-41 |
| 3958 | ac-7 | ta-42 | sp-7 | an-42 |
| 3959 | ac-7 | ta-44 | sp-7 | an-44 |
| 3960 | ac-7 | ta-45 | sp-7 | an-45 |
| 3961 | ac-7 | ta-47 | sp-7 | an-47 |
| 3962 | ac-7 | ta-49 | sp-7 | an-49 |
| 3963 | ac-7 | ta-67 | sp-7 | an-67 |
| 3964 | ac-7 | ta-88 | sp-7 | an-88 |
| 3965 | ac-7 | ta-89 | sp-7 | an-89 |
| 3966 | ac-7 | ta-98 | sp-7 | an-98 |
| 3967 | ac-7 | ta-99 | sp-7 | an-99 |
| 3968 | ac-7 | ta-100 | sp-7 | an-100 |
| 3969 | ac-7 | ta-101 | sp-7 | an-101 |
| 3970 | ac-7 | ta-107 | sp-7 | an-107 |
| 3971 | ac-7 | ta-115 | sp-7 | an-115 |
| 3972 | ac-7 | ta-287 | sp-7 | an-287 |
| 3973 | ac-7 | ta-288 | sp-7 | an-288 |
| 3974 | ac-7 | ta-289 | sp-7 | an-289 |
| 3975 | ac-7 | ta-290 | sp-7 | an-290 |
| 3976 | ac-7 | ta-291 | sp-7 | an-291 |
| 3977 | ac-7 | ta-292 | sp-7 | an-292 |
| 3978 | ac-7 | ta-293 | sp-7 | an-293 |
| 3979 | ac-7 | ta-294 | sp-7 | an-294 |
| 3980 | ac-7 | ta-295 | sp-7 | an-295 |
| 3981 | ac-7 | ta-296 | sp-7 | an-296 |
| 3982 | ac-7 | ta-297 | sp-7 | an-297 |
| 3983 | ac-7 | ta-298 | sp-7 | an-298 |
| 3984 | ac-7 | ta-299 | sp-7 | an-299 |
| 3985 | ac-8 | ta-1 | sp-8 | an-1 |
| 3986 | ac-8 | ta-2 | sp-8 | an-2 |
| 3987 | ac-8 | ta-3 | sp-8 | an-3 |
| 3988 | ac-8 | ta-4 | sp-8 | an-4 |
| 3989 | ac-8 | ta-5 | sp-8 | an-5 |
| 3990 | ac-8 | ta-6 | sp-8 | an-6 |
| 3991 | ac-8 | ta-21 | sp-8 | an-21 |
| 3992 | ac-8 | ta-25 | sp-8 | an-25 |
| 3993 | ac-8 | ta-26 | sp-8 | an-26 |
| 3994 | ac-8 | ta-32 | sp-8 | an-32 |
| 3995 | ac-8 | ta-34 | sp-8 | an-34 |
| 3996 | ac-8 | ta-38 | sp-8 | an-38 |
| 3997 | ac-8 | ta-41 | sp-8 | an-41 |
| 3998 | ac-8 | ta-42 | sp-8 | an-42 |
| 3999 | ac-8 | ta-44 | sp-8 | an-44 |
| 4000 | ac-8 | ta-45 | sp-8 | an-45 |
| 4001 | ac-8 | ta-47 | sp-8 | an-47 |
| 4002 | ac-8 | ta-49 | sp-8 | an-49 |
| 4003 | ac-8 | ta-67 | sp-8 | an-67 |
| 4004 | ac-8 | ta-88 | sp-8 | an-88 |
| 4005 | ac-8 | ta-89 | sp-8 | an-89 |
| 4006 | ac-8 | ta-98 | sp-8 | an-98 |
| 4007 | ac-8 | ta-99 | sp-8 | an-99 |
| 4008 | ac-8 | ta-100 | sp-8 | an-100 |
| 4009 | ac-8 | ta-101 | sp-8 | an-101 |
| 4010 | ac-8 | ta-107 | sp-8 | an-107 |
| 4011 | ac-8 | ta-115 | sp-8 | an-115 |
| 4012 | ac-8 | ta-287 | sp-8 | an-287 |
| 4013 | ac-8 | ta-288 | sp-8 | an-288 |
| 4014 | ac-8 | ta-289 | sp-8 | an-289 |
| 4015 | ac-8 | ta-290 | sp-8 | an-290 |
| 4016 | ac-8 | ta-291 | sp-8 | an-291 |
| 4017 | ac-8 | ta-292 | sp-8 | an-292 |
| 4018 | ac-8 | ta-293 | sp-8 | an-293 |
| 4019 | ac-8 | ta-294 | sp-8 | an-294 |
| 4020 | ac-8 | ta-295 | sp-8 | an-295 |
| 4021 | ac-8 | ta-296 | sp-8 | an-296 |
| 4022 | ac-8 | ta-297 | sp-8 | an-297 |
| 4023 | ac-8 | ta-298 | sp-8 | an-298 |
| 4024 | ac-8 | ta-299 | sp-8 | an-299 |
| 4025 | ac-9 | ta-1 | sp-9 | an-1 |
| 4026 | ac-9 | ta-2 | sp-9 | an-2 |
| 4027 | ac-9 | ta-3 | sp-9 | an-3 |
| 4028 | ac-9 | ta-4 | sp-9 | an-4 |
| 4029 | ac-9 | ta-5 | sp-9 | an-5 |
| 4030 | ac-9 | ta-6 | sp-9 | an-6 |
| 4031 | ac-9 | ta-21 | sp-9 | an-21 |
| 4032 | ac-9 | ta-25 | sp-9 | an-25 |
| 4033 | ac-9 | ta-26 | sp-9 | an-26 |
| 4034 | ac-9 | ta-32 | sp-9 | an-32 |
| 4035 | ac-9 | ta-34 | sp-9 | an-34 |
| 4036 | ac-9 | ta-38 | sp-9 | an-38 |
| 4037 | ac-9 | ta-41 | sp-9 | an-41 |
| 4038 | ac-9 | ta-42 | sp-9 | an-42 |
| 4039 | ac-9 | ta-44 | sp-9 | an-44 |
| 4040 | ac-9 | ta-45 | sp-9 | an-45 |
| 4041 | ac-9 | ta-47 | sp-9 | an-47 |
| 4042 | ac-9 | ta-49 | sp-9 | an-49 |
| 4043 | ac-9 | ta-67 | sp-9 | an-67 |
| 4044 | ac-9 | ta-88 | sp-9 | an-88 |
| 4045 | ac-9 | ta-89 | sp-9 | an-89 |
| 4046 | ac-9 | ta-98 | sp-9 | an-98 |
| 4047 | ac-9 | ta-99 | sp-9 | an-99 |
| 4048 | ac-9 | ta-100 | sp-9 | an-100 |
| 4049 | ac-9 | ta-101 | sp-9 | an-101 |
| 4050 | ac-9 | ta-107 | sp-9 | an-107 |
| 4051 | ac-9 | ta-115 | sp-9 | an-115 |
| 4052 | ac-9 | ta-287 | sp-9 | an-287 |
| 4053 | ac-9 | ta-288 | sp-9 | an-288 |
| 4054 | ac-9 | ta-289 | sp-9 | an-289 |
| 4055 | ac-9 | ta-290 | sp-9 | an-290 |
| 4056 | ac-9 | ta-291 | sp-9 | an-291 |
| 4057 | ac-9 | ta-292 | sp-9 | an-292 |
| 4058 | ac-9 | ta-293 | sp-9 | an-293 |
| 4059 | ac-9 | ta-294 | sp-9 | an-294 |
| 4060 | ac-9 | ta-295 | sp-9 | an-295 |
| 4061 | ac-9 | ta-296 | sp-9 | an-296 |
| 4062 | ac-9 | ta-297 | sp-9 | an-297 |
| 4063 | ac-9 | ta-298 | sp-9 | an-298 |
| 4064 | ac-9 | ta-299 | sp-9 | an-299 |

End of Table 3

[Example 4065] 1-{5-[4-(3,3-Dibutyl-7-dimethylamino-1,1-dioxo- 2,3,4,5-tetrahydro-1,4-benzothiazepin-5-yl)phenylthiocarbamoyl]- pentyl}-1-azoniabicyclo[2.2.2]octafle bromide Step a: Synthesis of 4-methoxybenzoic acid-4-fluorophenyl ester To a solution of 6.0 g of 4-fluorophenol (manufactured by TOKYO CHEMICAL INDUSTRIES, LTD.) in 60 ml of chloroform were added 6 ml of triethylamine and a solution of 4.0 g of 4-methoxybenzoyl chloride (manufactured by TOKYO CHEMICAL INDUSTRIES, LTD.) in 40 ml of chloroform, and the mixture was stirred at 55° C for 1 hour. The reaction solution was separated by adding to it 100 ml of dichloromethane, 200 ml of water, and 25 ml of a 1N aqueous solution of sodium hydroxide. The organic layer was dried over anhydrous sodium sulfate and then concentrated to obtain 8.1 g of the title compound.

Step b: Synthesis of 4-fluoro-2-(4-methoxybenzoyl)phenol 10 ml of titanium tetrachloride (manufactured by WAKO PURE CHEMICAL INDUSTRIES, LTD.) was added to 6.55 g of the compound obtained in the step a and the mixture was heated at 160° C for 4 hours. Under ice cooling, 10 ml of water was dropwise added to the reaction mixture and further 400 ml of ether and 400 ml of water were added to the mixture at room temperature to separate it. The organic layer was dried over anhydrous sodium sulfate and then concentrated. The residue was charged in a silica gel column and eluted with hexane-ethyl acetate (8:1) to obtain 3.44 g of the title compound.

Step c: Synthesis of O-[4-fluoro-2-(4-methoxybenzoyl)phenyl]N,N-dimethylthiocarbamate To a solution of 3.44 g of the compound obtained in the step b in 70 ml of dioxane were added 4.24 g of triethylamine, 0.34 g of dimethylaminopyridine (manufactured by WAKO PURE CHEMICAL INDUSTRIES, LTD.), and 2.10 g of N,N-dimethylthiocarbamoyl chloride (manufactured by TOKYO CHEMICAL INDUSTRIES, LTD.), and the mixture was stirred at 100° C for 24 hours. The reaction suspension was separated by adding to it 200 ml of ethyl acetate and 200 ml of water. The organic layer was dried over anhydrous sodium sulfate and then concentrated. The residue was charged in a silica gel column and eluted with hexane-ethyl acetate (3:1) to obtain 4.65 g of the title compound.

Step d: Synthesis of S-[4-fluoro-2-(4-methoxybenzoyl)phenyl]N,N-dimethylthiocarbamate A suspension of 4.65 g of the compound obtained in the step c in 30 ml of tetradecane (manufactured by WAKO PURE CHEMICAL INDUSTRIES, LTD.) was heated at 250° C for 5 hours. 12 ml of chloroform was added to the reaction suspension at room temperature to dissolve the reaction product. This solution was charged in a silica gel column and eluted with hexane-ethyl acetate (2:1) to obtain 2.10 g of the title compound.

Step e: Synthesis of 4-fluoro-2-(4-methoxybenzoyl)thiophenol

To a solution of 2.10 g of the compound obtained in the step d in 20 ml of THF were added 20 ml of methanol and 1.88 g of potassium hydroxide, and the mixture was stirred at 60° C for 2 hours. Under ice cooling, 30 ml of 1N hydrochloric acid was dropwise added to the reaction suspension and then 100 ml of ethyl acetate and 100 ml of water were added to the resultant at room temperature to separate it. The organic layer was washed with 150 ml of saturated saline, dried over anhydrous sodium sulfate, and then concentrated to obtain 1.63 g of the title compound.

Step f: Synthesis of 3,3-dibutyl-2,3-dihydro-7-fluoro-5-(4- methoxyphenyl)-1,4-benzothiazepine-1,1-dioxide The procedure in the steps g to i in Example 1 was followed except that the compound obtained in the step e in this example was used to obtain the title compound.

Step g: Synthesis of 3,3-dibutyl-2,3-dihydro-7-dimethylamino-5- (4-methoxyphenyl)-1,4-benzothiazepine-1,1-dioxide The procedure in the step k in Example 1 was followed except that the compound obtained in the step f in this example was used to obtain the title compound.

Step h: Synthesis of 3,3-dibutyl-7-dimethylamino-2, 3,4,5-tetrahydro-5- (4-methoxyphenyl)-1,4-benzothiazepine-1,1-dioxide The procedure in the step m in Example 1 was followed except that the compound obtained in the step g in this example was used to obtain the title compound.

Step i: Synthesis of 3,3-dibutyl-7-dimethylamino-2, 3,4,5-tetrahydro-5- (4-hydroxyphenyl)-1,4-benzothiazepine-1,1-dioxide To a solution of 1.15 g of the compound obtained in the step h in 10 ml of dichloromethane was dropwise added 9 ml of a dichloromethane solution of 1 mol/l boron tribromide (manufactured by ALDRICH CHEMICAL COMPANY) at −20° C and the mixture was stirred under ice cooling for 1 hour. The reaction solution was dropwise added to 200 ml of 5% sodium bicarbonate water under ice cooling. The mixture was then separated by adding to it 100 ml of dichloromethane at room temperature. The organic layer was dried over anhydrous sodium sulfate and then concentrated. The residue was charged in a silica gel column and eluted with hexane-ethyl acetate (2:1) to obtain 1.00 g of the title compound.

Step j: Trifluoromethanesulfonic acid 4-(3,3-dibutyl-7-dimethylamino- 1,1-dioxo-2,3,4,5-tetrahydro-1,4-benzothiazepin-5-yl)phenyl ester To a solution of 735 mg of the compound obtained in the step in 3.3 ml of pyridine was dropwise added 388 μl of trifluoromethanesulfonic acid anhydride (manufactured by ALDRICH CHEMICAL COMPANY) at 0° C, and the mixture was stirred at room temperature for 1 hour. The reaction solution was separated by adding to it 10 ml of ethyl acetate and 10 ml of water. The organic layer was washed with 10 ml of saturated aqueous copper sulfate solution, then washed with 10 ml of saturated sodium bicarbonate water, and further washed with 10 ml of saturated saline. The organic layer was dried over anhydrous sodium sulfate and then concentrated to obtain 916 mg of the title compound.

Step k: Synthesis of 3,3-dibutyl-7-dimethylamino-2, 3,4,5-tetrahydro-5- (4-aminophenyl)-1,4-benzothiazepine-1,1-dioxide To a solution of 3.77 g of the compound obtained in the step j in 38 ml of THF were added 303 mg of palladium II acetate (manufactured by ALDRICH CHEMICAL COMPANY), 986 mg of 2,2-bis- (diphenylphosphenyl)-1,1'-binaphthyl (manufactured by ALDRICH CHEMICAL COMPANY), and 4.42 g of cesium carbonate (manufactured by WAKO PURE CHEMICAL INDUSTRIES, LTD.). Further, 2.2 ml of benzophenonimine (manufactured by ALDRICH CHEMICAL COMPANY) was added and the mixture was refluxed under heating for 2 hours while stirring. The insoluble matter in the reaction suspension was removed by filtration and the filtrate was concentrated. The residue was dissolved in 65 ml of methanol, and 2.15 g of sodium acetate (manufactured by WAKO PURE CHEMICAL INDUSTRIES, LTD.) and 1.38 g of hydroxylamine hydrochloride (manufactured by TOKYO CHEMICAL INDUSTRIES, LTD.) were added to the solution, and the mixture was stirred at room temperature for 1 hour. The reaction suspension was separated by adding to it 70 ml of dichloromethane and 70 ml of saturated sodium bicarbonate water. The organic layer was washed with 70 ml of saturated saline, dried over anhydrous sodium sulfate, and then concentrated. The residue was charged in a silica gel column and eluted with hexane-ethyl acetate (2:1) to obtain 2.48 g of the title compound.

Step l: Synthesis of 1-{5-[4-(3,3-dibutyl-7-dimethylamino-1,1-dioxo- 2,3,4,5-tetrahydro-1,4-benzothiazepin-5-yl)phenylthiocarbamoyl]- pentyl}-1-azoniabicyclo[2.2.2]octane bromide The procedure in the steps n to p was followed except that the compound obtained in the step k in this example was used to obtain the title compound. $^1$H-NMR (CDCl$_3$) δ: 0.85 (3H, t); 0.90 (3H, t); 1.12-1.48 (8H, m); 1.53-2.25 (17H, m); 2.82 (6H, 5); 2.99 (1H, d); 3.10-3.51 (5H, m); 3.61 (6H, t); 5.94 (1H, d); 6.01 (1H, s); 6.47 (1H, dd); 7.41 (2H, d); 7.87 (1H, d); 8.22 (2H, d); 11.62 (1H, s). MS (m/z): 667 (M$^+$).

[Example 4066] 1-(3-{3-[4-(3,3-dibutyl-7-dimethylamino-1,1-dioxo- 2,3,4,5-tetrahydro-1,4-benzothiazepin-5-yl)phenyl]thioureido}propyl)-1- azoniabicyclo[2.2.2]octane bromide The procedure in the step b in Example 9 was followed except that instead of the compound obtained in the step m in Example 1, the compound obtained in the step k in Example 4065 was used to obtain the title compound. MS (m/z): 654 (M$^+$).

[Example 5405] Benzyl-(4-{3-[4-(3,3-dibutyl-7-dimethylamino-1,1- dioxo-2,3,4,5-tetrahydro-1,4-benzothiazepin-5-yl)phenyl] thioureido}- benzyl) dimethylammonium bromide Step a: Synthesis of benzyl-(4-isothiocyanatobenzyl)dimethylaminonium bromide The procedure in the step a in Example 9 was followed except that instead of 3-bromopropyl isothiocyanate, 4-(bromomethyl)phenyl isothiocyanate (is-14 mentioned earlier) was used and instead of quinuclidine, N,N-diinethylbenzylainine (ta-32 mentioned earlier) was used to obtain the title compound.

Step b: Synthesis of benzyl-(4-{3-[4-(3,3-dibutyl-7-dimethylamino-1,1- dioxo-2,3,4,5-tetrahydro-1,4-benzothiazepin-5-yl)phenyl]thioureido}- benzyl) dimethylammonium bromide The procedure in the step b in Example 9 was followed except that the compound obtained in the step a in this example and the compound obtained in the step k in Example 4065 were used to obtain the title compound.

[Example 5406] 1-(3-{3-[4-(3,3-Dibutyl-7-dimethylamino-1,1-dioxo- 2,3,4,5-tetrahydro-1,4-benzothiazepin-5-yl)phenyl]thioureido}benzyl)1- azoniabicyclo[2.2.2]octane bromide Step a: Synthesis of 1-(3-isothiocyanatobenzyl)-1-azoniabicyclo[2.2.2]-octane bromide The procedure in the step a in Example 9 was followed except that instead of 3-bromopropyl isothiocyanate, 3-(bromomethyl)phenyl isothiocyanate (is-15 mentioned earlier) was used to obtain the title compound.

Step b: Synthesis of 1-(3-{3-[4-(3,3-dibutyl-7-dimethylamino-1,1-dioxo- 2,3,4,5-tetrahydro-1,4-benzothiazepin-5-yl)phenyl]thioureido}benzyl)-1- azoniabicyclol2.2.2]octane bromide The procedure in the step b in Example 9 was followed except that the compound obtained in the step a in this example and the compound obtained in the step k in Example 4065 were used to obtain the title compound.

[Examples 5449 to 5858]

As shown in the following figure,

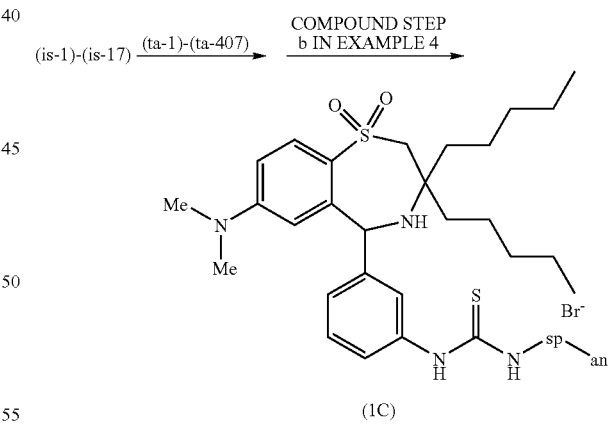

the procedure in the steps a and b in Example 9 is followed except that any one of the various isothiocyanates (is-14) and (is-17) represented by the formula (5-2b), any one of the various tertiary amines (ta-1) to (ta-407) represented by the formula (2), and the compound obtained in the step b in Example 4 are used to obtain compounds of Examples 5449 to 5858 as represented by the formula (1C) as shown in Table 4. In the formula (1C), "-sp-" indicates any one of the (sp-14) and (sp-25) described above and "-an" indicates any one of the (an-1) to (an-407) described above.

TABLE 4

| Example No. | Reagent is | Reagent ta | Example Compound sp | Example Compound an |
|---|---|---|---|---|
| 5449 | is-14 | ta-1 | sp-14 | an-1 |
| 5450 | is-14 | ta-2 | sp-14 | an-2 |
| 5451 | is-14 | ta-3 | sp-14 | an-3 |
| 5452 | is-14 | ta-4 | sp-14 | an-4 |
| 5453 | is-14 | ta-5 | sp-14 | an-5 |
| 5454 | is-14 | ta-6 | sp-14 | an-6 |
| 5455 | is-14 | ta-7 | sp-14 | an-7 |
| 5456 | is-14 | ta-8 | sp-14 | an-8 |
| 5457 | is-14 | ta-9 | sp-14 | an-9 |
| 5458 | is-14 | ta-10 | sp-14 | an-10 |
| 5459 | is-14 | ta-11 | sp-14 | an-11 |
| 5460 | is-14 | ta-12 | sp-14 | an-12 |
| 5461 | is-14 | ta-13 | sp-14 | an-13 |
| 5462 | is-14 | ta-14 | sp-14 | an-14 |
| 5463 | is-14 | ta-15 | sp-14 | an-15 |
| 5464 | is-14 | ta-16 | sp-14 | an-16 |
| 5465 | is-14 | ta-17 | sp-14 | an-17 |
| 5466 | is-14 | ta-18 | sp-14 | an-18 |
| 5467 | is-14 | ta-19 | sp-14 | an-19 |
| 5468 | is-14 | ta-20 | sp-14 | an-20 |
| 5469 | is-14 | ta-21 | sp-14 | an-21 |
| 5470 | is-14 | ta-22 | sp-14 | an-22 |
| 5471 | is-14 | ta-23 | sp-14 | an-23 |
| 5472 | is-14 | ta-24 | sp-14 | an-24 |
| 5473 | is-14 | ta-25 | sp-14 | an-25 |
| 5474 | is-14 | ta-26 | sp-14 | an-26 |
| 5475 | is-14 | ta-27 | sp-14 | an-27 |
| 5476 | is-14 | ta-28 | sp-14 | an-28 |
| 5477 | is-14 | ta-29 | sp-14 | an-29 |
| 5478 | is-14 | ta-30 | sp-14 | an-30 |
| 5479 | is-14 | ta-31 | sp-14 | an-31 |
| 5480 | is-14 | ta-32 | sp-14 | an-32 |
| 5481 | is-14 | ta-33 | sp-14 | an-33 |
| 5482 | is-14 | ta-34 | sp-14 | an-34 |
| 5483 | is-14 | ta-35 | sp-14 | an-35 |
| 5484 | is-14 | ta-36 | sp-14 | an-36 |
| 5485 | is-14 | ta-37 | sp-14 | an-37 |
| 5486 | is-14 | ta-38 | sp-14 | an-38 |
| 5487 | is-14 | ta-39 | sp-14 | an-39 |
| 5488 | is-14 | ta-40 | sp-14 | an-40 |
| 5489 | is-14 | ta-41 | sp-14 | an-41 |
| 5490 | is-14 | ta-42 | sp-14 | an-42 |
| 5491 | is-14 | ta-43 | sp-14 | an-43 |
| 5492 | is-14 | ta-44 | sp-14 | an-44 |
| 5493 | is-14 | ta-45 | sp-14 | an-45 |
| 5494 | is-14 | ta-46 | sp-14 | an-46 |
| 5495 | is-14 | ta-47 | sp-14 | an-47 |
| 5496 | is-14 | ta-48 | sp-14 | an-48 |
| 5497 | is-14 | ta-49 | sp-14 | an-49 |
| 5498 | is-14 | ta-50 | sp-14 | an-50 |
| 5499 | is-14 | ta-51 | sp-14 | an-51 |
| 5500 | is-14 | ta-52 | sp-14 | an-52 |
| 5501 | is-14 | ta-53 | sp-14 | an-53 |
| 5654 | is-14 | ta-206 | sp-14 | an-206 |
| 5655 | is-14 | ta-207 | sp-14 | an-207 |
| 5656 | is-14 | ta-208 | sp-14 | an-208 |
| 5657 | is-14 | ta-209 | sp-14 | an-209 |
| 5658 | is-14 | ta-210 | sp-14 | an-210 |
| 5659 | is-14 | ta-211 | sp-14 | an-211 |
| 5660 | is-14 | ta-212 | sp-14 | an-212 |
| 5661 | is-14 | ta-213 | sp-14 | an-213 |
| 5662 | is-14 | ta-214 | sp-14 | an-214 |
| 5663 | is-14 | ta-215 | sp-14 | an-215 |
| 5664 | is-14 | ta-216 | sp-14 | an-216 |
| 5665 | is-14 | ta-217 | sp-14 | an-217 |
| 5666 | is-14 | ta-218 | sp-14 | an-218 |
| 5667 | is-14 | ta-219 | sp-14 | an-219 |
| 5668 | is-14 | ta-220 | sp-14 | an-220 |
| 5669 | is-14 | ta-221 | sp-14 | an-221 |
| 5670 | is-14 | ta-222 | sp-14 | an-222 |
| 5671 | is-14 | ta-223 | sp-14 | an-223 |
| 5672 | is-14 | ta-224 | sp-14 | an-224 |
| 5673 | is-14 | ta-225 | sp-14 | an-225 |
| 5674 | is-14 | ta-226 | sp-14 | an-226 |
| 5675 | is-14 | ta-227 | sp-14 | an-227 |
| 5676 | is-14 | ta-228 | sp-14 | an-228 |
| 5677 | is-14 | ta-229 | sp-14 | an-229 |
| 5678 | is-14 | ta-230 | sp-14 | an-230 |
| 5679 | is-14 | ta-231 | sp-14 | an-231 |
| 5680 | is-14 | ta-232 | sp-14 | an-232 |
| 5681 | is-14 | ta-233 | sp-14 | an-233 |
| 5682 | is-14 | ta-234 | sp-14 | an-234 |
| 5683 | is-14 | ta-235 | sp-14 | an-235 |
| 5684 | is-14 | ta-236 | sp-14 | an-236 |
| 5685 | is-14 | ta-237 | sp-14 | an-237 |
| 5686 | is-14 | ta-238 | sp-14 | an-238 |
| 5687 | is-14 | ta-239 | sp-14 | an-239 |
| 5688 | is-14 | ta-240 | sp-14 | an-240 |
| 5689 | is-14 | ta-241 | sp-14 | an-241 |
| 5690 | is-14 | ta-242 | sp-14 | an-242 |
| 5691 | is-14 | ta-243 | sp-14 | an-243 |
| 5692 | is-14 | ta-244 | sp-14 | an-244 |
| 5693 | is-14 | ta-245 | sp-14 | an-245 |
| 5694 | is-14 | ta-246 | sp-14 | an-246 |
| 5695 | is-14 | ta-247 | sp-14 | an-247 |
| 5696 | is-14 | ta-248 | sp-14 | an-248 |
| 5697 | is-14 | ta-249 | sp-14 | an-249 |
| 5698 | is-14 | ta-250 | sp-14 | an-250 |
| 5699 | is-14 | ta-251 | sp-14 | an-251 |
| 5700 | is-14 | ta-252 | sp-14 | an-252 |
| 5701 | is-14 | ta-253 | sp-14 | an-253 |
| 5702 | is-14 | ta-254 | sp-14 | an-254 |
| 5703 | is-14 | ta-255 | sp-14 | an-255 |
| 5704 | is-14 | ta-256 | sp-14 | an-256 |
| 5705 | is-14 | ta-257 | sp-14 | an-257 |
| 5706 | is-14 | ta-258 | sp-14 | an-258 |
| 5449 | is-14 | ta-1 | sp-14 | an-1 |
| 5450 | is-14 | ta-2 | sp-14 | an-2 |
| 5451 | is-14 | ta-3 | sp-14 | an-3 |
| 5452 | is-14 | ta-4 | sp-14 | an-4 |
| 5453 | is-14 | ta-5 | sp-14 | an-5 |
| 5454 | is-14 | ta-6 | sp-14 | an-6 |
| 5455 | is-14 | ta-7 | sp-14 | an-7 |
| 5456 | is-14 | ta-8 | sp-14 | an-8 |
| 5457 | is-14 | ta-9 | sp-14 | an-9 |
| 5458 | is-14 | ta-10 | sp-14 | an-10 |
| 5459 | is-14 | ta-11 | sp-14 | an-11 |
| 5460 | is-14 | ta-12 | sp-14 | an-12 |
| 5461 | is-14 | ta-13 | sp-14 | an-13 |
| 5462 | is-14 | ta-14 | sp-14 | an-14 |
| 5463 | is-14 | ta-15 | sp-14 | an-15 |
| 5464 | is-14 | ta-16 | sp-14 | an-16 |
| 5465 | is-14 | ta-17 | sp-14 | an-17 |
| 5466 | is-14 | ta-18 | sp-14 | an-18 |
| 5467 | is-14 | ta-19 | sp-14 | an-19 |
| 5468 | is-14 | ta-20 | sp-14 | an-20 |
| 5469 | is-14 | ta-21 | sp-14 | an-21 |
| 5470 | is-14 | ta-22 | sp-14 | an-22 |
| 5471 | is-14 | ta-23 | sp-14 | an-23 |
| 5472 | is-14 | ta-24 | sp-14 | an-24 |
| 5473 | is-14 | ta-25 | sp-14 | an-25 |
| 5474 | is-14 | ta-26 | sp-14 | an-26 |
| 5475 | is-14 | ta-27 | sp-14 | an-27 |
| 5476 | is-14 | ta-28 | sp-14 | an-28 |
| 5477 | is-14 | ta-29 | sp-14 | an-29 |
| 5478 | is-14 | ta-30 | sp-14 | an-30 |
| 5479 | is-14 | ta-31 | sp-14 | an-31 |
| 5480 | is-14 | ta-32 | sp-14 | an-32 |
| 5481 | is-14 | ta-33 | sp-14 | an-33 |
| 5482 | is-14 | ta-34 | sp-14 | an-34 |
| 5483 | is-14 | ta-35 | sp-14 | an-35 |
| 5484 | is-14 | ta-36 | sp-14 | an-36 |
| 5485 | is-14 | ta-37 | sp-14 | an-37 |
| 5486 | is-14 | ta-38 | sp-14 | an-38 |
| 5487 | is-14 | ta-39 | sp-14 | an-39 |
| 5488 | is-14 | ta-40 | sp-14 | an-40 |
| 5489 | is-14 | ta-41 | sp-14 | an-41 |
| 5490 | is-14 | ta-42 | sp-14 | an-42 |
| 5491 | is-14 | ta-43 | sp-14 | an-43 |
| 5492 | is-14 | ta-44 | sp-14 | an-44 |

TABLE 4-continued

| Example No. | Reagent is | Reagent ta | Example Compound sp | Example Compound an |
|---|---|---|---|---|
| 5493 | is-14 | ta-45 | sp-14 | an-45 |
| 5494 | is-14 | ta-46 | sp-14 | an-46 |
| 5495 | is-14 | ta-47 | sp-14 | an-47 |
| 5496 | is-14 | ta-48 | sp-14 | an-48 |
| 5497 | is-14 | ta-49 | sp-14 | an-49 |
| 5498 | is-14 | ta-50 | sp-14 | an-50 |
| 5499 | is-14 | ta-51 | sp-14 | an-51 |
| 5500 | is-14 | ta-52 | sp-14 | an-52 |
| 5501 | is-14 | ta-53 | sp-14 | an-53 |
| 5654 | is-14 | ta-206 | sp-14 | an-206 |
| 5655 | is-14 | ta-207 | sp-14 | an-207 |
| 5656 | is-14 | ta-208 | sp-14 | an-208 |
| 5657 | is-14 | ta-209 | sp-14 | an-209 |
| 5658 | is-14 | ta-210 | sp-14 | an-210 |
| 5659 | is-14 | ta-211 | sp-14 | an-211 |
| 5660 | is-14 | ta-212 | sp-14 | an-212 |
| 5661 | is-14 | ta-213 | sp-14 | an-213 |
| 5662 | is-14 | ta-214 | sp-14 | an-214 |
| 5663 | is-14 | ta-215 | sp-14 | an-215 |
| 5664 | is-14 | ta-216 | sp-14 | an-216 |
| 5665 | is-14 | ta-217 | sp-14 | an-217 |
| 5666 | is-14 | ta-218 | sp-14 | an-218 |
| 5667 | is-14 | ta-219 | sp-14 | an-219 |
| 5668 | is-14 | ta-220 | sp-14 | an-220 |
| 5669 | is-14 | ta-221 | sp-14 | an-221 |
| 5670 | is-14 | ta-222 | sp-14 | an-222 |
| 5671 | is-14 | ta-223 | sp-14 | an-223 |
| 5672 | is-14 | ta-224 | sp-14 | an-224 |
| 5673 | is-14 | ta-225 | sp-14 | an-225 |
| 5674 | is-14 | ta-226 | sp-14 | an-226 |
| 5675 | is-14 | ta-227 | sp-14 | an-227 |
| 5676 | is-14 | ta-228 | sp-14 | an-228 |
| 5677 | is-14 | ta-229 | sp-14 | an-229 |
| 5678 | is-14 | ta-230 | sp-14 | an-230 |
| 5679 | is-14 | ta-231 | sp-14 | an-231 |
| 5680 | is-14 | ta-232 | sp-14 | an-232 |
| 5681 | is-14 | ta-233 | sp-14 | an-233 |
| 5682 | is-14 | ta-234 | sp-14 | an-234 |
| 5683 | is-14 | ta-235 | sp-14 | an-235 |
| 5684 | is-14 | ta-236 | sp-14 | an-236 |
| 5685 | is-14 | ta-237 | sp-14 | an-237 |
| 5686 | is-14 | ta-238 | sp-14 | an-238 |
| 5687 | is-14 | ta-239 | sp-14 | an-239 |
| 5688 | is-14 | ta-240 | sp-14 | an-240 |
| 5689 | is-14 | ta-241 | sp-14 | an-241 |
| 5690 | is-14 | ta-242 | sp-14 | an-242 |
| 5691 | is-14 | ta-243 | sp-14 | an-243 |
| 5692 | is-14 | ta-244 | sp-14 | an-244 |
| 5693 | is-14 | ta-245 | sp-14 | an-245 |
| 5694 | is-14 | ta-246 | sp-14 | an-246 |
| 5695 | is-14 | ta-247 | sp-14 | an-247 |
| 5696 | is-14 | ta-248 | sp-14 | an-248 |
| 5697 | is-14 | ta-249 | sp-14 | an-249 |
| 5698 | is-14 | ta-250 | sp-14 | an-250 |
| 5699 | is-14 | ta-251 | sp-14 | an-251 |
| 5700 | is-14 | ta-252 | sp-14 | an-252 |
| 5701 | is-14 | ta-253 | sp-14 | an-253 |
| 5702 | is-14 | ta-254 | sp-14 | an-254 |
| 5703 | is-14 | ta-255 | sp-14 | an-255 |
| 5704 | is-14 | ta-256 | sp-14 | an-256 |
| 5705 | is-14 | ta-257 | sp-14 | an-257 |
| 5706 | is-14 | ta-258 | sp-14 | an-258 |
| 5449 | is-14 | ta-1 | sp-14 | an-1 |
| 5450 | is-14 | ta-2 | sp-14 | an-2 |
| 5451 | is-14 | ta-3 | sp-14 | an-3 |
| 5452 | is-14 | ta-4 | sp-14 | an-4 |
| 5453 | is-14 | ta-5 | sp-14 | an-5 |
| 5454 | is-14 | ta-6 | sp-14 | an-6 |
| 5455 | is-14 | ta-7 | sp-14 | an-7 |
| 5456 | is-14 | ta-8 | sp-14 | an-8 |
| 5457 | is-14 | ta-9 | sp-14 | an-9 |
| 5458 | is-14 | ta-10 | sp-14 | an-10 |
| 5459 | is-14 | ta-11 | sp-14 | an-11 |
| 5460 | is-14 | ta-12 | sp-14 | an-12 |
| 5461 | is-14 | ta-13 | sp-14 | an-13 |
| 5462 | is-14 | ta-14 | sp-14 | an-14 |
| 5463 | is-14 | ta-15 | sp-14 | an-15 |
| 5464 | is-14 | ta-16 | sp-14 | an-16 |
| 5465 | is-14 | ta-17 | sp-14 | an-17 |
| 5466 | is-14 | ta-18 | sp-14 | an-18 |
| 5467 | is-14 | ta-19 | sp-14 | an-19 |
| 5468 | is-14 | ta-20 | sp-14 | an-20 |
| 5469 | is-14 | ta-21 | sp-14 | an-21 |
| 5470 | is-14 | ta-22 | sp-14 | an-22 |
| 5471 | is-14 | ta-23 | sp-14 | an-23 |
| 5472 | is-14 | ta-24 | sp-14 | an-24 |
| 5473 | is-14 | ta-25 | sp-14 | an-25 |
| 5474 | is-14 | ta-26 | sp-14 | an-26 |
| 5475 | is-14 | ta-27 | sp-14 | an-27 |
| 5476 | is-14 | ta-28 | sp-14 | an-28 |
| 5477 | is-14 | ta-29 | sp-14 | an-29 |
| 5478 | is-14 | ta-30 | sp-14 | an-30 |
| 5479 | is-14 | ta-31 | sp-14 | an-31 |
| 5480 | is-14 | ta-32 | sp-14 | an-32 |
| 5481 | is-14 | ta-33 | sp-14 | an-33 |
| 5482 | is-14 | ta-34 | sp-14 | an-34 |
| 5483 | is-14 | ta-35 | sp-14 | an-35 |
| 5484 | is-14 | ta-36 | sp-14 | an-36 |
| 5485 | is-14 | ta-37 | sp-14 | an-37 |
| 5486 | is-14 | ta-38 | sp-14 | an-38 |
| 5487 | is-14 | ta-39 | sp-14 | an-39 |
| 5488 | is-14 | ta-40 | sp-14 | an-40 |
| 5489 | is-14 | ta-41 | sp-14 | an-41 |
| 5490 | is-14 | ta-42 | sp-14 | an-42 |
| 5491 | is-14 | ta-43 | sp-14 | an-43 |
| 5492 | is-14 | ta-44 | sp-14 | an-44 |
| 5493 | is-14 | ta-45 | sp-14 | an-45 |
| 5494 | is-14 | ta-46 | sp-14 | an-46 |
| 5495 | is-14 | ta-47 | sp-14 | an-47 |
| 5496 | is-14 | ta-48 | sp-14 | an-48 |
| 5497 | is-14 | ta-49 | sp-14 | an-49 |
| 5498 | is-14 | ta-50 | sp-14 | an-50 |
| 5499 | is-14 | ta-51 | sp-14 | an-51 |
| 5500 | is-14 | ta-52 | sp-14 | an-52 |
| 5501 | is-14 | ta-53 | sp-14 | an-53 |
| 5654 | is-14 | ta-206 | sp-14 | an-206 |
| 5655 | is-14 | ta-207 | sp-14 | an-207 |
| 5656 | is-14 | ta-208 | sp-14 | an-208 |
| 5657 | is-14 | ta-209 | sp-14 | an-209 |
| 5658 | is-14 | ta-210 | sp-14 | an-210 |
| 5659 | is-14 | ta-211 | sp-14 | an-211 |
| 5660 | is-14 | ta-212 | sp-14 | an-212 |
| 5661 | is-14 | ta-213 | sp-14 | an-213 |
| 5662 | is-14 | ta-214 | sp-14 | an-214 |
| 5663 | is-14 | ta-215 | sp-14 | an-215 |
| 5664 | is-14 | ta-216 | sp-14 | an-216 |
| 5665 | is-14 | ta-217 | sp-14 | an-217 |
| 5666 | is-14 | ta-218 | sp-14 | an-218 |
| 5667 | is-14 | ta-219 | sp-14 | an-219 |
| 5668 | is-14 | ta-220 | sp-14 | an-220 |
| 5669 | is-14 | ta-221 | sp-14 | an-221 |
| 5670 | is-14 | ta-222 | sp-14 | an-222 |
| 5671 | is-14 | ta-223 | sp-14 | an-223 |
| 5672 | is-14 | ta-224 | sp-14 | an-224 |
| 5673 | is-14 | ta-225 | sp-14 | an-225 |
| 5674 | is-14 | ta-226 | sp-14 | an-226 |
| 5675 | is-14 | ta-227 | sp-14 | an-227 |
| 5676 | is-14 | ta-228 | sp-14 | an-228 |
| 5677 | is-14 | ta-229 | sp-14 | an-229 |
| 5678 | is-14 | ta-230 | sp-14 | an-230 |
| 5679 | is-14 | ta-231 | sp-14 | an-231 |
| 5680 | is-14 | ta-232 | sp-14 | an-232 |
| 5681 | is-14 | ta-233 | sp-14 | an-233 |
| 5682 | is-14 | ta-234 | sp-14 | an-234 |
| 5683 | is-14 | ta-235 | sp-14 | an-235 |
| 5684 | is-14 | ta-236 | sp-14 | an-236 |
| 5685 | is-14 | ta-237 | sp-14 | an-237 |
| 5686 | is-14 | ta-238 | sp-14 | an-238 |
| 5687 | is-14 | ta-239 | sp-14 | an-239 |
| 5688 | is-14 | ta-240 | sp-14 | an-240 |

TABLE 4-continued

| Example No. | Reagent is | ta | Example Compound sp | an |
|---|---|---|---|---|
| 5689 | is-14 | ta-241 | sp-14 | an-241 |
| 5690 | is-14 | ta-242 | sp-14 | an-242 |
| 5691 | is-14 | ta-243 | sp-14 | an-243 |
| 5692 | is-14 | ta-244 | sp-14 | an-244 |
| 5693 | is-14 | ta-245 | sp-14 | an-245 |
| 5694 | is-14 | ta-246 | sp-14 | an-246 |
| 5695 | is-14 | ta-247 | sp-14 | an-247 |
| 5696 | is-14 | ta-248 | sp-14 | an-248 |
| 5697 | is-14 | ta-249 | sp-14 | an-249 |
| 5698 | is-14 | ta-250 | sp-14 | an-250 |
| 5699 | is-14 | ta-251 | sp-14 | an-251 |
| 5700 | is-14 | ta-252 | sp-14 | an-252 |
| 5701 | is-14 | ta-253 | sp-14 | an-253 |
| 5702 | is-14 | ta-254 | sp-14 | an-254 |
| 5703 | is-14 | ta-255 | sp-14 | an-255 |
| 5704 | is-14 | ta-256 | sp-14 | an-256 |
| 5705 | is-14 | ta-257 | sp-14 | an-257 |
| 5706 | is-14 | ta-258 | sp-14 | an-258 |
| 5449 | is-14 | ta-1 | sp-14 | an-1 |
| 5450 | is-14 | ta-2 | sp-14 | an-2 |
| 5451 | is-14 | ta-3 | sp-14 | an-3 |
| 5452 | is-14 | ta-4 | sp-14 | an-4 |
| 5453 | is-14 | ta-5 | sp-14 | an-5 |
| 5454 | is-14 | ta-6 | sp-14 | an-6 |
| 5455 | is-14 | ta-7 | sp-14 | an-7 |
| 5456 | is-14 | ta-8 | sp-14 | an-8 |
| 5457 | is-14 | ta-9 | sp-14 | an-9 |
| 5458 | is-14 | ta-10 | sp-14 | an-10 |
| 5459 | is-14 | ta-11 | sp-14 | an-11 |
| 5460 | is-14 | ta-12 | sp-14 | an-12 |
| 5461 | is-14 | ta-13 | sp-14 | an-13 |
| 5462 | is-14 | ta-14 | sp-14 | an-14 |
| 5463 | is-14 | ta-15 | sp-14 | an-15 |
| 5464 | is-14 | ta-16 | sp-14 | an-16 |
| 5465 | is-14 | ta-17 | sp-14 | an-17 |
| 5466 | is-14 | ta-18 | sp-14 | an-18 |
| 5467 | is-14 | ta-19 | sp-14 | an-19 |
| 5468 | is-14 | ta-20 | sp-14 | an-20 |
| 5469 | is-14 | ta-21 | sp-14 | an-21 |
| 5470 | is-14 | ta-22 | sp-14 | an-22 |
| 5471 | is-14 | ta-23 | sp-14 | an-23 |
| 5472 | is-14 | ta-24 | sp-14 | an-24 |
| 5473 | is-14 | ta-25 | sp-14 | an-25 |
| 5474 | is-14 | ta-26 | sp-14 | an-26 |
| 5475 | is-14 | ta-27 | sp-14 | an-27 |
| 5476 | is-14 | ta-28 | sp-14 | an-28 |
| 5477 | is-14 | ta-29 | sp-14 | an-29 |
| 5478 | is-14 | ta-30 | sp-14 | an-30 |
| 5479 | is-14 | ta-31 | sp-14 | an-31 |
| 5480 | is-14 | ta-32 | sp-14 | an-32 |
| 5481 | is-14 | ta-33 | sp-14 | an-33 |
| 5482 | is-14 | ta-34 | sp-14 | an-34 |
| 5483 | is-14 | ta-35 | sp-14 | an-35 |
| 5484 | is-14 | ta-36 | sp-14 | an-36 |
| 5485 | is-14 | ta-37 | sp-14 | an-37 |
| 5486 | is-14 | ta-38 | sp-14 | an-38 |
| 5487 | is-14 | ta-39 | sp-14 | an-39 |
| 5488 | is-14 | ta-40 | sp-14 | an-40 |
| 5489 | is-14 | ta-41 | sp-14 | an-41 |
| 5490 | is-14 | ta-42 | sp-14 | an-42 |
| 5491 | is-14 | ta-43 | sp-14 | an-43 |
| 5492 | is-14 | ta-44 | sp-14 | an-44 |
| 5493 | is-14 | ta-45 | sp-14 | an-45 |
| 5494 | is-14 | ta-46 | sp-14 | an-46 |
| 5495 | is-14 | ta-47 | sp-14 | an-47 |
| 5496 | is-14 | ta-48 | sp-14 | an-48 |
| 5497 | is-14 | ta-49 | sp-14 | an-49 |
| 5498 | is-14 | ta-50 | sp-14 | an-50 |
| 5499 | is-14 | ta-51 | sp-14 | an-51 |
| 5500 | is-14 | ta-52 | sp-14 | an-52 |
| 5501 | is-14 | ta-53 | sp-14 | an-53 |
| 5654 | is-14 | ta-206 | sp-14 | an-206 |
| 5655 | is-14 | ta-207 | sp-14 | an-207 |
| 5656 | is-14 | ta-208 | sp-14 | an-208 |
| 5657 | is-14 | ta-209 | sp-14 | an-209 |
| 5658 | is-14 | ta-210 | sp-14 | an-210 |
| 5659 | is-14 | ta-211 | sp-14 | an-211 |
| 5660 | is-14 | ta-212 | sp-14 | an-212 |
| 5661 | is-14 | ta-213 | sp-14 | an-213 |
| 5662 | is-14 | ta-214 | sp-14 | an-214 |
| 5663 | is-14 | ta-215 | sp-14 | an-215 |
| 5664 | is-14 | ta-216 | sp-14 | an-216 |
| 5665 | is-14 | ta-217 | sp-14 | an-217 |
| 5666 | is-14 | ta-218 | sp-14 | an-218 |
| 5667 | is-14 | ta-219 | sp-14 | an-219 |
| 5668 | is-14 | ta-220 | sp-14 | an-220 |
| 5669 | is-14 | ta-221 | sp-14 | an-221 |
| 5670 | is-14 | ta-222 | sp-14 | an-222 |
| 5671 | is-14 | ta-223 | sp-14 | an-223 |
| 5672 | is-14 | ta-224 | sp-14 | an-224 |
| 5673 | is-14 | ta-225 | sp-14 | an-225 |
| 5674 | is-14 | ta-226 | sp-14 | an-226 |
| 5675 | is-14 | ta-227 | sp-14 | an-227 |
| 5676 | is-14 | ta-228 | sp-14 | an-228 |
| 5677 | is-14 | ta-229 | sp-14 | an-229 |
| 5678 | is-14 | ta-230 | sp-14 | an-230 |
| 5679 | is-14 | ta-231 | sp-14 | an-231 |
| 5680 | is-14 | ta-232 | sp-14 | an-232 |
| 5681 | is-14 | ta-233 | sp-14 | an-233 |
| 5682 | is-14 | ta-234 | sp-14 | an-234 |
| 5683 | is-14 | ta-235 | sp-14 | an-235 |
| 5684 | is-14 | ta-236 | sp-14 | an-236 |
| 5685 | is-14 | ta-237 | sp-14 | an-237 |
| 5686 | is-14 | ta-238 | sp-14 | an-238 |
| 5687 | is-14 | ta-239 | sp-14 | an-239 |
| 5688 | is-14 | ta-240 | sp-14 | an-240 |
| 5689 | is-14 | ta-241 | sp-14 | an-241 |
| 5690 | is-14 | ta-242 | sp-14 | an-242 |
| 5691 | is-14 | ta-243 | sp-14 | an-243 |
| 5692 | is-14 | ta-244 | sp-14 | an-244 |
| 5693 | is-14 | ta-245 | sp-14 | an-245 |
| 5694 | is-14 | ta-246 | sp-14 | an-246 |
| 5695 | is-14 | ta-247 | sp-14 | an-247 |
| 5696 | is-14 | ta-248 | sp-14 | an-248 |
| 5697 | is-14 | ta-249 | sp-14 | an-249 |
| 5698 | is-14 | ta-250 | sp-14 | an-250 |
| 5699 | is-14 | ta-251 | sp-14 | an-251 |
| 5700 | is-14 | ta-252 | sp-14 | an-252 |
| 5701 | is-14 | ta-253 | sp-14 | an-253 |
| 5702 | is-14 | ta-254 | sp-14 | an-254 |
| 5703 | is-14 | ta-255 | sp-14 | an-255 |
| 5704 | is-14 | ta-256 | sp-14 | an-256 |
| 5705 | is-14 | ta-257 | sp-14 | an-257 |
| 5706 | is-14 | ta-258 | sp-14 | an-258 |

[Test Example 1]

Blood cholesterol lowering effect in rats fed on a high cholesterol diet

In this test example, blood cholesterol level lowering effect in rats fed on a high cholesterol diet was tested according to the method described in J. Lipid, Res., 1995, 36, 1098-1105.

That is, a diet containing 0.4% cholesterol and 0.5% of bile acid was given to 7 to 9 weeks old SD (IGS) male rats for 5 days before the test to increase the blood cholesterol level. Rats which showed an evident increase in blood cholesterol level as compared with that before feeding were selected and used in the test. Cholestimide (trade name: CHOLEBINE GRANULE 70% manufactured by MITSUBISHI TOKYO PHARMACEUTICALS, INC.), which is an anion exchange resin, was suspended in distilled water while the test compound was either dissolved or suspended in distilled water. These were forcibly orally administered twice a day every day from the day of beginning of the test (each n =8). After 3 hours from the administration of the drug on the last day of the test, a blood sample was taken from a jugular vein pool and serum cholesterol level was measured to study the effect of the test compound. Further, as a control group, a group (n=8) fed on only high cholesterol diet and given distilled water (1 ml/kg) was prepared and the same test procedure was followed. A commercially available kit was used for the measurement of total cholesterol and HDL cholesterol. The value obtained by subtracting an HDL cholesterol value from the total cholesterol value was taken as an LDL+VLDL cholesterol value. Assuming the LDL+VLDL cholesterol value of the control group, for which the test compound was not used, as 100%, the rate of decrease (percentage of decrease) of LDL+VLDL cholesterol value when a fixed amount of the test compound was used, was determined.

The results are shown in Table 5 below. It has been verified that the compounds of the present invention decrease the LDL+VLDL cholesterol level and have excellent blood cholesterol lowering effect. Therefore, the compounds of the present invention have proved to be useful as drugs for the treatment and prevention of hyperlipidemia. Moreover, it has been verified that the compounds of the present invention have an inhibitory effect on increase of cholesterol even when a diet containing 0.4% cholesterol and 0.5% bile acid is fed and at the same time the compound of the present invention was forcibly orally administered, so that the compounds of the present invention are useful as drug for the prevention of hyperlipidemia. Note that it has also been verified that the compounds of other examples of the present invention not shown in Table 5 have excellent blood cholesterol lowering effect and thus the compounds have proved to be useful in particular as drugs for the treatment and prevention of hyperlipidemia.

TABLE 5

| Compound in example | Rat model loaded with high cholesterol diet (treatment model) Rate of decrease (%) of LDL + VLDL Dosage of drug at a time is indicated in parenthesis |
| --- | --- |
| Comparative Example* | 29.0 (25 mg/kg) |
| Example 1 | 68.4 (1 mg/kg) |
| Example 1 | 49 (0.3 mg/kg) |
| Example 3713 | 41 (0.3 mg/kg) |
| Example 3747 | 48 (0.3 mg/kg) |
| Example 3752 | 50 (0.3 mg/kg) |
| Example 5408 | 43 (0.3 mg/kg) |
| Example 3696 | 25 (0.3 mg/kg) |
| Example 3440 | 36 (0.3 mg/kg) |
| Example 3448 | 20 (0.3 mg/kg) |
| Example 3605 | 28 (0.3 mg/kg) |

*In Comparative Example, Cholestimide (trade name: CHOLEBINE KARYU 70% manufactured by MITSUBISHI TOKYO PHARMACEUTICALS, INC.) was used.

[Test Example 2]

Bile acid-decreasing effect in portal vein of rats loaded with cholic acid

In this test example, the test for confirming the bile acid-decreasing effect in portal vein of cholic acid-loaded rats was carried out according to the method described in Pharmacology and Therapeutics [Jpn Pharmacol. Ther., Vol. 24 Supplement, 1996, 103 (S-577)-110 (S-584)].

That is, 7 to 9 weeks old SD (IGS) rats were starved on the day before the test and thereafter. Cholic acid (200 mg/kg) and the test compound as drug to be administered, were either dissolved or suspended in distilled water containing a surfactant (trade name: Tween 20, BIO-RAD or HCO-60, manufactured by NIPPON CHEMICALS COMPANY, LTD.) to a final concentration of 0.5% or 1% and the solution or suspension was forcibly orally administered to the rats. After 2 hours from the administration, a sample of blood was taken from a portal vein and total serum bile acid level was measured to study the effect of the test compound (n=6). Further, as a control group, a group (n=6) loaded with cholic acid (200 mg/kg) only was prepared and the same test procedure was followed. A commercially available kit (trade name: SOTANJUSAN-TEST WAKO- (SOTANJUSAN=total bile acid), manufactured by WAKO PURE CHEMICAL INDUSTRIES, LTD.) was used for the measurement of bile acid. Assuming the value of the control group, which is a group in which no test compound was used, as 100%, the rate of decrease (percentage (%) of decrease) of the bile acid level when a fixed amount of the test compound was used was determined.

The results are shown in Table 6 below. It has been verified that the compounds of the present invention decrease the bile acid level and proved to have excellent bile acid resorption inhibiting effect. Therefore, it has been verified that the compounds of the present invention are useful as drugs for the treatment and prevention of hyperlipidemia and further useful as drugs for the treatment of cholestasis-caused hepatopathy. Note that it has also been verified that the compounds of other examples of the present invention not shown in Table 6 below have excellent bile acid resorption inhibiting effects and thus the compounds of the present invention have proved to be useful as drugs for the treatment and prevention of hyperlipidemia and as drugs for the treatment of cholestasis-caused hepatopathy.

TABLE 6

| Compound of Example | Cholic acid-loaded rat model Rate of decrease (%) of bile acid Dosage of drug at a time is indicated in parenthesis |
| --- | --- |
| Comparative Example 1* | 16 (25 mg/kg) # |
| Comparative Example 2** | 3 (0.1 mg/kg) # |
| Example 3835 | 23 (0.1 mg/kg) # |
| Example 1 | 51 (0.1 mg/kg) # |
| Example 3932 | 30 (0.1 mg/kg) # |
| Example 9 | 13 (0.1 mg/kg) # |
| Example 425 | 21 (0.1 mg/kg) # |
| Example 801 | 33 (0.1 mg/kg) ## |
| Example 1178 | 18 (0.1 mg/kg) ## |
| Example 3440 | 26 (0.1 mg/kg) ## |
| Example 3695 | 23 (0.1 mg/kg) ## |
| Example 3853 | 36 (0.1 mg/kg) ## |
| Example 3607 | 36 (0.1 mg/kg) ## |
| Example 3608 | 43 (0.1 mg/kg) ## |
| Example 5405 | 16 (0.1 mg/kg) ## |
| Example 4512 | 37 (0.1 mg/kg) ## |
| Example 4257 | 30 (0.1 mg/kg) ## |
| Example 4424 | 17 (0.1 mg/kg) ## |
| Example 4425 | 22 (0.1 mg/kg) ## |
| Example 4905 | 28 (0.1 mg/kg) ## |
| Example 3696 | 13 (0.1 mg/kg) ## |
| Example 3605 | 24 (0.1 mg/kg) ## |
| Example 3475 | 19 (0.1 mg/kg) ## |
| Example 3448 | 25 (0.1 mg/kg) ## |
| Example 5406 | 15 (0.1 mg/kg) ## |
| Example 3409 | 28 (0.1 mg/kg) ## |
| Example 3783 | 16 (0.1 mg/kg) ## |
| Example 3710 | 20 (0.1 mg/kg) ## |
| Example 3713 | 32 (0.1 mg/kg) ## |
| Example 3753 | 8.5 (0.3 mg/kg) ## |
| Example 3759 | 36 (0.3 mg/kg) ## |

TABLE 6-continued

| Compound of Example | Cholic acid-loaded rat model Rate of decrease (%) of bile acid Dosage of drug at a time is indicated in parenthesis |
|---|---|
| Example 5043 | 39 (0.3 mg/kg) ## |
| Example 5298 | 40 (0.3 mg/kg) ## |
| Example 3747 | 40 (0.1 mg/kg) ## |
| Example 3752 | 42 (0.1 mg/kg) ## |
| Example 5408 | 35 (0.1 mg/kg) ## |

*In Comparative Example 1, Cholestimide (trade name: CHOLEBINE KARYU (GRANULATED POWDER) 70% manufactured by MITSUBISHI TOKYO PHARMACEUTICALS, INC.) was used.
**In Comparative Example 2, compound 5 that shows the most potent activity among the compounds specifically described in WO02/08211 (synthesis Example 19); 1-{4-[4-(3,3-dibutyl-7-dimethylamino-1,1-dioxo-2,3,4,5-tetrahydro-1,4-benzothiazepin-5-yl)phenoxymethyl]benzyl}-4-aza-1-azoniabicyclo[2.2.2]octance chloride (compound A mentioned later was used).
Tween 20 having a final concentration of 0.05% was used as a surfactant.
HCO-60 having a final concentration of 0.1% was used as a surfactant.

[Test Example 3]

Effect on rat liver cholesterol 7-α-hydroxylase activity (7α-OHase)

In this test example, the test for confirming the effect on rat liver cholesterol 7-α-hydroxylase activity (7α-OHase) was carried out according to the method described in [Analytical Biochemistry, 1986, 158, 228-232].

That is, the test compound and vehicle (injectable water, trade name: manufactured by OHTSUKA PHARMACEUTICAL CO., LTD.) were administered to 6 weeks old SD (IGS) rats using an oral sonde for 14 days (n=5). Solid diet (trade name: CRF-1, manufactured by ORIENTAL YEAST CO., LTD.) was given as a diet and a sterilized tap water was given as drink water, and the rats were allowed to take them freely. The rats were dissected and the livers were extracted. The livers were preserved temporarily at −80° C. Thawed liver samples were homogenized in 1.15% KCl and then centrifuged to prepare liver microsomes. Final pelletized materials were resuspended in a buffer solution of sodium phosphate/potassium phosphate, followed by incubation of an aliquot at 37° C for 20 minutes in the presence of NADPH. The 7α-hydroxy-cholesterol formed was converted into 7α-hydroxy-4-cholesten-3-one by cholesterol oxidase. After extraction of this in petroleum ether, the organic solvent was evaporated and the residue was dissolved in isopropanol. An enzyme product was separated by injecting the aliquot of the extract into a reverse phase HPLC column (trade name: Finepack SIL-5, JASCO) and the substance eluted was quantated by using a 240 nm UV detector.

It has been verified that the compounds of the present invention have potent enhancing effects on the activity of liver cholesterol 7-α-hydroxylase (7α-OHase) which is included in the mechanism of blood cholesterol-lowering effects (Arterioscler Thromb Vasc. Biol., 1998, 18, 1304-1311) due to IBAT, which is an ileal bile acid transporter and that the compounds of the present invention can be used as drugs for the treatment and prevention of hyperlipidemia and so forth.

[Test example 4]

Cholestasis-caused hepatopathy (liver cell apoptosis) model

The "cholestasis-caused hepatopathy" model in this test example was handled by referring to apoptosis induction in liver cells of hypercholesterolemia model described in [Am. J. Physiol., 1995, 268, G613-G621].

That is, a diet containing 0.4% of cholesterol and 0.5% of bile acid was given to 7 to 9 weeks old SD (IGS) male rats for 4 days. The test compounds were forcibly orally administered twice a day everyday from the day of starting of feeding with the high cholesterol diet (n=8). As a control group, a group (n=8) fed with only the high cholesterol diet was prepared. After 3 hours from the administration of the drug on the last day of the experiment, the livers were extracted from the rats immediately after bloodletting from the abdominal aorta and fixed with a 10% neutral buffered formalin solution (trade name: FA-F96 manufactured by KOKUSAN CHEMICAL CO, LTD.). After the fixation, the livers were dewatered and embedded by use of a closed automatic embedding apparatus (trade name: ETP-180B, manufactured by SAKURA CO., LTD.) and thin slices of a thickness within the range of 2 μm to 5 μm were prepared with a microtome (trade name; IVS-410, manufactured by SAKURA CO., LTD.). Then, hematoxylin-eosin staining was performed on these thin sections using an automatic dyeing apparatus (trade name: DRS-60, manufactured by SAKURA CO. LTD.). Total number of mitotic cells in each slice was obtained by measuring for each section the number of mitotic cells at 10 different places in an area of 200 μm×200 μm in the same section.

The results are shown in Table 7 below. It has been verified that the compounds of the present invention exhibit a decreased number of mitotic cells in the liver and have effects of ameliorating cholestasis-caused hepatopathy. Therefore, the compounds of the present invention have proven to be useful as drugs for the treatment and prevention of cholestasis-caused hepatopathy.

TABLE 7

| Compound of Example | Number of mitotic cells in liver (average ± standard error, n = 8) In parenthesis, dosage of drug at a time is indicated. |
|---|---|
| Example 1 | 50 ± 13 (control group) |
|  | 28 ± 7 (1 mg/kg) |
|  | 36 ± 13 (0.1 mg/kg) |

[Test Example 5]

"Cholestasis-caused hepatopathy" model (bile duct partial ligation model)

The "cholestasis-caused hepatopathy" model by partial ligation surgery of bile duct in this test example was handled by referring to the method by Kanno et al. [Kanzo (Liver) 43 Suppl (1): A126, 2002].

That is, the abdomen of a 7 to 10 weeks old SD (IGS) male rat was cut open under anesthesia with pentobarbital and partial ligation surgery of the bile duct was carried out. A blood sample was taken from the femoral vein before the surgery and this was taken as pre-administration value. The test compound and 200 mg/kg of bile acid were forcibly orally administered twice a day for 3.5 days from the next day of the surgery (protocol A). The test compound and 200 mg/kg of bile acid were forcibly orally administered twice a day for 3.5 days without carrying out the partial ligation surgery (protocol B). In both the cases, the test compound was dissolved or suspended in distilled water or an aqueous solution of 1% HCO60 (manufactured by NIPPON CHEMICALS COMPANY, LTD.). Physiological saline was administered to a control group, while 25 mg/kg of cholestyramine (manufactured by SIGMA CHEMICAL COMPANY) or 50 mg/kg of ursodeoxycholic acid (manufactured by MITSUBISHI PHARMA CO., LTD.) as a comparative example was administered. Moreover, to consider the influence of the surgery, a pseudo operation group (a Sham group) was established as necessary. After 6 hours from the administration of the drug on the last day of the test, a blood sample was taken from the abdominal aorta and AST (GOT), ALT (GPT), and ALP in the blood were measured by using a measurement kit (GOTII-HA TEST WAKO, GPTII-HA TEST WAKO, and ALKALINE PHOSPHER-HA TEST WAKO respectively, all manufactured by WAKO PURE CHEMICAL INDUSTRIES, LTD.) with an auto analyzer (NITTECH ANALYZER SUPER Z818).

The results are shown in Tables 8 to 10 below. It has been verified that the compounds of the present invention inhibit the rise in AST, ALT, and ALP caused by partial ligation of the liver and loading of bile acid and have effects of ameliorating cholestasis-caused hepatopathy. Therefore, the compounds of the present invention have proved to be useful as drugs for the treatment and prevention of cholestasis-caused hepatopathy, in particular as drugs for the treatment and prevention of primary biliary cirrhosis and primary sclerosing cholangitis. Moreover, it has also been verified that the compounds of other examples of the present invention not shown in Tables 8 to 10 have excellent ameliorating effect on cholestasis-caused hepatopathy.

TABLE 8

| | (Protocol A) | | |
|---|---|---|---|
| Compound of Example | AST (IU/L) | ALT (IU/L) | ALP (IU/L) |
| (Pre-administration value) | 108 ± 6 | 38 ± 2 | 591 ± 116 |
| Control group | 400 ± 160 | 200 ± 81 | 1120 ± 410 |
| Comparative Example 1 | 385 ± 214 | 208 ± 123 | 1280 ± 660 |
| Comparative Example 2 | 256 ± 64 | 98 ± 25 | 785 ± 120 |
| Example 1 (0.1 mg/kg) | 182 ± 42 | 61 ± 4 | 603 ± 78 |

(For all the cases, N = 8, average ± standard error) In Comparative Example 1, 25 mg/kg of cholestyramine was administered while in Comparative Example 2, 50 mg/kg of ursodeoxycholic acid was administered. Distilled water was used as a solvent.

TABLE 9

| | (Protocol A) | | |
|---|---|---|---|
| Compound of Example | AST (IU/L) | ALT (IU/L) | ALP (IU/L) |
| Sham group | 141 ± 26 | 43 ± 1 | 665 ± 94 |
| Control group | 589 ± 221 | 417 ± 185 | 2318 ± 583 |
| Comparative Example | 916 ± 146 | 527 ± 118 | 2042 ± 235 |
| Example 3440 (1 mg/kg) | 309 ± 37 | 155 ± 38 | 1614 ± 189 |
| Example 3605 (1 mg/kg) | 487 ± 382 | 258 ± 219 | 1489 ± 533 |

TABLE 9-continued

| | (Protocol A) | | |
|---|---|---|---|
| Compound of Example | AST (IU/L) | ALT (IU/L) | ALP (IU/L) |
| Example 3448 (1 mg/kg) | 352 ± 210 | 181 ± 79 | 1148 ± 332 |
| Sham group | 128 ± 18 | 48 ± 5 | 630 ± 87 |
| Control group | 643 ± 125 | 384 ± 156 | 2204 ± 327 |
| Example 3696 (1 mg/kg) | 325 ± 87 | 191 ± 21 | 1209 ± 125 |
| Example 3713 (1 mg/kg) | 280 ± 61 | 163 ± 96 | 1008 ± 289 |
| Example 3747 (1 mg/kg) | 245 ± 81 | 146 ± 70 | 960 ± 259 |
| Example 3752 (1 mg/kg) | 358 ± 87 | 165 ± 47 | 1112 ± 184 |
| Example 5408 (1 mg/kg) | 198 ± 65 | 197 ± 45 | 1005 ± 102 |

(For all the cases, N = 8, average ± standard error) In comparative example, 25 mg/kg of cholestyramine was administered. In the case of the compounds of examples, aqueous solution of 1% HCO60 was used as a solvent.

TABLE 10

| | (Protocol B) | | |
|---|---|---|---|
| Compound of Example | AST (IU/L) | ALT (IU/L) | ALP (IU/L) |
| (Pre-administration value) | 102 ± 5 | 38 ± 5 | 508 ± 54 |
| Control group | 157 ± 35 | 82 ± 17 | 593 ± 77 |
| Comparative Example 1 | 149 ± 10 | 70 ± 6 | 602 ± 78 |
| Comparative Example 2 | 109 ± 11 | 62 ± 9 | 453 ± 58 |
| Example 1 (0.1 mg/kg) | 100 ± 2 | 53 ± 6 | 453 ± 50 |

(For all the cases, N = 8, average ± standard error) In Comparative Example 1, 25 mg/kg of cholestyramine and in Comparative Example 2, 50 mg/kg of ursodeoxycholic acid was administered. Distilled water was used as a solvent.

[Test Example 6]

Obesity and fatty liver model

The obesity and fatty liver model in this test example was handled by referring to the method described in WO02/09757.

That is, 10 weeks old KKA$^y$/Ta Jcl male mice were used as obese mice (N=from 4 to 7). The test compounds dissolved or suspended in an aqueous solution of 1% HCO60 (manufactured by NIPPON CHEMICALS COMPANY, LTD.) and an aqueous solution of 1% HCO60 (manufactured by NIPPON CHEMICALS COMPANY, LTD.) as a control group were administered once a day for 2 weeks continuously. The weights of the mice were measured every day and compared with the weights measured on the day before the administration. On the day next to the final day of administration of the drug, the livers were extracted and concentrations of triglycerides in the liver tissues were measured by using a measurement kit (TRIGLYCERIDE TEST WAKO, manufactured by WAKO PURE CHEMICAL INDUSTRIES, LTD.). The results are shown in Table 11 below.

It has been verified that the compounds of the present invention exhibit a body weight suppressing effect and a liver triglyceride lowering effect in obese mice, so that the compounds of the present invention have proved to be useful as drugs for the treatment and prevention of obesity and fatty liver. Moreover, it has also been verified that the compounds of other examples of the present invention not shown in Table 11 have excellent body weight suppressing effects and excellent triglyceride reduction effects.

TABLE 11

| Compound of Example | Body Weight (g) | | | Liver triglyceride (mg/g) |
|---|---|---|---|---|
| | Before administration | 2 weeks later | Variation amount | |
| Control group (N = 7) | 42.8 ± 0.4 | 42.0 ± 0.7 | −0.8 ± 0.5 | 94 ± 18 |
| Example 1 (N = 7) (1 mg/kg) | 43.0 ± 0.5 | 41.0 ± 0.6 | −1.9 ± 0.3 | 71 ± 13 |
| Example 3605 (N = 4) (1 mg/kg) | 42.9 ± 1.1 | 41.4 ± 1.0 | −1.5 ± 0.4 | 65 ± 7 |
| Control group (N = 7) | 44.1 ± 0.6 | 44.8 ± 0.9 | −0.7 ± 0.4 | 103 ± 19 |
| Example 3713 (N = 4) (1 mg/kg) | 44.0 ± 1.1 | 41.5 ± 2.4 | −2.5 ± 0.6 | 59 ± 33 |
| Example 3747 (N = 4) (1 mg/kg) | 44.3 ± 0.8 | 42.2 ± 1.8 | −2.1 ± 1.0 | 47 ± 23 |
| Example 3752 (N = 4) (1 mg/kg) | 43.8 ± 1.2 | 41.5 ± 1.0 | −2.3 ± 0.9 | 56 ± 23 |
| Example 5408 (N = 4) (1 mg/kg) | 44.0 ± 0.9 | 42.2 ± 1.6 | −1.8 ± 0.5 | 70 ± 11 |
| Example 3696 (N = 4) (1 mg/kg) | 43.5 ± 1.3 | 42.2 ± 2.2 | −1.3 ± 0.3 | 76 ± 12 |
| Example 3440 (N = 4) (1 mg/kg) | 44.6 ± 0.8 | 43.9 ± 1.8 | −0.7 ± 1.0 | 88 ± 6 |
| Example 3448 (N = 4) (1 mg/kg) | 44.1 ± 0.7 | 42.1 ± 3.2 | −2.0 ± 0.7 | 74 ± 8 |

(average ± standard error)

[Test Example 7]

In vitro assay of compounds inhibiting ileal bile acid transporter (IBAT) using Caco-2 cells In this test example, the in vitro assay of compounds inhibiting ileal bile acid transporter using Caco-2 cells was carried out according to the Test Example 1 described in WO00/35889.

That is, 1×10$^5$ cells/well Caco-2 cells were inoculated on a 24-well cell plate. For the assay, cells cultured for 14 days or more were used and the following procedure was followed. The cells were washed once with an assay buffer, Hank's buffer solution containing 25 mM glucose and 10 mM HEPES (pH 7.4), and then the buffer was replaced by an assay buffer to which the test compound was added. After adding [$^3$H] taurocholate (trade name: NET-322, manufactured by DAIICHI CHEMICAL CO., LTD.) to a final concentration of 8 μM, the cells were incubated at 37° C for 30 minutes to allow [$^3$H] taurocholate to be incorporated in Caco-2 cells by IBAT. The reaction was stopped by washing twice with a buffer prepared by adding 1mM taurocholate (trade name: T-4009, manufactured by SIGMA CHEMICAL COMPANY) to the assay buffer and lyzing the cells with 0.2 M NaOH. Measurement of the radioactivity was carried out by introducing the cell lyzate in 4 ml of liquid scintillation cocktail (trade name: Clearzol 1, manufactured by NACALAITESC), stirring the mixture well, and then measuring the radioactivity on a liquid scintillation counter (manufactured by PACKARD CO., LTD.). The inhibition rate (%) was determined from the radioactivity of a control which did not use the test compound and the radioactivity when the test compound having a fixed concentration was used and the concentration of the test compound at which 50% of the IBAT activity was inhibited was determined. This method has verified that the compounds of the present invention have potent inhibiting activity against IBAT, so that the compounds of the present invention have proven to be useful as drugs for the treatment and prevention of hyperlipidemia.

[Test Example 8]

In vitro assay of compounds which inhibit temporarily expressed human IBAT transporter or rat IBAT transporter using Cos 7 cells In this test example, the in vitro assay of the compounds which inhibit temporarily expressed human IBAT transporter or rat IBAT transporter using Cos cells was carried out according to the method described in Am. J. Physiol., 274, G157-169.

That is, 2.5×10$^{-5}$ cells/well Cos 7 were inoculated on a 24-well cell plate. One day later, 0.3 μg per well of cDNA of a human IBAT or a rat IBAT was transfected by using FuGENE6 (manufactured by ROCHE PHARMACEUTICAL CO., LTD.). For the assay, the cells cultured for one day after the transfection were used and the following procedure was followed. The cells were washed once with an assay buffer, Hank's buffer solution containing 25 mM glucose and with 10 mM HEPES (pH 7.4), and then the assay buffer was replaced by an assay buffer to which the test compound was added. After adding [$^3$H] taurocholate to a final concentration of 8 μM, the cells were incubated at 37° C for 60 minutes. [$^3$H] taurocholate was allowed to be incorporated in Cos 7 cells through human IBAT or rat IBAT. The reaction was stopped by washing twice with a buffer prepared by adding 1mM taurocholate to the assay buffer and lyzing the cells with 0.2M NaOH. Measurement of radioactivity was carried out by introducing the cell lyzate in 4 ml of liquid scintillation cocktail, stirring the mixture well, and then measuring the radioactivity by a scintillation counter. The inhibition rate (%) was determined from the radioactivity of a control which did not use the test compound and the radioactivity when the test compound having a fixed concentration was used. The concentration of the test compound at which 50% of human IBAT activity or rat IBAT activity was inhibited was determined.

The results are shown in Table 12 below. It has been verified that the compounds of the present invention have potent inhibitory activity against human BAT and rat IBAT. Therefore, the compounds of the present invention have proven to be useful as drugs for the treatment and prevention of hyperlipidemia. Moreover, it has also been verified that the compounds of other examples of the present invention not shown in Table 12 have potent inhibition activity against human IBAT and rat IBAT.

TABLE 12

| Compound of Example | Cos 7 human IBAT IC$_{50}$ (μM) | Cos 7 rat IBAT IC$_{50}$ (μM) |
|---|---|---|
| Comparative Example* | 10 | 0.2 |
| Example 3835 | 0.043 | Not tested |
| Example 1 | 0.025 | 0.007 |
| Example 3932 | 0.036 | 0.009 |
| Example 9 | 0.076 | 0.036 |
| Example 425 | 0.17 | Not tested |
| Example 801 | 0.1 | Not tested |
| Example 1056 | 0.1 | Not tested |
| Example 1178 | 0.093 | Not tested |
| Example 1433 | 0.103 | Not tested |
| Example 1555 | 0.153 | Not tested |
| Example 1810 | 0.167 | Not tested |
| Example 3440 | 0.037 | 0.010 |
| Example 3695 | 0.037 | 0.005 |
| Example 969 | 0.1 | Not tested |
| Example 968 | 0.038 | Not tested |
| Example 593 | 0.092 | Not tested |
| Example 592 | 0.1 | Not tested |
| Example 3853 | 0.028 | 0.009 |
| Example 3607 | 0.041 | Not tested |
| Example 3608 | 0.059 | Not tested |
| Example 4512 | 0.063 | Not tested |
| Example 4424 | 0.091 | Not tested |
| Example 4425 | 0.089 | Not tested |
| Example 4905 | 0.1 | Not tested |
| Example 1069 | 0.1 | Not tested |
| Example 867 | 0.1 | Not tested |
| Example 3708 | 0.07 | Not tested |
| Example 3506 | 0.127 | Not tested |
| Example 3696 | 0.039 | Not tested |
| Example 3605 | 0.039 | Not tested |
| Example 3475 | 0.1 | Not tested |
| Example 3558 | 0.07 | Not tested |
| Example 3448 | 0.037 | Not tested |
| Example 3572 | 0.1 | Not tested |
| Example 3593 | 0.07 | Not tested |
| Example 3554 | 0.065 | Not tested |
| Example 3698 | 0.072 | Not tested |
| Example 4210 | 0.1 | Not tested |
| Example 3409 | 0.045 | Not tested |
| Example 3433 | 0.055 | Not tested |
| Example 3449 | 0.055 | Not tested |
| Example 3441 | 0.085 | Not tested |
| Example 3444 | 0.1 | Not tested |
| Example 3567 | 0.1 | Not tested |
| Example 3662 | 0.1 | Not tested |
| Example 3709 | 0.049 | Not tested |
| Example 3717 | 0.03 | Not tested |
| Example 3722 | 0.039 | Not tested |
| Example 3725 | 0.052 | Not tested |
| Example 3783 | 0.048 | Not tested |
| Example 3429 | 0.055 | Not tested |
| Example 3568 | 0.094 | Not tested |
| Example 3587 | 0.07 | Not tested |
| Example 3705 | 0.054 | Not tested |
| Example 3724 | 0.069 | Not tested |
| Example 3764 | 0.08 | Not tested |
| Example 3723 | 0.025 | Not tested |
| Example 3768 | 0.072 | Not tested |
| Example 3770 | 0.057 | Not tested |
| Example 3774 | 0.1 | Not tested |
| Example 3454 | 0.068 | Not tested |
| Example 3544 | 0.1 | Not tested |
| Example 3599 | 0.054 | Not tested |
| Example 3604 | 0.045 | Not tested |
| Example 3697 | 0.069 | Not tested |
| Example 4226 | 0.099 | Not tested |
| Example 4250 | 0.1 | Not tested |
| Example 4266 | 0.1 | Not tested |
| Example 4258 | 0.1 | Not tested |
| Example 4261 | 0.1 | Not tested |
| Example 4232 | 0.099 | Not tested |
| Example 4248 | 0.1 | Not tested |
| Example 4384 | 0.1 | Not tested |
| Example 4405 | 0.062 | Not tested |
| Example 4456 | 0.1 | Not tested |
| Example 4458 | 0.1 | Not tested |
| Example 4479 | 0.078 | Not tested |
| Example 4526 | 0.1 | Not tested |
| Example 4534 | 0.076 | Not tested |
| Example 4539 | 0.064 | Not tested |
| Example 4600 | 0.078 | Not tested |
| Example 3414 | 0.088 | Not tested |
| Example 3410 | 0.068 | Not tested |
| Example 3710 | 0.052 | Not tested |
| Example 3714 | 0.058 | Not tested |
| Example 3719 | 0.1 | Not tested |
| Example 3412 | 0.075 | Not tested |
| Example 3434 | 0.071 | Not tested |
| Example 3426 | 0.058 | Not tested |
| Example 3713 | 0.037 | Not tested |
| Example 3729 | 0.088 | Not tested |
| Example 3413 | 0.073 | Not tested |
| Example 3416 | 0.1 | Not tested |
| Example 3711 | 0.063 | Not tested |
| Example 3716 | 0.089 | Not tested |
| Example 3727 | 0.066 | Not tested |
| Example 3726 | 0.073 | Not tested |
| Example 3730 | 0.084 | Not tested |
| Example 3765 | 0.1 | Not tested |
| Example 3772 | 0.089 | Not tested |
| Example 3854 | 0.028 | Not tested |
| Example 4233 | 0.046 | Not tested |
| Example 4259 | 0.067 | Not tested |
| Example 4408 | 0.073 | Not tested |
| Example 4412 | 0.1 | Not tested |
| Example 4528 | 0.091 | Not tested |
| Example 4543 | 0.082 | Not tested |
| Example 4547 | 0.072 | Not tested |
| Example 4589 | 0.046 | Not tested |
| Example 4402 | 0.043 | Not tested |
| Example 4613 | 0.1 | Not tested |
| Example 4246 | 0.072 | Not tested |
| Example 4263 | 0.072 | Not tested |
| Example 4258 | 0.074 | Not tested |
| Example 4268 | 0.1 | Not tested |
| Example 4247 | 0.091 | Not tested |
| Example 4234 | 0.1 | Not tested |
| Example 4385 | 0.1 | Not tested |
| Example 4460 | 0.1 | Not tested |
| Example 4522 | 0.097 | Not tested |
| Example 4527 | 0.073 | Not tested |
| Example 4531 | 0.1 | Not tested |
| Example 4581 | 0.1 | Not tested |
| Example 4540 | 0.1 | Not tested |
| Example 4585 | 0.078 | Not tested |
| Example 4587 | 0.060 | Not tested |
| Example 4251 | 0.1 | Not tested |
| Example 4371 | 0.074 | Not tested |
| Example 4260 | 0.074 | Not tested |
| Example 4243 | 0.078 | Not tested |
| Example 4236 | 0.10 | Not tested |
| Example 4513 | 0.092 | Not tested |
| Example 4546 | 0.087 | Not tested |
| Example 4401 | 0.061 | Not tested |
| Example 4605 | 0.079 | Not tested |
| Example 4448 | 0.10 | Not tested |
| Example 3733 | 0.057 | Not tested |
| Example 3736 | 0.05 | Not tested |
| Example 3747 | 0.045 | Not tested |
| Example 3748 | 0.081 | Not tested |
| Example 3750 | 0.075 | Not tested |
| Example 3752 | 0.041 | Not tested |
| Example 3754 | 0.092 | Not tested |
| Example 5043 | 0.062 | Not tested |
| Example 5298 | 0.076 | Not tested |
| Example 4551 | 0.076 | Not tested |
| Example 5416 | 0.077 | Not tested |
| Example 5417 | 0.026 | Not tested |
| Example 5407 | 0.052 | Not tested |
| Example 5408 | 0.032 | Not tested |
| Example 5409 | 0.042 | Not tested |

TABLE 12-continued

| Compound of Example | Cos 7 human IBAT IC$_{50}$ (μM) | Cos 7 rat IBAT IC$_{50}$ (μM) |
|---|---|---|
| Example 4221 | 0.043 | Not tested |
| Example 4223 | 0.025 | Not tested |
| Example 5410 | 0.1 | Not tested |
| Example 5411 | 0.097 | Not tested |
| Example 5412 | 0.037 | Not tested |
| Example 5418 | 0.069 | Not tested |
| Example 5419 | 0.039 | Not tested |
| Example 5420 | 0.068 | Not tested |
| Example 5413 | 0.065 | Not tested |
| Example 5414 | 0.1 | Not tested |
| Example 5415 | 0.44 | Not tested |

*In Comparative Example, the compound specifically described in Synthesis Example 1 of WO93/16055: (−)-trans-3-butyl-3-ethyl-2,3,4,5-tetrahydro-5-phenyl-1,4-benzothio-azepine-1,1-dioxide was used.

[Test Example 9]

In vitro assay of compounds inhibiting temporarily expressed human IBAT transporter in which alanine 171 was substituted by serine using Cos 7 cells The in vitro assay of the compounds inhibiting temporarily expressed human BAT transporter in which alanine 171 was substituted by serine was carried out in the same manner as in Test Example 4 except for using the cDNA of IBAT in which alanine 171 was substituted by serine in the human IBAT amino acid sequence.

Note that actually in the case of humans, the proportion of individuals having the IBAT transporter in which alanine 171 has been substituted by serine is said to be 28% [J. Clin. Invest., 1997, 99, 1880-1887].

The results are shown in Table 13 below. The value is a rate of inhibition (%) of the radioactivity of the test compound at a test compound concentration of 10 nM with respect to the radioactivity of the control without the test compound. It has been verified that the compound of the present invention has a potent inhibiting activity on the human IBAT in which alanine 171 is substituted by serine which is equivalent to that of the human IBAT in which alanine 171 is not substituted by serine. Therefore, the compound has proven to be useful as a drug for the treatment and prevention of hyperlipidemia. Moreover, it has been verified that the compounds of other examples of the present invention not shown in Table 13 have inhibitory effect against the human IBAT in which alanine 171 is substituted by serine.

TABLE 13

| Compound of Example | Cos 7, human IBAT in which alanine 171 is substituted by serine; Rate of inhibition (%) at a test compound concentration of 10 nM |
|---|---|
| Example 1 | 53 |

[Test Example 10]

In vitro assay of effects of compounds on Na$^+$ dependent amino acid transporter and Na$^+$ dependent water-soluble vitamin transporter using Cos 7 cells In this test example, the in vitro assays of the compound on various transporters using Cos 7 cells were carried out according to the method described in Published Translation of Japanese Patent Application No. 10-503830.

That is, $2.5 \times 10^{-5}$ cells/well of Cos 7 cells were inoculated on a 24-well cell plate. Two days later, the cells were washed once with an assay buffer, Hank's buffer solution containing 25 mM glucose and with 10 mM HEPES (ph 7.4), and then the buffer was replaced by an assay buffer to which the test compound was added. After adding to this, [$^3$H] alanine (trade name; NET-348, manufactured by DAIICHI CHEMICAL CO., LTD.), [$^3$H] leucine (trade name: NET-460, manufactured by DAIICHI CHEMICAL CO., LTD.), [$^3$H] phenylalanine (trade name: MT903, MORAVEK), [$^3$H] methionine (trade name: MT862, MORAVEK), [$^3$H] lysine (trade name: MT909, MORAKEK), or [$^3$H]choline (trade name: TRK593, AMERSHAM BIOSCIENCES CO., LTD.) to a final concentration of 8 μM, the mixture was incubated at 37° C for 60 minutes to allow Cos 7 cells to incorporate them. The reaction was stopped by washing the cells twice with the assay buffer and then lyzing them with 0.2 M NaOH. Measurement of the radioactivity was carried out by introducing the lyzate in 4 ml of liquid scintillation cocktail, stirring the mixture well, and then measuring on a liquid scintillation counter. The inhibition rate (%) was determined from the radioactivity of a control without test compounds and the radioactivity when the test compound having a fixed concentration was used, and then the concentration of the test compound at which 50% of the transporter activity was inhibited was determined.

In the small intestine epithelial cells having IBAT therein, there are also Na$^+$ dependent transporters, which further include an amino acid transporter and a water-soluble vitamin transporter. Essential amino acids are indispensable for normal growth and healthy life support [TOKYO KAGAKU DOZIN CO., LTD., 2nd edition of SEIKAGAKU JITEN (Dictionary of Biochemistry), P1052]. Choline is a water-soluble vitamin, deficiency of which in human body causes fatty liver and hepatocirrhosis [TOKYO KAGAKU DOZIN CO., LTD., 2nd edition, SEIKAGAKU JITEN (Dictionary of Biochemistry), P1050].

The results are shown in Table 14. It has been verified that the compound of the present invention has significant inhibitory specificity against human IBAT and rat IBAT and it has been shown that the compound of the present invention can serve as a drug for the treatment and prevention of hyperlipidemia. Similar effects were obtained for other amino acids, such as leucine, phenylalanine, methionine, and lysine, and even choline, which is a water-soluble vitamin. Moreover, it has also been verified that compounds of other examples of the present invention not shown in Table 14 have significant inhibitory specificities against human IBAT and rat IBAT.

TABLE 14

| Compound of Example | IC$_{50}$ (μM) against alanine transporter |
|---|---|
| Example 1 | 33 |

[Test Example 11]

Microbial mutagenicity (Ames test)

In this test example, the microbial mutagenicity test was carried out according to Ames Salmonella Mutation Assay. [0533]

The strains used are *Salmonella typhimurium* TA98 and *Salmonella typhimurium* TA100 strains. In an L-shaped tube containing a sterilized preculture medium (trade name: Nutrient Broth No. 2, manufactured by KANTO KAGAKU) was added a loopful of *Salmonella typhimurium* TA98 or *Salmonella typhimurium* TA100, which then was cultured in a shaking incubator at 37° C, for 8 hours with 100 shakes per minute. 0.1 ml of this microbial culture broth was added to 2 ml of sterilized soft agar warmed at 45° C, containing 0.05 mM of L - histidine and 0.05 mM (+)-biotin. After stirring, the mixture was spread on a minimum glucos agar plate medium (trade name: TESMEDIA AN, manufactured by ORIENTAL YEAST CO., LTD.) in a Petri dish and allowed to solidify. A circular filter paper was made by punching a filter paper (trade name: Quantitative Ashless No. 7, manufactured by ADVANTECH COMPANY, LTD.), sterilized, and disposed on the solidified agar. Then, 1 µl of the test compound having a concentration of 10 mM was put on the filter paper and culturing was performed at 37° C for 48 hours. For the judgment of the microbial mutagenicity, the occurrence of a mutant colony centered on the filter paper where the test compound was diffused was judged as positive and no occurrence of mutant colonies in that area was judged as negative.

As a result, it has been verified that all the compounds of the examples of the present invention were negative on both TA98 and TA100 in the microbial mutagenicity test (Ames test) and have no mutagenicity. Thus, the compounds of the present invention have proven to be safe. Therefore, it has been indicated that the compounds of the present invention can be drugs for the treatment and prevention of hyperlipidemia.

[Test Example 12]

Toxicity with respect to alimentary canal

To evaluate the toxicity of the compounds of the present invention to the alimentary canal, the cytotoxicity to Caco 2, which is a human originated small intestine epithelial cell line, was tested by referring to the method of Bestwick CS et al. [Biochimica et Biophysica Acta 1474: 47-55, 1999].

That is, Caco 2 cells (purchased from ATCC) were inoculated on a 96-well plate such that there were 10,000 cells/well [MEM-E medium, 10% FBS (Fetal Bovine Serum), 1% NEAA (Non Essential Amino Acid) solution, (both manufactured by GIBCO PHARMACEUTICAL COMPANY)]. After culturing for 48 hours, the test compounds were diluted with the culture medium and added to the respective wells. After 2 hours, 50 µl of the culture broth was collected and the LDH activity in the collected culture broth was measured by using an LDH activity measuring kit (CytoTox 96 Non-Radioactive Cytotoxicity Assay, manufactured by PROMEGA CORPORATION). Relative activities were calculated assuming the LDH activity as 100% when the Caco 2 cells were treated with the cytolytic agent and the obtained relative activities were taken as cytotoxicities to Caco 2 cell.

The results are shown in Table 15 below. From the results, it is apparent that the compounds of the present invention have low cytotoxicity or no cytotoxicity to Caco 2 cells and that the compounds of the present invention have very little toxicity or no toxicity to the alimentary canal. Note that the IBAT inhibiting agent having a structure of quaternary ammonium salt used as a control to the present invention (compound 5 (Synthesis Example 19) having the highest activity among the compounds specifically described in WO02/08211: 1-{4-[4-(3,3-dibutyl-7-dimethyl-amino-1,1-dioxo-2,3,4,5-tetrahydro-1,4- benzothiazepin-5-yl)phe- noxy-methyl]benzyl}-4-aza-1-azoniabycyclo- [2.2.2]octane chloride (the compound A mentioned later)) showed cytotoxicity to small intestine epithelial cell line at low concentrations and thus has toxicity to alimentary canal. In contrast, it has been verified that the compounds of the present invention have little toxicity or no toxicity to the alimentary canal, or are less toxic, so that they are more preferable as pharmaceuticals.

TABLE 15

| Compound of Example | Toxicity (%) to Caco 2 | | |
|---|---|---|---|
| | 30 µM | 10 µM | 3 µM |
| Comparative Example* | 79 | 22 | 1.5 |
| Example 3853 | <1 | <1 | <1 |
| Example 3605 | <1 | <1 | <1 |
| Example 3835 | <1 | <1 | <1 |
| Example 3440 | <1 | <1 | <1 |
| Example 3695 | <1 | <1 | <1 |
| Example 3607 | <1 | <1 | <1 |
| Example 3608 | <1 | <1 | <1 |
| Example 3696 | <1 | <1 | <1 |
| Example 3448 | <1 | <1 | <1 |
| Example 3409 | <1 | <1 | <1 |
| Example 3709 | <1 | <1 | <1 |
| Example 3783 | <1 | <1 | <1 |
| Example 3723 | <1 | <1 | <1 |
| Example 3710 | <1 | <1 | <1 |
| Example 3713 | <1 | <1 | <1 |
| Example 3759 | <1 | <1 | <1 |
| Example 5043 | <1 | <1 | <1 |
| Example 5298 | <1 | <1 | <1 |
| Example 5480 | <1 | <1 | <1 |
| Example 5735 | <1 | <1 | <1 |
| Example 5856 | <1 | <1 | <1 |
| Example 5857 | <1 | <1 | <1 |
| Example 3705 | <1 | <1 | <1 |
| Example 3747 | <1 | <1 | <1 |
| Example 3752 | <1 | <1 | <1 |
| Example 5408 | <1 | <1 | <1 |

*In Comparative Example, the compound 5 (Synthesis Example 19) having the highest activity among the compounds specifically described in WO02/08211: 1-{4-[4-(3,3-dibutyl-7-dimethylamino-1,1-dioxo-2,3,4,5-tetrahydro-1,4-benzothiazepin-5-yl)-phenoxymethyl]benzyl}-4-aza-1-azoniabicyclo-[2.2.2]octane chloride (compound A mentioned later) was used.

[Test example 13]

"Cholestasis-caused hepatopathy" model (bile duct partial ligation model)

In this test example, the model of cholestasis-caused hepatopathy was tested according to the method described in Test Example 5.

That is, the abdomens of 8 to 10 weeks old SD (IGS) male rats were cut open under anesthesia with pentobarbital and partial ligation surgery of the bile duct was carried out. After the surgery, 200 mg/kg of bile acid and an BAT inhibiting compound were forcibly orally administered to the rats (each n=3). As a control group, physiological saline (n=6) was administered (n=3). To observe the effect of the partial ligation surgery, a sham group (the abdomen was cut open under anesthesia with pentobarbital but partial ligation surgery of the bile duct was not carried out) and an untreated group were established (each n=3). After 24 hours-from the administration a blood sample was taken from the abdominal aorta and AST, ALT, and ALP in the blood were measured using the method described in Test Example 5.

The results are shown in Tables 16 and 17 below. It has been verified that the IBAT inhibiting compounds inhibit the rise in AST, ALT, and ALP caused by partial ligation of the liver and have ameliorating effects on cholestasis-caused hepatopathy. Therefore, it has been indicated that the compounds are useful as drugs for the treatment and prevention of cholestasis-caused hepatopathy, in particular as drugs for the treatment and prevention of primary biliary cirrhosis and primary sclerosing cholangitis. Moreover, it has also been verified that compounds of other examples of the present invention not shown in Table 16, can be expected to have excellent ameliorating effects on cholestasis-caused hepatopathy.

TABLE 16

| Compound of Example | AST (IU/L) | ALT (IU/L) | ALP (IU/L) |
|---|---|---|---|
| Untreated group | 119 ± 2 | 35 ± 2 | 769 ± 149 |
| Sham group | 174 ± 5 | 41 ± 3 | 567 ± 44 |
| Control group | 509 ± 86 | 245 ± 48 | 1135 ± 125 |
| Compound C (10 mg/kg) | 313 ± 82 | 113 ± 44 | 948 ± 208 |
| Compound D (10 mg/kg) | 275 ± 12 | 73 ± 17 | 715 ± 24 |

(For all the cases, N = 3, average ± standard error)

TABLE 17

| Compound of Example | AST (IU/L) | ALT (IU/L) | ALP (IU/L) |
|---|---|---|---|
| Sham group | 141 ± 26 | 43 ± 1 | 665 ± 94 |
| Control group | 589 ± 221 | 417 ± 185 | 2318 ± 583 |
| Comparative Example | 916 ± 146 | 527 ± 118 | 2042 ± 235 |
| Compound A (10 mg/kg) | 547 ± 159 | 281 ± 103 | 1266 ± 160 |
| Compound B (1 mg/kg) | 261 ± 63 | 138 ± 54 | 1335 ± 116 |
| Compound E (10 mg/kg) | 280 ± 72 | 180 ± 68 | 1345 ± 145 |
| Compound F (10 mg/kg) | 320 ± 66 | 214 ± 53 | 1423 ± 115 |

(For all the cases, N = 3, average ± standard error) In Comparative Example, 25 mg/kg of cholestyramine was administered.

[Test Example 14]

"Cholestasis-caused hepatopathy" model (bile acid loaded model)

In this test example, the model of hepatopathy due to loading of bile acid was carried out similarly to the protocol B in Test Example 5. However, the administration period in this test example was changed to 4.5 days. The results are shown in Tables 18 and 19 below. It has been verified that the IBAT inhibiting compounds inhibit the rise in AST and ALT caused by the loading of bile acid and have an ameliorating effect on cholestasis-caused hepatopathy. Therefore, the compounds have proven to be useful as drugs for the treatment and prevention of cholestasis-caused hepatopathy, in particular as drugs for the treatment and prevention of primary biliary cirrhosis and primary sclerosing cholangitis. Moreover, the compounds of other examples of the present invention not shown in Tables 18 and 19 can be expected to have excellent ameliorating effects on cholestasis-caused hepatopathy.

TABLE 18

| Compound of Example | AST (IU/L) | ALT (IU/L) |
|---|---|---|
| (Pre-administration value) | 108 ± 6 | 38 ± 2 |
| Control group | 157 ± 35 | 82 ± 17 |
| Comparative Example 1 | 149 ± 10 | 70 ± 6 |
| Comparative Example 2 | 109 ± 11 | 62 ± 9 |
| Compound C (10 mg/kg) | 100 ± 2 | 53 ± 6 |
| Compound D (10 mg/kg) | 100 ± 9 | 46 ± 4 |

(For all the examples, N = 6, average ± standard error) In Comparative Example 1, 25 mg/kg of cholestyramine was administered and in Comparative Example 2, 50 mg/kg of ursodeoxycholic acid was administered.

TABLE 19

| Compound of Example | AST (IU/L) | ALT (IU/L) |
|---|---|---|
| Untreated group | 97 ± 5 | 36 ± 3 |
| Control group | 156 ± 14 | 76 ± 8 |
| Compound B (0.1 mg/kg) | 110 ± 4 | 54 ± 6 |
| Compound E (10 mg/kg) | 105 ± 11 | 46 ± 3 |
| Compound F (10 mg/kg) | 123 ± 16 | 58 ± 5 |

(For all the cases, N = 6, average standard error)

Note that the IBAT inhibitors and production methods therefor used in the test examples are as follows.

Compound A; a compound having the following structure and chemical name

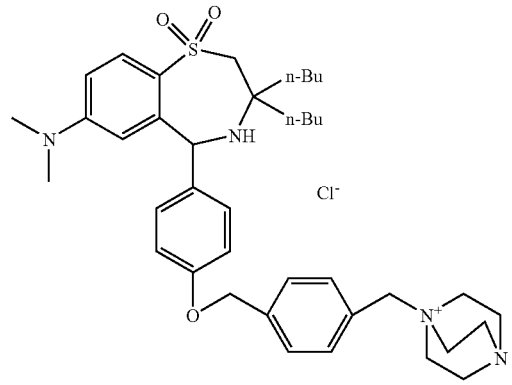

Chemical name: 1-{4-[4-(3,3-Dibutyl-7-dimethylamino-1,1-dioxo- 2,3,4,5-tetrahydro-1,4-benzothiazepin-5-yl)phenoxymethyl]benzyl}-4- aza-1-azoniabicyclo[2.2.2]octane chloride (manufactured according to the method described in WO02/08211)

Compound B; a compound having the following structure and chemical name

Chemical name: Trans-3-butyl-3-ethyl-2,3,4,5-tetrahydro-7,8-dimethoxy-5-phenyl-1,4-benzothiazepine-1,1-dioxide (manufactured according to the method described in Published Translation of Patent Application No. Hei10-504035)

Compound C; a compound having the following structure and chemical name

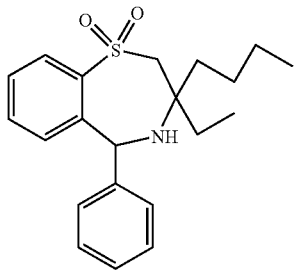

Chemical name: Trans-3-butyl-3-ethyl-2,3,4,5-tetrahydro-5-phenyl-1,4-benzothiazepine-1,1-dioxide (manufactured according to the method described in WO93/16055)

Compound D; a compound having the following structure and chemical name

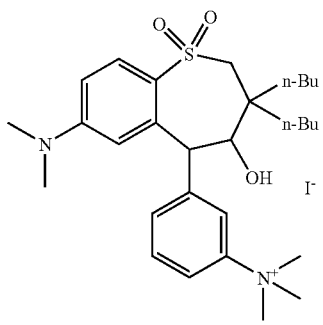

Chemical name: Cis-[3-(3,3-dibutyl-7-dimethylamino-4-hydroxy-1,1-dioxo-2,3,4,5-tetrahydro-1-benzothiepin-5-yl) phenyl]trimethyl- ammonium iodide (manufactured according to the method described in Published Translation of Patent Application No. 2001-526627)

Compound E; a compound having the following structure and chemical name

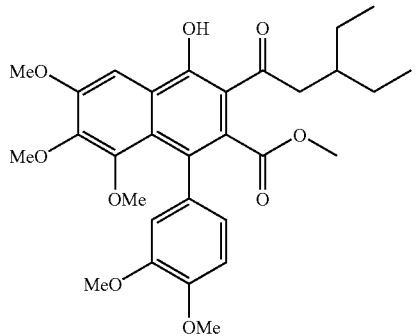

Chemical name: Methyl 1-(3,4-dimethoxyphenyl)-3-(3-ethylvaleryl)-4-hydroxy-6,7,8-trimethoxy-2-naphthoate (manufactured according to the method described in Japanese Patent No. 2839805)

Compound F; a compound having the following structure and chemical name

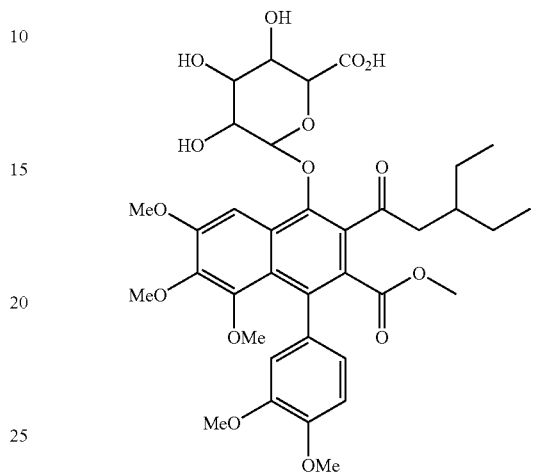

Chemical name: {1-O-[4-(3,4-dimethoxyphenyl)-2-(3-ethyl-pentanoyl)-5,6,7-trimethoxy-3-(methoxycarbonyl) naphthalen-1-yl]- β-D-glucopyranosido}uronic acid (manufactured according to the method described in Japanese Patent Application No. Hei 9-241206).

[Test Example 15]

Steatohepatitis model

In this test example, the steatohepatitis model was examined referring to the method of Okan A., et al. (Dig Dis Sci 47:2389-2397, 2002).

That is, 7 weeks old Wistar rats were fed with a choline-deficient diet (manufactured by Oriental Yeast Co., Ltd.) for 2 weeks to prepare a steatohepatitis model. A suspension of a test compound in an aqueous solution of 0.5% methyl cellulose (manufactured by WAKO PURE CHEMICAL INDUSTRIES, LTD.) and an aqueous solution of 0.5% methyl cellulose (manufactured by WAKO PURE CHEMICAL INDUSTRIES, LTD.) as a control were orally administered once a day for consecutive 2 weeks. On the day next to the last day of administration, a blood sample was taken from the abdominal aorta and AST (GOT) and ALT (GPT) in the blood were measured by using measuring kits (GOTII-HA TEST WAKO and GPTII-HA TEST WAKO, respectively, the both were manufactured by WAKO PURE CHEMICAL INDUSTRIES, LTD.) on an auto analyzer (NITTECH ANALYZER SUPER Z818). The results are shown in Table 20 below. It has been verified that the compounds of the present invention exhibit blood AST and ALT level-decreasing effects on steatohepatitis model rats, so that it has been shown that the compounds of the present invention are useful for the treatment and prevention of steatohepatitis. Moreover, it has also been verified that the compounds of other examples of the present invention not shown in Table 20 have excellent AST and ALT level-decreasing effects.

TABLE 20

| Compound of Example | AST (IU/L) | ALT (IU/L) |
|---|---|---|
| Control group (n = 6) | 180 ± 46 | 245 ± 57 |
| Example 3713 (3 mg/kg, n = 4) | 77 ± 37 | 118 ± 36 |
| Example 3747 (3 mg/kg, n = 4) | 63 ± 86 | 102 ± 50 |
| Example 3752 (3 mg/kg, n = 4) | 69 ± 98 | 88 ± 45 |
| Example 5408 (3 mg/kg, n = 4) | 103 ± 45 | 149 ± 38 |
| Example 3696 (3 mg/kg, n = 4) | 98 ± 23 | 145 ± 34 |
| Example 3440 (3 mg/kg, n = 4) | 125 ± 34 | 167 ± 93 |
| Example 3448 (3 mg/kg, n = 4) | 134 ± 23 | 143 ± 79 |
| Example 3605 (3 mg/kg, n = 4) | 80 ± 34 | 121 ± 36 |

(Average ± standard error)

Although the invention has been described with respect to a specific embodiment for a complete and clear disclosure, the appended claims are not to be thus limited but are to be construed as embodying all modifications and alternative constructions which may occur to one skilled in the art which fairly fall within the basic teaching herein set forth.

The invention claimed is:

1. A compound represented by formula (1) below

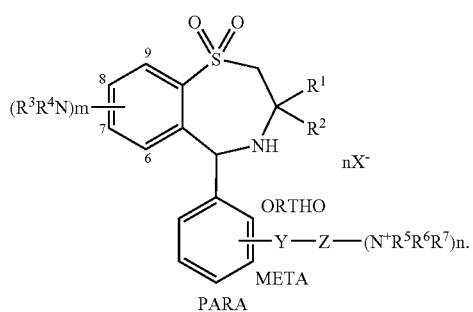

wherein $R^1$ and $R^2$, which may be mutually different, each represents an alkyl group having from 1 to 10 carbon atoms;

m represents an integer of 1 or 2, and $R^3$ and $R^4$, which may be mutually different, each represents an alkyl group having from 1 to 5 carbon atoms;

Y represents any one of —NHCS—, —NHCSNH—, and —NHCSO— where the —NH in the —NHCS— represents a bond which links with an adjacent benzene ring and the CS— in the —NHCS— represents a bond which links with an adjacent Z, and the —NH in the —NHCSO— represents a bond which links with an adjacent benzene ring and the CSO— in the —NHCSO— represents a bond which links with an adjacent Z;

Z— $(N^+R^5R^6R^7)_n$ represents an alkyl group having from 2 to 10 carbon atoms or an alkenyl group having from 2 to 10 carbon atoms which is substituted with n (—$N^+R^5R^6R^7$)s, where at least one of methylenes which constitute Z may be replaced by any one of a phenylene and an —O—; n is an integer of 1 or 2; and $N^+R^5R^6R^7$ is any one of I), II), and III) given below which are mutually independent I) $R^5$, $R^6$, and $R^7$, which may be mutually different, each represents any one of an alkyl group having from 1 to 10 carbon atoms, an alkenyl group having from 2 to 10 carbon atoms, and an alkynyl group having from 2 to 10 carbon atoms, where the alkyl group, the alkenyl group, and the alkynyl group may be substituted with at least one of a phenyl group, a naphthyl group, a pyridyl group, a quinolyl group, a thienyl group, a furyl group, a piperidyl group, a pyrrolidyl group, a morpholyl group, a cycloalkyl group having from 3 to 7 carbon atoms, a cyano group, a nitro group, a hydroxyl group, an oxo group, a thioxo group, a carboxyl group, a —$CONH_2$ group, an —$SO_3H$ group, and further, at least one of methylenes which constitute the alkyl group, the alkenyl group, and the alkynyl group may be replaced by any one of a phenylene, a thienylene, a furylene, a cyclohexylene, a cyclopentylene, an —O—, an —S—, a —$CO_2$—, an —NHCO—, an —$NR^8$—, and an —$N^+W^-R^9R^{10}$— where $R^8$ represents an alkyl group having from 1 to 5 carbon atoms or an alkenyl group having from 2 to 5 carbon atoms and the alkyl group and alkenyl group represented by R may be substituted with at least one of a phenyl group, a cycloalkyl group having from 3 to 7 carbon atoms, and a hydroxyl group; $R^9$ and $R^{10,}$ which may be mutually different, each represents an alkyl group having from 1 to 5 carbon atoms or alkenyl group having from 2 to 5 carbon atoms and may be substituted with at least one of a phenyl group, a cycloalkyl group having from 3 to 7 carbon atoms, and a hydroxyl group; and $W^-$ represents a counter anion, II) $N^+R^5R^6R^7$ represents a monocyclic ring or a bicyclic ring which is formed by 4 to 9 carbon atoms in addition to an ammonium nitrogen atom, provided that the position of its bonding with Z is the ammonium nitrogen atom, where one of the carbon atoms which constitute the ring in the monocyclic ring and the bicyclic ring may be replaced by any one atom of oxygen, nitrogen, and sulfur, and moreover, the monocyclic ring and the bicyclic ring may be substituted with at least one of a hydroxyl group, an oxo group, a thioxo group, a cyano group, a phenyl group, a naphthyl group, a thienyl group, a pyridyl group, a cycloalkyl group having from 3 to 7 carbon atoms, a carboxyl group, a —$CONH_2$ group, an —$SO_3H$ group, and an $R^{11}$ group; $R^{11}$ represents an alkyl group having from 1 to 8 carbon atoms or an alkenyl group having from 2 to 8 carbon atoms, where the alkyl group and the alkenyl group represented by $R^{11}$ may be substituted with at least one of a phenyl group, a naphthyl group, a pyridyl group, a quinolyl group, a thienyl group, a furyl group, a piperidyl group, a pyrrolidyl group, a morpholyl group, a cycloalkyl group having from 3 to 7 carbon atoms, a cyano group, a nitro group, a hydroxyl group, an oxo group, a thioxo group, a carboxyl group, a —$CONH_2$ group, and an —$SO_3H$ group; moreover, at least one of methylenes which constitute the alkyl group and the alkenyl group may be replaced by any one of a phenylene, a thienylene, a furylene, a cyclohexylene, a cyclopentylene, an —O—, an —S—, a —$CO_2$—, an —NHCO—, an —$NR^8$—, and an —$N^+W^-R^9R^{10}$—, where $R^8$, $R^9$, $R^{10}$, and $W^-$ are as described above; among $R^5$, $R^6$, and $R^7$, a group which is not involved in formation of the monocyclic ring and the bicyclic ring is the same as that in I) described above, III) $N^+R^5R^6R^7$ represents a pyridinium ring, a quinolinium ring, or an isoquinolinium ring, provided that the position of its bonding with Z is an ammonium nitrogen atom; the pyridinium ring, the quinolinium ring, and the isoquinolinium ring may be substituted with at least one of a cyano group, a nitro group, a phenyl group, a naphthyl group, a thienyl group, a pyridyl group, a cycloalkyl group having from 3 to 7 carbon atoms, an alkoxy group having from 1 to 5 carbon atoms, a carboxyl group, a —CONH$_2$ group, an —SO$_3$H group, and an —R$^{12}$ group; R$^{12}$ represents an alkyl group having from 1 to 9 carbon atoms or an alkenyl group having from 2 to 9 carbon atoms; and the alkyl group and the alkenyl group represented by R$^{12}$ may be substituted with at least one of a phenyl group, a naphthyl group, a pyridyl group, a quinolyl group, a thienyl group, a furyl group, a cycloalkyl group having from 3 to 7 carbon atoms, a cyano group, a nitro group, a hydroxyl group, an oxo group, a thioxo group, a carboxyl group, a —CONH$_2$ group, and an —SO$_3$H group; and further, at least one of methylenes which constitute the alkyl group and the alkenyl group may be replaced by any one of a phenylene, a thienylene, a furylene, a cyclohexylene, a cyclopentylene, an —S—, a —CO$_2$—, an —NHCO—, an —NR$^8$—, and an —N$^+$W$^-$R$^9$R$^{10}$—, where R$^8$, R$^9$, R$^{10}$, and W$^-$ are as described above, and X represents a counter anion.

2. The compound according to claim 1, wherein the Z-(N$\cdot$R$^5$R$^6$R$^7$)$_n$ represents an alkyl group having from 2 to 10 carbon atoms which is substituted with n (—N$^+$R$^5$R$^6$R$^7$)s and at least one of methylenes which constitute Z may be replaced by any one of a phenylene and an —O—.

3. The compound according to claim 2, wherein the Z-(N$\cdot$R$^5$R$^6$R$^7$)$_n$ represents a straight chain alkyl group having from 2 to 10 carbon atoms which is substituted with one —N$^+$R$^5$R$^6$R$^7$ and at least one of methylenes which constitute Z may be replaced by any one of a phenylene and an —O—.

4. The compound according to claim 3, wherein the Z-(N$\cdot$R$^5$R$^6$R$^7$)$_n$ represents a straight chain alkyl group having from 2 to 10 carbon atoms which is substituted with one —N$^+$R$^5$R$^6$R$^7$, a straight chain alkyl group having from 2 to 10 carbon atoms which is substituted with one —N$^+$R$^5$R$^6$R$^7$ and one of methylenes which constitute Z is replaced by a phenylene, a straight chain alkyl group having from 2 to 10 carbon atoms which is substituted with one —N$^+$R$^5$R$^6$R$^7$ and one of methylenes which constitute Z is replaced by an —O—, or a straight chain alkyl group having from 2 to 10 carbon atoms which is substituted with one —N$^+$R$^5$R$^6$R$^7$ and one of methylenes which constitute Z is replaced by a phenylene and another of methylenes which constitute Z is replaced by an —O—.

5. The compound according to claim 4, wherein Z represents a straight chain methylene group having from 2 to 10 carbon atoms, a straight chain methylene group having from 2 to 10 carbon atoms of which one methylene is replaced by a phenylene, a straight chain methylene group having from 2 to 10 carbon atoms of which one methylene is replaced by an —O—, or a straight chain methylene group having from 2 to 10 carbon atoms of which one methylene is replaced by a phenylene and another methylene is replaced by an —O—.

6. The compound according to claim 5, wherein Z represents a straight chain methylene group having from 2 to 10 carbon atoms.

7. The compound according to claim 5, wherein Y represents —NHCS— or —NHCSNH— at the para- or meta-position.

8. The compound according to claim 6, wherein Y represents —NHCS— or —NHCSNH— at the para- or meta-position.

9. The compound according to claim 8, wherein Y represents —NHCSNH— at the meta-position; and Z represents a straight chain methylene group having from 2 to 10 carbon atoms.

10. The compound according to claim 8, wherein Y represents —NHCS— at the meta-position; and Z represents a straight chain methylene group having from 2 to 10 carbon atoms.

11. The compound according to claim 10, wherein Y represents —NHCS— at the meta-position; and Z represents a straight chain methylene group having 5 carbon atoms.

12. The compound according to claim 5, wherein Y represents —NHCSNH— at the meta-position; and Z represents a straight chain methylene group having from 2 to 10 carbon atoms of which one methylene is replaced by a phenylene.

13. The compound according to claim 7, wherein Y represents —NHCS— or —NHCSNH— at the meta-position; and Z is represented by formula (sp-14)

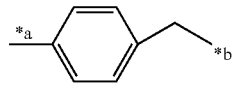

(sp-14)

wherein *a is bonded to Y in the formula (1) and *b is bonded to N$^+$R$^5$R$^6$R$^7$.

14. The compound according to claim 12, wherein Y represents —NHCSNH— at the meta-position; and Z is represented by formula (sp-14)

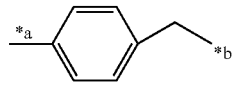

(sp-14)

wherein *a is bonded to Y in the formula (1) and *b is bonded to N$^+$R$^5$R$^6$R$^7$.

15. The compound according to claim 1, wherein N$^+$R$^5$R$^6$R$^7$ is any one of I), II), and III) given below which are mutually independent:

I) R$^5$, R$^6$, and R$^7$, which may be mutually different, each represents any one of an alkyl group having from 1 to 10 carbon atoms, an alkenyl group having from 3 to 8 carbon atoms, and an alkynyl group having from 3 to 9 carbon atoms, where the alkyl group, the alkenyl group, and the alkynyl group may be substituted with at least one of a phenyl group, a thienyl group, a cyclohexyl group, a cyano group, a hydroxyl group, an oxo group, a carboxyl group, a —CONH$_2$ group, and an —SO$_3$H group, and further, at least one of methylenes which constitute the alkyl group, the alkenyl group, and the alkynyl group may be replaced by any one of a phenylene, a thienylene, a furylene, an —O—, a —CO$_2$—, an —NHCO—, an —NR$^8$—, and an —N$^{30}$W$^-$R$^9$R$^{10}$— where R$^8$ represents an alkyl group having from 1 to 3 carbon atoms or an alkenyl group having 3 carbon atoms and the alkyl group may be substituted with at least one of a phenyl group and a hydroxyl group; R9 and R10, which may be mutually different, each represents an alkyl group having from 1 to 3 carbon atoms or an alkenyl group having 3 carbon atoms and the alkyl group may be substituted with at least one of a phenyl group and a hydroxyl group, II) N$^+$R$^5$R$^6$R$^7$ represents a monocyclic ring or a bicyclic ring which is any one of a pyrrolidinium ring, a piperidinium ring, a morpholinium ring, a thiomorpholinium ring, a piperazinium ring, an azepanium ring, a quinuclidinium ring, and a 1,4- diazabicyclo[2.2.2]octanium ring, provided that the position of its bonding with Z is an ammonium nitrogen atom; the monocyclic ring and the bicyclic ring may be substituted with at least one of a hydroxyl group, an oxo group, a cyano group, a phenyl group, a —$CONH_2$ group, and an —$R^{11}$ group; $R^{11}$ represents an alkyl group having from 1 to 6 carbon atoms or an alkenyl group having 3 carbon atoms, where the alkyl group represented by $R^{11}$ may be substituted with at least one of a hydroxyl group, a cyano group, a phenyl group, and a —$CONH_2$ group; moreover, at least one of methylenes which constitute the alkyl group may be replaced by any one of an —O—, a —$CO_2$—, and an —NHCO—; among $R^5$, $R^6$, and $R^7$, a group which is not involved in formation of the ring represents an alkyl group having 1 to 6 carbon atoms, an alkenyl group having 3 to 4 carbon atoms, or an alkynyl group having 3 to 6 carbon atoms; the alkyl group, the alkenyl group, and the alkynyl group represented by $R^5$, $R^6$, or $R^7$ may be substituted with at least one of a phenyl group, a thienyl group, a furyl group, a piperidyl group, a pyrrolidyl group, a morpholyl group, a cyclopropyl group, a cyclopentyl group, a cyano group, a hydroxyl group, an oxo group, a nitro group, a carboxyl group, an —$CONH_2$ group, and an —$SO_3H$ group; and moreover, at least one of methylenes which constitute the alkyl group may be replaced by any one of a phenylene, an —O—, and a —$CO_2$—, III) $N^+R^5R^6R^7$ represents a pyridinium ring, a quinolinium ring, or an isoquinolinium ring, provided that the position of its bonding with Z is an ammonium nitrogen atom; the pyridinium ring and the quinolinium ring may be substituted with at least one of a cyano group, a nitro group, a phenyl group, a thienyl group, a pyridyl group, an alkoxy group having from 1 to 3 carbon atoms, a carboxyl group, a —$CONH_2$ group, and an —$R^{12}$ group; $R^{12}$ represents an alkyl group having from 1 to 9 carbon atoms or an alkenyl group having from 2 to 4 carbon atoms; and the alkyl group and the alkenyl group represented by $R^{12}$ may be substituted with at least one of a phenyl group, a naphthyl group, a pyridyl group, a cyano group, a nitro group, a hydroxyl group, an oxo group, a carboxyl group, and an —$SO_3H$ group; and further, at least one of methylenes which constitute the alkyl group and the alkenyl group may be replaced by any one of an —S—, a —$CO_2$—, an —NHCO—, and an —$NR^8$— where $R^8$ represents an alkyl group having 1 to 3 carbon atoms and the alkyl group may be substituted with at least one hydroxyl group.

16. The compound according to claim 1, wherein $N^+R^5R^6R^7$ is any one of I), II), and III) given below which are mutually independent:

I) $R^5$, $R^6$, and $R^7$, which may be mutually different, each represents a straight chain alkyl group having from 1 to 10 carbon atoms, a straight chain alkenyl group having from 3 to 6, or 8 carbon atoms, a branched alkenyl group having 4, 6, or 7 carbon atoms, a straight chain alkynyl group having from 3, 5, 6, 7, or 9 carbon atoms, or a branched alkynyl group having 6 carbon atoms, in which 1) the alkyl group, alkenyl group, and alkynyl group represented by $R^5$, $R^6$, and $R^7$ are substituted with any one of a phenyl group, a thienyl group, a cyclohexyl group, a cyano group, a hydroxyl group, an oxo group, a carboxyl group, a —$CONH_2$ group, and an —$SO_3H$ group, 2) the alkyl group, the alkenyl group, and the alkynyl group are substituted with two hydroxyl groups, 3) the alkyl group, the alkenyl group, and the alkynyl group are substituted with one hydroxyl group and one —$SO_3H$ group, 4) the alkyl group, the alkenyl group, and the alkynyl group are substituted with one oxo group and one phenyl group, 5) the alkyl group, the alkenyl group, and the alkynyl group are substituted with one hydroxyl group and two phenyl groups, 6) one of methylenes which constitute the alkyl group, the alkenyl group, and the alkynyl group is replaced by any one of a phenylene, a furylene, a —$CO_2$—, an —NHCO—, an —$NR^8$— (where $R^8$ represents a methyl group, an ethyl group, an n-propyl group, a 2-propenyl group, a 2-hydroxyethyl group, a 2-hydroxypropyl group, or a benzyl group), and an —$N^+W^-R^9R^{10}$— (where $R^9$ and $R^{10}$ each represents a methyl group, an ethyl group, an n-propyl group, a 2-propenyl group, a 2-hydroxyethyl group, or a benzyl group), 7) two of methylenes which constitute the alkyl group, the alkenyl group, and the alkynyl group are replaced by any one selected from two (—O—)s, one phenylene and one —O—, one —O— and one —$NR^8$—, and one —NHCO— and one —O—, 8) three of methylenes which constitute the alkyl group, the alkenyl group, and the alkynyl group are replaced by any one selected from two (—O—)s and one —$NR^8$—, or one phenylene and two (—NHCO—)s, 9) the alkyl group, the alkenyl group, and the alkynyl group are substituted with one hydroxyl group, and moreover, one of methylenes which constitute the alkyl group, the alkenyl group, and the alkynyl group is replaced by an —O—, 10) the alkyl group, the alkenyl group, and the alkynyl group are substituted with one hydroxyl group, and moreover, one of methylenes which constitute the alkyl group, the alkenyl group, and the alkynyl group is replaced by an —$NR^8$—, 11) the alkyl group, the alkenyl group, and the alkynyl group are substituted with one hydroxyl group, and moreover one of methylenes which constitute the alkyl group, the alkenyl group, and the alkynyl group is replaced by a furylene, 12) the alkyl group, the alkenyl group, and the alkynyl group are substituted with one oxo group, and moreover, one of methylenes which constitute the alkyl group, the alkenyl group, and the alkynyl group is replaced by a thienylene, or 13) the alkyl group, the alkenyl group, and the alkynyl group are substituted with one oxo group, and moreover, two of methylenes which constitute the alkyl group, the alkenyl group, and the alkynyl group are replaced by one —O— and one phenylene, or the alkyl group, alkenyl group, and alkynyl group are neither substituted nor replaced, II) $N^+R^5R^6R^7$ represents a monocyclic ring or a bicyclic ring which is any one of a pyrrolidinium ring, a piperidinium ring, a morpholinium ring, a thiomorpholinium ring, a piperazinium ring, an azepanium ring, a quinuclidinium ring, and a 1,4- diazabicyclo[2.2.2]octanium ring, provided that the position of its bonding with Z is an ammonium nitrogen atom; the monocyclic ring and the bicyclic ring are 1) substituted with any one of a hydroxyl group, an oxo group, a cyano group, a phenyl group, a —$CONH_2$ group, and an —$R^{11}$ group, 2) substituted with one cyano group and one hydroxyl group, 3) substituted with one hydroxyl group and one —$R^{11}$, 4) substituted with one oxo group and one —$R^{11}$, 5) substituted with two oxo groups, or 6) substituted with two (—$R^{11}$)s, or the monocyclic ring and the bicyclic ring are unsubstituted, where $R^{11}$ represents any one of a methyl group, an ethyl group, an n-propyl group, an n-butyl group, an n-pentyl group, a 2-propenyl group, a benzyl group, an acetylamino group, a t-butoxycarbonylamino group, a hydroxymethyl group, a 2- hydroxyethyl group, a 3-hydroxypropyl group, a 2-cyanoethoxy group, a (2-cyanoethoxy)methyl group, a 2-carbamoylethoxy group, an ethoxycarbonyl group, a t-butoxycarbonyl group, a benzoyloxy group, a phenylacetylamino group, a butanoylamino group, and a pentanoylamino group; among $R^5$, $R^6$, and $R^7$, a group which is not involved in formation of the ring represents a straight chain alkyl group having from 1 to 6 carbon atoms, a straight chain alkenyl group having from 3 to 4 carbon atoms, or a straight chain alkynyl group having 3, 4, or 6 carbon atoms, and 1) the alkyl group, the alkenyl group, and the alkynyl group represented by $R^5$, $R^6$, or $R^7$ are substituted with any one of a phenyl group, a thienyl group, a furyl group, a piperidyl group, a pyrrolidyl group, a morpholyl group, a cyclopropyl group, a cyclopentyl group, a cyano group, a hydroxyl group, a carboxyl group, and an —$SO_3H$ group, 2) the alkyl group, the alkenyl group, and the alkynyl group are substituted with two hydroxyl groups, 3) the alkyl group, the alkenyl group, and the alkynyl group are substituted with one hydroxyl group and one —$SO_3H$, 4) the alkyl group, the alkenyl group, and the alkynyl group are substituted with four hydroxyl groups and one oxo group, 5) the alkyl group, the alkenyl group, and the alkynyl group are substituted with one nitro group and one morpholyl group, 6) one of methylenes which constitute the alkyl group, the alkenyl group, and the alkynyl group is replaced by a —$CO_2$—, or 7) the alkyl group, the alkenyl group, and the alkynyl group are substituted with one morpholyl group and moreover, one of methylenes which constitute the alkyl group, the alkenyl group, and the alkynyl group is replaced by an —O—, or the alkyl group, the alkenyl group, and the alkynyl group are neither substituted nor replaced, III) $N^+R^5R^6R^7$ represents any one of 1) a pyridinium ring substituted with any one of a cyano group, a phenyl group, a thienyl group, a pyridyl group, a methoxy group, an ethoxy group, a propoxy group, a carboxyl group, a —$CONH_2$ group, and a group, 2) a pyridinium ring substituted with two cyano groups, 3) a pyridinium ring substituted with two (—$R^{12}$)s, 4) a pyridinium ring substituted with one cyano group and one —$R^{12}$, 5) a pyridinium ring substituted with one phenyl group and one $R^{12}$, 6) a quinolinium ring substituted with any one of a cyano group, a nitro group, a carboxyl group, a methoxy group, an ethoxy group, a propoxy group, and —$R^{12}$, 7) a quinolinium ring substituted with one methoxy group and one —$R^{12}$, 8) a quinolinium ring substituted with one nitro group and one —$R^{12}$, 9) an unsubstituted pyridinium ring, 10) an unsubstituted quinolinium ring, and 11) an unsubstituted isoquinolinium ring, where $R^{12}$ represents any one of a methyl group, an ethyl group, an n-propyl group, an i-propyl group, an n-butyl group, a t-butyl group, an n-pentyl group, a 3-pentyl group, a 5-nonyl group, a vinyl group, a benzyl group, a 3-phenylpropyl group, a 2-(1-naphthyl)vinyl group, a hydroxymethyl group, a 2-hydroxyethyl group, a 3- hydroxypropyl group, a formyl group, an acetyl group, a propionyl group, a benzoyl group, a methoxycarbonyl group, an ethoxycarbonyl group, a butoxycarbonyl group, a hexoxycarbonyl group, a benzyloxycarbonyl group, a 2-propenyloxycarbonyl group, an ethoxycarbonylmethyl group, a 2-(methoxycarbonyl)ethyl group, an ethoxycarbonylmethylcarbonyl group, a 2- hydroxyethylaminocarbonyl group, a bis (2- hydroxyethyl)aminocarbonyl group, a 2-carboxyvinyl group, a carboxymethylthio group, a cyanomethyl group, a 2-nitrovinyl group, a 2-(4-pyridyl)ethyl group, a 2-(4-pyridyl)vinyl group, a 3-(4-pyridyl)propyl group, a 2-(4-pyridyl)-1,2-dihydroxyethyl group, and a 2-sulfoethyl group, provided that the position of its bonding with Z is an ammonium nitrogen atom.

17. The compound according to claim 1, wherein $N^+R^5R^6R^7$ is any one of I), II), and III) given below which are mutually independent:

I) $R^5$, $R^6$, and $R^7$, which may be mutually different, each represents any one of a straight chain alkyl group having from 1 to 10 carbon atoms, a straight chain alkyl group having from 1 to 10 carbon atoms which is substituted with one phenyl group, a straight chain alkyl group having from 1 to 10 carbon atoms which is substituted with one hydroxyl group, a straight chain alkenyl group having from 3 to 6, or 8 carbon atoms, a branched alkenyl group having 4, 6, or 7 carbon atoms, a straight chain alkynyl group having 3, 5, 6, 7, or 9 carbon atoms, and a branched alkynyl group having 6 carbon atoms, II) $N^+R^5R^6R^7$ represents a pyrrolidinium ring, a piperidinium ring, an azepanium ring, a quinuclidinium ring, or a 1,4- diazabicyclo[2.2.2]-octanium ring, substituted with any one of a methyl group, an ethyl group, an n-propyl group, an n-butyl group, an n-pentyl group, a 2-propenyl group, a phenyl group, a benzyl group, a hydroxyl group, a hydroxymethyl group, a 2- hydroxyethyl group, and a 3-hydroxypropyl group, or unsubstituted, provided that the position of its bonding with Z is an ammonium nitrogen atom; among $R^5$, $R^6$, and $R^7$, a group which is not involved in formation of the ring represents any one of a straight chain alkyl group having from 1 to 6 carbon atoms, a straight chain alkyl group having from 1 to 6 carbon atoms which is substituted with one phenyl group, a straight chain alkyl group having from 1 to 6 carbon atoms which is substituted with one hydroxyl group, a straight chain alkenyl group having from 3 to 4 carbon atoms, and a straight chain alkynyl group having 3, 4, or 6 carbon atoms, III) $N^+R^5R^6R^7$ represents an unsubstituted pyridinium ring, an unsubstituted quinolinium ring, an unsubstituted isoquinolinium ring, a pyridinium ring substituted with any one of a methyl group, an ethyl group, an n-propyl group, an i-propyl group, an n-butyl group, a t-butyl group, an n-pentyl group, a vinyl group, a phenyl group, a benzyl group, a 3-phenylpropyl group, a hydroxymethyl group, a 2-hydroxyethyl group, and a 3- hydroxypropyl group, a pyridinium ring substituted with any one selected from two methyl groups or two ethyl groups, a pyridinium ring substituted with one phenyl group and one methyl group, or a quinolinium ring substituted with any one of a methyl group and an i-propyl group, provided that the position of its bonding with Z is ammonium nitrogen atom.

18. The compound according to claim 15, wherein $R^1$ and $R^2$, which may be mutually different, each represents a straight chain alkyl group having 2 to 6 carbon atoms, and $(NR^3R^4)_m$ represents any one of a dimethylamino group substituting at the 7-position, a diethylamino group substituting at the 7- position, an ethylmethylamino group substituting at the 7- position, a dimethylamino group substituting at the 9-position, and dimethylamino groups substituting at the 7- and 9-positions.

19. The compound according to claim 16, wherein $R^1$ and $R^2$, which may be mutually different, each represents a straight chain alkyl group having 2 to 6 carbon atoms, and $(NR^3R^4)_m$ represents any one of a dimethylamino group substituting at the 7-position, a diethylamino group substituting at the 7- position, an ethylmethylamino group substituting at the 7- position, a dimethylamino group substituting at the 9-position, and dimethylamino groups substituting at the 7- and 9-positions.

20. The compound according to claim 17, wherein $R^1$ and $R^2$, which may be mutually different, each represents a straight chain alkyl group having 2 to 6 carbon atoms, and $(NR^3R^4)_m$ represents any one of a dimethylamino group substituting at the 7-position, a diethylamino group substituting at the 7- position, an ethylmethylamino group substituting at the 7- position, a dimethylamino group substituting at the 9-position, and dimethylamino groups substituting at the 7- and 9-positions.

21. The compound according to claim 18, wherein $(NR^3R^4)_m$ represents any one of a dimethylamino group substituting at the 7-position, a diethylamino group substituting at the 7- position, and an ethylmethylamino group substituting at the 7- position, and $N^+R^5R^6R^7$ represents any one of a 4-t-butylpyridinium group, a 3-(3-hydroxypropyl)-pyridinium group, a 3-[2- (methoxycarbonyl)ethyl]-pyridinium group, a 2-(n-propyl)- pyridinium group, a 4-phenyiquinuclidinium group, and a 1,4- diazabicyclo[2.2.2]octanium group.

22. A pharmaceutical composition containing the compound according to claim 1 as an active ingredient.

* * * * *